US007812131B2

(12) United States Patent
Larrinua et al.

(10) Patent No.: US 7,812,131 B2
(45) Date of Patent: Oct. 12, 2010

(54) SOURCES FOR, AND TYPES OF, INSECTICIDALLY ACTIVE PROTEINS, AND POLYNUCLEOTIDES THAT ENCODE THE PROTEINS

(75) Inventors: Ignacio Mario Larrinua, Indianapolis, IN (US); Aaron Todd Woosley, Fishers, IN (US); Thomas Meade, Zionsville, IN (US); Donald Joseph Merlo, Carmel, IN (US); Timothy Denver Hey, Zionsville, IN (US); Stephanie Love Burton, Indianapolis, IN (US)

(73) Assignee: Doe AgroSciences LLC, Indianapolis, IN (US)

( * ) Notice: Subject to any disclaimer, the term of this patent is extended or adjusted under 35 U.S.C. 154(b) by 503 days.

(21) Appl. No.: 11/366,918

(22) Filed: Mar. 2, 2006

(65) Prior Publication Data

US 2006/0205653 A1 Sep. 14, 2006

Related U.S. Application Data

(60) Provisional application No. 60/657,965, filed on Mar. 2, 2005, provisional application No. 60/704,533, filed on Aug. 2, 2005.

(51) Int. Cl.
*C07K 14/415* (2006.01)
*A61K 38/56* (2006.01)
*A61K 38/00* (2006.01)

(52) U.S. Cl. ........................ 530/370; 530/858; 530/350; 514/2

(58) Field of Classification Search ........................ None
See application file for complete search history.

(56) References Cited

U.S. PATENT DOCUMENTS

| | | | | |
|---|---|---|---|---|
| 2002/0078478 | A1* | 6/2002 | Ffrench-Constant et al. | 800/320.1 |
| 2003/0215803 | A1* | 11/2003 | Garcia et al. | 435/6 |
| 2004/0103455 | A1 | 5/2004 | Ffrench-Constant et al. | |
| 2004/0194164 | A1 | 9/2004 | Bintrim et al. | |
| 2004/0208907 | A1* | 10/2004 | Hey et al. | 424/405 |
| 2006/0168683 | A1 | 7/2006 | Hey et al. | |

FOREIGN PATENT DOCUMENTS

| | | |
|---|---|---|
| WO | WO 98/22595 | 5/1998 |
| WO | WO 99/24581 | 5/1999 |
| WO | WO 01/13731 | 3/2001 |
| WO | WO 2004/044217 | 5/2004 |
| WO | WO 2004/067727 A3 | 8/2004 |
| WO | WO 2004/067750 A3 | 8/2004 |

OTHER PUBLICATIONS

Springer T. A. (1997) Folding of the N-terminal, ligand-binding region of integrin alpha-subunits into a beta-propeller domain, Proc. Natl. Acad. Sci. U S A., vol. 94, No. 1, pp. 65-72.*

Gotoch et al. (2003) Extracellular secretion of the virulence plasmid-encoded ADP-ribosyltransferase SpvB in Salmonella, Microb. Pathog., vol. 34, No. 5, pp. 227-238.*

Bringaud et al. (2002) A new, expressed multigene family containing a hot spot for insertion of retroelements is associated with polymorphic subtelomeric regions of *Trypanosoma brucei*, Eukaryot. Cell., vol. 1, No. 1, pp. 137-151.*

Bockett, N.A. et al. "Utilization of the Rhs Core Region of tx-sepC Orthologues as a Degenerate System for the Rapid . . . ", Molecular Ecology Notes, 2006, pp. 616-620, vol. 6.

Ffrench-Constant, R. et al. "Photorhabdus: Towards a Functional Genomic Analysis of a Symbiont and Pathogen", FEMS Microbiology Reviews, 2003, pp. 433-456, vol. 26.

Hurst, M.R.H. et al. "Utilisation of the Rhs Core Region of tc-sepC Orthologes . . . " 38th Annual Meeting of the Soc. for Invert. Path., Aug. 7-11, 2005, Anchorage, Alaska.

Hurst, M. R. H. et al. "Plasmid-Located Pathogenicity Determinants of *Serratia entomophila*, the Causal Agent . . . ", Journal of Bact., Sep. 2000, pp. 5127-2138, vol. 182, No. 18.

NCBI database, Accession No. AACM01000442.1, "*Fusarium graminearum* genome sequence", (2007).

NCBI Database, Accession No. EAA68452, "Hypothetical Protein FG10566.1", Feb. 13, 2004. XP-002395819.

UNIPROT Database, "Hypothetical Protein FG10566.1", Aug. 16, 2005. XP-002395821.

Waterfield, N. R. et al. "The tc Genes of Photorhabdus: a Growing Family", TRENDS in Microbiology, Apr. 2001, pp. 185-191, vol. 9, No. 4.

* cited by examiner

*Primary Examiner*—Anand U Desai
*Assistant Examiner*—Samuel Liu
(74) *Attorney, Agent, or Firm*—Donald R. Stuart; Baker & Daniels LLP

(57) ABSTRACT

The subject invention provides exciting new sources for surprising, new types of toxin complex ("TC") proteins. The subject invention includes these new classes and types of TC proteins. The subject invention also includes polynucleotides that encode the subject proteins. The subject invention further provides vectors and cells comprising these polynucleotides. The subject invention also provides novel methods of controlling insects. The subject invention relates in part to the surprising discovery that new types of TC proteins can be obtained from a widely diverse phylogenetic spectrum of organisms including, most notably and surprisingly, eukaryotic fungus.

3 Claims, 7 Drawing Sheets

>Natural BC fusion in Tannerella

MRIINISIEIICTCLIIGVTGYAQKTNVYYAAGNEASSDNYDPSGYRIWGN
YRNETSDANELDARQLPSFYYKILKNRLENNYSPEEKRTFAPAPLSRGMA
VGSTAGMAEITLTGAANYSVPIEVPEGIAGFKPEVSVRYSSQSGVGLLGY
GWNLSAFSVISRSGKTFYHDGMSKAPALSYEDNVMLDGQRLMLISGQNLM
NGAKYRLENDPTIDITYKMIGSFQGFTVRSKDGTIREFGVTSDSNIETSD
GTALFWLLSRVIDKQGNVISYQYEEVINNGEFYLNRIEYASGRSIRFSYE
TRKDKQTGYYAGAVLNSNKILKNISTYIGQMQFKQYQFNYNTYENGLYTQ
LTEIIESGQNGQRYNPTRIYYGYPDPYKNEDIVTLSEHRKGNKPLFADFN
GDGRMDFLSYPEELSDNPKEDVATLFLSLHGLGGTYFAKKCTIPMRAFGE
FRYFMLADVNGDKKMDVIHVSRADNGTERYNYYVFDGEKLVYQYKGFNTH
GDEAFVGDFDGDGRHDILIKNNSKVYDGEGREIASGGITDWGSDYIKYYY
PNSRYICDLNGNGKSELLVIDKHGAKVYELNERQFVELPEFRTSLIKNYY
FPYFGDFNGDGKTDVLIQRWHQGDYDDVSILFSTGKGYVKQDVLNADIRA
KVFVADFNKDGKSDIFHMEIVNNAVRMKVGIFHGNGFHTTYHSSNLRLED
VYLSYNNIEYDNYLFQVADFDGDGSSEFCCARHMNAYIIRSFSDPQNLLV
ETISDGLGAYTSFQYAPITSNSVCTVTGNNEAFPVTDSRFPLYVVSNITQ
STGGYSETTRYRYKDPRSHMQGKGFLGFGEVESIDDNKDRKVITTYGYEK
DYFYPFIKEQKIMTRSGMKISTSVYENSYVYNGSKRVVPYVRKSTTTDHL
TGVVKTAECTQIDTWANPLSIVTRHGNDVTETVTASYINREAENLWIIGL
PQSVEKRVTKGTGTWIDKQVFTYNAGYLPQKIVNFTGDGNKQTSEDVFDY
DRYGNMITHSTRAYASPHVLTTRTEYSSDGLYMLRTIDPLSRVTTHTYNS
SGQLASTKDFLNTTTAYEYDGMGRLVKTVYPDQTQSSVVYSWENAVVNSV
YGMTETLTGKPERKIYFDAFGRKVRECIRQTDGQDVCTDTKYDNAGRVSQ
ESLPFKGGAASKWNTYGYDGYGRLSQQTHASGKTTTYTYAGNSITETKNG
ISHKSVYNAMGEQVSVTDPAGTITYTLRPDGQPVTITAPGNVKTTFSYDA
YGRQTAIHDPSAGNRTFAYDASGNLQRETDADNRVKTMSYDVYGRLTSKV
LPEFTTSYAYNGYGQLTTETSNNGISSVYEYDSYGRLAKERNNVPDGKWL
EKTYTYAAGNLASVRYASQSGAIGTEAYTYSHGHMNGIRWGSSPVWTLNA
ENPFSQPLSVTTGPVTRTYTYDVYGIPTGRTAQSTAGGTFLNSTYGFDAA
RGNLTYRKDNRRNKQENFTYDNLNRLKTYGGIVMDYDPKGNITKKGDVGT
FHYQTPYKPYALSGADIGTNKVIPPREQTIRYTSFDRPSVITENGYEASF
IYNASGDRQKMTVKKGGKPFYTRYYLGGRYETDVMGNSQKHRLYIGGDAY
TAPAVYMNTGNGWALYYICRDYLGNMTHLVASNGTVVQELSYDAWGRLRN
PETHAVYLPDNETELMLGRGYTGHEHLSMFGLINMNARLYDPVLGRFLSP
DPYVQMPDFTQSFNRYSYCLNNPLVYVDQDGE*IAWFVPVIVGAVIGAYSG*
*GVIANEGQYNPVKWDYNSGKTWGYMLGGAVVGGISGSLGWAVSISGMPMA*
*NTAGIISASFVNSVGTHIYTGGQTPVSMSLGVASYDFTNGSFGHLGKKGN*
*KWYENLGYGLGAMANLSDILIGFKPQKVDLVTENSDAIGHSAIVKHDTRT*
*GIKGKTDINGLISVGPDRVSQPDGSWHWMKGTNKWSTYSAKENSRWMQSL*
*DVNYNTINRYSNWLNKMENTGKLVYSLELSSCVTHTSLALNASGVFNIGI*
*HPYLLHAQMYLWGNGIRPWSFNHFFNR*

Fig. 2

>gi|46138103|ref|XP_390742.1| hypothetical protein FG10566.1 fused BC toxin protein [Gibberella zeae PH-1]
MSTLSSRPGDPRALHSGQNNGAPETLTNSKSNATLSGNRTTAPASASSFA
PQVRTLGEGIPGFRTSFNVAGKGGGAFRSISEDFEVSPANGTMSLAIPVR
TSPTRGGYGPDLKLSYDSGSGNGPFGFGWSMSMPSIHRKTTHAIPRYVDD
EDDFLMSGGDIIKRLNSEGIQETRNESGICGKFLVTTYRPRVDSGNIRIE
RWVRREDLEDVHWRTISSSNETKIYGDSDSSRIFDASGPSKRIFSWLLSR
SYDASGNAIEYVYKEEDSLGISDATGAMPVWEKNREQDARYRERYIKRVK
YGNRKPNRDLTTWEVSDWPEEWMFEVVFDYGEHDKGSPSTEESHSWPVRQ
DVFSQSRPGFEIRTYRLCRRVLMFHHFPEHTQESETFVFSTDLQYNESRQ
RTVLASLVATGYSSYKDNNDGKQRYRSESLPPWSFEYTSSPEASEIELME
AKTFNLLELPTSDARVSEWLDLDGDGMPGLLTRSVDGALYYQRNLGSISG
DDDPQFCGPVLLAQQPSMTGGTFQDLDRNGNLNYVLRNEHGHLEGYYERG
NSDTWKNYIEFPETSNGDIWQSTIDIDLTGDGHPDLICAADDSQVLIWQQ
NLGKKGLSSYQRVICGHDWESCPRLIKNQDVQTYVGDMTGSGMSDLVEIS
VSSVRYWPNLGYGTFGAAVDMGNPPAFAAKDYFDHSRVRLMDTDGSGTMD
LLYALPTGGAALYYNLAGNSWSNMVFLPHLPAIITPMSIFTLDLIGKGAD
CLCWADTSTDGNRIMYLDITGETKPHLLKSYSNGWGATTSVDYAPSTKFF
AEDTRNGHPWSSKLPFPVQCVSKVQVEDAITGNRQSTEYIYHNGCYNPTE
KQFSGFEMVEQFQSERVIVGEDETYEPPVTHTKSWFNVGLSLVVDESRFL
TKPAILSSLQDYHTDPAELVNALKGLNVRSEIYSQDGSPKSHLPYVIKEV
SYHVKISQARDTNKYSAVQVLPRETFSRAYERDMSDPRVTHDMVIKTNDF
GDVEESLSIVYPRAGKTTFEDVNKNQKAGNMSYTQNWYTKMVSEPEQEHF
RKPAAYRQQEHEILSFPFNGTLKFDDALAFNFNGLPTTKCSKTWKALRSE
NKAFYKDSLLQRRLDEGELQTFSLLDQTYALAFTPDILAKVEIGLRNCNV
PGSVEELLTKGSYVKLKDSDGWWAPSSQSFFCSSKTASAAEELKEARKSF
YTPSRFVDLFGNSSRLNMDKDFLLATEVEDAIGTATSFKNSYEHLQPVEI
IDANSNSVQVVLDPLGESIAVAASTRRDGVIEEIDSLENMVLDASPEDVD
DILRDPTGEVSTRLLGNAASRTIHYRDRYAQWKSRQNETSTSVDPEPALS
LVLSRDLSFKESSSPEIRVIVSYMNGLGSQYQEQHLSDPTTLEKRWLVPG
LAIPDTQGQVVCTYQPRFATLAAPIPSSLMKTNAAFTFYDAMGRNVASLA
ADCTWSKTVYTPWTTVEHGAGSMVLQSNARDDPDVGHFFSRIASSRYSQS
WYDKRKLGTAQEKRAAEKSAVYSDTPLTTHSGSCGLPVRTIQQAGGKTYT
RSSMYDLQTTGMDCGESWLLLDAQGGEILSWNCRGYSFITRYDPLRRETE
RLVAKAAEMPKLISRITYGETCGDAINLNLNGQVWKVEDQAGVHINTHYN
IRGHCLGKTLQFTKEYKQLVDWKLDQTLETEVYPHTYFYDNYGQVLQEED
EQGNRTRRNYSRQGHVVSVDFSSIKGRDWKSYLSGATFSADGLPITIKYG
NGVVSDFFYDDESRNLISQRTTRPCRGRRELLQDRTHVYDYVGRRIFTSD
GSEQVKYFGESRVKPEWDYTYNATGALVIATGRAQLSGKIGNGNQLTPHN
AMNGLNPSRGGGDGNLLYQYRETYDYDREGNILMMKHEAPDIKGVTSWTR
NYHYDEKSLLSDDPRVKSNRLSRTSIGDTNEGKYMYEGSAGLSGCITTLP
KFSELDWNMNNMLSFSSTQYVNAGTPERTYYVYDHAGNRVRKVTETAAKS
GEEPRKQRDTLFFGGVELQTKSNGSLLWTTRVKGDGIVAVVEVNRNQETP
LVRFQAGRDMEFDDQAQLISYEEYSPFGAVVYAAMYGNIEAPRAYRFARY
EHDSETGLYHCGQRYYCPWLGRWTSPDPLGDVDGPNLFVYVNNDPVNSHD
PSG*TSGKKTKEGTREMYAAPDDQGKRRLVDENKAVADRIAKYERKLQRQE*
*RKQQRAIARMSGTDPILGSRARYAVGIAAMGNALGRISGSTELHHTYPQE*
*YREEFSDIDINVDRTSVSISKEAHYICTYGSILDNLVATNKRWKSEYFDT*
*PDTGYYEQMEQHEWYDDDPGMQYAIRLHLAYEARTLNGKIMADFGINPKG*
*EDGRSMFVNYDAVTKMRTAGQRRGVRNDNLIHHETWPGRPFNTGNSDTDN*
*AGGPVHFQVAEEQYNGLDADAQAKFDDLRNQMEALLGKR*

Fig. 3

```
Tannerella    1 MRIINISIEIICTCLIIGVTGYAQKTNVYAAGNEASSDNYDPSGYRIWGN   50

Gibberella    1                                                       0

Tannerella   51 YRNETSDANELDARQLPSFYYKILKNRLENNYSPEE------------KR   88
                  ..|..:...|.|.|.|.          :||.:||.            .|
Gibberella       1   MSTLSSRPGDPRALHSG---------QNNGAPETLTNSKSNATLSGNR   39

Tannerella   89 TFAP------APLSRGMAVG--------STAGMA-----------EIT-L  112
                |.||      ||..|.:..|        :.||..           |:: .
Gibberella   40 TTAPASASSFAPQVRTLGEGIPGFRTSFNVAGKGGGAFRSISEDFEVSPA   89

Tannerella  113 TGAANYSVPIEVPEGIAGFKPEVSVRYSSQSGVGLLGYGWNLSAFSVISR  162
                .|..:.::|:.......|:.|::.:.|.|.||.|..|:||::|..|:..:
Gibberella   90 NGTMSLAIPVRTSPTRGGYGPDLKLSYDSGSGNGPFGFGWSMSMPSIHRK  139

Tannerella  163 SGKTF--YHDGMSKAPALSYEDNVMLDGQRLMLISGQNLMNGAKYRLEND  210
                :....  |.|.            ||:.:.:.|..::   :.|.:.......|:
Gibberella  140 TTHAIPRYVDD---------EDDFLMSGGDII----KRLNSEGIQETRNE  176

Tannerella  211 PTIDITYKMIGSFQGFTVRSK--DGTIR-------------EFGVTSDSN  245
                ..|      .|.|...|.|.:  .|.||             .:...|.||
Gibberella  177 SGI------CGKFLVTTYRPRVDSGNIRIERWVRREDLEDVHWRTISSSN  220

Tannerella  246 IET-----SDGTALF-----------WLLSRVIDKQGNVISYQYEEVINN  279
                 ||      ||.::|           |||||..|..||.|.|.|:|..:.
Gibberella  221 -ETKIYGDSDSSRIFDASGPSKRIFSWLLSRSYDASGNAIEYVYKEEDSL  269

Tannerella  280 G----------------------EFYLNRIEYASGRSIR-----------  296
                |                      |.|:.|::|.:.:.|
Gibberella  270 GISDATGAMPVWEKNREQDARYRERYIKRVKYGNRKPNRDLTTWEVSDWP  319

Tannerella  297 ------------------------FSYETRKDKQTGYYAGAVLNSNKILK  322
                                        .|:..|:|..:....|..:.:.:::.:
Gibberella  320 EEWMFEVVFDYGEHDKGSPSTEESHSWPVRQDVFSQSRPGFEIRTYRLCR  369

Tannerella  323 NISTYIGQMQFKQYQFNYNTYENGLYTQLTEIIESGQNGQRYNPTR----  368
                .:.:.:              :.|..:|.|.|:.:...|::          :||.:|
Gibberella  370 RVLMF--------HHFPEHTQESETFVFSTDL--------QYNESRQRTV  403

Tannerella  369 ----IYYGYPDPYKNEDIVTLSEHRKGNKPLFADFNGDGRMDFLS-----  409
                    :..|| ..||:                   |.||:..:.|
Gibberella  404 LASLVATGY-SSYKD-------------------NNDGKQRYRSESLPP  432

Tannerella  410 YPEELSDNPKEDVATLFLSLHGLGGTYFAKKCTIPMRAFGEFRYFMLADV  459
                :..|.:.:|:.....|.          .||...:.......:.|.....|:
Gibberella  433 WSFEYTSSPEASEIELM----------EAKTFNLLELPTSDARVSEWLDL  472

Tannerella  460 NGDKKMDVIHVSRADNGTERYNYYVFDGEKLVYQYKGFNTHGDE--AFVG  507
                :||.....::  :|:.:|.          |.||....:..||:  .|.|
Gibberella  473 DGDGMPGLL--TRSVDGA------------LYYQRNLGSISGDDDPQFCG  508

Tannerella  508 ----------------DFDGDGRHDILIKNNSKVYDGEGREIASGGITDW  541
                                |.|.:|.:.:::|.....:|     ....|.:|.
Gibberella  509 PVLLAQQPSMTGGTFQDLDRNGNLNYVLRNEHGHLEG----YYERGNSDT  554
```

Fig. 4A

```
Tannerella     542 GSDYIKYYYPNSRYI------CDLNGNGKSELLV-------------IDK   572
                   ..:||::....::..|      .||.|:|..:|:.              :.|
Gibberella     555 WKNYIEFPETSNGDIWQSTIDIDLTGDGHPDLICAADDSQVLIWQQNLGK  604

Tannerella     573 HGAKVYE--LNERQFVELPEFRTSLIKNY-YFPYFGDFNGDGKTDVL---  616
                   .|...|:  :.......|.    ||||. ...|.||..|.|.:|::
Gibberella     605 KGLSSYQRVICGHDWESCPR----LIKNQDVQTYVGDMTGSGMSDLVEIS  650

Tannerella     617 ---IQRWHQGDYDDVSILFSTGK--GYVKQDVLNADIRAKVFVADFNKDG  661
                      ::.|....|.........|.  .:..:|..:   .::|.:.|.:..|
Gibberella     651 VSSVRYWPNLGYGTFGAAVDMGNPPAFAAKDYFD---HSRVRLMDTDGSG  697

Tannerella     662 KSDIFHMEIVNNAVRMKVGIFH---GNGFHTTYHSSNLRLEDVYLSYNNI  708
                   ..|:.:.....|      .:::  ||.:      ||:    |:|.:...
Gibberella     698 TMDLLYALPTGGA-----ALYYNLAGNSW------SNM----VFLPHLPA  732

Tannerella     709 EYDNYLFQVADFDGDGSSEFCCA-------RHMNAYI-IRSFSDPQNLLV  750
                   ..........|..|.|:...|.|        |.|  |: |...:.|.  |:
Gibberella     733 IITPMSIFTLDLIGKGADCLCWADTSTDGNRIM--YLDITGETKPH--LL  778

Tannerella     751 ETISDGLGAYTSFQYAPITSNSVCTVTGNNEAFPVTDSR---------F  790
                   ::.|:|.||.||..|||.|.            |...|:|         |
Gibberella     779 KSYSNGWGATTSVDYAPSTK-----------FFAEDTRNGHPWSSKLPF  816

Tannerella     791 PLYVVS--NITQSTGGYSETTRYRYKDPRSHMQGKGFLGFGEVESIDDNK  838
                   |:..||  .:..:..|..::|.|.|.:......|.|.||  |.::..:
Gibberella     817 PVQCVSKVQVEDAITGNRQSTEYIYHNGCYNPTEKQFSGF---EMVEQFQ  863

Tannerella     839 DRKVITTYGYEKDYFYP--------------FIKEQKIMTR---------  865
                   ..:||.  |.::.|..|              .:.|.:.:|:
Gibberella     864 SERVIV--GEDETYEPPVTHTKSWFNVGLSLVVDESRFLTKPAILSSLQD  911

Tannerella     866 ------------SGMKISTSVYENSYVYNGS-KRVVPYVRKSTT------  896
                               .|:.:.:.:|..    :||  |..:|||.|..:
Gibberella     912 YHTDPAELVNALKGLNVRSEIYSQ----DGSPKSHLPYVIKEVSYHVKIS  957

Tannerella     897 ----TDHLTG-------------------------VVKTAECTQIDTWA  916
                       |:..:.                         |:||.:....::
Gibberella     958 QARDTNKYSAVQVLPRETFSRAYERDMSDPRVTHDMVIKTNDFGDVE---  1004

Tannerella     917 NPLSIV-TRHGNDVTETVT------------------------------A  935
                   ..|||| .|.|....|.|.                              |
Gibberella    1005 ESLSIVYPRAGKTTFEDVNKNQKAGNMSYTQNWYTKMVSEPEQEHFRKPA  1054

Tannerella     936 SYINREAENL-----------------------------W----------  946
                   :|..:|.|.|                             |
Gibberella    1055 AYRQQEHEILSFPFNGTLKFDDALAFNFNGLPTTKCSKTWKALRSENKAF  1104

Tannerella     947 ------------------------------------IIGL-----PQSV  954
                                                       .|||     |.||
XP_390742.1   1105 YKDSLLQRRLDEGELQTFSLLDQTYALAFTPDILAKVEIGLRNCNVPGSV  1154

Tannerella     955 EKRVTKGT--------GTWI-DKQVF-----TYNAG----------YLPQ  980
                   |:.:|||:        |.|. ..|.|     |.:|.           |.|.
Gibberella    1155 EELLTKGSYVKLKDSDGWWAPSSQSFFCSSKTASAAEELKEARKSFYTPS  1204

Tannerella     981 KIVNFTG---------------------------------------DGN  990
                   :.|:..|                                       |.|
Gibberella    1205 RFVDLFGNSSRLNMDKDFLLATEVEDAIGTATSFKNSYEHLQPVEIIDAN  1254
```

Fig. 4B

```
Tannerella   991 KQTSEDVFD--------------------YDRYGNMITH-----------  1009
                 ..:.:.|.|                    .|...||:..
Gibberella  1255 SNSVQVVLDPLGESIAVAASTRRDGVIEEIDSLENMVLDASPEDVDDILR  1304

Tannerella  1010 ------STR-----AYASPHVLTTRTEYSSDGLYMLRTIDP-------LS  1041
                       |||     |..:.|.......::.|.......::||       ||
Gibberella  1305 DPTGEVSTRLLGNAASRTIHYRDRYAQWKSRQNETSTSVDPEPALSLVLS  1354

Tannerella  1042 RVTTHTYNSS----------------------------------------  1051
                 |..:...:||
Gibberella  1355 RDLSFKESSSPEIRVIVSYMNGLGSQYQEQHLSDPTTLEKRWLVPGLAIP  1404

Tannerella  1052 ---GQLAST-------------KDFLNTTTAYE-YDGMGRLVKTVYPDQT  1084
                    ||:..|             ...:.|..|:. ||.|||.|.::..|.|
Gibberella  1405 DTQGQVVCTYQPRFATLAAPIPSSLMKTNAAFTFYDAMGRNVASLAADCT  1454

Tannerella  1085 QSSVVYS-W-------------ENA------------VVNSVY-------  1101
                 .|..||: |             .||            :.:|.|
Gibberella  1455 WSKTVYTPWTTVEHGAGSMVLQSNARDDPDVGHFFSRIASSRYSQSWYDK  1504

Tannerella  1102 ---GMTETLTGKPERKIYFD--------AFGRKVRECIRQTDGQDVCTDT  1140
                    |..:........:..:|.|        :.|..|| .|:|..|:.....:
Gibberella  1505 RKLGTAQEKRAAEKSAVYSDTPLTTHSGSCGLPVR-TIQQAGGKTYTRSS  1553

Tannerella  1141 KYD--NAGRVSQES---LPFKGGAASKWNTYGYD---GYGRLSQQT----  1178
                 .||  ..|....||   |..:||....||..||.   .|..|.:|
Gibberella  1554 MYDLQTTGMDCGESWLLLDAQGGEILSWNCRGYSFITRYDPLRRETERLV  1603

Tannerella  1179 --------------------------------------------------  1178

Gibberella  1604 AKAAEMPKLISRITYGETCGDAINLNLNGQVWKVEDQAGVHINTHYNIRG  1653

Tannerella  1179 HASGKTTTYTYAGNSITETK-------NGISHKSVYNAMGEQVSVTDPAG  1221
                 |..|||..:|.....:.:.|       ....|...|:..|:.:...|..|
Gibberella  1654 HCLGKTLQFTKEYKQLVDWKLDQTLETEVYPHTYFYDNYGQVLQEEDEQG  1703

Tannerella  1222 TIT-----------------------------YTLRPDGQPVTITAPGNV  1242
                 ..|                             .|...||.|:||.....|
Gibberella  1704 NRTRRNYSRQGHVVSVDFSSIKGRDWKSYLSGATFSADGLPITIKYGNGV  1753

Tannerella  1243 KTTFSYD--------------AYGRQTAIHDPSAGNRTFAYDASGNLQRE  1278
                 .:.|.||              ..||:..:.|     ||..||..|.....
Gibberella  1754 VSDFFYDDESRNLISQRTTRPCRGRRELLQD-----RTHVYDYVGRRIFT  1798

Tannerella  1279 TDADNRVKTMSYDVYGRLTSKVLPEFTTSYAYNGYGQLTTETSNNGISSV  1328
                 :|...:||     .:|.  |:|.||:  .|.||..|.|...|
Gibberella  1799 SDGSEQVK-----YFGE--SRVKPEW--DYTYNATGALVIAT--------  1831

Tannerella  1329 YEYDSYGRLAKERNNVPDGKWLEKTYTYAAGNLASVRYASQSGAIGTEAY  1378
                       ||                              |..||.||....
Gibberella  1832 ------GR------------------------------AQLSGKIGNGNQ  1845

Tannerella  1379 TYSHGHMNGIRWGSSPVWTLNAENPFSQPLSVTTGPVTRTYTYDVYGIPT  1428
                 ...|..|||:             ||     |...|.....|.|
Gibberella  1846 LTPHNAMNGL-------------NP-----SRGGGDGNLLYQY-------  1870
```

Fig. 4C

```
Tannerella   1429 GRTAQSTAGGTFLNSTYGFDAARGNLTYRKDNRRNKQ------ENFTYDN   1472
                               ..||.:|  ..||:...|.....:.:      .|:.||.
Gibberella   1871 -------------RETYDYD-REGNILMMKHEAPDIKGVTSWTRNYHYDE  1906

Tannerella   1473 LNRLKTYGGIVMDYDP--KGN---ITKKGDVGTFHYQTPYKPYA-LSGA-   1515
                  .:.|..         ||  |.|   .|..||.....|.  |:..| |||.
Gibberella   1907 KSLLSD--------DPRVKSNRLSRTSIGDTNEGKYM--YEGSAGLSGCI  1946

Tannerella   1516 ---------DIGTNKVIPPREQTIRYTSFDRPSVITENGYEASFIYNASG  1556
                           |...|.::  ...:.:|.:...|     |..|   ::|:.:|
Gibberella   1947 TTLPKFSELDWNMNNML--SFSSTQYVNAGTP----ERTY---YVYDHAG  1987

Tannerella   1557 DR-QKMT---VKKGGKPFYTRYYLGGRYETDVMGNSQKHRLYIGGDAYTA  1602
                   :| :|:|   .|.|.:|                 ..|:..|:.||
Gibberella   1988 NRVRKVTETAAKSGEEP-----------------RKQRDTLFFGG-----  2015

Tannerella   1603 PAVYMNTGNGWALYYICRDYLGNMTHLVASNGTV-VQELSYDAWGRLRNP  1651
                    |.:.|.:..:|.:..|         |..:|.| |.|::        ||.
Gibberella   2016 --VELQTKSNGSLLWTTR---------VKGDGIVAVVEVN-------RNQ  2047

Tannerella   1652 ETHAVYLP-------DNETEL----------------MLG-----RGY--  1671
                  ||..|...       |::.:|                |.|     |.|
Gibberella   2048 ETPLVRFQAGRDMEFDDQAQLISYEEYSPFGAVVYAAMYGNIEAPRAYRF  2097

Tannerella   1672 TGHEHLSMFGLINMNARLYDPVLGRFLSPDPY--VQMPDFTQSFNRYSYC  1719
                  ..:||.|..||.:...|.|.|.|.||:.||||.  |..|       |.:.|.
Gibberella   2098 ARYEHDSETGLYHCGQRYYCPWLGRWTSPDPLGDVDGP------NLFVYV  2141

Tannerella   1720 LNNPLVYVDQDGEIAWFVPVIVGAVIGAYSGGVIANEGQYNPVKWDYNSG  1769
                  .|:|:...|..|                 :.|....||.........:.|
Gibberella   2142 NNDPVNSHDPSG-----------------TSGKKTKEGTREMYAAPDDQG  2174

Tannerella   1770 KTWGYMLGGAV--------------------VGGISGS---LG----WA  1791
                  |........||                    :..:||:   ||    :|
Gibberella   2175 KRRLVDENKAVADRIAKYERKLQRQERKQQRAIARMSGTDPILGSRARYA  2224

Tannerella   1792 VSISGMPMANTAGIISASFVNSVGTHIY-------------TGGQTPVSM  1828
                  |.|:.  |.|..|.||.|   :...|.|             ...:|.||:
Gibberella   2225 VGIAA--MGNALGRISGS---TELHHTYPQEYREEFSDIDINVDRTSVSI  2269

Tannerella   1829 SLGVASYDFTNGSF---------------------GHLGK-KGNKWYE--  1854
                  | ..|.|..|.||.                     |:..: :.::||:
Gibberella   2270 S-KEAHYICTYGSILDNLVATNKRWKSEYFDTPDTGYYEQMEQHEWYDDD  2318

Tannerella   1855 ---------NLGYGLGAMANLSDILIGFKPQKVDLVTENSDAIGHSAIVK  1895
                           :|.|.....:.........|..|:..|          |.|..|.
Gibberella   2319 PGMQYAIRLHLAYEARTLNGKIMADFGINPKGED---------GRSMFVN  2359

Tannerella   1896 HDTRTGIKGKTDINGLISVGPDRVSQPDGSWH---WMKGTNKWSTYSAKE  1942
                  :|..|.::          :.|..|..:.|...|   | .|....:..|..:
Gibberella   2360 YDAVTKMR---------TAGQRRGVRNDNLIHHETW-PGRPFNTGNSDTD  2399

Tannerella   1943 NSR---WMQSLDVNYNTIN-----RYSNWLNKMEN-TGKLVYSLELSSCV  1983
                  |:.    ..|..:..||.::      ::.:..|:||. .||.
Gibberella   2400 NAGGPVHFQVAEEQYNGLDADAQAKFDDLRNQMEALLGKR           2439

Tannerella   1984 THTSLALNASGVFNIGIHPYLLHAQMYLWGNGIRPWSFNHFFNR   2027

Gibberella   2440                                              2439
```

Fig. 4D

SOURCES FOR, AND TYPES OF, INSECTICIDALLY ACTIVE PROTEINS, AND POLYNUCLEOTIDES THAT ENCODE THE PROTEINS

CROSS-REFERENCE TO RELATED APPLICATIONS

The subject application claims priority of U.S. provisional patent application Ser. No. 60/657,965, filed Mar. 2, 2005, and of U.S. provisional patent application Ser. No. 60/704,533, filed Aug. 2, 2005.

BACKGROUND

Billions of dollars are spent each year to control insects, and additional billions of dollars are lost because of crop damage inflicted by insects. Synthetic organic chemical insecticides have been the primary tools used to control insects, but biological insecticides are playing an important role in some areas. Insect-resistant plants transformed with insecticidal protein genes, such as the insecticidal proteins derived from *Bacillus thuringiensis* (B.t.), have revolutionized modern agriculture and heightened the importance and value of insecticidal proteins and their genes.

Toxin Complex (TC) proteins and genes, found primarily in bacteria of the genera *Photorhabdus* and *Xenorhabdus* (but also in other bacterial genera such as *Serratia, Pseudomonas*, and *Paenibacillus*) are an important, relatively new source of insecticidal proteins and genes. There are at least three distinct classes of TC proteins. Native Class A TC proteins are approximately 280 kDa in size and possess insecticidal activity. Class B TC proteins (approximately 170 kDa) and Class C TC proteins (approximately 107 kDa), in combination, enhance the insecticidal potency of Class A TC proteins but possess little to no insecticidal activity in the absence of a Class A TC protein. That is to say, Class B and Class C TC proteins in combination potentiate the insecticidal activity of Class A TC proteins. See e.g. US-2004-0208907 and WO 2004/067727 for a more detailed review of the art. Class A TC proteins possess insecticidal activity, but this activity is relatively low. When a Class A TC protein is combined with a Class B and a Class C TC protein, they form a complex that is much more potent than the Class A TC protein alone.

Unlike *Bacillus thuringiensis, Xenorhabdus*, and *Photorhabdus*, which are organisms that are known to be insecticidal and to have insecticidal proteins, organisms such as *Fusarium graminaerum* (now known as *Gibberella zeae*) and *Methanosarcina* were not known to be insecticidal and were not known to produce insecticidally active proteins.

BRIEF SUMMARY

The subject invention provides new classes and types of toxin complex ("TC") proteins, and exciting new sources for TC proteins. The subject invention also includes polynucleotides that encode the subject proteins. The subject invention further provides vectors and cells comprising these polynucleotides. The subject invention also provides novel methods of controlling insects.

The subject invention relates in part to the surprising discovery that new types of TC proteins can be obtained from a widely diverse phylogenetic spectrum of organisms including, most notably, eukaryotic fungi.

BRIEF DESCRIPTION OF THE FIGURES

FIG. 2 shows the amino acid sequence of SEQ ID NO:2 for the natural BC fusion in *Tannerella*, where underlined amino acids show the spvB (Salmonella virulence plasmid B protein) domain using the standard spvB-ls.hmm ("hmm" ="hidden Markov model") model; amino acids with double underlining show the FG-GAP domain using the BMode17.hmm model; amino acids in bold show the RHS (recombination hot spot) domains using Pfam rhs_ls.hmm model (where "ls" mode requires a sequence model to match the entire HMM profile); and amino acids in italics show the HVR mapped by lack of homology to other proteins.

FIG. 3 shows the amino acid sequence of SEQ ID NO:4 for the hypothetical protein FG10566.1 fused BC toxin protein [*Gibberella zeae* PH-1], where the underlined amino acids indicate the spvB domain using the standard spvB-ls.hmm model; amino acids with double underlining indicate three FG-GAP domains found with the BModels3 .hmm model; amino acids in bold indicate RHS domains using the Pfam rhs_ls.hmm model; and italics indicates HVR mapped by lack of homology to other proteins.

FIGS. 4A-D show the global alignment of the two BC fused toxin proteins from *Tannerella* of SEQ ID NO:2 and *Gibberella* of SEQ ID NO:4.

BRIEF DESCRIPTION OF THE SEQUENCES

Figure 1:
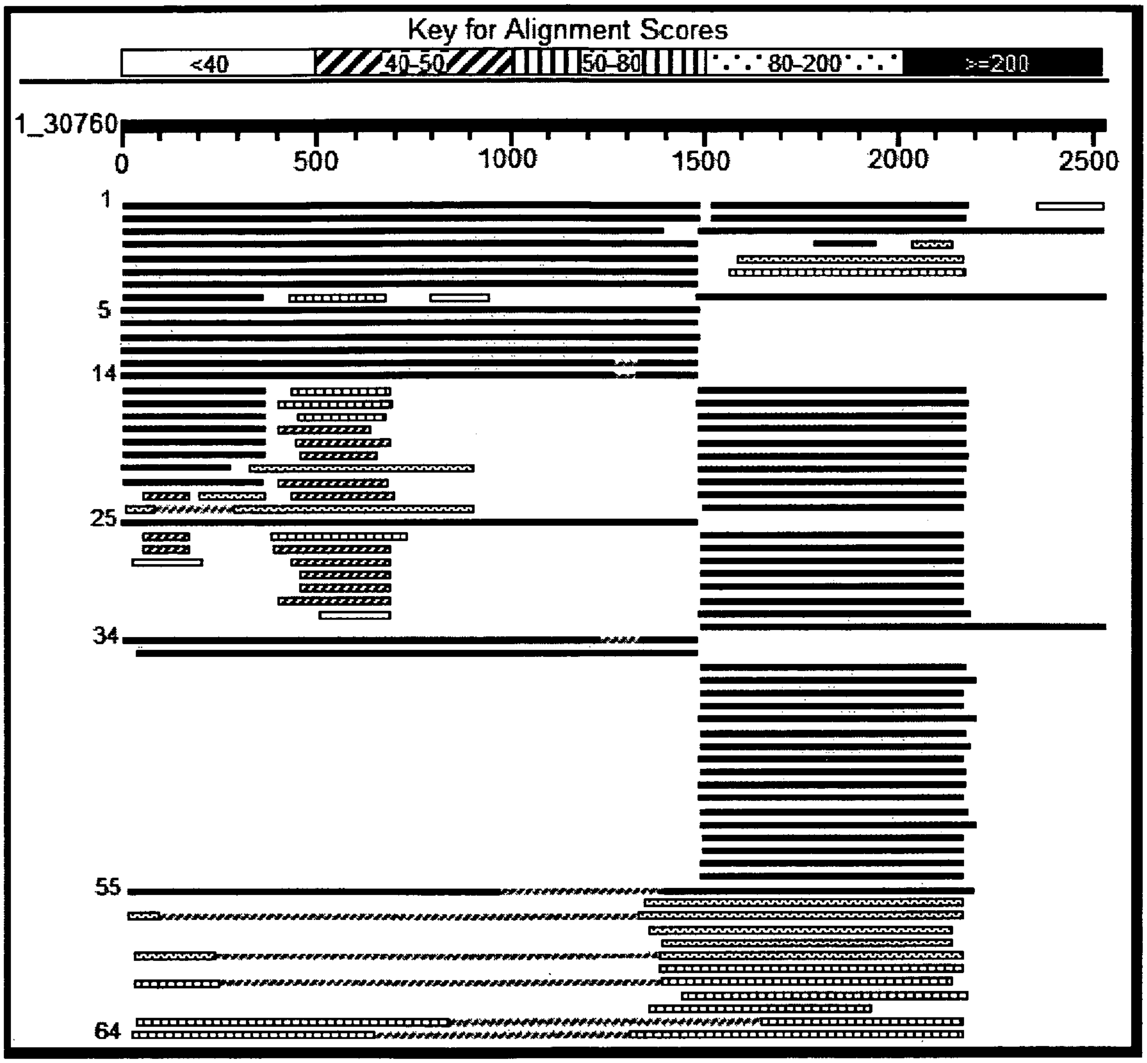
FIG. 1 presents the graphical output of a search using the artificial fusion protein sequence of SEQ ID NO:6 in a standard protein-protein BLAST search of the NCBI nonredundant protein database, using the following default values: Filter set to low complexity; Expect 10; Word size 3; Matrix BLOSUM62; Gap Costs: Existence 11, Extension 1.

SEQ ID NO:1 is the native genomic DNA sequence $tcp1_{Gz}$ which encodes the protein of SEQ ID NO:2.

SEQ ID NO:2 shows the native amino acid sequence of the $Tcp1_{Gz}$ protein (including readthrough of putative intron).

SEQ ID NO:3 shows the native, hypothetical cDNA sequence with the putative intron removed. This sequence encodes the protein of SEQ ID NO:4.

SEQ ID NO:4 is the native amino acid sequence of the $Tcp1_{Gz}$ protein with the intron-encoded sequence removed.

SEQ ID NO:5 is an *E. coli*-optimized polynucleotide sequence which codes for the $Tcp1_{Gz}$ protein of SEQ ID NO:2.

SEQ ID NO:6 is an example of a fusion protein generated from the amino acid sequences of TcaC (GenBank Accession AAC38625.1) and TccC1 (GenBank Accession AAL18473.1) (both from *Photorhabdus luminescens* strain W-14).

SEQ ID NO:7 is the genomic sequence from *Methanosarcina acetivorans* strain C2A that codes for a two-domain toxin complex protein.

SEQ ID NO:8 is the amino acid sequence encoded by SEQ ID NO:7.

SEQ ID NO:9 is the genomic sequence (from *Gibberella zeae* PH-1 strain PH-1; NRRL 31084 chromosome 1) that encodes a Class A TC protein.

SEQ ID NO:10 is the amino acid sequence encoded by SEQ ID NO:9.

SEQ ID NO:11 is the full length sequence of the Class B/C fusion gene in *Tannerella forsythensis* (ATCC 43037).

SEQ ID NO:12 is the protein encoded by SEQ ID NO:11.

SEQ ID NO:13 is primer P1 used for PCR according to the subject invention.

SEQ ID NO:14 is primer P2 used for PCR according to the subject invention.

SEQ ID NO:15 is primer P3 used for PCR according to the subject invention.

SEQ ID NO:16 is primer P4 used for PCR according to the subject invention.

SEQ ID NO:17 is primer P5 used for PCR according to the subject invention.

SEQ ID NO:18 is primer P6 used for PCR according to the subject invention.

SEQ ID NO:19 is the nucleotide sequence of fusion 8884 (TcdB2/Tcp$1_{Gz}$C). Nucleotides 1-4422 encode TcdB2; nucleotides 4423-4464 encode the TcdB2/Tcp$1_{Gz}$C linker peptide; and nucleotides 4465-7539 encode Tcp$1_{Gz}$C.

SEQ ID NO:20 is the amino acid sequence of the 8884 TcdB2/Tcp$1_{Gz}$C fusion peptide encoded by SEQ ID NO:19. Amino acids 1-1474: TcdB2; amino acids 1475-1488: TcdB2/Tcp$1_{Gz}$C linker peptide; amino acids 1489-2513: Tcp$1_{Gz}$C.

SEQ ID NO:21 is the nucleotide sequence of fusion 8883 (tcp$1_{Gz}$B/tccC3). Nucleotides 1-4536 encode Tcp$1_{Gz}$B; nucleotides encode the Tcp$1_{Gz}$B/TccC3 linker peptide; and nucleotides 4576-7455 encode TccC3.

SEQ ID NO:22 is the amino acid sequence of the 8883 fusion protein Tcp$1_{Gz}$B/TccC3 encoded by SEQ ID NO:21. Amino acids 1-1512: Tcp$1_{Gz}$B; amino acids 1513-1525: Linker; amino acids 1526-2485: TccC3.

SEQ ID NO:23 is the plant-optimized nucleotide sequence encoding a variant of *Gibberella zeae* fused Class B/Class C Tcp$1_{Gz}$ protein.

SEQ ID NO:24 is the variant of *Gibberella zeae* fused Class B/Class C Tcp$1_{Gz}$ protein encoded by SEQ ID NO:23.

SEQ ID NO:25 is the nucleotide sequence extracted from AContig12 of *Fusarium verticillioides*. The Threonine codon (ACG) that serves as the beginning of the open reading frame for the coding region of the first segment of the deduced putative TC Class A protein is noted as a misc_feature at nucleotides 21-23. The AAA Lysine codon which serves as the start of the open reading frame for the second portion of the deduced putative TC Class A protein is noted as a misc_feature at nucleotides 3022-3024.

SEQ ID NO:26 is the first segment of the deduced putative TC Class A protein encoded by SEQ ID NO:25.

SEQ ID NO:27 is the second segment of the deduced putative TC Class A protein encoded by SEQ ID NO:25.

SEQ ID NO:28 is the nucleotide sequence extracted from Acontig34 of *Fusarium verticillioides*. The beginning of the coding region corresponding to the first Asparagine of the putative TC Class A encoded protein in SEQ ID NO:29 is noted as a misc_feature at nucleotides 20-22. The second part of the open reading frame starts 4 bases downstream of the TGA stop codon, comprises 690 bases, and encodes the 230 amino acids shown in SEQ ID NO:30. The third portion of the open reading frame starts 11 bases downstream of the TAA stop codon, comprises 1122 bases, and encodes the 374 amino acids shown in SEQ ID NO:31. A large gap in the DNA sequence, indicated as a string of 2098 n's, is noted in a misc_feature at nucleotides 3299-5396. The portion of the DNA sequence following the Ns comprises a fourth portion of the deduced putative TC Class A protein open reading frame, and encodes the 1273 amino acids shown in SEQ ID NO:32. The GGA codon for the first Glycine of this portion of the deduced putative TC Class A protein is indicated as a misc_feature at nucleotides 5451-5453.

SEQ ID NO:29 is the first portion of the putative TC Class A protein encoded by SEQ ID NO:28.

SEQ ID NO:30 is the second portion of the putative TC Class A protein encoded by SEQ ID NO:28.

SEQ ID NO:31 is the third portion of the putative TC Class A protein encoded by SEQ ID NO:28.

SEQ ID NO:32 is the fourth potion of the putative TC Class A protein encoded by SEQ ID NO:28.

SEQ ID NO:33 is the nucleotide sequence extracted from BCContig12 of *Fusarium verticillioides*. The beginning of the coding region corresponding to the first Alanine of the encoded putative TC fused ClassB/Class C protein in SEQ ID NO:34 (GCC) is noted as a misc_feature from nucleotides 22-24. A large gap in the DNA sequence, indicated as a string of 659 n's, is noted as a misc_feature from nucleotides 5483-6141. The in-frame Histidine codon (CAT) that starts the second portion of the putative TC fused ClassB/Class C protein is noted as a misc_feature from nucleotides 6203-6205.

SEQ ID NO:34 is the first portion of the putative fused TC ClassB/Class C protein encoded by SEQ ID NO:33.

SEQ ID NO:35 is the second portion of the putative fused TC ClassB/Class C protein encoded by SEQ ID NO:33.

SEQ ID NO:36 is the nucleotide sequence extracted from BCContig6 of *Fusarium verticillioides*. The beginning of the coding region corresponding to the first Glutamine of the deduced putative TC fused Class B/Class C protein (CAG) is noted as a misc_feature from nucleotides 20-22. The Aspartic Acid codon (GAT) that starts the second portion of the putative TC fused Class B/Class C protein is noted as a misc_feature at nucleotides 619-621.

SEQ ID NO:37 is the first portion of the putative fused TC Class B/Class C protein encoded by SEQ ID NO:36.

SEQ ID NO:38 is the second portion of the putative fused TC Class B/Class C protein encoded by SEQ ID NO:36.

SEQ ID NO:39 is the nucleotide sequence extracted from BCContig46 from BCContig6 of *Fusarium verticillioides*. The beginning of the coding region (GAG), corresponding to the first Glutamic Acid of the first portion of the deduced putative TC fused Class B/Class C protein, is noted as a misc_feature at nucleotides 21-23. A large gap in the DNA sequence, indicated as a string of 1009 n's, is noted as a misc_feature from nucleotides 3424-4432. The TTG codon that specifies the first Leucine of the second portion of the deduced TC fused Class B/Class C protein following the n's is noted as a misc_feature at nucleotides 4435-4437.

SEQ ID NO:40 is the first portion of the putative fused TC Class B/Class C protein encoded by SEQ ID NO:39.

SEQ ID NO:41 is a second portion of the putative fused TC Class B/Class C protein encoded by SEQ ID NO:39.

SEQ ID NO:42 is the ClustalX sequence alignment for the FG_GAP Domain 4 extracted from the protein (represented under the GenBank Accession number 16416891).

SEQ ID NO:43 is the ClustalX sequence alignment for the FG_GAP Domain 4 extracted from the protein (represented under the GenBank Accession number 66047263).

SEQ ID NO:44 is the ClustalX sequence alignment for the FG_GAP Domain 3 extracted from the protein (represented under the GenBank Accession number 16416891).

SEQ ID NO:45 is the ClustalX sequence alignment for the FG_GAP Domain 3 extracted from the protein (represented under the GenBank Accession number 66047263).

SEQ ID NO:46 is the ClustalX sequence alignment for the FG_GAP Domain 6 extracted from the protein (represented under the GenBank Accession number 16416891).

SEQ ID NO:47 is the ClustalX sequence alignment for the FG_GAP Domain 6 extracted from the protein (represented under the GenBank Accession number 66047263).

SEQ ID NO:48 is the ClustalX sequence alignment for the FG_GAP Domain 2 extracted from the protein (represented under the GenBank Accession number 16416891).

SEQ ID NO:49 is the ClustalX sequence alignment for the FG_GAP Domain 2 extracted from the protein (represented under the GenBank Accession number 66047263).

SEQ ID NO:50 is the ClustalX sequence alignment for the FG_GAP Domain 5 extracted from the protein (represented under the GenBank Accession number 16416891).

SEQ ID NO:51 is the ClustalX sequence alignment for the FG_GAP Domain 5 extracted from the protein (represented under the GenBank Accession number 66047263).

SEQ ID NO:52 is the ClustalX sequence alignment for the FG_GAP Domain 1 extracted from the protein (represented under the GenBank Accession number 16416891).

SEQ ID NO:53 is the ClustalX sequence alignment for the FG_GAP Domain 1 extracted from the protein (represented under the GenBank Accession number 66047263).

SEQ ID NO:54 is the ClustalX sequence alignment of the RHS domain_1 extracted from the protein (represented under the GenBank Accession number 27479639).

SEQ ID NO:55 is the ClustalX sequence alignment of the RHS domain_1 extracted from the protein (represented under the GenBank Accession number 37524966).

SEQ ID NO:56 is the ClustalX sequence alignment of the RHS domain_1 extracted from the protein (represented under the GenBank Accession number 45441893).

SEQ ID NO:57 is the ClustalX sequence alignment of the RHS domain_1 extracted from the protein (represented under the GenBank Accession number 51596557).

SEQ ID NO:58 is the ClustalX sequence alignment of the RHS domain_2 extracted from the protein (represented under the GenBank Accession number 48730374).

SEQ ID NO:59 is the ClustalX sequence alignment of the RHS domain_2 extracted from the protein (represented under the GenBank Accession number 48730376).

SEQ ID NO:60 is the ClustalX sequence alignment of the RHS domain_2 extracted from the protein (represented under the GenBank Accession number 28871477).

SEQ ID NO:61 is the ClustalX sequence alignment of the RHS domain_1 extracted from the protein (represented under the GenBank Accession number 66047265).

SEQ ID NO:62 is the ClustalX sequence alignment of the RHS domain_1 extracted from the protein (represented under the GenBank Accession number 28871480).

SEQ ID NO:63 is the ClustalX sequence alignment of the RHS domain_2 extracted from the protein (represented under the GenBank Accession number 28868442).

SEQ ID NO:64 is the ClustalX sequence alignment of the RHS domain_2 extracted from the protein (represented under the GenBank Accession number 45443601).

SEQ ID NO:65 is the ClustalX sequence alignment of the RHS domain_2 extracted from the protein (represented under the GenBank Accession number 66044304).

SEQ ID NO:66 is the ClustalX sequence alignment of the RHS domain_3 extracted from the protein (represented under the GenBank Accession number 66045648).

SEQ ID NO:67 is the ClustalX sequence alignment of the RHS domain_3 extracted from the protein (represented under the GenBank Accession number 66047260).

SEQ ID NO:68 is the ClustalX sequence alignment of the RHS domain_2 extracted from the protein (represented under the GenBank Accession number 66043853).

SEQ ID NO:69 is the ClustalX sequence alignment of the RHS domain_1 extracted from the protein (represented under the GenBank Accession number 66045648).

SEQ ID NO:70 is the ClustalX sequence alignment of the RHS domain_1 extracted from the protein (represented under the GenBank Accession number 66047260).

SEQ ID NO:71 is the ClustalX sequence alignment of the RHS domain_1 extracted from the protein (represented under the GenBank Accession number 66047259).

SEQ ID NO:72 is the ClustalX sequence alignment of the RHS domain_1 extracted from the protein (represented under the GenBank Accession number 66047264).

SEQ ID NO:73 is the ClustalX sequence alignment of the RHS domain_3 extracted from the protein (represented under the GenBank Accession number 27479639).

SEQ ID NO:74 is the ClustalX sequence alignment of the RHS domain_4 extracted from the protein (represented under the GenBank Accession number 27479683).

SEQ ID NO:75 is the ClustalX sequence alignment of the RHS domain_2 extracted from the protein (represented under the GenBank Accession number 27479669).

SEQ ID NO:76 is the ClustalX sequence alignment of the RHS domain_4 extracted from the protein (represented under the GenBank Accession number 27479677).

SEQ ID NO:77 is the ClustalX sequence alignment of the RHS domain_4 extracted from the protein (represented under the GenBank Accession number 45441893).

SEQ ID NO:78 is the ClustalX sequence alignment of the RHS domain_3 extracted from the protein (represented under the GenBank Accession number 28871480).

SEQ ID NO:79 is the ClustalX sequence alignment of the RHS domain_4 extracted from the protein (represented under the GenBank Accession number 66047265).

SEQ ID NO:80 is the ClustalX sequence alignment of the RHS domain_4 extracted from the protein (represented under the GenBank Accession number 28868442).

SEQ ID NO:81 is the ClustalX sequence alignment of the RHS domain_4 extracted from the protein (represented under the GenBank Accession number 66043853).

SEQ ID NO:82 is the ClustalX sequence alignment of the RHS domain_2 extracted from the protein (represented under the GenBank Accession number 27479683).

SEQ ID NO:83 is the ClustalX sequence alignment of the RHS domain_3 extracted from the protein (represented under the GenBank Accession number 51597848).

SEQ ID NO:84 is the ClustalX sequence alignment of the RHS domain_2 extracted from the protein (represented under the GenBank Accession number 27479677).

SEQ ID NO:85 is the ClustalX sequence alignment of the RHS domain_2 extracted from the protein (represented under the GenBank Accession number 37524950).

SEQ ID NO:86 is the ClustalX sequence alignment of the RHS domain_3 extracted from the protein (represented under the GenBank Accession number 66047264).

SEQ ID NO:87 is the ClustalX sequence alignment of the RHS domain_4 extracted from the protein (represented under the GenBank Accession number 48730374).

SEQ ID NO:88 is the ClustalX sequence alignment of the RHS domain_4 extracted from the protein (represented under the GenBank Accession number 28871477).

SEQ ID NO:89 is the ClustalX sequence alignment of the RHS domain_3 extracted from the protein (represented under the GenBank Accession number 66047259).

SEQ ID NO:90 is the ClustalX sequence alignment of the ref NP_995139.1 from the protein (represented under the GenBank Accession number 45443600).

SEQ ID NO:91 is the ClustalX sequence alignment of the RHS domain_1 extracted from the protein (represented under the GenBank Accession number 51597848).

SEQ ID NO:92 is the ClustalX sequence alignment of the RHS domain__1 extracted from the protein (represented under the GenBank Accession number 27479639).

SEQ ID NO:93 is the ClustalX sequence alignment of the RHS domain__1 extracted from the protein (represented under the GenBank Accession number 37524966).

SEQ ID NO:94 is the ClustalX sequence alignment of the RHS domain__1 extracted from the protein (represented under the GenBank Accession number 45441893).

SEQ ID NO:95 is the ClustalX sequence alignment of the RHS domain__1 extracted from the protein (represented under the GenBank Accession number 51596557).

SEQ ID NO:96 is the ClustalX sequence alignment of the RHS domain__2 extracted from the protein (represented under the GenBank Accession number 48730374).

SEQ ID NO:97 is the ClustalX sequence alignment of the RHS domain__2 extracted from the protein (represented under the GenBank Accession number 48730376).

SEQ ID NO:98 is the ClustalX sequence alignment of the RHS domain__2 extracted from the protein (represented under the GenBank Accession number 28871477).

SEQ ID NO:99 is the ClustalX sequence alignment of the RHS domain__1 extracted from the protein (represented under the GenBank Accession number 66047265).

SEQ ID NO:100 is the ClustalX sequence alignment of the RHS domain__1 extracted from the protein (represented under the GenBank Accession number 28871480).

SEQ ID NO:101 is the ClustalX sequence alignment of the RHS domain__2 extracted from the protein (represented under the GenBank Accession number 28868442).

SEQ ID NO:102 is the ClustalX sequence alignment of the RHS domain__2 extracted from the protein (represented under the GenBank Accession number 45443601).

SEQ ID NO:103 is the ClustalX sequence alignment of the RHS domain__2 extracted from the protein (represented under the GenBank Accession number 66044304).

SEQ ID NO:104 is the ClustalX sequence alignment of the RHS domain__3 extracted from the protein (represented under the GenBank Accession number 66045648).

SEQ ID NO:105 is the ClustalX sequence alignment of the RHS domain__3 extracted from the protein (represented under the GenBank Accession number 66047260).

SEQ ID NO:106 is the ClustalX sequence alignment of the RHS domain__2 extracted from the protein (represented under the GenBank Accession number 66043853).

SEQ ID NO:107 is the ClustalX sequence alignment of the RHS domain__1 extracted from the protein (represented under the GenBank Accession number 66045648).

SEQ ID NO:108 is the ClustalX sequence alignment of the RHS domain__1 extracted from the protein (represented under the GenBank Accession number 66047260).

SEQ ID NO:109 is the ClustalX sequence alignment of the RHS domain__1 extracted from the protein (represented under the GenBank Accession number 66047259).

SEQ ID NO:110 is the ClustalX sequence alignment of the RHS domain__1 extracted from the protein (represented under the GenBank Accession number 66047264).

SEQ ID NO:111 is the ClustalX sequence alignment of the RHS domain__3 extracted from the protein (represented under the GenBank Accession number 27479639).

SEQ ID NO:112 is the ClustalX sequence alignment of the RHS domain__4 extracted from the protein (represented under the GenBank Accession number 27479683).

SEQ ID NO:113 is the ClustalX sequence alignment of the RHS domain__2 extracted from the protein (represented under the GenBank Accession number 27479669).

SEQ ID NO:114 is the ClustalX sequence alignment of the RHS domain__4 extracted from the protein (represented under the GenBank Accession number 27479677).

SEQ ID NO:115 is the ClustalX sequence alignment of the RHS domain__4 extracted from the protein (represented under the GenBank Accession number 45441893).

SEQ ID NO:116 is the ClustalX sequence alignment of the RHS domain__3 extracted from the protein (represented under the GenBank Accession number 28871480).

SEQ ID NO:117 is the ClustalX sequence alignment of the RHS domain__4 extracted from the protein (represented under the GenBank Accession number 66047265).

SEQ ID NO:118 is the ClustalX sequence alignment of the RHS domain__4 extracted from the protein (represented under the GenBank Accession number 28868442).

SEQ ID NO:119 is the ClustalX sequence alignment of the RHS domain__4 extracted from the protein (represented under the GenBank Accession number 66043853).

SEQ ID NO:120 is the ClustalX sequence alignment of the RHS domain__2 extracted from the protein (represented under the GenBank Accession number 27479683).

SEQ ID NO:121 is the ClustalX sequence alignment of the RHS domain__3 extracted from the protein (represented under the GenBank Accession number 51597848).

SEQ ID NO:122 is the ClustalX sequence alignment of the RHS domain__2 extracted from the protein (represented under the GenBank Accession number 27479677).

SEQ ID NO:123 is the ClustalX sequence alignment of the RHS domain__2 extracted from the protein (represented under the GenBank Accession number 37524950).

SEQ ID NO:124 is the ClustalX sequence alignment of the RHS domain__3 extracted from the protein (represented under the GenBank Accession number 66047264).

SEQ ID NO:125 is the ClustalX sequence alignment of the RHS domain__4 extracted from the protein (represented under the GenBank Accession number 48730374).

SEQ ID NO:126 is the ClustalX sequence alignment of the RHS domain__4 extracted from the protein (represented under the GenBank Accession number 28871477).

SEQ ID NO:127 is the ClustalX sequence alignment of the RHS domain__3 extracted from the protein (represented under the GenBank Accession number 66047259).

SEQ ID NO:128 is the ClustalX sequence alignment of the ref NP__995139.1 from the protein (represented under the GenBank Accession number 45113600).

SEQ ID NO:129 is the ClustalX sequence alignment of the RHS domain__1 extracted from the protein (represented under the GenBank Accession number 51597848).

SEQ ID NO:130 is the ClustalX sequence alignment of the FG_GAP domain 7 of the protein represented under the GenBank Acession number 48862345.

SEQ ID NO:131 is the ClustalX sequence alignment of the FG_GAP domain 5 of the protein represented under the GenBank Acession number 13475700.

SEQ ID NO:132 is the ClustalX sequence alignment of the FG_GAP domain 3 of the protein represented under the GenBank Acession number 48862345.

SEQ ID NO:133 is the ClustalX sequence alignment of the FG_GAP domain 4 of the protein represented under the GenBank Acession number 48862345.

SEQ ID NO:134 is the ClustalX sequence alignment of the FG_GAP domain 1 of the protein represented under the GenBank Acession number 48862345.

SEQ ID NO:135 is the ClustalX sequence alignment of the FG_GAP domain 2 of the protein represented under the GenBank Acession number 48862345.

SEQ ID NO:136 is the ClustalX sequence alignment of the FG_GAP domain 4 of the protein represented under the GenBank Acession number 13475700.

SEQ ID NO:137 is the ClustalX sequence alignment of the FG_GAP domain 5 of the protein represented under the GenBank Acession number 48862345.

SEQ ID NO:138 is the ClustalX sequence alignment of the FG_GAP domain 9 of the protein represented under the GenBank Acession number 48862345.

SEQ ID NO:139 is the ClustalX sequence alignment of the FG_GAP domain 8 of the protein represented under the GenBank Acession number 48862345.

SEQ ID NO:140 is the ClustalX sequence alignment of the FG_GAP domain 3 of the protein represented under the GenBank Acession number 13475700.

SEQ ID NO:141 is the ClustalX sequence alignment of the FG_GAP domain 6 of the protein represented under the GenBank Acession number 48862345.

SEQ ID NO:142 is the ClustalX sequence alignment of the FG_GAP domain 1 of the protein represented under the GenBank Acession number 13475700.

SEQ ID NO:143 is the ClustalX sequence alignment of the FG_GAP domain 2 of the protein represented under the GenBank Acession number 13475700.

SEQ ID NO:144 is a synthetic syntchtic peptide as discussed in Example 25.

SEQ ID NO:145 is a synthetic cyntchtic peptide as discussed in Example 25.

DETAILED DESCRIPTION

The subject invention relates in part to the surprising discovery that new types of TC proteins can be obtained from a widely diverse phylogenetic spectrum of organisms including, most notably, eukaryotic fungi. This is the first known disclosure of anti-insect toxins in, for example, *Gibberella zeae* (formerly known as *Fusarium graminaerum*) and *Methanosarcina*. These organisms were not known to be insecticidal and were not, heretofore, suspected of possessing genomic segments that encode insecticidally active proteins.

This discovery broadens the scope of organisms in which TC-like genes have been found. Thus, the subject invention generally relates to TC-like proteins obtainable from such species, to methods of screening these species for such proteins, and the like.

Considering the "role" that some source organisms play in nature can also lead to novel approaches for discovering additional TC proteins and genes. For example, *Gibberella zeae* (formerly known as *Fusarium graminaerum*) is a known plant pathogen. Having the benefit of the subject disclosure, one theory is that microbes that use crops, such as corn, as a food source evolved anti-insect toxins to help them outcompete insects that also feed on the crops. Thus, the subject invention can include methods of screening plant-pathogenic microbes for anti-insect proteins and the like.

This is also the first known discovery of naturally occurring, functionally active two-domain toxin complex ("TC") proteins, wherein one domain has functional and some level of sequence relatedness to "Class B" TC proteins (as discussed in more detail below), and the other domain has functional and some level of sequence relatedness to "Class C" TC proteins (as discussed in more detail below). As used herein, "B domains," "B segments," "C domains," and "C segments" refer to polypeptide domains or segments having structural and functional similarities to "Class B" and "Class C" TC proteins as discussed in detail in, for example, US-2004-0208907 and WO 2004/067727. Likewise, "Class A" proteins of the subject invention are discussed generally in, for example, US-2004-0208907 and WO 2004/067727.

Although the sequence of the *Gibberella zeae* genome (for example) was published in GENBANK, heretofore, there was no prior suggestion or expectation that the subject proteins would be active like known TC proteins. For example, there is a very low degree of sequence relatedness and unique conformations of the presently identified domains. The same is true for the bacterial sequences disclosed herein. There was not even a motivation to test these genomic sequences for any activity of hypothetically encoded proteins, considering, for example, the low degree of sequence relatedness, the unique conformations of the proteins, and the organisms possessing the genomic sequences. There was no reason to expect TCs in these sources, let alone active, naturally "fused" proteins like $Tcp1_{Gz}$. There was certainly no motivation to clone these genes into plant cells, for example. There was also no motivation to screen culture collections of isolates of these species to determine if the subject genes are more widely present in various strains of these organisms.

One exemplified anti-insect protein (a potentiator of Class A toxins) is referred to herein as $Tcp1_{Gz}$. For ease of reference, these two-domain proteins of the subject invention are sometimes referred to herein as "natural fusions" and as $Tcp1_{Gz}$-like proteins. The subject invention thus includes these new classes and types of TC proteins. The subject invention also includes polynucleotides that encode the subject proteins. The subject invention further provides vectors and cells comprising these polynucleotides. In some preferred embodiments, the subject invention also provides novel methods of controlling insects and other like pests, using the novel toxin protein of the subject invention.

Having discovered and shown that naturally occurring (but not heretofore "isolated") two-domain TC proteins of the subject invention are active, one will now be motivated to test and use other naturally occurring, two-domain TC proteins. *Methanosarcina* is preferred for such embodiments. In addition to *Methanosarcina* and *Gibberella*, novel source organisms for use according to the subject invention include species of the genera *Treponema, Leptospira, Microbulbifer, Burkholderia*, and *Nitrosospora.*

The subject invention also relates to screening new source organisms for novel Class A type proteins and genes, as disclosed herein. Eukaryotes, fungi, *Gibberella, Fusarium*, and *Aspergillus* are some preferred sources, as are bacteria of the genus *Burkholderia.*

$Tcp1_{Gz}$-like (natural fusion) proteins of the subject invention are typically in the molecular weight range of approximately 220 kDa to approximately 295 kDa, although this is just an approximate size range. A preferred weight, for example, is in the approximate range of 280-285 kDa. Another example of a naturally occurring, two-domain/BC-type toxin complex protein is obtainable from *Methanosarcina acetivorans* str. C2A. The sequences of the native gene and protein are set forth in SEQ ID NOs:7-8.

Another surprising feature of the exemplified $Tcp1_{Gz}$ protein is that it has an apparent intron. Thus, the subject invention includes isolated TC proteins comprising an intron sequence. The subject invention also includes searching for, identifying, and/or screening for TC proteins that contain intron-like sequences.

The subject invention provides exciting new sources for surprising, new types of toxin complex ("TC") proteins. Thus, the subject invention relates generally to *Gibberella, Fusarium*, and *Methanosarcina* species, for example, that have active TC proteins. The subject invention also includes methods of screening these and other species (some of which are identified herein) for these new classes of TC genes and proteins (as well as for known Class A-, Class B-, and Class C-type TC proteins). The subject invention also includes methods of isolating and/or purifying TC proteins from these species and testing them for toxin activity as disclosed herein. The subject invention further includes preparing and screening libraries of genes cloned (or otherwise produced) from these organisms. In some preferred embodiments, the organisms are eukaryotic. The subject proteins and genes of eukaryotic origin are particularly promising for high levels of expression in plants.

This is the first known report of these organisms having functionally active TC-like proteins, of any kind. This discovery was even more surprising because of the unique, two-domain conformation of proteins of the subject invention. Thus, the subject invention relates to methods of screening these species for TC-like genes and proteins. These pioneering observations have broad implications and thus enable one skilled in the art to screen appropriate species of bacteria and fungi for unique operons of the subject invention.

$Tcp1_{Gz}$-like proteins of the subject invention are shown herein to be useful to enhance or potentiate the activity of “stand-alone” *Xenorhabdus* and/or *Photorhabdus* “Class A” toxin proteins, for example. One or more TC proteins of the subject invention can be used as a novel element combined with techniques known in the art. See e.g. US-2004-0208907 and WO 2004/067727.

The subject invention also provides novel “Class A”-type TC proteins, which, as a Class, have “stand-alone” toxin activity. See e.g. US-2004-0208907 and WO 2004/067727 for a more detailed explanation. One exemplified Class A gene and protein of this type can be derived from the *Gibberella* organism disclosed herein. See SEQ ID NOs:9-10.

While the subject TC-like proteins have some sequence relatedness to, and characteristics in common with, TC proteins of *Xenorhabdus* and *Photorhabdus* for example, the sequences of the subject TC-like proteins are distinct from previously known TC proteins. Thus, the subject application provides new classes of TC-like proteins and genes that encode these proteins, which are obtainable from bacterial and fungal genera identified and suggested herein.

Other objects, advantages, and features of the subject invention will be apparent to one skilled in the art having the benefit of the subject disclosure.

Administration of the Subject Proteins, and Function, Activity, and Utility Thereof. Individual Class A, Class B, and Class C TC proteins, as the term is used herein, were known in the art. Such proteins include stand-alone toxins (Class A TC proteins) and potentiators (Class B and C TC proteins). Bacteria known to produce TC proteins include those of the following genera: *Photorhabdus, Xenorhabdus, Paenibacillus, Serratia*, and *Pseudomonas*. See, e.g., *Pseudomonas syringae* pv. *Syringae* B728a (GenBank Accession Numbers gi:23470933 and gi:23472543).

As mentioned above in the Background section, although “Toxin A” proteins have some insecticidal activity, alone, the high insecticidal potency of the “A+B+C” complex is much preferred for commercial applications of TC proteins. However, the exact mechanism(s) of action of TC proteins remains unknown. Likewise, it is unknown exactly how (and if) each of the A, B, and C components interact with each other. Thus, there was no way to a priori predict whether proteins of the subject invention would allow for proper functioning in the insect gut.

It came with surprise that the subject proteins were found to be highly effective for controlling insects. There was no expectation that the subject natural fusion proteins would be active (i.e., toxic in combination with a Class A TC protein) after ingestion by the target insect. It is shown herein that the subject proteins surprisingly function quite well in the insect gut.

The subject invention can be performed in many different ways. For example, a plant can be engineered to produce one or more types of Class A TC proteins together with a $Tcp1_{Gz}$-type protein of the subject invention, the latter of which potentiate the activity of the Class A TC protein. Every cell of the plant, or every cell in a given type of tissue (such as roots or leaves) can be designed to have genes to encode the A proteins and the $Tcp1_{Gz}$-type protein. Alternatively, different cells of the plant can produce only one (or more) of each of these proteins. In this situation, when an insect bites and eats tissues of the plant, it could eat a cell that produces a first Class A TC protein, another cell that produces a second Class A TC protein, and another cell that produces the $Tcp1_{Gz}$-type protein. Thus, the plant (not necessarily each plant cell) can produce one or more types of Class A TC proteins and the $Tcp1_{Gz}$-type protein of the subject invention so that insect pests eat all these types of proteins when they eat tissue of the plant.

Aside from transgenic plants, there are many other ways of administering the proteins, in a combination of the subject invention, to the target pest. Spray-on applications are known in the art. Some or all of the Class A and $Tcp1_{Gz}$-type proteins can be sprayed (the plant could produce one or more of the proteins and the others could be sprayed). Various types of bait granules for soil applications, for example, are also known in the art and can be used according to the subject invention.

The present invention provides easily administered, functional proteins. The present invention also provides a method for delivering insecticidal proteins that are functionally active and effective against many orders of insects, preferably lepidopteran and/or coleopteran insects. By “functional activity” (or “active against”) it is meant herein that the proteins function as orally active insect control agents (alone or in combination with other proteins), that the proteins have a toxic effect (alone or in combination with other proteins), or are able to disrupt or deter insect growth and/or feeding which may or may not cause death of the insect. When an insect comes into contact with an “effective amount” of an “insecticidal protein” of the subject invention delivered via transgenic plant expression, formulated protein composition(s), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the proteins available to the insects.

Thus, insects that ingest an effective amount of a Class A TC protein and a $Tcp1_{Gz}$-type protein, for example, can be deterred from feeding, have their growth stunted, and/or be killed, for example. A $Tcp1_{Gz}$-type protein of the invention has “functionality” or toxin activity if it enhances the functional activity of a Class A TC protein when used in combination therewith.

Complete lethality to feeding insects is preferred, but is not required to achieve functional activity. If an insect avoids the protein or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

Transfer of the functional activity to plant, bacterial, or other systems typically requires nucleic acid sequences, encoding the amino acid sequences for the toxins, integrated into a protein expression vector appropriate to the host in which the vector will reside. One way to obtain a nucleic acid sequence encoding a protein with functional activity is to isolate the native genetic material from the native source species that produces the toxins, using information deduced from the toxin's amino acid sequence, as disclosed herein. The native sequences can be optimized for expression in plants, for example, as discussed in more detail below. Optimized polynucleotides can also be designed based on the protein sequence.

There are many other ways in which TC proteins can be incorporated into an insect's diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, DNA for producing the protein could be genetically engineered directly into an insect food source. For instance, the major food source for many insect larvae is plant material. Therefore the genes encoding toxins can be transferred to plant material so that said plant material produces the toxin of interest.

When $Tcp1_{Gz}$-type proteins of the subject invention are said to have two domains, it should be noted that this does not exclude the existence of various subdomains, regions, and protein motifs, for example, in each of the two main domains. In addition, as the two main domains have homology to Class B and Class C TC proteins, respectively, and given that $Tcp1_{Gz}$-type proteins of the subject invention are shown herein to function like and to be useful like Class B and Class C TC proteins, the subject invention includes the use of either or both domains of the $Tcp1_{Gz}$-type proteins individually. That is, the Class C-like domain of a $Tcp1_{Gz}$-type protein can be used with a *Xenorhabdus* or *Photorhabdus* Class B protein, for example. The same is true for the Class B-like domain of $Tcp1_{Gz}$-type protein. Various methods for cutting proteins and corresponding DNA, to isolate and re-ligate fragments of interest, are described below in the section entitled "Modification of genes and proteins" for example. (Such DNA and protein fragments, for example, are within the scope of the subject invention.) A great number of possible combinations and utilities can be envisioned. For example, in some embodiments, a fragment of a $Tcp1_{Gz}$-type protein (preferably a B domain fragment or a C domain fragment) can be isolated (from the remaining fragment), swapped (fused or unfused) and "mixed and matched" according to the teachings of US-2004-0208907 and WO 2004/067727. (Any of the Class B and Class C sequences, for example, disclosed therein can also be used to define embodiments of the subject invention. For example, in the full-length sequences exemplified herein, the Class B and Class C domains can be identified, by comparison to sequences in US-2004-0208907 and WO 2004/067727, and used separately accordingly.) As discussed below, a Class C domain of the subject invention can also be synthetically ligated to a Class B TC protein. Likewise, a Class B domain can be synthetically ligated to a Class C TC protein.

Ligations and Other Terminology and Definitions. $Tcp1_{Gz}$-type proteins of the invention can be ligated to Class A TC proteins. See e.g. U.S. Ser. No. 60/549,516, filed Mar. 2, 2004. As mentioned above, other possibilities are that a Class B and/or a Class C domain of the subject invention (corresponding fragments of two-domain proteins of the subject invention) can be synthetically ligated to another TC protein. See e.g. U.S. Ser. No. 60/549,502, filed Mar. 2, 2004. As used herein, it is understood that ligation of normally separate proteins or protein domains can be brought about as a consequence of translation of a polynucleotide containing coding sequence regions that encode the amino acid sequences of the normally separate proteins or protein domains.

As used herein, the terms "linker" and "linker sequence" refer to nucleotides used to join a first protein coding region to a subsequent, immediately following protein coding region, such that both the first and second (and/or subsequent) protein coding regions form a single longer protein coding region in the +1 reading frame, as defined by the open reading frame of the first protein coding region. Such linker or linker sequence therefore cannot include translation termination codons in the +1 reading frame. As a consequence of translation of the linker or linker sequence, the protein encoded by the first protein coding region is joined by one or more amino acids to the protein encoded by the second protein coding region. A linker is optional, as the polypeptide components can be ligated directly, without a linker sequence.

As used herein, reference to "isolated" polynucleotides and/or proteins, and "purified" proteins refers to these molecules when they are not associated with the other molecules with which they would be found in nature. Thus, reference to "isolated" and/or "purified" signifies the involvement of the "hand of man" as described herein. For example, a bacterial or fungal polynucleotide (or "gene") of the subject invention put into a plant for expression is an "isolated polynucleotide." Likewise, a protein of the subject invention when produced by a plant is an "isolated protein." The term "ligated" can also be used to signify involvement of the "hand of man." That is, one polypeptide component (such as a $Tcp1_{Gz}$-type protein) can be synthetically joined or "ligated" to another polypeptide component (such as a Class A protein) to form a fusion protein of the subject invention.

A "recombinant" molecule refers to a molecule that has been recombined. When made in reference to a nucleic acid molecule, the term refers to a molecule that is comprised of nucleic acid sequences that are joined together by means of molecular biological techniques. The term "recombinant" when made in reference to a protein or a polypeptide refers to a protein molecule that is produced using one or more recombinant nucleic acid molecules.

The term "heterologous" when made in reference to a nucleic acid sequence refers to a nucleotide sequence that is ligated to, or is manipulated to become ligated to, a nucleic acid sequence to which it is not joined in nature, or to which it is joined at a different location in nature. The term "heterologous" therefore indicates that the nucleic acid molecule has been manipulated using genetic engineering, i.e. by human intervention. Thus, a gene of the subject invention can be operably linked to a heterologous promoter (or a "transcriptional regulatory region" which means a nucleotide sequence capable of mediating or modulating transcription of a nucleotide sequence of interest, when the transcriptional regulatory region is operably linked to the sequence of interest). Preferred heterologous promoters can be plant promoters. A promoter and/or a transcriptional regulatory region and a sequence of interest are "operably linked" when the sequences are functionally connected so as to permit transcription of the sequence of interest to be mediated or modulated by the transcriptional regulatory region. In some embodiments, to be operably linked, a transcriptional regulatory region may be located on the same strand as the sequence of interest. The transcriptional regulatory region may in some embodiments be located 5' of the sequence of interest. In such embodiments, the transcriptional regulatory region may be directly 5' of the sequence of interest or there may be intervening sequences between these regions. The operable linkage of the transcriptional regulatory region and the sequence of interest may require appropriate molecules (such as transgenic activator proteins) to be bound to the transcriptional regulatory region, the invention therefore encompasses embodiments in which such molecules are provided, either in vitro or in vivo.

There are a number of methods for obtaining the proteins for use according to the subject invention. For example, antibodies to the proteins disclosed herein can be used to identify and isolate other proteins from a mixture. Specifically, antibodies may be raised to the portions of the proteins that are most constant and most distinct from other proteins. These antibodies can then be used to specifically identify equivalent proteins with the characteristic activity by immunoprecipitation, enzyme linked immunosorbent assay (ELISA), or immuno-blotting. Antibodies to the proteins disclosed herein, or to equivalent proteins, or to fragments of these proteins, can be readily prepared using standard procedures. Such antibodies are an aspect of the subject invention. Proteins of the subject invention can be obtained from a variety of sources/source microorganisms.

One skilled in the art would readily recognize that proteins (and genes) of the subject invention can be obtained from a variety of sources. A protein "from" or "obtainable from" any of the subject isolates referred to or suggested herein means that the protein (or a similar protein) can be obtained from the exemplified isolate or some other source, such as another fungal or bacterial strain, or a plant (for example, a plant engineered to produce the protein). "Derived from" also has this connotation, and includes polynucleotides (and proteins) obtainable from a given type of fungus or bacterium wherein the polynucleotide is modified for expression in a plant, for example. One skilled in the art will readily recognize that, given the disclosure of a microbial gene and protein, a plant can be engineered to produce the protein. Antibody preparations, nucleic acid probes (DNA and RNA), and the like may be prepared using the polynucleotide and/or amino acid sequences disclosed herein and used to screen and recover other protein genes from other (natural) sources.

Identification of Proteins and Genes of the Subject Invention. Proteins and genes for use according to the subject invention can be identified and obtained by using oligonucleotide probes, for example. These probes are detectable nucleotide sequences which may be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization with a given polynucleotide is a technique that can be used to identify, find, and/or define proteins and genes of the subject invention. As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}P$-labeled gene-specific probes was performed by standard methods (see, e.g., Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266-285):

1) Tm=81.5° C.+16.6 Log[Na+]+0.41(% G+C)−0.61(% formamide)−600/length of duplex in base pairs.
2) Washes are typically carried out as follows:
3) Twice at room temperature for 15 minutes in 1×SSPE, 0.1% SDS (low stringency wash).
4) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes was determined by the following formula: Tm (° C.)=2(number T/A base pairs)+4(number G/C base pairs) (Suggs, S. V., T.

Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683-693).

Washes were typically carried out as follows:

1) Twice at room temperature for 15 minutes 1×SSPE, 0.1% SDS (low stringency wash).

2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes that can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of genes and proteins. The genes and proteins useful according to the subject invention include not only the specifically exemplified full-length sequences, but also portions, segments and/or fragments (including internal and/or terminal deletions compared to the full-length molecules) of these sequences, variants, mutants, chimerics, and fusions thereof. Proteins used in the subject invention can have substituted amino acids so long as they retain the characteristic pesticidal/functional activity of the proteins specifically exemplified herein. "Variant" genes have nucleotide sequences that encode the same proteins or equivalent proteins having functionality equivalent to an exemplified protein. The terms "variant proteins" and "equivalent proteins" refer to proteins having the same or essentially the same biological/functional activity as the exemplified proteins. As used herein, reference to an "equivalent" sequence refers to sequences having amino acid substitutions, deletions, additions, or insertions that improve or do not adversely affect functionality. Fragments retaining functionality are also included in this definition. Fragments and other equivalents that retain the same or similar function, as a corresponding fragment of an exemplified protein are within the scope of the subject invention. Changes, such as amino acid substitutions or additions, can be made for a variety of purposes, such as increasing (or decreasing) protease stability of the protein (without materially/substantially decreasing the functionality of the protein).

Variations of genes may be readily constructed using standard techniques for making point mutations, for example. In addition, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes that encode active fragments may be obtained using a variety of restriction enzymes. Proteases may be used to directly obtain active fragments of these proteins.

It is within the scope of the invention as disclosed herein that TC proteins may be truncated and still retain functional activity. By "truncated protein" it is meant that a portion of a protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said protein are removed either through digestion with restriction endonucleases or other techniques available to the skilled artisan. After truncation, said proteins can be expressed in heterologous systems such as *Escherichia coli*, baculoviruses, plant-based viral systems, yeast and the like and then placed in insect assays as disclosed herein to determine activity. It is well-known in the art that truncated proteins can be successfully produced so that they retain functional activity while having less than the entire, full-length sequence. It is well known in the art that B.t. toxins can be used in a truncated (core toxin) form. See, e.g., Adang et al., *Gene* 36:289-300 (1985), "Characterized full-length and truncated plasmid clones of the crystal protein of *Bacillus thuringiensis* subsp *kurstaki* HD-73 and their toxicity to *Manduca sexta*." There are other examples of truncated proteins that retain insecticidal activity, including the insect juvenile hormone esterase (U.S. Pat. No. 5,674,485 to the Regents of the University of California). As used herein, the term "toxin" is also meant to include functionally active truncations.

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

The subject invention include, for example:

1) proteins obtained from wild type organisms;

2) variants arising from mutations;

3) variants designed by making conservative amino acid substitutions; and 4) variants produced by random fragmentation and reassembly of a plurality of different sequences that encode the subject TC proteins (DNA shuffling). See e.g. U.S. Pat. No. 5,605,793.

The DNA sequences encoding the subject proteins can be wild type sequences, mutant sequences, or synthetic sequences designed to express a predetermined protein. DNA sequences designed to be highly expressed in plants by, for example, avoiding polyadenylation signals, and using plant preferred codons, are particularly useful.

Certain proteins and genes have been specifically exemplified herein. As these proteins and genes are merely exemplary, it should be readily apparent that the subject invention comprises use of variant or equivalent proteins (and nucleotide sequences coding for equivalents thereof) having the same or similar functionality as the exemplified proteins. Equivalent proteins will have amino acid similarity (and/or homology) with an exemplified TC protein. Preferred polynucleotides and proteins of the subject invention can be defined in terms of narrower identity and/or similarity ranges. For example, the identity and/or similarity of the Class A, B, and/or C TC protein can be 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein and, the identity and/or similarity of the Class C TC protein can be 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein. Any number listed above can be used to define the upper and lower limits. For example, a protein of the subject invention can be defined as having 50-90% identity, for example, with an exemplified protein.

Unless otherwise specified, as used herein, percent sequence identity and/or similarity of two nucleic acids is determined using the algorithm of Karlin and Altschul (1990), *Proc. Natl. Acad. Sci. USA* 87:2264-2268, modified as in Karlin and Altschul (1993), *Proc. Natl. Acad. Sci. USA* 90:5873-5877. Such an algorithm is incorporated into the NBLAST and XBLAST programs of Altschul et al. (1990), *J. Mol. Biol.* 215:402-410. BLAST nucleotide searches are performed with the NBLAST program, score=100, wordlength=12. Gapped BLAST can be used as described in Altschul et al. (1997), *Nucl. Acids Res.* 25:3389-3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above.

To obtain gapped alignments for comparison purposes, the AlignX function of Vector NTI Suite 8 (InforMax, Inc., North Bethesda, Md., U.S.A.), was used employing the default parameters. These were: a Gap opening penalty of 15, a Gap extension penalty of 6.66, and a Gap separation penalty range of 8. Two or more sequences can be aligned and compared in this manner or using other techniques that are well-known in the art. By analyzing such alignments, relatively conserved and non-conserved areas of the subject polypeptides can be identified. This can be useful for, for example, assessing whether changing a polypeptide sequence by modifying or substituting one or more amino acid residues can be expected to be tolerated.

The amino acid homology/similarity/identity will typically (but not necessarily) be highest in regions of the protein that account for its activity or that are involved in the determination of three-dimensional configurations that are ultimately responsible for the activity. In this regard, certain amino acid substitutions are acceptable and can be expected to be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

Various properties and three-dimensional features of the protein can also be changed without adversely affecting the toxin activity/functionality of the protein. Conservative amino acid substitutions can be expected to be tolerated/to not adversely affect the three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 1 provides a listing of examples of amino acids belonging to each class.

TABLE 1

Classes of amino acids.

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the functional/biological/toxin activity of the protein.

Equivalent TC proteins and/or genes encoding these equivalent proteins can be obtained/derived from wild-type or recombinant bacteria and/or from other wild-type or recombinant organisms using the teachings provided herein. Various species of fungi and bacteria can now be used as source isolates, as disclosed herein.

Optimization of sequence for expression in heterologous organisms. To obtain high expression of heterologous genes in plants, for example, it may be preferred to reengineer said genes so that they are more efficiently expressed in plant cells. Maize is one such plant where it may be preferred to re-design the heterologous gene(s) prior to transformation to increase the expression level thereof in said plant. Therefore, an additional step in the design of genes encoding a bacterial or fungal toxin, for example, is reengineering of a heterologous gene for optimal expression in a different type of organism. Guidance regarding the production of synthetic genes that are optimized for plant expression can be found in, for example, U.S. Pat. No. 5,380,831. A sequence optimized for expression in *E. coli* is also exemplified, as discussed in the Examples below.

Transgenic hosts. The genes encoding Toxin Complex proteins of the subject invention can be introduced into a wide variety of microbial or plant hosts. In preferred embodiments, transgenic plant cells and plants are used. Preferred plants (and plant cells) are corn (maize), cotton, canola, sunflowers, and soybeans.

In preferred embodiments, expression of the gene results, directly or indirectly, in the intracellular production (and maintenance) of the protein. Plants can be rendered insect-resistant in this manner. When transgenic/recombinant/transformed/transfected host cells (or contents thereof) are ingested by the pests, the pests will ingest the toxin. This is the preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluorescens*, can be applied where target pests are present; the microbes can proliferate there, and are ingested by the target pests. The microbe hosting the toxin gene can be treated under conditions that prolong the activity of the toxin and stabilize the cell. The treated cell, which retains the toxic activity, can then be applied to the environment of the target pest. The subject invention also includes the administration of a combination of cells, with some cells expressing one or more types of proteins and other cells expressing other types of proteins (such as some cells producing Class A toxin proteins and other cells producing "potentiating" $Tcp1_{Gz}$-type proteins of the subject invention, for example).

Where the toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilus, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium meliloti, Alcaligenes entrophus*, and *Azotobacter vinelandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Also of interest are pigmented microorganisms.

Insertion of genes to form transgenic hosts. One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System*, Offset-durkkerij Kanters B.V., Alblasserdam, Chapter 5; Fraley et al., *Crit. Rev. Plant Sci.* 4:1-46; and An et al. (1985) *EMBO J.* 4:277-287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacterium* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacterium*. The intermediate vector can be transferred into *Agrobacterium tumefaciens* by means of a helper plasmid (conjugation). Binary vectors can replicate themselves both in *E. coli* and in *Agrobacterium*. They comprise a selection marker gene and a linker or polylinker which are framed by the right and left T-DNA border regions. They can be transformed directly into *Agrobacterium* (Holsters et al. [1978] *Mol. Gen. Genet.* 163:181-187). The *Agrobacterium* used as host cell is to comprise a plasmid carrying a vir region. The vir region is necessary for the transfer of the T-DNA into the plant cell.

Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S. Pat. No. 5,141,131 to DowElanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149,645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants producing the protein of interest. For example, monocotyledonous plant can be transformed with a viral vector using the methods described in U.S. Pat. No. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method that provides for efficient transformation can be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA (1980) 77:7347-7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacterium* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue that is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17-19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

Standard molecular biology techniques may be used to clone and sequence the genes (and toxins) described herein. Additional information may be found in Sambrook, J., Fritsch, E. F., and Maniatis, T. (1989), Molecular Cloning, A Laboratory Manual, Cold Spring Harbor Press, which is incorporated herein by reference.

Resistance Management. With increasing commercial use of insecticidal proteins in transgenic plants, one consideration is resistance management. That is, there are numerous companies using *Bacillus thuringiensis* toxins in their products, and there is concern about insects developing resistance to B.t. toxins. One strategy for insect resistance management would be to combine the TC insecticidal proteins produced by *Xenorhabdus, Photorhabdus, Gibberella*, and the like with toxins such as B.t. crystal toxins, soluble insecticidal proteins from *Bacillus* stains (see, e.g., WO 98/18932 and WO 99/57282), or other insect toxins. The combinations could be formulated for a sprayable application or could be molecular combinations. Plants could be transformed with genes that produce two or more different insect toxins (see, e.g., Gould, 38 *Bioscience* 26-33 (1988) and U.S. Pat. No. 5,500,365; likewise, European Patent Application 0 400 246 A1 and U.S. Pat. Nos. 5,866,784; 5,908,970; and 6,172,281 also describe transformation of a plant with two B.t. crystal toxins). Another method of producing a transgenic plant that contains more than one insect resistant gene would be to first produce two plants, with each plant containing an insect resistance gene. These plants could then be crossed using traditional plant breeding techniques to produce a plant containing more than one insect resistance gene. Thus, it should be apparent that the phrase "comprising a polynucleotide" as used herein means at least one polynucleotide (and possibly more, contiguous or not) unless specifically indicated otherwise.

Formulations and Other Delivery Systems. Formulated bait granules containing cells and/or proteins of the subject invention (including recombinant microbes comprising the genes described herein) can be applied to the soil. Formulated product can also be applied as a seed-coating or root treatment or total plant treatment at later stages of the crop cycle. Plant and soil treatments of cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Another delivery scheme is the incorporation of the genetic material of toxins into a baculovirus vector. Baculoviruses infect particular insect hosts, including those desirably targeted with the toxins. Infectious baculovirus harboring an expression construct for the toxins could be introduced into areas of insect infestation to thereby intoxicate or poison infected insects.

Insect viruses, or baculoviruses, are known to infect and adversely affect certain insects. The effect of the viruses on insects is slow, and viruses do not immediately stop the feeding of insects. Thus, viruses are not viewed as being optimal as insect pest control agents. However, combining the toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to produce an anti-insect toxin protein. In so doing, the gene encoding a toxin can be inserted into the coat promoter region of a suitable plant virus that will infect the host plant of interest. The toxin can then be expressed thus providing protection of the plant from insect damage. Plant RNA viral based systems are described in U.S. Pat. No. 5,500,360 to Mycogen Plant Sciences, Inc. and U.S. Pat. Nos. 5,316,931 and 5,589,367 to Biosource Genetics Corp.

In addition to producing a transformed plant, there are other delivery systems where it may be desirable to engineer the toxin-encoding gene(s). For example, a protein toxin can be constructed by fusing together a molecule attractive to insects as a food source with a toxin. After purification in the laboratory such a toxic agent with "built-in" bait could be packaged inside standard insect trap housings.

Mutants. Mutants of bacterial and fungal isolates (and other organisms) can be made by procedures that are well known in the art. For example, mutants can be obtained through ethylmethane sulfonate (EMS) mutagenesis of an isolate. The mutants can be made using ultraviolet light and nitrosoguanidine by procedures well known in the art.

Examples of Various Specific Embodiments. (As used in this specification, the terms "a" and "an" signify at least one, unless specifically indicated otherwise.) The subject invention can include, but is not limited to, an isolated, eukaryotic protein comprising a B domain and a C domain, wherein said protein potentiates the insecticidal activity of a Class A toxin complex protein, wherein said B domain comprises an spvB subdomain followed by at least one FG-GAP subdomain, and said C domain comprises at least one RHS subdomain followed by a hyper-variable region. (It should be noted that these subdomains are sometimes referred to herein as "domains." It should be understood that such "domains" can be subparts of fusion proteins, of the subject invention, having two main domains—B and C with each main domain having domains of their own). In some embodiments, said protein can further comprise a transmembrane domain (or subdomain). In some embodiments, said protein is a fungal protein, including a *Gibberella* protein. Some preferred proteins have a molecular weight of approximately 200-300 kDa. In some other embodiments, said protein has the domains as described above but is prokaryotic or archaeal (not eukaryotic) obtainable from a naturally occurring organism of a genus selected from *Methanosarcina, Treponema, Leptospira, Tannerella*, and *Microbulbifer*. Novel bacterial sources (other than *Xenorhabdus, Photorhabdus*, and the like) are also described herein. Variations (such as conservative substitutions) of the naturally occurring amino acid sequences are also possible.

The subject invention includes an isolated polynucleotide that encodes any of these proteins. Some preferred polynucleotides have a codon composition optimized for expression in a plant. The invention includes a transgenic cell comprising any of these polynucleotides. In some preferred embodiments, the transgenic cell further comprises a nucleic acid molecule that encodes a Class A toxin.

The subject invention further includes a method of screening polynucleotide sequences for a polynucleotide that encodes a protein mentioned (and/or suggested) above, wherein said method comprises providing a reference sequence, comparing said reference sequence to a sequence database using an algorithm, assigning a score to a sequence in said database, selecting a minimum value, identifying said polynucleotide in said database that has a said score above said minimum value, producing a protein that is encoded by said polynucleotide, and assaying said protein for ability to potentiate the activity of a Class A toxin complex protein.

Still further included is a method of screening a culture of naturally occurring eukaryotic cells for a protein selected from the group of a Class A toxin complex protein and a BC fusion protein mentioned above. A naturally occurring organism of a genus selected from *Methanosarcina, Treponema, Leptospira, Tannerella*, and *Microbulbifer* can be substituted for the eukaryote in such screening methods.

The subject invention also includes a method of identifying a BC fusion protein, mentioned above, from a naturally occurring organism wherein said method comprises analyzing a sequence for a sequence of subdomains discussed above and elsewhere herein.

The subject invention also includes a method of screening a plurality of naturally occurring (microbial) isolates for an approximately 220 kDa to approximately 295 kDa protein that potentiates anti-insect toxin activity of a Class A toxin complex toxin protein wherein said method comprises obtaining protein from said isolates and screening said protein for said potentiating activity, said protein comprising a B domain and a C domain, wherein said B domain and said C domain comprise subdomains discussed above and elsewhere herein. Said microbes can be fungal. Said microbes can also be selected from *Gibberella, Methanosarcina, Treponema, Leptospira, Tannerella*, and *Microbulbifer.*

The subject invention also includes a method of screening a plurality of *Gibberella* isolates for a gene that encodes an approximately 220 kDa to approximately 295 kDa protein that potentiates anti-insect toxin activity of a Class A toxin complex toxin protein wherein said method comprises obtaining nucleic acid molecules from said isolates and contacting said nucleic acid molecules with a polynucleotide that hybridizes with said gene. The step of obtaining DNA from said culture can comprise creating a library of clones from said DNA and assaying at least one of said clones for the presence of said gene. The step of assaying said clone for the presence of said polynucleotide can comprise assaying said clone for lepidopteran toxin activity, thereby indicating the presence of said polynucleotide. The step of assaying said DNA can comprise performing polymerase chain reaction with at least one primer that is designed to indicate the presence of said gene. The step of assaying said DNA can comprise hybridizing a nucleic acid probe to said DNA wherein said probe is designed to indicate the presence of said gene. The method can also comprise assaying for said protein, comprising (for example) immunoreacting an antibody for said protein with a protein sample wherein said antibody is designed to indicate the presence of said protein.

The subject invention further provides a method of controlling an insect, or like pest, wherein said method comprises the step of contacting said insect with a BC fusion protein discussed above and a Class A toxin complex toxin protein. Also included is a method of potentiating the toxin activity of a Class A toxin complex toxin protein wherein said method comprises providing a BC fusion protein discussed above to an insect for ingestion. Novel B and/or C domains from these novel fusion proteins can also be used individually (not in the form of a fusion).

The subject invention still further includes a synthetic BC fusion protein comprising a B or a C domain obtainable from (or derived from) a novel source (naturally occurring) organism discussed above, wherein said B domain or said C domain is fused to a heterologous C domain or B domain. Various combinations are possible. Such synthetic fusions can also be fused to a Class A toxin complex toxin protein.

In some other embodiments, the subject invention includes a method of producing a transgenic cell, wherein said method comprises inserting a polynucleotide into said cell, wherein said polynucleotide encodes an approximately 220 kDa to approximately 295 kDa *Gibberella* (or other subject organism) protein, wherein said protein potentiates anti-insect toxin activity of a Class A toxin complex toxin protein. The subject invention also includes a transgenic cell comprising a heterologous polynucleotide from a culture of a *Gibberella* (or other subject organism) isolate, wherein said polynucleotide encodes an approximately 220 kDa to approximately 295 kDa protein that potentiates anti-insect toxin activity of a Class A toxin complex toxin protein. The subject invention includes a method of screening a plurality of *Gibberella* isolates for an approximately 220 kDa to approximately 295 kDa protein that potentiates anti-insect toxin activity of a Class A toxin complex toxin protein wherein said method comprises obtaining protein from said isolates and screening said protein for said potentiating activity. The subject invention still further includes a method of screening a plurality of *Gibberella* isolates for a gene that encodes an approximately 220 kDa to approximately 295 kDa protein that potentiates anti-insect toxin activity of a Class A toxin complex toxin protein wherein said method comprises obtaining nucleic acid molecules from said isolates and contacting said nucleic acid molecules with a polynucleotide that hybridizes with said gene.

Other organisms, proteins, and genes can be substituted in the above methods and embodiments. For example, *Methanosarcina* anti-insect proteins and genes can be identified or used according to the above methods. Likewise, Class A TC proteins and genes from *Gibberella* can identified or used according to the above methods. Novel strains identified using the subject methods are also within the scope of the subject invention.

Various approaches can be used for performing the above methods. For example, a library of clones can be constructed in performing some of the above methods. Some of these methods can include a step of performing polymerase chain reaction with at least one primer that is designed to indicate the presence of a gene of interest. The above methods can include a step of hybridizing a nucleic acid probe to DNA of interest wherein said probe is designed to indicate the presence of said gene. Proteins can be assayed by immunoreacting an antibody with said protein wherein said antibody is designed to indicate the presence of said protein.

The subject invention also includes an isolated protein that potentiates anti-insect toxin activity of a Class A toxin complex toxin wherein a polynucleotide sequence that encodes said protein hybridizes under stringent conditions with the complement of a sequence selected from SEQ ID NOs:1, 3, 5, 7, 9, and 11. In some preferred embodiments, the protein comprises an amino acid sequence selected from SEQ ID NO:2, SEQ ID NO:4, SEQ ID NO:6, SEQ ID NO:8, SEQ ID NO:10, and SEQ ID NO:12. An isolated polynucleotide that encodes any of these proteins is also within the scope of the subject invention, as are transgenic cells (such as microbial and plant cells) comprising said polynucleotides. The subject invention still further includes a method of controlling an insect pest wherein said method comprises the step of contacting said pest with a protein of the subject invention.

Again, other organisms, proteins, and genes can be substituted in the above methods and embodiments. This includes, for example, *Methanosarcina* anti-insect proteins and genes, and Class A TC proteins and genes from *Gibberella.*

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Discovery of Class B and Class C Gene Homologs in *Gibberella zeae*

A DNA sequence encoding a hypothetical protein with similarity to the *Photorhabdus luminescens* Toxin Complex TcaC (Class B) and TccC1 (Class C) proteins (GenBank Accession Numbers AAC38625.1 and AAL18473.1, respectively) was discovered by tblastn analysis of the *Gibberella zeae* genome. The analysis was done using the NCBI (National Center for Biotechnology Information) genomic BLAST algorithm at the World Wide Web site (ncbi.nlm.nih.gov/sutils/genom_table.cgi), using the following default values:

Expect 10;

Filter Default.

One hit for each protein was found within GenBank Accession Number AACM01000442 using tblastn. Both of the hits mapped to a single hypothetical protein which was annotated as follows:

CDS; join (52114 . . . 56781, 56863 . . . 59514);

locus_tag="FG10566.1";

codon_start=1;

product="hypothetical protein";

protein_id="EAA68452.1";

db_xref="GI:42545609".

The DNA sequence from AACM01000442 was translated using DNA Translator (a program that allows the user to select start and stop parameters for protein coding regions). The resulting predicted translation products were used to search a nonredundant local protein database using blastp. A similar blastp analysis was performed with all the proteins annotated in GenBank within the AACM01000442 sequence. In both cases, a single polypeptide (EAA68452.1) was identified that has significant homology to both the TcaC and TccC1 *Photorhabdus* Toxin Complex proteins.

Further analysis of the relationship between the EAA68452.1 protein and the TcaC and TccC1 proteins was performed with the program "Blast 2 sequences" which contains the blastp comparison algorithm [Tatiana A. Tatusova, Thomas L. Madden (1999), "Blast 2 sequences—a new tool for comparing protein and nucleotide sequences", FEMS Microbiol Lett. 174:247-250]. The default search/comparison parameters were used, as listed below:

Matrix Blosum62;

Open Gap 11;

Extension Gap 1;

Gap x dropoff 50;

Expect value 10;

Word size 3;

Filter off.

The "Blast2 sequences" comparison results for the TcaC protein are given below:

Length=2439

Score=318 bits (814);

Expect=9e-85;

Identities=333/1291 (25%);

Positives=527/1291 (40%),

Gaps=187/1291 (14%)

Analysis of the protein-protein alignment identified in this search revealed that the region of homology between TcaC and the *Gibberella zeae* EAA68452.1 hypothetical protein comprises amino acids 72-1266 of EAA68452.1.

The "Blast 2 sequences" comparison results for the TccC1 protein are given below:

Length=2439;

Score=192 bits (489);

Expect=3e-47;

Identities=198/723 (27%);

Positives=317/723 (43%);

Gaps=89/723 (12%)

Analysis of the protein-protein alignment identified in this search revealed that the region of homology between TccC1 and the *Gibberella zeae* EAA68452.1 hypothetical protein comprises amino acids 1557-2239 of EAA68452.1. Thus, it is apparent that the *Gibberella zeae* EAA68452.1 hypothetical protein comprises two consecutive domains, the first having some homology to the Class B TcaC protein, and a second domain having some homology to the Class C TccC1 protein.

GenBank Accession AACM01000442 is a 95095 base linear DNA sequence obtained via whole genome shotgun sequencing of the *Gibberella zeae* strain PH1 (NRRL 31084) chromosome 1, and has a deposit date of Feb. 13, 2004. It is noted that the CDS annotation above suggests the presence of an intron (intervening) sequence within the genomic sequence, comprising bases 56782 to 56862. Although annotated as an intron sequence, it should be noted that all the bases comprising the putative intron are in the +1 reading frame relative to exon1 preceding the intron (i.e. bases 52114 to 56781 of Accession AACM01000442). Therefore, an uninterrupted open reading frame extends from base 52114 to base 59514 of Accession AACM01000442. The predicted translation product provided by the DNA Translator program, and which was used in the above searches and comparisons, was larger than that annotated within AACM01000442, since the putative in-frame intron was not removed.

The sequence of the *Gibberella zeae* DNA which encodes a hypothetical protein with homology to toxin complex potentiator proteins, complete with translated intron, is shown in SEQ ID NO:1. The sequence is also referred to herein as $tcp1_{Gz}$ (toxin complex potentiator 1 of *Gibberella zeae*). The translation of SEQ ID NO:1 is shown in SEQ ID NO:2, and is referred to herein as $Tcp1_{Gz}$. The DNA sequence of $tcp1_{Gz}$ without the intron is shown in SEQ ID NO:3. The translation of SEQ ID NO:3 is shown in SEQ ID NO:4. According to some embodiments of the subject invention, the $Tcp1_{Gz}$ protein can potentiate the activities of the TC Class A proteins TcdA and XptA2 against their respective target insects. This observation is surprising and previously unexpected, since the $Tcp1_{Gz}$ protein has as its source a eukaryotic organism, and the TcdA and XptA2 proteins are derived from bacterial sources.

EXAMPLE 2

Design and Synthesis of a $Tcp1_{Gz}$-Encoding Gene for Expression in Bacteria This example teaches the design of a new DNA sequence that encodes the $Tcp1_{Gz}$ protein of SEQ ID NO:2, but is optimized for expression in *Escherichia coli* cells. Table 2, Columns D and H, present the distributions (in % of usage for all codons for that amino acid) of synonymous codons for each amino acid, as found in the coding regions of Class II genes of *E. coli*. [Class II genes are those that are highly expressed during the exponential growth phase of *E. coli* cells, as reported in: Henaut, A. and Danchin, A. (1996) *Escherichia coli and Salmonella typhimurium cellular and molecular biology*, vol. 2, pp. 2047-2066. [Neidhardt, F., Curtiss III, R., Ingraham, J., Lin, E., Low, B., Magasanik, B., Reznikoff, W., Riley, M., Schaechter, M. and Umbarger, H. (eds.). American Society for Microbiology, Washington, D.C.]. It is evident that some synonymous codons for some amino acids are present only rarely in those highly expressed genes (e.g. Leucine codon CTA and Arginine codon CGG). In the design process of creating a protein-encoding DNA sequence that approximates the codon distribution of highly expressed *E. coli* genes, any codon that is used infrequently relative to the other synonymous codons for that amino acid was not included (indicated by NA in Columns C and G of Table 2). Usually, a codon was considered to be rarely used if it was represented in the Class II genes at about 18% or less of the time to encode the relevant amino acid.

To balance the distribution of the remaining codon choices for an amino acid, a weighted average representation for each codon was calculated, using the formula:

$$\text{Weighted \% of } C1 = 1/(\%\ C1 + \%\ C2 + \%\ C3 + \text{ etc.}) \times \%\ C1 \times 100$$

where C1 is the codon in question, C2, C3, etc. represent the remaining synonymous codons, and the % values for the relevant codons are taken from columns D and H of Table 2 (ignoring the rare codon values in bold font). The Weighted % value for each codon is given in Columns C and G of Table 2.

Design of the *E. coli*-optimized DNA sequence was initiated by reverse translation of the protein sequence of SEQ ID NO:2 using a codon bias table constructed from Table 2, Columns C and G. The initial sequence was then modified by compensating codon changes (while retaining overall weighted average representation) to remove or add restriction enzyme recognition sites, remove highly stable intrastrand secondary structures, and other sequences that might be detrimental to cloning manipulations or expression of the engineered gene. An example of such detrimental sequence to avoid within a coding region is a 16S ribosomal RNA binding sequence ("Shine-Dalgarno sequence") such as AGGAGG, which could encode, for example, two consecutive arginine amino acids, but which might also serve as an intragenic (and therefore undesirable) translation initiation signal.

The *E.-coli*-biased DNA sequence that encodes the protein of SEQ ID NO:2 is given as bases 23-7420 of SEQ ID NO:5. To facilitate cloning and to ensure efficient translation initiation, a 5' terminal XbaI restriction enzyme recognition sequence (TCTAGA) and Shine Dalgarno sequence (AAGAAGGAG) were placed upstream of the ATG translation start codon (bases 1-22 of SEQ ID NO:5). Also to facilitate cloning, and to ensure proper translation termination, bases encoding two TAA translation stop codons and an XhoI restriction enzyme recognition site (CTCGAG) were included at the 3' end of the coding region (bases 7421-7440 of SEQ ID NO:5). Synthesis of a DNA fragment comprising SEQ ID NO:5 was performed by a commercial supplier (Entelechon GmbH, Regensburg, Germany).

It is presently noted that the *Gibberella zeae* genomic DNA sequence $tcp1_{Gz}$, disclosed in SEQ ID NO:1, as annotated in GenBank Accession AACM01000442, comprises a putative intron sequence (bases 4669-4749 of SEQ ID NO:1). Analysis of the open reading frame of SEQ ID NO:1 reveals that the bases comprising the putative intron maintain the +1 reading frame initiated by the ATG start codon at bases 1-3. In other words, SEQ ID NO:1 comprises a single open reading frame of 7398 bases that encodes a theoretical protein of 2466 amino acids. Thus, if the primary transcript derived from the DNA of SEQ ID NO:1 is not spliced (i.e. the intron sequence is not cleaved from the mRNA) translation would produce the $Tcp1_{Gz}$ protein disclosed in SEQ ID NO:2. On the other hand, if the primary transcript is spliced (that, is the intron sequences are removed) the mRNA would have a sequence corresponding to SEQ ID NO:3, and translation would produce the 2439 amino acid protein disclosed as SEQ ID NO:4.

For the purposes of this example, an *E. coli*-biased DNA sequence encoding the theoretical protein derived from the entire 7398 base open reading frame of SEQ ID NO:1 was designed and synthesized. The encoded protein of 2466 amino acids is identical in sequence to SEQ ID NO:2 ($Tcp1_{Gz}$,) and thus includes the amino acids encoded by the putative intron identified in the genomic sequence. As seen in the further Examples, this protein, derived from a eukaryotic organism, has the surprising activity of potentiating the insect toxicity of bacterially derived Class A TC proteins.

TABLE 2

Synonymous codon representation in highly expressed genes of *E. coli*, and calculation of a biased codon representation set for *E. coli*-optimized synthetic gene design.

| A Amino Acid | B Codon | C Weighted % | D Class II Genes % | E Amino Acid | F Codon | G Weighted % | H Class II Genes % |
|---|---|---|---|---|---|---|---|
| Ala (A) | GCA | 28.6 | 24.0 | Leu (L) | CTA | NA | 0.8 |
| | GCC | NA | 16.1 | | CTC | NA | 8.0 |
| | GCG | 38.5 | 32.3 | | CTG | 100.0 | 76.7 |
| | GCT | 32.8 | 27.5 | | CTT | NA | 5.6 |
| Arg (R) | AGA | NA | 0.6 | | TTA | NA | 3.4 |
| | AGG | NA | 0.3 | | TTG | NA | 5.5 |
| | CGA | NA | 1.1 | Lys (K) | AAA | 78.6 | 78.6 |
| | CGC | 33.9 | 33.0 | | AAG | 21.5 | 21.5 |
| | CGG | NA | 0.8 | Met (M) | ATG | 100.0 | 100.0 |
| | CGT | 66.1 | 64.3 | Phe (F) | TTC | 70.9 | 70.9 |
| Asn(N) | AAC | 100.0 | 82.8 | | TTT | 29.1 | 29.1 |
| | AAT | NA | 17.3 | Pro (P) | CCA | 17.5 | 15.3 |
| Asp (D) | GAC | 54.0 | 54.0 | | CCC | NA | 1.6 |
| | GAT | 46.1 | 46.1 | | CCG | 82.5 | 71.9 |
| Cys(C) | TGC | 61.2 | 61.2 | | CCT | NA | 11.2 |
| | TGT | 38.9 | 38.9 | Ser (S) | AGC | 29.2 | 24.3 |
| END | TAA | 100.0 | | | AGT | NA | 4.5 |
| | TAG | | | | TCA | NA | 4.8 |
| | TGA | | | | TCC | 31.9 | 26.6 |
| Gln(Q) | CAA | 18.7 | 18.7 | | TCG | NA | 7.4 |
| | CAG | 81.4 | 81.4 | | TCT | 38.9 | 32.4 |
| Glu (E) | GAA | 75.4 | 75.4 | Thr (T) | ACA | NA | 4.7 |
| | GAG | 24.7 | 24.7 | | ACC | 64.8 | 53.6 |

TABLE 2-continued

Synonymous codon representation in highly expressed genes of *E. coli*, and calculation of a biased codon representation set for *E. coli*-optimized synthetic gene design.

| A Amino Acid | B Codon | C Weighted % | D Class II Genes % | E Amino Acid | F Codon | G Weighted % | H Class II Genes % |
|---|---|---|---|---|---|---|---|
| Gly (G) | GGA | NA | 2.0 | | ACG | NA | 12.7 |
| | GGC | 45.7 | 42.8 | | ACT | 35.2 | 29.1 |
| | GGG | NA | 4.4 | Trp (W) | TGG | 100.0 | 100.0 |
| | GGT | 54.3 | 50.8 | Tyr (Y) | TAC | 64.8 | 64.8 |
| His (H) | CAC | 70.2 | 70.2 | | TAT | 35.2 | 35.2 |
| | CAT | 29.8 | 29.8 | Val (V) | GTA | 23.1 | 20.0 |
| Ile (I) | ATA | NA | 0.6 | | GTC | NA | 13.5 |
| | ATC | 66.3 | 65.9 | | GTG | 31.0 | 26.8 |
| | ATT | 33.7 | 33.5 | | GTT | 46.0 | 39.8 |

EXAMPLE 3

Engineering of the Synthetic Bacterial DNA Encoding $Tcp1_{Gz}$

The synthetic, bacterial biased DNA (SEQ ID NO:5) encoding the protein $Tcp1_{Gz}$, was engineered for expression by inserting it into two different *E. coli* expression vectors to assist in optimizing expression conditions. The first was vector pBT (U.S. application Ser. No. 10/754,115, filed Jan. 7, 2003), which uses a standard *E. coli* promoter. The pBT based plasmid was designated pDAB8828. The second was a pET expression vector (Novagen, Madison Wis.), which utilizes a bacteriophage T7 promoter. The pET based expression plasmid was designated pDAB8829. Each of these expression plasmids was constructed using standard molecular biology techniques. The engineering was done in such a way as to maintain appropriate bacterial transcription and translation signals. Both plasmids pDAB8828 and pDAB8829 encode the protein $Tcp1_{Gz}$, yet differ in promoter, selectable marker and various other features of the vector backbones.

EXAMPLE 4

Expression Conditions of pDAB8828 and Lysate Preparations

The expression plasmids pBT (empty vector control described in U.S. application Ser. No. 10/754,115, filed Jan. 7, 2003), and pDAB8828 were transformed into the *E. coli* expression strain BL21 (Novagen, Madison, Wis.) using standard methods. Expression cultures were initiated with 10-200 freshly transformed colonies placed into 250 mL LB medium containing 50 μg/mL antibiotic and 75 μM IPTG (isopropyl-α-D-thiogalactopyranoside). The cultures were grown at 28° C. for 48 hours at 180-200 rpm, and the cells were collected by centrifugation at 5,000×g for 20 minutes at 4° C. Cell pellets were suspended in 4-4.5 mL Butterfield's Phosphate solution (Hardy Diagnostics, Santa Maria, Calif.; 0.3 mM potassium phosphate pH 7.2), transferred to 50 mL polypropylene screw cap centrifuge tubes with 1 mL of 0.1 mm diameter glass beads (Biospec, Bartlesville, Okla., catalog number 1107901), and then were chilled on ice. The cells were lysed by sonication with two 45 second bursts using a 2 mm probe with a Branson Sonifier 250 (Danbury Conn.) at an output of ~30, chilling completely between bursts. The lysates were transferred to 2 mL Eppendorf tubes and centrifuged 10 minutes at 16,000×g. Supernatants were collected and the protein concentration measured. Bio-Rad Protein Dye Assay Reagent was diluted 1:5 with $H_2O$ and 1 mL was added to 10 μL of a 1:10 dilution of each sample and to bovine serum albumin (BSA) at concentrations of 5, 10, 15, 20 and 25 μg/mL. The optical densities of the samples were then read at 595 nm wavelength in a SpectraMax Plus spectrophotometer (Sunnyvale, Calif.). The lysates were assayed fresh.

EXAMPLE 5

Expression Conditions of pDAB8829 and Lysate Preparations

The expression plasmids pET (empty vector control), pDAB8920 and pDAB8829 were transformed into the *E. coli* T7 expression strain BL21(DE3) STAR (Invitrogen, Carlsbad, Calif.) using standard methods. Plasmid pDAB8920 was used as a positive potentiation control. It contains a fused potentiator gene consisting of the *Photorhabdus luminescens* genes tcdB2 and tccC3 fused via a 14 amino acid linker. Plasmid pDAB8920 is the subject of a separate application (U.S. Ser. No. 60/549,516, filed Mar. 2, 2004). Expression cultures were initiated with 10-200 freshly transformed colonies placed into 250 mL LB medium containing 50 μg/mL antibiotic and 75 μM IPTG (isopropyl-α-D-thiogalactopyranoside). The cultures were grown, lysed, and otherwise processed as described in Example 4 above.

EXAMPLE 6

Bioassay Conditions for pDAB8828 and pDAB8829 Lysates

Insect bioassays were conducted with neonate larvae on artificial diets in 128-well trays specifically designed for insect bioassays (C-D International, Pitman, N.J.). The species assayed were the southern corn rootworm, *Diabrotica undecimpunctata howardi* (Barber), and the corn earworm, *Helicoverpa zea* (Boddie).

Bioassays were incubated under controlled environmental conditions (28° C., ~40% relative humidity, 16 h:8 h [Light: Dark]) for 5 days, at which point the total number of insects in the treatment, the number of dead insects, and the weights of surviving insects were recorded.

The biological activity of the crude lysates alone or with added Toxin Complex Class A proteins TcdA or $XptA2_{xwi}$ was assayed as follows. Crude *E. coli* lysates (40 μL) (3-21 mg/mL) of either control cultures or those expressing potentiator proteins were applied to the surface of artificial diet in 8 wells of a bioassay tray. The average surface area of treated diet in each well was ~1.5 $cm^2$. The TcdA or XptA$2_{xwi}$ proteins were added as highly purified fractions from bacterial cultures heterologously expressing the individual proteins. The final concentrations of XptA$2_{xwi}$ and TcdA on the diet were 250 ng/$cm^2$ and 50 ng/$cm^2$, respectively. At these doses, these proteins have essentially no significant effect on the growth of the test insect larvae.

EXAMPLE 7

Bioassay Results for pDAB8828 Lysates

Table 3 shows the bioassay results for lysates of cells programmed to express the Tcp$1_{Gz}$ protein from plasmid pDAB8828, as compared to control cell lysates. Examination of the data show that TcdA (coleopteran active) and XptA$2_{xwi}$ (lepidopteran active) had negligible impact when mixed with vector only control lysates. It should be noted that the amount of TcdA and XptA$2_{xwi}$ added to the lysates was adjusted to highlight the potentiation affect of the potentiator encoding genes. Lysates from cells containing pDAB8828 did not kill insects. However, when mixed with TcdA or XptA$2_{xwi}$ proteins, significant growth inhibition was noted, with the expected spectrum of activity. Analysis of the various lysates by SDS-PAGE (sodium dodecyl sulfate polyacrylamide gel elctrophoresis) showed the presence of a ~280 kDa band in pDAB8828 samples but not in the control samples. The migration of the band is consistent with the calculated size of Tcp$1_{Gz}$ (i.e. 277.7 kDa). These results demonstrate that the plasmid pDAB8828 produces the protein Tcp$1_{Gz}$ and this protein exhibits the surprising function of potentiating the activity of the Class A proteins TcdA and XptA2 against their target insects.

TABLE 3

Response of *coleopteran* and *lepidopteran* species to *E. coli* lysates and purified proteins. Seven to nine insects used per replicate.

| Sample | Lysate Tested | Southern Corn Rootworm | Corn Earworm |
|---|---|---|---|
| pBT | Control | 0 | + |
| pBT + TcdA | Control | + | nt |
| pBT + XptA$2_{Xwi}$ | Control | nt | 0 |
| pDAB8828 | Tcp$1_{Gz}$ | 0 | 0 |
| pDAB8828 + TcdA | Tcp$1_{Gz}$ | ++++ | nt |
| pDAB8828 + XptA$2_{Xwi}$ | Tcp$1_{Gz}$ | nt | ++++ |

Data are for two independent replicates.
Growth Inhibition Scale:
0 = 0-20%;
+ = 21-40%;
++ = 41-60%;
+++ = 61-80%;
++++ = 81-100%;
nt = not tested.

EXAMPLE 8

Bioassay Results pDAB8829 Lysates

Table 4 shows the bioassay results for lysates of cells programmed to express the Tcp$1_{Gz}$ protein from plasmid pDAB8829, as compared to control cell lysates, and lysates of cells programmed to express the fused potentiator 8920. Examination of the data show that TcdA (coleopteran toxin) and XptA$2_{xwi}$ (lepidopteran toxin) had negligible impact when mixed with vector only control lysates. It should be noted that the amount of TcdA and XptA$2_{xwi}$ added to the lysates was adjusted to highlight the potentiation affect of the TcdB2 and TccC3 encoding genes. Lysates from pDAB8920 containing cells alone did not kill insects. However, when mixed with TcdA or XptA$2_{xwi}$, significant insect inhibition was noted with the expected spectrum. Surprisingly, lysates of cells programmed to produce the Tcp$1_{Gz}$ protein exhibited a similar activity profile as the 8920 potentiator. Analysis of the various lysates by SDS-PAGE showed the presence of a ~280 kDa in pDAB8829 samples as compared to vector lysates. The migration of the band is consistent with the predicted molecular weight of Tcp$1_{Gz}$. These results demonstrate that the plasmid pDAB8829 produces the protein Tcp$1_{Gz}$ and this protein potentiates the activity of the insect active Class A TcdA and XptA2 proteins.

TABLE 4

Response of *coleopteran* and *lepidopteran* species to *E. coli* lysates and purified proteins. Seven to nine insects used per replicate.

| Sample | Lysate Tested | Southern Corn Rootworm | Corn Earworm |
|---|---|---|---|
| pET | Control | + | + |
| pET + TcdA | Control | 0 | nt |
| pET + XptA2 | Control | nt | 0 |
| pDAB8920 | 8920 (TcdB2/TccC3) | 0 | 0 |
| pDAB8920 + TcdA | 8920 (TcdB2/TccC3) | ++++ | nt |
| pDAB8920 + XptA$2_{Xwi}$ | 8920 (TcdB2/TccC3) | nt | ++++ |
| pDAB8829 | Tcp$1_{Gz}$ | 0 | 0 |
| pDAB8829 + TcdA | Tcp$1_{Gz}$ | ++++ | nt |
| pDAB8829 + XptA$2_{Xwi}$ | Tcp$1_{Gz}$ | nt | ++++ |

Data are for two independent replicates.
Growth Inhibition:
0 = 0-20%;
+ = 21-40%;
++ = 41-60%;
+++ = 61-80%;
++++ = 81-100%;
nt = not tested.

EXAMPLE 9

Identification of Other Naturally Occurring Fused Class B/Class C Proteins

This example provides a further illustration of an approach that could be used to search a protein database for candidate proteins having homology to Class B and Class C TC proteins. An artificially generated fusion protein sequence was first constructed using a DNA/Protein analysis program [Vector NTI (Informax, Inc.)]. One skilled in the art would recognize that several other DNA/Protein analysis programs could alternatively be used. An example of such fusion protein, generated from the amino acid sequences of TcaC (GenBank Accession AAC38625.1) and TccC1 (GenBank Accession AAL18473.1) (both from *Photorhabdus luminescens* strain W-14) is disclosed in SEQ ID NO:6. This artificial fusion protein sequence was used in a standard protein-protein BLAST search of the NCBI nonredundant protein database, using default values as listed below:

Filter set to low complexity;
Expect 10;
Word size 3;
Matrix BLOSUM62
Gap Costs: Existence 11, Extension 1

FIG. 1 presents the graphical output of such a search. [The actual ouput of the computer search is presented in colors on a computer monitor; it is understood that the figure, as printed, is not exactly the same as the computer monitor output. This does not limit the interpretations presented herein.] Across the top of the figure is a bar with differently shaded segments to represent Alignment Scores calculated from different amounts of amino acid sequence homology of the query sequence to a sequence identified in the search. The values shown are: <40, 40-50, 50-80, 80-200- and >=200. The next horizontal line under the Alignment Score bar represents the amino sequence of the artificial fusion query sequence of 2858 amino acids, with divisions of 500 amino acids. This artificial fusion protein used as the query sequence is comprised of TcaC amino acids from residues 1 to 1485, and TccC1 amino acids from residues 1486 to 2858. The horizontal lines in the data portion of FIG. 1 represent individual proteins, identified by the BLAST algorithm as possessing an amino acid sequence related (within the parameters of the search) to the query sequence. For clarity and ease of reference, numbers have been added to certain of the landmark lines; such numbers are not a part of the original output. Inspection of FIG. 1 reveals that there were 64 lines representing protein sequences identified as having significant homology regions to the query sequence. It is noted that several of the horizontal lines do not represent single proteins. For example, the larger, left-hand portion of line 1 was identified by the output as "gi|3265037|gb|AAC38625.1| insecticidal toxin complex protein TcaC [*Photorhabdus luminescens*]" (i.e., part of the query sequence), whereas the right-hand, smaller portion of line 1 is identified as ">gi|53693249|ref|ZP_00127870.2| COG3209: Rhs family protein [*Pseudomonas syringae* pv. *syringae* B728a]." The gap in line 1 between the left-hand and right-hand portions of the line indicates that the two homology regions belong to separately encoded proteins.

In some instances, however, the homology lines represent a single protein. For example, line 53 has the left-hand and right-hand homology regions joined by a slashed line. The BLAST output identified this protein as the subject of this invention: ">gi|42545609|gb|EAA68452.1| hypothetical protein FG10566.1 [*Gibberella zeae* PH-1]". Other single proteins with homology regions to the query sequence are identified in Table 5. Although discovered by their homologies to a Class B and a Class C protein, it is understood that the biological functions/activities of the deduced proteins have not been confirmed. However, given the subject disclosure (but not prior to it), one is now motivated to assess the functionality of these proteins for their ability to potentiate the activity of Class A Toxin Complex proteins.

TABLE 5

Hypothetical fusion proteins identified by BLAST search of NCBI nonredundant protein database.

| Output | Identified Sequence Listing |
|---|---|
| Line 55 | >gi|42527066|ref|NP_972164.1|<br>YD repeat protein [*Treponema denticola* ATCC 35405]<br>Length = 3320<br>Left-hand portion:<br>Score = 49.7 bits (117), Expect = 0.001<br>Identities = 37/106 (34%), Positives = 54/106 (50%), Gaps = 19/106 (17%)<br>Right-hand portion:<br>Score = 116 bits (290), Expect = 1e−23<br>Identities = 199/931 (21%), Positives = 324/931 (34%), Gaps = 208/931 (22%) |
| Line 58 | >gi|45657896|ref|YP_001982.1|<br>cytoplasmic membrane protein [*Leptospira interrogans* serovar Copenhageni str. Fiocruz L1-130]<br>Length = 2554<br>Left-hand portion:<br>Score = 62.8 bits (151), Expect = 1e−07<br>Identities = 55/214 (25%), Positives = 93/214 (43%), Gaps = 37/214 (17%)<br>Right-hand portion:<br>Score = 84.3 bits (207), Expect = 4e−14<br>Identities = 185/818 (22%), Positives = 309/818 (37%), Gaps = 141/818 (17%) |
| Line 60 | >gi|24214465|ref|NP_711946.1| Rhs family protein [*Leptospira interrogans* serovar Lai str. 56601]<br>Length = 2321<br>Left-hand portion:<br>Score = 62.4 bits (150), Expect = 2e−07<br>Identities = 55/214 (25%), Positives = 93/214 (43%), Gaps = 37/214 (17%)<br>Right-hand portion:<br>Score = 77.4 bits (189), Expect = 5e−12<br>Identities = 177/792 (22%), Positives = 300/792 (37%), Gaps = 145/792 (18%) |
| Line 63 | >gi|20090892|ref|NP_616967.1|<br>hypothetical protein MA2045 [*Methanosarcina acetivorans* C2A]<br>Length = 2217<br>Left-hand portion:<br>Score = 63.9 bits (154), Expect = 6e−08<br>Identities = 174/872 (19%), Positives = 302/872 (34%), Gaps = 219/872 (25%)<br>Right-hand portion:<br>Score = 63.5 bits (153), Expect = 8e−08<br>Identities = 127/542 (23%), Positives = 210/542 (38%), Gaps = 114/542 (21%) |
| Line 64 | >gi|48863870|ref|ZP_00317763.1|<br>COG3209: Rhs family protein [*Microbulbifer degradans* 2-40]<br>Length = 2480<br>Left-hand portion:<br>Score = 62.0 bits (149), Expect = 2e−07 |

TABLE 5-continued

| Hypothetical fusion proteins identified by BLAST search of NCBI nonredundant protein database. | |
|---|---|
| Output | Identified Sequence Listing |
| | Identities = 140/647 (21%), Positives = 233/647 (36%), Gaps = 102/647 (15%)<br>Right-hand portion:<br>Score = 54.7 bits (130), Expect = 4e−05<br>Identities = 177/914 (19%), Positives = 318/914 (34%), Gaps = 188/914 (20%) |

EXAMPLE 10

Cloning of a Gene Encoding a Class B/C Fusion Protein of Toxin Complex Potentiators from *Tannerella forsythensis*

Pfam model analysis and scanning of publicly available DNA and protein sequence databases (NCBI and TIGR Microbial) identified a gene encoding a candidate fused Class B/C Toxin Complex (TC) potentiator protein and another four potential Class C TC genes in the genome of *Tannerella forsythensis*. (Also known as *Bacteroides forsythus*. As of the subject filing date, this genome was not known to be available from Entrez, and at the TIGR Microbial Database it was listed as unfinished with no target date for completion.) These Class C TC genes are located downstream of the gene encoding the fused Class B/C TC protein. The putative gene encoding the fused Class B/C TC protein was cloned.

Genomic DNA of *Tannerella forsythensis* (ATCC 43037) was purchased from the American Type Tissue Culture Collection (ATCC, Manassas, Va.). Primers for amplifying various regions of the fused Class B/C TC gene and its flanking sequences were designed based on the sequence in the public database. In the initial PCR reactions, a 4541 bp product corresponding to the region from 431 bp upstream of the Class B/C fusion gene to 4110 bp downstream of the putative start codon (ATG) was obtained using primers P1 and P2 (Table 6) with PfuTurbo hotstart DNA polymerase (Stratagene, La Jolla, Calif.). This PCR product was inserted into the pCRII Blunt TOPO vector (Invitrogen, Carlsbad, Calif.) and the DNA sequence of the insert DNA was determined. The sequencing results showed that the homology between the PCR fragment and the corresponding region of the fused Class B/C gene in the public database was only 97.1%. This implied that the bacterial strain on which the sequence in the public database was based might be different from that which we obtained from the ATCC (i.e. strain 43037). Multiple attempts were made to amplify the 3' end of the fused Class B/C gene based on the sequence in the public database. Alternative primers were designed to amplify DNA fragments beginning at the 3' end of the confirmed sequence region and extending to various regions downstream of the Class B/C fusion gene (based on the published sequence). An approximately 6.5 kb PCR fragment was obtained using primers P3 and P4 (Table 6) with Takara EX Taq™ DNA polymerase (Fisher Scientific, Pittsburg, Pa.). This DNA fragment was cloned into the pCR2.1-TOPO vector (Invitrogen, Carlsbad, Calif.) and partially sequenced. The results from sequencing the two ends of this PCR product indicated that, although the forward primer (P3) annealed to the expected location in the Class B/C fusion gene, the reverse primer (P4) had attached to the 5' end of the fourth Class C TC related gene downstream of the Class B/C fusion gene. Moreover, the size of PCR product (~6.5 kb) was smaller than the size predicted from the published genomic sequence (11201 bp), which indicated that there was a deletion or re-arrangement of DNA sequence in that region. The full sequence of the 3' end of the Class B/C fusion gene represented in the 6.5 kb PCR product was obtained by stepwise walking from the confirmed region at the 5' end all the way to the first in-frame stop codon. The full length sequence of the Class B/C fusion gene in Tannerella forsythensis (ATCC 43037) is disclosed in SEQ ID NO:11.

In parallel, three GenomeWalking "libraries" were constructed by digesting the genomic DNA of *T. forsythensis* (ATCC 43037) with Afe I, BsaB I, and Stu I restriction enzymes and using the BD GenomeWalker™ Universal Kit (BD Biosciences, San Jose, Calif.). The first round PCR was performed using primer P5 (Table 6) and AP1 (provided with the kit). The second round PCR was carried out using a pair of nested primers, P6 (Table 6) and AP2 (provided with the kit). Takara LA Taq™ DNA polymerase was used in both rounds of PCR reactions. Specific amplification was obtained from the libraries generated by BsaB I and Stu I digestions. These PCR products were cloned into the pCR2.1 TOPO vector and sequenced. The sequencing results matched with the corresponding region of SEQ ID NO:11 except for a few single nucleotide mutations that were possibly introduced during the PCR process. These results confirmed that the sequence disclosed in SEQ ID NO:11 was the actual sequence of the Class B/C fusion gene in *Tannerella forsythensis* (ATCC 43037), with very few discrepancies.

To further confirm this result, Southern blot analyses were performed using *T. forsythensis* genomic DNA digested with Hind III and BsaB I in separate reactions. The blots were probed with a 1030 bp DNA fragment representing part of the coding region for a Class B TC related protein in the Class B/C fusion gene. This probe was obtained by PCR amplification of the genomic DNA from *T. forsythensis* (ATCC 43037) using primers P2/P3. The results from the Southern blot analysis revealed that the probe hybridized to Hind III and BsaB I fragments of *T. forsythensis* (ATCC 43037) genomic DNA with the same sizes as those predicted from SEQ ID NO:11 [2792 bp for Hind III digestion, and 3598 bp for BsaB I].

It is noted that the DNA sequence of the *T. forsythensis* (ATCC 43037) Class B/C fusion gene disclosed as SEQ ID NO:11 was obtained from PCR products amplified from genomic DNA. It is well known in the art that such PCR amplifications can introduce small numbers of base incorporation errors. Thus, it is possible that the actual sequence of the gene as present in the *T. forsythensis* (ATCC 43037) genome may be slightly different from that disclosed in SEQ ID NO:11. Given that the sequence disclosed in SEQ ID NO:11 was determined from multiple PCR products, it is reasonable to expect that the genomic copy of the Class B/C fusion gene should be at least 99% identical to SEQ ID NO:11. Comparison of SEQ ID NO:11 to the corresponding sequence of the Class B/C fusion gene in the public databases reveals that the two sequences share 97% homology in the region comprising approximately 5.2 kb at the 5' end, which corresponds to the entire coding region for an amino acid sequence related to a Class B TC protein plus the core region of a Class C TC protein. Downstream of the 5.2 kb region, there is an approximately 460 bp sequence with high homology to the hyper-variable region of the third Class C TC related gene downstream of the Class B/C fusion gene, then there is an additional ~420 bp at the 3' end which currently exhibits relatively lower homology (less than 60%) than any other part of the published *Tannerella forsythensis* (ATCC 43037) partial genome sequence database. This indicated that the sequence of the putative gene encoding the fused Class B/C TC protein cloned from the genomic DNA of *Tannerella forsythensis* (ATCC 43037) (SEQ ID NO:11) was different from that in the public databases.

TABLE 6

Primers used for PCR

| Primer ID | Sequence | SEQ ID NO: |
|---|---|---|
| P1 | AGGATCGTACGATGGAACAAGAGG | 13 |
| P2 | CGACTGTGATGCGTAACGAACAGA | 14 |
| P3 | GTCCGACGGTCTGTATATGCTTAG | 15 |
| P4 | CCGAAGAAATCAATGCCTGCCGAT | 16 |
| P5 | TAATGTCCCCGACGGTAAATGGCTTGAA | 17 |
| P6 | GCGTCTGTTCGTTACGCATCACAGTCG | 18 |

EXAMPLE 11

Identification of Further Multi-Domain TC Proteins

In light of the subject disclosure of the activity of naturally fused “BC” toxin complex proteins, one skilled in the art now has the motivation to find other such fusion proteins with the expectation that they can potentiate the insecticidal activity of a Class A toxin complex toxin protein. It is well known in the art that standard BLAST searches of protein databases can be used to identify proteins related to one another by amino acid sequence homology. This example teaches how one may analyze a database of protein sequences and extract those having particular domain structures that predict their function as Class B or Class C Toxin Complex (TC) potentiators. The Class B and Class C TC gene families encode proteins that are relatively large and have distinctive protein domain structures. These two factors can be used in tandem to extract sequences of individual Class B and Class C TC proteins from large protein databases. Similarly, when the Class B and C TC proteins are fused into a single polypeptide, their large size and distinctive combinations of protein domains can be used to set up specific searches to extract sequences of related structure and function from protein databases. This is now possible because of the subject disclosure.

Protein domain searches are routinely performed utilizing a Pfam search algorithm (E.L.L. Sonnhamrner, S.R. Eddy, and R. Durbin), either at the Pfam web site (pfam.wustl.edu/), at a “mirror” site (e.g. website at sanger.ac.uk/Software/Pfam/), or with a local installation of the database. While these Pfam models are very helpful, they could miss existing domains, especially if those domains are reasonably divergent from the model. Therefore, to increase sensitivity of domain detection, it is desirable to establish protein domain models specific to the gene families being studied. This can be done with the same set of analysis tools as was used in generating the Pfam families (i.e. HMMER; R. Durbin, S.R. Eddy, A. Krogh, and G. Mitchison) and will often allow identification of protein domains missed by the more general models.

The workflow is conceptually simple. First, a search is performed on a protein database to extract a subset of the database sequences. Second, this subset is tested against an HMM model generated using HMMER. The hits generated against the model, and which have an appropriate significance level, will either encompass the set of proteins that can be selected for experimental characterization, or can serve as a smaller database that is screened against a second HMM model. This screening can be iterated as necessary until the desired level of resolution has been attained.

The examples below exemplify the utility of this approach for four distinct sets of TC protein families: the single Class B TC proteins, the single Class C TC proteins, and the fused Class B/C TC proteins from eukaryotic and prokaryotic archaeal sources.

Class B TC Proteins. All the Class B TC genes discovered to date come from prokaryotes; therefore, the initial search set was restricted to prokaryotic protein sequences. A protein search at the website ncbi.nlm.nih.gov/ was performed using the search terms: “1400:1600[SLEN] AND Prokaryota”. These terms restricted the search to those proteins that are between 1400 and 1600 amino acids in length and have prokaryotic sources. A total of 3522 protein sequences were identified and downloaded as a searchable database. It should be noted that, while these restrictions are useful in the present context, the interval length of the sequences and the kingdom searched can be modified to meet the parameters of the individual protein set to be examined.

All known Class B TC proteins examined to date contain two distinct sets of domains. (The domain terminology used herein is taken from the Pfam site and the domains can be searched for by name at that site.) At the amino terminal end is a highly conserved spvB domain. This domain is so well conserved that it was not necessary to construct a more specific HMM domain model, and the general model (spvB_ls.hmm) was downloaded directly from the Pfam web site. See also M. L. Lesnick, N. E. Reiner, J. Fierer, and D. G. Guiney, *Mol. Microbiol.* March 2001, 39(6):1464-70.

The spvB domain is followed by multiple FG-GAP domains. See, e.g., T. A. Spring, “Folding of the N-terminal, ligand-binding region of integrin alpha-subunits into a beta-propeller domain,” *Proc. Natl. Acad. Sci. U.S.A.* 1997, 94:65-72. The FG-GAP domain model utilized by the general Pfam model miss many domains within a single protein, and all domains in certain proteins when default Pfam gathering threshold values are used (for example GenBank Accessions 66047263, 28871479 and 48730377, which are identified by our model, see below). If a more relaxed cutoff value is used, [E-value=1.0], more domains are found, including those in the above proteins, but some domains may not be discovered. Therefore, it was necessary to create a tailored FG-GAP HMM model.

Creation of an HMM model of a protein family typically requires three steps. First, a set of domains is chosen as a “seed,” and a multiple sequence alignment is created using ClustalX. Second, the multiple sequence alignment is used as an input for hmmbuild, a program that generates the HMM model. Finally, hmmcalibrate is used to correct the statistics of the particular model (hmmcalibrate, hmmbuild, and hmmsearch are components of the HMMER package). The seed domain set used to generate the HMM model is a key component of the success of the model. It must be diverse enough to capture all the diversity of the relevant domains. However, the seed set cannot contain all the known domain members since the test of the predictive power of the model requires its ability to identify the domain containing members not included in the seed set.

A set of Class B TC proteins to be used as the source of FG-GAP domains was acquired using the BLink resource for GenBank Accession 16416891 (TcaC from *Photorhabdus luminescens*). This extraction yielded 15 related, nonredundant prokaryotic proteins with scores higher than 2000. [The number of related proteins accessible through BLink of any given protein can vary with time, since GenBank can be a dynamic list.] The GenBank Accession numbers of the extracted proteins were: 16416891, 37524951, 16416930, 37524959, 27479675, 51597844, 22124105, 45443595, 50956508, 14041732, 32699986, 10956817, 66047263, 28871479, and 48730377.

An intermediate HMM model was generated by extracting the FG-GAP domains found in the above proteins using the general Pfam model, supplemented with the known FG-GAP domains from GenBank Accession 16416891 (i.e. TcaC). The domains used in the final model were obtained by extracting the domains from the two protein sequences which had the best and worst scores of proteins containing six FG-GAP domains (GenBank Accessions 16416891 and 66047263, respectively). [Note that six represents the canonical number of FG-GAP domains in most FG-GAP containing proteins.] It is not surprising that GenBank Accession 16416891 is the best hit, since it is part of the model itself. The ClustalX multiple sequence alignments of the six FG_GAP domains in these two proteins is shown below. These alignments can be used with hmmbuild to generate the FG-GAP HMM model used in this example.

This multiple sequence alignment was used with hmmbuild and hmmcalibrate to generate BModels3.hmm. The BModels3.hmm model was then tested against the 15 protein sample set above and was able to identify all expected FG-GAP domains. Conversely, when the BModels3.hmm model was tested against 20 randomly selected proteins, no FG-GAP domains were found. The BModels3.hmm model was then tested with hmmsearch against the 3522 member database containing all prokaryotic proteins between 1400 and 1600 amino acids, yielding the results below.

hmmsearch—search a sequence database with a profile HMM

HMMER 2.3.1 (June 2003)

Copyright (C) 1992-2003 HHMI/Washington University School of Medicine

Freely distributed under the GNU General Public License (GPL)

HMM file: FinalTest/BModels3.hmm [BDomainsModel3Sequences]

Sequence database: FinalTest/Prokaryotic1400-1600.fasta per-sequence score cutoff: [none]

per-domain score cutoff: [none]

per-sequence Eval cutoff: <=10 per-domain Eval cutoff: [none]

Query HMM: BDomainsModel3Sequences

Accession: [none]

Description: [none]

[HMM has been calibrated; E-values are empirical estimates]

CLUSTALX (1.83) multiple sequence alignment of derived FG-GAP domains.

| | | |
|---|---|---|
| gi\|16416891\|Domain_4 | DARKLVAFSDMLGSGQQHLVEIKAN-RVTCWP-NLGHGRFGQP- | SEQ ID NO: 42 |
| gi\|66047263\|Domain_4 | -STELVAFSDLLGTGQQHLIRIRHN-EIRVWP-NLGRGRFGKG- | SEQ ID NO: 43 |
| gi\|16416891\|Domain_3 | --HPSIQFADLTGAGLSDLVLIGPK-SVRLYA-NQR-NGWRKGE | SEQ ID NO: 44 |
| gi\|66047263\|Domain_3 | --HPQGQMADLVGDGLSDLALIGPR-SVRLYA-NRRADGFAAA- | SEQ ID NO: 45 |
| gi\|16416891\|Domain_6 | -NTCQLQVADIQGLGIASLILTVPHIAPHHWRCDLSLTKPW--- | SEQ ID NO: 46 |
| gi\|66047263\|Domain_6 | -RFCQFSAVDLLGLGFSSLVLTVPHMAPRHWSLYYAADRTG--- | SEQ ID NO: 47 |
| gi\|16416891\|Domain_2 | --QDNASLMDINGDGQLDWVVTASG-IRGYHS-QQPDGKWTH-- | SEQ ID NO: 48 |
| gi\|66047263\|Domain_2 | -APVRQTLTDLTGDGRLDWVVAQPG-MAGFFT-LNPDRSWSK- | SEQ ID NO: 49 |
| gi\|16416891\|Domain_5 | -NPERLFLADIDGSGTTDLIYAQSG-SLLIYL-NQSGNQFDAP- | SEQ ID NO: 50 |
| gi\|66047263\|Domain_5 | -DSSRVRLADLDGSGASDVLYLQAD-GFQVFM-NQGGNGLAAA- | SEQ ID NO: 51 |
| gi\|16416891\|Domain_1 | --QQRYQLVDLRGEGLPGMLYQDRG--AWWYK-APQRQEDGDS- | SEQ ID NO: 52 |
| gi\|66047263\|Domain_1 | --GQQYQLVDLYGDGLPGILYRDDK--AWLYR-EPIRDTAGTA- | SEQ ID NO: 53 |

Scores for complete sequences (score includes all domains):

| Sequence | Description | Score | E-value | N |
|---|---|---|---|---|
| gi\|16416891\|gb\|AAL18451.1\| | toxin complex pr | 323.9 | 1.1e−94 | 6 |
| gi\|3265037\|gb\|AAC38625.1\| | insecticidal tox | 323.9 | 1.1e−94 | 6 |
| gi\|66047263\|ref\|YP__237104.1\| | *Salmonella* virul | 323.7 | 1.3e−94 | 6 |
| gi\|63257970\|gb\|AAY39066.1\| | *Salmonella* virul | 323.7 | 1.3e−94 | 6 |
| gi\|36783948\|emb\|CAE12810.1\| | Insecticidal tox | 321.0 | 8.3e−94 | 6 |
| gi\|37524524\|ref\|NP__927868.1\| | Insecticidal tox | 321.0 | 8.3e−94 | 6 |
| gi\|28854730\|gb\|AAO57793.1\| | insecticidal tox | 312.1 | 4e−91 | 6 |
| gi\|28871479\|ref\|NP__794098.1\| | insecticidal tox | 312.1 | 4e−91 | 6 |
| gi\|36784385\|emb\|CAE13264.1\| | Insecticidal tox | 248.0 | 8e−72 | 6 |
| gi\|37524959\|ref\|NP__928303.1\| | Insecticidal tox | 248.0 | 8e−72 | 6 |
| gi\|51510118\|emb\|CAH19031.1\| | unnamed protein | 244.2 | 1.1e−70 | 6 |
| gi\|49021690\|emb\|CAG38449.1\| | unnamed protein | 244.2 | 1.1e−70 | 6 |
| gi\|27479675\|gb\|AAO17202.1\| | TcdB2 [Photorhab | 244.2 | 1.1e−70 | 6 |
| gi\|36784377\|emb\|CAE13256.1\| | Insecticidal tox | 229.4 | 3.2e−66 | 6 |
| gi\|37524951\|ref\|NP__928295.1\| | Insecticidal tox | 229.4 | 3.2e−66 | 6 |
| gi\|50956508\|gb\|AAT90757.1\| | putative insecti | 229.0 | 4.2e−66 | 6 |
| gi\|16416930\|gb\|AAL18487.1\| | TcdB1; toxin com | 227.6 | 1.1e−65 | 6 |
| gi\|9963679\|gb\|AAG09643.1\| | SepB [*Serratia* e | 214.1 | 1.2e−61 | 6 |
| gi\|10956817\|ref\|NP__065277.1\| | SepB [*Serratia* e | 214.1 | 1.2e−61 | 6 |
| gi\|13444938\|emb\|CAC34920.1\| | unnamed protein | 214.1 | 1.2e−61 | 6 |
| gi\|51591126\|emb\|CAH22791.1\| | insecticidal tox | 211.8 | 5.9e−61 | 6 |
| gi\|51597844\|ref\|YP__072035.1\| | insecticidal tox | 211.8 | 5.9e−61 | 6 |
| gi\|45477499\|gb\|AAS66065.1\| | YO185-like prote | 211.8 | 5.9e−61 | 6 |
| gi\|32699986\|gb\|AAP57764.1\| | TcYF2 [*Yersinia* | 207.9 | 8.9e−60 | 6 |
| gi\|15981600\|emb\|CAC93148.1\| | insecticidal tox | 201.9 | 6e−58 | 6 |
| gi\|45443595\|ref\|NP__995134.1\| | insecticidal tox | 201.9 | 6e−58 | 6 |
| gi\|25511233\|pir\|AH0447 | insecticidal tox | 201.9 | 6e−58 | 6 |
| gi\|16123821\|ref\|NP__407134.1\| | insecticidal tox | 201.9 | 6e−58 | 6 |
| gi\|22124105\|ref\|NP__667528.1\| | putative toxin s | 201.9 | 6e−58 | 6 |
| gi\|45438465\|gb\|AAS64011.1\| | insecticidal tox | 201.9 | 6e−58 | 6 |
| gi\|21956856\|gb\|AAM83779.1\|AE013618__4 | putative toxin s | 201.9 | 6e−58 | 6 |
| gi\|14041732\|emb\|CAC38403.1\| | XptC1 protein [X | 178.3 | 7.7e−51 | 5 |
| gi\|48730377\|ref\|ZP__00264125.1\| | hypothetical pro | 138.4 | 7.5e−39 | 6 |
| gi\|39576632\|emb\|CAE80796.1\| | hypothetical pro | 13.5 | 0.044 | 2 |
| gi\|42524423\|ref\|NP__969803.1\| | hypothetical pro | 13.5 | 0.044 | 2 |
| gi\|23129574\|ref\|ZP__00111400.1\| | COG2931: RTX tox | 5.7 | 0.39 | 2 |
| gi\|11360961\|pir\|\|H82802 | fimbrial assembl | 2.4 | 0.99 | 1 |
| gi\|15837080\|ref\|NP__297768.1\| | fimbrial assembl | 2.4 | 0.99 | 1 |
| gi\|28199488\|ref\|NP__779802.1\| | fimbrial assembl | 2.4 | 0.99 | 1 |
| gi\|53800360\|ref\|ZP__00359737.1\| | COG3419: Tfp pil | 2.4 | 0.99 | 1 |
| gi\|9105326\|gb\|AAF83288.1\|AE003897__13 | fimbrial assembl | 2.4 | 0.99 | 1 |
| gi\|28057603\|gb\|AAO29451.1\| | fimbrial assembl | 2.4 | 0.99 | 1 |
| gi\|19704886\|ref\|NP__602381.1\| | *Fusobacterium* ou | −2.0 | 3.4 | 1 |
| gi\|19712775\|gb\|AAL93680.1\| | *Fusobacterium* ou | −2.0 | 3.4 | 1 |
| gi\|67760705\|ref\|ZP__00499423.1\| | COG3321: Polyket | −2.3 | 3.7 | 1 |
| gi\|67756256\|ref\|ZP__00495142.1\| | COG3321: Polyket | −2.3 | 3.7 | 1 |
| gi\|67738861\|ref\|ZP__00489483.1\| | COG3321: Polyket | −2.3 | 3.7 | 1 |
| gi\|67710424\|ref\|ZP__00480230.1\| | COG3321: Polyket | −2.3 | 3.7 | 1 |
| gi\|67683110\|ref\|ZP__00477256.1\| | COG3321: Polyket | −2.3 | 3.7 | 1 |
| gi\|52212615\|emb\|CAH38641.1\| | putative non-rib | −2.3 | 3.7 | 1 |
| gi\|53722201\|ref\|YP__111186.1\| | putative non-rib | −2.3 | 3.7 | 1 |
| gi\|28199386\|ref\|NP__779700.1\| | hemolysin-type c | −2.4 | 3.8 | 1 |
| gi\|28057492\|gb\|AAO29349.1\| | hemolysin-type c | −2.4 | 3.8 | 1 |
| gi\|67157564\|ref\|ZP__00418813.1\| | CobN/magnesium c | −2.7 | 4.1 | 1 |
| gi\|67085472\|gb\|EAM04946.1\| | CobN/magnesium c | −2.7 | 4.1 | 1 |
| gi\|49532277\|emb\|CAG69989.1\| | competence facto | −2.7 | 4.2 | 1 |
| gi\|50086301\|ref\|YP__047811.1\| | competence facto | −2.7 | 4.2 | 1 |
| gi\|20803923\|emb\|CAD31501.1\| | HYPOTHETICAL PRO | −2.8 | 4.3 | 1 |
| gi\|52857125\|ref\|ZP__00341419.1\| | COG3419: Tfp pil | −3.2 | 4.8 | 1 |
| gi\|67546318\|ref\|ZP__00424233.1\| | Amino acid adeny | −3.5 | 5.1 | 1 |
| gi\|67532466\|gb\|EAM29252.1\| | Amino acid adeny | −3.5 | 5.1 | 1 |
| gi\|56750225\|ref\|YP__170926.1\| | hypothetical pro | −4.0 | 6 | 1 |
| gi\|56685184\|dbj\|BAD78406.1\| | hypothetical pro | −4.0 | 6 | 1 |
| gi\|46129819\|ref\|ZP__00164431.2\| | COG2931: RTX tox | −4.0 | 6 | 1 |
| gi\|67935982\|ref\|ZP__00528997.1\| | conserved hypoth | −4.7 | 7.2 | 1 |
| gi\|67775076\|gb\|EAM34747.1\| | conserved hypoth | −4.7 | 7.2 | 1 |
| gi\|18466717\|ref\|NP__569524.1\| | putative phage t | −4.9 | 7.5 | 1 |
| gi\|16506033\|emb\|CAD09919.1\| | putative phage t | −4.9 | 7.5 | 1 |
| gi\|28199311\|ref\|NP__779625.1\| | bacteriocin [Xyl | −5.4 | 8.7 | 1 |
| gi\|28057417\|gb\|AAO29274.1\| | bacteriocin [Xyl | −5.4 | 8.7 | 1 |
| gi\|5834691\|emb\|CAB55188.1\| | putative phage t | −5.7 | 9.5 | 1 |

-continued

| Scores for complete sequences (score includes all domains): | | | | |
|---|---|---|---|---|
| Sequence | Description | Score | E-value | N |
| gi\|7467447\|pir\|\|T14966 | phage lambda-rel | −5.7 | 9.5 | 1 |
| gi\|31795379\|ref\|NP_857832.1\| | host specificity | −5.7 | 9.5 | 1 |
| gi\|45478595\|ref\|NP_995451.1\| | phage lambda-rel | −5.7 | 9.5 | 1 |
| gi\|45357248\|gb\|AAS58642.1\| | phage lambda-rel | −5.7 | 9.5 | 1 |
| gi\|16082788\|ref\|NP_395342.1\| | host specificity | −5.7 | 9.5 | 1 |
| gi\|3883049\|gb\|AAC82709.1\| | lambda host spec | −5.7 | 9.5 | 1 |

It is noted that there is a very clean break of E-values between gi|48730377| and gi|39576632| (double-underlined for clarity). The proteins with E-values below that of gi|48730377| (7.5e-39) were extracted. This dataset was then searched using the spvB_ls.hmm model and hmmsearch. The results are presented below:

hmmsearch—search a sequence database with a profile HMM

HMMER 2.3.1 (June 2003)

Copyright (C) 1992-2003 HHMI/Washington University School of Medicine

Freely distributed under the GNU General Public License (GPL)

HMM file: FinalTest/spvB_ls.hmm [SpvB]

Sequence database: FinalTest/ProBBModel3Hits.fasta per-sequence score cutoff: [none]

per-domain score cutoff: [none]

per-sequence Eval cutoff: <=10 per-domain Eval cutoff: [none]

Query HMM: SpvB

Accession: PF03534.3

Description: *Salmonella* virulence plasmid 65 kDa B protein

[HMM has been calibrated; E-values are empirical estimates]

| Scores for complete sequences (score includes all domains): | | | | |
|---|---|---|---|---|
| Sequence | Description | Score | E-value | N |
| gi\|16416891\|gb\|AAL18451.1\| | toxin complex pr | 871.6 | 1.4e−261 | 1 |
| gi\|3265037\|gb\|AAC38625.1\| | insecticidal tox | 871.6 | 1.4e−261 | 1 |
| gi\|36783948\|emb\|CAE12810.1\| | Insecticidal tox | 843.0 | 5.6e−253 | 1 |
| gi\|37524524\|ref\|NP_927868.1\| | Insecticidal tox | 843.0 | 5.6e−253 | 1 |
| gi\|9963679\|gb\|AAG09643.1\| | SepB [*Serratia* e | 821.5 | 1.7e−246 | 1 |
| gi\|10956817\|ref\|NP_065277.1\| | SepB [*Serratia* e | 821.5 | 1.7e−246 | 1 |
| gi\|13444938\|emb\|CAC34920.1\| | unnamed protein | 821.5 | 1.7e−246 | 1 |
| gi\|32699986\|gb\|AAP57764.1\| | TcYF2 [*Yersinia* | 730.4 | 4.3e−219 | 1 |
| gi\|36784377\|emb\|CAE13256.1\| | Insecticidal tox | 586.6 | 8.5e−176 | 1 |
| gi\|37524951\|ref\|NP_928295.1\| | Insecticidal tox | 586.6 | 8.5e−176 | 1 |
| gi\|16416930\|gb\|AAL18487.1\| | TcdB1; toxin com | 578.4 | 2.5e−173 | 1 |
| gi\|36784385\|emb\|CAE13264.1\| | Insecticidal tox | 574.5 | 3.9e−172 | 1 |
| gi\|37524959\|ref\|NP_928303.1\| | Insecticidal tox | 574.5 | 3.9e−172 | 1 |
| gi\|51510118\|emb\|CAH19031.1\| | unnamed protein | 572.1 | 2e−171 | 1 |
| gi\|49021690\|emb\|CAG38449.1\| | unnamed protein | 572.1 | 2e−171 | 1 |
| gi\|27479675\|gb\|AAO17202.1\| | TcdB2 [Photorhab | 572.1 | 2e−171 | 1 |
| gi\|50956508\|gb\|AAT90757.1\| | putative insecti | 472.8 | 1.6e−141 | 1 |
| gi\|15981600\|emb\|CAC93148.1\| | insecticidal tox | 465.9 | 1.8e−139 | 1 |
| gi\|45443595\|ref\|NP_995134.1\| | insecticidal tox | 465.9 | 1.8e−139 | 1 |
| gi\|25511233\|pir\|\|AH0447 | insecticidal tox | 465.9 | 1.8e−139 | 1 |
| gi\|16123821\|ref\|NP_407134.1\| | insecticidal tox | 465.9 | 1.8e−139 | 1 |
| gi\|22124105\|ref\|NP_667528.1\| | putative toxin s | 465.9 | 1.8e−139 | 1 |
| gi\|45438465\|gb\|AAS64011.1\| | insecticidal tox | 465.9 | 1.8e−139 | 1 |
| gi\|21956856\|gb\|AAM83779.1\|AE013618_4 | putative toxin s | 465.9 | 1.8e−139 | 1 |
| gi\|51591126\|emb\|CAH22791.1\| | insecticidal tox | 460.1 | 1e−137 | 1 |
| gi\|51597844\|ref\|YP_072035.1\| | insecticidal tox | 460.1 | 1e−137 | 1 |
| gi\|45477499\|gb\|AAS66065.1\| | YO185-like prote | 460.1 | 1e−137 | 1 |
| gi\|14041732\|emb\|CAC38403.1\| | XptC1 protein [X | 451.3 | 4.6e−135 | 1 |
| gi\|66047263\|ref\|YP_237104.1\| | *Salmonella* virul | 288.4 | 5.2e−86 | 1 |
| gi\|63257970\|gb\|AAY39066.1\| | *Salmonella* virul | 288.4 | 5.2e−86 | 1 |
| gi\|28854730\|gb\|AAO57793.1\| | insecticidal tox | 277.8 | 7.6e−83 | 1 |
| gi\|28871479\|ref\|NP_794098.1\| | insecticidal tox | 277.8 | 7.6e−83 | 1 |
| gi\|48730377\|ref\|ZP_00264125.1\| | hypothetical pro | 191.9 | 5.6e−57 | 1 |

The above set was dereplicated to remove duplicates, leaving a set of proteins that known are Class B TC proteins, as previously identified by standard BLAST searches. [The duplications are of two kinds—duplicate entries of the same gene, and identical proteins from closely related strains of the same organism.] The dereplicated list is presented below:

| Sequence | Description | Score | E-value | N |
|---|---|---|---|---|
| gi\|16416891\|gb\|AAL18451.1\| | toxin complex pr | 871.6 | 1.4e−261 | 1 |
| gi\|36783948\|emb\|CAE12810.1\| | Insecticidal tox | 843.0 | 5.6e−253 | 1 |
| gi\|37524524\|ref\|NP_927868.1\| | Insecticidal tox | 843.0 | 5.6e−253 | 1 |
| gi\|10956817\|ref\|NP_065277.1\| | SepB [*Serratia* e | 821.5 | 1.7e−246 | 1 |
| gi\|13444938\|emb\|CAC34920.1\| | unnamed protein | 821.5 | 1.7e−246 | 1 |
| gi\|32699986\|gb\|AAP57764.1\| | TcYF2 [*Yersinia* | 730.4 | 4.3e−219 | 1 |
| gi\|37524951\|ref\|NP_928295.1\| | Insecticidal tox | 586.6 | 8.5e−176 | 1 |
| gi\|16416930\|gb\|AAL18487.1\| | TcdB1; toxin com | 578.4 | 2.5e−173 | 1 |
| gi\|37524959\|ref\|NP_928303.1\| | Insecticidal tox | 574.5 | 3.9e−172 | 1 |
| gi\|27479675\|gb\|AAO17202.1\| | TcdB2 [Photorhab | 572.1 | 2e−171 | 1 |
| gi\|50956508\|gb\|AAT90757.1\| | putative insecti | 472.8 | 1.6e−141 | 1 |
| gi\|15981600\|emb\|CAC93148.1\| | insecticidal tox | 465.9 | 1.8e−139 | 1 |
| gi\|22124105\|ref\|NP_667528.1\| | putative toxin s | 465.9 | 1.8e−139 | 1 |
| gi\|45443595\|ref\|NP_995134.1\| | insecticidal tox | 465.9 | 1.8e−139 | 1 |
| gi\|51597844\|ref\|YP_072035.1\| | insecticidal tox | 460.1 | 1e−137 | 1 |
| gi\|14041732\|emb\|CAC38403.1\| | XptC1 protein [X | 451.3 | 4.6e−135 | 1 |
| gi\|66047263\|ref\|YP_237104.1\| | *Salmonella* virul | 288.4 | 5.2e−86 | 1 |
| gi\|28871479\|ref\|NP_794098.1\| | insecticidal tox | 277.8 | 7.6e−83 | 1 |
| gi\|48730377\|ref\|ZP_00264125.1\| | hypothetical pro | 191.9 | 5.6e−57 | 1 |
| gi\|45443595\|ref\|NP_995134.1\| | insecticidal tox | 465.9 | 1.8e−139 | 1 |

Thus, this example demonstrates the surprising result that, in contrast to standard BLAST searches used to identify proteins related by overall amino acid sequence homology, it is possible to additionally identify related proteins by using combinations of protein domain search strategies. These protein domain strategies can be acquired from a relatively few examples of proteins containing domains that may not be revealed by standard domain search algorithms. For this example, it is immaterial to the search end result whether the spvB_ls.hmm search is done first or second.

Class C TC Proteins. Class C TC proteins as annotated in GenBank are members of the RHS domain superfamily, which are characterized by containing multiple copies of the RHS domain. [Note: The domain terminology used herein is taken from the Pfam site and the domains can be searched for by name at that site.] See also C.W. Hill, C.H. Sandt, and D.A. Vlazny, "Rhs elements of *Escherichia coli*: a family of genetic composites each encoding a large mosaic protein," *Mol. Microbiol.* June 1994, 12(6):865-71; A.D. Minet, B.P. Rubin, R.P. Tucker, S. Baumgartner, and R. Chiquet-Ehrismann, "Teneurin-1, a vertebrate homologue of the *Drosophila* pair-rule gene ten-m, is a neuronal protein with a novel type of heparin-binding domain," *J. Cell Sci.* 1999, 112:2019-2032. All the Class C TC genes discovered to date come from prokaryotes; therefore, the initial search set was restricted to prokaryotic protein sequences. A protein search at the website ncbi.nlm.Nih.gov/ was performed using the search terms: "800:1100[SLEN] AND Prokaryota". These terms restricted the search to those proteins that are between 800 and 1100 amino acids in length and have prokaryotic sources. A total of 54323 protein sequences were identified and downloaded as a searchable database. It should be noted that, while these restrictions are useful in the present context, the interval length of the sequences and the kingdom searched can be modified to meet the parameters of the individual protein set to be examined.

A set of Class C TC proteins to be used as the source of RHS domains was acquired using the BLink resource for GenBank Accession 27479677 (TccC3 from *Photorhabdus luminescens*). This extraction yielded 38 related, nonredundant prokaryotic proteins with scores higher than 800. [The number of related proteins accessible through BLink of any given protein can vary with time, since GenBank can be a dynamic list.] The GenBank Accession numbers of the extracted proteins were: 27479677, 27479683, 27479669, 37524966, 37528020, 37528005, 16416915, 27479639, 37524950, 37528309, 42742522, 32699988, 10956818, 51596618, 51596557, 45441893, 45441958, 14041731, 45443601, 51597848, 25511229, 45443600, 50956512, 28871477, 28871480, 66044304, 66043853, 66047265, 66045648, 66047259, 66047264, 66047260, 28868442, 48730374, 48730375, 48730376, 48732572, and 48732573.

An intermediate HMM model was generated by extracting the RHS domains found in the above proteins using the general Pfam RHS model as above. The list of domains was divided into two parts, one to be used as a seed set and one to be used for testing the model. The ClustalX multiple sequence alignments of the RHS domains of the seed set is shown below. These alignments can be used with hmmbuild to generate the RHS HMM model used in this example.

| CLUSTALX (1.83) multiple sequence alignment | | |
| --- | --- | --- |
| gi\|27479639 \|RHS_domain_1 | -----------------ADATGALLTQT----DAKGNI------------ | SEQ ID NO: 54 |
| gi\|37524966\|RHS_domain_1 | -----------------FDATGALLTQT----DAKSNI------------ | SEQ ID NO: 55 |
| gi\|45441893\|RHS_domain_1 | -----------------ADATGAVLTTT----DAKGNL------------ | SEQ ID NO: 56 |
| gi\|51596557\|RHS_domain_1 | -----------------ADATGAVLTTT----DAKGNL------------ | SEQ ID NO: 57 |
| gi\|48730374\|RHS_domain_2 | -----------------YSPLGAVLTQT----DAGGHQ------------ | SEQ ID NO: 58 |
| gi\|48730376\|RHS_domain_2 | -----------------FSAVGALLQTT----DAGGHL------------ | SEQ ID NO: 59 |
| gi\|28871477\|RHS_domain_2 | -----------------FNAQGEDLAQT----DANGNV------------ | SEQ ID NO: 60 |
| gi\|66047265\|RHS_domain_1 | -----------------FNALGDALAQT----DAMGNT------------ | SEQ ID NO: 61 |
| gi\|28871480\|RHS_domain_1 | -----------------FNAQGEVLKQT----DASGNS------------ | SEQ ID NO: 62 |
| gi\|28868442\|RHS_domain_2 | -----------------YTVAGLLKSSRL---QMNGQAE----------- | SEQ ID NO: 63 |
| gi\|45443601\|RHS_domain_2 | -----------------YNRAGQLIGSWL---TIKNSAE----------- | SEQ ID NO: 64 |
| gi\|66044304\|RHS_domain_2 | -----------------YDAQQRVVSET----AGNGVI------------ | SEQ ID NO: 65 |
| gi\|66045648\|RHS_domain_3 | -----------------YDAQGHVTSET----AGNGVM------------ | SEQ ID NO: 66 |
| gi\|66047260\|RHS_domain_3 | -----------------YDAFNQVEQET----AGNGVV------------ | SEQ ID NO: 67 |
| gi\|66043853\|RRS_domain_2 | -----------------YDAHGRIESQT----AGNGVI------------ | SEQ ID NO: 68 |
| gi\|66045648\|RHS_domain_1 | -----------------YDAQLRPVAII-----ENGRCV----------- | SEQ ID NO: 69 |
| gi\|66047260\|RHS_domain_1 | -----------------YDAQLRPLAIN-----ESGRMT----------- | SEQ ID NO: 70 |
| gi\|66047259\|RHS_domain_1 | -----------------YDSSLRPVSVT-----EQGLVV----------- | SEQ ID NO: 71 |
| gi\|66047264\|RHS_domain_1 | -----------------YDLHLRPTRII-----EQNRCA----------- | SEQ ID NO: 72 |
| gi\|27479639\|RHS_domain_3 | -----------------WTPRGELKQVN----NGPGN------------- | SEQ ID NO: 73 |
| gi\|27479683\|RHS_domain_4 | -----------------WTPRGELKQAN----NSAGN------------- | SEQ ID NO: 74 |
| gi\|27479669\|RHS_domain_2 | -----------------WNTRGELKQVTPVSRESAS--D----------- | SEQ ID NO: 75 |
| gi\|27479677\|RHS_domain_4 | -----------------WNTRGELQQVTLVKRDKGANDD----------- | SEQ ID NO: 76 |
| gi\|45441893\|RHS_domain_4 | -----------------WTARNELLKVTPVVRDGSTD-D----------- | SEQ ID NO: 77 |
| gi\|28871480\|RHS_domain_3 | -----------------WDARNQLQHITTVQREDGSNDD----------- | SEQ ID NO: 78 |
| gi\|66047265\|RHS_domain_4 | -----------------WDVRNQLQHITTVQREDGSSDD----------- | SEQ ID NO: 79 |
| gi\|28868442\|RHS_domain_4 | FDASGNLLALQAGQHLSWDRRNQLQHVRPVIRENGMDDS----------- | SEQ ID NO: 80 |
| gi\|66043853\|RHS_domain_4 | -----------------WDSGNRLIKVDAVTRSEQPEDG----------- | SEQ ID NO: 81 |
| gi\|27479683\|RHS_domain_2 | -----------------YSAAGQ-----KLREEHGNGIV----------- | SEQ ID NO: 82 |
| gi\|51597848\|ref\|RHS_domain_3 | -----------------YSAAGQ-----KLREESGNGVI----------- | SEQ ID NO: 83 |
| gi\|27479677\|RHS_domain_2 | -----------------YEPETQRLIGIKTRRPSDTKVL----------- | SEQ ID NO: 84 |
| gi\|37524950\|RHS_domain_2 | ------YDSL-------YQLISATGREMANIGQQNNQLP-SPALPS-DNN | SEQ ID NO: 85 |
| gi\|66047264\|RHS_domain_3 | ------YDTL-------YQLIEASGREVRNGASHGPALPGLQSLPTIDPC | SEQ ID NO: 86 |
| gi\|48730374\|RHS_domain_4 | ------YDTL-------YRLISATGYSDAPPSDR-LGLP-----QSTNPD | SEQ ID NO: 87 |
| gi\|28871477\|RHS_domain_4 | ------YDAAGNLLQMRHEGAHNFTRNMHVDPDSNRSLP--------DND | SEQ ID NO: 88 |
| gi\|66047259\|RHS_domain_3 | ------YDAAGNLLQMRHEGAHNFTRNMHVDPDSNRSLP--------DDE | SEQ ID NO: 89 |
| gi\|45443600\|ref\|NP_995139.1\| | -----------------YDPVGNILAIHN--DAEATRFYR---------- | SEQ ID NO: 90 |
| gi\|51597848\|RHS_domain_1 | -----------------YNAFGQLIASR----DPRLEVDN---------- | SEQ ID NO: 91 |
| gi\|27479639\|RHS_domain_1 | ------QRLAYDVA---GQLKGCWLTLKGQA | SEQ ID NO: 92 |

-continued

| CLUSTALX (1.83) multiple sequence alignment | | |
|---|---|---|
| gi\|37524966\|RHS_domain_1 | ------QRLAYNVA---GQLKGSWLTLKNQSEQV-- | SEQ ID NO: 93 |
| gi\|45441893\|RHS_domain_1 | ------QRMAYDVA---GLLSGSW-TLKDGTE---- | SEQ ID NO: 94 |
| gi\|51596557\|RHS_domain_1 | ------QRMAYDVA---GLLSGSWLTLKDGTE---- | SEQ ID NO: 95 |
| gi\|48730374\|RHS_domain_2 | ------QQSTYDVA---GQLNRVQLQINGQT----- | SEQ ID NO: 96 |
| gi\|48730376\|RHS_domain_2 | ------QQSTYDIA---GQLVQVQLQLDGQA----- | SEQ ID NO: 97 |
| gi\|28871477\|RHS_domain_2 | ------QRFSHGVA---GQLHAVELTLANTAQRQT- | SEQ ID NO: 98 |
| gi\|66047265\|RHS_domain_1 | ------QAFGMTVA---GQLKAAGLT---------- | SEQ ID NO: 99 |
| gi\|28871480\|RHS_domain_1 | ------QLSTHNLA---GQLHSTDL----------- | SEQ ID NO: 100 |
| gi\|28868442\|RHS_domain_2 | ------QVLVSAIQY-DAQERVVSETAGNGVM---- | SEQ ID NO: 101 |
| gi\|45443601\|RHS_domain_2 | ------QVILRSLTY-SAAGQKLREESGNG------ | SEQ ID NO: 102 |
| gi\|66044304\|RHS_domain_2 | ------STALYATE--DGRLLALSARRADGLM---- | SEQ ID NO: 103 |
| gi\|66045648\|RHS_domain_3 | ------TKALHDAA--NGRLIELKGTRADGQL---- | SEQ ID NO: 104 |
| gi\|66047260\|RHS_domain_3 | ------SRYVYDLQ--DGRLIELSALSADGSV---- | SEQ ID NO: 105 |
| gi\|66043853\|RHS_domain_2 | ------SCASFDLA--DGRMSELITYRP-GVK---- | SEQ ID NO: 106 |
| gi\|66045648\|RHS_domain_1 | ------ERRQYGGAD-TQGHNQCNQCIRHDDPAGSR | SEQ ID NO: 107 |
| gi\|66047260\|RHS_domain_1 | ------ERFTYGGPA-TAERNQCNQLIRHDDTAGSR | SEQ ID NO: 108 |
| gi\|66047259\|RHS_domain_1 | ------ERLAYGGAD-AAEHNQCNQLIRHDDTAGSR | SEQ ID NO: 109 |
| gi\|66047264\|RHS_domain_1 | ------ERFTYGQAG-AAAHNQCNQLVRHDDTAGSR | SEQ ID NO: 110 |
| gi\|27479639\|RHS_domain_3 | ------EWYRYDSN---GMRQLKVSEQPTQ------ | SEQ ID NO: 111 |
| gi\|27479683\|RHS_domain_4 | ------EWYRYDSN---GIRQLKVNEQQTQ------ | SEQ ID NO: 112 |
| gi\|27479669\|RHS_domain_2 | -----REWYRYGND---GMRRLKVSEQQ-------- | SEQ ID NO: 113 |
| gi\|27479677\|RHS_domain_4 | -----REWYRYSGD---GRRMLKINEQQASNNAQT- | SEQ ID NO: 114 |
| gi\|45441893\|RHS_domain_4 | -----SESYRYDAA---SQRILKVSRQKTNT----- | SEQ ID NO: 115 |
| gi\|28871480\|RHS_domain_3 | -----E-RYVYDGQ---GQRCRLISTAQASGRT--- | SEQ ID NO: 116 |
| gi\|66047265\|RHS_domain_4 | -----E-RYVYDGQ---GQRCRKISTAQASGRM--- | SEQ ID NO: 117 |
| gi\|28868442\|RHS_domain_4 | -----E-RYSYDAS---GQRLRKVRTTQAKT----- | SEQ ID NO: 118 |
| gi\|66043853\|RHS_domain_4 | -----E-HYAYDAS---GQRLR--KTAKA------- | SEQ ID NO: 119 |
| gi\|27479683\|RHS_domain_2 | --TEY--SYEPETQ---RLIGITTRRPSDAK----- | SEQ ID NO: 120 |
| gi\|51597848\|ref\|RHS_domain_3 | --TEY--RYEPQTQ---RLIGIKTTRP--AK----- | SEQ ID NO: 121 |
| gi\|27479E77\|RHS_domain_2 | --QDL--RYEYDPV---GNV-ISIRNDAEAT----- | SEQ ID NO: 122 |
| gi\|37524950\|RHS_domain_2 | TYTNYTRRYSYDHS---GNL-TQIRHSSSAT----- | SEQ ID NO: 123 |
| gi\|66047264\|RHS_domain_3 | QVSNYTQSYSYDAA---GNL-LQMRHEGA------- | SEQ ID NO: 124 |
| gi\|48730374\|RHS_domain_4 | DRRNYVEHYDYDHG---DNL-VKTIHVRDGTS---- | SEQ ID NO: 125 |
| gi\|28871477\|RHS_domain_4 | RYVDF--ATSFDAN---GNL-LQLVRGQT------- | SEQ ID NO: 126 |
| gi\|66047259\|RHS_domain_3 | GEVDF--ATSFDAN---GNL-LQLVRGQT------- | SEQ ID NO: 127 |
| gi\|45443600\|ref\|NP_995139.1\| | -----NQKIVPETTYRYDALYQLIEATGREADT--- | SEQ ID NO: 128 |
| gi\|51597848\|RHS_domain_1 | ------FRYQYSLS---GVPLRTDSVDSGSTL---- | SEQ ID NO: 129 |

This multiple sequence alignment was used with hmmbuild and hmmcalibrate to generate CModel1.hmm. The CModel1.hmm model was then tested against the 38 protein sample set above and was able to identify all expected RHS domains. Conversely, when the CModel1.hmm model was tested against 20 randomly selected proteins, no RHS domains were found. The CModel1.hmm model was then tested with hmmsearch against the 54323 member database containing all prokaryotic proteins between 800 and 1100 amino acids, yielding the results below.

hmmsearch—search a sequence database with a profile HMM

HMMER 2.3.1 (June 2003)

Copyright (C) 1992-2003 HHMI/Washington University School of Medicine

Freely distributed under the GNU General Public License (GPL)

HMM file: FinalTest/CModel1.hmm [CDomainsUniqueCreate2]

Sequence database: FinalTest/Prokaryotic800-1100.fasta per-sequence score cutoff: [none]

per-domain score cutoff: [none]

per-sequence Eval cutoff: <=10 per-domain Eval cutoff: [none]

Query HMM: CDomainsUniqueCreate2

Accession: [none]

Description: [none]

[HMM has been calibrated; E-values are empirical estimates]

Scores for complete sequences (score includes all domains):

| Sequence | Description | Score | E-value | N |
|---|---|---|---|---|
| gi\|66047260\|ref\|YP_237101.1\| | YD repeat [Pseu | 202.3 | 7e−57 | 6 |
| gi\|63257967\|gb\|AAY39063.1\| | YD repeat [Pseu | 202.3 | 7e−57 | 6 |
| gi\|28854728\|gb\|AAO57791.1\| | insecticidal to | 200.6 | 2.3e−56 | 6 |
| gi\|28871477\|ref\|NP_794096.1\| | insecticidal to | 200.6 | 2.3e−56 | 6 |
| gi\|66047265\|ref\|YP_237106.1\| | YD repeat [Pseu | 178.4 | 1.1e−49 | 7 |
| gi\|63257972\|gb\|AAY39068.1\| | YD repeat [Pseu | 178.4 | 1.1e−49 | 7 |
| gi\|28854731\|gb\|AAO57794.1\| | insecticidal to | 171.2 | 1.6e−47 | 7 |
| gi\|28871480\|ref\|NP_794099.1\| | insecticidal to | 171.2 | 1.6e−47 | 7 |
| gi\|66047264\|ref\|YP_237105.1\| | YD repeat [Pseu | 155.3 | 1e−42 | 7 |
| gi\|63257971\|gb\|AAY39067.1\| | YD repeat [Pseu | 155.3 | 1e−42 | 7 |
| gi\|66047259\|ref\|YP_237100.1\| | YD repeat [Pseu | 146.6 | 4e−40 | 6 |
| gi\|63257966\|gb\|AAY39062.1\| | YD repeat [Pseu | 146.6 | 4e−40 | 6 |
| gi\|51510120\|emb\|CAH19032.1\| | unnamed protein | 143.2 | 4.3e−39 | 4 |
| gi\|49021696\|emb\|CAG38450.1\| | unnamed protein | 143.2 | 4.3e−39 | 4 |
| gi\|27479677\|gb\|AAO17204.1\| | TccC3 [Photorha | 143.2 | 4.3e−39 | 4 |
| gi\|28851680\|gb\|AAO54756.1\| | insecticidal to | 135.0 | 1.3e−36 | 5 |
| gi\|28868442\|ref\|NP_791061.1\| | insecticidal to | 135.0 | 1.3e−36 | 5 |
| gi\|66045648\|ref\|YP_235489.1\| | YD repeat [Pseu | 134.9 | 1.4e−36 | 4 |
| gi\|63256355\|gb\|AAY37451.1\| | YD repeat [Pseu | 134.9 | 1.4e−36 | 4 |
| gi\|15981595\|emb\|CAC93143.1\| | putative insect | 134.1 | 2.3e−36 | 6 |
| gi\|45443601\|ref\|NP_995140.1\| | putative insect | 134.1 | 2.3e−36 | 6 |
| gi\|25511227\|pir\|\|AC0447 | probable insect | 134.1 | 2.3e−36 | 6 |
| gi\|16123816\|ref\|NP_407129.1\| | putative insect | 134.1 | 2.3e−36 | 6 |
| gi\|22124111\|ref\|NP_667534.1\| | putative toxin | 134.1 | 2.3e−36 | 6 |
| gi\|45438471\|gb\|AAS64017.1\| | putative insect | 134.1 | 2.3e−36 | 6 |
| gi\|21956863\|gb\|AAM83785.1\|AE013619_6 | putative toxin | 134.1 | 2.3e−36 | 6 |
| gi\|15981596\|emb\|CAC93144.1\| | putative insect | 128.3 | 1.3e−34 | 6 |
| gi\|45443600\|ref\|NP_995139.1\| | putative toxin | 128.3 | 1.3e−34 | 6 |
| gi\|25511229\|pir\|\|AD0447 | probable insect | 128.3 | 1.3e−34 | 6 |
| gi\|16123817\|ref\|NP_407130.1\| | putative insect | 128.3 | 1.3e−34 | 6 |
| gi\|22124110\|ref\|NP_667533.1\| | putative toxin | 128.3 | 1.3e−34 | 6 |
| gi\|45438470\|gb\|AAS64016.1\| | putative toxin | 128.3 | 1.3e−34 | 6 |
| gi\|21956862\|gb\|AAM83784.1\|AE013619_5 | putative toxin | 128.3 | 1.3e−34 | 6 |
| gi\|51591130\|emb\|CAH22795.1\| | putative insect | 127.9 | 1.7e−34 | 6 |
| gi\|51597848\|ref\|YP_072039.1\| | putative insect | 127.9 | 1.7e−34 | 6 |
| gi\|27479639\|gb\|AAL18492.2\| | TccC2 [Photorha | 127.0 | 3.2e−34 | 4 |
| gi\|36784376\|emb\|CAE13255.1\| | Insecticidal to | 124.0 | 2.6e−33 | 4 |
| gi\|37524950\|ref\|NP_928294.1\| | Insecticidal to | 124.0 | 2.6e−33 | 4 |
| gi\|36784383\|emb\|CAE13262.1\| | Insecticidal to | 122.1 | 9.4e−33 | 5 |
| gi\|37524957\|ref\|NP_928301.1\| | Insecticidal to | 122.1 | 9.4e−33 | 5 |
| gi\|49021701\|emb\|CAG38451.1\| | unnamed protein | 120.5 | 2.9e−32 | 4 |
| gi\|27479669\|gb\|AAO17196.1\| | TccC4 [Photorha | 120.5 | 2.9e−32 | 4 |
| gi\|66044304\|ref\|YP_234145.1\| | YD repeat [Pseu | 119.1 | 7.8e−32 | 5 |
| gi\|63255011\|gb\|AAY36107.1\| | YD repeat [Pseu | 119.1 | 7.8e−32 | 5 |
| gi\|51589839\|emb\|CAH21471.1\| | putative insect | 118.6 | 1.1e−31 | 5 |
| gi\|15980309\|emb\|CAC91117.1\| | putative insect | 118.6 | 1.1e−31 | 5 |
| gi\|45441893\|ref\|NP_993432.1\| | putative insect | 118.6 | 1.1e−31 | 5 |
| gi\|25510685\|pir\|\|AI0281 | probable insect | 118.6 | 1.1e−31 | 5 |
| gi\|16122536\|ref\|NP_405849.1\| | putative insect | 118.6 | 1.1e−31 | 5 |
| gi\|51596557\|ref\|YP_070748.1\| | putative insect | 118.6 | 1.1e−31 | 5 |
| gi\|22125912\|ref\|NP_669335.1\| | putative compon | 118.6 | 1.1e−31 | 5 |
| gi\|45436756\|gb\|AAS62309.1\| | putative insect | 118.6 | 1.1e−31 | 5 |
| gi\|21958849\|gb\|AAM85586.1\|AE013804_10 | putative compon | 118.6 | 1.1e−31 | 5 |
| gi\|15980376\|emb\|CAC91185.1\| | insecticial tox | 114.6 | 1.8e−30 | 6 |
| gi\|45441958\|ref\|NP_993497.1\| | insecticial tox | 114.6 | 1.8e−30 | 6 |

-continued

| Scores for complete sequences (score includes all domains): | | | | |
|---|---|---|---|---|
| Sequence | Description | Score | E-value | N |
| gi\|25510725\|pir\|\|AE0290 | insecticial tox | 114.6 | 1.8e−30 | 6 |
| gi\|16122603\|ref\|NP__405916.1\| | insecticial tox | 114.6 | 1.8e−30 | 6 |
| gi\|45436821\|gb\|AAS62374.1\| | insecticial tox | 114.6 | 1.8e−30 | 6 |
| gi\|36784392\|emb\|CAE13271.1\| | Insecticidal to | 114.1 | 2.5e−30 | 4 |
| gi\|37524966\|ref\|NP__928310.1\| | Insecticidal to | 114.1 | 2.5e−30 | 4 |
| gi\|9963680\|gb\|AAG09644.1\| | SepC [*Serratia* | 113.9 | 2.8e−30 | 4 |
| gi\|10956818\|ref\|NP__065279.1\| | SepC [*Serratia* | 113.9 | 2.8e−30 | 4 |
| gi\|13444939\|emb\|CAC34921.1\| | unnamed protein | 113.9 | 2.8e−30 | 4 |
| gi\|51589900\|emb\|CAH21532.1\| | insecticial tox | 111.8 | 1.2e−29 | 6 |
| gi\|51596618\|ref\|YP__070809.1\| | insecticial tox | 111.8 | 1.2e−29 | 6 |
| gi\|36787747\|emb\|CAE16860.1\| | Insecticidal to | 110.7 | 2.6e−29 | 4 |
| gi\|37528309\|ref\|NP__931654.1\| | Insecticidal to | 110.7 | 2.6e−29 | 4 |
| gi\|49021704\|emb\|CAG38452.1\| | unnamed protein | 107.5 | 2.4e−28 | 4 |
| gi\|27479683\|gb\|AAO17210.1\| | TccC5 [Photorha | 107.5 | 2.4e−28 | 4 |
| gi\|16416915\|gb\|AAL18473.1\| | toxin complex p | 106.5 | 4.6e−28 | 5 |
| gi\|3265044\|gb\|AAC38630.1\| | insecticidal to | 106.5 | 4.6e−28 | 5 |
| gi\|36787442\|emb\|CAE16539.1\| | Insecticidal to | 105.5 | 9.8e−28 | 5 |
| gi\|37528005\|ref\|NP__931350.1\| | Insecticidal to | 105.5 | 9.8e−28 | 5 |
| gi\|48730374\|ref\|ZP__00264122.1\| | COG3209: Rhs fa | 99.0 | 8.7e−26 | 6 |
| gi\|36787457\|emb\|CAE16554.1\| | Insecticidal to | 98.9 | 9e−26 | 5 |
| gi\|37528020\|ref\|NP__931365.1\| | Insecticidal to | 98.9 | 9e−26 | 5 |
| gi\|36784380\|emb\|CAE13259.1\| | Insecticidal to | 96.0 | 6.9e−25 | 4 |
| gi\|37524954\|ref\|NP__928298.1\| | Insecticidal to | 96.0 | 6.9e−25 | 4 |
| gi\|66043853\|ref\|YP__233694.1\| | YD repeat [Pseu | 93.1 | 5e−24 | 5 |
| gi\|63254560\|gb\|AAY35656.1\| | YD repeat [Pseu | 93.1 | 5e−24 | 5 |
| gi\|32699988\|gb\|AAP57765.1\| | TcYF3 [*Yersinia* | 91.4 | 1.7e−23 | 5 |
| gi\|66045559\|ref\|YP__235400.1\| | YD repeat [Pseu | 86.1 | 6.8e−22 | 9 |
| gi\|63256266\|gb\|AAY37362.1\| | YD repeat [Pseu | 86.1 | 6.8e−22 | 9 |
| gi\|56414584\|ref\|YP__151659.1\| | Rhs-family prot | 83.2 | 4.9e−21 | 11 |
| gi\|56128841\|gb\|AAV78347.1\| | Rhs-family prot | 83.2 | 4.9e−21 | 11 |
| gi\|16759284\|ref\|NP__454901.1\| | Rhs-family prot | 82.2 | 9.6e−21 | 11 |
| gi\|16501575\|emb\|CAD08754.1\| | Rhs-family prot | 82.2 | 9.6e−21 | 11 |
| gi\|25511763\|pir\|\|AB0539 | Rhs-family prot | 82.2 | 9.6e−21 | 11 |
| gi\|29142943\|ref\|NP__806285.1\| | Rhs-family prot | 82.2 | 9.6e−21 | 11 |
| gi\|29138575\|gb\|AAO70145.1\| | Rhs-family prot | 82.2 | 9.6e−21 | 11 |
| gi\|58581261\|ref\|YP__200277.1\| | hypothetical pr | 76.0 | 7e−19 | 9 |
| gi\|58425855\|gb\|AAW74892.1\| | conserved hypot | 76.0 | 7e−19 | 9 |
| gi\|50955422\|ref\|YP__062710.1\| | RHS-related pro | 72.4 | 8.4e−18 | 9 |
| gi\|50951904\|gb\|AAT89605.1\| | RHS-related pro | 72.4 | 8.4e−18 | 9 |
| gi\|21223079\|ref\|NP__628858.1\| | putative Rhs pr | 72.0 | 1.2e−17 | 8 |
| gi\|7321289\|emb\|CAB82067.1\| | putative Rhs pr | 72.0 | 1.2e−17 | 8 |
| gi\|50956512\|gb\|AAT90761.1\| | putative insect | 69.9 | 4.8e−17 | 4 |
| gi\|32042609\|ref\|ZP__00140192.1\| | COG3209: Rhs fa | 65.7 | 9.1e−16 | 9 |
| gi\|25496542\|pir\|\|B86084 | hypothetical pr | 64.8 | 1.7e−15 | 6 |
| gi\|12518845\|gb\|AAG59134.1\|AE005624__10 | orf; Unknown fu | 64.8 | 1.7e−15 | 6 |
| gi\|15804530\|ref\|NP__290570.1\| | hypothetical pr | 64.8 | 1.7e−15 | 6 |
| gi\|46164196\|ref\|ZP__00136739.2\| | COG3209: Rhs fa | 64.5 | 2.1e−15 | 10 |
| gi\|14041731\|emb\|CAC38402.1\| | XptB1 protein [ | 63.4 | 4.5e−15 | 5 |
| gi\|42742522\|gb\|AAS45281.1\| | TccC1/XptB1 pro | 63.4 | 4.5e−15 | 5 |
| gi\|48730376\|ref\|ZP__00264124.1\| | COG3209: Rhs fa | 61.5 | 1.7e−14 | 6 |
| gi\|48730375\|ref\|ZP__00264123.1\| | COG3209: Rhs fa | 60.2 | 4.1e−14 | 6 |
| gi\|17547189\|ref\|NP__520591.1\| | PROBABLE RHS-RE | 58.5 | 1.3e−13 | 6 |
| gi\|17429491\|emb\|CAD16177.1\| | PROBABLE RHS-RE | 58.5 | 1.3e−13 | 6 |
| gi\|58581262\|ref\|YP__200278.1\| | hypothetical pr | 57.7 | 2.4e−13 | 6 |
| gi\|58425856\|gb\|AAW74893.1\| | conserved hypot | 57.7 | 2.4e−13 | 6 |
| gi\|48732572\|ref\|ZP__00266315.1\| | COG3209: Rhs fa | 56.4 | 5.8e−13 | 4 |
| gi\|48732573\|ref\|ZP__00266316.1\| | COG3209: Rhs fa | 51.5 | 1.8e−11 | 4 |
| gi\|17430552\|emb\|CAD17236.1\| | PUTATIVE RHS-RE | 50.3 | 4e−11 | 5 |
| gi\|17548306\|ref\|NP__521646.1\| | PUTATIVE RHS-RE | 50.3 | 4e−11 | 5 |
| gi\|67660484\|ref\|ZP__00457830.1\| | YD repeat [Burk | 49.0 | 9.9e−11 | 6 |
| gi\|67091947\|gb\|EAM09510.1\| | YD repeat [Burk | 49.0 | 9.9e−11 | 6 |
| gi\|67932920\|ref\|ZP__00526052.1\| | YD repeat [Soli | 47.9 | 2e−10 | 7 |
| gi\|67859831\|gb\|EAM54893.1\| | YD repeat [Soli | 47.9 | 2e−10 | 7 |
| gi\|15981529\|emb\|CAC93077.1\| | putative export | 45.7 | 9.5e−10 | 5 |
| gi\|45443670\|ref\|NP__995209.1\| | hypothetical pr | 45.7 | 9.5e−10 | 5 |
| gi\|25511182\|pir\|\|AI0438 | probable export | 45.7 | 9.5e−10 | 5 |
| gi\|16123750\|ref\|NP__407063.1\| | hypothetical pr | 45.7 | 9.5e−10 | 5 |
| gi\|22124186\|ref\|NP__667609.1\| | Rhs-like protei | 45.7 | 9.5e−10 | 5 |
| gi\|45438540\|gb\|AAS64086.1\| | putative export | 45.7 | 9.5e−10 | 5 |
| gi\|21956945\|gb\|AAM83860.1\|AE013626__7 | Rhs-like protei | 45.7 | 9.5e−10 | 5 |

-continued

| Scores for complete sequences (score includes all domains): | | | | |
|---|---|---|---|---|
| Sequence | Description | Score | E-value | N |
| gi\|66048214\|ref\|YP_238055.1\| | YD repeat [Pseu | 44.1 | 3e−09 | 5 |
| gi\|63258921\|gb\|AAY40017.1\| | YD repeat [Pseu | 44.1 | 3e−09 | 5 |
| gi\|50841691\|ref\|YP_054918.1\| | RHS-family prot | 43.8 | 3.5e−09 | 3 |
| gi\|50839293\|gb\|AAT81960.1\| | RHS-family prot | 43.8 | 3.5e−09 | 3 |
| gi\|66963410\|ref\|ZP_00410982.1\| | YD repeat [Arth | 41.8 | 1.4e−08 | 9 |
| gi\|66871070\|gb\|EAL98434.1\| | YD repeat [Arth | 41.8 | 1.4e−08 | 9 |
| gi\|17432059\|emb\|CAD18736.1\| | PUTATIVE RHS-RE | 36.0 | 7.7e−07 | 4 |
| gi\|17549804\|ref\|NP_523144.1\| | PUTATIVE RHS-RE | 36.0 | 7.7e−07 | 4 |
| gi\|67757182\|ref\|ZP_00496060.1\| | COG3209: Rhs fa | 31.1 | 2.4e−05 | 4 |
| gi\|17430924\|emb\|CAD17606.1\| | PROBABLE RHS-RE | 26.8 | 0.00045 | 4 |
| gi\|17548676\|ref\|NP_522016.1\| | PROBABLE RHS-RE | 26.8 | 0.00045 | 4 |
| gi\|50841692\|ref\|YP_054919.1\| | RHS-family prot | 26.6 | 0.00054 | 4 |
| gi\|50839294\|gb\|AAT81961.1\| | RHS-family prot | 26.6 | 0.00054 | 4 |
| gi\|67760154\|ref\|ZP_00498879.1\| | COG3209: Rhs fa | 24.9 | 0.0018 | 5 |
| gi\|67756692\|ref\|ZP_00495573.1\| | COG3209: Rhs fa | 24.9 | 0.0018 | 5 |
| gi\|67711658\|ref\|ZP_00481464.1\| | COG3209: Rhs fa | 24.9 | 0.0018 | 5 |
| gi\|67685220\|ref\|ZP_00479096.1\| | COG3209: Rhs fa | 24.9 | 0.0018 | 5 |
| gi\|67671863\|ref\|ZP_00468647.1\| | COG3209: Rhs fa | 24.9 | 0.0018 | 5 |
| gi\|29826985\|ref\|NP_821619.1\| | putative cell w | 23.9 | 0.0036 | 4 |
| gi\|29604082\|dbj\|BAC68154.1\| | putative cell w | 23.9 | 0.0036 | 4 |
| gi\|67738391\|ref\|ZP_00489054.1\| | COG3209: Rhs fa | 23.6 | 0.0042 | 5 |
| gi\|66963411\|ref\|ZP_00410983.1\| | YD repeat [Arth | 21.8 | 0.015 | 3 |
| gi\|66871071\|gb\|EAL98435.1\| | YD repeat [Arth | 21.8 | 0.015 | 3 |
| gi\|28850838\|gb\|AAO53917.1\| | Rhs family prot | 21.0 | 0.026 | 3 |
| gi\|28867603\|ref\|NP_790222.1\| | Rhs family prot | 21.0 | 0.026 | 3 |
| gi\|67941206\|ref\|ZP_00533425.1\| | YD repeat [Chlo | 19.5 | 0.071 | 2 |
| gi\|67912581\|gb\|EAM62210.1\| | YD repeat [Chlo | 19.5 | 0.071 | 2 |
| gi\|28852674\|gb\|AAO55747.1\| | YD repeat prote | 17.8 | 0.24 | 2 |
| gi\|28869433\|ref\|NP_792052.1\| | YD repeat prote | 17.8 | 0.24 | 2 |
| gi\|24112019\|ref\|NP_706529.1\| | putative Rhs-fa | 16.9 | 0.38 | 2 |
| gi\|24050837\|gb\|AAN42236.1\| | putative Rhs-fa | 16.9 | 0.38 | 2 |
| gi\|67158725\|ref\|ZP_00419586.1\| | PAS [Azotobacte | 12.9 | 1.6 | 1 |
| gi\|67084598\|gb\|EAM04080.1\| | PAS [Azotobacte | 12.9 | 1.6 | 1 |
| gi\|26988616\|ref\|NP_744041.1\| | hypothetical pr | 12.7 | 1.7 | 1 |
| gi\|24983394\|gb\|AAN67505.1\|AE016378_4 | hypothetical pr | 12.7 | 1.7 | 1 |
| gi\|46311839\|ref\|ZP_00212441.1\| | COG3501: Unchar | 10.0 | 4.3 | 1 |

While most of the hits in this list are Class C TC proteins, in contrast to the Class B TC proteins described above, there is not a clear-cut E-value defining a boundary between the Class C TC proteins and all other proteins scored. Nevertheless, the vast majority of hits better than e-10 are Class C TC proteins, and there are no known Class C TC proteins below that mark. In fact, the first 80 hits (up to gi|32699988|) are all Class C TC proteins, and at least 75% [88/116] of the proteins with scores better than e-10 are known Class C TC proteins or are annotated as such. None of the 38 selected Class C TC proteins had a score below 1.8e-11. Therefore, refinement of search criteria as represented in this HMM model demonstrates that it is an effective tool to search for Class C TC proteins in a database. The identification of approximately 88 hits out of 54323 proteins represents an increase in search efficiency and stringency by a factor of more than 600-fold. Some uncertainty exists in that some of the proteins scored in this model, but not annotated as Class C TC proteins may, in fact, be Class C TC proteins.

The inability of the CModel1.hmm to generate scores that allow complete separation between Class C TC proteins and all other proteins in the 800-1100 amino acid size class is probably due to the fact that the Class C TC protein family is a member of a larger superfamily of RHS proteins. Although most other members of the superfamily are larger than the Class C TC proteins, there may be a sufficient overlap in size to prevent complete discrimination. As will be seen below, the use of an RHS model in conjunction with other domain models is an effective method of distinguishing fused Class B/C TC proteins from other entries in a protein database.

Prokaryotic and Archaeal Fused Class B/C TC Proteins. Proteins corresponding to fused Class B/C Toxin Complex proteins are found in all three kingdoms, and all have the general domain format of an spvB domain followed by multiple FG-GAP domains followed by multiple RHS domains. However, some differences in the structure of these domains (or subdomains) does not allow for a simple set of HMM models to cover all three cases, so they are analyzed separately.

In contrast to single Class B TC proteins (see above) the spvB domains of fused Class B/C TC proteins from prokaryotes are not highly conserved, so the Pfam spvB model was inappropriate for model generation. Although there are three domain classes represented in the prokaryotic and archaeal fused Class B/C TC proteins, it is presently demonstrated that the use of HMM models for only two of them is sufficient to select the fused B/C TC proteins from a data set.

A protein search at the website ncbi.nlm.nih.gov was performed using the search terms: "1700:2800[SLEN] AND Prokaryota". These terms restricted the search to those proteins that are between 1700 and 2800 amino acids in length and have prokaryotic and archaeal sources. [It is an inherent GenBank feature that a search limited to Prokaryota will also extract Archaeal genes]. A total of 3303 protein sequences were identified and downloaded as a searchable database. It should be noted that, while these restrictions are useful in the present context, the interval length of the sequences and the kingdom searched can be modified to meet the parameters of the individual protein set to be examined.

Neither the Pfam FG-GAP model nor the nonfused (single) Class B TC protein HMM model (above) proved satisfactory for finding FG-GAP domains in fused Class B/C TC proteins from prokaryotes and archaea. A satisfactory new model was therefore created from GenBank Accession numbers 48862345 and 13475700 by taking the FG-GAP domains found by Pfam and setting the cutoff score to 1. The ClustalX multiple sequence alignments of the FG-GAP domains is shown below. These alignments can be used with hmmbuild to generate the FG-GAP HMM model (BModel7.hmm) used in this example.

Domain1 from the fused Class B/C TC protein of GenBank Accession number 13475700 was considerably longer and was trimmed to improve the model. The BModel.hmm model was then tested with hmmsearch against the 3303 member database containing all prokaryotic (and archaeal) proteins between 1700 and 2800 amino acids in length, yielding the results below. [The original output list was truncated to remove a large number of proteins with very high scores.]

hmmsearch—search a sequence database with a profile HMM

HMMER 2.3.1 (June 2003)

Copyright (C) 1992-2003 HHMI/Washington University School of Medicine

Freely distributed under the GNU General Public License (GPL)

HMM file: FinalTest/BModel7.hmm [BDomainsModel7Sequences]

Sequence database: FinalTest/Prokaryotic1700-2800.fasta per-sequence score cutoff: [none]

per-domain score cutoff: [none]

per-sequence Eval cutoff: <=10 per-domain Eval cutoff: [none]

Query HMM: BDomainsModel7Sequences

Accession: [none]

Description: [none]

[HMM has been calibrated; E-values are empirical estimates]

| CLUSTAL X (1.83) multiple sequence alignment | | |
|---|---|---|
| gi\|48862345\|BDomain7 | PESGISVGDINADGLTDVLYHNNGQV----EVYLS-- | SEQ ID NO: 130 |
| gi\|13475700\|BDomain5 | ISSGTTIGDFNGDGLPDF------------------ | SEQ ID NO: 131 |
| gi\|48862345\|BDomain3 | PTTQFQPIDINGDGELDVAWL--------------- | SEQ ID NO: 132 |
| gi\|48862345\|BDomain4 | --------DYNADGHADVAIY--------------- | SEQ ID NO: 133 |
| gi\|48862345\|BDomain1 | --ADYFSGDMNGDREEDYFIRGYQAG----EPAL--- | SEQ ID NO: 134 |
| gi\|48862345\|BDamain2 | RRNTIALQDYNLDGRMDLVLLSGVGGY---VVDVI-- | SEQ ID NO: 135 |
| gi\|13475700\|BDomain4 | SGTTGVLRDFDNDGKADVVTITG-GG-----IGS--- | SEQ ID NO: 136 |
| gi\|48862345\|BDomains | ----------DVNGDGLTDALTESR------VY---- | SEQ ID NO: 137 |
| gi\|48862345\|BDomain9 | EDKVIRLLDVNGDGLLDLVSESKSDSTTKFNVYHW-- | SEQ ID NO: 138 |
| gi\|48862345\|BDomain8 | GGANYVFSDVNGDSHTDLITFYDER----LSIH---- | SEQ ID NO: 139 |
| gi\|13475700\|BDomain3 | GSGTCVLADVNGDGATDIVRYDGLN----LSAGVWLS | SEQ ID NO: 140 |
| gi\|48862345\|BDomain6 | -----GFGDFNGDGRLDLLVGD-------------- | SEQ ID NO: 141 |
| gi\|13475700\|BDomain1 | TEAPREVGDLDFDGRDEIFGDYSEATDQRSGGREGET | SEQ ID NO: 142 |
| gi\|13475700\|BDomain2 | --GASGIG----VG--DFLGN----------GR---- | SEQ ID NO: 143 |

| Scores for complete sequences (score includes all domains): | | | | |
|---|---|---|---|---|
| Sequence | Description | Score | E-value | N |
| gi\|48862345\|ref\|ZP_00316242.1\| | COG3209: Rhs f | 236.4 | 2.2e−68 | 10 |
| gi\|13475700\|ref\|NP_107267.1\| | hypothetical p | 124.1 | 1.5e−34 | 5 |
| gi\|14026456\|dbj\|BAB53053.1\| | mll6838 [Mesor | 124.1 | 1.5e−34 | 5 |
| gi\|27367604\|ref\|NP_763131.1\| | Rhs family pro | 101.4 | 1e−27 | 7 |
| gi\|27359176\|gb\|AAO08121.1\|AE016812_103 | Rhs family pro | 101.4 | 1e−27 | 7 |
| gi\|48863870\|ref\|ZP_00317763.1\| | COG3209: Rhs f | 95.0 | 8.6e−26 | 8 |
| gi\|48833214\|ref\|ZP_00290236.1\| | COG2931: RTX t | 87.0 | 2.1e−23 | 11 |
| gi\|45657896\|ref\|YP_001982.1\| | cytoplasmic me | 79.7 | 3.4e−21 | 7 |
| gi\|45601137\|gb\|AAS70619.1\| | cytoplasmic me | 79.7 | 3.4e−21 | 7 |
| gi\|24214465\|ref\|NP_711946.1\| | Rhs family pro | 78.2 | 9.3e−21 | 7 |
| gi\|24195416\|gb\|AAN48964.1\|AE011353_4 | Rhs family pro | 78.2 | 9.3e−21 | 7 |
| gi\|45656716\|ref\|YP_000802.1\| | cytoplasmic me | 74.8 | 1e−19 | 6 |
| gi\|45599952\|gb\|AAS69439.1\| | cytoplasmic me | 74.8 | 1e−19 | 6 |
| gi\|67919346\|ref\|ZP_00512927.1\| | Integrins alph | 69.1 | 5.1e−18 | 6 |
| gi\|67783058\|gb\|EAM42456.1\| | Integrins alph | 69.1 | 5.1e−18 | 6 |
| gi\|39576631\|emb\|CAE80795.1\| | hypothetical p | 67.9 | 1.2e−17 | 8 |
| gi\|42524422\|ref\|NP_969802.1\| | hypothetical p | 67.9 | 1.2e−17 | 8 |
| gi\|20090892\|ref\|NP_616967.1\| | hypothetical p | 63.0 | 3.6e−16 | 6 |
| gi\|19915968\|gb\|AAM05447.1\| | hypothetical p | 63.0 | 3.6e−16 | 6 |
| gi\|24216032\|ref\|NP_713513.1\| | hypothetical p | 59.6 | 3.9e−15 | 7 |
| gi\|24197262\|gb\|AAN50531.1\|AE011493_4 | conserved hypo | 59.6 | 3.9e−15 | 7 |
| gi\|33632688\|emb\|CAE07500.1\| | conserved hypo | 58.7 | 7.2e−15 | 10 |
| gi\|33865519\|ref\|NP_897078.1\| | hypothetical p | 58.7 | 7.2e−15 | 10 |
| gi\|48893475\|ref\|ZP_00326711.1\| | COG3391: Uncha | 38.5 | 8.7e−09 | 7 |
| gi\|67932250\|ref\|ZP_00525397.1\| | Integrins alph | 38.3 | 1e−08 | 2 |
| gi\|67860476\|gb\|EAM55523.1\| | Integrins alph | 38.3 | 1e−08 | 2 |
| gi\|67762147\|ref\|ZP_00500850.1\| | COG3209: Rhs f | 32.2 | 6.5e−07 | 4 |
| gi\|67739010\|ref\|ZP_00489616.1\| | COG3209: Rhs f | 32.2 | 6.5e−07 | 4 |
| gi\|67670205\|ref\|ZP_00467015.1\| | COG3209: Rhs f | 32.2 | 6.5e−07 | 4 |
| gi\|67653219\|ref\|ZP_00450636.1\| | COG3209: Rhs f | 32.2 | 6.5e−07 | 4 |
| gi\|67648765\|ref\|ZP_00446993.1\| | COG3209: Rhs f | 32.2 | 6.5e−07 | 4 |
| gi\|67642373\|ref\|ZP_00441130.1\| | COG3209: Rhs f | 32.2 | 6.5e−07 | 4 |
| gi\|67636722\|ref\|ZP_00435666.1\| | COG3209: Rhs f | 32.2 | 6.5e−07 | 4 |
| gi\|67629702\|ref\|ZP_00429560.1\| | COG3209: Rhs f | 32.2 | 6.5e−07 | 4 |
| gi\|53718233\|ref\|YP_107219.1\| | putative membr | 32.2 | 6.5e−07 | 4 |
| gi\|52208647\|emb\|CAH34583.1\| | putative membr | 32.2 | 6.5e−07 | 4 |
| gi\|53724907\|ref\|YP_101869.1\| | FG-GAP/YD repe | 32.2 | 6.5e−07 | 4 |
| gi\|52428330\|gb\|AAU48923.1\| | FG-GAP/YD repe | 32.2 | 6.5e−07 | 4 |
| gi\|67713631\|ref\|ZP_00482992.1\| | COG3209: Rhs f | 31.0 | 1.6e−06 | 4 |
| gi\|67683974\|ref\|ZP_00478003.1\| | COG3209: Rhs f | 31.0 | 1.6e−06 | 4 |
| gi\|20089734\|ref\|NP_615809.1\| | cell surface p | 27.6 | 1.7e−05 | 6 |
| gi\|19914667\|gb\|AAM04289.1\| | cell surface p | 27.6 | 1.7e−05 | 6 |
| gi\|20092500\|ref\|NP_618575.1\| | cell surface p | 21.7 | 0.00067 | 5 |
| gi\|19917767\|gb\|AAM07055.1\| | cell surface p | 21.7 | 0.00067 | 5 |
| gi\|48838750\|ref\|ZP_00295689.1\| | COG3291: FOG: | 16.4 | 0.0067 | 4 |
| gi\|32446373\|emb\|CAD76201.1\| | probable fibri | 14.6 | 0.014 | 2 |
| gi\|32475830\|ref\|NP_868824.1\| | probable fibri | 14.6 | 0.014 | 2 |
| gi\|20092499\|ref\|NP_618574.1\| | cell surface p | 10.0 | 0.1 | 2 |
| gi\|19917765\|gb\|AAM07054.1\| | cell surface p | 10.0 | 0.1 | 2 |
| gi\|15597071\|ref\|NP_250565.1\| | hypothetical p | 7.9 | 0.26 | 1 |
| gi\|11349338\|pir\|\|A83412 | hypothetical p | 7.9 | 0.26 | 1 |
| gi\|32041947\|ref\|ZP_00139530.1\| | COG5295: Autot | 7.9 | 0.26 | 1 |
| gi\|9947864\|gb\|AAG05263.1\|AE004613_8 | hypothetical p | 7.9 | 0.26 | 1 |
| gi\|67936217\|ref\|ZP_00529228.1\| | Hemolysin-type | 7.6 | 0.29 | 3 |
| gi\|67774841\|gb\|EAM34516.1\| | Hemolysin-type | 7.6 | 0.29 | 3 |
| gi\|33440441\|gb\|AAQ19127.1\| | putative adhes | 7.2 | 0.35 | 1 |
| gi\|31616734\|emb\|CAD60101.1\| | peptide synthe | 7.0 | 0.38 | 1 |
| gi\|31505496\|gb\|AAO62586.1\| | peptide sythet | 7.0 | 0.38 | 1 |
| gi\|67756274\|ref\|ZP_00495160.1\| | COG3209: Rhs f | 6.6 | 0.45 | 3 |
| gi\|67754231\|ref\|ZP_00493144.1\| | COG3209: Rhs f | 6.6 | 0.45 | 3 |
| gi\|67754221\|ref\|ZP_00493134.1\| | COG3209: Rhs f | 6.6 | 0.45 | 3 |
| gi\|67752361\|ref\|ZP_00491350.1\| | COG3209: Rhs f | 6.6 | 0.45 | 3 |
| gi\|67752064\|ref\|ZP_00491084.1\| | COG3209: Rhs f | 6.6 | 0.45 | 3 |
| gi\|67710451\|ref\|ZP_00480257.1\| | COG3209: Rhs f | 6.6 | 0.45 | 3 |
| gi\|67710442\|ref\|ZP_00480248.1\| | COG3209: Rhs f | 6.6 | 0.45 | 3 |
| gi\|67682395\|ref\|ZP_00476633.1\| | COG3209: Rhs f | 6.6 | 0.45 | 3 |
| gi\|17431402\|emb\|CAD18081.1\| | SKWP PROTEIN 3 | 6.4 | 0.5 | 1 |
| gi\|17549151\|ref\|NP_522491.1\| | SKWP PROTEIN 3 | 6.4 | 0.5 | 1 |
| gi\|48731764\|ref\|ZP_00265508.1\| | COG2132: Putat | 6.3 | 0.52 | 1 |

It is noted that gi|19914667|, with an E-value of 1.7e-5 (double-underlined for clarity), is the last entry protein with 6 FG-GAP domains. Proteins with this score or better were extracted from GenBank and were used to create the searchable dataset for the next round of analysis. The general RHS Pfam model rhs_ls.hmm was used in lieu of creating a new RHS HMM model specific to fused B/C proteins. The results of the search are below:

hmmsearch—search a sequence database with a profile HMM

HMMER 2.3.1 (June 2003)

Copyright (C) 1992-2003 HHMI/Washington University School of Medicine

Freely distributed under the GNU General Public License (GPL)

HMM file: FinalTest/rhs_ls.hmm [RHS_repeat]

Sequence database: FinalTest/ProLargeModel7Hits.fasta per-sequence score cutoff: [none]

per-domain score cutoff: [none]

per-sequence Eval cutoff: <=10 per-domain Eval cutoff: [none]

Query HMM: RHS_repeat

Accession: PF05593.3

Description: RHS Repeat

[HMM has been calibrated; E-values are empirical estimates]

Scores for complete sequences (score includes all domains):

| Sequence | Description | Score | E-value | N |
|---|---|---|---|---|
| gi\|19915968\|gb\|AAM05447.1\| | hypothetical p | 153.0 | 3.5e−45 | 9 |
| gi\|20090892\|ref\|NP_616967.1\| | hypothetical p | 153.0 | 3.5e−45 | 9 |
| gi\|45656716\|ref\|YP_000802.1\| | cytoplasmic me | 151.7 | 9e−45 | 11 |
| gi\|45599952\|gb\|AAS69439.1\| | cytoplasmic me | 151.7 | 9e−45 | 11 |
| gi\|24197262\|gb\|AAN50531.1\|AE011493_4 | conserved hypo | 145.6 | 6.3e−43 | 11 |
| gi\|24216032\|ref\|NP_713513.1\| | hypothetical p | 145.6 | 6.3e−43 | 11 |
| gi\|14026456\|dbj\|BAB53053.1\| | mll6838 [Mesor | 133.2 | 3.4e−39 | 7 |
| gi\|13475700\|ref\|NP_107267.1\| | hypothetical p | 133.2 | 3.4e−39 | 7 |
| gi\|45601137\|gb\|AAS70619.1\| | cytoplasmic me | 125.5 | 6.8e−37 | 8 |
| gi\|45657896\|ref\|YP_001982.1\| | cytoplasmic me | 125.5 | 6.8e−37 | 8 |
| gi\|24195416\|gb\|AAN48964.1\|AE011353_4 | Rhs family pro | 122.8 | 4.5e−36 | 8 |
| gi\|24214465\|ref\|NP_711946.1\| | Rhs family pro | 122.8 | 4.5e−36 | 8 |
| gi\|67739010\|ref\|ZP_00489616.1\| | COG3209: Rhs f | 116.4 | 3.8e−34 | 9 |
| gi\|53718233\|ref\|YP_107219.1\| | putative membr | 116.4 | 3.8e−34 | 9 |
| gi\|52208647\|emb\|CAH34583.1\| | putative membr | 116.4 | 3.8e−34 | 9 |
| gi\|67713631\|ref\|ZP_00482992.1\| | COG3209: Rhs f | 116.4 | 3.8e−34 | 9 |
| gi\|67683974\|ref\|ZP_00478003.1\| | COG3209: Rhs f | 116.4 | 3.8e−34 | 9 |
| gi\|67653219\|ref\|ZP_00450636.1\| | COG3209: Rhs f | 114.0 | 2e−33 | 9 |
| gi\|67636722\|ref\|ZP_00435666.1\| | COG3209: Rhs f | 114.0 | 2e−33 | 9 |
| gi\|67642373\|ref\|ZP_00441130.1\| | COG3209: Rhs f | 114.0 | 2e−33 | 9 |
| gi\|53724907\|ref\|YP_101869.1\| | FG-GAP/YD repe | 114.0 | 2e−33 | 9 |
| gi\|52428330\|gb\|AAU48923.1\| | FG-GAP/YD repe | 114.0 | 2e−33 | 9 |
| gi\|67762147\|ref\|ZP_00500850.1\| | COG3209: Rhs f | 113.4 | 2.9e−33 | 9 |
| gi\|67648765\|ref\|ZP_00446993.1\| | COG3209: Rhs f | 113.4 | 3.1e−33 | 9 |
| gi\|67629702\|ref\|ZP_00429560.1\| | COG3209: Rhs f | 113.4 | 3.1e−33 | 9 |
| gi\|67670205\|ref\|ZP_00467015.1\| | COG3209: Rhs f | 113.3 | 3.2e−33 | 9 |
| gi\|27359176\|gb\|AAO08121.1\|AE016812_103 | Rhs family pro | 95.5 | 7.1e−28 | 8 |
| gi\|27367604\|ref\|NP_763131.1\| | Rhs family pro | 95.5 | 7.1e−28 | 8 |
| gi\|48863870\|ref\|ZP_00317763.1\| | COG3209: Rhs f | 67.6 | 1.8e−19 | 9 |
| gi\|19915968\|gb\|AAM05447.1\| | hypothetical p | 63.0 | 3.6e−16 | 6 |
| gi\|24216032\|ref\|NP_713513.1\| | hypothetical p | 59.6 | 3.9e−15 | 7 |
| gi\|48862345\|ref\|ZP_00316242.1\| | COG3209: Rhs f | 53.3 | 3.6e−15 | 11 |
| gi\|48833214\|ref\|ZP_00290236.1\| | COG2931: RTX t | −2.4 | 0.41 | 1 |
| gi\|20089734\|ref\|NP_615809.1\| | cell surface p | −3.5 | 0.57 | 1 |
| gi\|19914667\|gb\|AAM04289.1\| | cell surface p | −3.5 | 0.57 | 1 |
| gi\|67860476\|gb\|EAM55523.1\| | Integrins alph | −6.1 | 1.2 | 1 |
| gi\|67932250\|ref\|ZP_00525397.1\| | Integrins alph | −6.1 | 1.2 | 1 |
| gi\|33632688\|emb\|CAE07500.1\| | conserved hypo | −9.5 | 3.3 | 1 |
| gi\|33865519\|ref\|NP_897078.1\| | hypothetical p | −9.5 | 3.3 | 1 |
| gi\|67919346\|ref\|ZP_00512927.1\| | Integrins alph | −10.2 | 4 | 1 |
| gi\|67783058\|gb\|EAM42456.1\| | Integrins alph | −10.2 | 4 | 1 |
| gi\|39576631\|emb\|CAE80795.1\| | hypothetical p | −12.6 | 7.6 | 1 |
| gi\|42524422\|ref\|NP_969802.1\| | hypothetical p | −12.6 | 7.6 | 1 |
| gi\|48893475\|ref\|ZP_00326711.1\| | COG3391: Uncha | −12.6 | 7.7 | 1 |

It is noted that there is a very clean break of E-values between gi|48862345| (E-value ~e-15) and gi|48833214| (E-value 0.41) (double-underlined for clarity). A dereplicated list of proteins follows below:

| Scores for complete sequences (score includes all domains): | | | | |
|---|---|---|---|---|
| Sequence | Description | Score | E-value | N |
| gi\|20090892\|ref\|NP_616967.1\| | hypothetical p | 153.0 | 3.5e−45 | 9 |
| gi\|45656716\|ref\|YP_000802.1\| | cytoplasmic me | 151.7 | 9e−45 | 11 |
| gi\|24197262\|gb\|AAN50531.1\|AE011493_4 | conserved hypo | 145.6 | 6.3e−43 | 11 |
| gi\|14026456\|dbj\|BAB53053.1\| | mll6838 [Mesor | 133.2 | 3.4e−39 | 7 |
| gi\|45601137\|gb\|AAS70619.1\| | cytoplasmic me | 125.5 | 6.8e−37 | 8 |
| gi\|24195416\|gb\|AAN48964.1\|AE011353_4 | Rhs family pro | 122.8 | 4.5e−36 | 8 |
| gi\|67739010\|ref\|ZP_00489616.1\| | COG3209: Rhs f | 116.4 | 3.8e−34 | 9 |
| gi\|67653219\|ref\|ZP_00450636.1\| | COG3209: Rhs f | 114.0 | 2e−33 | 9 |
| gi\|67762147\|ref\|ZP_00500850.1\| | COG3209: Rhs f | 113.4 | 2.9e−33 | 9 |
| gi\|67648765\|ref\|ZP_00446993.1\| | COG3209: Rhs f | 113.4 | 3.1e−33 | 9 |
| gi\|67670205\|ref\|ZP_00467015.1\| | COG3209: Rhs f | 113.3 | 3.2e−33 | 9 |
| gi\|27359176\|gb\|AAO08121.1\|AE016812_103 | Rhs family pro | 95.5 | 7.1e−28 | 8 |
| gi\|48863870\|ref\|ZP_00317763.1\| | COG3209: Rhs f | 67.6 | 1.8e−19 | 9 |
| gi\|48862345\|ref\|ZP_00316242.1\| | COG3209: Rhs f | 53.3 | 3.6e−15 | 11 |

Thus, this example demonstrates that fused Class B/C TC protein sequences within large datasets can be identified from their shared protein domain structures, in the absence of other amino acid sequence information aside from length.

Eukaryotic Fused Class B/C TC Proteins. Models to identify eukaryotic proteins corresponding to fused Class B/C TC proteins were developed in a slightly different fashion from the Prokaryotic/Archaeal model. The only known example, from *Gibberella zeae*, has an spvB domain (rarely found in eukaryotic proteins) which closely fits the Pfam model. The *G. zeae* fused Class B/C TC protein also has FG-GAP domains which are discoverable using the FG-GAP BModels3.hmm model developed for the nonfused Class B TC proteins above. When used together, these two models were powerful enough to select the *G. zeae* protein from a database, so an RHS HMM model was not developed. One skilled in the art would realize that such an RHS model could easily be developed using these teachings. Such an additional RHS model might be useful, for example, if all of the GenBank proteins were to be searched instead of the subset tested below.

A protein search at the website ncbi.nlm.nih.gov/ was performed using the search terms: "1700:2800[SLEN] AND Eukaryota". These terms restricted the search to those proteins that are between 1700 and 2800 amino acids in length and have a eukaryotic source. A total of 19550 protein sequences were identified and downloaded as a searchable database. It should be noted that, while these restrictions are useful in the present context, the interval length of the sequences and the kingdom searched can be modified to meet the parameters of the individual protein set to be examined.

The data set was tested against the FG-GAP model first. This model was considered to be the less discriminating one of the two used, since eukaryotic proteins containing FG-GAP domains are known to exist. However as shown below, only a single member of the 19550 proteins of the search set had a significant hit. [GenBank Accessions gi|46138103| and gi|42545609| are duplicate entries.] This result indicates that the FG-GAP model is substantiality discriminatory for known proteins within the 1700 and 2800 sequence length range.

hmmsearch—search a sequence database with a profile HMM

HMMER 2.3.1 (June 2003)

Copyright (C) 1992-2003 HHMI/Washington University School of Medicine

Freely distributed under the GNU General Public License (GPL)

HMM file: FinalTest/BModels3.hmm [BDomainsModel3Sequences]

Sequence database: FinalTest/EukaryoticGenBank1700-2800.fasta per-sequence score cutoff: [none]

per-domain score cutoff: [none]

per-sequence Eval cutoff: <=10 per-domain Eval cutoff: [none]

Query HMM: BDomainsModel3Sequences

Accession: [none]

Description: [none]

[HMM has been calibrated; E-values are empirical estimates]

| Scores for complete sequences (score includes all domains): | | | | |
|---|---|---|---|---|
| Sequence | Description | Score | E-value | N |
| gi\|46138103\|ref\|XP_390742.1\| | hypothetical protei | 61.6 | 5.5e−15 | 3 |
| gi\|42545609\|gb\|EAA68452.1\| | hypothetical protei | 61.6 | 5.5e−15 | 3 |
| gi\|55620227\|ref\|XP_526172.1\| | PREDICTED: similar | 8.3 | 1.1 | 1 |
| gi\|34978363\|sp\|P39061\|COIA1_MOUSE | Collagen alpha 1(XV | 3.6 | 3.9 | 1 |
| gi\|7446033\|pir\|\|B56101 | collagen alpha 1(XV | 3.6 | 3.9 | 1 |
| gi\|1167906\|gb\|AAC52903.1\| | alpha-1(XVIII) coll | 3.6 | 3.9 | 1 |
| gi\|57916309\|ref\|XP_555970.1\| | ENSANGP00000027590 | 1.9 | 6.4 | 1 |

-continued

| Scores for complete sequences (score includes all domains): | | | | |
|---|---|---|---|---|
| Sequence | Description | Score | E-value | N |
| gi\|55238148\|gb\|EAL39797.1\| | ENSANGP00000027590 | 1.9 | 6.4 | 1 |
| gi\|55656175\|ref\|XP_531500.1\| | PREDICTED: hypothet | 1.7 | 6.6 | 1 |
| gi\|40231526\|gb\|AAR83296.1\| | type XVIII collagen | 1.7 | 6.6 | 1 |
| gi\|57112907\|ref\|XP_549331.1\| | PREDICTED: similar | 0.3 | 9.8 | 1 |

We tested this protein with the spvB_ls.hmm model to show that this model can find the appropriate protein. The results are below:

hmmsearch—search a sequence database with a profile HMM

HMMER 2.3.1 (June 2003)

Copyright (C) 1992-2003 HHMI/Washington University School of Medicine

Freely distributed under the GNU General Public License (GPL)

HMM file: FinalTest/spvB_ls.hmm [SpvB]

Sequence database: FinalTest/EukBCModel3Hits.fasta per-sequence score cutoff: [none]

per-domain score cutoff: [none]

per-sequence Eval cutoff: <=10 per-domain Eval cutoff: [none]

Query HMM: SpvB

Accession: PF03534.3

Description: *Salmonella* virulence plasmid 65 kDa B protein

[HMM has been calibrated; E-values are empirical estimates]

| Scores for complete sequences (score includes all domains): | | | | |
|---|---|---|---|---|
| Sequence | Description | Score | E-value | N |
| gi\|46138103\|ref\|XP_390742.1\| | hypothetical protein FG1 | 159.7 | 1.7e−48 | 1 |
| gi\|42545609\|gb\|EAA68452.1\| | hypothetical protein FG1 | 159.7 | 1.7e−48 | 1 |

Since only a single example of a eukaryotic Class B/C TC fusion protein has been discovered to date, it is not possible to provide a stringent test of this search strategy. However, it is clear that the two-model domain search strategy will be useful to discriminate proteins within the sequence length range that have FG-GAP domains but that are not fused Class B/C TC proteins. In addition, the models provided here can be used to extract Class B/C TC fusion proteins from a wider sequence range, when necessary. As with previous demonstrations, the order in which the models are used does not alter the final results. It is also important to note that an RHS model could be added to the above search criteria if necessary to obtain further discrimination.

The above examples teach that a combination of (1) sequence length filtering and (2) domain searching constitute a powerful method for extracting Class B, Class C and fused Class B/C TC proteins from protein sequence databases. The domains are taken from the spvB, FG-GAP and RHS domain families, using either general Pfam HMM models or particular HMM domain models tailored to the particular protein class. The sequence length intervals used in these examples were chosen to encompass the known range of these proteins, and to show that these proteins can be separated, not just from all other proteins, but also from other members of these protein families. Since the same HMM models were used for both the prokaryotic Class B TC proteins and the eukaryotic fused Class BC TC proteins, both results sets would have been extracted together if no sequence length or kingdom limits had initially been placed on the search. Optionally, an RHS model could easily be developed to discriminate between these protein sets. If such discrimination is undesired or unnecessary, the whole GenBank protein data set could be used as input. However, given the large and ever-expanding size of the GenBank databases, this would make the searches significantly slower.

For further guidance, see E. L. L. Sonnhammer, S. R. Eddy, and R. Durbin. *Proteins* 28:405-420, 1997 (describes the Pfam database of multiple sequence alignments and HMMs, and its use in large scale genome analysis), and Richard Durbin, Sean Eddy, Anders Krogh, and Graeme Mitchison (Cambridge University Press, 1998), Biological Sequence Analysis: Probabilistic Models of Proteins and Nucleic Acids.

EXAMPLE 12

Localization of spvB, FG-GAP, RHS, and HVR Subdomains in BC Fusion Proteins of *Tannerella* and *Gibberella*

FIGS. 2 and 3 illustrate the locations of the above subdomains in the B and C domains of the BC fusion proteins of *Tannerella* and *Gibberella*, respectively. For *Tannerella* (FIG. 2), the spvB domain (standard spvB-ls.hmm model) is illustrated with underlining from residues 51-374 (of FIG. 2 and also SEQ ID NO:12). The FG-GAP domains (using the BModel7.hmm model; there are six in this molecule) are indicated with double underlining and occur at residues 392-421, 453-486, 502-531, 552-581, 604-625, and 650-681. The foregoing features are observable in the B domain. Following a transition into the C domain, eight RHS domains (using Pfam rhs_ls.hmm model) are determinable in the C domain at residues 1048-1085, 1168-1201, 1207-1243, 1248-1285, 1290-1326, 1331-1369, 1447-1482, and 1620-1652. These are indicated in bold in FIG. 2. A hypervariable region (HVR), common in "Class C" TC proteins, is also identified at the C terminus of the molecule (residues 1733-2027). This is indicated in italics in FIG. 2.

Similarly, in FIG. 3 (and SEQ ID NO:4) for *Gibberella*, an spvB subdomain (shown with underlining in FIG. 3) in the B domain is observable at residues 51-374. Three FG-GAP domains/subdomains are accordingly determined to occur at residues 570-609, 630-669, and 685-700. These are indicated with double underlining in FIG. 3. (The intron of SEQ ID NO:2, residues 1557-1583, is not shown in FIG. 3.) Two RHS domains are located at residues 1738-1774 and 1972-2002 in the C domain (indicated in bold in FIG. 3), as is a HVR at residues 2154-2439 (the C terminal region), indicated in italics in FIG. 3.

For the *Gibberella* model discussed above, the spvB domain was determined using the standard spvB-Is.hmm model. The three FG-GAP domains were found with the Bmodels3.hmm model. As only one eukaryotic protein is presently known, it is difficult to test for the best model. As more eukaryotic fused BC toxin proteins are discovered the model will likely improve. The RHS domains were found using the Pfam rhs_ls.hmm model. As with the FG-GAP domains, two RHS domains were found. As more eukaryotic examples are found, the model is expected to improve. Under a slightly different domain search—NCBI's CD (conserved domain) search—the section from amino acid residues 1493-2153 is labeled as RHSA [Marchler-Bauer A, Bryant SH (2004), "*CD-Search: protein domain annotations on the Fly*.", Nucleic Acids Res. 32:W327-331.] As with the Tannerella model, the HVR was mapped by lack of homology to other proteins. However, HVRs are recognizable in other "Class C" TC proteins. Due to the differences in length of various natural proteins as illustrated above, the exact residue locations for each subdomain cannot be predicted for future proteins. However, the subject invention includes naturally occurring proteins wherein the Spy domain is located in the first half of the molecule followed by at least one F-Gap domain, followed by at least one RHS domain in the last two thirds of the molecule, followed by a hypervariable region at the end of the protein. Some software programs may also predict a transmembrane domain. This is the case for the program TMAP (transmembrane detection based on multiple sequence alignment: Karolinska Institut, Sweden). Thus, it is possible that the subject proteins further comprise a transmembrane domain.

EXAMPLE 13

Alignment and Further Comparison of BC Fused Toxin Proteins from *Tannerella* and *Gibberella*

A global alignment of the two BC fused toxin proteins from *Tannerella* and *Gibberella* was performed with needle, an EMBOSS program (*EMBOSS: The European Molecular Biology Open Software Suite* (2000), Rice, P., Longden, I., and Bleasby, A., Trends in Genetics 16(6):276-277) using the Needleman-Wunsch algorithm (same as GCG's GAP). See FIG. 4.

Additional settings used were: Align_format: srspair; Report_file: outfile; Matrix: EBLOSUM62; Gap_penalty: 10.0; Extend_penalty: 0.5.

For a length of 2894 amino acid residues, the following scores were obtained: Identity: 517/2894 (17.9%); Similarity: 796/2894 (27.5%); Gaps: 1322/2894 (45.7%); Score: 441.0.

EXAMPLE 14

Construction of a Gene Encoding the 8884 Fusion Protein (TcdB2/$Tcp1_{Gz}$C)

Fusion protein 8884 is comprised of the entire *Photorhabdus* TcdB2 (a Class B protein) fused to a portion of the *Gibberella zeae* $Tcp1_{Gz}$ protein. The segment of the $Tcp1_{Gz}$ protein present in the 8884 fusion protein is herein called $Tcp1_{Gz}$C, to reflect its functional similarity to other Class C proteins.

To construct the coding region for the 8884 fusion protein, the 3' end of the TcdB2 coding region was modified using standard molecular biology techniques. Likewise, the 5' end of the coding region of the C-like region of $Tcp1_{Gz}$ was modified in a multi step process, and the two modified coding regions were joined with a linker fragment to create a single open reading frame. The novel DNA encoding the 8884 gene fusion is disclosed in SEQ ID NO:19 and encodes polypeptide 8884 (presented in SEQ ID NO:20). Nucleotides 1-4422 of the 8884 fusion protein coding region correspond to the same numbered bases of the *Photorhabdus luminescens* strain W-14 tcdB2 gene (Genbank Accession AF346500.2) and encode the entire TcdB2 protein. This sequence is followed by 42 bases of linker sequence (encoding 14 amino acids), which is then followed by a DNA sequence corresponding to nucleotides 4346-7423 of a DNA sequence encoding the $Tcp1_{Gz}$ protein optimized for expression in *E. coli* cells (SEQ ID NO:5). The fused gene consisting of the coding regions for TcdB2 and $Tcp1_{Gz}$C (disclosed as SEQ ID NO:19). was cloned into a pET expression plasmid vector (Novagen, Madison Wis.). The construction was done in such a way as to maintain appropriate bacterial transcription and translation signals. The plasmid was designated pDAB8884. The cassette in SEQ ID NO:19 is 7542 nucleotides in length and contains coding regions for TcdB2 (nts 1-4422), the TcdB2/$Tcp1_{Gz}$C linker peptide (nts 4423-4464) and $Tcp1_{Gz}$C (nts 4465-7539). The polypeptide encoded by the fused gene in SEQ ID NO:19 is shown in SEQ ID NO:20. The fusion protein is predicted to contain 2,513 amino acids with segments representing TcdB2 (residues 1-1474), the TcdB2/$Tcp1_{Gz}$C linker peptide (residues 1475-1488), and $Tcp1_{Gz}$C (residues 1489-2513).

EXAMPLE 15

Expression Conditions for pDAB8884 and Lysate Preparations

The Class A TC protein $XptA2_{Xwi}$ was utilized in a purified form prepared from cultures of *Pseudomonas fluorescens* heterologously expressing the gene. The expression plasmids pET280 (empty vector control), pDAB8920 (encoding a TcdB2/TccC3 fusion protein), pDAB8829 (encoding the $Tcp1_{Gz}$ protein) and pDAB8884 were transformed into the *E. coli* T7 expression strain BL21(DE3) (Invitrogen, Carlsbad, Calif.) using standard methods. Expression cultures were initiated with 10-200 freshly transformed colonies into 250 mL LB medium containing 50 μg/mL antibiotic and 75 μM IPTG (isopropyl-α-D-thiogalactopyranoside). The cultures were grown at 28° C. for 24 hours at 180-200 rpm. The cells were collected by centrifugation in 500 mL Nalgene bottles at 5,000×g for 20 minutes at 4° C. The pellets were suspended in 4-4.5 mL Butterfield's Phosphate solution (Hardy Diagnostics, Santa Maria, Calif.; 0.3 mM potassium phosphate pH 7.2). The suspended cells were transferred to 50 mL polypropylene screw cap centrifuge tubes with 1 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of ~30, chilling completely between bursts. The lysates were transferred to 2 mL Eppendorf tubes and centrifuged 5 minutes at 16,000×g.

EXAMPLE 16

Bioassay Conditions for the 8884 Lysates

Insect bioassays were conducted with neonate corn earworm larvae (*Helicoverpa zea* (Boddie)) on artificial diets in 128-well trays specifically designed for insect bioassays (C-D International, Pitman, N.J.). Bioassays were incubated under controlled environmental conditions (28° C., ~40% relative humidity, 16 hr:8 hr [Light:Dark]) for 5 days, at which point the total number of insects in the treatment, the number of dead insects, and the weights of surviving insects were recorded.

The biological activity of the crude lysates alone or with added XptA2$_{Xwi}$ toxin protein was assayed as follows. Crude *E. coli* lysates (40 μL) of either control cultures or those expressing Toxin Complex proteins were applied to the surface of artificial diet in 8 wells of a bioassay tray. The average surface area of treated diet in each well was ~1.5 cm$^2$. The lysates from bacterial cultures harboring the empty vector control, or lysates from cultures producing the 8920 TcdB2/TccC3 fusion protein, the 8829 Tcp1$_{Gz}$ protein, and the 8884 TcdB2/Tcp1$_{Gz}$C fusion protein were applied with and without XptA2$_{Xwi}$. The XptA2$_{Xwi}$ protein added was a highly purified preparation from bacterial cultures heterologously expressing the protein. Additionally, purified XptA2$_{Xwi}$; without any crude lysate was mixed with Butterfield's Phosphate solution as a control. The final concentration of XptA2$_{Xwi}$ on the diet was 250 ng/cm$^2$.

EXAMPLE 17

Construction of a Gene Encoding the 8883 Fusion Protein (Tcp1$_{Gz}$B/TccC3)

Fusion protein 8883 is comprised of a portion of the *Gibberella zeae* Tcp1$_{Gz}$ protein fused to the entire *Photorhabdus* TccC3 protein (a Class C protein). The segment of the Tcp1$_{Gz}$ protein present in the 8883 fusion protein is herein called Tcp1$_{Gz}$B, to reflect its functional similarity to other Class B proteins.

To construct the 8883 fusion protein coding region, the 3' end of the coding region for the B-like region of Tcp1$_{Gz}$ was modified in a multi step process using standard molecular biology techniques. Likewise, the 5' end of the TccC3 coding region was modified in a multi-step process, and the two modified coding regions were joined with a linker fragment to create a single open reading frame. The novel DNA encoding the 8883 gene fusion is disclosed in SEQ ID NO:21 and encodes polypeptide 8883 (presented in SEQ ID NO:22). The portion of the *Gibberella zeae* protein Tcp1$_{Gz}$ corresponding to the Tcp1$_{Gz}$B protein is encoded by bases 23-4558 of a DNA sequence encoding the Tcp1$_{Gz}$ protein optimized for expression in *E. coli* cells (disclosed in SEQ ID NO:5). This sequence comprises bases 1-4536 of SEQ ID NO:21. These bases are followed by a linker fragment of 39 bases (encoding 13 amino acids), then by the entire coding region for the *Photorhabdus luminescens* strain W-14 TccC3 protein (a Class C protein; Genbank Accession AF346500.2). [In SEQ ID NO:21, base number 12 (T of the native sequence) was changed to C to accommodate a ClaI restriction enzyme recognition site. This silent base change does not alter the encoded amino acid sequence of the TccC3 protein.] This novel fusion gene is called 8883 (SEQ ID NO:21) and encodes polypeptide 8883 (SEQ ID NO:22).

The fused gene consisting of the coding regions for Tcp1$_{Gz}$B and TccC3 was engineered as a single open reading frame in a pET expression plasmid vector (Novagen, Madison Wis.). The construction was done in such a way as to maintain appropriate bacterial transcription and translation signals. The plasmid was designated pDAB8883. The DNA sequence of the fused coding region cassette is shown in SEQ ID NO:21. The cassette is 7458 nucleotides in length and contains coding regions of Tcp1$_{Gz}$B (nts 1-4536), the Tcp1$_{Gz}$B/TccC3 linker peptide (nts 4537-4575) and TccC3 (nts 4576-7455). The polypeptide encoded by the fused gene in SEQ ID NO:21 is shown in SEQ ID NO:22. The fusion protein is predicted to contain 2,485 amino acids with segments representing Tcp1$_{Gz}$B (residues 1-1512), the Tcp1$_{Gz}$B/TccC3 linker peptide (residues 1513-1525), and TccC3 (residues 1526-2485).

Lysates containing the 8883 fusion protein demonstrated excellent functional activity, as demonstrated in following examples. Thus, this invention demonstrates the retained synergistic activity of a fusion between the Tcp1$_{Gz}$B peptide, the product of a eukaryotic gene, with TccC3, the product of a prokaryotic gene, when used in combination with the Toxin Complex Protein XptA2$_{Xwi}$.

EXAMPLE 18

Expression Conditions for pDAB8883 and Lysate Preparations

The Class A TC protein XptA2$_{Xwi}$; was utilized in a purified form prepared from cultures of *Pseudomonas fluorescens* heterologously expressing the gene. The expression plasmids pET280 (empty vector control), pDAB8920 (encoding a TcdB2/TccC3 fusion protein), pDAB8829 (encoding the Tcp1$_{Gz}$ protein), and pDAB8883 were transformed into the *E. coli* T7 expression strain BL21(DE3) (Invitrogen, Carlsbad, Calif.) using standard methods. Expression cultures were initiated with 10-200 freshly transformed colonies into 250 mL LB medium containing 50 μg/mL antibiotic and 75 μM IPTG (isopropyl-α-D-thiogalactopyranoside). The cultures were grown at 28° C. for 24 hours at 180-200 rpm. The cells were collected by centrifugation in 500 mL Nalgene bottles at 5,000×g for 20 minutes at 4° C. The pellets were suspended in 4-4.5 mL Butterfield's Phosphate solution (Hardy Diagnostics, Santa Maria, Calif.; 0.3 mM potassium phosphate pH 7.2). The suspended cells were transferred to 50 mL polypropylene screw cap centrifuge tubes with 1 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of ~30, chilling completely between bursts. The lysates were transferred to 2 mL Eppendorf tubes and centrifuged 5 minutes at 16,000×g.

EXAMPLE 19

Bioassay Conditions for the 8883 Lysates

Insect bioassays were conducted with neonate corn earworm larvae, *Helicoverpa zea* (Boddie), on artificial diets in 128-well trays specifically designed for insect bioassays (C-D International, Pitman, N.J.). Bioassays were incubated under controlled environmental conditions (28° C., ~40% relative humidity, 16 hr:8 hr [Light:Dark]) for 5 days, at which point the total number of insects in the treatment, the number of dead insects, and the weights of surviving insects were recorded.

The biological activity of the crude lysates alone or with added XptA2$_{Xwi}$ toxin protein was assayed as follows. Crude *E. coli* lysates (40 μL) of either control cultures or those expressing Toxin Complex proteins were applied to the surface of artificial diet in 8 wells of a bioassay tray. The average surface area of treated diet in each well was ~1.5 cm$^2$. The lysates from bacterial cultures harboring the empty vector control, or lysates from cultures producing the 8920 TcdB2/TccC3 fusion protein, the 8829 Tcp1$_{Gz}$ protein, and the 8883

$Tcp1_{Gz}B/TccC3$ fusion protein were applied with and without $XptA2_{Xwi}$. The $XptA2_{Xwi}$ protein added was a highly purified preparation from bacterial cultures heterologously expressing the protein. Additionally, purified $XptA2_{Xwi}$ without any crude lysate was mixed with Butterfield's Phosphate solution as a control. The final concentration of $XptA2_{Xwi}$ on the diet was 250 ng/cm$^2$.

EXAMPLE 20

Bioassay Results for 8883 $Tcp1_{Gz}B/TccC3$ Fusion Lysates

Table 7 shows the bioassay results for control lysates, lysates of cells programmed to express the 8920 TcdB2/TccC3 fusion protein, lysates of cells programmed to express the 8829 $Tcp1_{Gz}$ protein, and lysates of cells programmed to express the 8883 $Tcp1_{Gz}$ B/TccC3 fusion protein. All of the lysates were bioassayed plus and minus purified $XptA2_{Xwi}$. The data show that control lysates, with and without $XptA2_{xwi}$, had little effect on the insects. Lysates containing only the 8920 TcdB2/TccC3 fusion protein had no effect without added $XptA2_{Xwi}$. However, with added $XptA2_{Xwi}$, the 8920 lysate was a potent inhibitor of insect growth. Lysates containing only the 8829 $Tcp1_{Gz}$ protein had no effect without added $XptA2_{Xwi}$. However, with added $XptA2_{Xwi}$, the 8829 lysate was a potent inhibitor of insect growth. Lysates programmed to express the 8883 $Tcp1_{Gz}B/TccC3$ fusion protein had no effect without added $XptA2_{Xwi}$. However, with added $XptA2_{Xwi}$, the 8883 lysate was a potent inhibitor of insect growth. These data demonstrate that when the $Tcp1_{Gz}B$ and TccC3 peptides are fused together they retain a synergistic effect when combined with $XptA2_{Xwi}$.

TABLE 7

Response of corn earworm (*Helicoverpa zea* (Boddie) neonate larvae to *E. coli* lysates expressing Toxin Complex proteins.

| Sample | Lysate Tested | Growth Inhibition Corn Earworm |
|---|---|---|
| pET280 | Empty vector control | 0 |
| pET280 + $XptA2_{Xwi}$ | Empty vector control | 0 |
| Purified $XptA2_{xXwi}$ | $XptA2_{xwi}$ | 0 |
| pDAB8920 | 8920 (TcdB2/TccC3) | 0 |
| pDAB8920 + $XptA2_{Xwi}$ | 8920 (TcdB2/TccC3) | ++++ |
| pDAB8829 | 8829 ($Tcp1_{Gz}$) | 0 |
| pDAB8829 + $XptA2_{Xwi}$ | 8829 ($Tcp1_{Gz}$) | ++++ |
| pDAB8883 | 8883 ($Tcp1_{Gz}B/TccC3$) | 0 |
| pDAB8883 + $XptA2_{Xwi}$ | 8883 ($Tcp1_{Gz}B/TccC3$) | ++++ |

24 insects used per test.
Growth Inhibition Scale:
0 = 0-20%;
+ = 21-40%;
++ = 41-60%;
+++ = 61-80%;
++++ = 81-100%.

EXAMPLE 21

Design and Synthesis of a Plant-Optimized Gene Encoding $Tcp1_{Gz}$ for Expression in Plants To obtain higher levels of expression of a fungal gene in plants, it may be preferred to re-engineer the protein-encoding sequence of the gene so that it is more efficiently expressed in plant cells. This example teaches the design of a new DNA sequence that encodes the $Tcp1_{Gz}$ protein of SEQ ID NO: 2, but is optimized for expression in plant cells.

One motive for the re-engineering of a gene encoding a fungal protein for expression in plants is due to the non-optimal G+C content of the heterologous gene. For example, the low G+C content of many native fungal gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a fungal protein for plant expression, more preferably referred to as plant optimized gene(s), is to generate a DNA sequence having a G+C content close to that of the average of plant gene coding regions. Another goal in the design of the plant optimized gene(s) encoding a fungal protein is to generate a DNA sequence in which the sequence modifications do not hinder translation.

Due to the plasticity afforded by the redundancy/degeneracy of the genetic code (i.e., some amino acids are specified by more than one codon), evolution of the genomes in different organisms, or classes of organisms, has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third codon position. It is thought that the presence of "minor" codons within an mRNA may reduce the absolute translation rate of that mRNA, especially when the relative abundance of the charged tRNA corresponding to the minor codon is low. An extension of this concept is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

To assist in engineering genes encoding a fungal protein for expression in plants the codon bias of plant genes can be determined. The codon bias for genes of a particular plant is represented by the statistical codon distribution found in the protein coding regions of the plant genes. In Table 8, Columns C, D, I, and J present the distributions (in % of usage for all codons for that amino acid) of synonomous codons for each amino acid, as found in the coding regions of *Zea mays* (maize) and dicot genes. The codons most preferred by each plant type are indicated in bold font, and the second, third, or fourth choices of preferred codons can be identified when multiple choices exist. It is evident that some synonomous codons for some amino acids are found only rarely in plant genes, and further, that maize and dicot plants differ in codon usage (e.g. Alanine codon GCG occurs more frequently in maize genes, while Arginine codon AGA is more often used in dicot genes). A new DNA sequence which encodes the amino acid sequence of the fungal $Tcp1_{gz}$ protein was designed for optimal expression in both maize and dicot plants. The new DNA sequence differs from the native fungal DNA sequence encoding the $Tcp1_{gz}$ protein by the substitution of plant (first preferred, second preferred, third preferred, or fourth preferred) codons to specify the appropriate amino acid at each position within the protein amino acid sequence. In the design process of creating a fungal protein-encoding DNA sequence that approximates an average codon distribution of both maize and dicot genes, any codon that is used infrequently relative to the other synonymous codons for that amino acid in either type of plant was not included (indicated by DNU in Columns F and L of Table 8). Usually, a codon was considered to be rarely used if it was represented at about 10% or less of the time to encode the relevant amino acid in genes of either plant type (indicated by NA in Columns E and K of Table 9).

To balance the distribution of the remaining codon choices for an amino acid, a weighted average representation for each codon was calculated, using the formula:

$$\text{Weighted \% of } C1=1/(\%\ C1+\%\ C2+\%\ C3+\text{ etc.})\times\%\ C1\times 100$$

where C1 is the codon in question and C2, C3, etc. represent the averages of the % values for maize and dicots of remaining synonymous codons (average % values for the relevant codons are taken from Columns E and K) of Table 8. The Weighted % value for each codon is given in Columns F and L of Table 8.

Design of the plant-optimized DNA sequence was initiated by reverse-translation of the protein sequence of SEQ ID NO: 2 using a balanced maize-dicot codon bias table constructed from Table 8 Columns F and L. The initial sequence was then modified by compensating codon changes (while retaining overall weighted average codon representation) to remove or add restriction enzyme recognition sites, remove highly stable intrastrand secondary structures, and other sequences that might be detrimental to cloning manipulations or expression of the engineered gene in plants.

The new sequence was then re-analyzed for restriction enzyme recognition sites that might have been created by the modifications. The identified sites are further modified by replacing the relevant codons with first, second, third, or fourth choice preferred codons. Other sites in the sequence which could affect transcription or translation of the gene of interest include the exon:intron junctions (5' or 3'), poly A addition signals, or RNA polymerase termination signals. The modified sequence is further analyzed and further modified to reduce the frequency of TA or CG doublets, and to increase the frequency of TG or CT doublets. In addition to these doublets, sequence blocks that have more than about five consecutive residues of [G+C] or [A+T] can affect transcription or translation of the sequence. Therefore, these sequence blocks are also modified by replacing the codons of first or second choice, etc. with other preferred codons of choice. Rarely used codons are not included to a substantial extent in the gene design, being used only when necessary to accommodate a different design criterion than codon composition per se (e.g. addition or deletion of restriction enzyme recognition sites).

The method described above enables one skilled in the art to design modified gene(s) that are foreign to a particular plant so that the genes are optimally expressed in plants. The method is further described and illustrated in U.S. Pat. No. 5,380,831 and patent application WO 97/13402.

Thus, in order to design plant optimized genes encoding a fungal protein, a DNA sequence is designed to encode the amino acid sequence of said protein utilizing a redundant genetic code established from a codon bias table compiled from the gene sequences for the particular plant or plants. The resulting DNA sequence has a higher degree of codon diversity, a desirable base composition, can contain strategically placed restriction enzyme recognition sites, and lacks sequences that might interfere with transcription of the gene, or translation of the product mRNA. Thus, synthetic genes that are functionally equivalent to the proteins/genes of the subject invention can be used to transform hosts, including plants. Additional guidance regarding the production of synthetic genes can be found in, for example, U.S. Pat. No. 5,380,831.

Once said DNA sequence has been designed on paper or in silico, actual DNA molecules can be synthesized in the laboratory to correspond in sequence precisely to the designed sequence. Such synthetic DNA molecules can be cloned and otherwise manipulated exactly as if they were derived from natural or native sources.

The plant optimized, codon biased DNA sequence that encodes a variant of the $Tcp1_{gz}$ fusion protein of SEQ ID NO: 2 is given as bases 3-7403 of SEQ ID NO:23 (referred to herein as the 8842 gene). To facilitate cloning and to ensure efficient translation initiation, a 5' terminal NcoI restriction enzyme recognition sequence (CCTAGG) was engineered to include the ATG translation start codon (bases 1-6 of SEQ ID NO:23). This design feature introduced a GCT codon specifying Alanine as the second amino acid of the encoded protein. Thus, the protein encoded by SEQ ID NO:23, as disclosed in SEQ ID NO:24 (referred to herein as the 8842 protein), differs from the native $Tcp1_{gz}$ protein of SEQ ID NO:2 by the addition of an Alanine at the second residue. Also, to ensure proper translation termination and to facilitate cloning, bases encoding translation stop codons in the six reading frames of double-stranded DNA, plus a SacI restriction enzyme recognition site (GAGCTC), were included at the 3' end of the coding region (bases 7404-7432 of SEQ ID NO:23). Synthesis of a DNA fragment comprising SEQ ID NO: 10 was performed by a commercial supplier (PicoScript, Houston. Tex USA).

It is to be noted that the *Gibberella zeae* genomic DNA sequence $tcp1_{Gz}$, disclosed in SEQ ID NO: 1, as annotated in Genbank Accession AACM01000442, comprises a putative intron sequence (bases 4669-4749 of SEQ ID NO:1). The plant-optimized, codon biased DNA sequence that encodes a variant of the $Tcp1_{gz}$ fusion protein and disclosed in SEQ ID NO:23 has been designed in such a manner that plant intron splice site recognition sequences were removed. Thus, the protein encoded by SEQ ID NO:23 and disclosed in SEQ ID NO:24, and expected to be produced by plant cells, includes amino acids encoded by the putative fungal intron sequences.

TABLE 8

Synonomous codon representation in coding regions of 706 *Zea mays* genes (Columns C and I), and 154 dicot plant genes (Columns D and J). Values for a balanced-biased codon representation set for a plant-optimized synthetic gene design are in Columns F and L.

| A Amino Acid | B Codon | C Maize % | D Dicot* % | E Maize-Dicot Average | F Weighted Average | G Amino Acid | H Codon | I Maize % | J Dicot* % | K Maize-Dicot Average | L Weighted Average |
|---|---|---|---|---|---|---|---|---|---|---|---|
| ALA (A) | GCA | 18 | 25 | 21.7 | 25.5 | LEU (L) | CTA | 8 | 8 | NA | DNU |
| | GCC | 34 | 27 | 30.3 | 35.6 | | CTC | 26 | 19 | 22.5 | 34.3 |
| | CCC | 24 | 6 | NA* | DNU*** | | CTG | 29 | 9 | NA | DNU |
| | GCF | 24 | 42 | 33.2 | 39.0 | | CTT | 17 | 28 | 22.5 | 34.3 |
| ARG (R) | AGA | 15 | 30 | 22.4 | 27.4 | | TTA | 5 | 10 | NA | DNU |
| | AGC | 26 | 25 | 25.7 | 31.5 | | TTG | 15 | 26 | 20.6 | 31.4 |
| | CGA | 9 | 8 | NA | DNU | LYS (K) | AAA | 22 | 39 | 30.6 | 30.6 |
| | CCC | 24 | 11 | 17.7 | 21.7 | | AAG | 78 | 61 | 69.4 | 69.4 |
| | CGG | 15 | 4 | NA | DNU | MET(M) | ATG | 100 | 100 | 100 | 100 |
| | CGT | 11 | 21 | 15.8 | 19.4 | PHE (F) | TTC | 71 | 55 | 63.2 | 63.2 |
| ASN (N) | AAC | 68 | 55 | 61.4 | 61.4 | | TTT | 29 | 45 | 36.8 | 36.8 |
| | AAT | 32 | 45 | 38.6 | 38.6 | PRO (P) | CCA | 26 | 42 | 33.8 | 41.4 |
| ASP (D) | GAC | 63 | 42 | 52.6 | 52.6 | | CCC | 24 | 17 | 20.7 | 25.3 |
| | GAT | 37 | 58 | 47.4 | 47.4 | CCG | 28 | 9 | NA | DNU | |
| CYS (C) | TGC | 68 | 56 | 61.8 | 61.8 | | CCT | 22 | 32 | 27.2 | 33.3 |
| | TGT | 32 | 44 | 38.2 38.2 | SER (S) | AGC | 23 | 18 | 20.4 | 26.0 | |
| END | TAA | 20 | 48 | 33.8 | | | AGT | 9 | 14 | NA | DNU |
| | TAG | 21 | 19 | 20.1 | DNU | TCA | 16 | 19 | 17.5 | 22.4 | |
| | TGA | 59 | 33 | 46.1 | TCC | 23 | 18 | 20.6 | 26.3 | | |
| GLN (Q) | CAA | 38 | 59 | 48.4 | 48.4 | | TCG | 14 | 6 | NA | DNU |
| | CAG | 62 | 41 | 51.6 | 51.6 | | TCT | 15 | 25 | 19.9 | 25.4 |
| GLU (E) | GAA | 29 | 49 | 38.8 | 38.8 | THR (T) | ACA | 21 | 27 | 23.8 | 28.0 |
| | GAG | 71 | 51 | 61.2 | 61.2 | | ACC | 37 | 30 | 33.6 | 39.5 |
| GLY (G) | GGA | 19 | 38 | 28.5 | 28.5 | | ACG | 22 | 8 | NA | DNU |
| | GGC | 42 | 16 | 29.1 | 29.0 | | ACT | 20 | 35 | 27.7 | 32.5 |
| | GGG | 20 | 12 | 16.1 | 16.0 | TRP (W) | TGG | 100 | 100 | 100 | 100 |
| | GGT | 20 | 33 | 26.7 | 26.6 | TYR (Y) | TAC | 73 | 57 | 65.0 | 65.0 |
| HIS (H) | CAC | 62 | 46 | 54.1 | 54.1 | | TAT | 27 | 43 | 35.0 | 35.0 |
| | CAT | 38 | 54 | 45.9 | 45.9 | VAL (V) | GTA | 8 | 12 | NA | DNU |
| ILE (I) | ATA | 14 | 18 | 15.9 | 15.9 | | GTC | 32 | 20 | 25.8 | 28.7 |
| | ATC | 58 | 37 | 47.6 | 47.9 | | GTG | 39 | 29 | 34.1 | 38.0 |
| | ATT | 28 | 45 | 36.4 | 36.4 | | GTT | 21 | 39 | 29.9 | 33.3 |

*Murray E. E., Lotzer, J., & Eberle, M. (1989) Codon usage in plant genes. Nuci. Acids Res. 17:477-498.
**NA = Not Applicable
***DNU = Do Not Use

EXAMPLE 22

Construction of a Binary Plant Expression Vector Containing a First Version of a Gene Expressing the 8842 Protein (Variant Tcp1$_{Gz}$)

Protein 8842 is comprised of a variant of the entire *Gibberella zeae* Tcp1$_{Gz}$ protein (a Class B protein fused to a Class C protein). The DNA encoding the 8842 gene fusion as disclosed in SEQ ID NO:23 has been optimized for expression in plants. Nucleotides 3-7403 of SEQ ID NO:23 encode the entire Tcp1$_{Gz}$ protein variant as disclosed in SEQ ID NO:24.

The 8842 gene was cloned on an NcoI/SacI DNA fragment into an intermediate plasmid by standard molecular biology techniques. The 8842 gene expression cassette in the intermediate vector consisted of (in the 5' to 3' direction) a Cassava Vein Mosaic Virus (CsVMV) promoter (essentially bases 7160 to 7678 of Genbank Accession CVU58751), the *Nicotiana tabacum* osmotin 5' stabilizing sequence (See US Patent Application Publication US20050102713 A1), the 8842 variant gene coding region, a *Nicotiana tabacum* osmotin 3' stabilizing sequence (See U.S. Patent Application Publication US20050102713 A1), and the ORF24 3' untranslated region from *Agrobacterium tumefaciens* pTi-15955 (essentially the complement of bases 18621 to 19148 of Genbank Accession ATACH5). The 8842 gene plant expression cassette was then moved via Gateway LR clonase (Invitrogen, Carlsbad, Calif.) into an *Agrobacterium tumefaciens* plant transformation binary vector, and the resulting plasmid was named pDAB8842. The 8842 gene plant expression cassette in pDAB8842 is directly preceded by the RB7 matrix attachment region (MAR) from *Nicotiana tabacum* (Hall, Gerald, Jr.; Allen, George C.; Loer, Deborah S.; Thompson, William F.; Spiker, Steven. *Nuclear scaffolds and scaffold-attachment regions in higher plants*. Proc. Natl. Acad. Sci. USA (1991) 88:9320-9324.) To provide in planta selection for transformed cells, the binary vector included, immediately following the 8842 gene plant expression cassette, a selectable marker gene in the form of an *Arabidopsis thaliana* ubiquitin 10 promoter (Genbank Accession L05399), a coding region for phosphinothricin acetyl transferase (PAT; Genbank Accession 143995), and a 3' untranslated region (3' UTR) from ORF1 of *Agrobacterium tumefaciens* pTi-15955 (essentially bases 2180 to 2887 of Genbank Accession ATACH5).

The final order of the elements and expression cassettes in the binary plasmid pDAB8842 is as follows: pTi 15955 T-DNA Border B, *Nicotiana tabacum* RB7 MAR, the gene 8842 expression cassette, the PAT gene expression cassette, and three tandem copies of pTi-15955 T-DNA Border A. The constructions were done in such a way as to maintain appropriate plant transcription and translation signals. For plant transformation, the pDAB8842 plasmid was introduced into cells of *Agrobacterium tumefaciens* strain LBA4404 by electroporation.

EXAMPLE 23

Construction of a Binary Plant Expression Vector Containing a Second Version of a Gene Expressing the 8842 Protein (Variant $Tcp1_{Gz}$)

The 8842 protein coding region of SEQ ID NO:23 was cloned on an NcoI/SacI DNA fragment into an intermediate plasmid by standard molecular biology techniques. The 8842 gene expression cassette in the intermediate vector consisted of (in the 5' to 3' direction) an *Arabidopsis thaliana* Actin 2 promoter (Act2; Genbank Accession U41998), the 8842 variant gene coding region, and the ORF24 3' untranslated region from *Agrobacterium tumefaciens* pTi-15955 (essentially the complement of bases 18621 to 19148 of Genbank Accession ATACH5). The 8842 gene plant expression cassette was then moved via Gateway LR clonase (Invitrogen, Carlsbad, Calif.) into an *Agrobacterium tumefaciens* plant transformation binary vector, and the resulting plasmid was named pDAB8844. In plasmid DAB8844, all the elements and expression cassettes are present in the same order as described in Example 22 for plasmid pDAB8842, except that the 8842 gene cassette under the control of the CsVMV promoter present in pDAB8842 was replaced by this version of the 8842 gene under the control of the Act2 promoter. For plant transformation, the pDAB8844 plasmid was introduced into cells of *Agrobacterium tumefaciens* strain LBA4404 by electroporation.

EXAMPLE 24

Transformation of Cotton Cells

Seeds of cotton variety Coker 310 were surface-sterilized in 95% alcohol for 1 minute, rinsed with sterile distilled water, sterilized with 50% commercial bleach for 20 minutes, then rinsed again 3 times with sterile distilled water. Treated seeds were germinated at 28° C. on G-medium [Murashige and Skoog, 1962 (MS) basal salts with B5 vitamins (Gamborg et al., 1965) and 3% sucrose] in Magenta GA-7 vessels maintained under a high light intensity of 40-60μE/$m^2$, with a photoperiod of 16 hrs light and 8 hrs dark.

Cotyledon segments (~5 mm square) were isolated from 7-10 day old seedlings into liquid M-medium (MS-based medium with 1-5 μM 2,4-Dichlorophenoxyacetic acid and 1-5 μM Kinetin) in Petri plates. For each construct (i.e. pDAB8842 and pDAB8844), 200 cut segments were treated with a recombinant *Agrobacterium tumefaciens* strain LBA4404 suspension (approximately $10^6$ cells/mL), then transferred to semi-solid M-medium and co-cultivated for 2-3 days (in this and subsequent steps, incubation was carried out under light at 28° C.). Following co-cultivation, segments were transferred to MG5 medium, which contains 5 mg/L glufosinate-ammonium (to select for plant cells that contain the transferred gene) and 500 mg/L carbenicillin (to eliminate residual *Agrobacterium tumefaciens* cells). After 3 weeks, callus from the cotyledon segments was isolated and transferred to fresh MG5 medium then a second transfer to MG5 medium was made 3 weeks later. After an additional 3 weeks, callus was transferred to C-medium (MS-based medium containing 10-20 μM Napthaleneacetic Acid and 5-10 μM Kinetin) containing glufosinate-ammonium and carbenicillin as above, and transferred again to fresh selection medium after 3 weeks. For the pDAB8842 construct, 26 callus lines were obtained, and 25 callus lines were obtained for the pDAB8844 construct.

EXAMPLE 25

Expression of Variant $Tcp1_{Gz}$ in Cotton Callus

Callus plant tissues (200 mg) isolated following transformation with constructs pDAB8842 and pDAB8844 were frozen at −80° C. The frozen plant material was placed into a 1.2 mL polypropylene tube containing a 0.188 inch diameter tungsten bead with 450 μL of extraction buffer [Phosphate Buffered Saline with 0.1% Triton X-100, 10 mM Dithiothreitol and 5 μL/mL of protease inhibitor cocktail (Sigma Chemical Company, St. Louis, Mo.; catalog number P9599)] and homogenized for four minutes at maximum speed using a Kleco Pulverizer bead mill (Kleco, Visalia, Calif.). The resulting homogenate was centrifuged at 4,000×g for 10 min at 4° C., and the supernatant removed using a pipette. The protein concentration of the supernatant was determined by the method of Bradford [Bradford, M. M., (1976) *A rapid and sensitive method for the quantitation of microgram quantities of protein utilizing the principle of protein-dye binding*. Anal. Biochem.: 72:248-254.]. The volume of supernatant required to provide 2-5 μg of total protein was mixed 4:1 with 4×Tris-HCl, SDS, 2-mercaptoethanol sample buffer, (consisting of 0.125M Tris HCl, 10% sucrose, 0.02% bromophenol blue, 2.0% SDS, and 5% 2-mercaptoethanol). The solution was heated to 90° C. for 4 minutes, loaded into wells of a 4-20% Tris-glycine polyacrylamide gel (BioRad, Hercules, Calif.), and the proteins were separated by applying 100 volts of electricity for 60 minutes using the method of Laemmli [Laemmli, U. K:, (1970) *Cleavage of structural proteins during the assembly of the head of bacteriophage T*4. Nature: 227:680-685.]

Characterization of the expressed variant $Tcp1_G$ protein was done by immunoblot analysis [Towbin, H., Staehelin, T., and Gordon, J., (1979) *Electrophoretic transfer of proteins from polyacrylamide gels to nitrocellulose sheets: procedure and some applications*. Proc. Natl. Acad. Sci. USA 76:4350-4354.] Briefly, the protein samples separated by SDS-polyacrylamide gel electrophoresis (above) were electrophoretically transferred onto nitrocellulose at 100 V for 1 hour, blocked with 1% non-fat milk, and probed with a 1:3,000 dilution of one of two different primary monoclonal antibodies prepared from different sequences of the $Tcp1_{Gz}$ protein. One antibody (1184) was derived using a 17 amino acid synthetic peptide containing the sequence of residues 1184-1200 (from SEQ ID NO:2) from $Tcp1_{Gz}$ (SKTASAAEELKEARKSF as disclosed in SEQ ID NO:144 in the region corresponding to the "B" protein. The other antibody (1929) was derived from a synthetic 22 amino acid peptide containing the sequence from residues 1929-1950 (from SEQ ID NO:2) (YHYDEKSLLSDDPRVKSNRLSR as disclosed in SEQ ID NO:145 that resides in the area of the protein corresponding to the "C" protein. The nitrocellulose membrane containing the transferred proteins was allowed to incubate with either the 1184 or 1929 antibody overnight at 4° C. while gently rocking. After extensive washing of the nitrocellulose membrane, proteins related to $Tcp1_{Gz}$ produced by the callus tissues were detected using anti mouse ECL-conjugated secondary antibody (BioRad) and developed using ECL reagents (Amersham Biosciences, Arlington Heights, IL) according to the supplier's instructions. Relative molecular weights of the protein bands were determined by including a sample of SeeBlue™ prestained protein molecular weight markers (Invitrogen) in one well of the gel. Negative controls consisted of plant tissues from non-transformed callus processed in the same manner as described above. Positive controls consisted of insoluble proteins obtained from an extract of *E. coli* cells transformed with the *E. coli*-optimized $tcp1_{Gz}$ gene (construct pDAB8829).

Fifteen cotton calli from construct pDAB8842 and 13 calli from construct pDAB8844 were analyzed. The protein extracts were blotted in duplicate and probed separately with antibodies 1184 (B-region peptide) and 1929 (C-region peptide). Both antibodies revealed similar, but not identical, banding patterns. The calculated size of the intact variant $Tcp1_{Gz}$ protein (2467 amino acids; SEQ ID NO:24) is about 278 kDa. In all analyses, the positive control samples showed a smearing of proteins reactive to the antibodies, starting just below the position of the 250 kDa molecular weight standard, while there was no signal observed from the negative control samples of proteins extracted from non-transformed cotton calli. Of the 15 pDAB8842 construct samples (wherein the 8842 variant $Tcp1_{Gz}$ expression is driven by the CsVMV promoter), 11 showed a positive response, exhibiting a strong protein band at an apparent molecular weight just below 250 kDa, and a second protein band of generally less intensity above the 148 kDa molecular weight marker. Samples prepared from cotton calli transformed with the pDAB8844 construct (wherein the 8842 variant $Tcp1_{Gz}$ expression is driven by the Act2 promoter) resulted in significantly fewer positive responses compared to the pDAB8842 construct (only 2 of the 13 samples showed a positive response).

Cotton calli that expressed the 8842 variant $tcp1_{Gz}$ gene demonstrated different banding patterns when probed with the two peptide specific antibodies 1184 (B-region peptide) and 1929 (C-region peptide). Antibody 1184 bound to a single protein species having an apparent molecular weight greater than 148 kDa, but less than 250 kDa. Antibody 1929 bound to either one or two proteins (depending on the callus sample), both having an apparent molecular weight greater than 148 kDa, but less than 250 kDa.

Thus, these results show that proteins that are recognized by antibodies prepared against peptide fragments of the variant $Tcp1_{Gz}$ protein are produced by these plant tissues. Given the very large size of this protein, and the technical limitations of the resolution of the gel analyses, it is expected that the high molecular weight, immuno-reactive bands observed in both control samples and plant samples represent full-length $Tcp1_{Gz}$ proteins.

EXAMPLE 26

Toxin Complex Class A and Fused Class B/C Genes of *Fusarium verticillioides*

This example teaches a method to discover new Class A genes and new fused Class B/Class C genes present in the genome sequence of *Fusarium verticillioides* (teleomorph *Gibberella moniliformis*). It is to be noted that one life stage (anamorph) of *Gibberella zeae* is classsified as *Fusarium graminearum.*

Determination of the DNA sequence of the genome of the fungus *Fusarium verticillioides* is in progress at the Broad Institute (Cambridge, Mass.) and the partial genome is accessible to the public from the website (broad.mit.edu/annotation/fgi/). The DNA sequences of the *Gibberella zeae* Class A TC gene (SEQ ID NO:9) and of the *Gibberella zeae* $tcp1_{Gz}$ gene (SEQ ID NO:1) were used separately as query sequences in TBLASTN analyses of the partial sequence of the *F. verticillioides* genome (TBLASTN ver. 2.2.10; Oct. 19, 2004).

These analyses revealed the presence of two sequences corresponding to Class A TC genes, two sequences corresponding to fused ClassB/ClassC TC genes, as well as a partial Class A TC gene and a partial Class B TC gene. The contig sequences including and flanking these presumptive TC genes were extracted and further analyzed. The extracted contig sequences were named for convenience; AContig12, AContig34, BCContig12, BCContig6, and BCContig46.

The sequence of each contig was translated in silico to identify coding regions for peptides of 100 amino acids or longer (terminator to terminator), and each such putative protein was used as a query sequence in a BLAST analysis (BLASTP ver.2.2.3; Apr. 24, 2002) of the Genbank nonredundant protein database (National Center for Biotechnology Information; Database: db/nr.01; Posted date: Jan. 18, 2006 4:00 PM; Number of letters in database: 111,166,549; Number of sequences in database: 325,447).

Proteins with significant BLAST scores to a TC Class A, Class B or Class C gene were mapped back to the encoding DNA of the source contig. From each contig belonging to a single TC ClassA or TC ClassBC gene, the whole DNA sequence encompassing the region encoding the protein, plus 20 bp on either side, was extracted. In some cases, it was necessary to reverse and complement the DNA base sequence as present in a native contig in order to obtain a protein coding region in the standard 5' to 3' sense orientation.

The DNA sequence extracted from Acontig12 is presented as SEQ ID NO:25. This DNA sequence encodes a putative TC Class A protein in two overlapping segments, the deduced sequence of which is disclosed in SEQ ID NOs:26 and 27. The Threonine codon (ACG) that serves as the beginning of the open reading frame for the coding region of the first segment of the deduced putative TC Class A protein is residues 21-23 in SEQ ID NO:25. There is a probable sequencing error around base 3000 (not uncommon in large-scale genomic sequencing projects such as this), as the open reading frame encoding the first 1002 amino acids of the putative TC Class A protein is terminated by a TGA stop codon. However, the AAA Lysine codon (residues 3022-3024 in SEQ ID NO:25) which serves as the start of the open reading frame for the second portion of the deduced putative TC Class A protein begins 5 bases upstream of the TGA codon. By linking the two encoded peptides, comprising 1002 amino acids (SEQ ID NO:26) and 2057 amino acids (SEQ ID NO:26), and by analogy to the *G. zeae* genome sequence, it is likely that SEQ ID NO:25 is part of a complete open reading frame that encodes a TC Class A protein of approximately 3000 amino acids. The high relatedness of this deduced FV TC Class A protein to a *G. zeae* TC Class A protein is reflected by a BLAST score of e-146 for the first 1002 amino acids, and 0.0 for the second 2057 amino acids.

The DNA sequence extracted from Acontig34 is presented as SEQ ID NO:28. This DNA encodes a second putative TC Class A protein. The DNA sequence that encodes the putative TC Class A protein comprises a first portion of 3298 bases. This sequence is followed by a large gap in the DNA sequence, indicated as a string of 2098 Ns. Finally, the TC-encoding sequence comprises an additional 3773 bases. Residues 20-22 (AAT) at the beginning of the coding region in SEQ ID NO:28 correspond to the first Asparagine of the putative TC Class A encoded protein sequence in SEQ ID NO:29. This first portion of the DNA sequence preceding the Ns likely contains two sequencing errors which interrupt the deduced putative TC Class A protein reading frame into three parts. The first part of the open reading frame comprises 1452 bases and encodes 484 amino acids (SEQ ID NO:29). This part of the open reading frame is terminated with a TGA stop codon. The second part of the open reading frame starts 4 bases downstream of the TGA stop codon, comprises 690 bases, and encodes 230 amino acids (SEQ ID NO:30). This portion of the open reading frame is terminated with a TAA stop codon. The third portion of the open reading frame starts 11 bases downstream of the TAA stop codon, comprises 1122 bases, and encodes 374 amino acids (SEQ ID NO:31). The portion of the DNA sequence following the Ns comprises a fourth portion of the deduced putative TC Class A protein open reading frame, and encodes 1233 amino acids (SEQ ID NO:32). The GGA codon for the first Glycine of this portion of the deduced putative TC Class A protein corresponds to basepairs 5453-5453 of SEQ ID NO: 28. The total protein encoded by SEQ ID NO:28 thus is at least 2358 amino acids long. By analogy to the *G. zeae* genome sequence it is likely that SEQ ID NO:28 is part of a complete open reading frame that encodes a TC Class A protein of approximately 3000 amino acids. The high relatedness of this deduced FV TC Class A protein to a *G. zeae* TC Class A protein is reflected by a BLAST score of 4e-43 for the first 484 amino acids, 0.001 for the second 230 amino acids, 2e-14 for the next 374 amino acids, and 0.0 for the final 1233 amino acids.

The DNA sequence extracted from BCContig12 is presented as SEQ ID NO:33. This DNA sequence encodes a putative fused TC ClassB/Class C protein and comprises a first portion of 5482 bases. This sequence is followed by a large gap in the DNA sequence, indicated as a string of 659 Ns. Finally, the BCContig 12 sequence comprises an additional 1563 bases. Basepairs 22-24 (GCC) at the beginning of the coding region in SEQ ID NO:33 correspond to the first Alanine of the encoded putative TC fused ClassB/Class C protein in SEQ ID NO:33. This first portion of the encoded protein comprises 1820 amino acids (SEQ ID NO:34). There is a probable sequencing error just after the series of Ns, as the in-frame Histidine codon (CAT, bases 6203-6205 of SEQ ID NO:33) that starts the second portion of the putative TC fused ClassB/Class C protein is preceded by 61 out-of-frame bases. The second portion of the encoded putative TC fused ClassB/Class C protein comprises 494 amino acids (SEQ ID NO:35). The total protein encoded by SEQ ID NO:33 thus is at least 2314 amino acids long. By analogy to the *G. zeae* genome sequence it is likely that SEQ ID NO:33 is part of a complete open reading frame that encodes a TC fused ClassB/ClassC protein of approximately 2400 amino acids. The high relatedness of this deduced FV TC fused Class B/Class C protein to a *G. zeae* TC fused Class B/Class C protein is reflected by a BLAST score of 0.0 for the first 1820 amino acids and 5e-45 for the final 494 amino acids.

The DNA sequence extracted from BCContig6 is presented as SEQ ID NO:36. This DNA sequence encodes a portion of a putative fused TC Class B/Class C protein and comprises 962 bases. Residues 20-22 (CAG) at the beginning of the coding region in SEQ ID NO:36 correspond to the first Glutamine of the deduced putative TC fused Class B/Class C protein. This first portion of the deduced encoded protein comprises 194 amino acids (SEQ ID NO:37). There is a probable sequencing error just after the Leucine codon (TTG), as a Stop codon (TAG) terminates the reading frame. However, the Aspartic Acid codon (GAT, residues 619-621 of SEQ ID NO:36) that starts the second portion of the putative TC fused Class B/Class C protein is found 14 bases after the TAG codon. The second portion of the deduced putative TC fused Class B/Class C protein comprises 107 amino acids (SEQ ID NO:38). The protein encoded by SEQ ID NO:36 is thus likely to represent a portion of a TC fused Class B/Class C coding region. By analogy to the *G. zeae* genome sequence, it is likely that SEQ ID NO:36 is part of a complete open reading frame that encodes a TC fused Class B/Class C protein of approximately 2400 amino acids. The high relatedness of this deduced FV TC fused Class B/Class C protein to a *Photorhabdus* TC Class C protein is reflected by a BLAST score of 1e-11 for the first 194 amino acids. The remaining 107 amino acids has a BLAST score of 1e-10 to a *G. zeae* TC fused Class B/Class C protein.

The DNA sequence extracted from BCContig46 is presented as SEQ ID NO:39. This DNA sequence encodes a putative fused TC Class B/Class C protein. The DNA sequence that encodes the putative fused TC Class B/Class C protein comprises a first portion of 3423 bases. This sequence is followed by a large gap in the DNA sequence, indicated as a string of 1009 Ns. Finally, the TC-encoding sequence comprises an additional 3810 bases. Bases 21-23 (GAG) at the beginning of the coding region in SEQ ID NO:39 correspond to the first Glutamic Acid of the first portion of the deduced putative TC fused Class B/Class C protein. This first portion of the deduced encoded protein comprises 1134 amino acids (SEQ ID NO:40). The second portion of the deduced putative TC fused Class B/Class C protein comprises 1263 amino acids (SEQ ID NO:41). The TTG codon, which specifies the first Leucine of the second protion of the deduced TC fused Class B/Class C protein following the Ns, corresponds to residues 4435-4437 in SEQ ID NO:39. The protein encoded by SEQ ID NO:39 thus is likely to represent a TC fused Class B/Class C protein of at least 2309 amino acids. By analogy to the *G. zeae* genome sequence it is likely that SEQ ID NO:39 is part of a complete open reading frame that encodes a TC fused Class B/Class C protein of approximately 2400 amino acids. The high relatedness of this deduced FV TC fused Class B/Class C protein to a *G. zeae* TC fused Class B/Class C protein is reflected by a BLAST score of e-168 for the first 1134 amino acids and e-122 for the final 1263 amino acids.

EXAMPLE 27

Additional Natural B/C Fusions from *Burkholderia* and *Nitrosospora*

In light of the findings reported herein, additional BLAST searches (similar to those described in Examples above) were conducted. The results of TBLASTN of Genbank nonredundant nucleotide database with the *Gibberella zeae* fused Class B/Class C sequence are as follows:

LOCUS CP000125.1 3181762 bp DNA circular BCT 30-Sep.-2005
DEFINITION *Burkholderia pseudomallei* 1710b chromosome II, complete sequence.
BLAST score: 2e-92

LOCUS CP000103.1 3184243 bp DNA circular BCT 15-Nov.-2005
DEFINITION *Nitrosospira multiformis* ATCC 25196, complete genome.
BLAST score: 4e-68

LOCUS CP000086.1 3809201 bp DNA circular BCT 05-Jan.-2006
DEFINITION *Burkholderia thailandensis* E264 chromosome I, complete sequence.
BLAST score: 7e-47

LOCUS BX571965 4074542 bp DNA circular BCT 17-Apr.-2005
DEFINITION *Burkholderia pseudomallei* strain K96243, chromosome 1, complete sequence.

BLAST score: 1e-39

LOCUS CP000124.1 4126292 bp DNA circular BCT 30-Sep.-2005

DEFINITION *Burkholderia pseudomallei* 1710b chromosome I, complete sequence.

BLAST score: 3e-39

LOCUS CP000010.1 3510148 bp DNA circular BCT 22-Sep.-2004

DEFINITION *Burkholderia mallei* ATCC 23344 chromosome 1, complete sequence.

BLAST score: 3e-38

As *Burkholderia* and *Nitrosospira* are bacterial genera, these results, taken with the other results reported herein, further confirm that novel BC fusion proteins can be found in other naturally occurring organisms, particularly these novel bacterial sources.

EXAMPLE 28

Additional Class A Proteins from *Burkholderia* and *Aspergillus*

In light of the findings reported herein, additional BLAST searches (similar to those described in Examples above) were conducted. The results of TBLASTN of Genbank nonredundant nucleotide database with the *Gibberella zeae* Class A sequence are as follows:

LOCUS AP007171 2505489 bp DNA linear PLN 23-Dec.-2005

DEFINITION *Aspergillus oryzae* RIB40 genomic DNA, SC011.

BLAST score: 8e-97

LOCUS CP000125.1 3181762 bp DNA circular BCT 30-Sep.-2005

DEFINITION *Burkholderia pseudomallei* 1710b chromosome II, complete sequence.

BLAST score: 1e-63

LOCUS CP000010.1 3510148 bp DNA circular BCT 22-Sep.-2004

DEFINITION *Burkholderia mallei* ATCC 23344 chromosome 1, complete sequence.

BLAST score: 3e-08

LOCUS BX571965.1 4074542 bp DNA circular BCT 17-Apr.-2005

DEFINITION *Burkholderia pseudomallei* strain K96243, chromosome 1, complete sequence.

BLAST score: 3e-08

LOCUS CP000124.1 4126292 bp DNA circular BCT 30-Sep.-2005

DEFINITION *Burkholderia pseudomallei* 1710b chromosome I, complete sequence.

BLAST score: 3e-08

LOCUS CP000086.1 3809201 bp DNA circular BCT 05-Jan.-2006

DEFINITION *Burkholderia thailandensis* E264 chromosome I, complete sequence.

BLAST score: 8e-08

As *Burkholderia* is a bacterial genus, these results, taken with the other results reported herein, are particularly noteworthy because they confirm that Class A proteins can be found, along with novel BC fusion proteins of the subject invention, in novel bacterial sources. As *Aspergillus* is a (eukaryotic) fungal genus, these results are also particularly noteworthy because they confirm that Class A proteins can be found in various eukaryotic and fungal sources.

SEQUENCE LISTING

```
<160> NUMBER OF SEQ ID NOS: 145

<210> SEQ ID NO 1
<211> LENGTH: 7401
<212> TYPE: DNA
<213> ORGANISM: Artificial sequence
<220> FEATURE:
<223> OTHER INFORMATION: Native genomic DNA sequence tcp1Gz encoding a
      fused Class B/Class C protein of Gibberella zeae PH1 NRRL 31084

<400> SEQUENCE: 1

atgtcaactc tttccagtcg tcctggagac cctcgcgccc tccactctgg acagaacaac      60

ggagcacccg aaaccctgac caactcaaaa agcaatgcca ctctatctgg aaaccgcacc     120

acggctccag cctcggcatc ttcatttgct ccacaagtcc gtacactggg tgaaggaatc     180

ccaggctttc gtacctcatt caacgtcgca ggtaaaggcg gcggagcgtt caggtccatc     240

agcgaggact tcgaagtgag ccctgccaat ggcaccatgt cacttgccat ccctgtgcgc     300

acgtcaccta cccgtggagg ctacggacca gatctgaagc tctcgtacga ctcgggttcg     360

ggaaatggac cgttcggatt tggctggagt atgtcaatgc cgtccattca tcgtaagaca     420

acacatgcta taccgcgata tgtggacgat gaggatgatt ttctcatgtc tggtggagac     480

atcattaaga ggttgaatag tgagggtata caagagacaa gaaatgaatc tggcatttgt     540

ggaaagtttc ttgttaccac atatcgtcca cgagtcgact ctgggaacat acgaatcgag     600

agatgggttc gcagagagga tctcgaagac gtgcactgga ggacaatctc gtccagcaac     660
```

-continued

```
gagactaaaa tctacggtga tagtgacagc agccgcatct ttgacgcttc tggcccatca    720
aagaggatct tctcttggct tttaagccga tcttatgatg catcaggcaa tgcaattgag    780
tatgtataca aagaagaaga ctcgttgggc atttctgatg ctactggagc catgcctgtg    840
tgggaaaaga atcgggaaca agacgcaaga taccgcgaga gatatatcaa acgagtcaag    900
tacggaaaca gaaagccaaa ccgtgatctt actacttggg aagtatcgga ttggcccgaa    960
gaatggatgt ttgaggtcgt ctttgactat ggagaacacg ataaaggcag tccaagcact   1020
gaagaatccc attcctggcc agttcgtcaa gatgtgtttt cacagagtcg ccctggattt   1080
gaaatccgta cctatcgtct ttgtcgccga gttctcatgt tccaccactt ccccgaacac   1140
acccaagagt cagagacttt cgtcttctcg acagatcttc agtacaacga gtctcgacaa   1200
aggactgttt tggccagctt ggtcgcaaca ggatactcgt cctacaaaga caacaatgat   1260
gggaaacaaa ggtacagatc agagtctctg ccgccatggt catttgagta cacaagttcc   1320
cccgaggcca gcgagattga actcatggag gcaaagactt ttaacctact cgaacttcct   1380
acatctgatg cacgagtttc agagtggctg gatctcgacg gcgatggtat gccagggctg   1440
ttgacaaggt ctgtagatgg cgccctctat tatcaacgca atcttgggtc aatttctggt   1500
gacgatgacc cacagttctg tggtccagtc cttctcgcac aacagcccag tatgactggc   1560
gggactttcc aagaccttga tcgaaatgga aacctcaact acgttctccg taacgagcat   1620
ggtcaccttg agggatacta tgaacgaggc aattctgata cctggaagaa ctacatcgaa   1680
tttccagaaa caagcaacgg ggatatatgg cagagcacta tcgacatcga cttgacgggc   1740
gacggtcatc ccgaccttat ctgtgcagca gatgattccc aagtcttgat ttggcagcag   1800
aacctcggaa agaaaggcct ctccagctat caacgtgtca tatgcggaca tgattgggag   1860
tcttgtccac gcttgatcaa aaaccaagat gtccagacct atgttggaga tatgactggt   1920
agcggcatgt cggacctagt tgagatctca gtatcgtcgg ttagatattg gccaaacctt   1980
ggctatggaa catttggtgc tgcagtagat atgggaaacc caccagcatt tgctgccaag   2040
gactactttg atcacagtcg agttagactc atggacaccg atggtagtgg cactatggat   2100
ctcctctacg ctctgccaac agggggcgca gctttgtact acaaccttgc tggcaattca   2160
tggagtaaca tggtattcct tccccatctc ccggctatta tcacgcctat gtcgatattt   2220
accttggatc taattggcaa gggggcggat tgtctttgtt gggcagatac ttcaactgat   2280
gggaacagga ttatgtacct cgacatcacg ggagaaacaa aaccgcatct gttgaagtct   2340
tacagcaatg gttggggtgc aacaacgtca gtggactacg ctccatcgac caagttcttc   2400
gcggaagata ccagaaatgg acacccgtgg tcaagcaaat tgccattccc agttcaatgt   2460
gtctcaaagg tccaagtcga ggatgccatc actgggaatc gacagtctac cgaatacatc   2520
taccacaacg gttgctacaa cccgaccgag aagcaatttt ctggctttga gatggtagaa   2580
cagtttcaga gcgaaagagt catcgttgga gaggatgaga catatgagcc tcctgttaca   2640
cacaccaagt cgtggttcaa cgttggtctg agccttgtag ttgatgagtc gcgctttttg   2700
accaagccag ccattctctc tagtctacag gattaccaca cggatcccgc ggagcttgtg   2760
aacgcactga aagggctcaa cgtgcgatcg gagatatata gtcaggatgg aagccccaag   2820
tctcacttgc cctacgttat caaggaggtg tcgtaccatg tcaagatctc gcaagcacga   2880
gacacaaaca agtattccgc agtccaggta ctcccgcgtg agacattctc gagagcgtac   2940
gagagggata tgagtgatcc acgtgtcaca cacgatatgg tgatcaagac caacgacttt   3000
ggagacgttg aggaaagcct gagtatcgtg tatcctcgtg ctgggaagac cacattcgaa   3060
```

-continued

```
gatgtgaaca agaatcaaaa ggctggaaac atgtcctaca cccagaattg gtatacaaag   3120
atggtgtcag aacctgaaca ggaacacttc cgcaagcctg cagcgtacag gcaacaggaa   3180
cacgagatac tcagctttcc attcaatggg accctcaagt tcgacgacgc tcttgcgttc   3240
aacttcaatg gattgcccac cacaaaatgc tcgaaaacat ggaaggctct acgcagcgag   3300
aacaaggcgt tttacaaaga ctctctcttg cagagaagac ttgacgaagg cgagctgcag   3360
acgttttcac tgcttgatca gacctatgcc ctggccttta caccagacat cctagccaaa   3420
gtcgaaatag gtttacggaa ttgcaatgtt cccggctcag tcgaagagct tttgaccaaa   3480
gggtcatacg tgaagctgaa agacagtgac ggttggtggg ctccatcgtc tcagtcattt   3540
ttctgttcat ccaagactgc atcggcagct gaagagctca aagaggcacg caaatccttc   3600
tacacccctt cgcgcttcgt cgacctgttt ggcaactcgt cacggcttaa catggataag   3660
gacttcctat tagccacaga agttgaggat gctataggaa ctgcgacctc gttcaaaaac   3720
agctacgagc acttgcagcc tgtggagatc atcgatgcca atagtaattc cgtacaagtc   3780
gtgctggatc cactgggcga gtcgatcgcg gttgcagctt cgacaagacg cgacggggtt   3840
atagaagaga tagacagcct ggagaatatg gtcttagatg ccagccctga agatgtagac   3900
gacattcttc gcgatcctac gggcgaggtc tcgactcgtc ttttgggtaa tgctgcaagc   3960
aggactatcc attaccgcga tagatatgcc caatggaagt ctcgtcagaa tgagacatca   4020
acatcagtcg atccggaacc agcattgtca cttgttctat cacgggacct ttcattcaag   4080
gagtccagta gtcctgagat tcgagtcatc gtttcgtaca tgaatggact tgggtcgcag   4140
taccaggagc agcacctgag tgacccaact acgttggaaa aacgatggtt ggtacctggc   4200
cttgccattc cagacactca aggccaagtt gtgtgcacat accaacctcg gtttgcaact   4260
ttagcagcgc caattccatc cagtttgatg aagactaacg ctgcattcac cttttacgat   4320
gcaatgggtc gcaatgttgc gtcccttgct gccgattgca cttggtcgaa aacagtgtat   4380
accccatgga cgacagttga acatggagca ggaagcatgg tacttcagtc caacgcacga   4440
gatgatcctg atgttggcca tttcttctcc cgaatcgcat cctcccgata ctctcaaagt   4500
tggtacgaca agcgcaagct tggaacagca caagagaagc gagctgcaga gaaatcagct   4560
gtatactccg atactccact tactactcat tcgggtagct gcggacttcc tgttagaact   4620
atccaacaag ccggtggcaa gacatacaca cggagctcca tgtatgatgt gagtggcaat   4680
aggattcgag atgtcgactc gtatgaacgg accgtagaaa agatgctata cgataaactt   4740
ggtcgacagc ttcagactac aggcatggac tgcggtgaat catggctgct gctagatgcc   4800
cagggagggg agattctgtc ctggaattgt cgtggatact ctttcatcac tcgttacgat   4860
cccctacgtc gggagactga gagattagtt gcgaaagccg cagagatgcc gaagctcatc   4920
tcacgaatca cgtacggaga gacctgtggc gatgccatca acctgaactt gaatggccaa   4980
gtatggaaag tggaagatca agctggtgtt catatcaata cccattacaa catccgcggc   5040
cactgtctag ggaaaacatt acagttcaca aaagagtata agcaactggt cgattggaaa   5100
cttgatcaga cgcttgaaac ggaagtctac ccgcatacat acttctatga taactatggt   5160
caagtgttac aggaagagga tgagcaggga aaccgcacaa gaagaaatta ttcacgacaa   5220
gggcatgtcg tttcggtcga tttcagttcc ataaagggtc gtgactggaa gtcatatctc   5280
tcaggggcaa ccttttcagc tgatgggctg cctataacta tcaagtatgg gaatggagtc   5340
gtttctgact ttttctacga tgacgagtcc agaaacctca tctcgcaaag aactacgcgc   5400
```

-continued

```
ccatgccggg gtagaagaga gttgcttcaa gacaggacac acgtttatga ctacgtaggg   5460

cgtcgaatat ttacctccga tggctcagaa caagtcaagt actttggtga aagtcgcgtc   5520

aagcccgagt gggactacac atacaatgcg accggtgccc tggtgattgc cacagggaga   5580

gctcaactct ctggaaagat tggaaatggc aaccagttga caccccacaa cgcaatgaac   5640

ggactgaacc catcgcgcgg tggtggcgat ggcaatttac tttaccaata tcgcgagaca   5700

tatgattatg atcgtgaggg caatatcttg atgatgaagc atgaggcgcc tgacatcaaa   5760

ggggttacaa gctggacgag aaactatcat tacgatgaga agagtttact aagcgacgat   5820

ccccgcgtta agagcaaccg tcttagtcgg acgtcaattg gagacacaaa cgagggcaag   5880

tacatgtatg aaggcagtgc cggtctctca ggctgcataa cgacgctacc gaaattctcc   5940

gagctcgatt ggaacatgaa caatatgctc tccttctcgt caacgcagta cgtcaacgct   6000

ggcactccag agagaacata ctatgtctac gaccacgcgg gcaaccgtgt gcgaaaggtg   6060

accgagactg cagccaaatc tggtgaggag cctcgtaaac aaagggatac attgtttttc   6120

ggtggagtcg aactgcaaac aaaaaagcaac ggatcactct tatggaccac gcgtgtcaag   6180

ggtgatggta tcgtggctgt ggtggaggtc aatagaaatc aagagacacc gttggtgcga   6240

ttccaggcgg gacgcgacat ggagttcgac gaccaagcac agctcatctc atatgaagag   6300

tactcgccct tcggtgccgt ggtttacgcg gctatgtacg ggaatatcga agcgcctcgg   6360

gcatatcgtt tcgccaggta tgagcatgac agcgagacgg gcttgtacca ctgtggacag   6420

cgctactatt gcccatggct gggccgttgg acgtctccag atcctcttgg tgacgtagat   6480

gggccgaacc tttttgtata tgtgaataac gatcctgtaa actcgcacga tccttcggga   6540

acatctggca agaaaacgaa agagggcacc agagaaatgt acgcggcacc cgacgatcaa   6600

gggaagagac gtcttgtgga tgagaataag gcagtggccg accgcatagc gaagtatgag   6660

aggaaattac aacgacaaga acggaaacag caacgagcca tagctagaat gtctggcaca   6720

gatcccatcc taggttccag ggcacggtac gcggttggca tagccgcaat gggcaatgca   6780

ctgggccgca tttcaggaag tacagaactc catcatacct atccacaaga gtacagggag   6840

gagttttccg acatcgacat caatgttgac aggacttcgg tgtctatttc aaaggaggca   6900

cattatatct gcacttatgg cagcattctg gacaaccttg ttgccaccaa caaacgatgg   6960

aagagcgagt attttgatac accggacact ggttattatg agcagatgga gcaacacgag   7020

tggtatgacg atgaccctgg tatgcagtac gcgatacgtc tgcatttggc ctatgaggct   7080

cgcaccctaa acggtaaaat catggctgat tttggcataa accccaaagg cgaagatggg   7140

aggagtatgt ttgtgaatta cgatgccgtg acaaaaatga ggacggcagg gcaaaggagg   7200

ggcgtgcgga atgataattt gatacaccac gaaacatggc ctggtaggcc gtttaatact   7260

ggtaacagcg atacggacaa cgctggcgga cctgtgcatt tccaagtggc tgaggagcag   7320

tataatggcc ttgatgctga tgcgcaggcg aagtttgatg acttaaggaa ccagatggaa   7380

gctcttttgg ggaagagata g                                             7401
```

<210> SEQ ID NO 2
<211> LENGTH: 2466
<212> TYPE: PRT
<213> ORGANISM: Artificial Sequence
<220> FEATURE:
<223> OTHER INFORMATION: Native amino sequence of fused Class B/Class C protein Tcp1Gz of Gibberella zeae PH1 NRRL 31084.

<400> SEQUENCE: 2

-continued

```
Met Ser Thr Leu Ser Ser Arg Pro Gly Asp Pro Arg Ala Leu His Ser
1               5                   10                  15

Gly Gln Asn Asn Gly Ala Pro Glu Thr Leu Thr Asn Ser Lys Ser Asn
            20                  25                  30

Ala Thr Leu Ser Gly Asn Arg Thr Thr Ala Pro Ala Ser Ala Ser Ser
        35                  40                  45

Phe Ala Pro Gln Val Arg Thr Leu Gly Glu Gly Ile Pro Gly Phe Arg
    50                  55                  60

Thr Ser Phe Asn Val Ala Gly Lys Gly Gly Gly Ala Phe Arg Ser Ile
65                  70                  75                  80

Ser Glu Asp Phe Glu Val Ser Pro Ala Asn Gly Thr Met Ser Leu Ala
                85                  90                  95

Ile Pro Val Arg Thr Ser Pro Thr Arg Gly Gly Tyr Gly Pro Asp Leu
            100                 105                 110

Lys Leu Ser Tyr Asp Ser Gly Ser Gly Asn Gly Pro Phe Gly Phe Gly
        115                 120                 125

Trp Ser Met Ser Met Pro Ser Ile His Arg Lys Thr Thr His Ala Ile
    130                 135                 140

Pro Arg Tyr Val Asp Asp Glu Asp Asp Phe Leu Met Ser Gly Gly Asp
145                 150                 155                 160

Ile Ile Lys Arg Leu Asn Ser Glu Gly Ile Gln Glu Thr Arg Asn Glu
                165                 170                 175

Ser Gly Ile Cys Gly Lys Phe Leu Val Thr Thr Tyr Arg Pro Arg Val
            180                 185                 190

Asp Ser Gly Asn Ile Arg Ile Glu Arg Trp Val Arg Arg Glu Asp Leu
        195                 200                 205

Glu Asp Val His Trp Arg Thr Ile Ser Ser Ser Asn Glu Thr Lys Ile
    210                 215                 220

Tyr Gly Asp Ser Asp Ser Ser Arg Ile Phe Asp Ala Ser Gly Pro Ser
225                 230                 235                 240

Lys Arg Ile Phe Ser Trp Leu Leu Ser Arg Ser Tyr Asp Ala Ser Gly
                245                 250                 255

Asn Ala Ile Glu Tyr Val Tyr Lys Glu Glu Asp Ser Leu Gly Ile Ser
            260                 265                 270

Asp Ala Thr Gly Ala Met Pro Val Trp Glu Lys Asn Arg Glu Gln Asp
        275                 280                 285

Ala Arg Tyr Arg Glu Arg Tyr Ile Lys Arg Val Lys Tyr Gly Asn Arg
    290                 295                 300

Lys Pro Asn Arg Asp Leu Thr Thr Trp Glu Val Ser Asp Trp Pro Glu
305                 310                 315                 320

Glu Trp Met Phe Glu Val Val Phe Asp Tyr Gly Glu His Asp Lys Gly
                325                 330                 335

Ser Pro Ser Thr Glu Glu Ser His Ser Trp Pro Val Arg Gln Asp Val
            340                 345                 350

Phe Ser Gln Ser Arg Pro Gly Phe Glu Ile Arg Thr Tyr Arg Leu Cys
        355                 360                 365

Arg Arg Val Leu Met Phe His His Phe Pro Glu His Thr Gln Glu Ser
    370                 375                 380

Glu Thr Phe Val Phe Ser Thr Asp Leu Gln Tyr Asn Glu Ser Arg Gln
385                 390                 395                 400

Arg Thr Val Leu Ala Ser Leu Val Ala Thr Gly Tyr Ser Ser Tyr Lys
                405                 410                 415

Asp Asn Asn Asp Gly Lys Gln Arg Tyr Arg Ser Glu Ser Leu Pro Pro
```

-continued

```
            420                 425                 430

Trp Ser Phe Glu Tyr Thr Ser Ser Pro Glu Ala Ser Glu Ile Glu Leu
        435                 440                 445

Met Glu Ala Lys Thr Phe Asn Leu Leu Glu Leu Pro Thr Ser Asp Ala
    450                 455                 460

Arg Val Ser Glu Trp Leu Asp Leu Asp Gly Asp Gly Met Pro Gly Leu
465                 470                 475                 480

Leu Thr Arg Ser Val Asp Gly Ala Leu Tyr Tyr Gln Arg Asn Leu Gly
                485                 490                 495

Ser Ile Ser Gly Asp Asp Asp Pro Gln Phe Cys Gly Pro Val Leu Leu
            500                 505                 510

Ala Gln Gln Pro Ser Met Thr Gly Gly Thr Phe Gln Asp Leu Asp Arg
        515                 520                 525

Asn Gly Asn Leu Asn Tyr Val Leu Arg Asn Glu His Gly His Leu Glu
    530                 535                 540

Gly Tyr Tyr Glu Arg Gly Asn Ser Asp Thr Trp Lys Asn Tyr Ile Glu
545                 550                 555                 560

Phe Pro Glu Thr Ser Asn Gly Asp Ile Trp Gln Ser Thr Ile Asp Ile
                565                 570                 575

Asp Leu Thr Gly Asp Gly His Pro Asp Leu Ile Cys Ala Ala Asp Asp
            580                 585                 590

Ser Gln Val Leu Ile Trp Gln Gln Asn Leu Gly Lys Lys Gly Leu Ser
        595                 600                 605

Ser Tyr Gln Arg Val Ile Cys Gly His Asp Trp Glu Ser Cys Pro Arg
    610                 615                 620

Leu Ile Lys Asn Gln Asp Val Gln Thr Tyr Val Gly Asp Met Thr Gly
625                 630                 635                 640

Ser Gly Met Ser Asp Leu Val Glu Ile Ser Val Ser Ser Val Arg Tyr
                645                 650                 655

Trp Pro Asn Leu Gly Tyr Gly Thr Phe Gly Ala Ala Val Asp Met Gly
            660                 665                 670

Asn Pro Pro Ala Phe Ala Ala Lys Asp Tyr Phe Asp His Ser Arg Val
        675                 680                 685

Arg Leu Met Asp Thr Asp Gly Ser Gly Thr Met Asp Leu Leu Tyr Ala
    690                 695                 700

Leu Pro Thr Gly Gly Ala Ala Leu Tyr Tyr Asn Leu Ala Gly Asn Ser
705                 710                 715                 720

Trp Ser Asn Met Val Phe Leu Pro His Leu Pro Ala Ile Ile Thr Pro
                725                 730                 735

Met Ser Ile Phe Thr Leu Asp Leu Ile Gly Lys Gly Ala Asp Cys Leu
            740                 745                 750

Cys Trp Ala Asp Thr Ser Thr Asp Gly Asn Arg Ile Met Tyr Leu Asp
        755                 760                 765

Ile Thr Gly Glu Thr Lys Pro His Leu Leu Lys Ser Tyr Ser Asn Gly
    770                 775                 780

Trp Gly Ala Thr Thr Ser Val Asp Tyr Ala Pro Ser Thr Lys Phe Phe
785                 790                 795                 800

Ala Glu Asp Thr Arg Asn Gly His Pro Trp Ser Ser Lys Leu Pro Phe
                805                 810                 815

Pro Val Gln Cys Val Ser Lys Val Gln Val Glu Asp Ala Ile Thr Gly
            820                 825                 830

Asn Arg Gln Ser Thr Glu Tyr Ile Tyr His Asn Gly Cys Tyr Asn Pro
        835                 840                 845
```

-continued

```
Thr Glu Lys Gln Phe Ser Gly Phe Glu Met Val Glu Gln Phe Gln Ser
    850                 855                 860

Glu Arg Val Ile Val Gly Glu Asp Glu Thr Tyr Glu Pro Pro Val Thr
865                 870                 875                 880

His Thr Lys Ser Trp Phe Asn Val Gly Leu Ser Leu Val Val Asp Glu
                885                 890                 895

Ser Arg Phe Leu Thr Lys Pro Ala Ile Leu Ser Ser Leu Gln Asp Tyr
            900                 905                 910

His Thr Asp Pro Ala Glu Leu Val Asn Ala Leu Lys Gly Leu Asn Val
        915                 920                 925

Arg Ser Glu Ile Tyr Ser Gln Asp Gly Ser Pro Lys Ser His Leu Pro
    930                 935                 940

Tyr Val Ile Lys Glu Val Ser Tyr His Val Lys Ile Ser Gln Ala Arg
945                 950                 955                 960

Asp Thr Asn Lys Tyr Ser Ala Val Gln Val Leu Pro Arg Glu Thr Phe
                965                 970                 975

Ser Arg Ala Tyr Glu Arg Asp Met Ser Asp Pro Arg Val Thr His Asp
            980                 985                 990

Met Val Ile Lys Thr Asn Asp Phe  Gly Asp Val Glu Glu  Ser Leu Ser
        995                 1000                1005

Ile Val  Tyr Pro Arg Ala Gly  Lys Thr Thr Phe Glu  Asp Val Asn
    1010                 1015                 1020

Lys Asn  Gln Lys Ala Gly Asn  Met Ser Tyr Thr Gln  Asn Trp Tyr
    1025                 1030                 1035

Thr Lys  Met Val Ser Glu Pro  Glu Gln Glu His Phe  Arg Lys Pro
    1040                 1045                 1050

Ala Ala  Tyr Arg Gln Gln Glu  His Glu Ile Leu Ser  Phe Pro Phe
    1055                 1060                 1065

Asn Gly  Thr Leu Lys Phe Asp  Asp Ala Leu Ala Phe  Asn Phe Asn
    1070                 1075                 1080

Gly Leu  Pro Thr Thr Lys Cys  Ser Lys Thr Trp Lys  Ala Leu Arg
    1085                 1090                 1095

Ser Glu  Asn Lys Ala Phe Tyr  Lys Asp Ser Leu Leu  Gln Arg Arg
    1100                 1105                 1110

Leu Asp  Glu Gly Glu Leu Gln  Thr Phe Ser Leu Leu  Asp Gln Thr
    1115                 1120                 1125

Tyr Ala  Leu Ala Phe Thr Pro  Asp Ile Leu Ala Lys  Val Glu Ile
    1130                 1135                 1140

Gly Leu  Arg Asn Cys Asn Val  Pro Gly Ser Val Glu  Glu Leu Leu
    1145                 1150                 1155

Thr Lys  Gly Ser Tyr Val Lys  Leu Lys Asp Ser Asp  Gly Trp Trp
    1160                 1165                 1170

Ala Pro  Ser Ser Gln Ser Phe  Phe Cys Ser Ser Lys  Thr Ala Ser
    1175                 1180                 1185

Ala Ala  Glu Glu Leu Lys Glu  Ala Arg Lys Ser Phe  Tyr Thr Pro
    1190                 1195                 1200

Ser Arg  Phe Val Asp Leu Phe  Gly Asn Ser Ser Arg  Leu Asn Met
    1205                 1210                 1215

Asp Lys  Asp Phe Leu Leu Ala  Thr Glu Val Glu Asp  Ala Ile Gly
    1220                 1225                 1230

Thr Ala  Thr Ser Phe Lys Asn  Ser Tyr Glu His Leu  Gln Pro Val
    1235                 1240                 1245
```

-continued

```
Glu Ile  Ile Asp Ala Asn Ser  Asn Ser Val Gln Val  Val Leu Asp
    1250                 1255                 1260

Pro Leu  Gly Glu Ser Ile Ala  Val Ala Ala Ser Thr  Arg Arg Asp
    1265                 1270                 1275

Gly Val  Ile Glu Glu Ile Asp  Ser Leu Glu Asn Met  Val Leu Asp
    1280                 1285                 1290

Ala Ser  Pro Glu Asp Val Asp  Asp Ile Leu Arg Asp  Pro Thr Gly
    1295                 1300                 1305

Glu Val  Ser Thr Arg Leu Leu  Gly Asn Ala Ala Ser  Arg Thr Ile
    1310                 1315                 1320

His Tyr  Arg Asp Arg Tyr Ala  Gln Trp Lys Ser Arg  Gln Asn Glu
    1325                 1330                 1335

Thr Ser  Thr Ser Val Asp Pro  Glu Pro Ala Leu Ser  Leu Val Leu
    1340                 1345                 1350

Ser Arg  Asp Leu Ser Phe Lys  Glu Ser Ser Ser Pro  Glu Ile Arg
    1355                 1360                 1365

Val Ile  Val Ser Tyr Met Asn  Gly Leu Gly Ser Gln  Tyr Gln Glu
    1370                 1375                 1380

Gln His  Leu Ser Asp Pro Thr  Thr Leu Glu Lys Arg  Trp Leu Val
    1385                 1390                 1395

Pro Gly  Leu Ala Ile Pro Asp  Thr Gln Gly Gln Val  Val Cys Thr
    1400                 1405                 1410

Tyr Gln  Pro Arg Phe Ala Thr  Leu Ala Ala Pro Ile  Pro Ser Ser
    1415                 1420                 1425

Leu Met  Lys Thr Asn Ala Ala  Phe Thr Phe Tyr Asp  Ala Met Gly
    1430                 1435                 1440

Arg Asn  Val Ala Ser Leu Ala  Ala Asp Cys Thr Trp  Ser Lys Thr
    1445                 1450                 1455

Val Tyr  Thr Pro Trp Thr Thr  Val Glu His Gly Ala  Gly Ser Met
    1460                 1465                 1470

Val Leu  Gln Ser Asn Ala Arg  Asp Asp Pro Asp Val  Gly His Phe
    1475                 1480                 1485

Phe Ser  Arg Ile Ala Ser Ser  Arg Tyr Ser Gln Ser  Trp Tyr Asp
    1490                 1495                 1500

Lys Arg  Lys Leu Gly Thr Ala  Gln Glu Lys Arg Ala  Ala Glu Lys
    1505                 1510                 1515

Ser Ala  Val Tyr Ser Asp Thr  Pro Leu Thr Thr His  Ser Gly Ser
    1520                 1525                 1530

Cys Gly  Leu Pro Val Arg Thr  Ile Gln Gln Ala Gly  Gly Lys Thr
    1535                 1540                 1545

Tyr Thr  Arg Ser Ser Met Tyr  Asp Val Ser Gly Asn  Arg Ile Arg
    1550                 1555                 1560

Asp Val  Asp Ser Tyr Glu Arg  Thr Val Glu Lys Met  Leu Tyr Asp
    1565                 1570                 1575

Lys Leu  Gly Arg Gln Leu Gln  Thr Thr Gly Met Asp  Cys Gly Glu
    1580                 1585                 1590

Ser Trp  Leu Leu Leu Asp Ala  Gln Gly Gly Glu Ile  Leu Ser Trp
    1595                 1600                 1605

Asn Cys  Arg Gly Tyr Ser Phe  Ile Thr Arg Tyr Asp  Pro Leu Arg
    1610                 1615                 1620

Arg Glu  Thr Glu Arg Leu Val  Ala Lys Ala Ala Glu  Met Pro Lys
    1625                 1630                 1635

Leu Ile  Ser Arg Ile Thr Tyr  Gly Glu Thr Cys Gly  Asp Ala Ile
```

-continued

```
    1640                1645                1650

Asn Leu  Asn Leu Asn Gly Gln  Val Trp Lys Val Glu  Asp Gln Ala
    1655                1660                1665

Gly Val  His Ile Asn Thr His  Tyr Asn Ile Arg Gly  His Cys Leu
    1670                1675                1680

Gly Lys  Thr Leu Gln Phe Thr  Lys Glu Tyr Lys Gln  Leu Val Asp
    1685                1690                1695

Trp Lys  Leu Asp Gln Thr Leu  Glu Thr Glu Val Tyr  Pro His Thr
    1700                1705                1710

Tyr Phe  Tyr Asp Asn Tyr Gly  Gln Val Leu Gln Glu  Glu Asp Glu
    1715                1720                1725

Gln Gly  Asn Arg Thr Arg Arg  Asn Tyr Ser Arg Gln  Gly His Val
    1730                1735                1740

Val Ser  Val Asp Phe Ser Ser  Ile Lys Gly Arg Asp  Trp Lys Ser
    1745                1750                1755

Tyr Leu  Ser Gly Ala Thr Phe  Ser Ala Asp Gly Leu  Pro Ile Thr
    1760                1765                1770

Ile Lys  Tyr Gly Asn Gly Val  Val Ser Asp Phe Phe  Tyr Asp Asp
    1775                1780                1785

Glu Ser  Arg Asn Leu Ile Ser  Gln Arg Thr Thr Arg  Pro Cys Arg
    1790                1795                1800

Gly Arg  Arg Glu Leu Leu Gln  Asp Arg Thr His Val  Tyr Asp Tyr
    1805                1810                1815

Val Gly  Arg Arg Ile Phe Thr  Ser Asp Gly Ser Glu  Gln Val Lys
    1820                1825                1830

Tyr Phe  Gly Glu Ser Arg Val  Lys Pro Glu Trp Asp  Tyr Thr Tyr
    1835                1840                1845

Asn Ala  Thr Gly Ala Leu Val  Ile Ala Thr Gly Arg  Ala Gln Leu
    1850                1855                1860

Ser Gly  Lys Ile Gly Asn Gly  Asn Gln Leu Thr Pro  His Asn Ala
    1865                1870                1875

Met Asn  Gly Leu Asn Pro Ser  Arg Gly Gly Gly Asp  Gly Asn Leu
    1880                1885                1890

Leu Tyr  Gln Tyr Arg Glu Thr  Tyr Asp Tyr Asp Arg  Glu Gly Asn
    1895                1900                1905

Ile Leu  Met Met Lys His Glu  Ala Pro Asp Ile Lys  Gly Val Thr
    1910                1915                1920

Ser Trp  Thr Arg Asn Tyr His  Tyr Asp Glu Lys Ser  Leu Leu Ser
    1925                1930                1935

Asp Asp  Pro Arg Val Lys Ser  Asn Arg Leu Ser Arg  Thr Ser Ile
    1940                1945                1950

Gly Asp  Thr Asn Glu Gly Lys  Tyr Met Tyr Glu Gly  Ser Ala Gly
    1955                1960                1965

Leu Ser  Gly Cys Ile Thr Thr  Leu Pro Lys Phe Ser  Glu Leu Asp
    1970                1975                1980

Trp Asn  Met Asn Asn Met Leu  Ser Phe Ser Ser Thr  Gln Tyr Val
    1985                1990                1995

Asn Ala  Gly Thr Pro Glu Arg  Thr Tyr Tyr Val Tyr  Asp His Ala
    2000                2005                2010

Gly Asn  Arg Val Arg Lys Val  Thr Glu Thr Ala Ala  Lys Ser Gly
    2015                2020                2025

Glu Glu  Pro Arg Lys Gln Arg  Asp Thr Leu Phe Phe  Gly Gly Val
    2030                2035                2040
```

-continued

```
Glu Leu  Gln Thr Lys Ser Asn  Gly Ser Leu Leu Trp  Thr Thr Arg
    2045                 2050                 2055

Val Lys  Gly Asp Gly Ile Val  Ala Val Val Glu Val  Asn Arg Asn
    2060                 2065                 2070

Gln Glu  Thr Pro Leu Val Arg  Phe Gln Ala Gly Arg  Asp Met Glu
    2075                 2080                 2085

Phe Asp  Asp Gln Ala Gln Leu  Ile Ser Tyr Glu Glu  Tyr Ser Pro
    2090                 2095                 2100

Phe Gly  Ala Val Val Tyr Ala  Ala Met Tyr Gly Asn  Ile Glu Ala
    2105                 2110                 2115

Pro Arg  Ala Tyr Arg Phe Ala  Arg Tyr Glu His Asp  Ser Glu Thr
    2120                 2125                 2130

Gly Leu  Tyr His Cys Gly Gln  Arg Tyr Tyr Cys Pro  Trp Leu Gly
    2135                 2140                 2145

Arg Trp  Thr Ser Pro Asp Pro  Leu Gly Asp Val Asp  Gly Pro Asn
    2150                 2155                 2160

Leu Phe  Val Tyr Val Asn Asn  Asp Pro Val Asn Ser  His Asp Pro
    2165                 2170                 2175

Ser Gly  Thr Ser Gly Lys Lys  Thr Lys Glu Gly Thr  Arg Glu Met
    2180                 2185                 2190

Tyr Ala  Ala Pro Asp Asp Gln  Gly Lys Arg Arg Leu  Val Asp Glu
    2195                 2200                 2205

Asn Lys  Ala Val Ala Asp Arg  Ile Ala Lys Tyr Glu  Arg Lys Leu
    2210                 2215                 2220

Gln Arg  Gln Glu Arg Lys Gln  Gln Arg Ala Ile Ala  Arg Met Ser
    2225                 2230                 2235

Gly Thr  Asp Pro Ile Leu Gly  Ser Arg Ala Arg Tyr  Ala Val Gly
    2240                 2245                 2250

Ile Ala  Ala Met Gly Asn Ala  Leu Gly Arg Ile Ser  Gly Ser Thr
    2255                 2260                 2265

Glu Leu  His His Thr Tyr Pro  Gln Glu Tyr Arg Glu  Glu Phe Ser
    2270                 2275                 2280

Asp Ile  Asp Ile Asn Val Asp  Arg Thr Ser Val Ser  Ile Ser Lys
    2285                 2290                 2295

Glu Ala  His Tyr Ile Cys Thr  Tyr Gly Ser Ile Leu  Asp Asn Leu
    2300                 2305                 2310

Val Ala  Thr Asn Lys Arg Trp  Lys Ser Glu Tyr Phe  Asp Thr Pro
    2315                 2320                 2325

Asp Thr  Gly Tyr Tyr Glu Gln  Met Glu Gln His Glu  Trp Tyr Asp
    2330                 2335                 2340

Asp Asp  Pro Gly Met Gln Tyr  Ala Ile Arg Leu His  Leu Ala Tyr
    2345                 2350                 2355

Glu Ala  Arg Thr Leu Asn Gly  Lys Ile Met Ala Asp  Phe Gly Ile
    2360                 2365                 2370

Asn Pro  Lys Gly Glu Asp Gly  Arg Ser Met Phe Val  Asn Tyr Asp
    2375                 2380                 2385

Ala Val  Thr Lys Met Arg Thr  Ala Gly Gln Arg Arg  Gly Val Arg
    2390                 2395                 2400

Asn Asp  Asn Leu Ile His His  Glu Thr Trp Pro Gly  Arg Pro Phe
    2405                 2410                 2415

Asn Thr  Gly Asn Ser Asp Thr  Asp Asn Ala Gly Gly  Pro Val His
    2420                 2425                 2430
```

-continued

```
Phe Gln  Val Ala Glu Glu Gln  Tyr Asn Gly Leu Asp  Ala Asp Ala
    2435                 2440                 2445

Gln Ala  Lys Phe Asp Asp Leu  Arg Asn Gln Met Glu  Ala Leu Leu
    2450                 2455                 2460

Gly Lys  Arg
    2465
```

<210> SEQ ID NO 3
<211> LENGTH: 7320
<212> TYPE: DNA
<213> ORGANISM: Artificial Sequence
<220> FEATURE:
<223> OTHER INFORMATION: Native hypothetical cDNA sequence encoding fused Class B/Class C protein of Gibberella zeae PH1 NRRL 31084 (putative intron removed)

<400> SEQUENCE: 3

```
atgtcaactc tttccagtcg tcctggagac cctcgcgccc tccactctgg acagaacaac     60

ggagcacccg aaaccctgac caactcaaaa agcaatgcca ctctatctgg aaaccgcacc    120

acggctccag cctcggcatc ttcatttgct ccacaagtcc gtacactggg tgaaggaatc    180

ccaggctttc gtacctcatt caacgtcgca ggtaaaggcg gcggagcgtt caggtccatc    240

agcgaggact tcgaagtgag ccctgccaat ggcaccatgt cacttgccat ccctgtgcgc    300

acgtcaccta cccgtggagg ctacggacca gatctgaagc tctcgtacga ctcgggttcg    360

ggaaatggac cgttcggatt tggctggagt atgtcaatgc cgtccattca tcgtaagaca    420

acacatgcta taccgcgata tgtggacgat gaggatgatt ttctcatgtc tggtggagac    480

atcattaaga ggttgaatag tgagggtata caagagacaa gaaatgaatc tggcatttgt    540

ggaaagtttc ttgttaccac atatcgtcca cgagtcgact ctgggaacat acgaatcgag    600

agatgggttc gcagagagga tctcgaagac gtgcactgga ggacaatctc gtccagcaac    660

gagactaaaa tctacggtga tagtgacagc agccgcatct ttgacgcttc tggcccatca    720

aagaggatct tctcttggct tttaagccga tcttatgatg catcaggcaa tgcaattgag    780

tatgtataca aagaagaaga ctcgttgggc atttctgatg ctactggagc catgcctgtg    840

tgggaaaaga atcgggaaca agacgcaaga taccgcgaga gatatatcaa acgagtcaag    900

tacggaaaca gaaagccaaa ccgtgatctt actacttggg aagtatcgga ttggcccgaa    960

gaatggatgt ttgaggtcgt ctttgactat ggagaacacg ataaaggcag tccaagcact   1020

gaagaatccc attcctggcc agttcgtcaa gatgtgtttt cacagagtcg ccctggattt   1080

gaaatccgta cctatcgtct ttgtcgccga gttctcatgt tccaccactt ccccgaacac   1140

acccaagagt cagagacttt cgtcttctcg acagatcttc agtacaacga gtctcgacaa   1200

aggactgttt tggccagctt ggtcgcaaca ggatactcgt cctacaaaga caacaatgat   1260

gggaaacaaa ggtacagatc agagtctctg ccgccatggt catttgagta cacaagttcc   1320

cccgaggcca gcgagattga actcatggag gcaaagactt ttaacctact cgaacttcct   1380

acatctgatg cacgagtttc agagtggctg gatctcgacg gcgatggtat gccagggctg   1440

ttgacaaggt ctgtagatgg cgccctctat tatcaacgca atcttgggtc aatttctggt   1500

gacgatgacc cacagttctg tggtccagtc cttctcgcac aacagcccag tatgactggc   1560

gggactttcc aagaccttga tcgaaatgga aacctcaact acgttctccg taacgagcat   1620

ggtcaccttg agggatacta tgaacgaggc aattctgata cctggaagaa ctacatcgaa   1680

tttccagaaa caagcaacgg ggatatatgg cagagcacta tcgacatcga cttgacgggc   1740
```

-continued

```
gacggtcatc ccgaccttat ctgtgcagca gatgattccc aagtcttgat ttggcagcag   1800
aacctcggaa agaaaggcct ctccagctat caacgtgtca tatgcggaca tgattgggag   1860
tcttgtccac gcttgatcaa aaaccaagat gtccagacct atgttggaga tatgactggt   1920
agcggcatgt cggacctagt tgagatctca gtatcgtcgg ttagatattg gccaaacctt   1980
ggctatggaa catttggtgc tgcagtagat atgggaaacc caccagcatt tgctgccaag   2040
gactactttg atcacagtcg agttagactc atggacaccg atggtagtgg cactatggat   2100
ctcctctacg ctctgccaac agggggcgca gctttgtact acaaccttgc tggcaattca   2160
tggagtaaca tggtattcct tccccatctc ccggctatta tcacgcctat gtcgatattt   2220
accttggatc taattggcaa gggggcggat tgtctttgtt gggcagatac ttcaactgat   2280
gggaacagga ttatgtacct cgacatcacg ggagaaacaa aaccgcatct gttgaagtct   2340
tacagcaatg gttggggtgc aacaacgtca gtggactacg ctccatcgac caagttcttc   2400
gcggaagata ccagaaatgg acacccgtgg tcaagcaaat tgccattccc agttcaatgt   2460
gtctcaaagg tccaagtcga ggatgccatc actgggaatc gacagtctac cgaatacatc   2520
taccacaacg gttgctacaa cccgaccgag aagcaatttt ctggctttga gatggtagaa   2580
cagtttcaga gcgaaagagt catcgttgga gaggatgaga catatgagcc tcctgttaca   2640
cacaccaagt cgtggttcaa cgttggtctg agccttgtag ttgatgagtc gcgcttttttg   2700
accaagccag ccattctctc tagtctacag gattaccaca cggatcccgc ggagcttgtg   2760
aacgcactga aagggctcaa cgtgcgatcg gagatatata gtcaggatgg aagccccaag   2820
tctcacttgc cctacgttat caaggaggtg tcgtaccatg tcaagatctc gcaagcacga   2880
gacacaaaca agtattccgc agtccaggta ctcccgcgtg agacattctc gagagcgtac   2940
gagagggata tgagtgatcc acgtgtcaca cacgatatgg tgatcaagac caacgacttt   3000
ggagacgttg aggaaagcct gagtatcgtg tatcctcgtg ctgggaagac cacattcgaa   3060
gatgtgaaca agaatcaaaa ggctggaaac atgtcctaca cccagaattg gtatacaaag   3120
atggtgtcag aacctgaaca ggaacacttc cgcaagcctg cagcgtacag gcaacaggaa   3180
cacgagatac tcagctttcc attcaatggg accctcaagt tcgacgacgc tcttgcgttc   3240
aacttcaatg gattgcccac cacaaaatgc tcgaaaacat ggaaggctct acgcagcgag   3300
aacaaggcgt tttacaaaga ctctctcttg cagagaagac ttgacgaagg cgagctgcag   3360
acgttttcac tgcttgatca gacctatgcc ctggccttta caccagacat cctagccaaa   3420
gtcgaaatag gtttacggaa ttgcaatgtt cccggctcag tcgaagagct tttgaccaaa   3480
gggtcatacg tgaagctgaa agacagtgac ggttggtggg ctccatcgtc tcagtcattt   3540
ttctgttcat ccaagactgc atcggcagct gaagagctca aagaggcacg caaatccttc   3600
tacacccctt cgcgcttcgt cgacctgttt ggcaactcgt cacggcttaa catggataag   3660
gacttcctat tagccacaga agttgaggat gctataggaa ctgcgacctc gttcaaaaac   3720
agctacgagc acttgcagcc tgtggagatc atcgatgcca atagtaattc cgtacaagtc   3780
gtgctggatc cactgggcga gtcgatcgcg gttgcagctt cgacaagacg cgacggggtt   3840
atagaagaga tagacagcct ggagaatatg gtcttagatg ccagccctga agatgtagac   3900
gacattcttc gcgatcctac gggcgaggtc tcgactcgtc ttttgggtaa tgctgcaagc   3960
aggactatcc attaccgcga tagatatgcc caatggaagt ctcgtcagaa tgagacatca   4020
acatcagtcg atccggaacc agcattgtca cttgttctat cacgggacct ttcattcaag   4080
gagtccagta gtcctgagat tcgagtcatc gtttcgtaca tgaatggact tgggtcgcag   4140
```

-continued

```
taccaggagc agcacctgag tgacccaact acgttggaaa aacgatggtt ggtacctggc   4200
cttgccattc cagacactca aggccaagtt gtgtgcacat accaacctcg gtttgcaact   4260
ttagcagcgc caattccatc cagtttgatg aagactaacg ctgcattcac cttttacgat   4320
gcaatgggtc gcaatgttgc gtcccttgct gccgattgca cttggtcgaa aacagtgtat   4380
accccatgga cgacagttga acatggagca ggaagcatgg tacttcagtc caacgcacga   4440
gatgatcctg atgttggcca tttcttctcc cgaatcgcat cctcccgata ctctcaaagt   4500
tggtacgaca agcgcaagct tggaacagca caagagaagc gagctgcaga gaaatcagct   4560
gtatactccg atactccact tactactcat tcgggtagct gcggacttcc tgttagaact   4620
atccaacaag ccggtggcaa gacatacaca cggagctcca tgtatgatct tcagactaca   4680
ggcatggact gcggtgaatc atggctgctg ctagatgccc agggagggga gattctgtcc   4740
tggaattgtc gtggatactc tttcatcact cgttacgatc ccctacgtcg ggagactgag   4800
agattagttg cgaaagccgc agagatgccg aagctcatct cacgaatcac gtacggagag   4860
acctgtggcg atgccatcaa cctgaacttg aatggccaag tatggaaagt ggaagatcaa   4920
gctggtgttc atatcaatac ccattacaac atccgcggcc actgtctagg gaaaacatta   4980
cagttcacaa aagagtataa gcaactggtc gattggaaac ttgatcagac gcttgaaacg   5040
gaagtctacc cgcatacata cttctatgat aactatggtc aagtgttaca ggaagaggat   5100
gagcagggaa accgcacaag aagaaattat tcacgacaag ggcatgtcgt ttcggtcgat   5160
ttcagttcca taaagggtcg tgactggaag tcatatctct caggggcaac cttttcagct   5220
gatgggctgc ctataactat caagtatggg aatggagtcg tttctgactt tttctacgat   5280
gacgagtcca gaaacctcat ctcgcaaaga actacgcgcc catgccgggg tagaagagag   5340
ttgcttcaag acaggacaca cgtttatgac tacgtagggc gtcgaatatt tacctccgat   5400
ggctcagaac aagtcaagta ctttggtgaa agtcgcgtca agcccgagtg ggactacaca   5460
tacaatgcga ccggtgccct ggtgattgcc acagggagag ctcaactctc tggaaagatt   5520
ggaaatggca accagttgac accccacaac gcaatgaacg gactgaaccc atcgcgcggt   5580
ggtggcgatg gcaatttact ttaccaatat cgcgagacat atgattatga tcgtgagggc   5640
aatatcttga tgatgaagca tgaggcgcct gacatcaaag ggttacaag ctggacgaga   5700
aactatcatt acgatgagaa gagtttacta agcgacgatc cccgcgttaa gagcaaccgt   5760
cttagtcgga cgtcaattgg agacacaaac gagggcaagt acatgtatga aggcagtgcc   5820
ggtctctcag gctgcataac gacgctaccg aaattctccg agctcgattg gaacatgaac   5880
aatatgctct ccttctcgtc aacgcagtac gtcaacgctg gcactccaga gagaacatac   5940
tatgtctacg accacgcggg caaccgtgtg cgaaaggtga ccgagactgc agccaaatct   6000
ggtgaggagc ctcgtaaaca aagggataca ttgtttttcg gtggagtcga actgcaaaca   6060
aaaagcaacg gatcactctt atggaccacg cgtgtcaagg gtgatggtat cgtggctgtg   6120
gtggaggtca atagaaatca agagacaccg ttggtgcgat tccaggcggg acgcgacatg   6180
gagttcgacg accaagcaca gctcatctca tatgaagagt actcgccctt cggtgccgtg   6240
gtttacgcgg ctatgtacgg gaatatcgaa gcgcctcggg catatcgttt cgccaggtat   6300
gagcatgaca gcgagacggg cttgtaccac tgtggacagc gctactattg cccatggctg   6360
ggccgttgga cgtctccaga tcctcttggt gacgtagatg ggccgaacct tttgtatat    6420
gtgaataacg atcctgtaaa ctcgcacgat ccttcgggaa catctggcaa gaaaacgaaa   6480
```

-continued gagggcacca gagaaatgta cgcggcaccc gacgatcaag ggaagagacg tcttgtggat 6540
gagaataagg cagtggccga ccgcatagcg aagtatgaga ggaaattaca acgacaagaa 6600
cggaaacagc aacgagccat agctagaatg tctggcacag atcccatcct aggttccagg 6660
gcacggtacg cggttggcat agccgcaatg ggcaatgcac tgggccgcat ttcaggaagt 6720
acagaactcc atcataccta tccacaagag tacagggagg agttttccga catcgacatc 6780
aatgttgaca ggacttcggt gtctatttca aaggaggcac attatatctg cacttatggc 6840
agcattctgg acaaccttgt tgccaccaac aaacgatgga agagcgagta ttttgataca 6900
ccggacactg gttattatga gcagatggag caacacgagt ggtatgacga tgaccctggt 6960
atgcagtacg cgatacgtct gcatttggcc tatgaggctc gcaccctaaa cggtaaaatc 7020
atggctgatt ttggcataaa ccccaaaggc gaagatggga ggagtatgtt tgtgaattac 7080
gatgccgtga caaaaatgag gacggcaggg caaaggaggg gcgtgcggaa tgataatttg 7140
atacaccacg aaacatggcc tggtaggccg tttaatactg gtaacagcga tacggacaac 7200
gctggcggac ctgtgcattt ccaagtggct gaggagcagt ataatggcct tgatgctgat 7260
gcgcaggcga agtttgatga cttaaggaac cagatggaag ctcttttggg gaagagatag 7320

<210> SEQ ID NO 4
<211> LENGTH: 2439
<212> TYPE: PRT
<213> ORGANISM: Artificial Sequence
<220> FEATURE:
<223> OTHER INFORMATION: Native amino sequence of fused Class B/Class C
protein of Gibberella zeae PH1 NRRL 31084.
2439 amino acids encoded by SEQ ID NO:3

<400> SEQUENCE: 4

Met Ser Thr Leu Ser Ser Arg Pro Gly Asp Pro Arg Ala Leu His Ser
1 5 10 15

Gly Gln Asn Asn Gly Ala Pro Glu Thr Leu Thr Asn Ser Lys Ser Asn
20 25 30

Ala Thr Leu Ser Gly Asn Arg Thr Thr Ala Pro Ala Ser Ala Ser Ser
35 40 45

Phe Ala Pro Gln Val Arg Thr Leu Gly Glu Gly Ile Pro Gly Phe Arg
50 55 60

Thr Ser Phe Asn Val Ala Gly Lys Gly Gly Gly Ala Phe Arg Ser Ile
65 70 75 80

Ser Glu Asp Phe Glu Val Ser Pro Ala Asn Gly Thr Met Ser Leu Ala
85 90 95

Ile Pro Val Arg Thr Ser Pro Thr Arg Gly Gly Tyr Gly Pro Asp Leu
100 105 110

Lys Leu Ser Tyr Asp Ser Gly Ser Gly Asn Gly Pro Phe Gly Phe Gly
115 120 125

Trp Ser Met Ser Met Pro Ser Ile His Arg Lys Thr Thr His Ala Ile
130 135 140

Pro Arg Tyr Val Asp Asp Glu Asp Asp Phe Leu Met Ser Gly Gly Asp
145 150 155 160

Ile Ile Lys Arg Leu Asn Ser Glu Gly Ile Gln Glu Thr Arg Asn Glu
165 170 175

Ser Gly Ile Cys Gly Lys Phe Leu Val Thr Thr Tyr Arg Pro Arg Val
180 185 190

Asp Ser Gly Asn Ile Arg Ile Glu Arg Trp Val Arg Arg Glu Asp Leu
195 200 205

-continued

```
Glu Asp Val His Trp Arg Thr Ile Ser Ser Ser Asn Glu Thr Lys Ile
    210                 215                 220

Tyr Gly Asp Ser Asp Ser Ser Arg Ile Phe Asp Ala Ser Gly Pro Ser
225                 230                 235                 240

Lys Arg Ile Phe Ser Trp Leu Leu Ser Arg Ser Tyr Asp Ala Ser Gly
                245                 250                 255

Asn Ala Ile Glu Tyr Val Tyr Lys Glu Glu Asp Ser Leu Gly Ile Ser
            260                 265                 270

Asp Ala Thr Gly Ala Met Pro Val Trp Glu Lys Asn Arg Glu Gln Asp
        275                 280                 285

Ala Arg Tyr Arg Glu Arg Tyr Ile Lys Arg Val Lys Tyr Gly Asn Arg
    290                 295                 300

Lys Pro Asn Arg Asp Leu Thr Thr Trp Glu Val Ser Asp Trp Pro Glu
305                 310                 315                 320

Glu Trp Met Phe Glu Val Val Phe Asp Tyr Gly Glu His Asp Lys Gly
                325                 330                 335

Ser Pro Ser Thr Glu Glu Ser His Ser Trp Pro Val Arg Gln Asp Val
            340                 345                 350

Phe Ser Gln Ser Arg Pro Gly Phe Glu Ile Arg Thr Tyr Arg Leu Cys
        355                 360                 365

Arg Arg Val Leu Met Phe His His Phe Pro Glu His Thr Gln Glu Ser
    370                 375                 380

Glu Thr Phe Val Phe Ser Thr Asp Leu Gln Tyr Asn Glu Ser Arg Gln
385                 390                 395                 400

Arg Thr Val Leu Ala Ser Leu Val Ala Thr Gly Tyr Ser Ser Tyr Lys
                405                 410                 415

Asp Asn Asn Asp Gly Lys Gln Arg Tyr Arg Ser Glu Ser Leu Pro Pro
            420                 425                 430

Trp Ser Phe Glu Tyr Thr Ser Ser Pro Glu Ala Ser Glu Ile Glu Leu
        435                 440                 445

Met Glu Ala Lys Thr Phe Asn Leu Leu Glu Leu Pro Thr Ser Asp Ala
    450                 455                 460

Arg Val Ser Glu Trp Leu Asp Leu Asp Gly Asp Gly Met Pro Gly Leu
465                 470                 475                 480

Leu Thr Arg Ser Val Asp Gly Ala Leu Tyr Tyr Gln Arg Asn Leu Gly
                485                 490                 495

Ser Ile Ser Gly Asp Asp Asp Pro Gln Phe Cys Gly Pro Val Leu Leu
            500                 505                 510

Ala Gln Gln Pro Ser Met Thr Gly Gly Thr Phe Gln Asp Leu Asp Arg
        515                 520                 525

Asn Gly Asn Leu Asn Tyr Val Leu Arg Asn Glu His Gly His Leu Glu
    530                 535                 540

Gly Tyr Tyr Glu Arg Gly Asn Ser Asp Thr Trp Lys Asn Tyr Ile Glu
545                 550                 555                 560

Phe Pro Glu Thr Ser Asn Gly Asp Ile Trp Gln Ser Thr Ile Asp Ile
                565                 570                 575

Asp Leu Thr Gly Asp Gly His Pro Asp Leu Ile Cys Ala Ala Asp Asp
            580                 585                 590

Ser Gln Val Leu Ile Trp Gln Gln Asn Leu Gly Lys Lys Gly Leu Ser
        595                 600                 605

Ser Tyr Gln Arg Val Ile Cys Gly His Asp Trp Glu Ser Cys Pro Arg
    610                 615                 620

Leu Ile Lys Asn Gln Asp Val Gln Thr Tyr Val Gly Asp Met Thr Gly
```

-continued

```
625                 630                 635                 640

Ser Gly Met Ser Asp Leu Val Glu Ile Ser Val Ser Ser Val Arg Tyr
                645                 650                 655

Trp Pro Asn Leu Gly Tyr Gly Thr Phe Gly Ala Ala Val Asp Met Gly
            660                 665                 670

Asn Pro Pro Ala Phe Ala Ala Lys Asp Tyr Phe Asp His Ser Arg Val
        675                 680                 685

Arg Leu Met Asp Thr Asp Gly Ser Gly Thr Met Asp Leu Leu Tyr Ala
    690                 695                 700

Leu Pro Thr Gly Gly Ala Ala Leu Tyr Tyr Asn Leu Ala Gly Asn Ser
705                 710                 715                 720

Trp Ser Asn Met Val Phe Leu Pro His Leu Pro Ala Ile Ile Thr Pro
                725                 730                 735

Met Ser Ile Phe Thr Leu Asp Leu Ile Gly Lys Gly Ala Asp Cys Leu
            740                 745                 750

Cys Trp Ala Asp Thr Ser Thr Asp Gly Asn Arg Ile Met Tyr Leu Asp
        755                 760                 765

Ile Thr Gly Glu Thr Lys Pro His Leu Leu Lys Ser Tyr Ser Asn Gly
    770                 775                 780

Trp Gly Ala Thr Thr Ser Val Asp Tyr Ala Pro Ser Thr Lys Phe Phe
785                 790                 795                 800

Ala Glu Asp Thr Arg Asn Gly His Pro Trp Ser Ser Lys Leu Pro Phe
                805                 810                 815

Pro Val Gln Cys Val Ser Lys Val Gln Val Glu Asp Ala Ile Thr Gly
            820                 825                 830

Asn Arg Gln Ser Thr Glu Tyr Ile Tyr His Asn Gly Cys Tyr Asn Pro
        835                 840                 845

Thr Glu Lys Gln Phe Ser Gly Phe Glu Met Val Glu Gln Phe Gln Ser
    850                 855                 860

Glu Arg Val Ile Val Gly Glu Asp Glu Thr Tyr Glu Pro Pro Val Thr
865                 870                 875                 880

His Thr Lys Ser Trp Phe Asn Val Gly Leu Ser Leu Val Val Asp Glu
                885                 890                 895

Ser Arg Phe Leu Thr Lys Pro Ala Ile Leu Ser Ser Leu Gln Asp Tyr
            900                 905                 910

His Thr Asp Pro Ala Glu Leu Val Asn Ala Leu Lys Gly Leu Asn Val
        915                 920                 925

Arg Ser Glu Ile Tyr Ser Gln Asp Gly Ser Pro Lys Ser His Leu Pro
    930                 935                 940

Tyr Val Ile Lys Glu Val Ser Tyr His Val Lys Ile Ser Gln Ala Arg
945                 950                 955                 960

Asp Thr Asn Lys Tyr Ser Ala Val Gln Val Leu Pro Arg Glu Thr Phe
                965                 970                 975

Ser Arg Ala Tyr Glu Arg Asp Met Ser Asp Pro Arg Val Thr His Asp
            980                 985                 990

Met Val Ile Lys Thr Asn Asp Phe  Gly Asp Val Glu Glu  Ser Leu Ser
        995                 1000                1005

Ile Val  Tyr Pro Arg Ala Gly  Lys Thr Thr Phe Glu  Asp Val Asn
    1010                1015                1020

Lys Asn  Gln Lys Ala Gly Asn  Met Ser Tyr Thr Gln  Asn Trp Tyr
    1025                1030                1035

Thr Lys  Met Val Ser Glu Pro  Glu Gln Glu His Phe  Arg Lys Pro
    1040                1045                1050
```

-continued

```
Ala Ala  Tyr Arg Gln Gln Glu  His Glu Ile Leu Ser  Phe Pro Phe
    1055                 1060                 1065

Asn Gly  Thr Leu Lys Phe Asp  Asp Ala Leu Ala Phe  Asn Phe Asn
    1070                 1075                 1080

Gly Leu  Pro Thr Thr Lys Cys  Ser Lys Thr Trp Lys  Ala Leu Arg
    1085                 1090                 1095

Ser Glu  Asn Lys Ala Phe Tyr  Lys Asp Ser Leu Leu  Gln Arg Arg
    1100                 1105                 1110

Leu Asp  Glu Gly Glu Leu Gln  Thr Phe Ser Leu Leu  Asp Gln Thr
    1115                 1120                 1125

Tyr Ala  Leu Ala Phe Thr Pro  Asp Ile Leu Ala Lys  Val Glu Ile
    1130                 1135                 1140

Gly Leu  Arg Asn Cys Asn Val  Pro Gly Ser Val Glu  Glu Leu Leu
    1145                 1150                 1155

Thr Lys  Gly Ser Tyr Val Lys  Leu Lys Asp Ser Asp  Gly Trp Trp
    1160                 1165                 1170

Ala Pro  Ser Ser Gln Ser Phe  Phe Cys Ser Ser Lys  Thr Ala Ser
    1175                 1180                 1185

Ala Ala  Glu Glu Leu Lys Glu  Ala Arg Lys Ser Phe  Tyr Thr Pro
    1190                 1195                 1200

Ser Arg  Phe Val Asp Leu Phe  Gly Asn Ser Ser Arg  Leu Asn Met
    1205                 1210                 1215

Asp Lys  Asp Phe Leu Leu Ala  Thr Glu Val Glu Asp  Ala Ile Gly
    1220                 1225                 1230

Thr Ala  Thr Ser Phe Lys Asn  Ser Tyr Glu His Leu  Gln Pro Val
    1235                 1240                 1245

Glu Ile  Ile Asp Ala Asn Ser  Asn Ser Val Gln Val  Val Leu Asp
    1250                 1255                 1260

Pro Leu  Gly Glu Ser Ile Ala  Val Ala Ala Ser Thr  Arg Arg Asp
    1265                 1270                 1275

Gly Val  Ile Glu Glu Ile Asp  Ser Leu Glu Asn Met  Val Leu Asp
    1280                 1285                 1290

Ala Ser  Pro Glu Asp Val Asp  Asp Ile Leu Arg Asp  Pro Thr Gly
    1295                 1300                 1305

Glu Val  Ser Thr Arg Leu Leu  Gly Asn Ala Ala Ser  Arg Thr Ile
    1310                 1315                 1320

His Tyr  Arg Asp Arg Tyr Ala  Gln Trp Lys Ser Arg  Gln Asn Glu
    1325                 1330                 1335

Thr Ser  Thr Ser Val Asp Pro  Glu Pro Ala Leu Ser  Leu Val Leu
    1340                 1345                 1350

Ser Arg  Asp Leu Ser Phe Lys  Glu Ser Ser Ser Pro  Glu Ile Arg
    1355                 1360                 1365

Val Ile  Val Ser Tyr Met Asn  Gly Leu Gly Ser Gln  Tyr Gln Glu
    1370                 1375                 1380

Gln His  Leu Ser Asp Pro Thr  Thr Leu Glu Lys Arg  Trp Leu Val
    1385                 1390                 1395

Pro Gly  Leu Ala Ile Pro Asp  Thr Gln Gly Gln Val  Val Cys Thr
    1400                 1405                 1410

Tyr Gln  Pro Arg Phe Ala Thr  Leu Ala Ala Pro Ile  Pro Ser Ser
    1415                 1420                 1425

Leu Met  Lys Thr Asn Ala Ala  Phe Thr Phe Tyr Asp  Ala Met Gly
    1430                 1435                 1440
```

-continued

```
Arg Asn  Val Ala Ser Leu Ala  Ala Asp Cys Thr Trp  Ser Lys Thr
    1445                 1450                 1455

Val Tyr  Thr Pro Trp Thr Thr  Val Glu His Gly Ala  Gly Ser Met
    1460                 1465                 1470

Val Leu  Gln Ser Asn Ala Arg  Asp Asp Pro Asp Val  Gly His Phe
    1475                 1480                 1485

Phe Ser  Arg Ile Ala Ser Ser  Arg Tyr Ser Gln Ser  Trp Tyr Asp
    1490                 1495                 1500

Lys Arg  Lys Leu Gly Thr Ala  Gln Glu Lys Arg Ala  Ala Glu Lys
    1505                 1510                 1515

Ser Ala  Val Tyr Ser Asp Thr  Pro Leu Thr Thr His  Ser Gly Ser
    1520                 1525                 1530

Cys Gly  Leu Pro Val Arg Thr  Ile Gln Gln Ala Gly  Gly Lys Thr
    1535                 1540                 1545

Tyr Thr  Arg Ser Ser Met Tyr  Asp Leu Gln Thr Thr  Gly Met Asp
    1550                 1555                 1560

Cys Gly  Glu Ser Trp Leu Leu  Leu Asp Ala Gln Gly  Gly Glu Ile
    1565                 1570                 1575

Leu Ser  Trp Asn Cys Arg Gly  Tyr Ser Phe Ile Thr  Arg Tyr Asp
    1580                 1585                 1590

Pro Leu  Arg Arg Glu Thr Glu  Arg Leu Val Ala Lys  Ala Ala Glu
    1595                 1600                 1605

Met Pro  Lys Leu Ile Ser Arg  Ile Thr Tyr Gly Glu  Thr Cys Gly
    1610                 1615                 1620

Asp Ala  Ile Asn Leu Asn Leu  Asn Gly Gln Val Trp  Lys Val Glu
    1625                 1630                 1635

Asp Gln  Ala Gly Val His Ile  Asn Thr His Tyr Asn  Ile Arg Gly
    1640                 1645                 1650

His Cys  Leu Gly Lys Thr Leu  Gln Phe Thr Lys Glu  Tyr Lys Gln
    1655                 1660                 1665

Leu Val  Asp Trp Lys Leu Asp  Gln Thr Leu Glu Thr  Glu Val Tyr
    1670                 1675                 1680

Pro His  Thr Tyr Phe Tyr Asp  Asn Tyr Gly Gln Val  Leu Gln Glu
    1685                 1690                 1695

Glu Asp  Glu Gln Gly Asn Arg  Thr Arg Arg Asn Tyr  Ser Arg Gln
    1700                 1705                 1710

Gly His  Val Val Ser Val Asp  Phe Ser Ser Ile Lys  Gly Arg Asp
    1715                 1720                 1725

Trp Lys  Ser Tyr Leu Ser Gly  Ala Thr Phe Ser Ala  Asp Gly Leu
    1730                 1735                 1740

Pro Ile  Thr Ile Lys Tyr Gly  Asn Gly Val Val Ser  Asp Phe Phe
    1745                 1750                 1755

Tyr Asp  Asp Glu Ser Arg Asn  Leu Ile Ser Gln Arg  Thr Thr Arg
    1760                 1765                 1770

Pro Cys  Arg Gly Arg Arg Glu  Leu Leu Gln Asp Arg  Thr His Val
    1775                 1780                 1785

Tyr Asp  Tyr Val Gly Arg Arg  Ile Phe Thr Ser Asp  Gly Ser Glu
    1790                 1795                 1800

Gln Val  Lys Tyr Phe Gly Glu  Ser Arg Val Lys Pro  Glu Trp Asp
    1805                 1810                 1815

Tyr Thr  Tyr Asn Ala Thr Gly  Ala Leu Val Ile Ala  Thr Gly Arg
    1820                 1825                 1830

Ala Gln  Leu Ser Gly Lys Ile  Gly Asn Gly Asn Gln  Leu Thr Pro
```

-continued

```
    1835                1840                1845

His Asn  Ala Met Asn Gly Leu  Asn Pro Ser Arg Gly  Gly Gly Asp
    1850                1855                1860

Gly Asn  Leu Leu Tyr Gln Tyr  Arg Glu Thr Tyr Asp  Tyr Asp Arg
    1865                1870                1875

Glu Gly  Asn Ile Leu Met Met  Lys His Glu Ala Pro  Asp Ile Lys
    1880                1885                1890

Gly Val  Thr Ser Trp Thr Arg  Asn Tyr His Tyr Asp  Glu Lys Ser
    1895                1900                1905

Leu Leu  Ser Asp Asp Pro Arg  Val Lys Ser Asn Arg  Leu Ser Arg
    1910                1915                1920

Thr Ser  Ile Gly Asp Thr Asn  Glu Gly Lys Tyr Met  Tyr Glu Gly
    1925                1930                1935

Ser Ala  Gly Leu Ser Gly Cys  Ile Thr Thr Leu Pro  Lys Phe Ser
    1940                1945                1950

Glu Leu  Asp Trp Asn Met Asn  Asn Met Leu Ser Phe  Ser Ser Thr
    1955                1960                1965

Gln Tyr  Val Asn Ala Gly Thr  Pro Glu Arg Thr Tyr  Tyr Val Tyr
    1970                1975                1980

Asp His  Ala Gly Asn Arg Val  Arg Lys Val Thr Glu  Thr Ala Ala
    1985                1990                1995

Lys Ser  Gly Glu Glu Pro Arg  Lys Gln Arg Asp Thr  Leu Phe Phe
    2000                2005                2010

Gly Gly  Val Glu Leu Gln Thr  Lys Ser Asn Gly Ser  Leu Leu Trp
    2015                2020                2025

Thr Thr  Arg Val Lys Gly Asp  Gly Ile Val Ala Val  Val Glu Val
    2030                2035                2040

Asn Arg  Asn Gln Glu Thr Pro  Leu Val Arg Phe Gln  Ala Gly Arg
    2045                2050                2055

Asp Met  Glu Phe Asp Asp Gln  Ala Gln Leu Ile Ser  Tyr Glu Glu
    2060                2065                2070

Tyr Ser  Pro Phe Gly Ala Val  Val Tyr Ala Ala Met  Tyr Gly Asn
    2075                2080                2085

Ile Glu  Ala Pro Arg Ala Tyr  Arg Phe Ala Arg Tyr  Glu His Asp
    2090                2095                2100

Ser Glu  Thr Gly Leu Tyr His  Cys Gly Gln Arg Tyr  Tyr Cys Pro
    2105                2110                2115

Trp Leu  Gly Arg Trp Thr Ser  Pro Asp Pro Leu Gly  Asp Val Asp
    2120                2125                2130

Gly Pro  Asn Leu Phe Val Tyr  Val Asn Asn Asp Pro  Val Asn Ser
    2135                2140                2145

His Asp  Pro Ser Gly Thr Ser  Gly Lys Lys Thr Lys  Glu Gly Thr
    2150                2155                2160

Arg Glu  Met Tyr Ala Ala Pro  Asp Asp Gln Gly Lys  Arg Arg Leu
    2165                2170                2175

Val Asp  Glu Asn Lys Ala Val  Ala Asp Arg Ile Ala  Lys Tyr Glu
    2180                2185                2190

Arg Lys  Leu Gln Arg Gln Glu  Arg Lys Gln Gln Arg  Ala Ile Ala
    2195                2200                2205

Arg Met  Ser Gly Thr Asp Pro  Ile Leu Gly Ser Arg  Ala Arg Tyr
    2210                2215                2220

Ala Val  Gly Ile Ala Ala Met  Gly Asn Ala Leu Gly  Arg Ile Ser
    2225                2230                2235
```

-continued

```
Gly Ser  Thr Glu Leu His His  Thr Tyr Pro Gln Glu  Tyr Arg Glu
    2240                 2245                 2250

Glu Phe  Ser Asp Ile Asp Ile  Asn Val Asp Arg Thr  Ser Val Ser
    2255                 2260                 2265

Ile Ser  Lys Glu Ala His Tyr  Ile Cys Thr Tyr Gly  Ser Ile Leu
    2270                 2275                 2280

Asp Asn  Leu Val Ala Thr Asn  Lys Arg Trp Lys Ser  Glu Tyr Phe
    2285                 2290                 2295

Asp Thr  Pro Asp Thr Gly Tyr  Tyr Glu Gln Met Glu  Gln His Glu
    2300                 2305                 2310

Trp Tyr  Asp Asp Asp Pro Gly  Met Gln Tyr Ala Ile  Arg Leu His
    2315                 2320                 2325

Leu Ala  Tyr Glu Ala Arg Thr  Leu Asn Gly Lys Ile  Met Ala Asp
    2330                 2335                 2340

Phe Gly  Ile Asn Pro Lys Gly  Glu Asp Gly Arg Ser  Met Phe Val
    2345                 2350                 2355

Asn Tyr  Asp Ala Val Thr Lys  Met Arg Thr Ala Gly  Gln Arg Arg
    2360                 2365                 2370

Gly Val  Arg Asn Asp Asn Leu  Ile His His Glu Thr  Trp Pro Gly
    2375                 2380                 2385

Arg Pro  Phe Asn Thr Gly Asn  Ser Asp Thr Asp Asn  Ala Gly Gly
    2390                 2395                 2400

Pro Val  His Phe Gln Val Ala  Glu Glu Gln Tyr Asn  Gly Leu Asp
    2405                 2410                 2415

Ala Asp  Ala Gln Ala Lys Phe  Asp Asp Leu Arg Asn  Gln Met Glu
    2420                 2425                 2430

Ala Leu  Leu Gly Lys Arg
    2435
```

<210> SEQ ID NO 5
<211> LENGTH: 7440
<212> TYPE: DNA
<213> ORGANISM: Artificial Sequence
<220> FEATURE:
<223> OTHER INFORMATION: E. coli biased DNA sequence encoding Gibberella zeae fused Class B/Class C protein.

<400> SEQUENCE: 5

```
tctagaaaga aggagatata ccatgtctac cctgtcctct cgcccgggcg acccgcgtgc     60

gctccattcc ggccagaata acggtgcgcc agaaactctg accaacagca aatctaacgc    120

gaccctgtct ggtaaccgta ccactgcgcc ggcatctgct agctccttcg caccgcaggt    180

tcgtaccctg ggtgaaggta tcccaggctt ccgtacttct ttcaacgtag ctggtaaagg    240

tggcggtgcg tttcgctcta tttctgaaga cttcgaagtt tccccggcta acggcactat    300

gtctctggcg atcccggtac gcaccagccc gacccgtggt ggctatggtc cggacctgaa    360

actgagctac gatagcggtt ctggtaacgg cccgttcggc tttggttggt ccatgtctat    420

gccgtctatc caccgtaaaa ccactcatgc tattccgcgt tacgttgatg acgaagacga    480

tttcctgatg tctggtggcg acattatcaa acgtctgaac tccgaaggta ttcaggaaac    540

ccgcaacgag agcggcatct gcggtaaatt cctggtaacc acttatcgcc cgcgtgttga    600

ctccggtaac atccgcatcg aacgctgggt acgtcgcgaa gatctggaag atgtgcattg    660

gcgtactatc agctcctcta acgaaactaa aatctacggc gactccgatt cttcccgcat    720

cttcgatgct tccggtccgt ctaaacgtat cttttcctgg ctgctcagcc gctcttacga    780
```

-continued

```
cgcatccggc aacgcgattg aatacgtgta taaagaggaa gactccctgg gcatcagcga    840
cgcaaccggc gcgatgccag tatgggaaaa gaaccgtgaa caggacgctc gctaccgcga    900
acgttacatc aagcgtgtaa aatatggcaa ccgcaaaccg aaccgtgatc tgactacctg    960
ggaggtgtct gactggccgg aagagtggat gttcgaagtg gtattcgatt acggcgaaca   1020
tgataaaggt tctccgtcca ctgaggaatc ccactcttgg ccggttcgtc aggacgtttt   1080
ctctcagtcc cgtccaggtt tcgaaatccg tacttaccgt ctgtgtcgtc gcgttctgat   1140
gttccaccat ttcccggaac acactcagga gagcgaaacc tttgttttct ctaccgacct   1200
gcaatataac gaaagccgcc agcgtaccgt tctggcaagc ctggtggcga ctggttattc   1260
tagctacaaa gataacaacg atggtaagca gcgttaccgc tctgaaagcc tgccaccgtg   1320
gtcttttgaa tatacctcta gcccggaagc atctgagatc gaactgatgg aagctaaaac   1380
cttcaacctg ctcgaactgc cgacctccga cgcacgtgtg tctgagtggc tggacctgga   1440
tggtgacggc atgccgggcc ttctgacccg ttctgtggat ggcgcactgt actatcagcg   1500
caacctgggt tctatctccg gtgacgatga cccgcagttc tgcggtccgg ttcttctggc   1560
tcagcaaccg tccatgaccg gcggtacttt ccaggatctg gatcgtaacg gcaacctgaa   1620
ctacgtgctg cgtaacgaac acggtcacct ggaaggttac tatgagcgtg gtaactctga   1680
cacctggaag aactatatcg aattcccgga aacctctaac ggtgatatct ggcagtctac   1740
tatcgatatt gacctgaccg gcgatggtca tccggacctg atctgcgcgg cagacgatag   1800
ccaggtgctg atttggcagc aaaacctggg taagaaaggc ctgtctagct accagcgtgt   1860
aatttgcggc catgattggg agtcctgccc acgcctgatc aagaaccagg acgttcagac   1920
ctacgttggc gacatgaccg gcagcggcat gtctgacctg gtagaaatca gcgtaagctc   1980
cgtgcgctat tggccgaacc tgggttacgg tactttcggc gcggcagtag acatgggtaa   2040
cccgccagct ttcgcagcga aagattactt cgaccacagc cgtgtgcgcc tgatggacac   2100
cgacggtagc ggcactatgg atctgctcta cgcactgccg accggcggtg cagctctgta   2160
ctataacctg gctggcaaca gctggtctaa catggtgttc ctgccacacc tgccggcgat   2220
tatcaccccg atgagcatct tcaccctgga cctgattggc aaaggtgctg attgcctgtg   2280
ttgggctgac acttccaccg atggtaaccg tatcatgtat ctggacatca ccggcgaaac   2340
caaaccgcac ttgctgaaat cttatagcaa cggctggggt gctactacct ctgtggatta   2400
cgcgccgtcc accaaattct ttgcagaaga tacccgtaac ggccacccgt ggtctagcaa   2460
actgccgttt ccggtgcagt gcgtatctaa agttcaggtg gaagacgcta tcaccggcaa   2520
ccgtcagagc accgaataca tctatcataa cggttgttac aacccgactg aaaagcagtt   2580
ctctggtttc gaaatggtgg aacagttcca gtccgagcgt gttatcgtag gcgaagatga   2640
aacctacgaa ccgccagtta cccacaccaa aagctggttc aacgttggtc tgagcctggt   2700
agtggacgaa agccgtttcc tgactaaacc ggcgatcctg tcctctctgc aagattacca   2760
cactgacccg gcggaactgg tgaacgcact gaaaggtctg aacgtgcgtt ccgaaattta   2820
ctctcaagat ggctccccga aatctcacct gccgtatgta atcaaggaag tttcttatca   2880
cgttaagatt tcccaggcgc gtgacaccaa caaatattcc gcagttcagg ttctgccacg   2940
tgaaactttt agccgtgcgt acgaacgtga catgtccgac ccgcgtgtga ctcacgatat   3000
ggttattaag accaacgact ttggtgacgt tgaagagtct ctgtctattg tatatccgcg   3060
tgcaggcaaa accactttcg aagatgttaa caagaaccag aaagcgggca acatgtccta   3120
```

-continued

```
cactcagaac tggtacacca aaatggtgag cgaaccggaa caggagcact ttcgcaaacc   3180

ggcagcgtat cgccaacagg aacacgagat cctgtccttt ccgttcaacg gcactctgaa   3240

gtttgatgac gcactggcgt ttaacttcaa cggtctgccg actaccaaat gttctaaaac   3300

ttggaaagct ctgcgcagcg aaaacaaggc gttctacaaa gatagccttc tgcaacgccg   3360

tctggatgaa ggtgagctgc aaaccttctc cctcctggac cagacttacg cactggcgtt   3420

taccccggac atcctggcta aagtggaaat tggcctgcgt aactgtaacg taccgggttc   3480

tgtggaggaa ctgttgacta aaggtagcta cgtaaagctg aaagacagcg acggctggtg   3540

ggcaccgtct tcccagtctt tcttttgtag ctctaagacc gctagcgcag ctgaggaact   3600

gaaagaagcg cgcaaatcct tttataccc atcccgtttc gtggacctgt tcggcaactc   3660

cagccgcctg aacatggata aagactttct cctggctact gaagttgagg acgcaatcgg   3720

caccgcaacc tctttcaaaa actcctatga acacctgcaa ccagtggaga ttatcgacgc   3780

gaactctaac agcgttcagg tagttctgga cccactgggc gaatccattg cggtggcggc   3840

ttccactcgt cgcgacggtg ttatcgagga aattgactcc ctggaaaaca tggtgctgga   3900

tgcgtctccg gaagacgttg atgacatcct gcgtgatccg accggcgaag tgagcacccg   3960

ccttctgggt aacgcggctt ctcgtaccat tcattaccgt gatcgctacg ctcagtggaa   4020

gtctcgccag aacgaaacct ctaccagcgt tgatccggaa ccggctctgt ctctggttct   4080

gtcccgtgac ctgtccttca aggaatcctc tagcccggag atccgtgtta ttgtgagcta   4140

catgaacggc ctgggtagcc agtatcaaga gcagcatctg tccgatccga ccactctgga   4200

gaaacgttgg ctggttccgg gcctggcaat cccagataca cagggccagg tggtatgcac   4260

ctaccagccg cgtttcgcta ccctggctgc gccgattcca tcctctctga tgaaaactaa   4320

cgcggcattc accttctacg atgcgatggg ccgtaacgtg gcaagcttgg ctgcggattg   4380

tacctggtcc aaaaccgttt atactccgtg gaccactgtt gaacacggtg ctggtagcat   4440

ggttctgcaa tccaacgctc gtgatgaccc ggatgttggt cacttctttt cccgcatcgc   4500

gtcttcccgc tactcccaga gctggtacga taagcgtaaa ctgggtactg ctcaggaaaa   4560

acgcgcagct gagaaatccg cggtttattc cgatactccg ctgaccactc actccggttc   4620

ttgcggcctg ccggttcgca ccatccagca agcaggcggt aaaacctaca cccgcagctc   4680

tatgtatgat gtgtctggca accgtatccg cgacgttgac tcctacgaac gtaccgttga   4740

aaaaatgctg tacgacaaac tgggtcgtca gctgcagact accggtatgg attgtggcga   4800

atcctggctc ctgcttgacg cacagggtgg cgagatcctg agctggaact gtcgcggtta   4860

ctctttcatt actcgttacg acccgctgcg tcgcgaaacc gaacgcctgg ttgcgaaagc   4920

ggctgaaatg ccgaaactga tcagccgtat cacttacggc gaaacctgcg gtgacgcaat   4980

caacctgaac ctgaacggtc aggtatggaa agttgaggat caggcaggcg ttcacattaa   5040

cactcactat aacattcgtg gtcactgcct gggtaagacc ctgcaattca ccaaagaata   5100

taaacagctg gttgattgga aactggatca gaccctggaa actgaggttt atccgcatac   5160

ctatttctac gataactatg gccaggttct gcaagaggaa gacgaacagg gcaaccgtac   5220

ccgccgtaac tactcccgtc agggtcacgt ggtttctgta gacttctcta gcattaaagg   5280

ccgtgactgg aaatcttacc tgtctggtgc taccttctct gcggacggcc tgccgattac   5340

tatcaaatac ggcaacggtg tggtttccga ctttttctac gatgacgaaa gccgtaacct   5400

gattagccaa cgcaccactc gtccgtgccg tggtcgtcgc gaactgctcc aagatcgtac   5460

ccatgtttac gactatgttg gtcgtcgcat ttttacttcc gacggttccg aacaggtaaa   5520
```

-continued atatttcggt gagagccgtg ttaagccgga atgggactac acttacaacg cgactggcgc 5580
actggtaatc gcaaccggcc gtgcgcagct gtctggcaaa atcggtaacg gcaaccagct 5640
gaccccgcat aacgctatga acggcctgaa cccgtctcgc ggtggcggtg acggtaactt 5700
gctgtatcag tatcgcgaaa cttacgacta cgatcgtgag ggtaacattc tgatgatgaa 5760
acacgaagcg ccggacatca aaggcgttac cagctggacc cgtaactacc actacgatga 5820
aaagagcctg ttatccgacg atccacgtgt gaaatccaac cgtctgtctc gcacctccat 5880
cggcgatacc aacgaaggca aatacatgta cgaaggctct gctggcctgt ccggttgcat 5940
caccactctg ccaaagttct ccgaactgga ttggaacatg aacaacatgc tgagcttttc 6000
ttccactcag tacgtaaacg cggcaccccc ggaacgtacc tactatgtgt acgaccacgc 6060
tggtaaccgc gttcgtaaag ttaccgagac tgcggctaaa tctggtgagg aaccgcgtaa 6120
acagcgtgat accctgttct ttggtggcgt ggaactgcaa accaaatcca acggctctct 6180
tctgtggact acccgtgtta aaggtgatgg tatcgtggct gtagttgaag tgaaccgtaa 6240
ccaggaaacc ccgctggtac gcttccaggc tggtcgtgac atggaatttg acgatcaggc 6300
gcagctgatc agctacgagg aatattctcc gttcggtgct gtggtttacg ctgcgatgta 6360
cggcaacatt gaggcaccac gcgcttaccg tttcgcacgt tacgaacacg attctgaaac 6420
cggcctgtat cactgtggcc agcgttatta ctgcccgtgg ctgggtcgtt ggacctcccc 6480
agatccgctg ggtgacgtgg atggtccaaa cctgttcgta tacgtgaaca acgatccagt 6540
taactcccac gacccgtctg gtacttccgg caagaaaacc aaggaaggta ctcgcgaaat 6600
gtacgcagcg ccagatgacc agggcaaacg ccgtctggtt gacgagaaca aagctgttgc 6660
tgatcgcatc gcaaagtacg aacgcaaact gcaacgtcag gaacgtaaac aacagcgtgc 6720
gatcgcgcgt atgagcggca ccgacccgat cctgggttct cgtgcacgtt atgcggtagg 6780
cattgcggct atgggcaacg cgctgggtcg tatctctggt tccaccgaac tgcatcacac 6840
ctacccgcag gaatatcgtg aagagttctc tgacatcgac attaacgttg accgtacctc 6900
tgtgagcatt tccaaagagg cgcactatat ctgcacttac ggtagcatcc tggacaacct 6960
ggtagcaacc aacaaacgct ggaaatctga atactttgac actccagaca ctggttatta 7020
cgaacagatg gagcagcatg agtggtacga cgatgaccca ggcatgcagt acgcgatccg 7080
tctgcacctg gcatacgaag cgcgtactct gaacggtaaa atcatggcgg atttcggcat 7140
caacccgaaa ggcgaagacg gtcgttccat gtttgttaac tatgatgcgg taaccaaaat 7200
gcgtaccgct ggtcagcgtc gcggcgtacg taacgacaac ctgatccatc acgaaacctg 7260
gccgggtcgt ccgtttaaca ccggcaacag cgataccgat aacgcgggtg gcccggttca 7320
cttccaggtt gcagaggaac agtacaacgg cctggatgct gacgcgcagg cgaaattcga 7380
tgacctgcgc aaccaaatgg aggcgctcct aggcaaacgc taataattaa tgctctcgag 7440

<210> SEQ ID NO 6
<211> LENGTH: 2528
<212> TYPE: PRT
<213> ORGANISM: Artificial Sequence
<220> FEATURE:
<223> OTHER INFORMATION: Example of fusion protein generated from the amino acid sequences of TcaC (GenBank Accession AAC38625.1) and TccC1 (GenBank Accession AAL18473.1) (both from Photorhabdus luminescens strain W-14)

<400> SEQUENCE: 6

Met Gln Asp Ser Pro Glu Val Ser Ile Thr Thr Leu Ser Leu Pro Lys

-continued

```
1               5                   10                  15

Gly Gly Gly Ala Ile Asn Gly Met Gly Glu Ala Leu Asn Ala Ala Gly
            20                  25                  30

Pro Asp Gly Met Ala Ser Leu Ser Leu Pro Leu Pro Leu Ser Thr Gly
        35                  40                  45

Arg Gly Thr Ala Pro Gly Leu Ser Leu Ile Tyr Ser Asn Ser Ala Gly
    50                  55                  60

Asn Gly Pro Phe Gly Ile Gly Trp Gln Cys Gly Val Met Ser Ile Ser
65                  70                  75                  80

Arg Arg Thr Gln His Gly Ile Pro Gln Tyr Gly Asn Asp Asp Thr Phe
                85                  90                  95

Leu Ser Pro Gln Gly Glu Val Met Asn Ile Ala Leu Asn Asp Gln Gly
            100                 105                 110

Gln Pro Asp Ile Arg Gln Asp Val Lys Thr Leu Gln Gly Val Thr Leu
        115                 120                 125

Pro Ile Ser Tyr Thr Val Thr Arg Tyr Gln Ala Arg Gln Ile Leu Asp
    130                 135                 140

Phe Ser Lys Ile Glu Tyr Trp Gln Pro Ala Ser Gly Gln Glu Gly Arg
145                 150                 155                 160

Ala Phe Trp Leu Ile Ser Ser Pro Asp Gly Gln Leu His Ile Leu Gly
                165                 170                 175

Lys Thr Ala Gln Ala Cys Leu Ala Asn Pro Gln Asn Asp Gln Gln Ile
            180                 185                 190

Ala Gln Trp Leu Leu Glu Glu Thr Val Thr Pro Ala Gly Glu His Val
        195                 200                 205

Ser Tyr Gln Tyr Arg Ala Glu Asp Glu Ala His Cys Asp Asp Asn Glu
    210                 215                 220

Lys Thr Ala His Pro Asn Val Thr Ala Gln Arg Tyr Leu Val Gln Val
225                 230                 235                 240

Asn Tyr Gly Asn Ile Lys Pro Gln Ala Ser Leu Phe Val Leu Asp Asn
                245                 250                 255

Ala Pro Pro Ala Pro Glu Glu Trp Leu Phe His Leu Val Phe Asp His
            260                 265                 270

Gly Glu Arg Asp Thr Ser Leu His Thr Val Pro Thr Trp Asp Ala Gly
        275                 280                 285

Thr Ala Gln Trp Ser Val Arg Pro Asp Ile Phe Ser Arg Tyr Glu Tyr
    290                 295                 300

Gly Phe Glu Val Arg Thr Arg Arg Leu Cys Gln Gln Val Leu Met Phe
305                 310                 315                 320

His Arg Thr Ala Leu Met Ala Gly Glu Ala Ser Thr Asn Asp Ala Pro
                325                 330                 335

Glu Leu Val Gly Arg Leu Ile Leu Glu Tyr Asp Lys Asn Ala Ser Val
            340                 345                 350

Thr Thr Leu Ile Thr Ile Arg Gln Leu Ser His Glu Ser Asp Gly Ser
        355                 360                 365

Pro Val Thr Gln Pro Pro Leu Glu Leu Ala Trp Gln Arg Phe Asp Leu
    370                 375                 380

Glu Lys Met Pro Thr Trp Gln Arg Phe Asp Ala Leu Asp Asn Phe Asn
385                 390                 395                 400

Ser Gln Gln Arg Tyr Gln Leu Val Asp Leu Arg Gly Glu Gly Leu Pro
                405                 410                 415

Gly Met Leu Tyr Gln Asp Arg Gly Ala Trp Trp Tyr Lys Ala Pro Gln
            420                 425                 430
```

-continued

```
Arg Gln Glu Asp Gly Asp Ser Asn Ala Val Thr Tyr Asp Lys Ile Ala
        435                 440                 445

Pro Leu Pro Thr Leu Pro Asn Leu Gln Asp Asn Ala Ser Leu Met Asp
    450                 455                 460

Ile Asn Gly Asp Gly Gln Leu Asp Trp Val Val Thr Ala Ser Gly Ile
465                 470                 475                 480

Arg Gly Tyr His Ser Gln Gln Pro Asp Gly Lys Trp Thr His Phe Thr
                485                 490                 495

Pro Ile Asn Ala Leu Pro Val Glu Tyr Phe His Pro Ser Ile Gln Phe
            500                 505                 510

Ala Asp Leu Thr Gly Ala Gly Leu Ser Asp Leu Val Leu Ile Gly Pro
        515                 520                 525

Lys Ser Val Arg Leu Tyr Ala Asn Gln Arg Asn Gly Trp Arg Lys Gly
    530                 535                 540

Glu Asp Val Pro Gln Ser Thr Gly Ile Thr Leu Pro Val Thr Gly Thr
545                 550                 555                 560

Asp Ala Arg Lys Leu Val Ala Phe Ser Asp Met Leu Gly Ser Gly Gln
                565                 570                 575

Gln His Leu Val Glu Ile Lys Ala Asn Arg Val Thr Cys Trp Pro Asn
            580                 585                 590

Leu Gly His Gly Arg Phe Gly Gln Pro Leu Thr Leu Ser Gly Phe Ser
        595                 600                 605

Gln Pro Glu Asn Ser Phe Asn Pro Glu Arg Leu Phe Leu Ala Asp Ile
    610                 615                 620

Asp Gly Ser Gly Thr Thr Asp Leu Ile Tyr Ala Gln Ser Gly Ser Leu
625                 630                 635                 640

Leu Ile Tyr Leu Asn Gln Ser Gly Asn Gln Phe Asp Ala Pro Leu Thr
                645                 650                 655

Leu Ala Leu Pro Glu Gly Val Gln Phe Asp Asn Thr Cys Gln Leu Gln
            660                 665                 670

Val Ala Asp Ile Gln Gly Leu Gly Ile Ala Ser Leu Ile Leu Thr Val
        675                 680                 685

Pro His Ile Ala Pro His His Trp Arg Cys Asp Leu Ser Leu Thr Lys
    690                 695                 700

Pro Trp Leu Leu Asn Val Met Asn Asn Asn Arg Gly Ala His His Thr
705                 710                 715                 720

Leu His Tyr Arg Ser Ser Ala Gln Phe Trp Leu Asp Glu Lys Leu Gln
                725                 730                 735

Leu Thr Lys Ala Gly Lys Ser Pro Ala Cys Tyr Leu Pro Phe Pro Met
            740                 745                 750

His Leu Leu Trp Tyr Thr Glu Ile Gln Asp Glu Ile Ser Gly Asn Arg
        755                 760                 765

Leu Thr Ser Glu Val Asn Tyr Ser His Gly Val Trp Asp Gly Lys Glu
    770                 775                 780

Arg Glu Phe Arg Gly Phe Gly Cys Ile Lys Gln Thr Asp Thr Thr Thr
785                 790                 795                 800

Phe Ser His Gly Thr Ala Pro Glu Gln Ala Ala Pro Ser Leu Ser Ile
                805                 810                 815

Ser Trp Phe Ala Thr Gly Met Asp Glu Val Asp Ser Gln Leu Ala Thr
            820                 825                 830

Glu Tyr Trp Gln Ala Asp Thr Gln Ala Tyr Ser Gly Phe Glu Thr Arg
        835                 840                 845
```

-continued

```
Tyr Thr Val Trp Asp His Thr Asn Gln Thr Asp Gln Ala Phe Thr Pro
    850                 855                 860

Asn Glu Thr Gln Arg Asn Trp Leu Thr Arg Ala Leu Lys Gly Gln Leu
865                 870                 875                 880

Leu Arg Thr Glu Leu Tyr Gly Leu Asp Gly Thr Asp Lys Gln Thr Val
                885                 890                 895

Pro Tyr Thr Val Ser Glu Ser Arg Tyr Gln Val Arg Ser Ile Pro Val
            900                 905                 910

Asn Lys Glu Thr Glu Leu Ser Ala Trp Val Thr Ala Ile Glu Asn Arg
        915                 920                 925

Ser Tyr His Tyr Glu Arg Ile Ile Thr Asp Pro Gln Phe Ser Gln Ser
    930                 935                 940

Ile Lys Leu Gln His Asp Ile Phe Gly Gln Ser Leu Gln Ser Val Asp
945                 950                 955                 960

Ile Ala Trp Pro Arg Arg Glu Lys Pro Ala Val Asn Pro Tyr Pro Pro
                965                 970                 975

Thr Leu Pro Glu Thr Leu Phe Asp Ser Ser Tyr Asp Asp Gln Gln Gln
            980                 985                 990

Leu Leu Arg Leu Val Arg Gln Lys  Asn Ser Trp His His  Leu Thr Asp
        995                 1000                1005

Gly Glu  Asn Trp Arg Leu Gly  Leu Pro Asn Ala Gln  Arg Arg Asp
    1010                1015                1020

Val Tyr  Thr Tyr Asp Arg Ser  Lys Ile Pro Thr Glu  Gly Ile Ser
    1025                1030                1035

Leu Glu  Ile Leu Leu Lys Asp  Asp Gly Leu Leu Ala  Asp Glu Lys
    1040                1045                1050

Ala Ala  Val Tyr Leu Gly Gln  Gln Gln Thr Phe Tyr  Thr Ala Gly
    1055                1060                1065

Gln Ala  Glu Val Thr Leu Glu  Lys Pro Thr Leu Gln  Ala Leu Val
    1070                1075                1080

Ala Phe  Gln Glu Thr Ala Met  Met Asp Asp Thr Ser  Leu Gln Ala
    1085                1090                1095

Tyr Glu  Gly Val Ile Glu Glu  Gln Glu Leu Asn Thr  Ala Leu Thr
    1100                1105                1110

Gln Ala  Gly Tyr Gln Gln Val  Ala Arg Leu Phe Asn  Thr Arg Ser
    1115                1120                1125

Glu Ser  Pro Val Trp Ala Ala  Arg Gln Gly Tyr Thr  Asp Tyr Gly
    1130                1135                1140

Asp Ala  Ala Gln Phe Trp Arg  Pro Gln Ala Gln Arg  Asn Ser Leu
    1145                1150                1155

Leu Thr  Gly Lys Thr Thr Leu  Thr Trp Asp Thr His  His Cys Val
    1160                1165                1170

Ile Ile  Gln Thr Gln Asp Ala  Ala Gly Leu Thr Thr  Gln Ala His
    1175                1180                1185

Tyr Asp  Tyr Arg Phe Leu Thr  Pro Val Gln Leu Thr  Asp Ile Asn
    1190                1195                1200

Asp Asn  Gln His Ile Val Thr  Leu Asp Ala Leu Gly  Arg Val Thr
    1205                1210                1215

Thr Ser  Arg Phe Trp Gly Thr  Glu Ala Gly Gln Ala  Ala Gly Tyr
    1220                1225                1230

Ser Asn  Gln Pro Phe Thr Pro  Pro Asp Ser Val Asp  Lys Ala Leu
    1235                1240                1245

Ala Leu  Thr Gly Ala Leu Pro  Val Ala Gln Cys Leu  Val Tyr Ala
```

-continued

```
    1250                1255                1260

Val Asp  Ser Trp Met Pro Ser  Leu Ser Leu Ser Gln  Leu Ser Gln
    1265                1270                1275

Ser Gln  Glu Glu Ala Glu Ala  Leu Trp Ala Gln Leu  Arg Ala Ala
    1280                1285                1290

His Met  Ile Thr Glu Asp Gly  Lys Val Cys Ala Leu  Ser Gly Lys
    1295                1300                1305

Arg Gly  Thr Ser His Gln Asn  Leu Thr Ile Gln Leu  Ile Ser Leu
    1310                1315                1320

Leu Ala  Ser Ile Pro Arg Leu  Pro Pro His Val Leu  Gly Ile Thr
    1325                1330                1335

Thr Asp  Arg Tyr Asp Ser Asp  Pro Gln Gln Gln His  Gln Gln Thr
    1340                1345                1350

Val Ser  Phe Ser Asp Gly Phe  Gly Arg Leu Leu Gln  Ser Ser Ala
    1355                1360                1365

Arg His  Glu Ser Gly Asp Ala  Trp Gln Arg Lys Glu  Asp Gly Gly
    1370                1375                1380

Leu Val  Val Asp Ala Asn Gly  Val Leu Val Ser Ala  Pro Thr Asp
    1385                1390                1395

Thr Arg  Trp Ala Val Ser Gly  Arg Thr Glu Tyr Asp  Asp Lys Gly
    1400                1405                1410

Gln Pro  Val Arg Thr Tyr Gln  Pro Tyr Phe Leu Asn  Asp Trp Arg
    1415                1420                1425

Tyr Val  Ser Asp Asp Ser Ala  Arg Asp Asp Leu Phe  Ala Asp Thr
    1430                1435                1440

His Leu  Tyr Asp Pro Leu Gly  Arg Glu Tyr Lys Val  Ile Thr Ala
    1445                1450                1455

Lys Lys  Tyr Leu Arg Glu Lys  Leu Tyr Thr Pro Trp  Phe Ile Val
    1460                1465                1470

Ser Glu  Asp Glu Asn Asp Thr  Ala Ser Arg Thr Pro  Met Ser Pro
    1475                1480                1485

Ser Glu  Thr Thr Leu Tyr Thr  Gln Thr Pro Thr Val  Ser Val Leu
    1490                1495                1500

Asp Asn  Arg Gly Leu Ser Ile  Arg Asp Ile Gly Phe  His Arg Ile
    1505                1510                1515

Val Ile  Gly Gly Asp Thr Asp  Thr Arg Val Thr Arg  His Gln Tyr
    1520                1525                1530

Asp Ala  Arg Gly His Leu Asn  Tyr Ser Ile Asp Pro  Arg Leu Tyr
    1535                1540                1545

Asp Ala  Lys Gln Ala Asp Asn  Ser Val Lys Pro Asn  Phe Val Trp
    1550                1555                1560

Gln His  Asp Leu Ala Gly His  Ala Leu Arg Thr Glu  Ser Val Asp
    1565                1570                1575

Ala Gly  Arg Thr Val Ala Leu  Asn Asp Ile Glu Gly  Arg Ser Val
    1580                1585                1590

Met Thr  Met Asn Ala Thr Gly  Val Arg Gln Thr Arg  Arg Tyr Glu
    1595                1600                1605

Gly Asn  Thr Leu Pro Gly Arg  Leu Leu Ser Val Ser  Glu Gln Val
    1610                1615                1620

Phe Asn  Gln Glu Ser Ala Lys  Val Thr Glu Arg Phe  Ile Trp Ala
    1625                1630                1635

Gly Asn  Thr Thr Ser Glu Lys  Glu Tyr Asn Leu Ser  Gly Leu Cys
    1640                1645                1650
```

-continued

```
Ile Arg  His Tyr Asp Thr Ala  Gly Val Thr Arg Leu  Met Ser Gln
    1655                 1660                 1665

Ser Leu  Ala Gly Ala Met Leu  Ser Gln Ser His Gln  Leu Leu Ala
    1670                 1675                 1680

Glu Gly  Gln Glu Ala Asn Trp  Ser Gly Asp Asp Glu  Thr Val Trp
    1685                 1690                 1695

Gln Gly  Met Leu Ala Ser Glu  Val Tyr Thr Thr Gln  Ser Thr Thr
    1700                 1705                 1710

Asn Ala  Ile Gly Ala Leu Leu  Thr Gln Thr Asp Ala  Lys Gly Asn
    1715                 1720                 1725

Ile Gln  Arg Leu Ala Tyr Asp  Ile Ala Gly Gln Leu  Lys Gly Ser
    1730                 1735                 1740

Trp Leu  Thr Val Lys Gly Gln  Ser Glu Gln Val Ile  Val Lys Ser
    1745                 1750                 1755

Leu Ser  Trp Ser Ala Ala Gly  His Lys Leu Arg Glu  Glu His Gly
    1760                 1765                 1770

Asn Gly  Val Val Thr Glu Tyr  Ser Tyr Glu Pro Glu  Thr Gln Arg
    1775                 1780                 1785

Leu Ile  Gly Ile Thr Thr Arg  Arg Ala Glu Gly Ser  Gln Ser Gly
    1790                 1795                 1800

Ala Arg  Val Leu Gln Asp Leu  Arg Tyr Lys Tyr Asp  Pro Val Gly
    1805                 1810                 1815

Asn Val  Ile Ser Ile His Asn  Asp Ala Glu Ala Thr  Arg Phe Trp
    1820                 1825                 1830

Arg Asn  Gln Lys Val Glu Pro  Glu Asn Arg Tyr Val  Tyr Asp Ser
    1835                 1840                 1845

Leu Tyr  Gln Leu Met Ser Ala  Thr Gly Arg Glu Met  Ala Asn Ile
    1850                 1855                 1860

Gly Gln  Gln Ser Asn Gln Leu  Pro Ser Pro Val Ile  Pro Val Pro
    1865                 1870                 1875

Thr Asp  Asp Ser Thr Tyr Thr  Asn Tyr Leu Arg Thr  Tyr Thr Tyr
    1880                 1885                 1890

Asp Arg  Gly Gly Asn Leu Val  Gln Ile Arg His Ser  Ser Pro Ala
    1895                 1900                 1905

Thr Gln  Asn Ser Tyr Thr Thr  Asp Ile Thr Val Ser  Ser Arg Ser
    1910                 1915                 1920

Asn Arg  Ala Val Leu Ser Thr  Leu Thr Thr Asp Pro  Thr Arg Val
    1925                 1930                 1935

Asp Ala  Leu Phe Asp Ser Gly  Gly His Gln Lys Met  Leu Ile Pro
    1940                 1945                 1950

Gly Gln  Asn Leu Asp Trp Asn  Ile Arg Gly Glu Leu  Gln Arg Val
    1955                 1960                 1965

Thr Pro  Val Ser Arg Glu Asn  Ser Ser Asp Ser Glu  Trp Tyr Arg
    1970                 1975                 1980

Tyr Ser  Ser Asp Gly Met Arg  Leu Leu Lys Val Ser  Glu Gln Gln
    1985                 1990                 1995

Thr Gly  Asn Ser Thr Gln Val  Gln Arg Val Thr Tyr  Leu Pro Gly
    2000                 2005                 2010

Leu Glu  Leu Arg Thr Thr Gly  Val Ala Asp Lys Thr  Thr Glu Asp
    2015                 2020                 2025

Leu Gln  Val Ile Thr Val Gly  Glu Ala Gly Arg Ala  Gln Val Arg
    2030                 2035                 2040
```

-continued

```
Val Leu  His Trp Glu Ser Gly  Lys Pro Thr Asp Ile  Asp Asn Asn
    2045                 2050                 2055

Gln Val  Arg Tyr Ser Tyr Asp  Asn Leu Leu Gly Ser  Ser Gln Leu
    2060                 2065                 2070

Glu Leu  Asp Ser Glu Gly Gln  Ile Leu Ser Gln Glu  Glu Tyr Tyr
    2075                 2080                 2085

Pro Tyr  Gly Gly Thr Ala Ile  Trp Ala Ala Arg Asn  Gln Thr Glu
    2090                 2095                 2100

Ala Ser  Tyr Lys Phe Ile Arg  Tyr Ser Gly Lys Glu  Arg Asp Ala
    2105                 2110                 2115

Thr Gly  Leu Tyr Tyr Tyr Gly  Tyr Arg Tyr Tyr Gln  Pro Trp Val
    2120                 2125                 2130

Gly Arg  Trp Leu Ser Ala Asp  Pro Ala Gly Thr Val  Asp Gly Leu
    2135                 2140                 2145

Asn Leu  Tyr Arg Met Val Arg  Asn Asn Pro Ile Thr  Leu Thr Asp
    2150                 2155                 2160

His Asp  Gly Leu Ala Pro Ser  Pro Asn Arg Asn Arg  Asn Thr Phe
    2165                 2170                 2175

Trp Phe  Ala Ser Phe Leu Phe  Arg Lys Pro Asp Glu  Gly Met Ser
    2180                 2185                 2190

Ala Ser  Met Arg Arg Gly Gln  Lys Ile Gly Arg Ala  Ile Ala Gly
    2195                 2200                 2205

Gly Ile  Ala Ile Gly Gly Leu  Ala Ala Thr Ile Ala  Ala Thr Ala
    2210                 2215                 2220

Gly Ala  Ala Ile Pro Val Ile  Leu Gly Val Ala Ala  Val Gly Ala
    2225                 2230                 2235

Gly Ile  Gly Ala Leu Met Gly  Tyr Asn Val Gly Ser  Leu Leu Glu
    2240                 2245                 2250

Lys Gly  Gly Ala Leu Leu Ala  Arg Leu Val Gln Gly  Lys Ser Thr
    2255                 2260                 2265

Leu Val  Gln Ser Ala Ala Gly  Ala Ala Ala Gly Ala  Ser Ser Ala
    2270                 2275                 2280

Ala Ala  Tyr Gly Ala Arg Ala  Gln Gly Val Gly Val  Ala Ser Ala
    2285                 2290                 2295

Ala Gly  Ala Val Thr Gly Ala  Val Gly Ser Trp Ile  Asn Asn Ala
    2300                 2305                 2310

Asp Arg  Gly Ile Gly Gly Ala  Ile Gly Ala Gly Ser  Ala Val Gly
    2315                 2320                 2325

Thr Ile  Asp Thr Met Leu Gly  Thr Ala Ser Thr Leu  Thr His Glu
    2330                 2335                 2340

Val Gly  Ala Ala Ala Gly Gly  Ala Ala Gly Gly Met  Ile Thr Gly
    2345                 2350                 2355

Thr Gln  Gly Ser Thr Arg Ala  Gly Ile His Ala Gly  Ile Gly Thr
    2360                 2365                 2370

Tyr Tyr  Gly Ser Trp Ile Gly  Phe Gly Leu Asp Val  Ala Ser Asn
    2375                 2380                 2385

Pro Ala  Gly His Leu Ala Asn  Tyr Ala Val Gly Tyr  Ala Ala Gly
    2390                 2395                 2400

Leu Gly  Ala Glu Met Ala Val  Asn Arg Ile Met Gly  Gly Gly Phe
    2405                 2410                 2415

Leu Ser  Arg Leu Leu Gly Arg  Val Val Ser Pro Tyr  Ala Ala Gly
    2420                 2425                 2430

Leu Ala  Arg Gln Leu Val His  Phe Ser Val Ala Arg  Pro Val Phe
```

-continued

```
    2435                2440                2445

Glu Pro  Ile Phe Ser Val Leu  Gly Gly Leu Val Gly  Gly Ile Gly
    2450                2455                2460

Thr Gly  Leu His Arg Val Met  Gly Arg Glu Ser Trp  Ile Ser Arg
    2465                2470                2475

Ala Leu  Ser Ala Ala Gly Ser  Gly Ile Asp His Val  Ala Gly Met
    2480                2485                2490

Ile Gly  Asn Gln Ile Arg Gly  Arg Val Leu Thr Thr  Thr Gly Ile
    2495                2500                2505

Ala Asn  Ala Ile Asp Tyr Gly  Thr Ser Ala Val Gly  Ala Ala Arg
    2510                2515                2520

Arg Val  Phe Ser Leu
    2525
```

<210> SEQ ID NO 7
<211> LENGTH: 6654
<212> TYPE: DNA
<213> ORGANISM: Methanosarcina acetivorans

<400> SEQUENCE: 7

```
atgtttttca tggtactaca ggttccgatc cataccagaa gactgctttc aatttttatg     60
attattgtat tgctcacacc gaatgtatat tgtcttgaaa acacagaggc aagccaggac    120
gtaaattccg agggttcaca agttgattcc gagtcatacg aggaaaataa taaaaacata    180
gtagaatctg aggaagaaac gagtgaaaca atttccgatc ttgatagtga aagtgtggac    240
gatgatacag aaactgtttc tgaagatact atgttaactg caactacagt ttccgaagat    300
gaggagcctt taagggatgc aaaagcgtat cttagtccta ccctggaaaa tgaaaacaat    360
tactttgaca caagcctgtt tacaggttct tttgtttatt cttatccgat tgaaacttta    420
aaaggaagaa ctggattaga gccggaggtt tctctaacct attccagtgc tacaggctca    480
aaaggaacat acggttcact ggggattggg tggtcattga atgagaactg cattatcagg    540
gataccagat ataccccctga aaacacaaat gatgatagat ttattcttgt tttggacggc    600
tcaacatata aactcgtcta tgtggaaagt gacaactcat atcacaccga aactgaaagt    660
tttatgaaaa ttgaaaagag tgcaaccagt agcaattctt tcggggacta ctggaccctc    720
aacatgccgg acgggacaaa atatcgtttt ggttataata ttgattccga acaaagaaac    780
tccgttgaat caagaaatta tgtcagtaaa tggtggctcg atcttataga ggacgtcaat    840
ggcaacaaga ttaaatatac gtatcttgaa aatccggtaa gtggcgaggt cggaagcaca    900
tatcctgaca gcataaccta caacgacaat catgcagtta ttgattttga gttcacggaa    960
aaaccacgtg tattcactat ttatgaatat ggtaacaaaa ttatcgaaaa aaacttgatc   1020
tccagtatta ctgttcgtaa cgatgaaacc gttctctgga aatatgatct tgattatgaa   1080
acccaacagt taaaattaca tctgaaatcc attacaaaaa caggattaaa caatgaagag   1140
ttcccaccta ctgtttttga atatgactca ataaccgaag ggtggcagga aagtagttcc   1200
tggaccccac caacttccat gtcaggagac aagggaagaa gaattgcaga tgttaatggc   1260
gacggattag atgacatcct taaaggatat gtagatagtg acggggatgt ttattgctca   1320
acctggataa ataccggaga tgactgggaa ctgaacagtt cctggacaac accaacatat   1380
ttcaggcatt ataatcatga tgggggagct cgccttgcag atgtcaacgg ggacggatta   1440
gttgacatta tccagcacgg attttacatt tcctctgcct ggttgaatac cggtaccggt   1500
tgggaacaaa acaactcatg gatacctcca ctggattttg gctggtcaag tgattatggt   1560
```

-continued

```
gtaagagttt tagatgtcaa cggggacgga ttagttgaca taattaaggg ttacaaaaac   1620
gatcgtggaa ctatatacta tgatgcttat ctcaataccg gtgaaggctg gatacaggat   1680
aattcatgga acccgcctac ttacttctca tacgataata ttgatacagg cgtacgactc   1740
acggacctta acggagacga cctggtcgat atctttaaac tacgctcttc atggttaaac   1800
accggcagtg gatgggaaca ggataactcc tgggcgcccc caatatctct cgactcagat   1860
cagggtgtag tcttagtgga tgttaacgga gacggtttga ctgacattct taagagttat   1920
tataacgatg ccgggtacac ttacgatgcc tggataagca ctggcaatgg ctgggaaaac   1980
gataactcat ggaatccgcc aacgttgatc gcaagctacg gcaaagacca gggtgtacgg   2040
tttgctgatt tgaatggaga cggtttgaca gacattatca aagcaggcta tagcgattac   2100
tgtgcctgga caaacacgaa cactgagagt acagaaaatt acaaaactca gggcctgctc   2160
aaaaaaatac agcactcaac cggtggaagc acgaccataa aatatgaacc ttctacgctc   2220
ttcgataaca ccggggaaga cggcgtttcg gatttgacca tgagtatgtg ggtcacaagc   2280
agtgtgacag gagataatgg tattacaggc acgggaagcg tagtttcaac aacagattac   2340
acctataaaa acggaatgca gtacttcgac ccaccggaag aaatcgaatt cagaggattt   2400
ggtgaagtta ctgttgaaaa cgagtattcg atagtaaagc actttttcca ccaggacaac   2460
gtcctcaagg gcatcgaaca ccatactgaa gtctgggaca aaaacggaaa cctttacagt   2520
tcctcggaca cggaatatac tgctcaggaa atataccctg atgtcaacct gattttgctg   2580
gactcggagt ccaaaacaag gttcgacggg ctggtacaga acccgaccag ttcagccggc   2640
tggtcatatc tcaccgaata taacgaatat gacgattacg ggaacccgct ttccataaca   2700
gatcacggcg atgtgaacaa tgccggggat gaaaaatatt accattttgg atatgccaat   2760
gcagaaaatc cgtggatcct cggaaaaaaa acacatgaat gggtggaaga ctccgatcat   2820
gtaaagaaga gcgaatcatg gtactattat gacgaaacaa atgacaacag tgccattagc   2880
aaagggcagc tcactaaaac agtattatgg aacaatatgg gagataatcc caatgttctg   2940
tacgattacg ataactatgg aaatataatc cggattacaa atccggaagg ggcttcaaag   3000
aacataggat atgatgaaaa ccatttatac cccgtttaca tcgaaaacgc ctttggtcaa   3060
aaagagtgtt atgaattcaa cgaccttggc aggataacga aaataacaga cagtaacgac   3120
atttctatag cgtatatcta tgatgacctg cacagaataa caaaagtact gaaagtcaat   3180
gacacacttg attctccatc tattgagtat acgtactatc aggatggagt agcgcctgaa   3240
aaaattttaa ccacaacaaa agaatgtggt agtgaagaga acaattacgt cattaatggt   3300
tctgtattca gcaattataa acgtatcaca atttcaccat catcagacgg aaccctgact   3360
gattaccagg tgaagctgga tattaactat gaatcagaga tgcaatccga ttttgatgat   3420
cttcgttttg ttgatgaaaa tggcattcta cttccatatt ggatcgaaga aaaggttgat   3480
tccagttatg caaaagtctg ggtaaaggtt cctgtaatcg atggaattga tggtgctact   3540
atcaaaatgt attatgataa ctcatatgtt tcatcagcag agaatggcga tgatgttttt   3600
gaattctttg atgatttcga aagcggtgta atagacaatg ctaaatggaa tgaagttggc   3660
tcgccgacaa ttgttgatga caatggagac aaagtgctga aggtgacacc aagcaacgag   3720
gtaaatacat ttaataagtt ttccggtaca gagtacatcg ttgggggggtt gatgaagttt   3780
tcatcattcg gcgactacgg accacgcatg acacttgatg tcagaaggca aaatgaccaa   3840
acgatacttg cgacatgtcg tatagaatcg tatgcggatg ggacaggagg aacaggcacg   3900
```

-continued

```
tcaatacgat attatccggg ttcaggaagt ttcattacag ttgcacaagc tcggccatcg   3960
tggtctaccg gagtatggaa tagattttca ttttcctcaa cgaatagtac acagaaacta   4020
acaattaacg gccttgtcat ttctggcaca tgtgaaaaca atctttcagg ttcgataaat   4080
atacatacct gggacagtgg caatgacatt agactttctt atttatatgt ccgtaaattc   4140
gcatcgtctg agcccactgt tgtgcttgaa gaaaaaaact atgtctctac tttcgactcc   4200
actgactcat acgacggctt cggtcaattg atccagaaaa agtatgaagg ggaaggcggc   4260
tggattatcc agaacaccgc atataacgaa ctgggccttg tagaaagtgc cgaaatcccg   4320
cattattcgg accaaaccgg cttatccgta acctacgagt atgatgcagc cggacggcca   4380
acggttatca ccaatactga cagcactacc ctgacatacg attacaacct tgacgacacc   4440
acgattacca accagaacgg cgttgacaaa acactaacaa gtgatgtttt cggaaatatt   4500
gtcaaggtat atgagttcaa cgaaggcgaa acttacgtta catcctacag ttacgatgcc   4560
ctgaataatc tcatcgagat tacgccgggc ttcaatgacc ctcaggctcc gcccagtgtt   4620
tatttcacct acgattccct cggcaggaaa gtggcaatgg acgactctga catgggcagc   4680
tggacctatg aatacgacct gaacggaaac ctgataaacc agaccgattc acggggagtt   4740
tcgacaatcc tcagttatga tgacctggac agggttactg caatagatta ccctaacgat   4800
gaggacatca gtttcaccta cgaccttgaa tttaacggta cgctttcccg ggtaacaaaa   4860
ggacccgcat catcaagtta cgactacgac ctgcgctaca gggtagaaag cgaaacttta   4920
accattgacg gtacacccta caccacgtcc tacgattatg acagcatgga cagggtcacg   4980
ggaatcacct acccgaacgg cgaagccgtc agcctgacat acaatgcgca gacccttctt   5040
gaaagcgttg acggcgtgat tgacgacctt gactataacg caaggaacca gatcacaaga   5100
aaggaatatt ccaacggcgt aatcacaacc tacacctacg acagtcaaaa actgctgctg   5160
gacagaatct attccgcagg cctccaggac ctcaactacg atttcgataa cgtcggcaat   5220
gtcctcgaga tcgcggacaa cacccaaaat tccgtaaaaa cctacggata cgacgacctt   5280
gacaggctgg tcagcgcaga tatgtcggtc aacagcgtcc cgacctacca gagagatttc   5340
acctacgacc ggtatggcag tatcaggcag gtggataaca acggcgccac agtctcctct   5400
tacggatact ctgcgacccc gtcccacgca cctgttacct acaacggaaa caccctcgac   5460
tatgacgcaa acggaaacct tgtcgacgat gaggatttca tctacgtcta caacgatgcc   5520
aaccagttaa gtgaagtccg ttactctgcc aataattccc ttgtagaaaa gtactggtac   5580
gatgcaaacg gccagagaat caagaaacag aattccgatg gagaattcac ctattacatc   5640
aacaagttct acgaaatcga taacggcatc tctaccagct acttcttccg cgatgatgaa   5700
cgcgtagcca aagaaacatc cgaaagtatg gagtggtacc tctccgatca cataggcagc   5760
acttccctga tggttaacga gaatgggctt gaggtcgaac gcaccgattt cccatacgga   5820
caggttcggt caggcgggct ggagaaatac gggtttacag ggcaggaaaa tgatgccgat   5880
acagggctga tgtactacgg tgcgaggtat tactcgcctg agtacagggt tttcgttcag   5940
ccggatacaa tgcttcctga cccgtataat ccgcaggcgt tgaacaggta ttcttatgtg   6000
ctgaacaacc cggtgaagta tactgatccg agtgggcatg ttgtggacgt ccttgtggat   6060
ggcggatttc ttttgatgga tttagacgac atccgcaccg ggaatgctga taaatggaca   6120
tacatcggtc ttggtgttga ccttgtatgt gctttcgttc cgggtgtgac agggggaagg   6180
ctaggagttc aggctctgga ggaaacagtt actcatgcgg ataacgttga ggatttgttt   6240
aagctactgg ataaaacggt ggatgcagag aagaaagttg acgatgtgat agattctgga   6300
```

-continued

```
aaagttgcta aaaatagtaa ccaaatttac aacgttatca aaagagcgga cttgcctaat   6360

acaaaaatca caagttcgaa attacaacat gaatggaaac atgcaactga tttcggaata   6420

aaaggcaatt ggaataaagc taatggagat ctatatgaaa aagctattca gaatcatata   6480

aatactgcac ctgaagttta taaatcgact tatagacaaa atcaagatgt ttatgtttat   6540

ttgaataagg agacaggggt gggagtatac acagatcttt ctgggaatta tattggagct   6600

ggaaattcag tccggaacag attaagtatc atacaactaa tggacttaaa atag         6654


<210> SEQ ID NO 8
<211> LENGTH: 2217
<212> TYPE: PRT
<213> ORGANISM: Methanosarcina acetivorans

<400> SEQUENCE: 8

Met Phe Phe Met Val Leu Gln Val Pro Ile His Thr Arg Arg Leu Leu
1               5                   10                  15

Ser Ile Phe Met Ile Ile Val Leu Leu Thr Pro Asn Val Tyr Cys Leu
            20                  25                  30

Glu Asn Thr Glu Ala Ser Gln Asp Val Asn Ser Glu Gly Ser Gln Val
        35                  40                  45

Asp Ser Glu Ser Tyr Glu Glu Asn Asn Lys Asn Ile Val Glu Ser Glu
    50                  55                  60

Glu Glu Thr Ser Glu Thr Ile Ser Asp Leu Asp Ser Glu Ser Val Asp
65                  70                  75                  80

Asp Asp Thr Glu Thr Val Ser Glu Asp Thr Met Leu Thr Ala Thr Thr
                85                  90                  95

Val Ser Glu Asp Glu Glu Pro Leu Arg Asp Ala Lys Ala Tyr Leu Ser
            100                 105                 110

Pro Thr Leu Glu Asn Glu Asn Asn Tyr Phe Asp Thr Ser Leu Phe Thr
        115                 120                 125

Gly Ser Phe Val Tyr Ser Tyr Pro Ile Glu Thr Leu Lys Gly Arg Thr
    130                 135                 140

Gly Leu Glu Pro Glu Val Ser Leu Thr Tyr Ser Ser Ala Thr Gly Ser
145                 150                 155                 160

Lys Gly Thr Tyr Gly Ser Leu Gly Ile Gly Trp Ser Leu Asn Glu Asn
                165                 170                 175

Cys Ile Ile Arg Asp Thr Arg Tyr Thr Pro Glu Asn Thr Asn Asp Asp
            180                 185                 190

Arg Phe Ile Leu Val Leu Asp Gly Ser Thr Tyr Lys Leu Val Tyr Val
        195                 200                 205

Glu Ser Asp Asn Ser Tyr His Thr Glu Thr Glu Ser Phe Met Lys Ile
    210                 215                 220

Glu Lys Ser Ala Thr Ser Ser Asn Ser Phe Gly Asp Tyr Trp Thr Leu
225                 230                 235                 240

Asn Met Pro Asp Gly Thr Lys Tyr Arg Phe Gly Tyr Asn Ile Asp Ser
                245                 250                 255

Glu Gln Arg Asn Ser Val Glu Ser Arg Asn Tyr Val Ser Lys Trp Trp
            260                 265                 270

Leu Asp Leu Ile Glu Asp Val Asn Gly Asn Lys Ile Lys Tyr Thr Tyr
        275                 280                 285

Leu Glu Asn Pro Val Ser Gly Glu Val Gly Ser Thr Tyr Pro Asp Ser
    290                 295                 300

Ile Thr Tyr Asn Asp Asn His Ala Val Ile Asp Phe Glu Phe Thr Glu
```

-continued

```
305                 310                 315                 320

Lys Pro Arg Val Phe Thr Ile Tyr Glu Tyr Gly Asn Lys Ile Ile Glu
                325                 330                 335

Lys Asn Leu Ile Ser Ser Ile Thr Val Arg Asn Asp Glu Thr Val Leu
            340                 345                 350

Trp Lys Tyr Asp Leu Asp Tyr Glu Thr Gln Gln Leu Lys Leu His Leu
        355                 360                 365

Lys Ser Ile Thr Lys Thr Gly Leu Asn Asn Glu Glu Phe Pro Pro Thr
    370                 375                 380

Val Phe Glu Tyr Asp Ser Ile Thr Glu Gly Trp Gln Glu Ser Ser Ser
385                 390                 395                 400

Trp Thr Pro Pro Thr Ser Met Ser Gly Asp Lys Gly Arg Arg Ile Ala
                405                 410                 415

Asp Val Asn Gly Asp Gly Leu Asp Asp Ile Leu Lys Gly Tyr Val Asp
            420                 425                 430

Ser Asp Gly Asp Val Tyr Cys Ser Thr Trp Ile Asn Thr Gly Asp Asp
        435                 440                 445

Trp Glu Leu Asn Ser Ser Trp Thr Thr Pro Thr Tyr Phe Arg His Tyr
    450                 455                 460

Asn His Asp Gly Gly Ala Arg Leu Ala Asp Val Asn Gly Asp Gly Leu
465                 470                 475                 480

Val Asp Ile Ile Gln His Gly Phe Tyr Ile Ser Ser Ala Trp Leu Asn
                485                 490                 495

Thr Gly Thr Gly Trp Glu Gln Asn Asn Ser Trp Ile Pro Pro Leu Asp
            500                 505                 510

Phe Gly Trp Ser Ser Asp Tyr Gly Val Arg Val Leu Asp Val Asn Gly
        515                 520                 525

Asp Gly Leu Val Asp Ile Ile Lys Gly Tyr Lys Asn Asp Arg Gly Thr
    530                 535                 540

Ile Tyr Tyr Asp Ala Tyr Leu Asn Thr Gly Glu Gly Trp Ile Gln Asp
545                 550                 555                 560

Asn Ser Trp Asn Pro Pro Thr Tyr Phe Ser Tyr Asp Asn Ile Asp Thr
                565                 570                 575

Gly Val Arg Leu Thr Asp Leu Asn Gly Asp Asp Leu Val Asp Ile Phe
            580                 585                 590

Lys Leu Arg Ser Ser Trp Leu Asn Thr Gly Ser Gly Trp Glu Gln Asp
        595                 600                 605

Asn Ser Trp Ala Pro Pro Ile Ser Leu Asp Ser Asp Gln Gly Val Val
    610                 615                 620

Leu Val Asp Val Asn Gly Asp Gly Leu Thr Asp Ile Leu Lys Ser Tyr
625                 630                 635                 640

Tyr Asn Asp Ala Gly Tyr Thr Tyr Asp Ala Trp Ile Ser Thr Gly Asn
                645                 650                 655

Gly Trp Glu Asn Asp Asn Ser Trp Asn Pro Pro Thr Leu Ile Ala Ser
            660                 665                 670

Tyr Gly Lys Asp Gln Gly Val Arg Phe Ala Asp Leu Asn Gly Asp Gly
        675                 680                 685

Leu Thr Asp Ile Ile Lys Ala Gly Tyr Ser Asp Tyr Cys Ala Trp Thr
    690                 695                 700

Asn Thr Asn Thr Glu Ser Thr Glu Asn Tyr Lys Thr Gln Gly Leu Leu
705                 710                 715                 720

Lys Lys Ile Gln His Ser Thr Gly Gly Ser Thr Thr Ile Lys Tyr Glu
                725                 730                 735
```

-continued

```
Pro Ser Thr Leu Phe Asp Asn Thr Gly Glu Asp Gly Val Ser Asp Leu
            740                 745                 750

Thr Met Ser Met Trp Val Thr Ser Ser Val Thr Gly Asp Asn Gly Ile
        755                 760                 765

Thr Gly Thr Gly Ser Val Val Ser Thr Thr Asp Tyr Thr Tyr Lys Asn
    770                 775                 780

Gly Met Gln Tyr Phe Asp Pro Pro Glu Glu Ile Glu Phe Arg Gly Phe
785                 790                 795                 800

Gly Glu Val Thr Val Glu Asn Glu Tyr Ser Ile Val Lys His Phe Phe
                805                 810                 815

His Gln Asp Asn Val Leu Lys Gly Ile Glu His His Thr Glu Val Trp
            820                 825                 830

Asp Lys Asn Gly Asn Leu Tyr Ser Ser Ser Asp Thr Glu Tyr Thr Ala
        835                 840                 845

Gln Glu Ile Tyr Pro Asp Val Asn Leu Ile Leu Leu Asp Ser Glu Ser
    850                 855                 860

Lys Thr Arg Phe Asp Gly Leu Val Gln Asn Pro Thr Ser Ser Ala Gly
865                 870                 875                 880

Trp Ser Tyr Leu Thr Glu Tyr Asn Glu Tyr Asp Asp Tyr Gly Asn Pro
                885                 890                 895

Leu Ser Ile Thr Asp His Gly Asp Val Asn Asn Ala Gly Asp Glu Lys
            900                 905                 910

Tyr Tyr His Phe Gly Tyr Ala Asn Ala Glu Asn Pro Trp Ile Leu Gly
        915                 920                 925

Lys Lys Thr His Glu Trp Val Glu Asp Ser Asp His Val Lys Lys Ser
    930                 935                 940

Glu Ser Trp Tyr Tyr Tyr Asp Glu Thr Asn Asp Asn Ser Ala Ile Ser
945                 950                 955                 960

Lys Gly Gln Leu Thr Lys Thr Val Leu Trp Asn Asn Met Gly Asp Asn
                965                 970                 975

Pro Asn Val Leu Tyr Asp Tyr Asp Asn Tyr Gly Asn Ile Ile Arg Ile
            980                 985                 990

Thr Asn Pro Glu Gly Ala Ser Lys  Asn Ile Gly Tyr Asp  Glu Asn His
        995                 1000                 1005

Leu Tyr  Pro Val Tyr Ile Glu  Asn Ala Phe Gly Gln  Lys Glu Cys
    1010                 1015                 1020

Tyr Glu  Phe Asn Asp Leu Gly  Arg Ile Thr Lys Ile  Thr Asp Ser
    1025                 1030                 1035

Asn Asp  Ile Ser Ile Ala Tyr  Ile Tyr Asp Asp Leu  His Arg Ile
    1040                 1045                 1050

Thr Lys  Val Leu Lys Val Asn  Asp Thr Leu Asp Ser  Pro Ser Ile
    1055                 1060                 1065

Glu Tyr  Thr Tyr Tyr Gln Asp  Gly Val Ala Pro Glu  Lys Ile Leu
    1070                 1075                 1080

Thr Thr  Thr Lys Glu Cys Gly  Ser Glu Glu Asn Asn  Tyr Val Ile
    1085                 1090                 1095

Asn Gly  Ser Val Phe Ser Asn  Tyr Lys Arg Ile Thr  Ile Ser Pro
    1100                 1105                 1110

Ser Ser  Asp Gly Thr Leu Thr  Asp Tyr Gln Val Lys  Leu Asp Ile
    1115                 1120                 1125

Asn Tyr  Glu Ser Glu Met Gln  Ser Asp Phe Asp Asp  Leu Arg Phe
    1130                 1135                 1140
```

-continued

```
Val Asp  Glu Asn Gly Ile Leu  Leu Pro Tyr Trp Ile  Glu Glu Lys
    1145                 1150                 1155

Val Asp  Ser Ser Tyr Ala Lys  Val Trp Val Lys Val  Pro Val Ile
    1160                 1165                 1170

Asp Gly  Ile Asp Gly Ala Thr  Ile Lys Met Tyr Tyr  Asp Asn Ser
    1175                 1180                 1185

Tyr Val  Ser Ser Ala Glu Asn  Gly Asp Asp Val Phe  Glu Phe Phe
    1190                 1195                 1200

Asp Asp  Phe Glu Ser Gly Val  Ile Asp Asn Ala Lys  Trp Asn Glu
    1205                 1210                 1215

Val Gly  Ser Pro Thr Ile Val  Asp Asp Asn Gly Asp  Lys Val Leu
    1220                 1225                 1230

Lys Val  Thr Pro Ser Asn Glu  Val Asn Thr Phe Asn  Lys Phe Ser
    1235                 1240                 1245

Gly Thr  Glu Tyr Ile Val Gly  Gly Leu Met Lys Phe  Ser Ser Phe
    1250                 1255                 1260

Gly Asp  Tyr Gly Pro Arg Met  Thr Leu Asp Val Arg  Arg Gln Asn
    1265                 1270                 1275

Asp Gln  Thr Ile Leu Ala Thr  Cys Arg Ile Glu Ser  Tyr Ala Asp
    1280                 1285                 1290

Gly Thr  Gly Gly Thr Gly Thr  Ser Ile Arg Tyr Tyr  Pro Gly Ser
    1295                 1300                 1305

Gly Ser  Phe Ile Thr Val Ala  Gln Ala Arg Pro Ser  Trp Ser Thr
    1310                 1315                 1320

Gly Val  Trp Asn Arg Phe Ser  Phe Ser Ser Thr Asn  Ser Thr Gln
    1325                 1330                 1335

Lys Leu  Thr Ile Asn Gly Leu  Val Ile Ser Gly Thr  Cys Glu Asn
    1340                 1345                 1350

Asn Leu  Ser Gly Ser Ile Asn  Ile His Thr Trp Asp  Ser Gly Asn
    1355                 1360                 1365

Asp Ile  Arg Leu Ser Tyr Leu  Tyr Val Arg Lys Phe  Ala Ser Ser
    1370                 1375                 1380

Glu Pro  Thr Val Val Leu Glu  Glu Lys Asn Tyr Val  Ser Thr Phe
    1385                 1390                 1395

Asp Ser  Thr Asp Ser Tyr Asp  Gly Phe Gly Gln Leu  Ile Gln Lys
    1400                 1405                 1410

Lys Tyr  Glu Gly Glu Gly Gly  Trp Ile Ile Gln Asn  Thr Ala Tyr
    1415                 1420                 1425

Asn Glu  Leu Gly Leu Val Glu  Ser Ala Glu Ile Pro  His Tyr Ser
    1430                 1435                 1440

Asp Gln  Thr Gly Leu Ser Val  Thr Tyr Glu Tyr Asp  Ala Ala Gly
    1445                 1450                 1455

Arg Pro  Thr Val Ile Thr Asn  Thr Asp Ser Thr Thr  Leu Thr Tyr
    1460                 1465                 1470

Asp Tyr  Asn Leu Asp Asp Thr  Thr Ile Thr Asn Gln  Asn Gly Val
    1475                 1480                 1485

Asp Lys  Thr Leu Thr Ser Asp  Val Phe Gly Asn Ile  Val Lys Val
    1490                 1495                 1500

Tyr Glu  Phe Asn Glu Gly Glu  Thr Tyr Val Thr Ser  Tyr Ser Tyr
    1505                 1510                 1515

Asp Ala  Leu Asn Asn Leu Ile  Glu Ile Thr Pro Gly  Phe Asn Asp
    1520                 1525                 1530

Pro Gln  Ala Pro Pro Ser Val  Tyr Phe Thr Tyr Asp  Ser Leu Gly
```

-continued

```
    1535                1540                1545

Arg Lys Val Ala Met Asp Asp Ser Asp Met Gly Ser Trp Thr Tyr
    1550                1555                1560

Glu Tyr Asp Leu Asn Gly Asn Leu Ile Asn Gln Thr Asp Ser Arg
    1565                1570                1575

Gly Val Ser Thr Ile Leu Ser Tyr Asp Asp Leu Asp Arg Val Thr
    1580                1585                1590

Ala Ile Asp Tyr Pro Asn Asp Glu Asp Ile Ser Phe Thr Tyr Asp
    1595                1600                1605

Leu Glu Phe Asn Gly Thr Leu Ser Arg Val Thr Lys Gly Pro Ala
    1610                1615                1620

Ser Ser Ser Tyr Asp Tyr Asp Leu Arg Tyr Arg Val Glu Ser Glu
    1625                1630                1635

Thr Leu Thr Ile Asp Gly Thr Pro Tyr Thr Thr Ser Tyr Asp Tyr
    1640                1645                1650

Asp Ser Met Asp Arg Val Thr Gly Ile Thr Tyr Pro Asn Gly Glu
    1655                1660                1665

Ala Val Ser Leu Thr Tyr Asn Ala Gln Thr Leu Leu Glu Ser Val
    1670                1675                1680

Asp Gly Val Ile Asp Asp Leu Asp Tyr Asn Ala Arg Asn Gln Ile
    1685                1690                1695

Thr Arg Lys Glu Tyr Ser Asn Gly Val Ile Thr Thr Tyr Thr Tyr
    1700                1705                1710

Asp Ser Gln Lys Leu Leu Leu Asp Arg Ile Tyr Ser Ala Gly Leu
    1715                1720                1725

Gln Asp Leu Asn Tyr Asp Phe Asp Asn Val Gly Asn Val Leu Glu
    1730                1735                1740

Ile Ala Asp Asn Thr Gln Asn Ser Val Lys Thr Tyr Gly Tyr Asp
    1745                1750                1755

Asp Leu Asp Arg Leu Val Ser Ala Asp Met Ser Val Asn Ser Val
    1760                1765                1770

Pro Thr Tyr Gln Arg Asp Phe Thr Tyr Asp Arg Tyr Gly Ser Ile
    1775                1780                1785

Arg Gln Val Asp Asn Asn Gly Ala Thr Val Ser Ser Tyr Gly Tyr
    1790                1795                1800

Ser Ala Thr Pro Ser His Ala Pro Val Thr Tyr Asn Gly Asn Thr
    1805                1810                1815

Leu Asp Tyr Asp Ala Asn Gly Asn Leu Val Asp Asp Glu Asp Phe
    1820                1825                1830

Ile Tyr Val Tyr Asn Asp Ala Asn Gln Leu Ser Glu Val Arg Tyr
    1835                1840                1845

Ser Ala Asn Asn Ser Leu Val Glu Lys Tyr Trp Tyr Asp Ala Asn
    1850                1855                1860

Gly Gln Arg Ile Lys Lys Gln Asn Ser Asp Gly Glu Phe Thr Tyr
    1865                1870                1875

Tyr Ile Asn Lys Phe Tyr Glu Ile Asp Asn Gly Ile Ser Thr Ser
    1880                1885                1890

Tyr Phe Phe Arg Asp Asp Glu Arg Val Ala Lys Glu Thr Ser Glu
    1895                1900                1905

Ser Met Glu Trp Tyr Leu Ser Asp His Ile Gly Ser Thr Ser Leu
    1910                1915                1920

Met Val Asn Glu Asn Gly Leu Glu Val Glu Arg Thr Asp Phe Pro
    1925                1930                1935
```

-continued

```
Tyr Gly  Gln Val Arg Ser Gly  Gly Leu Glu Lys Tyr  Gly Phe Thr
    1940                 1945                 1950

Gly Gln  Glu Asn Asp Ala Asp  Thr Gly Leu Met Tyr  Tyr Gly Ala
    1955                 1960                 1965

Arg Tyr  Tyr Ser Pro Glu Tyr  Arg Val Phe Val Gln  Pro Asp Thr
    1970                 1975                 1980

Met Leu  Pro Asp Pro Tyr Asn  Pro Gln Ala Leu Asn  Arg Tyr Ser
    1985                 1990                 1995

Tyr Val  Leu Asn Asn Pro Val  Lys Tyr Thr Asp Pro  Ser Gly His
    2000                 2005                 2010

Val Val  Asp Val Leu Val Asp  Gly Gly Phe Leu Leu  Met Asp Leu
    2015                 2020                 2025

Asp Asp  Ile Arg Thr Gly Asn  Ala Asp Lys Trp Thr  Tyr Ile Gly
    2030                 2035                 2040

Leu Gly  Val Asp Leu Val Cys  Ala Phe Val Pro Gly  Val Thr Gly
    2045                 2050                 2055

Gly Arg  Leu Gly Val Gln Ala  Leu Glu Glu Thr Val  Thr His Ala
    2060                 2065                 2070

Asp Asn  Val Glu Asp Leu Phe  Lys Leu Leu Asp Lys  Thr Val Asp
    2075                 2080                 2085

Ala Glu  Lys Lys Val Asp Asp  Val Ile Asp Ser Gly  Lys Val Ala
    2090                 2095                 2100

Lys Asn  Ser Asn Gln Ile Tyr  Asn Val Ile Lys Arg  Ala Asp Leu
    2105                 2110                 2115

Pro Asn  Thr Lys Ile Thr Ser  Ser Lys Leu Gln His  Glu Trp Lys
    2120                 2125                 2130

His Ala  Thr Asp Phe Gly Ile  Lys Gly Asn Trp Asn  Lys Ala Asn
    2135                 2140                 2145

Gly Asp  Leu Tyr Glu Lys Ala  Ile Gln Asn His Ile  Asn Thr Ala
    2150                 2155                 2160

Pro Glu  Val Tyr Lys Ser Thr  Tyr Arg Gln Asn Gln  Asp Val Tyr
    2165                 2170                 2175

Val Tyr  Leu Asn Lys Glu Thr  Gly Val Gly Val Tyr  Thr Asp Leu
    2180                 2185                 2190

Ser Gly  Asn Tyr Ile Gly Ala  Gly Asn Ser Val Arg  Asn Arg Leu
    2195                 2200                 2205

Ser Ile  Ile Gln Leu Met Asp  Leu Lys
    2210                 2215
```

<210> SEQ ID NO 9
<211> LENGTH: 8961
<212> TYPE: DNA
<213> ORGANISM: Gibberella zeae

<400> SEQUENCE: 9

```
atggccaccg ttactgtaca agggcccttc ttcaaagatc tacccacgct atccgccaaa      60

atcaacagtt tactggcaga agacggaacc acacttgcag cagctattga cagcgcgttg     120

aagtctggtg gtctggattc tgttagtact cgccgtctgc ttttcttcca aggcctcact     180

gcagacaacc aactgcttct gtatttgaca acaaactacg gtaatgtgga gccttcactt     240

gctcggattg gtcttgaaaa ttacttcaat agctttgatg gtttcaacaa agatgtcgtg     300

aaggactttc ggtctcattt atgggagaaa gaacctttgg ccgttctcct tgcatctttg     360

cgccagacta agctattgac cactgtttgg attgaactga agcctcaaat cgataccgtc     420
```

-continued

```
ctccaactgt gcgtggataa agaactttcg ctgtcttcac ctgaagttca cacccgtgtg    480
aaagaattgg atgtcacaag accgaagaca gaggtaaaga aagacgtcaa ggggaaatcg    540
gtcgttgttc ctggcttgcg tgatgcaatt cttgctatac agcgccttca ctgtcttgtc    600
atcgatccga tgcatttgga agtgctactg agagaaggat ggcattccgc acatgatgtt    660
gccattctcc ctcgtggagt attcctttca gtcatcgaaa aagcagccaa aaaccaggat    720
cctatattca acatcgatga agaatctgca tcacgtatcc atgaccatgc cattaccatt    780
gactgccgga accaagaaac gtgggtcaag atacttgatg gtctcaaaag agactttacg    840
atcgttgtac cacagtctcg tcccgaggat gaagctgaga agaaacggaa gcaagaggag    900
attgagaaac aagcaagaaa agacggtgcc aacaaagacg ctcccagagt ggacgttctt    960
gcgcacaaaa actacaacat gtctaccatc tttgacctac agacttccag ctgcgaagag   1020
tgctgctcag ttacaggacc agccgcctac tttgttgacc tactcaattt tctcaaagcg   1080
agtccttgta ctggagctgg aagcaagttt tccactttgt tccaggcttt gatgcatcga   1140
cgtccagatt tgcaggactt ggaactatct tgtgcaaact ccaagaacat ggtgccctac   1200
atctccatcg tcaacgagac gctagagtct tttattgcat ctctcagcga acacgatgat   1260
gatgacaaat atgttgctac tgtcctggct gtcaatgaac aggaagcacc gggctcttat   1320
tcagggtcaa cacaggatac tcgattgaca gccgccaagt ctctcgacgg ggtcatgtcc   1380
cctttgaatg tgtttccaca caaccaaggt ctccagtcca tcaaaacata tcttcattcc   1440
ttcggaatca cggggataga agtcttgaaa acctttcgat ccgaggctag gctcttggaa   1500
gcggtgatag gagctttgcc cagtgacaaa ggcactcgtg caacacttct ctctgaagca   1560
ggtgttatct tggatcgtgc aactgttgct gcatcactga atctactacc gctagattta   1620
gcagccattg tgggagagaa gatttacacg ccacatgcaa tgaggagcat gatgggaatg   1680
cgacagaaac gaggaaagtc actcttgtcg gagctcgagg tcccaaaaac ttgccgtaac   1740
tggggctatt cgagtactag tgacatgatc gacacggatg agcgggcaaa gactggtctc   1800
tgcttcatca ggtctcagtt tatgccgcgt tcaggactgt cattcgaaga aatcctgcag   1860
cttctcaaga gcctttattt tggtggccgt cttgtcataa caaatgcaga caagacaaaa   1920
gcgtttactg gacagatttc cgagatgcgt ctacaggccc tcaatacggc ggctactgca   1980
cctaaagaga cggcagtcgg gcctttgact gatcaactct gtcacgagat tcaggccttt   2040
atcagactga agaatcgtct tggctggagt atcaaggagc ttgatggggc cttgtctgca   2100
atcttccaga gccaggttgc ttcaggcgtt atgcgcactc ctgatggtac ccgaggcatc   2160
tcttttgggg tgttgcaaga tctttccatg gcgaagagcc tcgctgaatc tgtgaatatg   2220
ccgatagacg ctatacttat tctctgggca ccgcttaaca cagaaagccc tctcttcagt   2280
cgtgtctttg gtggcccacg caatatgtct tcggataaca tcttcaccac gctcagcaac   2340
cgtgtgtcat taatcaagaa ccatcttcct gctgttatga ccgctctggg gcatagtcaa   2400
gatcaactga actgtctcat gcgagctgcc aatattgaca gcgcgaaaga caagctgacg   2460
atggacgtcc ttactaagtt gtatcgacac tcgactatga gccgaatact caaagccaca   2520
cctatggagt acttggaact tctctctctc cttcccgccg gacttgatgt actattagac   2580
ccgacaacga cgctgtcatt tgtcacgaaa tggcgtcagc ttgttgacag tcgctggtca   2640
ccacaagaga tcatcatggc aatacgtcca actcccgtaa ctagtatctc agacaactac   2700
accaatgtaa ctgatgctct cttcctatcg tcctctatta tcgacgaaat ggaagtaatg   2760
```

-continued

```
cggttactct ggcaagatcc tgtccgcgat atggttgtac ggcacgagga tatcgttcag   2820
atttgtggag agctctatga cgcgaccgca gctgcttcaa ttgtagagtt catcgaggga   2880
acccagtcaa ccgaagcaag aatccctttg tccaagcctc tcgccaccgc cctcatgacc   2940
atcaaagtat tgccatcaaa catgacgttg acagtcgagc ttgggtcgaa gacaaagccg   3000
ggtgtacttg ttctatccct cctgggcgtt ctctctggcg aaaaccgatt gatgatcgaa   3060
acgcttatca agaacaaaga cgccgggcta aaagcaccaa catccacact tggcacaggg   3120
cttcggaagg acctggatga gctatttgat gacttggatg tgcgctctag cggtgccagg   3180
aagacgttgg aagataggtt gctcaatact cttccagctg atcaacgtga agaacttggg   3240
ttaatgttcc agaatgatat tagagatgga accagcacga tgacactgga tgaagcattg   3300
attcaagctg agatggcagt caagaaacgc cggagtgctt tcatcttggc cgctctgcct   3360
gtattgcgcg cacaactggt agagagatca ttgattgggg caatcggcaa ggcagtccct   3420
ggccttgatc cgtcagtcct tgctatgctg ggaacacagg tttttaagca acatgacaag   3480
agtgcaacca aggttgtgga agatatttgc agtgattacg tgtctaacaa gggggcatcc   3540
gaagtctcta cggcgttctt ctgccctgca gcctcagata cttatcaatt tcatttcacg   3600
ccactgcaaa atgcggagca aaatggtcaa aacaactctt ctgtaccatt gttctcagtc   3660
aatggagtcg agatcccagt gctgaaggct ggcgatggaa acgggtggca gtcagttcca   3720
acactccttg cgactggcaa gccgtatctg ttgagttcat caacgagtct tggacatgct   3780
cagtggacga ccaaacaatc gactcagccc cagaaatttg tgaaatccac cttgatccct   3840
gctgatatca tcacatcggt ctccaacgag ctactaacag tcgttcactt tgcgcaactt   3900
atgaagaagc taaatctggg tcttgaagag ttcaagtatc tcagctctga ttccacctcc   3960
tctatgcaag tcgatctgaa caaactgacc attgatggtc tctgtcagct agagaagtat   4020
tgcacactca gagactcggt atctagtggt cccgactccc ttattggatt tttcgcctgg   4080
ttaggtagtg ggcaatacga tggaaagacg accttggcca cacgtctggc agccgccacc   4140
agatgggatc agcttcagtt gaatactact ctggagctca agtatcctgg tctgacggaa   4200
aaggacatca ttgacagatt tgcgtcctct cttgacgaac tctgctccct gggcgatgtc   4260
ataacgctat ctggccatct gggcggcgcc tcgggacgac gagcggccca gccgttgttg   4320
gttctgtaca aactcgctgt acctgcccct cccaccgaaa ccgactggga catggaaacg   4380
gcttcggcac ttgaactttg tctgggacct gaacaagctg cgcagtgcag atcagagtta   4440
cgcgagacgc aacggacagc atatgtgcaa tttctgctgc agcggaagta cttccaaaga   4500
ttgggcgtaa cagatgcgga cggctgtttt gcacatttca tgctagatgt ccagatggga   4560
gctcagctcg aaattacacg gatgaaggcg gccatctcga ctgtacagct gtttgtccag   4620
cgcgtgctgc ttggtttaga ggcaccaagt ggtgttctcg atgctcgtat cgacaaagac   4680
aagtgggcgt ggatgcagcg ccacaatatc tggcaggcaa caagaaaggc attcctctac   4740
ccagagaatt ggatagatcc aagcctacga gatgacaaga ctccattgtt tgaggcctat   4800
gagtcagcca tcatgtccaa ggacctaagc tgggattcgt tttctcagtc aatgaaggac   4860
tatgtacaat cacttctagg aattgctgat ctctcgattg aggcatacct acgggagcta   4920
cgacctgatg aggtcgaaat ttaccatttc tttggtagaa ctcgaagcgc gccttttgag   4980
ttttactatc gagcgatgca gattgtcaag tcgggatctg gcgaaggact tgtcttctgg   5040
tcaccctgga ccaaggtggg ggtagaagcc cctacatacg acacagattg gaatggcaag   5100
acacttgaca agggcggatg ctaccttgtt cctgttgttc gaaacaagcg tcttttcctg   5160
```

-continued

```
tacctgccac agctcatggc caagcccgtg gccccgacac ccaacatgac tatggaggat   5220
atggccaaga aagtccctgt cacaactggg gcatacacct gggaagtacg catgggatgg   5280
acagagtttg tagatggaca gtggacgcct aagcgggtgc tgcaaacacc tttggttgtc   5340
aactggattc ccccgactac agaaaagcct accgatatag agggcctacc ctctgtagac   5400
aagtttgtct ttagtgccga aacgactggg ccagatgtca aaatccaagt tgggtatcga   5460
ggaaccatag atgggatgct tcattatatt ggcaggtttg acgttatcga tgaacgtatc   5520
gagactatca aagttactag ccagaccgat aaactcggca aggcgctgga tacctccttt   5580
cacaagctca catgggaagc ggagccgaac atcaaggaga ccatgggaca ggctggagag   5640
ctcaaagagc ctgacagctc gttgtactcc atgctgacca aggccgagga gacaccgctc   5700
ttggcgatag gaaagcgtga ttataaacgt aacctgacat ggacactatc ctacgcggac   5760
aagaccaata ataccaacaa gacagcaggt ctcgtggtag atgagcgtcg agggggtgct   5820
gatggtacta ccttcttcat gtacccctat caaacgcctg aggataagaa gaagaagacg   5880
gtgccgcttg ctacaaacct catgtacgac caatccagag aggaaatcgt tgaacactct   5940
gctgcacgag aaatgatgga ggcggtctgt cagactgacg gtctgaacat gctttttgac   6000
acaatggata ccaacctcac caagaaccat gactacggta aagctgtggt ccggtccgac   6060
atgagcaact atcatgagct tacgacccca tacgccatct acaattggga gttgggtcta   6120
cacgctgtcc tcctagccat cgatcgcttc tacgccacgc agcagttcga gctcgcccta   6180
aaggccgcca ggctcatctt tgaccccacc accaacccgc cgaccggctg ctcggcggac   6240
gaggcggcgg cagcttgctg gaggttcagg ccgttccggg acctggccga acacaagatt   6300
ggtatggttg atgttttcaa gggctggccc tcagacggga acctcgagat cgcagtgtcg   6360
gagcgccgaa gtaatccttc cacggtacac tcgactgcac gcggacggcc ccaggcttac   6420
atgaagtggg ttatcatgaa gtacattgag atattgatct ctgctggtga cgagtacttc   6480
cgacagggaa gtatggagac gctgcctttg gcaattcatc actatgttga agcagctcac   6540
gtgcttggtc cagatccccc acgagtacca cagttggcca agtctgtggt caagacattc   6600
cgcgagatag gatcccccga gcacaaggtt gatctcgaac tcgcctttcc gttcctttgc   6660
gagattgaaa gacgtggtag taagagagca gacggtgata gtcgccgtag atcaccactg   6720
ctgtgcattc tcaccacgac ctacttcagc ctgccgccaa acccaaagta cgcgagcttg   6780
cgagtcctag ttcaggatag gctctacaag gctcggaaca atcttgacat caatggacgt   6840
cctatcgttt attccatgtc cgagcccttt attgatcctg gcgatgcgat gcgagcgttg   6900
gcacaaggtg gtgctggagc ggtcgggtca ctcatgaatg atagtgacag tccaatgccg   6960
taccaacgat tctccttcct catcagcaaa gctcttgaac tatgcaatga gctgaggagt   7020
atgggggagc aatttctttc cgtccgcgag agacatgatg cggagtcttt ggcacaattg   7080
aagaaccgcc aagattcaat gagacagaag atgatacttg aagtcagact gtcacagacg   7140
gaggagatcc tcaagaccat tgaatcactg caacagagtc gggcttctac tgtgtcacag   7200
ctggagtact atctccgcct caccggtgat tcactggatc ttattcccgg tgatgagaaa   7260
gatgagtggc aggacatccg gcaggacatc gcgactccaa tcagtgatga ccttcgaatg   7320
agccctttg aaactatgga gcttgcttcc gcagctgtag cttccacgct gaatgttgca   7380
gcagctggta tggatacact agccggcttc ctaaaagctt ttccaaacgt gacgacaaat   7440
gctcagccca tgggctgtgg tgtcaccgtc aaggctgacg caagcaatgc ggctcaattg   7500
```

-continued

```
acgttgggtt tggcatcagc tacaaagaca tatgctctta tcgcttcaga agctggatca   7560

atgtcagcgc gaatcggagg tctgaccaag caattacaag agcgtcgtat gcaagctaat   7620

atcaggggac gcgagatcaa gaatcttgat aagcaaatcg agattcagcg taagaggcta   7680

gatatcaatg ccaaggagat cctcgctcag agaagtgagg ttgagtatgc caatgagacc   7740

gaggtttggt atcgcagcaa atacacaaac gccaaccttt actcatggct cgagggatca   7800

gtccgttcta tacattacga cctttatggc ctcgcatccg acatgtgccg tcgcgccgag   7860

agagcctttc gttttgagcg tggtcatcaa gcatctgccg catttcttcg ttctggcggc   7920

tactgggaca acagtcgaga cggtttgctc gcggctcagc aactagcctt ggacctgcga   7980

cgcatggagg cagcctatct tcacaaaccg ggtcatgact gggaattgtc caagaatatt   8040

tctctgcgca agactaaccc ccatgctctg ctcacgctac gagagaaagg tacgacaact   8100

ttcagcatcc cagaattgct gtttgatctg gattttcccg gacactacat gcgacgtctc   8160

aagtcagtgg cggtgacaat cccgtgcgtt atcggtcctt ataccactct agctgcgact   8220

ctgtcactca cgcgacacac ataccgtgta tctgcagctg cacaatctgg tgatgactat   8280

ctgctagcaa actcctcaga tggttcgttc agaaccgacc ccatccccat ctctgctgtc   8340

gccacatcgc atgccgtgca agatacaggc tcgttcgact ttggcttcaa ccagagcaac   8400

attgcgaata ccgactacgg tccgttcgag ggtgccggtg ccatcagcaa ctggaaactc   8460

gaactaccac caaagacaac tcagccattt gattactcga ccatttcaga cgtggtactt   8520

catatcaagt atacttctat cgacggtgga ccgatcctta agcgttccgc ctccgatgcg   8580

gtgaaaaagc agtgcgcgcg tacagatagt ctgggtgttc acgacggtct ctggggcttc   8640

gtcgaggtac gcaatgaggc aacgaaccaa tggttcaagt ttagttccac gctctcccaa   8700

acggctttgg ctcgcaccgc aacacttgac cttggcccag caatcacgtc acgattaccc   8760

ttttggacaa agaatcggga tgtcaagatc gaaactttga cccttgcaat tacaggtgct   8820

gatgctggct tggccaaaga tttgtcaata cctgcattgg gatcaagtga ttgggattgt   8880

acaaccttgg gagacatagc actgctaagt atagctggtt taggagatat agtatctttg   8940

aagcaagagg aaggtcgcta a                                              8961
```

<210> SEQ ID NO 10
<211> LENGTH: 2986
<212> TYPE: PRT
<213> ORGANISM: Gibberella zeae

<400> SEQUENCE: 10

```
Met Ala Thr Val Thr Val Gln Gly Pro Phe Phe Lys Asp Leu Pro Thr
1               5                   10                  15

Leu Ser Ala Lys Ile Asn Ser Leu Leu Ala Glu Asp Gly Thr Thr Leu
            20                  25                  30

Ala Ala Ala Ile Asp Ser Ala Leu Lys Ser Gly Gly Leu Asp Ser Val
        35                  40                  45

Ser Thr Arg Arg Leu Leu Phe Phe Gln Gly Leu Thr Ala Asp Asn Gln
    50                  55                  60

Leu Leu Leu Tyr Leu Thr Thr Asn Tyr Gly Asn Val Glu Pro Ser Leu
65                  70                  75                  80

Ala Arg Ile Gly Leu Glu Asn Tyr Phe Asn Ser Phe Asp Gly Phe Asn
                85                  90                  95

Lys Asp Val Val Lys Asp Phe Arg Ser His Leu Trp Glu Lys Glu Pro
            100                 105                 110
```

-continued

```
Leu Ala Val Leu Leu Ala Ser Leu Arg Gln Thr Lys Leu Leu Thr Thr
        115                 120                 125

Val Trp Ile Glu Leu Lys Pro Gln Ile Asp Thr Val Leu Gln Leu Cys
    130                 135                 140

Val Asp Lys Glu Leu Ser Leu Ser Ser Pro Glu Val His Thr Arg Val
145                 150                 155                 160

Lys Glu Leu Asp Val Thr Arg Pro Lys Thr Glu Val Lys Lys Asp Val
                165                 170                 175

Lys Gly Lys Ser Val Val Val Pro Gly Leu Arg Asp Ala Ile Leu Ala
            180                 185                 190

Ile Gln Arg Leu His Cys Leu Val Ile Asp Pro Met His Leu Glu Val
        195                 200                 205

Leu Leu Arg Glu Gly Trp His Ser Ala His Asp Val Ala Ile Leu Pro
    210                 215                 220

Arg Gly Val Phe Leu Ser Val Ile Glu Lys Ala Ala Lys Asn Gln Asp
225                 230                 235                 240

Pro Ile Phe Asn Ile Asp Glu Glu Ser Ala Ser Arg Ile His Asp His
                245                 250                 255

Ala Ile Thr Ile Asp Cys Arg Asn Gln Glu Thr Trp Val Lys Ile Leu
            260                 265                 270

Asp Gly Leu Lys Arg Asp Phe Thr Ile Val Val Pro Gln Ser Arg Pro
        275                 280                 285

Glu Asp Glu Ala Glu Lys Lys Arg Lys Gln Glu Glu Ile Glu Lys Gln
    290                 295                 300

Ala Arg Lys Asp Gly Ala Asn Lys Asp Ala Pro Arg Val Asp Val Leu
305                 310                 315                 320

Ala His Lys Asn Tyr Asn Met Ser Thr Ile Phe Asp Leu Gln Thr Ser
                325                 330                 335

Ser Cys Glu Glu Cys Cys Ser Val Thr Gly Pro Ala Ala Tyr Phe Val
            340                 345                 350

Asp Leu Leu Asn Phe Leu Lys Ala Ser Pro Cys Thr Gly Ala Gly Ser
        355                 360                 365

Lys Phe Ser Thr Leu Phe Gln Ala Leu Met His Arg Arg Pro Asp Leu
    370                 375                 380

Gln Asp Leu Glu Leu Ser Cys Ala Asn Ser Lys Asn Met Val Pro Tyr
385                 390                 395                 400

Ile Ser Ile Val Asn Glu Thr Leu Glu Ser Phe Ile Ala Ser Leu Ser
                405                 410                 415

Glu His Asp Asp Asp Asp Lys Tyr Val Ala Thr Val Leu Ala Val Asn
            420                 425                 430

Glu Gln Glu Ala Pro Gly Ser Tyr Ser Gly Ser Thr Gln Asp Thr Arg
        435                 440                 445

Leu Thr Ala Ala Lys Ser Leu Asp Gly Val Met Ser Pro Leu Asn Val
    450                 455                 460

Phe Pro His Asn Gln Gly Leu Gln Ser Ile Lys Thr Tyr Leu His Ser
465                 470                 475                 480

Phe Gly Ile Thr Gly Ile Glu Val Leu Lys Thr Phe Arg Ser Glu Ala
                485                 490                 495

Arg Leu Leu Glu Ala Val Ile Gly Ala Leu Pro Ser Asp Lys Gly Thr
            500                 505                 510

Arg Ala Thr Leu Leu Ser Glu Ala Gly Val Ile Leu Asp Arg Ala Thr
        515                 520                 525

Val Ala Ala Ser Leu Asn Leu Leu Pro Leu Asp Leu Ala Ala Ile Val
```

-continued

```
    530                 535                 540

Gly Glu Lys Ile Tyr Thr Pro His Ala Met Arg Ser Met Met Gly Met
545                 550                 555                 560

Arg Gln Lys Arg Gly Lys Ser Leu Leu Ser Glu Leu Glu Val Pro Lys
                565                 570                 575

Thr Cys Arg Asn Trp Gly Tyr Ser Ser Thr Ser Asp Met Ile Asp Thr
            580                 585                 590

Asp Glu Arg Ala Lys Thr Gly Leu Cys Phe Ile Arg Ser Gln Phe Met
        595                 600                 605

Pro Arg Ser Gly Leu Ser Phe Glu Glu Ile Leu Gln Leu Leu Lys Ser
    610                 615                 620

Leu Tyr Phe Gly Gly Arg Leu Val Ile Thr Asn Ala Asp Lys Thr Lys
625                 630                 635                 640

Ala Phe Thr Gly Gln Ile Ser Glu Met Arg Leu Gln Ala Leu Asn Thr
                645                 650                 655

Ala Ala Thr Ala Pro Lys Glu Thr Ala Val Gly Pro Leu Thr Asp Gln
            660                 665                 670

Leu Cys His Glu Ile Gln Ala Phe Ile Arg Leu Lys Asn Arg Leu Gly
        675                 680                 685

Trp Ser Ile Lys Glu Leu Asp Gly Ala Leu Ser Ala Ile Phe Gln Ser
    690                 695                 700

Gln Val Ala Ser Gly Val Met Arg Thr Pro Asp Gly Thr Arg Gly Ile
705                 710                 715                 720

Ser Phe Gly Val Leu Gln Asp Leu Ser Met Ala Lys Ser Leu Ala Glu
                725                 730                 735

Ser Val Asn Met Pro Ile Asp Ala Ile Leu Ile Leu Trp Ala Pro Leu
            740                 745                 750

Asn Thr Glu Ser Pro Leu Phe Ser Arg Val Phe Gly Gly Pro Arg Asn
        755                 760                 765

Met Ser Ser Asp Asn Ile Phe Thr Thr Leu Ser Asn Arg Val Ser Leu
    770                 775                 780

Ile Lys Asn His Leu Pro Ala Val Met Thr Ala Leu Gly His Ser Gln
785                 790                 795                 800

Asp Gln Leu Asn Cys Leu Met Arg Ala Ala Asn Ile Asp Ser Ala Lys
                805                 810                 815

Asp Lys Leu Thr Met Asp Val Leu Thr Lys Leu Tyr Arg His Ser Thr
            820                 825                 830

Met Ser Arg Ile Leu Lys Ala Thr Pro Met Glu Tyr Leu Glu Leu Leu
        835                 840                 845

Ser Leu Leu Pro Ala Gly Leu Asp Val Leu Leu Asp Pro Thr Thr Thr
    850                 855                 860

Leu Ser Phe Val Thr Lys Trp Arg Gln Leu Val Asp Ser Arg Trp Ser
865                 870                 875                 880

Pro Gln Glu Ile Ile Met Ala Ile Arg Pro Thr Pro Val Thr Ser Ile
                885                 890                 895

Ser Asp Asn Tyr Thr Asn Val Thr Asp Ala Leu Phe Leu Ser Ser Ser
            900                 905                 910

Ile Ile Asp Glu Met Glu Val Met Arg Leu Leu Trp Gln Asp Pro Val
        915                 920                 925

Arg Asp Met Val Val Arg His Glu Asp Ile Val Gln Ile Cys Gly Glu
    930                 935                 940

Leu Tyr Asp Ala Thr Ala Ala Ala Ser Ile Val Glu Phe Ile Glu Gly
945                 950                 955                 960
```

-continued

```
Thr Gln Ser Thr Glu Ala Arg Ile Pro Leu Ser Lys Pro Leu Ala Thr
                965                 970                 975

Ala Leu Met Thr Ile Lys Val Leu Pro Ser Asn Met Thr Leu Thr Val
            980                 985                 990

Glu Leu Gly Ser Lys Thr Lys Pro  Gly Val Leu Val Leu  Ser Leu Leu
        995                  1000                 1005

Gly Val  Leu Ser Gly Glu Asn  Arg Leu Met Ile Glu  Thr Leu Ile
    1010                 1015                 1020

Lys Asn  Lys Asp Ala Gly Leu  Lys Ala Pro Thr Ser  Thr Leu Gly
    1025                 1030                 1035

Thr Gly  Leu Arg Lys Asp Leu  Asp Glu Leu Phe Asp  Asp Leu Asp
    1040                 1045                 1050

Val Arg  Ser Ser Gly Ala Arg  Lys Thr Leu Glu Asp  Arg Leu Leu
    1055                 1060                 1065

Asn Thr  Leu Pro Ala Asp Gln  Arg Glu Glu Leu Gly  Leu Met Phe
    1070                 1075                 1080

Gln Asn  Asp Ile Arg Asp Gly  Thr Ser Thr Met Thr  Leu Asp Glu
    1085                 1090                 1095

Ala Leu  Ile Gln Ala Glu Met  Ala Val Lys Lys Arg  Arg Ser Ala
    1100                 1105                 1110

Phe Ile  Leu Ala Ala Leu Pro  Val Leu Arg Ala Gln  Leu Val Glu
    1115                 1120                 1125

Arg Ser  Leu Ile Gly Ala Ile  Gly Lys Ala Val Pro  Gly Leu Asp
    1130                 1135                 1140

Pro Ser  Val Leu Ala Met Leu  Gly Thr Gln Val Phe  Lys Gln His
    1145                 1150                 1155

Asp Lys  Ser Ala Thr Lys Val  Val Glu Asp Ile Cys  Ser Asp Tyr
    1160                 1165                 1170

Val Ser  Asn Lys Gly Ala Ser  Glu Val Ser Thr Ala  Phe Phe Cys
    1175                 1180                 1185

Pro Ala  Ala Ser Asp Thr Tyr  Gln Phe His Phe Thr  Pro Leu Gln
    1190                 1195                 1200

Asn Ala  Glu Gln Asn Gly Gln  Asn Asn Ser Ser Val  Pro Leu Phe
    1205                 1210                 1215

Ser Val  Asn Gly Val Glu Ile  Pro Val Leu Lys Ala  Gly Asp Gly
    1220                 1225                 1230

Asn Gly  Trp Gln Ser Val Pro  Thr Leu Leu Ala Thr  Gly Lys Pro
    1235                 1240                 1245

Tyr Leu  Leu Ser Ser Ser Thr  Ser Leu Gly His Ala  Gln Trp Thr
    1250                 1255                 1260

Thr Lys  Gln Ser Thr Gln Pro  Gln Lys Phe Val Lys  Ser Thr Leu
    1265                 1270                 1275

Ile Pro  Ala Asp Ile Ile Thr  Ser Val Ser Asn Glu  Leu Leu Thr
    1280                 1285                 1290

Val Val  His Phe Ala Gln Leu  Met Lys Lys Leu Asn  Leu Gly Leu
    1295                 1300                 1305

Glu Glu  Phe Lys Tyr Leu Ser  Ser Asp Ser Thr Ser  Ser Met Gln
    1310                 1315                 1320

Val Asp  Leu Asn Lys Leu Thr  Ile Asp Gly Leu Cys  Gln Leu Glu
    1325                 1330                 1335

Lys Tyr  Cys Thr Leu Arg Asp  Ser Val Ser Ser Gly  Pro Asp Ser
    1340                 1345                 1350
```

-continued

```
Leu Ile  Gly Phe Phe Ala Trp  Leu Gly Ser Gly Gln  Tyr Asp Gly
    1355                 1360                 1365

Lys Thr  Thr Leu Ala Thr Arg  Leu Ala Ala Ala Thr  Arg Trp Asp
    1370                 1375                 1380

Gln Leu  Gln Leu Asn Thr Thr  Leu Glu Leu Lys Tyr  Pro Gly Leu
    1385                 1390                 1395

Thr Glu  Lys Asp Ile Ile Asp  Arg Phe Ala Ser Ser  Leu Asp Glu
    1400                 1405                 1410

Leu Cys  Ser Leu Gly Asp Val  Ile Thr Leu Ser Gly  His Leu Gly
    1415                 1420                 1425

Gly Ala  Ser Gly Arg Arg Ala  Ala Gln Pro Leu Leu  Val Leu Tyr
    1430                 1435                 1440

Lys Leu  Ala Val Pro Ala Pro  Pro Thr Glu Thr Asp  Trp Asp Met
    1445                 1450                 1455

Glu Thr  Ala Ser Ala Leu Glu  Leu Cys Leu Gly Pro  Glu Gln Ala
    1460                 1465                 1470

Ala Gln  Cys Arg Ser Glu Leu  Arg Glu Thr Gln Arg  Thr Ala Tyr
    1475                 1480                 1485

Val Gln  Phe Leu Leu Gln Arg  Lys Tyr Phe Gln Arg  Leu Gly Val
    1490                 1495                 1500

Thr Asp  Ala Asp Gly Leu Phe  Ala His Phe Met Leu  Asp Val Gln
    1505                 1510                 1515

Met Gly  Ala Gln Leu Glu Ile  Thr Arg Met Lys Ala  Ala Ile Ser
    1520                 1525                 1530

Thr Val  Gln Leu Phe Val Gln  Arg Val Leu Leu Gly  Leu Glu Ala
    1535                 1540                 1545

Pro Ser  Gly Val Leu Asp Ala  Arg Ile Asp Lys Asp  Lys Trp Ala
    1550                 1555                 1560

Trp Met  Gln Arg His Asn Ile  Trp Gln Ala Thr Arg  Lys Ala Phe
    1565                 1570                 1575

Leu Tyr  Pro Glu Asn Trp Ile  Asp Pro Ser Leu Arg  Asp Asp Lys
    1580                 1585                 1590

Thr Pro  Leu Phe Glu Ala Tyr  Glu Ser Ala Ile Met  Ser Lys Asp
    1595                 1600                 1605

Leu Ser  Trp Asp Ser Phe Ser  Gln Ser Met Lys Asp  Tyr Val Gln
    1610                 1615                 1620

Ser Leu  Leu Gly Ile Ala Asp  Leu Ser Ile Glu Ala  Tyr Leu Arg
    1625                 1630                 1635

Glu Leu  Arg Pro Asp Glu Val  Glu Ile Tyr His Phe  Phe Gly Arg
    1640                 1645                 1650

Thr Arg  Ser Ala Pro Phe Glu  Phe Tyr Tyr Arg Ala  Met Gln Ile
    1655                 1660                 1665

Val Lys  Ser Gly Ser Gly Glu  Gly Leu Val Phe Trp  Ser Pro Trp
    1670                 1675                 1680

Thr Lys  Val Gly Val Glu Ala  Pro Thr Tyr Asp Thr  Asp Trp Asn
    1685                 1690                 1695

Gly Lys  Thr Leu Asp Lys Gly  Gly Cys Tyr Leu Val  Pro Val Val
    1700                 1705                 1710

Arg Asn  Lys Arg Leu Phe Leu  Tyr Leu Pro Gln Leu  Met Ala Lys
    1715                 1720                 1725

Pro Val  Ala Pro Thr Pro Asn  Met Thr Met Glu Asp  Met Ala Lys
    1730                 1735                 1740

Lys Val  Pro Val Thr Thr Gly  Ala Tyr Thr Trp Glu  Val Arg Met
```

-continued

```
    1745                1750                1755

Gly Trp  Thr Glu Phe Val Asp  Gly Gln Trp Thr Pro  Lys Arg Val
    1760                1765                1770

Leu Gln  Thr Pro Leu Val Val  Asn Trp Ile Pro Pro  Thr Thr Glu
    1775                1780                1785

Lys Pro  Thr Asp Ile Glu Gly  Leu Pro Ser Val Asp  Lys Phe Val
    1790                1795                1800

Phe Ser  Ala Glu Thr Thr Gly  Pro Asp Val Lys Ile  Gln Val Gly
    1805                1810                1815

Tyr Arg  Gly Thr Ile Asp Gly  Met Leu His Tyr Ile  Gly Arg Phe
    1820                1825                1830

Asp Val  Ile Asp Glu Arg Ile  Glu Thr Ile Lys Val  Thr Ser Gln
    1835                1840                1845

Thr Asp  Lys Leu Gly Lys Ala  Leu Asp Thr Ser Phe  His Lys Leu
    1850                1855                1860

Thr Trp  Glu Ala Glu Pro Asn  Ile Lys Glu Thr Met  Gly Gln Ala
    1865                1870                1875

Gly Glu  Leu Lys Glu Pro Asp  Ser Ser Leu Tyr Ser  Met Leu Thr
    1880                1885                1890

Lys Ala  Glu Glu Thr Pro Leu  Leu Ala Ile Gly Lys  Arg Asp Tyr
    1895                1900                1905

Lys Arg  Asn Leu Thr Trp Thr  Leu Ser Tyr Ala Asp  Lys Thr Asn
    1910                1915                1920

Asn Thr  Asn Lys Thr Ala Gly  Leu Val Val Asp Glu  Arg Arg Gly
    1925                1930                1935

Gly Ala  Asp Gly Thr Thr Phe  Phe Met Tyr Pro Tyr  Gln Thr Pro
    1940                1945                1950

Glu Asp  Lys Lys Lys Lys Thr  Val Pro Leu Ala Thr  Asn Leu Met
    1955                1960                1965

Tyr Asp  Gln Ser Arg Glu Glu  Ile Val Glu His Ser  Ala Ala Arg
    1970                1975                1980

Glu Met  Met Glu Ala Val Cys  Gln Thr Asp Gly Leu  Asn Met Leu
    1985                1990                1995

Phe Asp  Thr Met Asp Thr Asn  Leu Thr Lys Asn His  Asp Tyr Gly
    2000                2005                2010

Lys Ala  Val Val Arg Ser Asp  Met Ser Asn Tyr His  Glu Leu Thr
    2015                2020                2025

Thr Pro  Tyr Ala Ile Tyr Asn  Trp Glu Leu Gly Leu  His Ala Val
    2030                2035                2040

Leu Leu  Ala Ile Asp Arg Phe  Tyr Ala Thr Gln Gln  Phe Glu Leu
    2045                2050                2055

Ala Leu  Lys Ala Ala Arg Leu  Ile Phe Asp Pro Thr  Thr Asn Pro
    2060                2065                2070

Pro Thr  Gly Cys Ser Ala Asp  Glu Ala Ala Ala Ala  Cys Trp Arg
    2075                2080                2085

Phe Arg  Pro Phe Arg Asp Leu  Ala Glu His Lys Ile  Gly Met Val
    2090                2095                2100

Asp Val  Phe Lys Gly Trp Pro  Ser Asp Gly Asn Leu  Glu Ile Ala
    2105                2110                2115

Val Ser  Glu Arg Arg Ser Asn  Pro Ser Thr Val His  Ser Thr Ala
    2120                2125                2130

Arg Gly  Arg Pro Gln Ala Tyr  Met Lys Trp Val Ile  Met Lys Tyr
    2135                2140                2145
```

-continued

Ile Glu Ile Leu Ile Ser Ala Gly Asp Glu Tyr Phe Arg Gln Gly
2150 2155 2160

Ser Met Glu Thr Leu Pro Leu Ala Ile His His Tyr Val Glu Ala
2165 2170 2175

Ala His Val Leu Gly Pro Asp Pro Pro Arg Val Pro Gln Leu Ala
2180 2185 2190

Lys Ser Val Val Lys Thr Phe Arg Glu Ile Gly Ser Pro Glu His
2195 2200 2205

Lys Val Asp Leu Glu Leu Ala Phe Pro Phe Leu Cys Glu Ile Glu
2210 2215 2220

Arg Arg Gly Ser Lys Arg Ala Asp Gly Asp Ser Arg Arg Arg Ser
2225 2230 2235

Pro Leu Leu Cys Ile Leu Thr Thr Thr Tyr Phe Ser Leu Pro Pro
2240 2245 2250

Asn Pro Lys Tyr Ala Ser Leu Arg Val Leu Val Gln Asp Arg Leu
2255 2260 2265

Tyr Lys Ala Arg Asn Asn Leu Asp Ile Asn Gly Arg Pro Ile Val
2270 2275 2280

Tyr Ser Met Ser Glu Pro Phe Ile Asp Pro Gly Asp Ala Met Arg
2285 2290 2295

Ala Leu Ala Gln Gly Gly Ala Gly Ala Val Gly Ser Leu Met Asn
2300 2305 2310

Asp Ser Asp Ser Pro Met Pro Tyr Gln Arg Phe Ser Phe Leu Ile
2315 2320 2325

Ser Lys Ala Leu Glu Leu Cys Asn Glu Leu Arg Ser Met Gly Glu
2330 2335 2340

Gln Phe Leu Ser Val Arg Glu Arg His Asp Ala Glu Ser Leu Ala
2345 2350 2355

Gln Leu Lys Asn Arg Gln Asp Ser Met Arg Gln Lys Met Ile Leu
2360 2365 2370

Glu Val Arg Leu Ser Gln Thr Glu Glu Ile Leu Lys Thr Ile Glu
2375 2380 2385

Ser Leu Gln Gln Ser Arg Ala Ser Thr Val Ser Gln Leu Glu Tyr
2390 2395 2400

Tyr Leu Arg Leu Thr Gly Asp Ser Leu Asp Leu Ile Pro Gly Asp
2405 2410 2415

Glu Lys Asp Glu Trp Gln Asp Ile Arg Gln Asp Ile Ala Thr Pro
2420 2425 2430

Ile Ser Asp Asp Leu Arg Met Ser Pro Phe Glu Thr Met Glu Leu
2435 2440 2445

Ala Ser Ala Ala Val Ala Ser Thr Leu Asn Val Ala Ala Ala Gly
2450 2455 2460

Met Asp Thr Leu Ala Gly Phe Leu Lys Ala Phe Pro Asn Val Thr
2465 2470 2475

Thr Asn Ala Gln Pro Met Gly Cys Gly Val Thr Val Lys Ala Asp
2480 2485 2490

Ala Ser Asn Ala Ala Gln Leu Thr Leu Gly Leu Ala Ser Ala Thr
2495 2500 2505

Lys Thr Tyr Ala Leu Ile Ala Ser Glu Ala Gly Ser Met Ser Ala
2510 2515 2520

Arg Ile Gly Gly Leu Thr Lys Gln Leu Gln Glu Arg Arg Met Gln
2525 2530 2535

-continued

```
Ala Asn Ile Arg Gly Arg Glu Ile Lys Asn Leu Asp Lys Gln Ile
    2540                2545                2550

Glu Ile Gln Arg Lys Arg Leu Asp Ile Asn Ala Lys Glu Ile Leu
    2555                2560                2565

Ala Gln Arg Ser Glu Val Glu Tyr Ala Asn Glu Thr Glu Val Trp
    2570                2575                2580

Tyr Arg Ser Lys Tyr Thr Asn Ala Asn Leu Tyr Ser Trp Leu Glu
    2585                2590                2595

Gly Ser Val Arg Ser Ile His Tyr Asp Leu Tyr Gly Leu Ala Ser
    2600                2605                2610

Asp Met Cys Arg Arg Ala Glu Arg Ala Phe Arg Phe Glu Arg Gly
    2615                2620                2625

His Gln Ala Ser Ala Ala Phe Leu Arg Ser Gly Gly Tyr Trp Asp
    2630                2635                2640

Asn Ser Arg Asp Gly Leu Leu Ala Ala Gln Gln Leu Ala Leu Asp
    2645                2650                2655

Leu Arg Arg Met Glu Ala Ala Tyr Leu His Lys Pro Gly His Asp
    2660                2665                2670

Trp Glu Leu Ser Lys Asn Ile Ser Leu Arg Lys Thr Asn Pro His
    2675                2680                2685

Ala Leu Leu Thr Leu Arg Glu Lys Gly Thr Thr Thr Phe Ser Ile
    2690                2695                2700

Pro Glu Leu Leu Phe Asp Leu Asp Phe Pro Gly His Tyr Met Arg
    2705                2710                2715

Arg Leu Lys Ser Val Ala Val Thr Ile Pro Cys Val Ile Gly Pro
    2720                2725                2730

Tyr Thr Thr Leu Ala Ala Thr Leu Ser Leu Thr Arg His Thr Tyr
    2735                2740                2745

Arg Val Ser Ala Ala Ala Gln Ser Gly Asp Asp Tyr Leu Leu Ala
    2750                2755                2760

Asn Ser Ser Asp Gly Ser Phe Arg Thr Asp Pro Ile Pro Ile Ser
    2765                2770                2775

Ala Val Ala Thr Ser His Ala Val Gln Asp Thr Gly Ser Phe Asp
    2780                2785                2790

Phe Gly Phe Asn Gln Ser Asn Ile Ala Asn Thr Asp Tyr Gly Pro
    2795                2800                2805

Phe Glu Gly Ala Gly Ala Ile Ser Asn Trp Lys Leu Glu Leu Pro
    2810                2815                2820

Pro Lys Thr Thr Gln Pro Phe Asp Tyr Ser Thr Ile Ser Asp Val
    2825                2830                2835

Val Leu His Ile Lys Tyr Thr Ser Ile Asp Gly Gly Pro Ile Leu
    2840                2845                2850

Lys Arg Ser Ala Ser Asp Ala Val Lys Lys Gln Cys Ala Arg Thr
    2855                2860                2865

Asp Ser Leu Gly Val His Asp Gly Leu Trp Gly Phe Val Glu Val
    2870                2875                2880

Arg Asn Glu Ala Thr Asn Gln Trp Phe Lys Phe Ser Ser Thr Leu
    2885                2890                2895

Ser Gln Thr Ala Leu Ala Arg Thr Ala Thr Leu Asp Leu Gly Pro
    2900                2905                2910

Ala Ile Thr Ser Arg Leu Pro Phe Trp Thr Lys Asn Arg Asp Val
    2915                2920                2925

Lys Ile Glu Thr Leu Thr Leu Ala Ile Thr Gly Ala Asp Ala Gly
```

-continued

```
    2930                2935                2940

Leu Ala  Lys Asp Leu Ser Ile  Pro Ala Leu Gly Ser  Ser Asp Trp
    2945                2950                2955

Asp Cys  Thr Thr Leu Gly Asp  Ile Ala Leu Leu Ser  Ile Ala Gly
    2960                2965                2970

Leu Gly  Asp Ile Val Ser Leu  Lys Gln Glu Glu Gly  Arg
    2975                2980                2985


<210> SEQ ID NO 11
<211> LENGTH: 6084
<212> TYPE: DNA
<213> ORGANISM: Tannerella forsythensis (ATCC 43037)

<400> SEQUENCE: 11

atgagaataa taaatatatc catagagata atatgtacct gccttatcat tggagtgaca     60

ggctatgcac agaagacaaa tgtttatgcg gcagggaacg aggcttcttc ggacaattat    120

gatccatccg gatatcgtat atggggaaac tatcgcaatg agacaagtga tgccaatgag    180

ttagacgctc ggcaactacc ctccttctat tacaagatat taaaaaacag gttagaaaac    240

aactattcac cggaagagaa aagaaccttt gcacctgcac ccttgtcaag aggtatggct    300

gtcggttcaa cagccggtat ggctgaaatt actctcacgg gagccgctaa ttatagtgtt    360

ccgatcgaag ttccggaggg tattgccgga tttaagcctg aggtatccgt tcggtatagt    420

agtcaatcgg gggtcggttt attgggatac gggtggaatt tgtcggcatt ttccgtcata    480

tcacgcagtg gtaagacatt ctatcatgat gggatgtcaa aagctcctgc gttatcgtat    540

gaagataacg tgatgttgga cggacaaagg ctgatgttga tttccgggca gaatctgatg    600

aacggagcta aatacaggct ggaaaatgat ccgacgatag atattacgta taagatgatc    660

ggttcattcc agggatttac agtaagaagt aaggatggaa caataagaga attcggtgtt    720

acttcagatt caaacatcga aacttcggat ggtactgctt tgttttggct gttatctcga    780

gtgattgata aacaaggaaa tgtaatctct tatcaatatg aagaagtaat aaacaacgga    840

gagttttatc taaatcgtat agaatatgca tccggacgca gtattcggtt ttcatacgaa    900

acaagaaaag ataagcaaac aggatattat gcaggagcgg tattaaacag caacaaaatt    960

ctgaaaaata tatctaccta tatcggtcag atgcagttta agcaatatca gtttaattat   1020

aatacgtacg agaacggtct ttatacccag ctgacggaaa ttattgaaag cggacaaaat   1080

ggccagagat ataatccgac ccgcatatat tatggttatc cggatccata taaaaatgag   1140

gatattgtta ctttgtcgga acatcgaaaa ggaaataagc cgctgtttgc cgattttaac   1200

ggcgatggac gtatggattt tctgtcgtat ccggaagaat tatcggataa tccgaaagaa   1260

gatgtagcca ccttgttttt atcgcttcac ggacttggcg gaacgtattt tgccaagaaa   1320

tgtacgatcc cgatgcgtgc tttcggagaa tttcgatatt ttatgttggc agacgtgaac   1380

ggcgataaga agatggatgt cattcatgtt tccagagcgg ataatggaac ggaacgctat   1440

aactattatg tgtttgacgg agagaagctc gtgtatcaat ataagggttt taatacacat   1500

ggagacgaag catttgtcgg agattttgat ggggatggga ggcatgatat tttaattaaa   1560

aacaattcga aggtgtatga tggcgaagga cgtgagattg cctcgggagg cattaccgac   1620

tggggatcgg attatattaa gtattactat ccgaacagta gatatatatg tgatttgaat   1680

ggaaacggaa agtcggaatt attagtcatc gacaagcatg gagctaaagt ttatgagttg   1740

aatgaacggc agtttgtgga attgccggaa ttcaggacct ccctgataaa aaattactat   1800
```

-continued

```
ttcccttatt tcggcgactt taacggagat ggtaaaacgg atgtcttgat acagcgatgg   1860
caccagggag attatgacga tgtaagtatc cttttttcaa ccgggaaagg atatgtaaaa   1920
caggatgttt taaatgcgga tattcgggct aaagtatttg tggcagattt taacaaagat   1980
gggaaatcgg atatttttca tatggagatc gtaaataatg ctgtcagaat gaaggtgggg   2040
atttttcacg gaaatggctt tcataccact tatcactcat cgaatttacg acttgaagat   2100
gtctatttat catataataa tatcgaatat gataattatc tgtttcaagt agctgatttt   2160
gatggggatg gcagttcgga gttctgttgt gcccgtcata tgaatgctta cattatcagg   2220
tctttttccg atcctcagaa tctgcttgtg gaaacaatct cggatggatt aggtgcatat   2280
acttcatttc aatatgcccc gataacaagt aattccgttt gtaccgtcac gggaaataac   2340
gaagcttttc ccgtaaccga cagtcgattc cctctatatg tagtcagcaa tatcacacag   2400
agtacgggag ggtattccga aacgacaaga tatcgatata aagaccctcg tagccatatg   2460
cagggaaaag gatttctggg attcggcgaa gtggaatcga tagatgataa taaagaccga   2520
aaagtaatta ctacatacgg atacgagaag gattattttt atccttttat taaggaacag   2580
aagatcatga cacgttccgg gatgaaaatt tctacttcgg tgtatgaaaa ttcatatgtc   2640
tataatggtt ccaaacgagt tgtcccctat gtgcggaaaa gtacaaccac cgatcatctg   2700
acaggagtag tgaagactgc tgaatgcact caaatcgata catgggctaa cccgttaagc   2760
attgttacac gccatggaaa tgatgtgact gaaacggtca ccgcatctta tattaaccgt   2820
gaagcagaga acctgtggat aatcggtctg cctcaatctg tagaaaagag agtaaccaag   2880
ggaacgggaa catggataga caagcaggta tttacgtata atgccggata tttgccccag   2940
aaaatagtca attttacagg ggatgggaac aaacagacat cagaagatgt ttttgattat   3000
gacagatacg gaaatatgat tacgcattcg acacgtgcct atgcatcgcc tcatgtattg   3060
acaaccagga cggaatactc gtccgacggt ctgtatatgc ttagaaccat cgacccgttg   3120
tcgagagtca cgactcatac ctacaattcg tcggggcagc ttgcttcaac aaaagatttt   3180
ctgaatacta cgactgcgta tgaatatgat ggtatgggaa gattggtaaa aaccgtctat   3240
ccggatcaaa cccagtcgtc ggttgtttat tcatgggaaa atgctgttgt aaacagcgtg   3300
tatggcatga cggagacgct cacgggaaaa ccggaacgaa aaatatattt cgatgccttc   3360
ggaagaaaag taagagagtg catccggcaa acggatggac aagacgtatg tacggatacg   3420
aaatatgaca atgccggccg tgtctcccag gaatcattgc cttttaaagg aggtgccgct   3480
tcaaaatgga atacttatgg atacgacggc tacggccgac tttcccaaca gacccatgct   3540
tccggaaaaa cgacgactta tacgtatgcc ggaaacagta ttacggaaac aaaaaacggg   3600
atatctcata aaagtgtcta taatgcaatg ggtgaacagg tcagtgttac ggatcctgcc   3660
ggtaccatta cttatacgtt gcgtcccgat ggccagccgg taacgatcac agctccggga   3720
aatgttaaaa caaccttttc ttatgacgct tacgggcgac agacagccat acatgatccg   3780
agcgccggta atcgcacctt cgcttacgat gcttcaggca atcttcaacg cgaaacggat   3840
gccgacaatc gtgtcaagac gatgagttat gacgtatatg ggaggcttac gtcgaaggtg   3900
ttacccgagt ttactacttc gtatgcatat aacggctatg gacaactgac gacggagact   3960
tcaaacaacg gaatatcatc cgtatacgaa tatgacagtt acggaagatt ggccaaagag   4020
cgcaataatg tccccgacgg taaatggctt gaaaaaacat atacgtatgc cgcagggaat   4080
cttgcgtctg ttcgttacgc atcacagtcg gggctatcg gtacggaagc atatacctac    4140
tcgcatggcc atatgaacgg tatccgctgg ggaagcagcc ctgtatggac actcaatgcg   4200
```

-continued

```
gaaaatccgt tcagccagcc tttgtcggtt acgacagggc cggtaacgcg tacttatacg   4260
tacgatgtct atgggattcc gacgggccgg accgctcaat cgacagccgg gggtacgttc   4320
ttgaattcca cctatggttt tgatgcggcg agggggaatc tgacttatcg gaaagataac   4380
cggaggaaca aacaggaaaa ctttacgtac gacaatctga atcgtctgaa aacgtatgga   4440
ggcatcgtta tggattatga cccgaaaggg aatattacga aaaaaggcga tgtgggtaca   4500
tttcattatc agacgccgta taagccgtac gccctctccg gtgcggatat aggcacaaat   4560
aaagtaatcc ctccgagaga gcagacgata agatatactt catttgatcg accgtccgtc   4620
attaccgaaa acggctacga agcctcgttt atatataatg cctcgggcga tcgccaaaag   4680
atgacggtaa agaaaggggg taaaccgttc tatacgcgtt actaccttgg cggccgttac   4740
gaaacggacg ttatggggaa ttctcaaaag caccggcttt atatcggtgg ggacgcttat   4800
acggctccgg ccgtgtatat gaatacggga aacggttggg cgctttatta tatctgtcgc   4860
gattatcttg gtaatatgac tcatcttgta gcgagcaacg gtacggttgt tcaggagctg   4920
agttatgatg cgtggggacg tttgcgtaat ccggagacgc atgccgtcta tcttcccgac   4980
aacgagacgg aattaatgct tggtcgcggt tatacgggtc atgaacatct ttcgatgttc   5040
gggttgatca atatgaacgc ccgtttatat gatcccgttc tcggccgctt tcttagtccc   5100
gacccatacg tgcagatgcc ggacttcacc caaagcttca accggtactc gtattgttta   5160
aacaatccgc tggtgtatgt ggatcaagat ggagaaatag cctggttcgt ccctgttatt   5220
gtgggggcag tgataggtgc ttatagtgga ggggttattg ctaacgaagg tcaatataac   5280
cctgtaaaat gggattacaa ctcaggtaaa acttggggct acatgcttgg tggtgctgtt   5340
gtaggcggta taagtggttc tctcggttgg gcagtctcaa tttcgggtat gccaatggca   5400
aacacagcgg gaataatatc tgcttcgttt gtaaattctg ttggcacgca tatttacaca   5460
ggagggcaaa caccagtttc aatgagttta ggtgttgcct cttatgattt tacgaatggt   5520
tcttttggtc atctcggcaa aaaaggcaac aagtggtatg aaaacttggg atatggatta   5580
ggggcaatgg cgaatttgag tgatatatta attggcttta aacctcaaaa agttgatttg   5640
gttactgaaa attcagatgc gataggtcat tctgctattg tcaaacacga tacaagaaca   5700
ggcatcaagg gcaaaacaga tataaatgga ttaatatcag tgggacctga tagagttagt   5760
caaccagatg gttcgtggca ctggatgaaa ggaactaata aatggtcaac ttattcagca   5820
aaagagaact caagatggat gcaatcactt gatgttaatt ataatacaat taatcgctat   5880
tctaattggc ttaacaaaat ggaaaatacg ggtaaacttg tgtatagttt agaactaagt   5940
agctgtgtga ctcacacgtc attagcactt aatgcgtcag gcgtttttaa tataggtata   6000
cacccgtatt tacttcatgc tcaaatgtat ttatggggta acggaattag accttggtct   6060
tttaatcatt tttttaatcg ttag                                          6084
```

<210> SEQ ID NO 12
<211> LENGTH: 2027
<212> TYPE: PRT
<213> ORGANISM: Tannerella forsythensis (ATCC 43037)

<400> SEQUENCE: 12

```
Met Arg Ile Ile Asn Ile Ser Ile Glu Ile Ile Cys Thr Cys Leu Ile
1               5                   10                  15

Ile Gly Val Thr Gly Tyr Ala Gln Lys Thr Asn Val Tyr Ala Ala Gly
            20                  25                  30
```

-continued

```
Asn Glu Ala Ser Ser Asp Asn Tyr Asp Pro Ser Gly Tyr Arg Ile Trp
        35                  40                  45

Gly Asn Tyr Arg Asn Glu Thr Ser Asp Ala Asn Glu Leu Asp Ala Arg
    50                  55                  60

Gln Leu Pro Ser Phe Tyr Tyr Lys Ile Leu Lys Asn Arg Leu Glu Asn
65                  70                  75                  80

Asn Tyr Ser Pro Glu Glu Lys Arg Thr Phe Ala Pro Ala Pro Leu Ser
                85                  90                  95

Arg Gly Met Ala Val Gly Ser Thr Ala Gly Met Ala Glu Ile Thr Leu
            100                 105                 110

Thr Gly Ala Ala Asn Tyr Ser Val Pro Ile Glu Val Pro Glu Gly Ile
        115                 120                 125

Ala Gly Phe Lys Pro Glu Val Ser Val Arg Tyr Ser Ser Gln Ser Gly
    130                 135                 140

Val Gly Leu Leu Gly Tyr Gly Trp Asn Leu Ser Ala Phe Ser Val Ile
145                 150                 155                 160

Ser Arg Ser Gly Lys Thr Phe Tyr His Asp Gly Met Ser Lys Ala Pro
                165                 170                 175

Ala Leu Ser Tyr Glu Asp Asn Val Met Leu Asp Gly Gln Arg Leu Met
            180                 185                 190

Leu Ile Ser Gly Gln Asn Leu Met Asn Gly Ala Lys Tyr Arg Leu Glu
        195                 200                 205

Asn Asp Pro Thr Ile Asp Ile Thr Tyr Lys Met Ile Gly Ser Phe Gln
    210                 215                 220

Gly Phe Thr Val Arg Ser Lys Asp Gly Thr Ile Arg Glu Phe Gly Val
225                 230                 235                 240

Thr Ser Asp Ser Asn Ile Glu Thr Ser Asp Gly Thr Ala Leu Phe Trp
                245                 250                 255

Leu Leu Ser Arg Val Ile Asp Lys Gln Gly Asn Val Ile Ser Tyr Gln
            260                 265                 270

Tyr Glu Glu Val Ile Asn Asn Gly Glu Phe Tyr Leu Asn Arg Ile Glu
        275                 280                 285

Tyr Ala Ser Gly Arg Ser Ile Arg Phe Ser Tyr Glu Thr Arg Lys Asp
    290                 295                 300

Lys Gln Thr Gly Tyr Tyr Ala Gly Ala Val Leu Asn Ser Asn Lys Ile
305                 310                 315                 320

Leu Lys Asn Ile Ser Thr Tyr Ile Gly Gln Met Gln Phe Lys Gln Tyr
                325                 330                 335

Gln Phe Asn Tyr Asn Thr Tyr Glu Asn Gly Leu Tyr Thr Gln Leu Thr
            340                 345                 350

Glu Ile Ile Glu Ser Gly Gln Asn Gly Gln Arg Tyr Asn Pro Thr Arg
        355                 360                 365

Ile Tyr Tyr Gly Tyr Pro Asp Pro Tyr Lys Asn Glu Asp Ile Val Thr
    370                 375                 380

Leu Ser Glu His Arg Lys Gly Asn Lys Pro Leu Phe Ala Asp Phe Asn
385                 390                 395                 400

Gly Asp Gly Arg Met Asp Phe Leu Ser Tyr Pro Glu Glu Leu Ser Asp
                405                 410                 415

Asn Pro Lys Glu Asp Val Ala Thr Leu Phe Leu Ser Leu His Gly Leu
            420                 425                 430

Gly Gly Thr Tyr Phe Ala Lys Lys Cys Thr Ile Pro Met Arg Ala Phe
        435                 440                 445

Gly Glu Phe Arg Tyr Phe Met Leu Ala Asp Val Asn Gly Asp Lys Lys
```

-continued

```
    450                 455                 460

Met Asp Val Ile His Val Ser Arg Ala Asp Asn Gly Thr Glu Arg Tyr
465                 470                 475                 480

Asn Tyr Tyr Val Phe Asp Gly Glu Lys Leu Val Tyr Gln Tyr Lys Gly
                485                 490                 495

Phe Asn Thr His Gly Asp Glu Ala Phe Val Gly Asp Phe Asp Gly Asp
            500                 505                 510

Gly Arg His Asp Ile Leu Ile Lys Asn Asn Ser Lys Val Tyr Asp Gly
        515                 520                 525

Glu Gly Arg Glu Ile Ala Ser Gly Gly Ile Thr Asp Trp Gly Ser Asp
    530                 535                 540

Tyr Ile Lys Tyr Tyr Tyr Pro Asn Ser Arg Tyr Ile Cys Asp Leu Asn
545                 550                 555                 560

Gly Asn Gly Lys Ser Glu Leu Leu Val Ile Asp Lys His Gly Ala Lys
                565                 570                 575

Val Tyr Glu Leu Asn Glu Arg Gln Phe Val Glu Leu Pro Glu Phe Arg
            580                 585                 590

Thr Ser Leu Ile Lys Asn Tyr Tyr Phe Pro Tyr Phe Gly Asp Phe Asn
        595                 600                 605

Gly Asp Gly Lys Thr Asp Val Leu Ile Gln Arg Trp His Gln Gly Asp
    610                 615                 620

Tyr Asp Asp Val Ser Ile Leu Phe Ser Thr Gly Lys Gly Tyr Val Lys
625                 630                 635                 640

Gln Asp Val Leu Asn Ala Asp Ile Arg Ala Lys Val Phe Val Ala Asp
                645                 650                 655

Phe Asn Lys Asp Gly Lys Ser Asp Ile Phe His Met Glu Ile Val Asn
            660                 665                 670

Asn Ala Val Arg Met Lys Val Gly Ile Phe His Gly Asn Gly Phe His
        675                 680                 685

Thr Thr Tyr His Ser Ser Asn Leu Arg Leu Glu Asp Val Tyr Leu Ser
    690                 695                 700

Tyr Asn Asn Ile Glu Tyr Asp Asn Tyr Leu Phe Gln Val Ala Asp Phe
705                 710                 715                 720

Asp Gly Asp Gly Ser Ser Glu Phe Cys Cys Ala Arg His Met Asn Ala
                725                 730                 735

Tyr Ile Ile Arg Ser Phe Ser Asp Pro Gln Asn Leu Leu Val Glu Thr
            740                 745                 750

Ile Ser Asp Gly Leu Gly Ala Tyr Thr Ser Phe Gln Tyr Ala Pro Ile
        755                 760                 765

Thr Ser Asn Ser Val Cys Thr Val Thr Gly Asn Asn Glu Ala Phe Pro
    770                 775                 780

Val Thr Asp Ser Arg Phe Pro Leu Tyr Val Val Ser Asn Ile Thr Gln
785                 790                 795                 800

Ser Thr Gly Gly Tyr Ser Glu Thr Thr Arg Tyr Arg Tyr Lys Asp Pro
                805                 810                 815

Arg Ser His Met Gln Gly Lys Gly Phe Leu Gly Phe Gly Glu Val Glu
            820                 825                 830

Ser Ile Asp Asp Asn Lys Asp Arg Lys Val Ile Thr Thr Tyr Gly Tyr
        835                 840                 845

Glu Lys Asp Tyr Phe Tyr Pro Phe Ile Lys Glu Gln Lys Ile Met Thr
    850                 855                 860

Arg Ser Gly Met Lys Ile Ser Thr Ser Val Tyr Glu Asn Ser Tyr Val
865                 870                 875                 880
```

-continued

```
Tyr Asn Gly Ser Lys Arg Val Val Pro Tyr Val Arg Lys Ser Thr Thr
                885                 890                 895

Thr Asp His Leu Thr Gly Val Val Lys Thr Ala Glu Cys Thr Gln Ile
            900                 905                 910

Asp Thr Trp Ala Asn Pro Leu Ser Ile Val Thr Arg His Gly Asn Asp
        915                 920                 925

Val Thr Glu Thr Val Thr Ala Ser Tyr Ile Asn Arg Glu Ala Glu Asn
    930                 935                 940

Leu Trp Ile Ile Gly Leu Pro Gln Ser Val Glu Lys Arg Val Thr Lys
945                 950                 955                 960

Gly Thr Gly Thr Trp Ile Asp Lys Gln Val Phe Thr Tyr Asn Ala Gly
                965                 970                 975

Tyr Leu Pro Gln Lys Ile Val Asn Phe Thr Gly Asp Gly Asn Lys Gln
            980                 985                 990

Thr Ser Glu Asp Val Phe Asp Tyr  Asp Arg Tyr Gly Asn  Met Ile Thr
        995                 1000                1005

His Ser  Thr Arg Ala Tyr Ala  Ser Pro His Val Leu  Thr Thr Arg
    1010                1015                1020

Thr Glu  Tyr Ser Ser Asp Gly  Leu Tyr Met Leu Arg  Thr Ile Asp
    1025                1030                1035

Pro Leu  Ser Arg Val Thr Thr  His Thr Tyr Asn Ser  Ser Gly Gln
    1040                1045                1050

Leu Ala  Ser Thr Lys Asp Phe  Leu Asn Thr Thr Thr  Ala Tyr Glu
    1055                1060                1065

Tyr Asp  Gly Met Gly Arg Leu  Val Lys Thr Val Tyr  Pro Asp Gln
    1070                1075                1080

Thr Gln  Ser Ser Val Val Tyr  Ser Trp Glu Asn Ala  Val Val Asn
    1085                1090                1095

Ser Val  Tyr Gly Met Thr Glu  Thr Leu Thr Gly Lys  Pro Glu Arg
    1100                1105                1110

Lys Ile  Tyr Phe Asp Ala Phe  Gly Arg Lys Val Arg  Glu Cys Ile
    1115                1120                1125

Arg Gln  Thr Asp Gly Gln Asp  Val Cys Thr Asp Thr  Lys Tyr Asp
    1130                1135                1140

Asn Ala  Gly Arg Val Ser Gln  Glu Ser Leu Pro Phe  Lys Gly Gly
    1145                1150                1155

Ala Ala  Ser Lys Trp Asn Thr  Tyr Gly Tyr Asp Gly  Tyr Gly Arg
    1160                1165                1170

Leu Ser  Gln Gln Thr His Ala  Ser Gly Lys Thr Thr  Thr Tyr Thr
    1175                1180                1185

Tyr Ala  Gly Asn Ser Ile Thr  Glu Thr Lys Asn Gly  Ile Ser His
    1190                1195                1200

Lys Ser  Val Tyr Asn Ala Met  Gly Glu Gln Val Ser  Val Thr Asp
    1205                1210                1215

Pro Ala  Gly Thr Ile Thr Tyr  Thr Leu Arg Pro Asp  Gly Gln Pro
    1220                1225                1230

Val Thr  Ile Thr Ala Pro Gly  Asn Val Lys Thr Thr  Phe Ser Tyr
    1235                1240                1245

Asp Ala  Tyr Gly Arg Gln Thr  Ala Ile His Asp Pro  Ser Ala Gly
    1250                1255                1260

Asn Arg  Thr Phe Ala Tyr Asp  Ala Ser Gly Asn Leu  Gln Arg Glu
    1265                1270                1275
```

-continued

```
Thr Asp Ala Asp Asn Arg Val Lys Thr Met Ser Tyr Asp Val Tyr
    1280                1285                1290

Gly Arg Leu Thr Ser Lys Val Leu Pro Glu Phe Thr Thr Ser Tyr
    1295                1300                1305

Ala Tyr Asn Gly Tyr Gly Gln Leu Thr Thr Glu Thr Ser Asn Asn
    1310                1315                1320

Gly Ile Ser Ser Val Tyr Glu Tyr Asp Ser Tyr Gly Arg Leu Ala
    1325                1330                1335

Lys Glu Arg Asn Asn Val Pro Asp Gly Lys Trp Leu Glu Lys Thr
    1340                1345                1350

Tyr Thr Tyr Ala Ala Gly Asn Leu Ala Ser Val Arg Tyr Ala Ser
    1355                1360                1365

Gln Ser Gly Ala Ile Gly Thr Glu Ala Tyr Thr Tyr Ser His Gly
    1370                1375                1380

His Met Asn Gly Ile Arg Trp Gly Ser Ser Pro Val Trp Thr Leu
    1385                1390                1395

Asn Ala Glu Asn Pro Phe Ser Gln Pro Leu Ser Val Thr Thr Gly
    1400                1405                1410

Pro Val Thr Arg Thr Tyr Thr Tyr Asp Val Tyr Gly Ile Pro Thr
    1415                1420                1425

Gly Arg Thr Ala Gln Ser Thr Ala Gly Gly Thr Phe Leu Asn Ser
    1430                1435                1440

Thr Tyr Gly Phe Asp Ala Ala Arg Gly Asn Leu Thr Tyr Arg Lys
    1445                1450                1455

Asp Asn Arg Arg Asn Lys Gln Glu Asn Phe Thr Tyr Asp Asn Leu
    1460                1465                1470

Asn Arg Leu Lys Thr Tyr Gly Gly Ile Val Met Asp Tyr Asp Pro
    1475                1480                1485

Lys Gly Asn Ile Thr Lys Lys Gly Asp Val Gly Thr Phe His Tyr
    1490                1495                1500

Gln Thr Pro Tyr Lys Pro Tyr Ala Leu Ser Gly Ala Asp Ile Gly
    1505                1510                1515

Thr Asn Lys Val Ile Pro Pro Arg Glu Gln Thr Ile Arg Tyr Thr
    1520                1525                1530

Ser Phe Asp Arg Pro Ser Val Ile Thr Glu Asn Gly Tyr Glu Ala
    1535                1540                1545

Ser Phe Ile Tyr Asn Ala Ser Gly Asp Arg Gln Lys Met Thr Val
    1550                1555                1560

Lys Lys Gly Gly Lys Pro Phe Tyr Thr Arg Tyr Tyr Leu Gly Gly
    1565                1570                1575

Arg Tyr Glu Thr Asp Val Met Gly Asn Ser Gln Lys His Arg Leu
    1580                1585                1590

Tyr Ile Gly Gly Asp Ala Tyr Thr Ala Pro Ala Val Tyr Met Asn
    1595                1600                1605

Thr Gly Asn Gly Trp Ala Leu Tyr Tyr Ile Cys Arg Asp Tyr Leu
    1610                1615                1620

Gly Asn Met Thr His Leu Val Ala Ser Asn Gly Thr Val Val Gln
    1625                1630                1635

Glu Leu Ser Tyr Asp Ala Trp Gly Arg Leu Arg Asn Pro Glu Thr
    1640                1645                1650

His Ala Val Tyr Leu Pro Asp Asn Glu Thr Glu Leu Met Leu Gly
    1655                1660                1665

Arg Gly Tyr Thr Gly His Glu His Leu Ser Met Phe Gly Leu Ile
```

-continued

```
    1670                1675                1680

Asn Met  Asn Ala Arg Leu Tyr  Asp Pro Val Leu Gly  Arg Phe Leu
    1685                1690                1695

Ser Pro  Asp Pro Tyr Val Gln  Met Pro Asp Phe Thr  Gln Ser Phe
    1700                1705                1710

Asn Arg  Tyr Ser Tyr Cys Leu  Asn Asn Pro Leu Val  Tyr Val Asp
    1715                1720                1725

Gln Asp  Gly Glu Ile Ala Trp  Phe Val Pro Val Ile  Val Gly Ala
    1730                1735                1740

Val Ile  Gly Ala Tyr Ser Gly  Gly Val Ile Ala Asn  Glu Gly Gln
    1745                1750                1755

Tyr Asn  Pro Val Lys Trp Asp  Tyr Asn Ser Gly Lys  Thr Trp Gly
    1760                1765                1770

Tyr Met  Leu Gly Gly Ala Val  Val Gly Gly Ile Ser  Gly Ser Leu
    1775                1780                1785

Gly Trp  Ala Val Ser Ile Ser  Gly Met Pro Met Ala  Asn Thr Ala
    1790                1795                1800

Gly Ile  Ile Ser Ala Ser Phe  Val Asn Ser Val Gly  Thr His Ile
    1805                1810                1815

Tyr Thr  Gly Gly Gln Thr Pro  Val Ser Met Ser Leu  Gly Val Ala
    1820                1825                1830

Ser Tyr  Asp Phe Thr Asn Gly  Ser Phe Gly His Leu  Gly Lys Lys
    1835                1840                1845

Gly Asn  Lys Trp Tyr Glu Asn  Leu Gly Tyr Gly Leu  Gly Ala Met
    1850                1855                1860

Ala Asn  Leu Ser Asp Ile Leu  Ile Gly Phe Lys Pro  Gln Lys Val
    1865                1870                1875

Asp Leu  Val Thr Glu Asn Ser  Asp Ala Ile Gly His  Ser Ala Ile
    1880                1885                1890

Val Lys  His Asp Thr Arg Thr  Gly Ile Lys Gly Lys  Thr Asp Ile
    1895                1900                1905

Asn Gly  Leu Ile Ser Val Gly  Pro Asp Arg Val Ser  Gln Pro Asp
    1910                1915                1920

Gly Ser  Trp His Trp Met Lys  Gly Thr Asn Lys Trp  Ser Thr Tyr
    1925                1930                1935

Ser Ala  Lys Glu Asn Ser Arg  Trp Met Gln Ser Leu  Asp Val Asn
    1940                1945                1950

Tyr Asn  Thr Ile Asn Arg Tyr  Ser Asn Trp Leu Asn  Lys Met Glu
    1955                1960                1965

Asn Thr  Gly Lys Leu Val Tyr  Ser Leu Glu Leu Ser  Ser Cys Val
    1970                1975                1980

Thr His  Thr Ser Leu Ala Leu  Asn Ala Ser Gly Val  Phe Asn Ile
    1985                1990                1995

Gly Ile  His Pro Tyr Leu Leu  His Ala Gln Met Tyr  Leu Trp Gly
    2000                2005                2010

Asn Gly  Ile Arg Pro Trp Ser  Phe Asn His Phe Phe  Asn Arg
    2015                2020                2025
```

<210> SEQ ID NO 13
<211> LENGTH: 24
<212> TYPE: DNA
<213> ORGANISM: Artificial Sequence
<220> FEATURE:
<223> OTHER INFORMATION: Primer P1

-continued

<400> SEQUENCE: 13
aggatcgtac gatggaacaa gagg 24

<210> SEQ ID NO 14
<211> LENGTH: 24
<212> TYPE: DNA
<213> ORGANISM: Artificial Sequence
<220> FEATURE:
<223> OTHER INFORMATION: Primer P2

<400> SEQUENCE: 14
cgactgtgat gcgtaacgaa caga 24

<210> SEQ ID NO 15
<211> LENGTH: 24
<212> TYPE: DNA
<213> ORGANISM: Artificial Sequence
<220> FEATURE:
<223> OTHER INFORMATION: Primer P3

<400> SEQUENCE: 15
gtccgacggt ctgtatatgc ttag 24

<210> SEQ ID NO 16
<211> LENGTH: 24
<212> TYPE: DNA
<213> ORGANISM: Artificial Sequence
<220> FEATURE:
<223> OTHER INFORMATION: Primer P4

<400> SEQUENCE: 16
ccgaagaaat caatgcctgc cgat 24

<210> SEQ ID NO 17
<211> LENGTH: 28
<212> TYPE: DNA
<213> ORGANISM: Artificial Sequence
<220> FEATURE:
<223> OTHER INFORMATION: Primer P5

<400> SEQUENCE: 17
taatgtcccc gacggtaaat ggcttgaa 28

<210> SEQ ID NO 18
<211> LENGTH: 27
<212> TYPE: DNA
<213> ORGANISM: Artificial Sequence
<220> FEATURE:
<223> OTHER INFORMATION: Primer P6

<400> SEQUENCE: 18
gcgtctgttc gttacgcatc acagtcg 27

<210> SEQ ID NO 19
<211> LENGTH: 7542
<212> TYPE: DNA
<213> ORGANISM: Artificial Sequence
<220> FEATURE:
<223> OTHER INFORMATION: Fusion 8884 (TcdB2/TcplGzC)

<400> SEQUENCE: 19
atgcaaaatt cacaagattt tagtattacg gaactgtcac tgcccaaagg ggggggcgct 60
atcacgggaa tgggtgaagc attaaccccc actggaccgg atggtatggc cgcgctatct 120
ctaccattgc ctatttctgc cgggcgcggt tatgctcccg cattcactct gaattacaac 180

-continued

```
agcggcgccg gtaacagtcc atttggtctg ggttgggatt gcaacgttat gactatccgc    240
cgccgcaccc attttggcgt cccccattat gacgaaaccg atacctttttt ggggccagaa    300
ggcgaagtgc tggtggtagc ggatcaacct cgcgacgaat ccacattaca gggtatcaat    360
ttaggcgcca cctttaccgt taccggctac cgttcccgtc tggaaagcca tttcagccga    420
ttggaatatt ggcaacccaa aacaacaggt aaaacagatt tttggttgat atatagccca    480
gatgggcagg tgcatctact gggtaaatca ccgcaagcgc ggatcagcaa cccatcccaa    540
acgacacaaa cagcacaatg gctgctggaa gcctctgtat catcacgtgg cgaacaaatt    600
tattatcaat atcgcgccga agatgacaca ggttgcgaag cagatgaaat tacgcaccat    660
ttacaggcta cagcgcaacg ttatttacac atcgtgtatt acggcaaccg tacagccagc    720
gaaacattac ccggtctgga tggcagcgcc ccatcacaag cagactggtt gttctatctg    780
gtatttgatt acggcgaacg cagtaacaac ctgaaaacgc caccagcatt ttcgactaca    840
ggtagctggc tttgccgtca ggaccgtttt tcccgttatg aatatggctt tgagattcgt    900
acccgccgct tatgccgtca ggtattgatg taccatcacc tgcaagcact ggatagtaag    960
ataacagaac acaacggacc aacgctggtt tcacgcctga tactcaatta cgacgaaagc   1020
gcgatagcca gcacgctagt attcgttcgc cgagtgggac acgagcaaga tggtaatgtc   1080
gtcaccctgc cgccattaga attggcatat caggattttt caccgcgaca tcacgctcac   1140
tggcaaccaa tggatgtact ggcaaacttc aatgccattc agcgctggca gctagtcgat   1200
ctaaaaggcg aaggattacc cggcctgtta tatcaggata aaggcgcttg gtggtaccgc   1260
tccgcacagc gtctgggcga aattggctca gatgccgtca cttgggaaaa gatgcaacct   1320
ttatcggtta ttccttcttt gcaaagtaat gcctcgttgg tggatatcaa tggagacggc   1380
caacttgact gggttatcac cggaccggga ttacggggat atcatagtca acgcccggat   1440
ggcagttgga cacgttttac cccactcaac gctctgccgg tggaatacac ccatccacgc   1500
gcgcaactcg cagatttaat gggagccggg ctatccgatt tggtgctgat cggccctaag   1560
agcgtgcgtt tatatgccaa tacccgcgac ggctttgcca aaggaaaaga tgtggtgcaa   1620
tccggtgata tcacactgcc ggtgccgggc gccgatccac gtaagttggt ggcgtttagt   1680
gatgtattgg gttcaggtca agcccatctg gttgaagtaa gcgcgactaa agtcacctgc   1740
tggcctaatc tggggcgcgg acgttttggt caacccatta ccttaccggg attcagccag   1800
ccagcaaccg agtttaaccc ggctcaagtt tatctggccg atctggatgg cagcggtcca   1860
acggatctga tttatgttca tacaaaccgt ctggatatct tcctgaacaa aagtggcaat   1920
ggctttgctg aaccagtgac attacgcttc ccggaaggtc tgcgttttga tcatacctgt   1980
cagttacaaa tggccgatgt acaaggatta ggcgtcgcca gcctgatact gagcgtgccg   2040
catatgtctc cccatcactg gcgctgcgat ctgaccaaca tgaagccgtg gttactcaat   2100
gaaatgaaca acaatatggg ggtccatcac accttgcgtt accgcagttc ctcccaattc   2160
tggctggatg aaaaagccgc ggcgctgact accggacaaa caccggtttg ctatctcccc   2220
ttcccgatcc acaccctatg gcaaacggaa acagaagatg aaatcagcgg caacaaatta   2280
gtcacaacac ttcgttatgc tcgtggcgca tgggacggac gcgagcggga atttcgcgga   2340
tttggttatg tagagcagac agacagccat caactggctc aaggcaacgc gccagaacgt   2400
acgccaccgg cgctgaccaa aaactggtat gccaccggac tgccggtgat agataacgca   2460
ttatcaaccg agtattggcg tgatgatcag gcttttgccg gtttctcacc gcgctttacg   2520
```

-continued

```
acttggcaag ataacaaaga tgtcccgtta acaccggaag atgataacag tcgttactgg   2580
ttcaaccgcg cgttgaaagg tcaactgcta cgtagtgaac tgtacggatt ggacgatagt   2640
acaaataaac acgttcccta tactgtcact gaatttcgtt cacaggtacg tcgattacag   2700
cataccgaca gccgataccc tgtactttgg tcatctgtag ttgaaagccg caactatcac   2760
tacgaacgta tcgccagcga cccgcaatgc agtcaaaata ttacgctatc cagtgatcga   2820
tttggtcagc cgctaaaaca gctttcggta cagtacccgc gccgccagca gccagcaatc   2880
aatctgtatc ctgatacatt gcctgataag ttgttagcca acagctatga tgaccaacaa   2940
cgccaattac ggctcaccta tcaacaatcc agttggcatc acctgaccaa caataccgtt   3000
cgagtattgg gattaccgga tagtacccgc agtgatatct ttacttatgg cgctgaaaat   3060
gtgcctgctg gtggtttaaa tctggaactt ctgagtgata aaaatagcct gatcgcggac   3120
gataaaccac gtgaatacct cggtcagcaa aaaaccgctt ataccgatgg acaaaataca   3180
acgccgttgc aaacaccaac acggcaagcc ctgattgcct ttaccgaaac aacggtattc   3240
aaccagtcca cattatcagc gtttaacgga agcatcccgt ccgataaatt atcaacgacg   3300
ctggagcaag ctggatatca gcaaacaaat tatctattcc ctcgcactgg agaagataaa   3360
gtttgggtag cccatcacgg ctataccgat tatggtacag cggcacagtt ctggcgcccg   3420
caaaaacaga gcaacaccca actcaccggt aaaatcaccc tcatctggga tgcaaactat   3480
tgcgttgtgg tacaaacccg ggatgctgct ggactgacaa cctcagccaa atatgactgg   3540
cgttttctga ccccggtgca actcaccgat atcaatgaca atcagcacct tatcacactg   3600
gatgcattgg gccgaccaat cacattgcgc ttttggggaa ctgaaaacgg caagatgaca   3660
ggttattcct caccggaaaa agcatcattt tctccaccat ccgatgttaa tgccgctatt   3720
gagttaaaaa aaccgctccc tgtagcacag tgtcaggtct acgcaccaga aagctggatg   3780
ccagtattaa gtcagaaaac cttcaatcga ctggcagaac aagattggca aaagttatat   3840
aacgcccgaa tcatcaccga agatggacgt atctgcacac tggcttatcg ccgctgggta   3900
caaagccaaa aggcaatccc tcaactcatt agcctgttaa acaacggacc ccgtttacct   3960
cctcacagcc tgacattgac gacggatcgt tatgatcacg atcctgagca acagatccgt   4020
caacaggtgg tattcagtga tggctttggc cgcttgctgc aagccgctgc ccgacatgag   4080
gcaggcatgg cccggcaacg caatgaagac ggctctttga ttataaatgt ccagcatact   4140
gagaaccgtt gggcagtgac tggacgaacg gaatatgaca ataaggggca accgatacgt   4200
acctatcagc cctatttcct caatgactgg cgatacgtca gcaatgatag tgcccggcag   4260
gaaaaagaag cttatgcaga tacccatgtc tatgatccca taggtcgaga aatcaaggtt   4320
atcaccgcaa aaggttggtt ccgtcgaacc ttgttcactc cctggtttac tgtcaatgaa   4380
gatgaaaatg acacagccgc tgaggtgaag aaggtaaaga tgccgggatc cgacaacaag   4440
ggtcagacta tccgcactag gcctatgggc cgtaacgtgg caagcttggc tgcggattgt   4500
acctggtcca aaaccgttta tactccgtgg accactgttg aacacggtgc tggtagcatg   4560
gttctgcaat ccaacgctcg tgatgacccg gatgttggtc acttcttttc ccgcatcgcg   4620
tcttcccgct actcccagag ctggtacgat aagcgtaaac tgggtactgc tcaggaaaaa   4680
cgcgcagctg agaaatccgc ggtttattcc gatactccgc tgaccactca ctccggttct   4740
tgcggcctgc cggttcgcac catccagcaa gcaggcggta aaacctacac ccgcagctct   4800
atgtatgatg tgtctggcaa ccgtatccgc gacgttgact cctacgaacg taccgttgaa   4860
aaaatgctgt acgacaaact gggtcgtcag ctgcagacta ccggtatgga ttgtggcgaa   4920
```

-continued

```
tcctggctcc tgcttgacgc acagggtggc gagatcctga gctggaactg tcgcggttac   4980
tctttcatta ctcgttacga cccgctgcgt cgcgaaaccg aacgcctggt tgcgaaagcg   5040
gctgaaatgc cgaaactgat cagccgtatc acttacggcg aaacctgcgg tgacgcaatc   5100
aacctgaacc tgaacggtca ggtatggaaa gttgaggatc aggcaggcgt tcacattaac   5160
actcactata acattcgtgg tcactgcctg ggtaagaccc tgcaattcac caaagaatat   5220
aaacagctgg ttgattggaa actggatcag accctggaaa ctgaggttta tccgcatacc   5280
tatttctacg ataactatgg ccaggttctg caagaggaag acgaacaggg caaccgtacc   5340
cgccgtaact actcccgtca gggtcacgtg gtttctgtag acttctctag cattaaaggc   5400
cgtgactgga aatcttacct gtctggtgct accttctctg cggacggcct gccgattact   5460
atcaaatacg gcaacggtgt ggtttccgac tttttctacg atgacgaaag ccgtaacctg   5520
attagccaac gcaccactcg tccgtgccgt ggtcgtcgcg aactgctcca agatcgtacc   5580
catgtttacg actatgttgg tcgtcgcatt tttacttccg acggttccga acaggtaaaa   5640
tatttcggtg agagccgtgt taagccggaa tgggactaca cttacaacgc gactggcgca   5700
ctggtaatcg caaccggccg tgcgcagctg tctggcaaaa tcggtaacgg caaccagctg   5760
accccgcata acgctatgaa cggcctgaac ccgtctcgcg gtggcggtga cggtaacttg   5820
ctgtatcagt atcgcgaaac ttacgactac gatcgtgagg gtaacattct gatgatgaaa   5880
cacgaagcgc cggacatcaa aggcgttacc agctggaccc gtaactacca ctacgatgaa   5940
aagagcctgt tatccgacga tccacgtgtg aaatccaacc gtctgtctcg cacctccatc   6000
ggcgatacca acgaaggcaa atacatgtac gaaggctctg ctggcctgtc cggttgcatc   6060
accactctgc caaagttctc cgaactggat tggaacatga acaacatgct gagcttttct   6120
tccactcagt acgtaaacgc gggcaccccg gaacgtacct actatgtgta cgaccacgct   6180
ggtaaccgcg ttcgtaaagt taccgagact gcggctaaat ctggtgagga accgcgtaaa   6240
cagcgtgata ccctgttctt tggtggcgtg gaactgcaaa ccaaatccaa cggctctctt   6300
ctgtggacta cccgtgttaa aggtgatggt atcgtggctg tagttgaagt gaaccgtaac   6360
caggaaaccc cgctggtacg cttccaggct ggtcgtgaca tggaatttga cgatcaggcg   6420
cagctgatca gctacgagga atattctccg ttcggtgctg tggtttacgc tgcgatgtac   6480
ggcaacattg aggcaccacg cgcttaccgt ttcgcacgtt acgaacacga ttctgaaacc   6540
ggcctgtatc actgtggcca gcgttattac tgcccgtggc tgggtcgttg gacctcccca   6600
gatccgctgg gtgacgtgga tggtccaaac ctgttcgtat acgtgaacaa cgatccagtt   6660
aactcccacg acccgtctgg tacttccggc aagaaaacca aggaaggtac tcgcgaaatg   6720
tacgcagcgc cagatgacca gggcaaacgc cgtctggttg acgagaacaa agctgttgct   6780
gatcgcatcg caaagtacga acgcaaactg caacgtcagg aacgtaaaca acagcgtgcg   6840
atcgcgcgta tgagcggcac cgacccgatc ctgggttctc gtgcacgtta tgcggtaggc   6900
attgcggcta tgggcaacgc gctgggtcgt atctctggtt ccaccgaact gcatcacacc   6960
tacccgcagg aatatcgtga agagttctct gacatcgaca ttaacgttga ccgtacctct   7020
gtgagcattt ccaaagaggc gcactatatc tgcacttacg gtagcatcct ggacaacctg   7080
gtagcaacca acaaacgctg gaaatctgaa tactttgaca ctccagacac tggttattac   7140
gaacagatgg agcagcatga gtggtacgac gatgacccag gcatgcagta cgcgatccgt   7200
ctgcacctgg catacgaagc gcgtactctg aacggtaaaa tcatggcgga tttcggcatc   7260
```

-continued aacccgaaag gcgaagacgg tcgttccatg tttgttaact atgatgcggt aaccaaaatg 7320
cgtaccgctg gtcagcgtcg cggcgtacgt aacgacaacc tgatccatca cgaaacctgg 7380
ccgggtcgtc cgtttaacac cggcaacagc gataccgata acgcgggtgg cccggttcac 7440
ttccaggttg cagaggaaca gtacaacggc ctggatgctg acgcgcaggc gaaattcgat 7500
gacctgcgca accaaatgga ggcgctccta ggcaaacgct aa 7542

<210> SEQ ID NO 20
<211> LENGTH: 2513
<212> TYPE: PRT
<213> ORGANISM: Artificial Sequence
<220> FEATURE:
<223> OTHER INFORMATION: 8884 TcdB2/Tcp1GzC fusion peptide

<400> SEQUENCE: 20

Met Gln Asn Ser Gln Asp Phe Ser Ile Thr Glu Leu Ser Leu Pro Lys
1 5 10 15

Gly Gly Gly Ala Ile Thr Gly Met Gly Glu Ala Leu Thr Pro Thr Gly
20 25 30

Pro Asp Gly Met Ala Ala Leu Ser Leu Pro Leu Pro Ile Ser Ala Gly
35 40 45

Arg Gly Tyr Ala Pro Ala Phe Thr Leu Asn Tyr Asn Ser Gly Ala Gly
50 55 60

Asn Ser Pro Phe Gly Leu Gly Trp Asp Cys Asn Val Met Thr Ile Arg
65 70 75 80

Arg Arg Thr His Phe Gly Val Pro His Tyr Asp Glu Thr Asp Thr Phe
85 90 95

Leu Gly Pro Glu Gly Glu Val Leu Val Val Ala Asp Gln Pro Arg Asp
100 105 110

Glu Ser Thr Leu Gln Gly Ile Asn Leu Gly Ala Thr Phe Thr Val Thr
115 120 125

Gly Tyr Arg Ser Arg Leu Glu Ser His Phe Ser Arg Leu Glu Tyr Trp
130 135 140

Gln Pro Lys Thr Thr Gly Lys Thr Asp Phe Trp Leu Ile Tyr Ser Pro
145 150 155 160

Asp Gly Gln Val His Leu Leu Gly Lys Ser Pro Gln Ala Arg Ile Ser
165 170 175

Asn Pro Ser Gln Thr Thr Gln Thr Ala Gln Trp Leu Leu Glu Ala Ser
180 185 190

Val Ser Ser Arg Gly Glu Gln Ile Tyr Tyr Gln Tyr Arg Ala Glu Asp
195 200 205

Asp Thr Gly Cys Glu Ala Asp Glu Ile Thr His His Leu Gln Ala Thr
210 215 220

Ala Gln Arg Tyr Leu His Ile Val Tyr Tyr Gly Asn Arg Thr Ala Ser
225 230 235 240

Glu Thr Leu Pro Gly Leu Asp Gly Ser Ala Pro Ser Gln Ala Asp Trp
245 250 255

Leu Phe Tyr Leu Val Phe Asp Tyr Gly Glu Arg Ser Asn Asn Leu Lys
260 265 270

Thr Pro Pro Ala Phe Ser Thr Thr Gly Ser Trp Leu Cys Arg Gln Asp
275 280 285

Arg Phe Ser Arg Tyr Glu Tyr Gly Phe Glu Ile Arg Thr Arg Arg Leu
290 295 300

Cys Arg Gln Val Leu Met Tyr His His Leu Gln Ala Leu Asp Ser Lys
305 310 315 320

-continued

```
Ile Thr Glu His Asn Gly Pro Thr Leu Val Ser Arg Leu Ile Leu Asn
                325                 330                 335

Tyr Asp Glu Ser Ala Ile Ala Ser Thr Leu Val Phe Val Arg Arg Val
            340                 345                 350

Gly His Glu Gln Asp Gly Asn Val Val Thr Leu Pro Pro Leu Glu Leu
        355                 360                 365

Ala Tyr Gln Asp Phe Ser Pro Arg His His Ala His Trp Gln Pro Met
    370                 375                 380

Asp Val Leu Ala Asn Phe Asn Ala Ile Gln Arg Trp Gln Leu Val Asp
385                 390                 395                 400

Leu Lys Gly Glu Gly Leu Pro Gly Leu Leu Tyr Gln Asp Lys Gly Ala
                405                 410                 415

Trp Trp Tyr Arg Ser Ala Gln Arg Leu Gly Glu Ile Gly Ser Asp Ala
            420                 425                 430

Val Thr Trp Glu Lys Met Gln Pro Leu Ser Val Ile Pro Ser Leu Gln
        435                 440                 445

Ser Asn Ala Ser Leu Val Asp Ile Asn Gly Asp Gly Gln Leu Asp Trp
    450                 455                 460

Val Ile Thr Gly Pro Gly Leu Arg Gly Tyr His Ser Gln Arg Pro Asp
465                 470                 475                 480

Gly Ser Trp Thr Arg Phe Thr Pro Leu Asn Ala Leu Pro Val Glu Tyr
                485                 490                 495

Thr His Pro Arg Ala Gln Leu Ala Asp Leu Met Gly Ala Gly Leu Ser
            500                 505                 510

Asp Leu Val Leu Ile Gly Pro Lys Ser Val Arg Leu Tyr Ala Asn Thr
        515                 520                 525

Arg Asp Gly Phe Ala Lys Gly Lys Asp Val Val Gln Ser Gly Asp Ile
    530                 535                 540

Thr Leu Pro Val Pro Gly Ala Asp Pro Arg Lys Leu Val Ala Phe Ser
545                 550                 555                 560

Asp Val Leu Gly Ser Gly Gln Ala His Leu Val Glu Val Ser Ala Thr
                565                 570                 575

Lys Val Thr Cys Trp Pro Asn Leu Gly Arg Gly Arg Phe Gly Gln Pro
            580                 585                 590

Ile Thr Leu Pro Gly Phe Ser Gln Pro Ala Thr Glu Phe Asn Pro Ala
        595                 600                 605

Gln Val Tyr Leu Ala Asp Leu Asp Gly Ser Gly Pro Thr Asp Leu Ile
    610                 615                 620

Tyr Val His Thr Asn Arg Leu Asp Ile Phe Leu Asn Lys Ser Gly Asn
625                 630                 635                 640

Gly Phe Ala Glu Pro Val Thr Leu Arg Phe Pro Glu Gly Leu Arg Phe
                645                 650                 655

Asp His Thr Cys Gln Leu Gln Met Ala Asp Val Gln Gly Leu Gly Val
            660                 665                 670

Ala Ser Leu Ile Leu Ser Val Pro His Met Ser Pro His His Trp Arg
        675                 680                 685

Cys Asp Leu Thr Asn Met Lys Pro Trp Leu Leu Asn Glu Met Asn Asn
    690                 695                 700

Asn Met Gly Val His His Thr Leu Arg Tyr Arg Ser Ser Ser Gln Phe
705                 710                 715                 720

Trp Leu Asp Glu Lys Ala Ala Ala Leu Thr Thr Gly Gln Thr Pro Val
                725                 730                 735
```

-continued

```
Cys Tyr Leu Pro Phe Pro Ile His Thr Leu Trp Gln Thr Glu Thr Glu
            740                 745                 750

Asp Glu Ile Ser Gly Asn Lys Leu Val Thr Thr Leu Arg Tyr Ala Arg
        755                 760                 765

Gly Ala Trp Asp Gly Arg Glu Arg Glu Phe Arg Gly Phe Gly Tyr Val
    770                 775                 780

Glu Gln Thr Asp Ser His Gln Leu Ala Gln Gly Asn Ala Pro Glu Arg
785                 790                 795                 800

Thr Pro Pro Ala Leu Thr Lys Asn Trp Tyr Ala Thr Gly Leu Pro Val
                805                 810                 815

Ile Asp Asn Ala Leu Ser Thr Glu Tyr Trp Arg Asp Asp Gln Ala Phe
            820                 825                 830

Ala Gly Phe Ser Pro Arg Phe Thr Thr Trp Gln Asp Asn Lys Asp Val
        835                 840                 845

Pro Leu Thr Pro Glu Asp Asp Asn Ser Arg Tyr Trp Phe Asn Arg Ala
    850                 855                 860

Leu Lys Gly Gln Leu Leu Arg Ser Glu Leu Tyr Gly Leu Asp Asp Ser
865                 870                 875                 880

Thr Asn Lys His Val Pro Tyr Thr Val Thr Glu Phe Arg Ser Gln Val
                885                 890                 895

Arg Arg Leu Gln His Thr Asp Ser Arg Tyr Pro Val Leu Trp Ser Ser
            900                 905                 910

Val Val Glu Ser Arg Asn Tyr His Tyr Glu Arg Ile Ala Ser Asp Pro
        915                 920                 925

Gln Cys Ser Gln Asn Ile Thr Leu Ser Ser Asp Arg Phe Gly Gln Pro
    930                 935                 940

Leu Lys Gln Leu Ser Val Gln Tyr Pro Arg Arg Gln Gln Pro Ala Ile
945                 950                 955                 960

Asn Leu Tyr Pro Asp Thr Leu Pro Asp Lys Leu Leu Ala Asn Ser Tyr
                965                 970                 975

Asp Asp Gln Gln Arg Gln Leu Arg Leu Thr Tyr Gln Gln Ser Ser Trp
            980                 985                 990

His His Leu Thr Asn Asn Thr Val  Arg Val Leu Gly Leu  Pro Asp Ser
        995                 1000                1005

Thr Arg  Ser Asp Ile Phe Thr  Tyr Gly Ala Glu Asn  Val Pro Ala
    1010                 1015                1020

Gly Gly  Leu Asn Leu Glu Leu  Leu Ser Asp Lys Asn  Ser Leu Ile
    1025                 1030                1035

Ala Asp  Asp Lys Pro Arg Glu  Tyr Leu Gly Gln Gln  Lys Thr Ala
    1040                 1045                1050

Tyr Thr  Asp Gly Gln Asn Thr  Thr Pro Leu Gln Thr  Pro Thr Arg
    1055                 1060                1065

Gln Ala  Leu Ile Ala Phe Thr  Glu Thr Thr Val Phe  Asn Gln Ser
    1070                 1075                1080

Thr Leu  Ser Ala Phe Asn Gly  Ser Ile Pro Ser Asp  Lys Leu Ser
    1085                 1090                1095

Thr Thr  Leu Glu Gln Ala Gly  Tyr Gln Gln Thr Asn  Tyr Leu Phe
    1100                 1105                1110

Pro Arg  Thr Gly Glu Asp Lys  Val Trp Val Ala His  His Gly Tyr
    1115                 1120                1125

Thr Asp  Tyr Gly Thr Ala Ala  Gln Phe Trp Arg Pro  Gln Lys Gln
    1130                 1135                1140

Ser Asn  Thr Gln Leu Thr Gly  Lys Ile Thr Leu Ile  Trp Asp Ala
```

-continued

```
    1145                1150                1155

Asn Tyr  Cys Val Val Val Gln  Thr Arg Asp Ala Ala  Gly Leu Thr
    1160                1165                1170

Thr Ser  Ala Lys Tyr Asp Trp  Arg Phe Leu Thr Pro  Val Gln Leu
    1175                1180                1185

Thr Asp  Ile Asn Asp Asn Gln  His Leu Ile Thr Leu  Asp Ala Leu
    1190                1195                1200

Gly Arg  Pro Ile Thr Leu Arg  Phe Trp Gly Thr Glu  Asn Gly Lys
    1205                1210                1215

Met Thr  Gly Tyr Ser Ser Pro  Glu Lys Ala Ser Phe  Ser Pro Pro
    1220                1225                1230

Ser Asp  Val Asn Ala Ala Ile  Glu Leu Lys Lys Pro  Leu Pro Val
    1235                1240                1245

Ala Gln  Cys Gln Val Tyr Ala  Pro Glu Ser Trp Met  Pro Val Leu
    1250                1255                1260

Ser Gln  Lys Thr Phe Asn Arg  Leu Ala Glu Gln Asp  Trp Gln Lys
    1265                1270                1275

Leu Tyr  Asn Ala Arg Ile Ile  Thr Glu Asp Gly Arg  Ile Cys Thr
    1280                1285                1290

Leu Ala  Tyr Arg Arg Trp Val  Gln Ser Gln Lys Ala  Ile Pro Gln
    1295                1300                1305

Leu Ile  Ser Leu Leu Asn Asn  Gly Pro Arg Leu Pro  Pro His Ser
    1310                1315                1320

Leu Thr  Leu Thr Thr Asp Arg  Tyr Asp His Asp Pro  Glu Gln Gln
    1325                1330                1335

Ile Arg  Gln Gln Val Val Phe  Ser Asp Gly Phe Gly  Arg Leu Leu
    1340                1345                1350

Gln Ala  Ala Ala Arg His Glu  Ala Gly Met Ala Arg  Gln Arg Asn
    1355                1360                1365

Glu Asp  Gly Ser Leu Ile Ile  Asn Val Gln His Thr  Glu Asn Arg
    1370                1375                1380

Trp Ala  Val Thr Gly Arg Thr  Glu Tyr Asp Asn Lys  Gly Gln Pro
    1385                1390                1395

Ile Arg  Thr Tyr Gln Pro Tyr  Phe Leu Asn Asp Trp  Arg Tyr Val
    1400                1405                1410

Ser Asn  Asp Ser Ala Arg Gln  Glu Lys Glu Ala Tyr  Ala Asp Thr
    1415                1420                1425

His Val  Tyr Asp Pro Ile Gly  Arg Glu Ile Lys Val  Ile Thr Ala
    1430                1435                1440

Lys Gly  Trp Phe Arg Arg Thr  Leu Phe Thr Pro Trp  Phe Thr Val
    1445                1450                1455

Asn Glu  Asp Glu Asn Asp Thr  Ala Ala Glu Val Lys  Lys Val Lys
    1460                1465                1470

Met Pro  Gly Ser Asp Asn Lys  Gly Gln Thr Ile Arg  Thr Arg Pro
    1475                1480                1485

Met Gly  Arg Asn Val Ala Ser  Leu Ala Ala Asp Cys  Thr Trp Ser
    1490                1495                1500

Lys Thr  Val Tyr Thr Pro Trp  Thr Thr Val Glu His  Gly Ala Gly
    1505                1510                1515

Ser Met  Val Leu Gln Ser Asn  Ala Arg Asp Asp Pro  Asp Val Gly
    1520                1525                1530

His Phe  Phe Ser Arg Ile Ala  Ser Ser Arg Tyr Ser  Gln Ser Trp
    1535                1540                1545
```

-continued

```
Tyr Asp Lys Arg Lys Leu Gly Thr Ala Gln Glu Lys Arg Ala Ala
    1550                1555                1560

Glu Lys Ser Ala Val Tyr Ser Asp Thr Pro Leu Thr Thr His Ser
    1565                1570                1575

Gly Ser Cys Gly Leu Pro Val Arg Thr Ile Gln Gln Ala Gly Gly
    1580                1585                1590

Lys Thr Tyr Thr Arg Ser Ser Met Tyr Asp Val Ser Gly Asn Arg
    1595                1600                1605

Ile Arg Asp Val Asp Ser Tyr Glu Arg Thr Val Glu Lys Met Leu
    1610                1615                1620

Tyr Asp Lys Leu Gly Arg Gln Leu Gln Thr Thr Gly Met Asp Cys
    1625                1630                1635

Gly Glu Ser Trp Leu Leu Leu Asp Ala Gln Gly Gly Glu Ile Leu
    1640                1645                1650

Ser Trp Asn Cys Arg Gly Tyr Ser Phe Ile Thr Arg Tyr Asp Pro
    1655                1660                1665

Leu Arg Arg Glu Thr Glu Arg Leu Val Ala Lys Ala Ala Glu Met
    1670                1675                1680

Pro Lys Leu Ile Ser Arg Ile Thr Tyr Gly Glu Thr Cys Gly Asp
    1685                1690                1695

Ala Ile Asn Leu Asn Leu Asn Gly Gln Val Trp Lys Val Glu Asp
    1700                1705                1710

Gln Ala Gly Val His Ile Asn Thr His Tyr Asn Ile Arg Gly His
    1715                1720                1725

Cys Leu Gly Lys Thr Leu Gln Phe Thr Lys Glu Tyr Lys Gln Leu
    1730                1735                1740

Val Asp Trp Lys Leu Asp Gln Thr Leu Glu Thr Glu Val Tyr Pro
    1745                1750                1755

His Thr Tyr Phe Tyr Asp Asn Tyr Gly Gln Val Leu Gln Glu Glu
    1760                1765                1770

Asp Glu Gln Gly Asn Arg Thr Arg Arg Asn Tyr Ser Arg Gln Gly
    1775                1780                1785

His Val Val Ser Val Asp Phe Ser Ser Ile Lys Gly Arg Asp Trp
    1790                1795                1800

Lys Ser Tyr Leu Ser Gly Ala Thr Phe Ser Ala Asp Gly Leu Pro
    1805                1810                1815

Ile Thr Ile Lys Tyr Gly Asn Gly Val Val Ser Asp Phe Phe Tyr
    1820                1825                1830

Asp Asp Glu Ser Arg Asn Leu Ile Ser Gln Arg Thr Thr Arg Pro
    1835                1840                1845

Cys Arg Gly Arg Arg Glu Leu Leu Gln Asp Arg Thr His Val Tyr
    1850                1855                1860

Asp Tyr Val Gly Arg Arg Ile Phe Thr Ser Asp Gly Ser Glu Gln
    1865                1870                1875

Val Lys Tyr Phe Gly Glu Ser Arg Val Lys Pro Glu Trp Asp Tyr
    1880                1885                1890

Thr Tyr Asn Ala Thr Gly Ala Leu Val Ile Ala Thr Gly Arg Ala
    1895                1900                1905

Gln Leu Ser Gly Lys Ile Gly Asn Gly Asn Gln Leu Thr Pro His
    1910                1915                1920

Asn Ala Met Asn Gly Leu Asn Pro Ser Arg Gly Gly Gly Asp Gly
    1925                1930                1935
```

-continued

```
Asn Leu  Leu Tyr Gln Tyr Arg  Glu Thr Tyr Asp Tyr  Asp Arg Glu
    1940                 1945                 1950

Gly Asn  Ile Leu Met Met Lys  His Glu Ala Pro Asp  Ile Lys Gly
    1955                 1960                 1965

Val Thr  Ser Trp Thr Arg Asn  Tyr His Tyr Asp Glu  Lys Ser Leu
    1970                 1975                 1980

Leu Ser  Asp Asp Pro Arg Val  Lys Ser Asn Arg Leu  Ser Arg Thr
    1985                 1990                 1995

Ser Ile  Gly Asp Thr Asn Glu  Gly Lys Tyr Met Tyr  Glu Gly Ser
    2000                 2005                 2010

Ala Gly  Leu Ser Gly Cys Ile  Thr Thr Leu Pro Lys  Phe Ser Glu
    2015                 2020                 2025

Leu Asp  Trp Asn Met Asn Asn  Met Leu Ser Phe Ser  Ser Thr Gln
    2030                 2035                 2040

Tyr Val  Asn Ala Gly Thr Pro  Glu Arg Thr Tyr Tyr  Val Tyr Asp
    2045                 2050                 2055

His Ala  Gly Asn Arg Val Arg  Lys Val Thr Glu Thr  Ala Ala Lys
    2060                 2065                 2070

Ser Gly  Glu Glu Pro Arg Lys  Gln Arg Asp Thr Leu  Phe Phe Gly
    2075                 2080                 2085

Gly Val  Glu Leu Gln Thr Lys  Ser Asn Gly Ser Leu  Leu Trp Thr
    2090                 2095                 2100

Thr Arg  Val Lys Gly Asp Gly  Ile Val Ala Val Val  Glu Val Asn
    2105                 2110                 2115

Arg Asn  Gln Glu Thr Pro Leu  Val Arg Phe Gln Ala  Gly Arg Asp
    2120                 2125                 2130

Met Glu  Phe Asp Asp Gln Ala  Gln Leu Ile Ser Tyr  Glu Glu Tyr
    2135                 2140                 2145

Ser Pro  Phe Gly Ala Val Val  Tyr Ala Ala Met Tyr  Gly Asn Ile
    2150                 2155                 2160

Glu Ala  Pro Arg Ala Tyr Arg  Phe Ala Arg Tyr Glu  His Asp Ser
    2165                 2170                 2175

Glu Thr  Gly Leu Tyr His Cys  Gly Gln Arg Tyr Tyr  Cys Pro Trp
    2180                 2185                 2190

Leu Gly  Arg Trp Thr Ser Pro  Asp Pro Leu Gly Asp  Val Asp Gly
    2195                 2200                 2205

Pro Asn  Leu Phe Val Tyr Val  Asn Asn Asp Pro Val  Asn Ser His
    2210                 2215                 2220

Asp Pro  Ser Gly Thr Ser Gly  Lys Lys Thr Lys Glu  Gly Thr Arg
    2225                 2230                 2235

Glu Met  Tyr Ala Ala Pro Asp  Asp Gln Gly Lys Arg  Arg Leu Val
    2240                 2245                 2250

Asp Glu  Asn Lys Ala Val Ala  Asp Arg Ile Ala Lys  Tyr Glu Arg
    2255                 2260                 2265

Lys Leu  Gln Arg Gln Glu Arg  Lys Gln Gln Arg Ala  Ile Ala Arg
    2270                 2275                 2280

Met Ser  Gly Thr Asp Pro Ile  Leu Gly Ser Arg Ala  Arg Tyr Ala
    2285                 2290                 2295

Val Gly  Ile Ala Ala Met Gly  Asn Ala Leu Gly Arg  Ile Ser Gly
    2300                 2305                 2310

Ser Thr  Glu Leu His His Thr  Tyr Pro Gln Glu Tyr  Arg Glu Glu
    2315                 2320                 2325

Phe Ser  Asp Ile Asp Ile Asn  Val Asp Arg Thr Ser  Val Ser Ile
```

-continued

```
    2330                2335                2340

Ser Lys  Glu Ala His Tyr Ile  Cys Thr Tyr Gly Ser  Ile Leu Asp
    2345                2350                2355

Asn Leu  Val Ala Thr Asn Lys  Arg Trp Lys Ser Glu  Tyr Phe Asp
    2360                2365                2370

Thr Pro  Asp Thr Gly Tyr Tyr  Glu Gln Met Glu Gln  His Glu Trp
    2375                2380                2385

Tyr Asp  Asp Asp Pro Gly Met  Gln Tyr Ala Ile Arg  Leu His Leu
    2390                2395                2400

Ala Tyr  Glu Ala Arg Thr Leu  Asn Gly Lys Ile Met  Ala Asp Phe
    2405                2410                2415

Gly Ile  Asn Pro Lys Gly Glu  Asp Gly Arg Ser Met  Phe Val Asn
    2420                2425                2430

Tyr Asp  Ala Val Thr Lys Met  Arg Thr Ala Gly Gln  Arg Arg Gly
    2435                2440                2445

Val Arg  Asn Asp Asn Leu Ile  His His Glu Thr Trp  Pro Gly Arg
    2450                2455                2460

Pro Phe  Asn Thr Gly Asn Ser  Asp Thr Asp Asn Ala  Gly Gly Pro
    2465                2470                2475

Val His  Phe Gln Val Ala Glu  Glu Gln Tyr Asn Gly  Leu Asp Ala
    2480                2485                2490

Asp Ala  Gln Ala Lys Phe Asp  Asp Leu Arg Asn Gln  Met Glu Ala
    2495                2500                2505

Leu Leu  Gly Lys Arg
    2510
```

<210> SEQ ID NO 21
<211> LENGTH: 7458
<212> TYPE: DNA
<213> ORGANISM: Artificial Sequence
<220> FEATURE:
<223> OTHER INFORMATION: fusion 8883 (tcp1GzB/tccC3)

<400> SEQUENCE: 21

```
atgtctaccc tgtcctctcg cccgggcgac ccgcgtgcgc tccattccgg ccagaataac     60

ggtgcgccag aaactctgac caacagcaaa tctaacgcga ccctgtctgg taaccgtacc    120

actgcgccgg catctgctag ctccttcgca ccgcaggttc gtaccctggg tgaaggtatc    180

ccaggcttcc gtacttcttt caacgtagct ggtaaaggtg gcggtgcgtt tcgctctatt    240

tctgaagact tcgaagtttc cccggctaac ggcactatgt ctctggcgat cccggtacgc    300

accagcccga cccgtggtgg ctatggtccg gacctgaaac tgagctacga tagcggttct    360

ggtaacggcc cgttcggctt tggttggtcc atgtctatgc cgtctatcca ccgtaaaacc    420

actcatgcta ttccgcgtta cgttgatgac gaagacgatt tcctgatgtc tggtggcgac    480

attatcaaac gtctgaactc cgaaggtatt caggaaaccc gcaacgagag cggcatctgc    540

ggtaaattcc tggtaaccac ttatcgcccg cgtgttgact ccggtaacat ccgcatcgaa    600

cgctgggtac gtcgcgaaga tctggaagat gtgcattggc gtactatcag ctcctctaac    660

gaaactaaaa tctacggcga ctccgattct tcccgcatct tcgatgcttc cggtccgtct    720

aaacgtatct tttcctggct gctcagccgc tcttacgacg catccggcaa cgcgattgaa    780

tacgtgtata aagaggaaga ctccctgggc atcagcgacg caaccggcgc gatgccagta    840

tgggaaaaga accgtgaaca ggacgctcgc taccgcgaac gttacatcaa gcgtgtaaaa    900

tatggcaacc gcaaaccgaa ccgtgatctg actacctggg aggtgtctga ctggccggaa    960
```

-continued

```
gagtggatgt tcgaagtggt attcgattac ggcgaacatg ataaaggttc tccgtccact   1020
gaggaatccc actcttggcc ggttcgtcag gacgttttct ctcagtcccg tccaggtttc   1080
gaaatccgta cttaccgtct gtgtcgtcgc gttctgatgt tccaccattt cccggaacac   1140
actcaggaga gcgaaacctt tgttttctct accgacctgc aatataacga aagccgccag   1200
cgtaccgttc tggcaagcct ggtggcgact ggttattcta gctacaaaga taacaacgat   1260
ggtaagcagc gttaccgctc tgaaagcctg ccaccgtggt cttttgaata tacctctagc   1320
ccggaagcat ctgagatcga actgatggaa gctaaaacct tcaacctgct cgaactgccg   1380
acctccgacg cacgtgtgtc tgagtggctg gacctggatg gtgacggcat gccgggcctt   1440
ctgacccgtt ctgtggatgg cgcactgtac tatcagcgca acctgggttc tatctccggt   1500
gacgatgacc cgcagttctg cggtccggtt cttctggctc agcaaccgtc catgaccggc   1560
ggtactttcc aggatctgga tcgtaacggc aacctgaact acgtgctgcg taacgaacac   1620
ggtcacctgg aaggttacta tgagcgtggt aactctgaca cctggaagaa ctatatcgaa   1680
ttcccggaaa cctctaacgg tgatatctgg cagtctacta tcgatattga cctgaccggc   1740
gatggtcatc cggacctgat ctgcgcggca gacgatagcc aggtgctgat ttggcagcaa   1800
aacctgggta agaaaggcct gtctagctac cagcgtgtaa tttgcggcca tgattgggag   1860
tcctgcccac gcctgatcaa gaaccaggac gttcagacct acgttggcga catgaccggc   1920
agcggcatgt ctgacctggt agaaatcagc gtaagctccg tgcgctattg gccgaacctg   1980
ggttacggta ctttcggcgc ggcagtagac atgggtaacc cgccagcttt cgcagcgaaa   2040
gattacttcg accacagccg tgtgcgcctg atggacaccg acggtagcgg cactatggat   2100
ctgctctacg cactgccgac cggcggtgca gctctgtact ataacctggc tggcaacagc   2160
tggtctaaca tggtgttcct gccacacctg ccggcgatta tcacccgat gagcatcttc    2220
accctggacc tgattggcaa aggtgctgat tgcctgtgtt gggctgacac ttccaccgat   2280
ggtaaccgta tcatgtatct ggacatcacc ggcgaaacca aaccgcactt gctgaaatct   2340
tatagcaacg gctggggtgc tactacctct gtggattacg cgccgtccac caaattcttt   2400
gcagaagata cccgtaacgg ccacccgtgg tctagcaaac tgccgtttcc ggtgcagtgc   2460
gtatctaaag ttcaggtgga agacgctatc accggcaacc gtcagagcac cgaatacatc   2520
tatcataacg gttgttacaa cccgactgaa aagcagttct ctggtttcga aatggtggaa   2580
cagttccagt ccgagcgtgt tatcgtaggc gaagatgaaa cctacgaacc gccagttacc   2640
cacaccaaaa gctggttcaa cgttggtctg agcctggtag tggacgaaag ccgtttcctg   2700
actaaaccgg cgatcctgtc ctctctgcaa gattaccaca ctgacccggc ggaactggtg   2760
aacgcactga aggtctgaa cgtgcgttcc gaaatttact ctcaagatgg ctccccgaaa    2820
tctcacctgc cgtatgtaat caaggaagtt tcttatcacg ttaagatttc ccaggcgcgt   2880
gacaccaaca aatattccgc agttcaggtt ctgccacgtg aaacttttag ccgtgcgtac   2940
gaacgtgaca tgtccgaccc gcgtgtgact cacgatatgg ttattaagac caacgacttt   3000
ggtgacgttg aagagtctct gtctattgta tatccgcgtg caggcaaaac cactttcgaa   3060
gatgttaaca agaaccagaa agcgggcaac atgtcctaca ctcagaactg gtacaccaaa   3120
atggtgagcg aaccggaaca ggagcacttt cgcaaaccgg cagcgtatcg ccaacaggaa   3180
cacgagatcc tgtcctttcc gttcaacggc actctgaagt ttgatgacgc actggcgttt   3240
aacttcaacg gtctgccgac taccaaatgt tctaaaactt ggaaagctct gcgcagcgaa   3300
```

-continued aacaaggcgt tctacaaaga tagccttctg caacgccgtc tggatgaagg tgagctgcaa 3360
accttctccc tcctggacca gacttacgca ctggcgttta ccccggacat cctggctaaa 3420
gtggaaattg gcctgcgtaa ctgtaacgta ccgggttctg tggaggaact gttgactaaa 3480
ggtagctacg taaagctgaa agacagcgac ggctggtggg caccgtcttc ccagtctttc 3540
ttttgtagct ctaagaccgc tagcgcagct gaggaactga aagaagcgcg caaatccttt 3600
tataccccat cccgtttcgt ggacctgttc ggcaactcca gccgcctgaa catggataaa 3660
gactttctcc tggctactga agttgaggac gcaatcggca ccgcaacctc tttcaaaaac 3720
tcctatgaac acctgcaacc agtggagatt atcgacgcga actctaacag cgttcaggta 3780
gttctggacc cactgggcga atccattgcg gtggcggctt ccactcgtcg cgacggtgtt 3840
atcgaggaaa ttgactccct ggaaaacatg gtgctggatg cgtctccgga agacgttgat 3900
gacatcctgc gtgatccgac cggcgaagtg agcacccgcc ttctgggtaa cgcggcttct 3960
cgtaccattc attaccgtga tcgctacgct cagtggaagt ctcgccagaa cgaaacctct 4020
accagcgttg atccggaacc ggctctgtct ctggttctgt cccgtgacct gtccttcaag 4080
gaatcctcta gcccggagat ccgtgttatt gtgagctaca tgaacggcct gggtagccag 4140
tatcaagagc agcatctgtc cgatccgacc actctggaga aacgttggct ggttccgggc 4200
ctggcaatcc cagatacaca gggccaggtg gtatgcacct accagccgcg tttcgctacc 4260
ctggctgcgc cgattccatc ctctctgatg aaaactaacg cggcattcac cttctacgat 4320
gcgatgggcc gtaacgtggc aagcttggct gcggattgta cctggtccaa aaccgtttat 4380
actccgtgga ccactgttga acacggtgct ggtagcatgg ttctgcaatc caacgctcgt 4440
gatgacccgg atgttggtca cttcttttcc cgcatcgcgt cttcccgcta ctcccagagc 4500
tggtacgata agcgtaaact gggtactgct caggaaggat ccgacaacaa gggtcagact 4560
atccgcacta ggcctatgaa aaacatcgat cccaaacttt atcaaaaaac ccctactgtc 4620
agcgtttacg ataaccgtgg tctgataatc cgtaacatcg attttcatcg tactaccgca 4680
aatggtgatc ccgatacccg tattacccgc catcaatacg atattcacgg acacctaaat 4740
caaagcatcg atccgcgcct atatgaagcc aagcaaacca acaatacgat caaacccaat 4800
tttctttggc agtatgattt gaccggtaat cccctatgta cagagagcat tgatgcaggt 4860
cgcactgtca ccttgaatga tattgaaggc cgtccgctac taacggtgac tgcaacaggg 4920
gttatacaaa ctcgacaata tgaaacttct tccctgcccg gtcgtctgtt atctgttgcc 4980
gaacaaacac ccgaggaaaa aacatcccgt atcaccgaac gcctgatttg ggctggcaat 5040
accgaagcag agaaagacca taaccttgcc ggccagtgcg tgcgtcacta tgacacggcg 5100
ggagttaccc ggttagagag tttatcactg accggtactg ttttatctca atccagccaa 5160
ctattgatcg acactcaaga ggcaaactgg acaggtgata acgaaaccgt ctggcaaaac 5220
atgctggctg atgacatcta cacaaccctg agcaccttcg atgccaccgg tgctttactg 5280
actcagaccg atgcgaaagg gaacattcag agactggctt atgatgtggc cgggcagcta 5340
aacgggagct ggctaacact caaaggccag acggaacaag tgattatcaa atccctgacc 5400
tactccgccg ccggacaaaa attacgtgag gaacacggca atgatgttat caccgaatac 5460
agttatgaac cggaaaccca acggctgatc ggtatcaaaa cccgccgtcc gtcagacact 5520
aaagtgctac aagacctgcg ctatgaatat gacccggtag gcaatgtcat cagcatccgt 5580
aatgacgcgg aagccacccg cttttggcac aatcagaaag tgatgccgga aaacacttat 5640
acctacgatt ccctgtatca gcttatcagc gccaccgggc gcgaaatggc gaatataggt 5700

-continued

```
caacaaagtc accaatttcc ctcacccgct ctaccttctg ataacaacac ctataccaac   5760

tatacccgta cttatactta tgaccgtggc ggcaatctga ccaaaatcca gcacagttca   5820

ccggcgacgc aaaacaacta caccaccaat atcacggttt caaatcgcag caaccgcgca   5880

gtactcagca cattgaccga agatccggcg caagtagatg ctttgtttga tgcaggcgga   5940

catcagaaca ccttgatatc aggacaaaac ctgaactgga atactcgtgg tgaactgcaa   6000

caagtaacac tggttaaacg ggacaagggc gccaatgatg atcgggaatg gtatcgttat   6060

agcggtgacg gaagaaggat gttaaaaatc aatgaacagc aggccagcaa caacgctcaa   6120

acacaacgtg tgacttattt gccgaactta gaacttcgtc taacacaaaa cagcacggcc   6180

acaaccgaag atttgcaagt tatcaccgta ggcgaagcgg gccgggcaca ggtacgagta   6240

ttacattggg agagcggtaa accggaagat atcgacaata atcagttgcg ttatagttac   6300

gataatctta tcggttccag tcaacttgaa ttagatagcg aaggacaaat tatcagtgaa   6360

gaagaatatt atccctatgg tggaacagca ttatgggccg ccaggaatca gacagaagcc   6420

agttataaaa ctatccgtta ttcaggcaaa gagcgggatg ccaccgggct atattactac   6480

ggctatcggt attaccaacc gtggatagga cggtggttaa gctccgatcc ggcaggaaca   6540

atcgatgggc tgaatttata tcggatggtg aggaataatc cagttaccct ccttgatcct   6600

gatggattaa tgccaacaat tgcagaacgc atagcagcac taaaaaaaaa taaagtaaca   6660

gactcagcgc cttcgccagc aaatgccaca aacgtagcga taaacatccg cccgcctgta   6720

gcaccaaaac ctagcttacc gaaagcatca acgagtagcc aaccaaccac acaccctatc   6780

ggagctgcaa acataaaacc aacgacgtct gggtcatcta ttgttgctcc attgagtcca   6840

gtaggaaata aatctacttc tgaaatctct ctgccagaaa gcgctcaaag cagttcttca   6900

agcactacct cgacaaatct acagaaaaaa tcatttactt tatatagagc agataacaga   6960

tcctttgaag aaatgcaaag taaattccct gaaggattta aagcctggac tcctctagac   7020

actaagatgg caaggcaatt tgctagtatc tttattggtc agaaagatac atctaattta   7080

cctaaagaaa cagtcaagaa cataagcaca tggggagcaa agccaaaact aaaagatctc   7140

tcaaattaca taaaatatac caaggacaaa tctacagtat gggtttctac tgcaattaat   7200

actgaagcag gtggacaaag ctcaggggct ccactccata aaattgatat ggatctctac   7260

gagtttgcca ttgatggaca aaaactaaat ccactaccgg agggtagaac taaaaacatg   7320

gtaccttccc ttttactcga caccccacaa atagagacat catccatcat tgcacttaat   7380

catggaccgg taaatgatgc agaaatttca tttctgacaa caattccgct taaaaatgta   7440

aaacctcata agagataa                                                 7458
```

<210> SEQ ID NO 22
<211> LENGTH: 2485
<212> TYPE: PRT
<213> ORGANISM: Artificial Sequence
<220> FEATURE:
<223> OTHER INFORMATION: 8883 fusion protein Tcp1GzB/TccC3

<400> SEQUENCE: 22

```
Met Ser Thr Leu Ser Ser Arg Pro Gly Asp Pro Arg Ala Leu His Ser
1               5                   10                  15

Gly Gln Asn Asn Gly Ala Pro Glu Thr Leu Thr Asn Ser Lys Ser Asn
            20                  25                  30

Ala Thr Leu Ser Gly Asn Arg Thr Thr Ala Pro Ala Ser Ala Ser Ser
        35                  40                  45
```

-continued

```
Phe Ala Pro Gln Val Arg Thr Leu Gly Glu Gly Ile Pro Gly Phe Arg
    50                  55                  60

Thr Ser Phe Asn Val Ala Gly Lys Gly Gly Gly Ala Phe Arg Ser Ile
65                  70                  75                  80

Ser Glu Asp Phe Glu Val Ser Pro Ala Asn Gly Thr Met Ser Leu Ala
                85                  90                  95

Ile Pro Val Arg Thr Ser Pro Thr Arg Gly Gly Tyr Gly Pro Asp Leu
            100                 105                 110

Lys Leu Ser Tyr Asp Ser Gly Ser Gly Asn Gly Pro Phe Gly Phe Gly
        115                 120                 125

Trp Ser Met Ser Met Pro Ser Ile His Arg Lys Thr Thr His Ala Ile
    130                 135                 140

Pro Arg Tyr Val Asp Asp Glu Asp Asp Phe Leu Met Ser Gly Gly Asp
145                 150                 155                 160

Ile Ile Lys Arg Leu Asn Ser Glu Gly Ile Gln Glu Thr Arg Asn Glu
                165                 170                 175

Ser Gly Ile Cys Gly Lys Phe Leu Val Thr Thr Tyr Arg Pro Arg Val
            180                 185                 190

Asp Ser Gly Asn Ile Arg Ile Glu Arg Trp Val Arg Arg Glu Asp Leu
        195                 200                 205

Glu Asp Val His Trp Arg Thr Ile Ser Ser Ser Asn Glu Thr Lys Ile
    210                 215                 220

Tyr Gly Asp Ser Asp Ser Ser Arg Ile Phe Asp Ala Ser Gly Pro Ser
225                 230                 235                 240

Lys Arg Ile Phe Ser Trp Leu Leu Ser Arg Ser Tyr Asp Ala Ser Gly
                245                 250                 255

Asn Ala Ile Glu Tyr Val Tyr Lys Glu Glu Asp Ser Leu Gly Ile Ser
            260                 265                 270

Asp Ala Thr Gly Ala Met Pro Val Trp Glu Lys Asn Arg Glu Gln Asp
        275                 280                 285

Ala Arg Tyr Arg Glu Arg Tyr Ile Lys Arg Val Lys Tyr Gly Asn Arg
    290                 295                 300

Lys Pro Asn Arg Asp Leu Thr Thr Trp Glu Val Ser Asp Trp Pro Glu
305                 310                 315                 320

Glu Trp Met Phe Glu Val Val Phe Asp Tyr Gly Glu His Asp Lys Gly
                325                 330                 335

Ser Pro Ser Thr Glu Glu Ser His Ser Trp Pro Val Arg Gln Asp Val
            340                 345                 350

Phe Ser Gln Ser Arg Pro Gly Phe Glu Ile Arg Thr Tyr Arg Leu Cys
        355                 360                 365

Arg Arg Val Leu Met Phe His His Phe Pro Glu His Thr Gln Glu Ser
    370                 375                 380

Glu Thr Phe Val Phe Ser Thr Asp Leu Gln Tyr Asn Glu Ser Arg Gln
385                 390                 395                 400

Arg Thr Val Leu Ala Ser Leu Val Ala Thr Gly Tyr Ser Ser Tyr Lys
                405                 410                 415

Asp Asn Asn Asp Gly Lys Gln Arg Tyr Arg Ser Glu Ser Leu Pro Pro
            420                 425                 430

Trp Ser Phe Glu Tyr Thr Ser Ser Pro Glu Ala Ser Glu Ile Glu Leu
        435                 440                 445

Met Glu Ala Lys Thr Phe Asn Leu Leu Glu Leu Pro Thr Ser Asp Ala
    450                 455                 460
```

-continued

```
Arg Val Ser Glu Trp Leu Asp Leu Asp Gly Asp Gly Met Pro Gly Leu
465                 470                 475                 480

Leu Thr Arg Ser Val Asp Gly Ala Leu Tyr Tyr Gln Arg Asn Leu Gly
                485                 490                 495

Ser Ile Ser Gly Asp Asp Asp Pro Gln Phe Cys Gly Pro Val Leu Leu
            500                 505                 510

Ala Gln Gln Pro Ser Met Thr Gly Gly Thr Phe Gln Asp Leu Asp Arg
        515                 520                 525

Asn Gly Asn Leu Asn Tyr Val Leu Arg Asn Glu His Gly His Leu Glu
    530                 535                 540

Gly Tyr Tyr Glu Arg Gly Asn Ser Asp Thr Trp Lys Asn Tyr Ile Glu
545                 550                 555                 560

Phe Pro Glu Thr Ser Asn Gly Asp Ile Trp Gln Ser Thr Ile Asp Ile
                565                 570                 575

Asp Leu Thr Gly Asp Gly His Pro Asp Leu Ile Cys Ala Ala Asp Asp
            580                 585                 590

Ser Gln Val Leu Ile Trp Gln Gln Asn Leu Gly Lys Lys Gly Leu Ser
        595                 600                 605

Ser Tyr Gln Arg Val Ile Cys Gly His Asp Trp Glu Ser Cys Pro Arg
    610                 615                 620

Leu Ile Lys Asn Gln Asp Val Gln Thr Tyr Val Gly Asp Met Thr Gly
625                 630                 635                 640

Ser Gly Met Ser Asp Leu Val Glu Ile Ser Val Ser Ser Val Arg Tyr
                645                 650                 655

Trp Pro Asn Leu Gly Tyr Gly Thr Phe Gly Ala Ala Val Asp Met Gly
            660                 665                 670

Asn Pro Pro Ala Phe Ala Ala Lys Asp Tyr Phe Asp His Ser Arg Val
        675                 680                 685

Arg Leu Met Asp Thr Asp Gly Ser Gly Thr Met Asp Leu Leu Tyr Ala
    690                 695                 700

Leu Pro Thr Gly Gly Ala Ala Leu Tyr Tyr Asn Leu Ala Gly Asn Ser
705                 710                 715                 720

Trp Ser Asn Met Val Phe Leu Pro His Leu Pro Ala Ile Ile Thr Pro
                725                 730                 735

Met Ser Ile Phe Thr Leu Asp Leu Ile Gly Lys Gly Ala Asp Cys Leu
            740                 745                 750

Cys Trp Ala Asp Thr Ser Thr Asp Gly Asn Arg Ile Met Tyr Leu Asp
        755                 760                 765

Ile Thr Gly Glu Thr Lys Pro His Leu Leu Lys Ser Tyr Ser Asn Gly
    770                 775                 780

Trp Gly Ala Thr Thr Ser Val Asp Tyr Ala Pro Ser Thr Lys Phe Phe
785                 790                 795                 800

Ala Glu Asp Thr Arg Asn Gly His Pro Trp Ser Ser Lys Leu Pro Phe
                805                 810                 815

Pro Val Gln Cys Val Ser Lys Val Gln Val Glu Asp Ala Ile Thr Gly
            820                 825                 830

Asn Arg Gln Ser Thr Glu Tyr Ile Tyr His Asn Gly Cys Tyr Asn Pro
        835                 840                 845

Thr Glu Lys Gln Phe Ser Gly Phe Glu Met Val Glu Gln Phe Gln Ser
    850                 855                 860

Glu Arg Val Ile Val Gly Glu Asp Glu Thr Tyr Glu Pro Pro Val Thr
865                 870                 875                 880

His Thr Lys Ser Trp Phe Asn Val Gly Leu Ser Leu Val Val Asp Glu
```

-continued

```
                885                 890                 895

Ser Arg Phe Leu Thr Lys Pro Ala Ile Leu Ser Ser Leu Gln Asp Tyr
            900                 905                 910

His Thr Asp Pro Ala Glu Leu Val Asn Ala Leu Lys Gly Leu Asn Val
        915                 920                 925

Arg Ser Glu Ile Tyr Ser Gln Asp Gly Ser Pro Lys Ser His Leu Pro
    930                 935                 940

Tyr Val Ile Lys Glu Val Ser Tyr His Val Lys Ile Ser Gln Ala Arg
945                 950                 955                 960

Asp Thr Asn Lys Tyr Ser Ala Val Gln Val Leu Pro Arg Glu Thr Phe
                965                 970                 975

Ser Arg Ala Tyr Glu Arg Asp Met Ser Asp Pro Arg Val Thr His Asp
            980                 985                 990

Met Val Ile Lys Thr Asn Asp Phe  Gly Asp Val Glu Glu  Ser Leu Ser
        995                 1000                1005

Ile Val  Tyr Pro Arg Ala Gly  Lys Thr Thr Phe Glu  Asp Val Asn
    1010                1015                1020

Lys Asn  Gln Lys Ala Gly Asn  Met Ser Tyr Thr Gln  Asn Trp Tyr
    1025                1030                1035

Thr Lys  Met Val Ser Glu Pro  Glu Gln Glu His Phe  Arg Lys Pro
    1040                1045                1050

Ala Ala  Tyr Arg Gln Gln Glu  His Glu Ile Leu Ser  Phe Pro Phe
    1055                1060                1065

Asn Gly  Thr Leu Lys Phe Asp  Asp Ala Leu Ala Phe  Asn Phe Asn
    1070                1075                1080

Gly Leu  Pro Thr Thr Lys Cys  Ser Lys Thr Trp Lys  Ala Leu Arg
    1085                1090                1095

Ser Glu  Asn Lys Ala Phe Tyr  Lys Asp Ser Leu Leu  Gln Arg Arg
    1100                1105                1110

Leu Asp  Glu Gly Glu Leu Gln  Thr Phe Ser Leu Leu  Asp Gln Thr
    1115                1120                1125

Tyr Ala  Leu Ala Phe Thr Pro  Asp Ile Leu Ala Lys  Val Glu Ile
    1130                1135                1140

Gly Leu  Arg Asn Cys Asn Val  Pro Gly Ser Val Glu  Glu Leu Leu
    1145                1150                1155

Thr Lys  Gly Ser Tyr Val Lys  Leu Lys Asp Ser Asp  Gly Trp Trp
    1160                1165                1170

Ala Pro  Ser Ser Gln Ser Phe  Phe Cys Ser Ser Lys  Thr Ala Ser
    1175                1180                1185

Ala Ala  Glu Glu Leu Lys Glu  Ala Arg Lys Ser Phe  Tyr Thr Pro
    1190                1195                1200

Ser Arg  Phe Val Asp Leu Phe  Gly Asn Ser Ser Arg  Leu Asn Met
    1205                1210                1215

Asp Lys  Asp Phe Leu Leu Ala  Thr Glu Val Glu Asp  Ala Ile Gly
    1220                1225                1230

Thr Ala  Thr Ser Phe Lys Asn  Ser Tyr Glu His Leu  Gln Pro Val
    1235                1240                1245

Glu Ile  Ile Asp Ala Asn Ser  Asn Ser Val Gln Val  Val Leu Asp
    1250                1255                1260

Pro Leu  Gly Glu Ser Ile Ala  Val Ala Ala Ser Thr  Arg Arg Asp
    1265                1270                1275

Gly Val  Ile Glu Glu Ile Asp  Ser Leu Glu Asn Met  Val Leu Asp
    1280                1285                1290
```

-continued

```
Ala Ser  Pro Glu Asp Val Asp  Asp Ile Leu Arg Asp  Pro Thr Gly
    1295                 1300                 1305

Glu Val  Ser Thr Arg Leu Leu  Gly Asn Ala Ala Ser  Arg Thr Ile
    1310                 1315                 1320

His Tyr  Arg Asp Arg Tyr Ala  Gln Trp Lys Ser Arg  Gln Asn Glu
    1325                 1330                 1335

Thr Ser  Thr Ser Val Asp Pro  Glu Pro Ala Leu Ser  Leu Val Leu
    1340                 1345                 1350

Ser Arg  Asp Leu Ser Phe Lys  Glu Ser Ser Ser Pro  Glu Ile Arg
    1355                 1360                 1365

Val Ile  Val Ser Tyr Met Asn  Gly Leu Gly Ser Gln  Tyr Gln Glu
    1370                 1375                 1380

Gln His  Leu Ser Asp Pro Thr  Thr Leu Glu Lys Arg  Trp Leu Val
    1385                 1390                 1395

Pro Gly  Leu Ala Ile Pro Asp  Thr Gln Gly Gln Val  Val Cys Thr
    1400                 1405                 1410

Tyr Gln  Pro Arg Phe Ala Thr  Leu Ala Ala Pro Ile  Pro Ser Ser
    1415                 1420                 1425

Leu Met  Lys Thr Asn Ala Ala  Phe Thr Phe Tyr Asp  Ala Met Gly
    1430                 1435                 1440

Arg Asn  Val Ala Ser Leu Ala  Ala Asp Cys Thr Trp  Ser Lys Thr
    1445                 1450                 1455

Val Tyr  Thr Pro Trp Thr Thr  Val Glu His Gly Ala  Gly Ser Met
    1460                 1465                 1470

Val Leu  Gln Ser Asn Ala Arg  Asp Asp Pro Asp Val  Gly His Phe
    1475                 1480                 1485

Phe Ser  Arg Ile Ala Ser Ser  Arg Tyr Ser Gln Ser  Trp Tyr Asp
    1490                 1495                 1500

Lys Arg  Lys Leu Gly Thr Ala  Gln Glu Gly Ser Asp  Asn Lys Gly
    1505                 1510                 1515

Gln Thr  Ile Arg Thr Arg Pro  Met Lys Asn Ile Asp  Pro Lys Leu
    1520                 1525                 1530

Tyr Gln  Lys Thr Pro Thr Val  Ser Val Tyr Asp Asn  Arg Gly Leu
    1535                 1540                 1545

Ile Ile  Arg Asn Ile Asp Phe  His Arg Thr Thr Ala  Asn Gly Asp
    1550                 1555                 1560

Pro Asp  Thr Arg Ile Thr Arg  His Gln Tyr Asp Ile  His Gly His
    1565                 1570                 1575

Leu Asn  Gln Ser Ile Asp Pro  Arg Leu Tyr Glu Ala  Lys Gln Thr
    1580                 1585                 1590

Asn Asn  Thr Ile Lys Pro Asn  Phe Leu Trp Gln Tyr  Asp Leu Thr
    1595                 1600                 1605

Gly Asn  Pro Leu Cys Thr Glu  Ser Ile Asp Ala Gly  Arg Thr Val
    1610                 1615                 1620

Thr Leu  Asn Asp Ile Glu Gly  Arg Pro Leu Leu Thr  Val Thr Ala
    1625                 1630                 1635

Thr Gly  Val Ile Gln Thr Arg  Gln Tyr Glu Thr Ser  Ser Leu Pro
    1640                 1645                 1650

Gly Arg  Leu Leu Ser Val Ala  Glu Gln Thr Pro Glu  Glu Lys Thr
    1655                 1660                 1665

Ser Arg  Ile Thr Glu Arg Leu  Ile Trp Ala Gly Asn  Thr Glu Ala
    1670                 1675                 1680
```

-continued

```
Glu Lys  Asp His Asn Leu Ala  Gly Gln Cys Val Arg  His Tyr Asp
    1685                 1690                 1695

Thr Ala  Gly Val Thr Arg Leu  Glu Ser Leu Ser Leu  Thr Gly Thr
    1700                 1705                 1710

Val Leu  Ser Gln Ser Ser Gln  Leu Leu Ile Asp Thr  Gln Glu Ala
    1715                 1720                 1725

Asn Trp  Thr Gly Asp Asn Glu  Thr Val Trp Gln Asn  Met Leu Ala
    1730                 1735                 1740

Asp Asp  Ile Tyr Thr Thr Leu  Ser Thr Phe Asp Ala  Thr Gly Ala
    1745                 1750                 1755

Leu Leu  Thr Gln Thr Asp Ala  Lys Gly Asn Ile Gln  Arg Leu Ala
    1760                 1765                 1770

Tyr Asp  Val Ala Gly Gln Leu  Asn Gly Ser Trp Leu  Thr Leu Lys
    1775                 1780                 1785

Gly Gln  Thr Glu Gln Val Ile  Ile Lys Ser Leu Thr  Tyr Ser Ala
    1790                 1795                 1800

Ala Gly  Gln Lys Leu Arg Glu  Glu His Gly Asn Asp  Val Ile Thr
    1805                 1810                 1815

Glu Tyr  Ser Tyr Glu Pro Glu  Thr Gln Arg Leu Ile  Gly Ile Lys
    1820                 1825                 1830

Thr Arg  Arg Pro Ser Asp Thr  Lys Val Leu Gln Asp  Leu Arg Tyr
    1835                 1840                 1845

Glu Tyr  Asp Pro Val Gly Asn  Val Ile Ser Ile Arg  Asn Asp Ala
    1850                 1855                 1860

Glu Ala  Thr Arg Phe Trp His  Asn Gln Lys Val Met  Pro Glu Asn
    1865                 1870                 1875

Thr Tyr  Thr Tyr Asp Ser Leu  Tyr Gln Leu Ile Ser  Ala Thr Gly
    1880                 1885                 1890

Arg Glu  Met Ala Asn Ile Gly  Gln Gln Ser His Gln  Phe Pro Ser
    1895                 1900                 1905

Pro Ala  Leu Pro Ser Asp Asn  Asn Thr Tyr Thr Asn  Tyr Thr Arg
    1910                 1915                 1920

Thr Tyr  Thr Tyr Asp Arg Gly  Gly Asn Leu Thr Lys  Ile Gln His
    1925                 1930                 1935

Ser Ser  Pro Ala Thr Gln Asn  Asn Tyr Thr Thr Asn  Ile Thr Val
    1940                 1945                 1950

Ser Asn  Arg Ser Asn Arg Ala  Val Leu Ser Thr Leu  Thr Glu Asp
    1955                 1960                 1965

Pro Ala  Gln Val Asp Ala Leu  Phe Asp Ala Gly Gly  His Gln Asn
    1970                 1975                 1980

Thr Leu  Ile Ser Gly Gln Asn  Leu Asn Trp Asn Thr  Arg Gly Glu
    1985                 1990                 1995

Leu Gln  Gln Val Thr Leu Val  Lys Arg Asp Lys Gly  Ala Asn Asp
    2000                 2005                 2010

Asp Arg  Glu Trp Tyr Arg Tyr  Ser Gly Asp Gly Arg  Arg Met Leu
    2015                 2020                 2025

Lys Ile  Asn Glu Gln Gln Ala  Ser Asn Asn Ala Gln  Thr Gln Arg
    2030                 2035                 2040

Val Thr  Tyr Leu Pro Asn Leu  Glu Leu Arg Leu Thr  Gln Asn Ser
    2045                 2050                 2055

Thr Ala  Thr Thr Glu Asp Leu  Gln Val Ile Thr Val  Gly Glu Ala
    2060                 2065                 2070

Gly Arg  Ala Gln Val Arg Val  Leu His Trp Glu Ser  Gly Lys Pro
```

-continued

```
    2075                2080                2085

Glu Asp  Ile Asp Asn Asn Gln  Leu Arg Tyr Ser Tyr  Asp Asn Leu
    2090                2095                2100

Ile Gly  Ser Ser Gln Leu Glu  Leu Asp Ser Glu Gly  Gln Ile Ile
    2105                2110                2115

Ser Glu  Glu Glu Tyr Tyr Pro  Tyr Gly Gly Thr Ala  Leu Trp Ala
    2120                2125                2130

Ala Arg  Asn Gln Thr Glu Ala  Ser Tyr Lys Thr Ile  Arg Tyr Ser
    2135                2140                2145

Gly Lys  Glu Arg Asp Ala Thr  Gly Leu Tyr Tyr Tyr  Gly Tyr Arg
    2150                2155                2160

Tyr Tyr  Gln Pro Trp Ile Gly  Arg Trp Leu Ser Ser  Asp Pro Ala
    2165                2170                2175

Gly Thr  Ile Asp Gly Leu Asn  Leu Tyr Arg Met Val  Arg Asn Asn
    2180                2185                2190

Pro Val  Thr Leu Leu Asp Pro  Asp Gly Leu Met Pro  Thr Ile Ala
    2195                2200                2205

Glu Arg  Ile Ala Ala Leu Lys  Lys Asn Lys Val Thr  Asp Ser Ala
    2210                2215                2220

Pro Ser  Pro Ala Asn Ala Thr  Asn Val Ala Ile Asn  Ile Arg Pro
    2225                2230                2235

Pro Val  Ala Pro Lys Pro Ser  Leu Pro Lys Ala Ser  Thr Ser Ser
    2240                2245                2250

Gln Pro  Thr Thr His Pro Ile  Gly Ala Ala Asn Ile  Lys Pro Thr
    2255                2260                2265

Thr Ser  Gly Ser Ser Ile Val  Ala Pro Leu Ser Pro  Val Gly Asn
    2270                2275                2280

Lys Ser  Thr Ser Glu Ile Ser  Leu Pro Glu Ser Ala  Gln Ser Ser
    2285                2290                2295

Ser Ser  Ser Thr Thr Ser Thr  Asn Leu Gln Lys Lys  Ser Phe Thr
    2300                2305                2310

Leu Tyr  Arg Ala Asp Asn Arg  Ser Phe Glu Glu Met  Gln Ser Lys
    2315                2320                2325

Phe Pro  Glu Gly Phe Lys Ala  Trp Thr Pro Leu Asp  Thr Lys Met
    2330                2335                2340

Ala Arg  Gln Phe Ala Ser Ile  Phe Ile Gly Gln Lys  Asp Thr Ser
    2345                2350                2355

Asn Leu  Pro Lys Glu Thr Val  Lys Asn Ile Ser Thr  Trp Gly Ala
    2360                2365                2370

Lys Pro  Lys Leu Lys Asp Leu  Ser Asn Tyr Ile Lys  Tyr Thr Lys
    2375                2380                2385

Asp Lys  Ser Thr Val Trp Val  Ser Thr Ala Ile Asn  Thr Glu Ala
    2390                2395                2400

Gly Gly  Gln Ser Ser Gly Ala  Pro Leu His Lys Ile  Asp Met Asp
    2405                2410                2415

Leu Tyr  Glu Phe Ala Ile Asp  Gly Gln Lys Leu Asn  Pro Leu Pro
    2420                2425                2430

Glu Gly  Arg Thr Lys Asn Met  Val Pro Ser Leu Leu  Leu Asp Thr
    2435                2440                2445

Pro Gln  Ile Glu Thr Ser Ser  Ile Ile Ala Leu Asn  His Gly Pro
    2450                2455                2460

Val Asn  Asp Ala Glu Ile Ser  Phe Leu Thr Thr Ile  Pro Leu Lys
    2465                2470                2475
```

-continued

```
Asn Val  Lys Pro His Lys Arg
    2480                2485


<210> SEQ ID NO 23
<211> LENGTH: 7432
<212> TYPE: DNA
<213> ORGANISM: Artificial Sequence
<220> FEATURE:
<223> OTHER INFORMATION: Plant-optimized DNA sequence encoding variant
      of Gibberella zeae fused Class B/Class C Tcp1Gz protein

<400> SEQUENCE: 23

ccatggcttc aaccctctcc tctcgtcctg gtgacccaag ggcactccac tctggtcaga     60

acaatggtgc cccagagact ttgaccaact caaagtccaa tgcaaccctt tctggcaaca    120

gaacaactgc cccagcctct gcaagctcat ttgctcccca agtcagaaca ttgggtgaag    180

gcatccctgg gttccgcacc agcttcaatg ttgctggcaa aggtggaggt gctttccgca    240

gcatctctga ggactttgaa gtttccccag ccaatggcac catgagcttg gccatcccag    300

tgaggacctc tcccacccgt ggtggatatg gaccagacct caaactcagc tatgattctg    360

gctctggaaa tggccctttt ggctttggat ggagcatgtc catgcccagc atacacagaa    420

agacaactca tgccattccc agatatgttg acgatgagga tgacttcctc atgtctggtg    480

gagacattat caaaaggttg aactctgagg gtattcaaga gactcgcaat gagtctggaa    540

tctgtgggaa gttccttgtg acaacctaca gacctcgtgt ggactctggg aacattcgca    600

tagagcgctg ggtgagaagg gaggatcttg aagatgtcca ctggaggaca atcagctcat    660

ccaatgagac caaaatctat ggtgattctg attcctctcg catctttgac gcatctggtc    720

caagcaaacg catcttcagc tggctccttt caaggagcta tgacgcctct gggaatgcca    780

tagagtatgt ttacaaagag gaagatagcc tcgggatttc tgatgcaact ggagccatgc    840

cagtgtggga gaagaacaga gagcaagatg ctcgctaccg tgaacgttac atcaagaggg    900

tcaagtatgg aaaccgcaaa cccaaccgtg atctcaccac ttgggaggtc tcagattggc    960

ctgaagagtg gatgtttgag gtggtctttg actatggtga acatgacaag ggatcaccca   1020

gcacagaaga gagccactca tggcctgtga ggcaagatgt tttctcccag tcacgccctg   1080

ggtttgagat tcgcacttac cgcctttgcc gcagagtgtt gatgttccat cacttcccag   1140

agcacaccca agagtctgaa acttttgtct tttctactga ccttcagtac aatgagtccc   1200

gtcaaaggac tgtcttggct tcccttgtgg ccactggcta cagctcatac aaggacaaca   1260

atgatggcaa gcagagatac cgctctgaga gcctccctcc ctggtccttt gagtacacct   1320

ccagcccaga ggcatctgag attgaattga tggaagccaa gaccttcaac ttgcttgagc   1380

ttcccacctc tgatgcaagg gtctcagagt ggcttgactt ggatggtgat gggatgcctg   1440

gcttgctcac cagatcagtg gatggagccc tttactatca gaggaacctt ggctccatct   1500

ctggtgatga cgatccacag ttctgtggac cagtgctctt ggctcagcag ccctccatga   1560

ctggtgggac cttccaagac ttggaccgca atggcaacct caactatgtc ttgaggaacg   1620

aacatgggca tcttgaaggt tactatgaac gtggaaactc agacacatgg aagaactaca   1680

ttgagttccc tgagacctcc aatggtgaca tctggcagtc caccatagac attgacctca   1740

ctggtgatgg ccatcccgat ctcatttgtg ccgcagatga cagccaagtg ctcatctggc   1800

aacagaacct tgggaagaaa ggtctcagct cctaccagag ggtgatctgc ggacatgact   1860

gggaatcctg cccaaggctc atcaagaacc aggatgtgca gacctatgtg ggagacatga   1920
```

-continued

```
caggttctgg aatgtctgac cttgttgaaa tctctgtcag ctctgtgcgt tactggccca   1980
accttggtta tgggacattt ggtgcagctg ttgacatggg gaaccctcca gcttttgctg   2040
ccaaggacta ctttgatcac tcaagagtcc gcctcatgga cactgatggg tctggcacaa   2100
tggacttgct ctatgctctc cccactggtg gagctgccct ctactacaac ttggctggca   2160
acagctggtc caacatggtg ttcctcccac acttgcctgc catcatcaca ccaatgtcca   2220
tcttcacctt ggatctcatt gggaaaggag ctgactgcct ttgctgggca gacacctcaa   2280
cagatgggaa ccgcataatg tacctcgaca tcactggtga gaccaagcca catcttctca   2340
agtcctacag caatggctgg ggtgccacca catctgtgga ctatgcccct tccaccaaat   2400
tctttgctga agatacaagg aatggtcatc cctggtcctc aaaactccca ttccctgtgc   2460
agtgtgtgtc caaggtccaa gttgaggacg ccatcactgg caacagacag tccaccgagt   2520
acatctacca caatggctgc tacaacccca ctgaaaagca gttctctggc tttgaaatgg   2580
ttgagcagtt ccagtctgag agggtgattg tgggagaaga tgagacttac gagcctccag   2640
tcacacacac caaatcatgg ttcaatgttg gcctctcact tgtggttgat gagtccagat   2700
tcttgaccaa gccagccatc ttgtccagcc tccaagacta ccacactgac ccagctgagc   2760
ttgtcaatgc tctcaaagga ctcaacgtga ggtctgagat atactcccaa gatggcagcc   2820
ccaagagcca tctcccctat gtcatcaagg aggtctccta ccatgtcaag atttcccaag   2880
caagggacac aaacaaatac tccgctgttc aagttttgcc aagggagact ttctccagag   2940
cttacgaaag ggacatgtca gacccaaggg tgacccatga catggtgatc aagaccaatg   3000
actttgggga tgttgaagag agcctttcaa ttgtctaccc acgtgctggc aagactacct   3060
ttgaggatgt caacaagaac cagaaagctg ggaacatgtc atacacacag aactggtaca   3120
caaagatggt ctcagagcca gaacaagagc acttccgcaa accagcagcc tacagacagc   3180
aagagcatga gattctcagc ttccccttca atgggacctt gaagtttgat gacgcacttg   3240
ccttcaactt caatgggttg ccaacaacta aatgctccaa gacctggaag gccctcagat   3300
cagagaacaa ggccttctac aaggactccc ttctccagag aaggttggat gaaggtgagt   3360
tgcagacctt ctcactcttg gaccagactt atgcccttgc tttcacccct gacattcttg   3420
ccaaagttga gattggattg aggaactgca atgtgcctgg ctcagtggaa gagcttctca   3480
caaagggaag ctacgtcaag ctcaaggatt cagatggatg gtgggcacct tcctctcagt   3540
cattcttctg tagctccaag acagcatccg cagctgagga actcaaggag gcaaggaaga   3600
gcttctacac tccctcaagg tttgttgact tgtttggaaa cagctcacgt ctcaacatgg   3660
acaaggactt cctcttggcc actgaggtgg aagatgcaat aggcactgca acatcattca   3720
agaactccta tgaacacctt cagccagttg agatcattga tgccaacagc aacagcgttc   3780
aagttgtcct tgacccactt ggtgagagca ttgctgttgc tgcatccacc agacgtgatg   3840
gagtcataga agagattgat tcacttgaga acatggtgtt ggatgccagc ccagaagatg   3900
ttgatgacat cctcagagac cccactggag aggtctccac aaggcttttg ggcaatgctg   3960
catcccgcac aatccactac agagaccgct atgctcagtg gaaatcacgt cagaatgaga   4020
catccacctc tgtggaccca gagcctgctc tcagccttgt gttgtcacgt gacttgagct   4080
tcaaggaatc ctcatcccca gaaatccgcg tcattgtttc ctacatgaat ggccttgggt   4140
cacagtacca agaacagcac ctctcagatc caaccacatt ggaaaagcgt tggttggtgc   4200
ctggccttgc catcccagac actcaaggac aagttgtctg cacataccag cctaggtttg   4260
ccaccttggc tgcacccatt ccttccagct tgatgaaaac caatgctgcc ttcacattct   4320
```

-continued

```
atgatgcaat gggacgcaat gtggccagcc ttgcagctga ctgcacttgg agcaagacag   4380
tctacactcc ttggacaact gtcgagcatg gcgctggttc tatggttctt cagtccaatg   4440
caagggatga cccagatgtg ggacactttt tctctcgcat agcatcatca cgctactccc   4500
agtcctggta tgacaagcgc aagttgggca ctgctcaaga gaaaagagcc gcggagaagt   4560
ctgctgttta ctctgacacc cccttgacca ctcactctgg aagctgtggt ctccctgtca   4620
gaaccatcca gcaagctggt ggcaaaactt acaccagatc atccatgtat gatgtttctg   4680
gcaacagaat cagagatgtg gactcttacg aaaggactgt tgagaagatg ttgtatgaca   4740
agttgggaag gcaattgcag actaccggta tggattgtgg agagtcatgg ttgctcttgg   4800
atgcacaagg tggagagatc ctttcatgga attgcagagg ctacagcttc atcacacgct   4860
atgatcctct cagaagggag actgaaaggc tcgttgccaa ggcagctgaa atgccaaagt   4920
tgatttcaag gatcacctat ggggagactt gtggggatgc catcaacctc aacctcaatg   4980
gccaagtgtg gaaggttgag gatcaagctg gggtccacat caacacacat tacaacatcc   5040
gtggtcactg ccttggaaag acccttcagt tcaccaaaga gtacaagcag ttggtggatt   5100
ggaagttgga ccaaaccctt gagactgagg tttacccaca cacctacttc tacgacaact   5160
atggtcaagt tttgcaagaa gaggatgagc aaggcaacag aacccgtcgc aactacagca   5220
gacaaggaca cgtagtttct gtggatttct ccagcatcaa gggaagggac tggaaatcct   5280
acttgtctgg agccacattc tcagcagatg gtttgcccat caccatcaag tatggcaatg   5340
gtgtggtctc agactttttc tacgacgatg aatctaggaa cctcatttct cagagaacca   5400
caaggccttg cagaggtcgc agagaactcc ttcaagacag aacccatgtt tatgactacg   5460
ttggaaggcg catattcact tctgatggtt cagagcaagt caaatacttt ggagagagcc   5520
gtgtcaaacc tgaatgggat tacacataca acgccactgg tgctcttgtc attgccactg   5580
gtcgtgctca gctttctggc aagattggca atggcaacca gctcactcct cacaatgcca   5640
tgaatggtct caaccccagc agaggtggag gtgatggcaa ccttttgtac cagtacagag   5700
aaacttacga ttatgatcgt gagggcaaca tattgatgat gaagcacgaa gctcctgaca   5760
tcaaaggggt gacaagctgg acaaggaatt accactacga cgaaaagtcc cttctctcag   5820
atgaccctcg tgtgaaatcc aatcgtttga gcagaaccag cattggtgac accaatgagg   5880
ggaagtacat gtatgaaggt tcagctggac tttctggttg catcaccact cttccaaagt   5940
tctcagaact tgactggaac atgaacaaca tgctctcatt ctccagcact cagtatgtga   6000
atgctggcac tcccgaaaga acttactatg tctatgacca tgctggcaat cgtgtgagaa   6060
aggtgactga gactgctgcc aagtctgggg aggaaccaag gaaacagagg gacacacttt   6120
tctttggtgg agttgagctt cagaccaaat caaatggcag ccttctctgg acaactcgtg   6180
tcaaggggga tggaatagtg gctgtggttg aggtgaacag aaatcaagag acacccttgg   6240
ttcgcttcca agctggcaga gacatggagt ttgatgacca agcccagctc ataagctacg   6300
aggaatactc cccccttcgga gctgttgtgt acgctgccat gtatggcaac attgaggctc   6360
ccagagctta ccgttttgca cgttatgagc atgacagcga aactggcttg taccactgtg   6420
ggcagcgcta ctactgtcct tggcttggga ggtggacctc ccctgatcca cttggagatg   6480
ttgatgggcc aaacttgttt gtctatgtca acaatgatcc agtgaactca catgacccat   6540
ctggcacctc tggaaagaaa actaaggagg gcacccgtga gatgtatgca gcccctgatg   6600
accaagggaa gaggcgtctt gttgatgaga acaaagcagt tgctgatcgc attgccaagt   6660
```

-continued

```
atgagaggaa actccagcgc caagagagga aacagcaaag agccattgct cgcatgtctg   6720

gaacagatcc cattcttggc tctcgtgccc gttatgcagt tggaatagct gcaatgggaa   6780

atgcacttgg aagaatttct ggaagcacag aacttcatca cacctaccct caagagtacc   6840

gtgaagagtt ctctgacatt gacatcaatg ttgatcgcac atctgtcagc atttccaagg   6900

aagcccacta catctgcacc tatggctcaa tccttgacaa ccttgttgcc acaaacaaga   6960

ggtggaagtc agaatacttt gacaccccag acactggtta ctatgaacaa atggagcagc   7020

atgaatggta tgatgacgat cctggaatgc aatatgccat aaggctccac ttggcctatg   7080

aagcacgcac actcaatggc aaaatcatgg cagactttgg gattaaccca aagggagagg   7140

atggaaggtc aatgtttgtc aactatgatg cagtgacaaa gatgaggact gctggccaaa   7200

ggagaggtgt gaggaatgac aacctcatcc atcacgaaac ttggcctggg aggcctttca   7260

acactggcaa ctccgacact gacaatgctg gtggccctgt ccacttccaa gttgctgagg   7320

aacagtacaa tggccttgat gcagatgccc aagccaagtt tgatgacctt cgcaaccaga   7380

tggaagccct tttgggaaag agatgagtag ttagcttaat cacctagagc tc           7432
```

```
<210> SEQ ID NO 24
<211> LENGTH: 2467
<212> TYPE: PRT
<213> ORGANISM: Artificial Sequence
<220> FEATURE:
<223> OTHER INFORMATION: Variant of Gibberella zeae fused Class B/Class
      C Tcp1Gz protein encoded by SEQ ID NO:17

<400> SEQUENCE: 24

Met Ala Ser Thr Leu Ser Ser Arg Pro Gly Asp Pro Arg Ala Leu His
1               5                   10                  15

Ser Gly Gln Asn Asn Gly Ala Pro Glu Thr Leu Thr Asn Ser Lys Ser
            20                  25                  30

Asn Ala Thr Leu Ser Gly Asn Arg Thr Thr Ala Pro Ala Ser Ala Ser
        35                  40                  45

Ser Phe Ala Pro Gln Val Arg Thr Leu Gly Glu Gly Ile Pro Gly Phe
    50                  55                  60

Arg Thr Ser Phe Asn Val Ala Gly Lys Gly Gly Gly Ala Phe Arg Ser
65                  70                  75                  80

Ile Ser Glu Asp Phe Glu Val Ser Pro Ala Asn Gly Thr Met Ser Leu
                85                  90                  95

Ala Ile Pro Val Arg Thr Ser Pro Thr Arg Gly Gly Tyr Gly Pro Asp
            100                 105                 110

Leu Lys Leu Ser Tyr Asp Ser Gly Ser Gly Asn Gly Pro Phe Gly Phe
        115                 120                 125

Gly Trp Ser Met Ser Met Pro Ser Ile His Arg Lys Thr Thr His Ala
    130                 135                 140

Ile Pro Arg Tyr Val Asp Asp Glu Asp Asp Phe Leu Met Ser Gly Gly
145                 150                 155                 160

Asp Ile Ile Lys Arg Leu Asn Ser Glu Gly Ile Gln Glu Thr Arg Asn
                165                 170                 175

Glu Ser Gly Ile Cys Gly Lys Phe Leu Val Thr Thr Tyr Arg Pro Arg
            180                 185                 190

Val Asp Ser Gly Asn Ile Arg Ile Glu Arg Trp Val Arg Arg Glu Asp
        195                 200                 205

Leu Glu Asp Val His Trp Arg Thr Ile Ser Ser Ser Asn Glu Thr Lys
    210                 215                 220
```

-continued

```
Ile Tyr Gly Asp Ser Asp Ser Ser Arg Ile Phe Asp Ala Ser Gly Pro
225                 230                 235                 240

Ser Lys Arg Ile Phe Ser Trp Leu Leu Ser Arg Ser Tyr Asp Ala Ser
                245                 250                 255

Gly Asn Ala Ile Glu Tyr Val Tyr Lys Glu Glu Asp Ser Leu Gly Ile
            260                 265                 270

Ser Asp Ala Thr Gly Ala Met Pro Val Trp Glu Lys Asn Arg Glu Gln
        275                 280                 285

Asp Ala Arg Tyr Arg Glu Arg Tyr Ile Lys Arg Val Lys Tyr Gly Asn
    290                 295                 300

Arg Lys Pro Asn Arg Asp Leu Thr Thr Trp Glu Val Ser Asp Trp Pro
305                 310                 315                 320

Glu Glu Trp Met Phe Glu Val Val Phe Asp Tyr Gly Glu His Asp Lys
                325                 330                 335

Gly Ser Pro Ser Thr Glu Glu Ser His Ser Trp Pro Val Arg Gln Asp
            340                 345                 350

Val Phe Ser Gln Ser Arg Pro Gly Phe Glu Ile Arg Thr Tyr Arg Leu
        355                 360                 365

Cys Arg Arg Val Leu Met Phe His His Phe Pro Glu His Thr Gln Glu
    370                 375                 380

Ser Glu Thr Phe Val Phe Ser Thr Asp Leu Gln Tyr Asn Glu Ser Arg
385                 390                 395                 400

Gln Arg Thr Val Leu Ala Ser Leu Val Ala Thr Gly Tyr Ser Ser Tyr
                405                 410                 415

Lys Asp Asn Asn Asp Gly Lys Gln Arg Tyr Arg Ser Glu Ser Leu Pro
            420                 425                 430

Pro Trp Ser Phe Glu Tyr Thr Ser Ser Pro Glu Ala Ser Glu Ile Glu
        435                 440                 445

Leu Met Glu Ala Lys Thr Phe Asn Leu Leu Glu Leu Pro Thr Ser Asp
    450                 455                 460

Ala Arg Val Ser Glu Trp Leu Asp Leu Asp Gly Asp Gly Met Pro Gly
465                 470                 475                 480

Leu Leu Thr Arg Ser Val Asp Gly Ala Leu Tyr Tyr Gln Arg Asn Leu
                485                 490                 495

Gly Ser Ile Ser Gly Asp Asp Asp Pro Gln Phe Cys Gly Pro Val Leu
            500                 505                 510

Leu Ala Gln Gln Pro Ser Met Thr Gly Gly Thr Phe Gln Asp Leu Asp
        515                 520                 525

Arg Asn Gly Asn Leu Asn Tyr Val Leu Arg Asn Glu His Gly His Leu
    530                 535                 540

Glu Gly Tyr Tyr Glu Arg Gly Asn Ser Asp Thr Trp Lys Asn Tyr Ile
545                 550                 555                 560

Glu Phe Pro Glu Thr Ser Asn Gly Asp Ile Trp Gln Ser Thr Ile Asp
                565                 570                 575

Ile Asp Leu Thr Gly Asp Gly His Pro Asp Leu Ile Cys Ala Ala Asp
            580                 585                 590

Asp Ser Gln Val Leu Ile Trp Gln Gln Asn Leu Gly Lys Lys Gly Leu
        595                 600                 605

Ser Ser Tyr Gln Arg Val Ile Cys Gly His Asp Trp Glu Ser Cys Pro
    610                 615                 620

Arg Leu Ile Lys Asn Gln Asp Val Gln Thr Tyr Val Gly Asp Met Thr
625                 630                 635                 640

Gly Ser Gly Met Ser Asp Leu Val Glu Ile Ser Val Ser Ser Val Arg
```

-continued

```
                645                 650                 655

Tyr Trp Pro Asn Leu Gly Tyr Gly Thr Phe Gly Ala Ala Val Asp Met
            660                 665                 670

Gly Asn Pro Pro Ala Phe Ala Ala Lys Asp Tyr Phe Asp His Ser Arg
        675                 680                 685

Val Arg Leu Met Asp Thr Asp Gly Ser Gly Thr Met Asp Leu Leu Tyr
    690                 695                 700

Ala Leu Pro Thr Gly Gly Ala Ala Leu Tyr Tyr Asn Leu Ala Gly Asn
705                 710                 715                 720

Ser Trp Ser Asn Met Val Phe Leu Pro His Leu Pro Ala Ile Ile Thr
                725                 730                 735

Pro Met Ser Ile Phe Thr Leu Asp Leu Ile Gly Lys Gly Ala Asp Cys
            740                 745                 750

Leu Cys Trp Ala Asp Thr Ser Thr Asp Gly Asn Arg Ile Met Tyr Leu
        755                 760                 765

Asp Ile Thr Gly Glu Thr Lys Pro His Leu Leu Lys Ser Tyr Ser Asn
    770                 775                 780

Gly Trp Gly Ala Thr Thr Ser Val Asp Tyr Ala Pro Ser Thr Lys Phe
785                 790                 795                 800

Phe Ala Glu Asp Thr Arg Asn Gly His Pro Trp Ser Ser Lys Leu Pro
                805                 810                 815

Phe Pro Val Gln Cys Val Ser Lys Val Gln Val Glu Asp Ala Ile Thr
            820                 825                 830

Gly Asn Arg Gln Ser Thr Glu Tyr Ile Tyr His Asn Gly Cys Tyr Asn
        835                 840                 845

Pro Thr Glu Lys Gln Phe Ser Gly Phe Glu Met Val Glu Gln Phe Gln
    850                 855                 860

Ser Glu Arg Val Ile Val Gly Glu Asp Glu Thr Tyr Glu Pro Pro Val
865                 870                 875                 880

Thr His Thr Lys Ser Trp Phe Asn Val Gly Leu Ser Leu Val Val Asp
                885                 890                 895

Glu Ser Arg Phe Leu Thr Lys Pro Ala Ile Leu Ser Ser Leu Gln Asp
            900                 905                 910

Tyr His Thr Asp Pro Ala Glu Leu Val Asn Ala Leu Lys Gly Leu Asn
        915                 920                 925

Val Arg Ser Glu Ile Tyr Ser Gln Asp Gly Ser Pro Lys Ser His Leu
    930                 935                 940

Pro Tyr Val Ile Lys Glu Val Ser Tyr His Val Lys Ile Ser Gln Ala
945                 950                 955                 960

Arg Asp Thr Asn Lys Tyr Ser Ala Val Gln Val Leu Pro Arg Glu Thr
                965                 970                 975

Phe Ser Arg Ala Tyr Glu Arg Asp Met Ser Asp Pro Arg Val Thr His
            980                 985                 990

Asp Met Val Ile Lys Thr Asn Asp  Phe Gly Asp Val Glu  Glu Ser Leu
        995                 1000                1005

Ser Ile  Val Tyr Pro Arg Ala  Gly Lys Thr Thr Phe  Glu Asp Val
    1010                1015                1020

Asn Lys  Asn Gln Lys Ala Gly  Asn Met Ser Tyr Thr  Gln Asn Trp
    1025                1030                1035

Tyr Thr  Lys Met Val Ser Glu  Pro Glu Gln Glu His  Phe Arg Lys
    1040                1045                1050

Pro Ala  Ala Tyr Arg Gln Gln  Glu His Glu Ile Leu  Ser Phe Pro
    1055                1060                1065
```

-continued

Phe Asn Gly Thr Leu Lys Phe Asp Asp Ala Leu Ala Phe Asn Phe
1070 1075 1080

Asn Gly Leu Pro Thr Thr Lys Cys Ser Lys Thr Trp Lys Ala Leu
1085 1090 1095

Arg Ser Glu Asn Lys Ala Phe Tyr Lys Asp Ser Leu Leu Gln Arg
1100 1105 1110

Arg Leu Asp Glu Gly Glu Leu Gln Thr Phe Ser Leu Leu Asp Gln
1115 1120 1125

Thr Tyr Ala Leu Ala Phe Thr Pro Asp Ile Leu Ala Lys Val Glu
1130 1135 1140

Ile Gly Leu Arg Asn Cys Asn Val Pro Gly Ser Val Glu Glu Leu
1145 1150 1155

Leu Thr Lys Gly Ser Tyr Val Lys Leu Lys Asp Ser Asp Gly Trp
1160 1165 1170

Trp Ala Pro Ser Ser Gln Ser Phe Phe Cys Ser Ser Lys Thr Ala
1175 1180 1185

Ser Ala Ala Glu Glu Leu Lys Glu Ala Arg Lys Ser Phe Tyr Thr
1190 1195 1200

Pro Ser Arg Phe Val Asp Leu Phe Gly Asn Ser Ser Arg Leu Asn
1205 1210 1215

Met Asp Lys Asp Phe Leu Leu Ala Thr Glu Val Glu Asp Ala Ile
1220 1225 1230

Gly Thr Ala Thr Ser Phe Lys Asn Ser Tyr Glu His Leu Gln Pro
1235 1240 1245

Val Glu Ile Ile Asp Ala Asn Ser Asn Ser Val Gln Val Val Leu
1250 1255 1260

Asp Pro Leu Gly Glu Ser Ile Ala Val Ala Ala Ser Thr Arg Arg
1265 1270 1275

Asp Gly Val Ile Glu Glu Ile Asp Ser Leu Glu Asn Met Val Leu
1280 1285 1290

Asp Ala Ser Pro Glu Asp Val Asp Asp Ile Leu Arg Asp Pro Thr
1295 1300 1305

Gly Glu Val Ser Thr Arg Leu Leu Gly Asn Ala Ala Ser Arg Thr
1310 1315 1320

Ile His Tyr Arg Asp Arg Tyr Ala Gln Trp Lys Ser Arg Gln Asn
1325 1330 1335

Glu Thr Ser Thr Ser Val Asp Pro Glu Pro Ala Leu Ser Leu Val
1340 1345 1350

Leu Ser Arg Asp Leu Ser Phe Lys Glu Ser Ser Ser Pro Glu Ile
1355 1360 1365

Arg Val Ile Val Ser Tyr Met Asn Gly Leu Gly Ser Gln Tyr Gln
1370 1375 1380

Glu Gln His Leu Ser Asp Pro Thr Thr Leu Glu Lys Arg Trp Leu
1385 1390 1395

Val Pro Gly Leu Ala Ile Pro Asp Thr Gln Gly Gln Val Val Cys
1400 1405 1410

Thr Tyr Gln Pro Arg Phe Ala Thr Leu Ala Ala Pro Ile Pro Ser
1415 1420 1425

Ser Leu Met Lys Thr Asn Ala Ala Phe Thr Phe Tyr Asp Ala Met
1430 1435 1440

Gly Arg Asn Val Ala Ser Leu Ala Ala Asp Cys Thr Trp Ser Lys
1445 1450 1455

-continued

```
Thr Val  Tyr Thr Pro Trp Thr  Thr Val Glu His Gly  Ala Gly Ser
    1460                 1465                 1470

Met Val  Leu Gln Ser Asn Ala  Arg Asp Asp Pro Asp  Val Gly His
    1475                 1480                 1485

Phe Phe  Ser Arg Ile Ala Ser  Ser Arg Tyr Ser Gln  Ser Trp Tyr
    1490                 1495                 1500

Asp Lys  Arg Lys Leu Gly Thr  Ala Gln Glu Lys Arg  Ala Ala Glu
    1505                 1510                 1515

Lys Ser  Ala Val Tyr Ser Asp  Thr Pro Leu Thr Thr  His Ser Gly
    1520                 1525                 1530

Ser Cys  Gly Leu Pro Val Arg  Thr Ile Gln Gln Ala  Gly Gly Lys
    1535                 1540                 1545

Thr Tyr  Thr Arg Ser Ser Met  Tyr Asp Val Ser Gly  Asn Arg Ile
    1550                 1555                 1560

Arg Asp  Val Asp Ser Tyr Glu  Arg Thr Val Glu Lys  Met Leu Tyr
    1565                 1570                 1575

Asp Lys  Leu Gly Arg Gln Leu  Gln Thr Thr Gly Met  Asp Cys Gly
    1580                 1585                 1590

Glu Ser  Trp Leu Leu Leu Asp  Ala Gln Gly Gly Glu  Ile Leu Ser
    1595                 1600                 1605

Trp Asn  Cys Arg Gly Tyr Ser  Phe Ile Thr Arg Tyr  Asp Pro Leu
    1610                 1615                 1620

Arg Arg  Glu Thr Glu Arg Leu  Val Ala Lys Ala Ala  Glu Met Pro
    1625                 1630                 1635

Lys Leu  Ile Ser Arg Ile Thr  Tyr Gly Glu Thr Cys  Gly Asp Ala
    1640                 1645                 1650

Ile Asn  Leu Asn Leu Asn Gly  Gln Val Trp Lys Val  Glu Asp Gln
    1655                 1660                 1665

Ala Gly  Val His Ile Asn Thr  His Tyr Asn Ile Arg  Gly His Cys
    1670                 1675                 1680

Leu Gly  Lys Thr Leu Gln Phe  Thr Lys Glu Tyr Lys  Gln Leu Val
    1685                 1690                 1695

Asp Trp  Lys Leu Asp Gln Thr  Leu Glu Thr Glu Val  Tyr Pro His
    1700                 1705                 1710

Thr Tyr  Phe Tyr Asp Asn Tyr  Gly Gln Val Leu Gln  Glu Glu Asp
    1715                 1720                 1725

Glu Gln  Gly Asn Arg Thr Arg  Arg Asn Tyr Ser Arg  Gln Gly His
    1730                 1735                 1740

Val Val  Ser Val Asp Phe Ser  Ser Ile Lys Gly Arg  Asp Trp Lys
    1745                 1750                 1755

Ser Tyr  Leu Ser Gly Ala Thr  Phe Ser Ala Asp Gly  Leu Pro Ile
    1760                 1765                 1770

Thr Ile  Lys Tyr Gly Asn Gly  Val Val Ser Asp Phe  Phe Tyr Asp
    1775                 1780                 1785

Asp Glu  Ser Arg Asn Leu Ile  Ser Gln Arg Thr Thr  Arg Pro Cys
    1790                 1795                 1800

Arg Gly  Arg Arg Glu Leu Leu  Gln Asp Arg Thr His  Val Tyr Asp
    1805                 1810                 1815

Tyr Val  Gly Arg Arg Ile Phe  Thr Ser Asp Gly Ser  Glu Gln Val
    1820                 1825                 1830

Lys Tyr  Phe Gly Glu Ser Arg  Val Lys Pro Glu Trp  Asp Tyr Thr
    1835                 1840                 1845

Tyr Asn  Ala Thr Gly Ala Leu  Val Ile Ala Thr Gly  Arg Ala Gln
```

-continued

```
    1850                1855                1860

Leu Ser  Gly Lys Ile Gly Asn  Gly Asn Gln Leu Thr  Pro His Asn
    1865                1870                1875

Ala Met  Asn Gly Leu Asn Pro  Ser Arg Gly Gly Gly  Asp Gly Asn
    1880                1885                1890

Leu Leu  Tyr Gln Tyr Arg Glu  Thr Tyr Asp Tyr Asp  Arg Glu Gly
    1895                1900                1905

Asn Ile  Leu Met Met Lys His  Glu Ala Pro Asp Ile  Lys Gly Val
    1910                1915                1920

Thr Ser  Trp Thr Arg Asn Tyr  His Tyr Asp Glu Lys  Ser Leu Leu
    1925                1930                1935

Ser Asp  Asp Pro Arg Val Lys  Ser Asn Arg Leu Ser  Arg Thr Ser
    1940                1945                1950

Ile Gly  Asp Thr Asn Glu Gly  Lys Tyr Met Tyr Glu  Gly Ser Ala
    1955                1960                1965

Gly Leu  Ser Gly Cys Ile Thr  Thr Leu Pro Lys Phe  Ser Glu Leu
    1970                1975                1980

Asp Trp  Asn Met Asn Asn Met  Leu Ser Phe Ser Ser  Thr Gln Tyr
    1985                1990                1995

Val Asn  Ala Gly Thr Pro Glu  Arg Thr Tyr Tyr Val  Tyr Asp His
    2000                2005                2010

Ala Gly  Asn Arg Val Arg Lys  Val Thr Glu Thr Ala  Ala Lys Ser
    2015                2020                2025

Gly Glu  Glu Pro Arg Lys Gln  Arg Asp Thr Leu Phe  Phe Gly Gly
    2030                2035                2040

Val Glu  Leu Gln Thr Lys Ser  Asn Gly Ser Leu Leu  Trp Thr Thr
    2045                2050                2055

Arg Val  Lys Gly Asp Gly Ile  Val Ala Val Val Glu  Val Asn Arg
    2060                2065                2070

Asn Gln  Glu Thr Pro Leu Val  Arg Phe Gln Ala Gly  Arg Asp Met
    2075                2080                2085

Glu Phe  Asp Asp Gln Ala Gln  Leu Ile Ser Tyr Glu  Glu Tyr Ser
    2090                2095                2100

Pro Phe  Gly Ala Val Val Tyr  Ala Ala Met Tyr Gly  Asn Ile Glu
    2105                2110                2115

Ala Pro  Arg Ala Tyr Arg Phe  Ala Arg Tyr Glu His  Asp Ser Glu
    2120                2125                2130

Thr Gly  Leu Tyr His Cys Gly  Gln Arg Tyr Tyr Cys  Pro Trp Leu
    2135                2140                2145

Gly Arg  Trp Thr Ser Pro Asp  Pro Leu Gly Asp Val  Asp Gly Pro
    2150                2155                2160

Asn Leu  Phe Val Tyr Val Asn  Asn Asp Pro Val Asn  Ser His Asp
    2165                2170                2175

Pro Ser  Gly Thr Ser Gly Lys  Lys Thr Lys Glu Gly  Thr Arg Glu
    2180                2185                2190

Met Tyr  Ala Ala Pro Asp Asp  Gln Gly Lys Arg Arg  Leu Val Asp
    2195                2200                2205

Glu Asn  Lys Ala Val Ala Asp  Arg Ile Ala Lys Tyr  Glu Arg Lys
    2210                2215                2220

Leu Gln  Arg Gln Glu Arg Lys  Gln Gln Arg Ala Ile  Ala Arg Met
    2225                2230                2235

Ser Gly  Thr Asp Pro Ile Leu  Gly Ser Arg Ala Arg  Tyr Ala Val
    2240                2245                2250
```

```
Gly Ile  Ala Ala Met Gly Asn  Ala Leu Gly Arg Ile  Ser Gly Ser
    2255                 2260                 2265

Thr Glu  Leu His His Thr Tyr  Pro Gln Glu Tyr Arg  Glu Glu Phe
    2270                 2275                 2280

Ser Asp  Ile Asp Ile Asn Val  Asp Arg Thr Ser Val  Ser Ile Ser
    2285                 2290                 2295

Lys Glu  Ala His Tyr Ile Cys  Thr Tyr Gly Ser Ile  Leu Asp Asn
    2300                 2305                 2310

Leu Val  Ala Thr Asn Lys Arg  Trp Lys Ser Glu Tyr  Phe Asp Thr
    2315                 2320                 2325

Pro Asp  Thr Gly Tyr Tyr Glu  Gln Met Glu Gln His  Glu Trp Tyr
    2330                 2335                 2340

Asp Asp  Asp Pro Gly Met Gln  Tyr Ala Ile Arg Leu  His Leu Ala
    2345                 2350                 2355

Tyr Glu  Ala Arg Thr Leu Asn  Gly Lys Ile Met Ala  Asp Phe Gly
    2360                 2365                 2370

Ile Asn  Pro Lys Gly Glu Asp  Gly Arg Ser Met Phe  Val Asn Tyr
    2375                 2380                 2385

Asp Ala  Val Thr Lys Met Arg  Thr Ala Gly Gln Arg  Arg Gly Val
    2390                 2395                 2400

Arg Asn  Asp Asn Leu Ile His  His Glu Thr Trp Pro  Gly Arg Pro
    2405                 2410                 2415

Phe Asn  Thr Gly Asn Ser Asp  Thr Asp Asn Ala Gly  Gly Pro Val
    2420                 2425                 2430

His Phe  Gln Val Ala Glu Glu  Gln Tyr Asn Gly Leu  Asp Ala Asp
    2435                 2440                 2445

Ala Gln  Ala Lys Phe Asp Asp  Leu Arg Asn Gln Met  Glu Ala Leu
    2450                 2455                 2460

Leu Gly  Lys Arg
    2465
```

```
<210> SEQ ID NO 25
<211> LENGTH: 9214
<212> TYPE: DNA
<213> ORGANISM: Fusarium verticillioides
<220> FEATURE:
<221> NAME/KEY: misc_feature
<222> LOCATION: (21)..(23)
<223> OTHER INFORMATION: Threonine codon (ACG) that serves as the
      beginning of the open reading frame for the coding region of the
      first segment of the deduced putative TC Class A protein
<220> FEATURE:
<221> NAME/KEY: misc_feature
<222> LOCATION: (3022)..(3024)
<223> OTHER INFORMATION: AAA Lysine codon which serves as the start of
      the open reading frame for the second portion of the deduced
      putative TC Class A protein

<400> SEQUENCE: 25

tcgcgtctcg agcctcgtaa acgaacttgg aagagatttt gtgcagtgta tcactataca     60

atttcaccaa aacttccttt gccttcaatc agcaattgct cgctattgat tcagagcatt    120

cttttcacca actctattct atcaccatgg cgcaagtctc atctttggtt gctgccatgt    180

tccgtggaaa cgatgagcta gtgaccagag ttcaaactgc cattgagaca cgacatgatg    240

ttattgctgc cattgaagtc gttgttggtc agggaggttt aagcttagac aacatcaaat    300

cacttcaatg gatgcgggag atattccaag caacccaaga ggatgagaag cttgcctgtt    360

acctattaca gaacttccca ggcccgaata gcctcagcag ggttgcactc gagtactacc    420
```

-continued

```
gtaaagaaga cttgccctgc aacgacaaag aaaatgccgc gcgtctcaga tcgtatctga    480
tgcttaaaga accactggct gttctcctgg cttccgttag ggcgaaggat ttccagttta    540
aaccagaatt gaacagcact atcgagtttg cgttgaaatg ggctgttgag aacgacgtat    600
caatcacctc tgataggttt cgaaaacagg tcaactccaa aggcttcttc gactcaatca    660
aggacagccg gaaggtcgaa gtcgaagagg tcatcggcag aatcatgacg ctacagagat    720
tgcagtatct ggtcacagaa ccacagcata taaaacatct cctggacctc aaatttgaga    780
gtgcacagga tatcgcttct acaaacagaa aagagtttgt tcagagcatg aggaagcgtc    840
tgcaggagga gactgcactc aagatccacg accatgcggt tgtagttgct tgtcggagtc    900
aggaaacctg ggtgaatctg ctcaccatga ttaacgaaga cttcatgcca accagaaaag    960
cgatcgcaga tgttggggca gaagagatca gtcgaccatc ggtacccgac gaagatcctt   1020
ccacggcggt ccctgacgca agcactaaga aggacttcaa catgacaagt atctttgatc   1080
tacaagatac tccatgcgaa gagtgttgct ctgttgtcag cgcctcggca tattttgttg   1140
acctgctcaa gttcctagaa cacagccgct gctctacaac ggttaatgaa gccgacaatg   1200
tcctaaaagc attggctctt cgacgtccag atttgcaaaa actgcaactc tcgtgcgcga   1260
atagcaagaa aatggtgccc tatatcacaa tcgtcaatga gattatggct tcatacatcg   1320
caagtgaggg agggtccatc ggcgtcattg atgaacagga tacctcaaca tccgaagttc   1380
atgtcagtgc agaagaagat cttgtagcca ctgcatgcga gaacaaaatt gcggaagcta   1440
tgtttcctct gaaccgattc ccgtatagct tgggccaaga ctcggccaga gtctatcttt   1500
cttcgatggg tatcgagccg tcggacgtgc gtgaaaactt caagtcaact accttcatgc   1560
tgaaacagct tatgaacttc gttccaagtg actcaaagtc gaggaaagag ctggaaaggg   1620
aggcagaggc tgtatggcac cgattcgacg ttgccgagac cttgcatatg ctccctcgcg   1680
accttgctgc tatttctaaa gaaaccatct ttacagacac ctttttagat cttcttgtcg   1740
gcctgtaccc agaggagctg gttcaagaga caatgctgcg agataggtcg atccccatgg   1800
tcaacgaatg ctggggctat gaaactattg acaagatgct tgacacctcc gagcagaatc   1860
tggcaggact ttgtttcata cgagatcagc ttcttccacg ctcggggcta tcgcttgagg   1920
aacttctgga gctttcgaac accactttct ttggtagaag acttgtaatc gtcaacaacc   1980
gaggctcaaa ggtgttcgac gggcagctgt cggaaatgcg acttcgactg cttgacaaca   2040
ccgcgagtgc cagtgggagg gatgcttctg aagaacctcc cattggtaat ctgacacaag   2100
agatttgcca cgaacttcaa agctttattc gactcagaaa taagctagga tggaccattg   2160
cagagcttga cgtcgtcatt tcaaccatca ctcagaatca cattgccaac agtgctactg   2220
catcagttga aggattcaga ggtattacgt tagcagtcct tgaagatgtc gctcacatcg   2280
taaagttgag taaactgaca gaggcaccag tggtctctct tctcccaatt tgggctccaa   2340
tcagcactca tggcgataag tccttatata gaaaggcgtt ccttgaacca atgagctatc   2400
tgagtaatga tccagtcttc aggccggact cttacggcgg atatctgagg gataaaggcg   2460
ccattgaagt ttacatggca cctctcacaa tgactttgaa gacgacttcg gaggatctga   2520
agattctttt ggctgttgct gggttgagcc cttcgtcacc gctcaacttg gatacgctgt   2580
ccaagatgta tcgtcatgcg ctgatgtgtc gacttcttgg agtacgtcca agagactatg   2640
atatggttct ttcagtcttc ccagacagga acatcttcat cgatccaaag acaactctcg   2700
ggaatatttc actctggagg cagttgactg atagtggctg gtcaattagc gacatcatgc   2760
```

-continued

```
tgcttgttgg caagagcgaa agtaccaaca ttccattatc tgaccatgcc cttcagttta   2820
cgtcgtctat tatggagaag gtcaatgcca acagcagtgt ctgggagcct cgcatacaaa   2880
acaatacggt tatatcgcga gatgttatgg atctgtgcgg ccagatattc gacgctgcaa   2940
cttccaagag cctgacgcag atagttgaag gttcgtcatc gagaccacca tgtctacacc   3000
accgtgctaa cgagactcta aaaaggtgat ttcgttctca acaagagcat taacatggag   3060
tctctggagt cgctgccttc cttcaacggc cttccttcaa aattgactat cgacatcaac   3120
agaagaaaca aaaagaccca ggcagctgtt gtaaccctca cgggggtcat gacagaggaa   3180
gaaaaagaga agagtataag tcaggtcgaa gaatttccaa ccctggccga cgcgatcaat   3240
gaacttgaca agttgacaaa gattccttat aatgccttgc tatccagatt ctcgggtaca   3300
gacaccactg agaagcagga tgttatcgac ttgatatgct ctgacgtggc tttgacaacc   3360
acagatcttg gaggccaatc cgacgactcg ctctgtacca gctcggagga agactcgagc   3420
gaggaagagg atagtgatgc agaatcctgt gagtcagatg agagtctggt cgacgagtcc   3480
gaagctatgg aatcgcctga agttgagaga gaaaagactt tacgtactag gcgattggaa   3540
ttcgtcaagt tgatgttacc aatattgcga tcacagacct tggtcgacct cgcgaccagg   3600
agtattggtg agaagctgga aggtgttgaa cacactctta tccccatgct tctgaacaag   3660
gagatggcgt gggaaaacaa caagtcagct atcaatatcc tagacgagat tcggggttac   3720
tctgcagaga agcctgcaag gacgcaaggc tactttctac caacggccac aggagagtac   3780
acgttcactt tgcggtcatc acagcctcag gacataccgg atccatgtct tagcatcaat   3840
ggtgccaagg tcattatgaa aaaatccggc aaagagtggt attccgatcc catccttatg   3900
acaacagggc agacctactt gcttgtatcg tctgttcaac ccatgcatat tacatgggcc   3960
accaagcaga cggtgccagc aagcttcacc gatacaacgt tcattgtgga agacgatgtc   4020
cagaaggctg attcagtatt gaaagaggtt ggccgattgg cctcgttgtt ccgaaagctg   4080
gagctgagct tggaggaagt aaagtaccta accactccca acgggctgat gtccgttgat   4140
ttaaactccc tgagtatcag tgacattgcg aagctacaga gttatcgcca gctgagagac   4200
aatgttgcca aggataagga ctctttagtc acgttgtttt catggctgga aaaccctgac   4260
agttcttcaa cgttgacttc caaactcata gctgcgacaa catggcccga agcacagcta   4320
tcaaccttga tcaatgccaa atatgactat gatggggcga cgacagaaga tataatcagc   4380
tctgtatcca gtctcagtga cctcgtgtcc attcaaacta tcatggagat ctctggcaat   4440
ctgaagccca attcaagtca ggaaggcgag catccgatca ctaatctttt caaattcgcc   4500
gctcccacac ttcttagttc gtccaaggat ttggaggttg cgaacgagct gagactcatg   4560
ctaggtaaac gacaactcaa gacatgtacc tcacagctac aagagaccca gcggacagtt   4620
ttcatcgagt atttgctgca acagccatat atcaagaaag ccaagatctc ggacgcgggc   4680
ggcttgtttg atctgctgtt gattgacgtt cagatgggct cgcagtttga gatcacgcga   4740
atgaaacaag ccatctcgac cgttcagtta tacgtacaac ggtgtctcct cggcatggaa   4800
actgaagctg gtgtgcaacc aagcaacata gatcagacca agtgggcgtg gatgcataag   4860
cacaatactt ggacggctac acgcaaggca ttcctatacc cggagaattg gatcgatcca   4920
accttgcgtg acgataagac tgctttgttt cgtgactacg aaacaacgat catgcaaaag   4980
gacctcagct gggatacatt ctcacaagct atccggacgt acgtgaaggg tctgtcagag   5040
atcgctgatc tagacatcca agcatatcta cggcatcatc ccacggatgg cctcgagacg   5100
taccatttct ttggcaagac gcgcagcgca ccatatcgtt tctactaccg taacatgagg   5160
```

-continued

```
cttacacagc ccagtgacgt tgcgatatgg acaccgtgga ctttgatgga cattggatct   5220
gtgacgtacg aggcagattg ggatggctcg agtgtcacca atgccggggc ctacctgatt   5280
cccgttatgc gtggaaaccg tctcagcgtc tatgtcccag agataatggt caaaactact   5340
actcctgaga ccccagcggg gaaaacgacg accaccatga cgttttcaga ggccgcgggc   5400
gagtcattga acacgacaaa gtcgccgagt aactgggaga tacggatggc atggactgaa   5460
ctacttaacg gggaatggac acccaagcga gtttcgcaac cggtactgaa tgtgaagtgg   5520
gataatgatt tcaacaaaga aaagctgcct tacatttcac gcttcacctt ttgggccaat   5580
acgaccgaac cggttgggga aacagtcact attaatgtgg gatgctggag aaaggaaaag   5640
aaaaccgaga ccacggcaac aaaaaccgac gtagccaacc actcatttct tggatctttt   5700
cagataagtg atgaccgcgc atctgtgaaa gaaaatgaga aacagtccga gtccacggca   5760
aaaacccttg agacggtgtt tcacaagtat acatggaagc aagactggga aacgagaaag   5820
acgtttgacg acgaccaggt cgagactcct gaacaacaag ttgcttcgtt tgggggagac   5880
caggtatctt ctcccttgct agctgttcct gttccaacct cttccagaac gcttgtttgg   5940
accatgtcgt atgatggaaa cgacaagctc ggcaaggcta caggctacgt cgtggacgtg   6000
caagtatcgg caccagatgg caagacaacc ttcatgtatc caaagcttgc ctacgcaaaa   6060
agcaacaaag tcaatcttgc atcgtcgaat cttgttcgga attcgatgac tgaagttatt   6120
gagcattctt catcaccaag tttcatgcag gatatcacga agacagacag cctgatacca   6180
ctctttgaga cgatgaacac aatgaacgag agagagtacg gaaaggctgt cgttgaagca   6240
aatatgtctc agtaccacga acaggcaact tcatatgctc tctacaactg ggaacttggt   6300
gcgcattgta ttcttctcgc tatggacagg ttcttagcaa cgcagcaata cgacctcgct   6360
cttcgcgttg caaggtttgt attcgacccg acagtagatg tccaagggca aactcgaaag   6420
caagcaaaga cggcatgctg gaggttccgt ccattcagag atattgcagc tgatccgact   6480
gagaaccaag acaagttcac tggctggcta gacgaatcta ccctcgacgt ggcagtgaca   6540
gaaaggagac gaaacccttc caacacgcat gcaacagcgc gaacacgacc gcgagcatac   6600
atgaaatgga tcgtcatgaa gtacatcgaa atcctcatag ctgctggcga tgagtacttc   6660
cgccagggta gcattgaatc tctccctatg gcgatccagc ggtacatcga ggcagcgcat   6720
gtcctcggcc cggagccacc caagatgccc aagcttggta aaactgcagt caagacctat   6780
gacactctga acaagaatgg cagaatgaga gtcgatctcg agctcacgtt tccttttctc   6840
tgtgatgttg agagacgagg gacaaatgcc tcgggcgatg acgcgcagga cagatatggc   6900
gtcttaggaa tcttaacaac gacatacttt tgcctgccag caaatccgaa gtatcagaca   6960
atgcggtcat tagtcaacga ccggctctac aaggctagga acaacttgga tatcaatgga   7020
cgaccacttg tgtatgccat gaacgagcag agtattgacc caggacaaat aggccgggcc   7080
ttgcaaggtg gtggaggggg agtgacttct ctgttgaatc agattgatgg tcccatgcca   7140
aatcagcgat tccaatacct aatctccaaa gcactggaga tatgtacgag ccttcaaggc   7200
atgggagagc agttcttaca aatcaaggaa aagaaggact cggaagctct ccagatcctc   7260
aaagcgaagc aagacacggc tcgacagcgg ctttccataa gtctcaaacg cctgcagagg   7320
gaggagatcg aaaggaacat cgagcttta gaaatgaaca gatcttctgc cgcatctcaa   7380
ctgagctact accttcaact tatgggcgag ccattgaacc gcataccaag cgaaacggag   7440
aagtgggtgg acatcgagca tgcgatcgat gcaccgttca cggacgacct tcgtatgaat   7500
```

-continued

```
cgactggagc tccaggaaat gaagggaacg gatctggcca ataagctgaa catcgctgct   7560

tcatacatag acatctgggc gtttatgctc aaggctctac cccaggtgac gtcgaatgtt   7620

gagccaatgg gtgttggtgc gtcgctcaag atggatggct cgatcctgtc atcagctgtt   7680

caagcttcgg ccatgaccct caggacaggc tccatggcag ccagcatggt agcatccgat   7740

gcccaacgca caaatgcgct cacgaaacag ctacaagaga ggcgactcca agcaaacatg   7800

aagggccagg agattaagtc gcttgacaaa caagcagaga tccaaagaaa gcgattagag   7860

ctcaatgaga aggaaacatg catccagcaa gcagagattg acaatgcagt tgagatggag   7920

cagtggtatc agtccaagta cacaaacgag aagctctacg cttggatgga gaacacggtc   7980

cgtaatgtcc attacgatct gtatcagctc gcatcagacc ttgcacgtcg cgctcagaac   8040

tcgttccgct tcgagaaggg atcttcagtg cagggattct tgcgacctgg tggttattgg   8100

gatagcagtc atgatggtct cctcgcagcg cagcagctgc aagctgacct tcgacgcatg   8160

gaggccgcgt atctggagcg atcttcgtat gactatgaga tagtcaagaa tatctcactc   8220

aggcaactca aacctgaagc tctactgaat cttagagccg acggtactgc cacctttgac   8280

attcctgagg tgttgtatga ctttgacttc ccaggtcatt acatgcgtcg gatcaagtca   8340

gtctcattgt ctgttccgtg tgttgtcggt ccccatactg gtctgaatgc aacactgcgt   8400

cttcttcagc accgttaccg tgttagctct gtggcagcct caggagaaga ctacgctgaa   8460

gatgatatgg cctcgggaca tttccgcaca gacatcgtgc ctataacttc agttgccatc   8520

agctctggta tccaggactc tggtgtattc gagctcaact tcaaggacga ccgcttccag   8580

ccattcgaag gtgctggtgc aattggttca tggtcccttg agctccccac gattgtccgt   8640

tcttttgact actccactat ctcggacgtt attctgcatg ttcggtatac agcagtcgac   8700

ggagggcctt tgctccgcaa tgctgccaat caagctgtca agactttccg atctcgtgtt   8760

gaaggcttga gctcagaagg gcctggtctc ttcgccatgt ttgatctcaa aaacgacttt   8820

agtaacgcat ggtacgcgtt ccggtcaggc ctgttgggca aaactattgc cgagttggac   8880

ctatctggta tcaaagacag atttccatac tgggcgctag gaaaaaccat cattgttacc   8940

agtttaagtc ttgttgtttc tggcaaggtg aataagaaaa agctggacca gaaatcgttt   9000

tcgatcactg ctttggggac gggaaaaccg tgggattcag ttcctttggg aagtgcgacg   9060

atgctgacct tgtcaccatt gaacactgag ttaaaaaatt cgaaccttga gtggaaattg   9120

aaggtatcga atgaaggggg cgacttcacg gcgttggaga acgtggtagt tgtgttgcgg   9180

tatgccttag cttgagctca ctagcctgga gaaa                               9214
```

<210> SEQ ID NO 26
<211> LENGTH: 1002
<212> TYPE: PRT
<213> ORGANISM: Fusarium verticillioides

<400> SEQUENCE: 26

```
Thr Asn Leu Glu Glu Ile Leu Cys Ser Val Ser Leu Tyr Asn Phe Thr
1               5                   10                  15

Lys Thr Ser Phe Ala Phe Asn Gln Gln Leu Leu Ala Ile Asp Ser Glu
            20                  25                  30

His Ser Phe His Gln Leu Tyr Ser Ile Thr Met Ala Gln Val Ser Ser
        35                  40                  45

Leu Val Ala Ala Met Phe Arg Gly Asn Asp Glu Leu Val Thr Arg Val
    50                  55                  60

Gln Thr Ala Ile Glu Thr Arg His Asp Val Ile Ala Ala Ile Glu Val
```

-continued

```
65                  70                  75                  80

Val Val Gly Gln Gly Gly Leu Ser Leu Asp Asn Ile Lys Ser Leu Gln
                85                  90                  95

Trp Met Arg Glu Ile Phe Gln Ala Thr Gln Glu Asp Glu Lys Leu Ala
            100                 105                 110

Cys Tyr Leu Leu Gln Asn Phe Pro Gly Pro Asn Ser Leu Ser Arg Val
        115                 120                 125

Ala Leu Glu Tyr Tyr Arg Lys Glu Asp Leu Pro Cys Asn Asp Lys Glu
    130                 135                 140

Asn Ala Ala Arg Leu Arg Ser Tyr Leu Met Leu Lys Glu Pro Leu Ala
145                 150                 155                 160

Val Leu Leu Ala Ser Val Arg Ala Lys Asp Phe Gln Phe Lys Pro Glu
                165                 170                 175

Leu Asn Ser Thr Ile Glu Phe Ala Leu Lys Trp Ala Val Glu Asn Asp
            180                 185                 190

Val Ser Ile Thr Ser Asp Arg Phe Arg Lys Gln Val Asn Ser Lys Gly
        195                 200                 205

Phe Phe Asp Ser Ile Lys Asp Ser Arg Lys Val Glu Val Glu Glu Val
    210                 215                 220

Ile Gly Arg Ile Met Thr Leu Gln Arg Leu Gln Tyr Leu Val Thr Glu
225                 230                 235                 240

Pro Gln His Ile Lys His Leu Leu Asp Leu Lys Phe Glu Ser Ala Gln
                245                 250                 255

Asp Ile Ala Ser Thr Asn Arg Lys Glu Phe Val Gln Ser Met Arg Lys
            260                 265                 270

Arg Leu Gln Glu Glu Thr Ala Leu Lys Ile His Asp His Ala Val Val
        275                 280                 285

Val Ala Cys Arg Ser Gln Glu Thr Trp Val Asn Leu Leu Thr Met Ile
    290                 295                 300

Asn Glu Asp Phe Met Pro Thr Arg Lys Ala Ile Ala Asp Val Gly Ala
305                 310                 315                 320

Glu Glu Ile Ser Arg Pro Ser Val Pro Asp Glu Asp Pro Ser Thr Ala
                325                 330                 335

Val Pro Asp Ala Ser Thr Lys Lys Asp Phe Asn Met Thr Ser Ile Phe
            340                 345                 350

Asp Leu Gln Asp Thr Pro Cys Glu Glu Cys Cys Ser Val Val Ser Ala
        355                 360                 365

Ser Ala Tyr Phe Val Asp Leu Leu Lys Phe Leu Glu His Ser Arg Cys
    370                 375                 380

Ser Thr Thr Val Asn Glu Ala Asp Asn Val Leu Lys Ala Leu Ala Leu
385                 390                 395                 400

Arg Arg Pro Asp Leu Gln Lys Leu Gln Leu Ser Cys Ala Asn Ser Lys
                405                 410                 415

Lys Met Val Pro Tyr Ile Thr Ile Val Asn Glu Ile Met Ala Ser Tyr
            420                 425                 430

Ile Ala Ser Glu Gly Gly Ser Ile Gly Val Ile Asp Glu Gln Asp Thr
        435                 440                 445

Ser Thr Ser Glu Val His Val Ser Ala Glu Glu Asp Leu Val Ala Thr
    450                 455                 460

Ala Cys Glu Asn Lys Ile Ala Glu Ala Met Phe Pro Leu Asn Arg Phe
465                 470                 475                 480

Pro Tyr Ser Leu Gly Gln Asp Ser Ala Arg Val Tyr Leu Ser Ser Met
                485                 490                 495
```

-continued

```
Gly Ile Glu Pro Ser Asp Val Arg Glu Asn Phe Lys Ser Thr Thr Phe
            500                 505                 510

Met Leu Lys Gln Leu Met Asn Phe Val Pro Ser Asp Ser Lys Ser Arg
        515                 520                 525

Lys Glu Leu Glu Arg Glu Ala Glu Ala Val Trp His Arg Phe Asp Val
    530                 535                 540

Ala Glu Thr Leu His Met Leu Pro Arg Asp Leu Ala Ala Ile Ser Lys
545                 550                 555                 560

Glu Thr Ile Phe Thr Asp Thr Phe Leu Asp Leu Leu Val Gly Leu Tyr
                565                 570                 575

Pro Glu Glu Leu Val Gln Glu Thr Met Leu Arg Asp Arg Ser Ile Pro
            580                 585                 590

Met Val Asn Glu Cys Trp Gly Tyr Glu Thr Ile Asp Lys Met Leu Asp
        595                 600                 605

Thr Ser Glu Gln Asn Leu Ala Gly Leu Cys Phe Ile Arg Asp Gln Leu
    610                 615                 620

Leu Pro Arg Ser Gly Leu Ser Leu Glu Glu Leu Leu Glu Leu Ser Asn
625                 630                 635                 640

Thr Thr Phe Phe Gly Arg Arg Leu Val Ile Val Asn Asn Arg Gly Ser
                645                 650                 655

Lys Val Phe Asp Gly Gln Leu Ser Glu Met Arg Leu Arg Leu Leu Asp
            660                 665                 670

Asn Thr Ala Ser Ala Ser Gly Arg Asp Ala Ser Glu Glu Pro Pro Ile
        675                 680                 685

Gly Asn Leu Thr Gln Glu Ile Cys His Glu Leu Gln Ser Phe Ile Arg
    690                 695                 700

Leu Arg Asn Lys Leu Gly Trp Thr Ile Ala Glu Leu Asp Val Val Ile
705                 710                 715                 720

Ser Thr Ile Thr Gln Asn His Ile Ala Asn Ser Ala Thr Ala Ser Val
                725                 730                 735

Glu Gly Phe Arg Gly Ile Thr Leu Ala Val Leu Glu Asp Val Ala His
            740                 745                 750

Ile Val Lys Leu Ser Lys Leu Thr Glu Ala Pro Val Val Ser Leu Leu
        755                 760                 765

Pro Ile Trp Ala Pro Ile Ser Thr His Gly Asp Lys Ser Leu Tyr Arg
    770                 775                 780

Lys Ala Phe Leu Glu Pro Met Ser Tyr Leu Ser Asn Asp Pro Val Phe
785                 790                 795                 800

Arg Pro Asp Ser Tyr Gly Gly Tyr Leu Arg Asp Lys Gly Ala Ile Glu
                805                 810                 815

Val Tyr Met Ala Pro Leu Thr Met Thr Leu Lys Thr Thr Ser Glu Asp
            820                 825                 830

Leu Lys Ile Leu Leu Ala Val Ala Gly Leu Ser Pro Ser Ser Pro Leu
        835                 840                 845

Asn Leu Asp Thr Leu Ser Lys Met Tyr Arg His Ala Leu Met Cys Arg
    850                 855                 860

Leu Leu Gly Val Arg Pro Arg Asp Tyr Asp Met Val Leu Ser Val Phe
865                 870                 875                 880

Pro Asp Arg Asn Ile Phe Ile Asp Pro Lys Thr Thr Leu Gly Asn Ile
                885                 890                 895

Ser Leu Trp Arg Gln Leu Thr Asp Ser Gly Trp Ser Ile Ser Asp Ile
            900                 905                 910
```

-continued

```
Met Leu Leu Val Gly Lys Ser Glu Ser Thr Asn Ile Pro Leu Ser Asp
        915                 920                 925

His Ala Leu Gln Phe Thr Ser Ser Ile Met Glu Lys Val Asn Ala Asn
    930                 935                 940

Ser Ser Val Trp Glu Pro Arg Ile Gln Asn Asn Thr Val Ile Ser Arg
945                 950                 955                 960

Asp Val Met Asp Leu Cys Gly Gln Ile Phe Asp Ala Ala Thr Ser Lys
                965                 970                 975

Ser Leu Thr Gln Ile Val Glu Gly Ser Ser Ser Arg Pro Pro Cys Leu
            980                 985                 990

His His Arg Ala Asn Glu Thr Leu  Lys Arg
        995                 1000


<210> SEQ ID NO 27
<211> LENGTH: 2057
<212> TYPE: PRT
<213> ORGANISM: Fusarium verticillioides

<400> SEQUENCE: 27

Lys Gly Asp Phe Val Leu Asn Lys Ser Ile Asn Met Glu Ser Leu Glu
1               5                   10                  15

Ser Leu Pro Ser Phe Asn Gly Leu Pro Ser Lys Leu Thr Ile Asp Ile
            20                  25                  30

Asn Arg Arg Asn Lys Lys Thr Gln Ala Ala Val Val Thr Leu Thr Gly
        35                  40                  45

Val Met Thr Glu Glu Glu Lys Glu Lys Ser Ile Ser Gln Val Glu Glu
    50                  55                  60

Phe Pro Thr Leu Ala Asp Ala Ile Asn Glu Leu Asp Lys Leu Thr Lys
65                  70                  75                  80

Ile Pro Tyr Asn Ala Leu Leu Ser Arg Phe Ser Gly Thr Asp Thr Thr
                85                  90                  95

Glu Lys Gln Asp Val Ile Asp Leu Ile Cys Ser Asp Val Ala Leu Thr
            100                 105                 110

Thr Thr Asp Leu Gly Gly Gln Ser Asp Asp Ser Leu Cys Thr Ser Ser
        115                 120                 125

Glu Glu Asp Ser Ser Glu Glu Glu Asp Ser Asp Ala Glu Ser Cys Glu
    130                 135                 140

Ser Asp Glu Ser Leu Val Asp Glu Ser Glu Ala Met Glu Ser Pro Glu
145                 150                 155                 160

Val Glu Arg Glu Lys Thr Leu Arg Thr Arg Arg Leu Glu Phe Val Lys
                165                 170                 175

Leu Met Leu Pro Ile Leu Arg Ser Gln Thr Leu Val Asp Leu Ala Thr
            180                 185                 190

Arg Ser Ile Gly Glu Lys Leu Glu Gly Val Glu His Thr Leu Ile Pro
        195                 200                 205

Met Leu Leu Asn Lys Glu Met Ala Trp Glu Asn Asn Lys Ser Ala Ile
    210                 215                 220

Asn Ile Leu Asp Glu Ile Arg Gly Tyr Ser Ala Glu Lys Pro Ala Arg
225                 230                 235                 240

Thr Gln Gly Tyr Phe Leu Pro Thr Ala Thr Gly Glu Tyr Thr Phe Thr
                245                 250                 255

Leu Arg Ser Ser Gln Pro Gln Asp Ile Pro Asp Pro Cys Leu Ser Ile
            260                 265                 270

Asn Gly Ala Lys Val Ile Met Lys Lys Ser Gly Lys Glu Trp Tyr Ser
        275                 280                 285
```

-continued

```
Asp Pro Ile Leu Met Thr Thr Gly Gln Thr Tyr Leu Leu Val Ser Ser
    290                 295                 300

Val Gln Pro Met His Ile Thr Trp Ala Thr Lys Gln Thr Val Pro Ala
305                 310                 315                 320

Ser Phe Thr Asp Thr Thr Phe Ile Val Glu Asp Asp Val Gln Lys Ala
                325                 330                 335

Asp Ser Val Leu Lys Glu Val Gly Arg Leu Ala Ser Leu Phe Arg Lys
            340                 345                 350

Leu Glu Leu Ser Leu Glu Glu Val Lys Tyr Leu Thr Thr Pro Asn Gly
        355                 360                 365

Leu Met Ser Val Asp Leu Asn Ser Leu Ser Ile Ser Asp Ile Ala Lys
    370                 375                 380

Leu Gln Ser Tyr Arg Gln Leu Arg Asp Asn Val Ala Lys Asp Lys Asp
385                 390                 395                 400

Ser Leu Val Thr Leu Phe Ser Trp Leu Glu Asn Pro Asp Ser Ser Ser
                405                 410                 415

Thr Leu Thr Ser Lys Leu Ile Ala Ala Thr Thr Trp Pro Glu Ala Gln
            420                 425                 430

Leu Ser Thr Leu Ile Asn Ala Lys Tyr Asp Tyr Asp Gly Ala Thr Thr
        435                 440                 445

Glu Asp Ile Ile Ser Ser Val Ser Ser Leu Ser Asp Leu Val Ser Ile
    450                 455                 460

Gln Thr Ile Met Glu Ile Ser Gly Asn Leu Lys Pro Asn Ser Ser Gln
465                 470                 475                 480

Glu Gly Glu His Pro Ile Thr Asn Leu Phe Lys Phe Ala Ala Pro Thr
                485                 490                 495

Leu Leu Ser Ser Ser Lys Asp Leu Glu Val Ala Asn Glu Leu Arg Leu
            500                 505                 510

Met Leu Gly Lys Arg Gln Leu Lys Thr Cys Thr Ser Gln Leu Gln Glu
        515                 520                 525

Thr Gln Arg Thr Val Phe Ile Glu Tyr Leu Leu Gln Gln Pro Tyr Ile
    530                 535                 540

Lys Lys Ala Lys Ile Ser Asp Ala Gly Gly Leu Phe Asp Leu Leu Leu
545                 550                 555                 560

Ile Asp Val Gln Met Gly Ser Gln Phe Glu Ile Thr Arg Met Lys Gln
                565                 570                 575

Ala Ile Ser Thr Val Gln Leu Tyr Val Gln Arg Cys Leu Leu Gly Met
            580                 585                 590

Glu Thr Glu Ala Gly Val Gln Pro Ser Asn Ile Asp Gln Thr Lys Trp
        595                 600                 605

Ala Trp Met His Lys His Asn Thr Trp Thr Ala Thr Arg Lys Ala Phe
    610                 615                 620

Leu Tyr Pro Glu Asn Trp Ile Asp Pro Thr Leu Arg Asp Asp Lys Thr
625                 630                 635                 640

Ala Leu Phe Arg Asp Tyr Glu Thr Thr Ile Met Gln Lys Asp Leu Ser
                645                 650                 655

Trp Asp Thr Phe Ser Gln Ala Ile Arg Thr Tyr Val Lys Gly Leu Ser
            660                 665                 670

Glu Ile Ala Asp Leu Asp Ile Gln Ala Tyr Leu Arg His His Pro Thr
        675                 680                 685

Asp Gly Leu Glu Thr Tyr His Phe Phe Gly Lys Thr Arg Ser Ala Pro
    690                 695                 700
```

-continued

```
Tyr Arg Phe Tyr Tyr Arg Asn Met Arg Leu Thr Gln Pro Ser Asp Val
705                 710                 715                 720

Ala Ile Trp Thr Pro Trp Thr Leu Met Asp Ile Gly Ser Val Thr Tyr
                725                 730                 735

Glu Ala Asp Trp Asp Gly Ser Ser Val Thr Asn Ala Gly Ala Tyr Leu
            740                 745                 750

Ile Pro Val Met Arg Gly Asn Arg Leu Ser Val Tyr Val Pro Glu Ile
        755                 760                 765

Met Val Lys Thr Thr Thr Pro Glu Thr Pro Ala Gly Lys Thr Thr Thr
    770                 775                 780

Thr Met Thr Phe Ser Glu Ala Ala Gly Glu Ser Leu Asn Thr Thr Lys
785                 790                 795                 800

Ser Pro Ser Asn Trp Glu Ile Arg Met Ala Trp Thr Glu Leu Leu Asn
                805                 810                 815

Gly Glu Trp Thr Pro Lys Arg Val Ser Gln Pro Val Leu Asn Val Lys
            820                 825                 830

Trp Asp Asn Asp Phe Asn Lys Glu Lys Leu Pro Tyr Ile Ser Arg Phe
        835                 840                 845

Thr Phe Trp Ala Asn Thr Thr Glu Pro Val Gly Glu Thr Val Thr Ile
    850                 855                 860

Asn Val Gly Cys Trp Arg Lys Glu Lys Lys Thr Glu Thr Thr Ala Thr
865                 870                 875                 880

Lys Thr Asp Val Ala Asn His Ser Phe Leu Gly Ser Phe Gln Ile Ser
                885                 890                 895

Asp Asp Arg Ala Ser Val Lys Glu Asn Glu Lys Gln Ser Glu Ser Thr
            900                 905                 910

Ala Lys Thr Leu Glu Thr Val Phe His Lys Tyr Thr Trp Lys Gln Asp
        915                 920                 925

Trp Glu Thr Arg Lys Thr Phe Asp Asp Asp Gln Val Glu Thr Pro Glu
    930                 935                 940

Gln Gln Val Ala Ser Phe Gly Gly Asp Gln Val Ser Ser Pro Leu Leu
945                 950                 955                 960

Ala Val Pro Val Pro Thr Ser Ser Arg Thr Leu Val Trp Thr Met Ser
                965                 970                 975

Tyr Asp Gly Asn Asp Lys Leu Gly Lys Ala Thr Gly Tyr Val Val Asp
            980                 985                 990

Val Gln Val Ser Ala Pro Asp Gly  Lys Thr Thr Phe Met  Tyr Pro Lys
        995                 1000                1005

Leu Ala  Tyr Ala Lys Ser Asn  Lys Val Asn Leu Ala  Ser Ser Asn
    1010                1015                1020

Leu Val  Arg Asn Ser Met Thr  Glu Val Ile Glu His  Ser Ser Ser
    1025                1030                1035

Pro Ser  Phe Met Gln Asp Ile  Thr Lys Thr Asp Ser  Leu Ile Pro
    1040                1045                1050

Leu Phe  Glu Thr Met Asn Thr  Met Asn Glu Arg Glu  Tyr Gly Lys
    1055                1060                1065

Ala Val  Val Glu Ala Asn Met  Ser Gln Tyr His Glu  Gln Ala Thr
    1070                1075                1080

Ser Tyr  Ala Leu Tyr Asn Trp  Glu Leu Gly Ala His  Cys Ile Leu
    1085                1090                1095

Leu Ala  Met Asp Arg Phe Leu  Ala Thr Gln Gln Tyr  Asp Leu Ala
    1100                1105                1110

Leu Arg  Val Ala Arg Phe Val  Phe Asp Pro Thr Val  Asp Val Gln
```

1115 1120 1125

Gly Gln Thr Arg Lys Gln Ala Lys Thr Ala Cys Trp Arg Phe Arg
1130 1135 1140

Pro Phe Arg Asp Ile Ala Ala Asp Pro Thr Glu Asn Gln Asp Lys
1145 1150 1155

Phe Thr Gly Trp Leu Asp Glu Ser Thr Leu Asp Val Ala Val Thr
1160 1165 1170

Glu Arg Arg Arg Asn Pro Ser Asn Thr His Ala Thr Ala Arg Thr
1175 1180 1185

Arg Pro Arg Ala Tyr Met Lys Trp Ile Val Met Lys Tyr Ile Glu
1190 1195 1200

Ile Leu Ile Ala Ala Gly Asp Glu Tyr Phe Arg Gln Gly Ser Ile
1205 1210 1215

Glu Ser Leu Pro Met Ala Ile Gln Arg Tyr Ile Glu Ala Ala His
1220 1225 1230

Val Leu Gly Pro Glu Pro Pro Lys Met Pro Lys Leu Gly Lys Thr
1235 1240 1245

Ala Val Lys Thr Tyr Asp Thr Leu Asn Lys Asn Gly Arg Met Arg
1250 1255 1260

Val Asp Leu Glu Leu Thr Phe Pro Phe Leu Cys Asp Val Glu Arg
1265 1270 1275

Arg Gly Thr Asn Ala Ser Gly Asp Asp Ala Gln Asp Arg Tyr Gly
1280 1285 1290

Val Leu Gly Ile Leu Thr Thr Thr Tyr Phe Cys Leu Pro Ala Asn
1295 1300 1305

Pro Lys Tyr Gln Thr Met Arg Ser Leu Val Asn Asp Arg Leu Tyr
1310 1315 1320

Lys Ala Arg Asn Asn Leu Asp Ile Asn Gly Arg Pro Leu Val Tyr
1325 1330 1335

Ala Met Asn Glu Gln Ser Ile Asp Pro Gly Gln Ile Gly Arg Ala
1340 1345 1350

Leu Gln Gly Gly Gly Gly Gly Val Thr Ser Leu Leu Asn Gln Ile
1355 1360 1365

Asp Gly Pro Met Pro Asn Gln Arg Phe Gln Tyr Leu Ile Ser Lys
1370 1375 1380

Ala Leu Glu Ile Cys Thr Ser Leu Gln Gly Met Gly Glu Gln Phe
1385 1390 1395

Leu Gln Ile Lys Glu Lys Lys Asp Ser Glu Ala Leu Gln Ile Leu
1400 1405 1410

Lys Ala Lys Gln Asp Thr Ala Arg Gln Arg Leu Ser Ile Ser Leu
1415 1420 1425

Lys Arg Leu Gln Arg Glu Glu Ile Glu Arg Asn Ile Glu Leu Leu
1430 1435 1440

Glu Met Asn Arg Ser Ser Ala Ala Ser Gln Leu Ser Tyr Tyr Leu
1445 1450 1455

Gln Leu Met Gly Glu Pro Leu Asn Arg Ile Pro Ser Glu Thr Glu
1460 1465 1470

Lys Trp Val Asp Ile Glu His Ala Ile Asp Ala Pro Phe Thr Asp
1475 1480 1485

Asp Leu Arg Met Asn Arg Leu Glu Leu Gln Glu Met Lys Gly Thr
1490 1495 1500

Asp Leu Ala Asn Lys Leu Asn Ile Ala Ala Ser Tyr Ile Asp Ile
1505 1510 1515

```
Trp Ala  Phe Met Leu Lys Ala  Leu Pro Gln Val Thr  Ser Asn Val
    1520                 1525                 1530

Glu Pro  Met Gly Val Gly Ala  Ser Leu Lys Met Asp  Gly Ser Ile
    1535                 1540                 1545

Leu Ser  Ser Ala Val Gln Ala  Ser Ala Met Thr Leu  Arg Thr Gly
    1550                 1555                 1560

Ser Met  Ala Ala Ser Met Val  Ala Ser Asp Ala Gln  Arg Thr Asn
    1565                 1570                 1575

Ala Leu  Thr Lys Gln Leu Gln  Glu Arg Arg Leu Gln  Ala Asn Met
    1580                 1585                 1590

Lys Gly  Gln Glu Ile Lys Ser  Leu Asp Lys Gln Ala  Glu Ile Gln
    1595                 1600                 1605

Arg Lys  Arg Leu Glu Leu Asn  Glu Lys Glu Thr Cys  Ile Gln Gln
    1610                 1615                 1620

Ala Glu  Ile Asp Asn Ala Val  Glu Met Glu Gln Trp  Tyr Gln Ser
    1625                 1630                 1635

Lys Tyr  Thr Asn Glu Lys Leu  Tyr Ala Trp Met Glu  Asn Thr Val
    1640                 1645                 1650

Arg Asn  Val His Tyr Asp Leu  Tyr Gln Leu Ala Ser  Asp Leu Ala
    1655                 1660                 1665

Arg Arg  Ala Gln Asn Ser Phe  Arg Phe Glu Lys Gly  Ser Ser Val
    1670                 1675                 1680

Gln Gly  Phe Leu Arg Pro Gly  Gly Tyr Trp Asp Ser  Ser His Asp
    1685                 1690                 1695

Gly Leu  Leu Ala Ala Gln Gln  Leu Gln Ala Asp Leu  Arg Arg Met
    1700                 1705                 1710

Glu Ala  Ala Tyr Leu Glu Arg  Ser Ser Tyr Asp Tyr  Glu Ile Val
    1715                 1720                 1725

Lys Asn  Ile Ser Leu Arg Gln  Leu Lys Pro Glu Ala  Leu Leu Asn
    1730                 1735                 1740

Leu Arg  Ala Asp Gly Thr Ala  Thr Phe Asp Ile Pro  Glu Val Leu
    1745                 1750                 1755

Tyr Asp  Phe Asp Phe Pro Gly  His Tyr Met Arg Arg  Ile Lys Ser
    1760                 1765                 1770

Val Ser  Leu Ser Val Pro Cys  Val Val Gly Pro His  Thr Gly Leu
    1775                 1780                 1785

Asn Ala  Thr Leu Arg Leu Leu  Gln His Arg Tyr Arg  Val Ser Ser
    1790                 1795                 1800

Val Ala  Ala Ser Gly Glu Asp  Tyr Ala Glu Asp Asp  Met Ala Ser
    1805                 1810                 1815

Gly His  Phe Arg Thr Asp Ile  Val Pro Ile Thr Ser  Val Ala Ile
    1820                 1825                 1830

Ser Ser  Gly Ile Gln Asp Ser  Gly Val Phe Glu Leu  Asn Phe Lys
    1835                 1840                 1845

Asp Asp  Arg Phe Gln Pro Phe  Glu Gly Ala Gly Ala  Ile Gly Ser
    1850                 1855                 1860

Trp Ser  Leu Glu Leu Pro Thr  Ile Val Arg Ser Phe  Asp Tyr Ser
    1865                 1870                 1875

Thr Ile  Ser Asp Val Ile Leu  His Val Arg Tyr Thr  Ala Val Asp
    1880                 1885                 1890

Gly Gly  Pro Leu Leu Arg Asn  Ala Ala Asn Gln Ala  Val Lys Thr
    1895                 1900                 1905
```

-continued

```
Phe Arg  Ser Arg Val Glu Gly  Leu Ser Ser Glu Gly  Pro Gly Leu
    1910                 1915                 1920

Phe Ala  Met Phe Asp Leu Lys  Asn Asp Phe Ser Asn  Ala Trp Tyr
    1925                 1930                 1935

Ala Phe  Arg Ser Gly Leu Leu  Gly Lys Thr Ile Ala  Glu Leu Asp
    1940                 1945                 1950

Leu Ser  Gly Ile Lys Asp Arg  Phe Pro Tyr Trp Ala  Leu Gly Lys
    1955                 1960                 1965

Thr Ile  Ile Val Thr Ser Leu  Ser Leu Val Val Ser  Gly Lys Val
    1970                 1975                 1980

Asn Lys  Lys Lys Leu Asp Gln  Lys Ser Phe Ser Ile  Thr Ala Leu
    1985                 1990                 1995

Gly Thr  Gly Lys Pro Trp Asp  Ser Val Pro Leu Gly  Ser Ala Thr
    2000                 2005                 2010

Met Leu  Thr Leu Ser Pro Leu  Asn Thr Glu Leu Lys  Asn Ser Asn
    2015                 2020                 2025

Leu Glu  Trp Lys Leu Lys Val  Ser Asn Glu Gly Gly  Asp Phe Thr
    2030                 2035                 2040

Ala Leu  Glu Asn Val Val Val  Val Leu Arg Tyr Ala  Leu Ala
    2045                 2050                 2055
```

<210> SEQ ID NO 28
<211> LENGTH: 9169
<212> TYPE: DNA
<213> ORGANISM: Fusarium verticillioides
<220> FEATURE:
<221> NAME/KEY: misc_feature
<222> LOCATION: (20)..(22)
<223> OTHER INFORMATION: Beginning of the coding region corresponding to the first Asparagine of the putative TC Class A encoded protein in SEQ ID NO:29
<220> FEATURE:
<221> NAME/KEY: misc_feature
<222> LOCATION: (3299)..(5396)
<223> OTHER INFORMATION: n = a, g, c, or t (large gap in the DNA sequence, indicated as a string of 2098 n's)
<220> FEATURE:
<221> NAME/KEY: misc_feature
<222> LOCATION: (5451)..(5453)
<223> OTHER INFORMATION: GGA codon for the first Glycine of this portion of the deduced putative TC Class A protein

<400> SEQUENCE: 28

```
aggcaagcat gtcttctaga atgcgtgtga cctttccggc gagagtaacc aggttgctat     60

gatcggcgcg gtcagcaagg actcgataaa acacgacttg gtattcccta agttgtttca    120

gtcaaagatg ataacagttc tgttgaagag gacagtacag atgatacagc tgcaataccg    180

agggccagaa gcctcggtcc aacgtcaccg tctcatggct cttagctcag cccccacaag    240

acaggtcgcg agctatacgg agatcattgg cgatattgtg atcggatctt gtgatgactg    300

taactcggtc accagtccag cggcatactt tgtcgacctc cttcgactgt tgaagaacac    360

tcctagtgat gctaaggcag gctcgcccag ccttctcgac aggattctcg tcaggcgccc    420

agatctgttg accttacagc tctcatatgt taacacaaac gtactgatcc cgtatattga    480

ccttgccaac gaagccatgg agtcattcat caagaatgtt gggactctcg ttccaccggc    540

tgccgtacca attcaagggt tcaacatgac ggatcaagat accagcgata tcagtctggc    600

tgagcccaag aacacggact acagtgtcta tcgtgatcaa atttccgccc agtatttccc    660

acttaccgta tttccttaca atcaggcact tgatttccaa cgccttttct tttccagtct    720

gaacacgtct ttttcagcgg tcattgactt atttggctcg gagtcacgtc ttcttcctca    780
```

-continued

```
agttggtagc aacatcgctc ctgatctggt caaactagcc aaggatgtag tagatgccgc    840
cagtgcagca gagtttcttg gtctctggcc tgcagactat gtagccatca ctggatcttc    900
tgtcttttca ttcgacttct tcaaggcggt ttacgatcag aatatacagc aggacgccta    960
caatcaaaag attggacgtc taggcactgg gcagtactgg ggctaccagg ctgctgatgg   1020
caagacagcc gagcaggtca tgttatctga agacaacgac cagggactgc cccttgtaaa   1080
ggcacaattg cttcgtcgta cagagctcac ctttgagcag ttgatagacc tcctcaaggc   1140
cagactgctc cagggccaac ttgtccttga gaacccggac aacacggcaa tcttttctgg   1200
aaagctggaa gagctcaggc tacgccatcc caccaaagag gtttctaacg cgccactgac   1260
ggagcgagac tgttggttat tgcagtctta catccgtctc tggcgtaaga cgggatggac   1320
tttgcaagac ctcgactgcg cggttgtctc gtttggtact ggcgacgcag ccagcggcct   1380
gaacatcact gcccagacca tcacttcaat ggcagctata cagcgcatct caaccctgac   1440
gggtcttgag atctatcaac taatgccttt ctgaggcatt attgatacta acggagacaa   1500
gtcactttat gcgaggctgt tcttgagagg caaggctggc cggaaggacc ctgttttcgg   1560
accagacgat caagggcgat accttcaggc tgatgcaagt ctccaagata acagagcgcc   1620
attactctca agactcggac tcacggaaga aagctttacg gccatcttag cagctgccaa   1680
gatcaccaat gacaaacttg atttggctaa tgtcaccact atttatcgga taactatttt   1740
ctgtcagata cttggggtaa gcccaatcta ctttcagtcg ttccaagcac tgctggactc   1800
cgatgaagct gcttttgttg ccccgcaggc tacactgaac attattaagc agtttcaaga   1860
gtgcgcagat gccggtctca gctcggagca gatgattttc ttcacaaacc acgacaaagt   1920
cttactctcg aagaacgtca actcgaggct ctcgattcag caaatcgcaa tagctgtatc   1980
agatatcatc aatagcctcc agagcagcta cgcggggccc ccgactatta acagcgacac   2040
aactacagct tctgcagccg atgtctccgc cgtttcaact aagatgtttg ctccggctac   2100
tgcgcagcaa gtgacggcgt ttcttcaaag tgagctccct acgcaagcaa cgagttgcta   2160
tcggtaacta acaatagtat ttagtgctcc ccggaacaga cctgacagat cagtcaaagg   2220
tgtacaataa tattctccgt ccattcttca gtgacacaca agcagcccac aaagtctttt   2280
ttgagcagcc agaaccaagc ggaacggagg aggagaaagc cattgccaaa gaaaataacc   2340
ttgattctcg acgcctgttt ttcttaaaag ctgttattaa accacttcaa gcccggattg   2400
ccagtgatac tgtcctgcag gtgctcactc ctctctacgt ggaatcagac cccactgttc   2460
ttggccacct actcgggacg gttgttggac aatctgaggg tgagcgacca gttgcgaaga   2520
tactaggtga tctcggggcc tctaatgagg cggcattaaa gaaaggctcg tcagatgtct   2580
tcttcatacc attgaatgta gacctatacc gcttcttctt tccggacaca agcttggaaa   2640
aggcccccac cgttactctg gatacgacag cccttgtgtt caacaaagac gtaggcgggt   2700
ggatttcgaa cgagatacgt ctatccaacg gacaagcgta taatttacgc cgctctaatg   2760
gtggattgac agagtgtttc tattctactc cgcgaaatcc tagacaatct tttccttcca   2820
acactctact tgcacacgat actatcaagt acgcccaaag ctccctgaaa ctgttgtcgc   2880
gagccgccgg tctgtgtacc agcttcaagt tgaatattga tgagctgcag ttcttccaga   2940
gtcaggagct aaacactgat cttgcaatcg acttggggaa cattgactgg aagactttgc   3000
agcttgtgca acggtacaga actctttcaa gaaggacaac agggactacg agccttctat   3060
ccttcctcaa atgggcctgt gtgtctcctc gggatggtac tctgatagca cagctcgtca   3120
```

-continued

```
ggctcacgaa tgtatcccaa acgcagatca aagattacac aactccaagg ttctcaagtc   3180
taactgagga tcagttggtt cagcgcttcc aagaaactgc ggagctcaga cacttacttg   3240
atagtgttgc cttcgtgcat cgcacaggtg tcccctggta tgacattcca actcttgtnn   3300
nnnnnnnnnn nnnnnnnnnn nnnnnnnnnn nnnnnnnnnn nnnnnnnnnn nnnnnnnnnn   3360
nnnnnnnnnn nnnnnnnnnn nnnnnnnnnn nnnnnnnnnn nnnnnnnnnn nnnnnnnnnn   3420
nnnnnnnnnn nnnnnnnnnn nnnnnnnnnn nnnnnnnnnn nnnnnnnnnn nnnnnnnnnn   3480
nnnnnnnnnn nnnnnnnnnn nnnnnnnnnn nnnnnnnnnn nnnnnnnnnn nnnnnnnnnn   3540
nnnnnnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnnnnnn nnnnnnnnnn   3720
nnnnnnnnnn nnnnnnnnnn nnnnnnnnnn nnnnnnnnnn nnnnnnnnnn nnnnnnnnnn   3780
nnnnnnnnnn nnnnnnnnnn nnnnnnnnnn nnnnnnnnnn nnnnnnnnnn nnnnnnnnnn   3840
nnnnnnnnnn nnnnnnnnnn nnnnnnnnnn nnnnnnnnnn nnnnnnnnnn nnnnnnnnnn   3900
nnnnnnnnnn nnnnnnnnnn nnnnnnnnnn nnnnnnnnnn nnnnnnnnnn nnnnnnnnnn   3960
nnnnnnnnnn nnnnnnnnnn nnnnnnnnnn nnnnnnnnnn nnnnnnnnnn nnnnnnnnnn   4020
nnnnnnnnnn nnnnnnnnnn nnnnnnnnnn nnnnnnnnnn nnnnnnnnnn nnnnnnnnnn   4080
nnnnnnnnnn nnnnnnnnnn nnnnnnnnnn nnnnnnnnnn nnnnnnnnnn nnnnnnnnnn   4140
nnnnnnnnnn nnnnnnnnnn nnnnnnnnnn nnnnnnnnnn nnnnnnnnnn nnnnnnnnnn   4200
nnnnnnnnnn nnnnnnnnnn nnnnnnnnnn nnnnnnnnnn nnnnnnnnnn nnnnnnnnnn   4260
nnnnnnnnnn nnnnnnnnnn nnnnnnnnnn nnnnnnnnnn nnnnnnnnnn nnnnnnnnnn   4320
nnnnnnnnnn nnnnnnnnnn nnnnnnnnnn nnnnnnnnnn nnnnnnnnnn nnnnnnnnnn   4380
nnnnnnnnnn nnnnnnnnnn nnnnnnnnnn nnnnnnnnnn nnnnnnnnnn nnnnnnnnnn   4440
nnnnnnnnnn nnnnnnnnnn nnnnnnnnnn nnnnnnnnnn nnnnnnnnnn nnnnnnnnnn   4500
nnnnnnnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnnnnnnnnn nnnnnnnnnn nnnnnnnnnn   4620
nnnnnnnnnn nnnnnnnnnn nnnnnnnnnn nnnnnnnnnn nnnnnnnnnn nnnnnnnnnn   4680
nnnnnnnnnn nnnnnnnnnn nnnnnnnnnn nnnnnnnnnn nnnnnnnnnn nnnnnnnnnn   4740
nnnnnnnnnn nnnnnnnnnn nnnnnnnnnn nnnnnnnnnn nnnnnnnnnn nnnnnnnnnn   4800
nnnnnnnnnn nnnnnnnnnn nnnnnnnnnn nnnnnnnnnn nnnnnnnnnn nnnnnnnnnn   4860
nnnnnnnnnn nnnnnnnnnn nnnnnnnnnn nnnnnnnnnn nnnnnnnnnn nnnnnnnnnn   4920
nnnnnnnnnn nnnnnnnnnn nnnnnnnnnn nnnnnnnnnn nnnnnnnnnn nnnnnnnnnn   4980
nnnnnnnnnn nnnnnnnnnn nnnnnnnnnn nnnnnnnnnn nnnnnnnnnn nnnnnnnnnn   5040
nnnnnnnnnn nnnnnnnnnn nnnnnnnnnn nnnnnnnnnn nnnnnnnnnn nnnnnnnnnn   5100
nnnnnnnnnn nnnnnnnnnn nnnnnnnnnn nnnnnnnnnn nnnnnnnnnn nnnnnnnnnn   5160
nnnnnnnnnn nnnnnnnnnn nnnnnnnnnn nnnnnnnnnn nnnnnnnnnn nnnnnnnnnn   5220
nnnnnnnnnn nnnnnnnnnn nnnnnnnnnn nnnnnnnnnn nnnnnnnnnn nnnnnnnnnn   5280
nnnnnnnnnn nnnnnnnnnn nnnnnnnnnn nnnnnnnnnn nnnnnnnnnn nnnnnnnnnn   5340
nnnnnnnnnn nnnnnnnnnn nnnnnnnnnn nnnnnnnnnn nnnnnnnnnn nnnnnnccgt   5400
atggaagatg ggacaccaaa gcaggtttct ccacaaaggc tactttctaa ggacatttag   5460
agggaggccc attgagtacg gatttcccca tgcagcatgc aagttctact gcgcctggta   5520
```

-continued

```
atgcatggaa tgaggcggta aaattacctg acgtctcatc gttcaagttc tggattcggt   5580
ctaggaaaag cgactcaatg ccccctgctt ctttggtcgc tccggctcct cccgcaccta   5640
gcaaggctcc agttcctagt acaagtattc tagtcatcga tgtggagcgt tgggttgatg   5700
caggcaaagg ccagaaccct cgatatgtca actatcctct aggacgtttc gagatgcgtg   5760
gctcgcaggt tatcctggtc aacctcggaa cagctgatgt ttcacctgac cccttcaaga   5820
agccctggcg atcaactatc cctaccaagt tcgctaaaat gtggtggcac atggagaagg   5880
acaaagaccc ggccgttccc ggtatagcta tcggcagagg cacgggcgcc gacaaggagc   5940
cgctgttggg tgttgttacg aagctcatgg ataatattcc caagaaggat gttcactgga   6000
cgctatcatt caacgattca caagccaaga atgccactgg ctttgttcag gacattgtta   6060
ccaccgaaag caccatctcc tacatcacct atccacccat cgcgtcttca tcaacctttg   6120
cgtccgatgt cttccagcac actttggaca gagacctagt ttcgatgtca actatgtaca   6180
atgggctcga tcaagtctac gcctttcttg gaagtgtacc accgaatgac acatatcttg   6240
cctttggaaa acgcaatggt cctgtccacg aactctcaac cccatatgcc ctttacaact   6300
gggaattggg cgcccattcc atcatgttgc tcatggaaag gctacaggtg acacagcagt   6360
atgatctcgc tctccaagta gcgcatttcg tttttgatcc aaccattgat ggcaccagtc   6420
tcacccgttg ttgggtcttc ccaccgttta aagagctggc ggctggtaag attgactccg   6480
tggaagacat tttgaagctt cttgagccat ctagtggttc agaggaggac atgaagacca   6540
gtattcttga gtggcgtaag aacccattca atgctcatgt cgtggcgcga gggagacctt   6600
tagcttacat gaggcgcatc atcatgaagt atgtggagat tcttatcgct agcggcgatg   6660
tctattttcg acagaatacc cttgagactt taccattggc tattcagcgt tacgttgaag   6720
catctcatgt cttcgggtca aagcctgtac gcgtgcctaa gctagctaag cctgtgtata   6780
aatcttatgc agatctcgac cgggacttta acgacttttc caacgctgcc ttcgacatgg   6840
aattggactt ccctttcttc agcgatcctg cctcacgtgg aggagtgcct ggggccagtg   6900
gcacttttgg cctaactggt attctgaaga ccacgtactt ctgtgtccct tctaatccga   6960
agcttgttgg acttcgggat cttatagacg accgtctttt caagattcgc aactgccagg   7020
atatatatgg tgtcgtccga agtttagctc tcttcgagcc accactagac cctgggatgc   7080
tcgtccgagc gactgccggt ggcgttgaca tttcccagct ggtgagcagt atagcaggcc   7140
ccatgccaaa ttatcgcttc cagtacttgc tccaaaaagc tcaggagatg tgtgcggagg   7200
tcaagtcgat gggtaccttg atgctgtcta tcaaggagag gaaggatgtg gaagcactcg   7260
caagtcttcg agcgcggcag gataaggtca ttcagaatct tatgattgag atgaaagaaa   7320
ctgccaagaa agaagctgaa tcgagtattg atgccctctt ggagacgcgc caggctcagg   7380
ttgcaagact ggagtactac cttgctctga cagggagtga tgacaagtct gcaccagatg   7440
agaaggagga ttgggaagac atcgcacagt caattgagaa gccgacaacc gatgatctac   7500
gtatgacgtc tcatgaaaag cttgagatgc aaaaggctga cgccgcctcg gatctaaatc   7560
aaaaggcgac tattctcgac attgcggcta gtatcatcaa gatcatacca gacatcaacg   7620
aggcagctga gcctcttgga gttggtgtat ctattgactc catcaccaaa aacatctgcg   7680
agtccatgat gatcaattcg aatgtcatgc gtgcccaggc tcaacacttt agtgatgaag   7740
gtgctcgcgc gtcgcggact ggcgggctca ttaaacagct ccaagagcgg cgcttgcaag   7800
ccaacatggc tggtcgtgac atcaaggaaa ctgacaagca aatcttgact gcgcgcatca   7860
```

-continued

```
gagtcgagat gtgcgagcgc aatattcaac tacagaagca acaggctgag tatgcacgcg   7920

acacagagga atggctgagg acgaagtaca gcagtgaaca gctctacgcc tggatggatg   7980

gtgtcgttcg gaatctgtac caccagacct atatgattgc cgatgatctg gcgcagaaag   8040

cccagaaggc gttccagttt gaaaagggtg atcaatttgt caacattatc agtccatgtt   8100

actgggatgc tggaagagat ggtttgttct ccggggaaaa cctctttttg tctctaaagc   8160

ggcttgaagg ggcatacatc gaacagcgca tgcacgactt tgaaatagtg aaaaacattt   8220

cgctacgtca ggttcggcct tgggctctga ttaacttacg tgaaactggc gcggcagagt   8280

ttgacttgcc agaggttctt ttcgactttg acttctccgg tcactattgt cgccgcatca   8340

agtccgtcgg aatgactatc ccatgtattg tgggacccta caccagcgtc aatgccacgc   8400

tgacactcct cgaataccaa tatcgcatca agtcagacgc caagggcgcc caagactatc   8460

cccaaaaagc gacagatgaa cggttccaaa ctgaccaggt gccgatccca tccattgccg   8520

ttagccacgg gcagcaggac agtggtgtct tgaatcttga cttcaaggac gagcgataca   8580

tgccctttga aggcgcggga gcagttagta gatggagact ggaacttcca actaccatca   8640

agcaattcga ctacaaccct attagtgaca ttgtcttgca catgaaatac acagctattc   8700

aaggctgtgc tgcctttcgc aaagctgcgg cagaatctgc ggctgctggc ctatcgctga   8760

atgaaggcat gtttgcagtg ttggatcttc ccaacgagtt tccttctgag tggcaccggc   8820

tagttatggc tgacaagacc caaccttcaa ctatgccgct tctatcttta caagatcgtc   8880

ttccattctt cacaaaaggc aagagtatca aggccggaag cgtgtctgtg catatcgagt   8940

cgtcgggtat caatctggaa gaagacatca ccttgactgc tgcgaatcgg ctgaacctca   9000

aggccggaac tggcattggg tccttccaag ttgctaccac atccacaaat atgagacaac   9060

ctgttaaaga ttggcgtctg accttgtcat caaaagctat gaatgcaagt atttctcgag   9120

ttttgatttt atataggtat tttttagtat aggccgtaat ccttttacc               9169
```

```
<210> SEQ ID NO 29
<211> LENGTH: 484
<212> TYPE: PRT
<213> ORGANISM: Fusarium verticillioides

<400> SEQUENCE: 29

Asn Ala Cys Asp Leu Ser Gly Glu Ser Asn Gln Val Ala Met Ile Gly
1               5                   10                  15

Ala Val Ser Lys Asp Ser Ile Lys His Asp Leu Val Phe Pro Lys Leu
            20                  25                  30

Phe Gln Ser Lys Met Ile Thr Val Leu Leu Lys Arg Thr Val Gln Met
        35                  40                  45

Ile Gln Leu Gln Tyr Arg Gly Pro Glu Ala Ser Val Gln Arg His Arg
    50                  55                  60

Leu Met Ala Leu Ser Ser Ala Pro Thr Arg Gln Val Ala Ser Tyr Thr
65                  70                  75                  80

Glu Ile Ile Gly Asp Ile Val Ile Gly Ser Cys Asp Asp Cys Asn Ser
                85                  90                  95

Val Thr Ser Pro Ala Ala Tyr Phe Val Asp Leu Leu Arg Leu Leu Lys
            100                 105                 110

Asn Thr Pro Ser Asp Ala Lys Ala Gly Ser Pro Ser Leu Leu Asp Arg
        115                 120                 125

Ile Leu Val Arg Arg Pro Asp Leu Leu Thr Leu Gln Leu Ser Tyr Val
    130                 135                 140
```

-continued

```
Asn Thr Asn Val Leu Ile Pro Tyr Ile Asp Leu Ala Asn Glu Ala Met
145                 150                 155                 160

Glu Ser Phe Ile Lys Asn Val Gly Thr Leu Val Pro Pro Ala Ala Val
                165                 170                 175

Pro Ile Gln Gly Phe Asn Met Thr Asp Gln Asp Thr Ser Asp Ile Ser
            180                 185                 190

Leu Ala Glu Pro Lys Asn Thr Asp Tyr Ser Val Tyr Arg Asp Gln Ile
        195                 200                 205

Ser Ala Gln Tyr Phe Pro Leu Thr Val Phe Pro Tyr Asn Gln Ala Leu
    210                 215                 220

Asp Phe Gln Arg Leu Phe Phe Ser Ser Leu Asn Thr Ser Phe Ser Ala
225                 230                 235                 240

Val Ile Asp Leu Phe Gly Ser Glu Ser Arg Leu Leu Pro Gln Val Gly
                245                 250                 255

Ser Asn Ile Ala Pro Asp Leu Val Lys Leu Ala Lys Asp Val Val Asp
            260                 265                 270

Ala Ala Ser Ala Ala Glu Phe Leu Gly Leu Trp Pro Ala Asp Tyr Val
        275                 280                 285

Ala Ile Thr Gly Ser Ser Val Phe Ser Phe Asp Phe Phe Lys Ala Val
    290                 295                 300

Tyr Asp Gln Asn Ile Gln Gln Asp Ala Tyr Asn Gln Lys Ile Gly Arg
305                 310                 315                 320

Leu Gly Thr Gly Gln Tyr Trp Gly Tyr Gln Ala Ala Asp Gly Lys Thr
                325                 330                 335

Ala Glu Gln Val Met Leu Ser Glu Asp Asn Asp Gln Gly Leu Pro Leu
            340                 345                 350

Val Lys Ala Gln Leu Leu Arg Arg Thr Glu Leu Thr Phe Glu Gln Leu
        355                 360                 365

Ile Asp Leu Leu Lys Ala Arg Leu Leu Gln Gly Gln Leu Val Leu Glu
    370                 375                 380

Asn Pro Asp Asn Thr Ala Ile Phe Ser Gly Lys Leu Glu Glu Leu Arg
385                 390                 395                 400

Leu Arg His Pro Thr Lys Glu Val Ser Asn Ala Pro Leu Thr Glu Arg
                405                 410                 415

Asp Cys Trp Leu Leu Gln Ser Tyr Ile Arg Leu Trp Arg Lys Thr Gly
            420                 425                 430

Trp Thr Leu Gln Asp Leu Asp Cys Ala Val Val Ser Phe Gly Thr Gly
        435                 440                 445

Asp Ala Ala Ser Gly Leu Asn Ile Thr Ala Gln Thr Ile Thr Ser Met
    450                 455                 460

Ala Ala Ile Gln Arg Ile Ser Thr Leu Thr Gly Leu Glu Ile Tyr Gln
465                 470                 475                 480

Leu Met Pro Phe


<210> SEQ ID NO 30
<211> LENGTH: 230
<212> TYPE: PRT
<213> ORGANISM: Fusarium verticillioides

<400> SEQUENCE: 30

Gly Ile Ile Asp Thr Asn Gly Asp Lys Ser Leu Tyr Ala Arg Leu Phe
1               5                   10                  15

Leu Arg Gly Lys Ala Gly Arg Lys Asp Pro Val Phe Gly Pro Asp Asp
            20                  25                  30
```

-continued

```
Gln Gly Arg Tyr Leu Gln Ala Asp Ala Ser Leu Gln Asp Asn Arg Ala
        35                  40                  45

Pro Leu Leu Ser Arg Leu Gly Leu Thr Glu Glu Ser Phe Thr Ala Ile
    50                  55                  60

Leu Ala Ala Ala Lys Ile Thr Asn Asp Lys Leu Asp Leu Ala Asn Val
65                  70                  75                  80

Thr Thr Ile Tyr Arg Ile Thr Ile Phe Cys Gln Ile Leu Gly Val Ser
                85                  90                  95

Pro Ile Tyr Phe Gln Ser Phe Gln Ala Leu Leu Asp Ser Asp Glu Ala
            100                 105                 110

Ala Phe Val Ala Pro Gln Ala Thr Leu Asn Ile Ile Lys Gln Phe Gln
        115                 120                 125

Glu Cys Ala Asp Ala Gly Leu Ser Ser Glu Gln Met Ile Phe Phe Thr
    130                 135                 140

Asn His Asp Lys Val Leu Leu Ser Lys Asn Val Asn Ser Arg Leu Ser
145                 150                 155                 160

Ile Gln Gln Ile Ala Ile Ala Val Ser Asp Ile Ile Asn Ser Leu Gln
                165                 170                 175

Ser Ser Tyr Ala Gly Pro Pro Thr Ile Asn Ser Asp Thr Thr Thr Ala
            180                 185                 190

Ser Ala Ala Asp Val Ser Ala Val Ser Thr Lys Met Phe Ala Pro Ala
        195                 200                 205

Thr Ala Gln Gln Val Thr Ala Phe Leu Gln Ser Glu Leu Pro Thr Gln
    210                 215                 220

Ala Thr Ser Cys Tyr Arg
225                 230


<210> SEQ ID NO 31
<211> LENGTH: 374
<212> TYPE: PRT
<213> ORGANISM: Fusarium verticillioides

<400> SEQUENCE: 31

Tyr Leu Val Leu Pro Gly Thr Asp Leu Thr Asp Gln Ser Lys Val Tyr
1               5                   10                  15

Asn Asn Ile Leu Arg Pro Phe Phe Ser Asp Thr Gln Ala Ala His Lys
            20                  25                  30

Val Phe Phe Glu Gln Pro Glu Pro Ser Gly Thr Glu Glu Glu Lys Ala
        35                  40                  45

Ile Ala Lys Glu Asn Asn Leu Asp Ser Arg Arg Leu Phe Phe Leu Lys
    50                  55                  60

Ala Val Ile Lys Pro Leu Gln Ala Arg Ile Ala Ser Asp Thr Val Leu
65                  70                  75                  80

Gln Val Leu Thr Pro Leu Tyr Val Glu Ser Asp Pro Thr Val Leu Gly
                85                  90                  95

His Leu Leu Gly Thr Val Val Gly Gln Ser Glu Gly Glu Arg Pro Val
            100                 105                 110

Ala Lys Ile Leu Gly Asp Leu Gly Ala Ser Asn Glu Ala Ala Leu Lys
        115                 120                 125

Lys Gly Ser Ser Asp Val Phe Phe Ile Pro Leu Asn Val Asp Leu Tyr
    130                 135                 140

Arg Phe Phe Phe Pro Asp Thr Ser Leu Glu Lys Ala Pro Thr Val Thr
145                 150                 155                 160

Leu Asp Thr Thr Ala Leu Val Phe Asn Lys Asp Val Gly Gly Trp Ile
                165                 170                 175
```

-continued

```
Ser Asn Glu Ile Arg Leu Ser Asn Gly Gln Ala Tyr Asn Leu Arg Arg
            180                 185                 190

Ser Asn Gly Gly Leu Thr Glu Cys Phe Tyr Ser Thr Pro Arg Asn Pro
        195                 200                 205

Arg Gln Ser Phe Pro Ser Asn Thr Leu Leu Ala His Asp Thr Ile Lys
    210                 215                 220

Tyr Ala Gln Ser Ser Leu Lys Leu Leu Ser Arg Ala Ala Gly Leu Cys
225                 230                 235                 240

Thr Ser Phe Lys Leu Asn Ile Asp Glu Leu Gln Phe Phe Gln Ser Gln
                245                 250                 255

Glu Leu Asn Thr Asp Leu Ala Ile Asp Leu Gly Asn Ile Asp Trp Lys
            260                 265                 270

Thr Leu Gln Leu Val Gln Arg Tyr Arg Thr Leu Ser Arg Arg Thr Thr
        275                 280                 285

Gly Thr Thr Ser Leu Leu Ser Phe Leu Lys Trp Ala Cys Val Ser Pro
    290                 295                 300

Arg Asp Gly Thr Leu Ile Ala Gln Leu Val Arg Leu Thr Asn Val Ser
305                 310                 315                 320

Gln Thr Gln Ile Lys Asp Tyr Thr Thr Pro Arg Phe Ser Ser Leu Thr
                325                 330                 335

Glu Asp Gln Leu Val Gln Arg Phe Gln Glu Thr Ala Glu Leu Arg His
            340                 345                 350

Leu Leu Asp Ser Val Ala Phe Val His Arg Thr Gly Val Pro Trp Tyr
        355                 360                 365

Asp Ile Pro Thr Leu Val
    370


<210> SEQ ID NO 32
<211> LENGTH: 1233
<212> TYPE: PRT
<213> ORGANISM: Fusarium verticillioides

<400> SEQUENCE: 32

Gly His Leu Glu Gly Gly Pro Leu Ser Thr Asp Phe Pro Met Gln His
1               5                   10                  15

Ala Ser Ser Thr Ala Pro Gly Asn Ala Trp Asn Glu Ala Val Lys Leu
            20                  25                  30

Pro Asp Val Ser Ser Phe Lys Phe Trp Ile Arg Ser Arg Lys Ser Asp
        35                  40                  45

Ser Met Pro Pro Ala Ser Leu Val Ala Pro Ala Pro Pro Ala Pro Ser
    50                  55                  60

Lys Ala Pro Val Pro Ser Thr Ser Ile Leu Val Ile Asp Val Glu Arg
65                  70                  75                  80

Trp Val Asp Ala Gly Lys Gly Gln Asn Pro Arg Tyr Val Asn Tyr Pro
                85                  90                  95

Leu Gly Arg Phe Glu Met Arg Gly Ser Gln Val Ile Leu Val Asn Leu
            100                 105                 110

Gly Thr Ala Asp Val Ser Pro Asp Pro Phe Lys Lys Pro Trp Arg Ser
        115                 120                 125

Thr Ile Pro Thr Lys Phe Ala Lys Met Trp Trp His Met Glu Lys Asp
    130                 135                 140

Lys Asp Pro Ala Val Pro Gly Ile Ala Ile Gly Arg Gly Thr Gly Ala
145                 150                 155                 160

Asp Lys Glu Pro Leu Leu Gly Val Val Thr Lys Leu Met Asp Asn Ile
```

-continued

```
                165                 170                 175

Pro Lys Lys Asp Val His Trp Thr Leu Ser Phe Asn Asp Ser Gln Ala
            180                 185                 190

Lys Asn Ala Thr Gly Phe Val Gln Asp Ile Val Thr Thr Glu Ser Thr
        195                 200                 205

Ile Ser Tyr Ile Thr Tyr Pro Pro Ile Ala Ser Ser Ser Thr Phe Ala
    210                 215                 220

Ser Asp Val Phe Gln His Thr Leu Asp Arg Asp Leu Val Ser Met Ser
225                 230                 235                 240

Thr Met Tyr Asn Gly Leu Asp Gln Val Tyr Ala Phe Leu Gly Ser Val
                245                 250                 255

Pro Pro Asn Asp Thr Tyr Leu Ala Phe Gly Lys Arg Asn Gly Pro Val
            260                 265                 270

His Glu Leu Ser Thr Pro Tyr Ala Leu Tyr Asn Trp Glu Leu Gly Ala
        275                 280                 285

His Ser Ile Met Leu Leu Met Glu Arg Leu Gln Val Thr Gln Gln Tyr
    290                 295                 300

Asp Leu Ala Leu Gln Val Ala His Phe Val Phe Asp Pro Thr Ile Asp
305                 310                 315                 320

Gly Thr Ser Leu Thr Arg Cys Trp Val Phe Pro Pro Phe Lys Glu Leu
                325                 330                 335

Ala Ala Gly Lys Ile Asp Ser Val Glu Asp Ile Leu Lys Leu Leu Glu
            340                 345                 350

Pro Ser Ser Gly Ser Glu Glu Asp Met Lys Thr Ser Ile Leu Glu Trp
        355                 360                 365

Arg Lys Asn Pro Phe Asn Ala His Val Val Ala Arg Gly Arg Pro Leu
    370                 375                 380

Ala Tyr Met Arg Arg Ile Ile Met Lys Tyr Val Glu Ile Leu Ile Ala
385                 390                 395                 400

Ser Gly Asp Val Tyr Phe Arg Gln Asn Thr Leu Glu Thr Leu Pro Leu
                405                 410                 415

Ala Ile Gln Arg Tyr Val Glu Ala Ser His Val Phe Gly Ser Lys Pro
            420                 425                 430

Val Arg Val Pro Lys Leu Ala Lys Pro Val Tyr Lys Ser Tyr Ala Asp
        435                 440                 445

Leu Asp Arg Asp Phe Asn Asp Phe Ser Asn Ala Ala Phe Asp Met Glu
    450                 455                 460

Leu Asp Phe Pro Phe Phe Ser Asp Pro Ala Ser Arg Gly Gly Val Pro
465                 470                 475                 480

Gly Ala Ser Gly Thr Phe Gly Leu Thr Gly Ile Leu Lys Thr Thr Tyr
                485                 490                 495

Phe Cys Val Pro Ser Asn Pro Lys Leu Val Gly Leu Arg Asp Leu Ile
            500                 505                 510

Asp Asp Arg Leu Phe Lys Ile Arg Asn Cys Gln Asp Ile Tyr Gly Val
        515                 520                 525

Val Arg Ser Leu Ala Leu Phe Glu Pro Pro Leu Asp Pro Gly Met Leu
    530                 535                 540

Val Arg Ala Thr Ala Gly Gly Val Asp Ile Ser Gln Leu Val Ser Ser
545                 550                 555                 560

Ile Ala Gly Pro Met Pro Asn Tyr Arg Phe Gln Tyr Leu Leu Gln Lys
                565                 570                 575

Ala Gln Glu Met Cys Ala Glu Val Lys Ser Met Gly Thr Leu Met Leu
            580                 585                 590
```

-continued

```
Ser Ile Lys Glu Arg Lys Asp Val Glu Ala Leu Ala Ser Leu Arg Ala
        595                 600                 605

Arg Gln Asp Lys Val Ile Gln Asn Leu Met Ile Glu Met Lys Glu Thr
    610                 615                 620

Ala Lys Lys Glu Ala Glu Ser Ser Ile Asp Ala Leu Leu Glu Thr Arg
625                 630                 635                 640

Gln Ala Gln Val Ala Arg Leu Glu Tyr Tyr Leu Ala Leu Thr Gly Ser
                645                 650                 655

Asp Asp Lys Ser Ala Pro Asp Glu Lys Glu Asp Trp Glu Asp Ile Ala
            660                 665                 670

Gln Ser Ile Glu Lys Pro Thr Thr Asp Asp Leu Arg Met Thr Ser His
        675                 680                 685

Glu Lys Leu Glu Met Gln Lys Ala Asp Ala Ala Ser Asp Leu Asn Gln
    690                 695                 700

Lys Ala Thr Ile Leu Asp Ile Ala Ala Ser Ile Ile Lys Ile Ile Pro
705                 710                 715                 720

Asp Ile Asn Glu Ala Ala Glu Pro Leu Gly Val Gly Val Ser Ile Asp
                725                 730                 735

Ser Ile Thr Lys Asn Ile Cys Glu Ser Met Met Ile Asn Ser Asn Val
            740                 745                 750

Met Arg Ala Gln Ala Gln His Phe Ser Asp Glu Gly Ala Arg Ala Ser
        755                 760                 765

Arg Thr Gly Gly Leu Ile Lys Gln Leu Gln Glu Arg Arg Leu Gln Ala
    770                 775                 780

Asn Met Ala Gly Arg Asp Ile Lys Glu Thr Asp Lys Gln Ile Leu Thr
785                 790                 795                 800

Ala Arg Ile Arg Val Glu Met Cys Glu Arg Asn Ile Gln Leu Gln Lys
                805                 810                 815

Gln Gln Ala Glu Tyr Ala Arg Asp Thr Glu Glu Trp Leu Arg Thr Lys
            820                 825                 830

Tyr Ser Ser Glu Gln Leu Tyr Ala Trp Met Asp Gly Val Val Arg Asn
        835                 840                 845

Leu Tyr His Gln Thr Tyr Met Ile Ala Asp Asp Leu Ala Gln Lys Ala
    850                 855                 860

Gln Lys Ala Phe Gln Phe Glu Lys Gly Asp Gln Phe Val Asn Ile Ile
865                 870                 875                 880

Ser Pro Cys Tyr Trp Asp Ala Gly Arg Asp Gly Leu Phe Ser Gly Glu
                885                 890                 895

Asn Leu Phe Leu Ser Leu Lys Arg Leu Glu Gly Ala Tyr Ile Glu Gln
            900                 905                 910

Arg Met His Asp Phe Glu Ile Val Lys Asn Ile Ser Leu Arg Gln Val
        915                 920                 925

Arg Pro Trp Ala Leu Ile Asn Leu Arg Glu Thr Gly Ala Ala Glu Phe
    930                 935                 940

Asp Leu Pro Glu Val Leu Phe Asp Phe Asp Phe Ser Gly His Tyr Cys
945                 950                 955                 960

Arg Arg Ile Lys Ser Val Gly Met Thr Ile Pro Cys Ile Val Gly Pro
                965                 970                 975

Tyr Thr Ser Val Asn Ala Thr Leu Thr Leu Leu Glu Tyr Gln Tyr Arg
            980                 985                 990

Ile Lys Ser Asp Ala Lys Gly Ala  Gln Asp Tyr Pro Gln  Lys Ala Thr
        995                 1000                 1005
```

-continued

```
Asp Glu  Arg Phe Gln Thr Asp  Gln Val Pro Ile Pro  Ser Ile Ala
    1010                 1015                 1020

Val Ser  His Gly Gln Gln Asp  Ser Gly Val Leu Asn  Leu Asp Phe
    1025                 1030                 1035

Lys Asp  Glu Arg Tyr Met Pro  Phe Glu Gly Ala Gly  Ala Val Ser
    1040                 1045                 1050

Arg Trp  Arg Leu Glu Leu Pro  Thr Thr Ile Lys Gln  Phe Asp Tyr
    1055                 1060                 1065

Asn Pro  Ile Ser Asp Ile Val  Leu His Met Lys Tyr  Thr Ala Ile
    1070                 1075                 1080

Gln Gly  Cys Ala Ala Phe Arg  Lys Ala Ala Ala Glu  Ser Ala Ala
    1085                 1090                 1095

Ala Gly  Leu Ser Leu Asn Glu  Gly Met Phe Ala Val  Leu Asp Leu
    1100                 1105                 1110

Pro Asn  Glu Phe Pro Ser Glu  Trp His Arg Leu Val  Met Ala Asp
    1115                 1120                 1125

Lys Thr  Gln Pro Ser Thr Met  Pro Leu Leu Ser Leu  Gln Asp Arg
    1130                 1135                 1140

Leu Pro  Phe Phe Thr Lys Gly  Lys Ser Ile Lys Ala  Gly Ser Val
    1145                 1150                 1155

Ser Val  His Ile Glu Ser Ser  Gly Ile Asn Leu Glu  Glu Asp Ile
    1160                 1165                 1170

Thr Leu  Thr Ala Ala Asn Arg  Leu Asn Leu Lys Ala  Gly Thr Gly
    1175                 1180                 1185

Ile Gly  Ser Phe Gln Val Ala  Thr Thr Ser Thr Asn  Met Arg Gln
    1190                 1195                 1200

Pro Val  Lys Asp Trp Arg Leu  Thr Leu Ser Ser Lys  Ala Met Asn
    1205                 1210                 1215

Ala Ser  Ile Ser Arg Val Leu  Ile Leu Tyr Arg Tyr  Phe Leu Val
    1220                 1225                 1230
```

<210> SEQ ID NO 33
<211> LENGTH: 7704
<212> TYPE: DNA
<213> ORGANISM: Fusarium verticillioides
<220> FEATURE:
<221> NAME/KEY: misc_feature
<222> LOCATION: (22)..(24)
<223> OTHER INFORMATION: Beginning of the coding region corresponding to the first Alanine of the encoded putative TC fused ClassB/Class C protein in SEQ ID NO:34 (GCC)
<220> FEATURE:
<221> NAME/KEY: misc_feature
<222> LOCATION: (5483)..(6141)
<223> OTHER INFORMATION: n = a, g, c, or t (large gap in the DNA sequence, indicated as a string of 659 n's)
<220> FEATURE:
<221> NAME/KEY: misc_feature
<222> LOCATION: (6203)..(6205)
<223> OTHER INFORMATION: In-frame Histidine codon (CAT) that starts the second portion of the putative TC fused ClassB/Class C protein

<400> SEQUENCE: 33

```
gacagcaatt gcaggccttg agccatagtt atgtctggca agatgaatcg caaatccaga     60

taccatccga gtgatgctgt agcacctaat accggcagct ccacgaaaag tccgccctcg    120

cattcagcgt ccacaccggc aggcaaggcc tcgcaaggag gaggccaaca tgctgcacag    180

acaggacaga gacttccagc tgtcatctcg accccaactc tacaaaaggg catcgccgga    240

ggcagtcatc gaccaattga ccagaccttc aagatgaacc ccttgaacgg tacaatggct    300
```

-continued

```
ttggccttac caatcccagt aactgagggc cgtggcgggt ttggtccgaa gttggaactc    360
tcgtacaatt cgggctcggg aaatggttac ttcggacttg gctggcaact gaatttgagt    420
tccatcaccc gtatgacctc caagcgtact cccatgtacg atgagaccga cactttcttg    480
ctgagcggcg aggacgagtt ggtccgtatg ggtgaccctg aacgcattgg cgatgaattt    540
tcggttcagt cgtatcaacc tcgagtcatg ggagatgctc tgaagatcga acaatggagt    600
cgattgacag atccttccga tgtccactgg aggacgattt cgggctctaa tgtgacttgc    660
atttatggcc agtcgagcca aacgcgaacc tcctgcaagg atcagtctgg ccgcacctat    720
atcttctctt ggctactatg cagttcatac gatcccttcg ggaacttaat cacctatgaa    780
tacaaggatg agaacacgca gggttttgac accttgtcgc ctgaagcgcg attgcaggaa    840
cagaatcgag ccatggaaac agttggacgt gcaaagtact tgaaggcgat caagtacggc    900
aatgcacttc ctaatcgaga tattagtagt tggaagccac tcgaacatga cgggcaatac    960
cacttccaag tagttcttga ctacggagaa catgacatcg acaacccgga tgttcaggca   1020
gaatcaccct gggtggtcag acaagacaga ttctcaacag cggcagccgg ctttgaagta   1080
cgctggctac ggctgtgtcg ccgcattctc atgttccatt actttccgaa ggagctgtca   1140
gagaagcatt gtctcgtgcg ttctgtttcg atgcagtatc aagagtcatc cgtggcctct   1200
ttcttatctt cactaacaga acgggggcat tggttcaatc acgaaacgaa tgagatgcaa   1260
catcaagcgc taccgccata cactttccag tataacatgc cgatcgatgt gtccagcgcc   1320
aaagtcgagc acatgaatac cgataatctg ccgaatttac ccagcccagg tgggaatgag   1380
tggcaatggg tggatttgtt gggagaggga gcgcctgggc tacttgaaca acgtcccgac   1440
ggttcttgga acttccgtaa gaactacaat atcatagatg aatcatcagt tccgaagttc   1500
gattcatcta tgaccatacc tgcccgaccg aaccgaaacc tgggcaaatc ggcttacttt   1560
gaggacttga accaagatgg aaagctcgaa ctagtgtgtc tagacgacat aaacaggttg   1620
gaaggcttct accaccaata tgatgaggga tggattggtt acactacctt ctcgtcaact   1680
ccaaatcgag ataccaccgc agtcttcttc aagcagcttg atctcactgg aaatgggctt   1740
gcagatcttg tggcagttga tgccgtgaat agagagatta tgtggcaaga aaacttgggc   1800
gcagctggat ttgctccatt gagggaatgc gtcaacagta cgggtgttcc gcagctgatg   1860
tctgatgacc ctacggtaca ggtcactctt gctgatatga caggtgacgg tcggtcagat   1920
gtcgtacagg tctcttcagg ctatgtcaag tactggcaga atctatcata cggacaattc   1980
agtgacccgg tctgtatgta caatgcccca aagctggata gtgatatctc cattgccgaa   2040
agaatacgcc ttgttgatat caatggatcg ggtaccaacg atctgatcta catgcctgca   2100
ggtggtggtc tgcacgttta tttcaaccaa gcaggaaacg gctggagtga tccacagatt   2160
ctggagtcat tcccgtcggt tgaccagctg agtagcgtct ctacggtgga cctgtttggt   2220
aaagggacgg catgtttatg ttggagcggc aaggtacttg ggtcaaactc agcgcagact   2280
ctctactatg tcgaccttgc ccctggacca aagcccaact gcctagctac ataccaaaat   2340
gggaggggat cgcgagtaga agtctcgtat cggtcttcca actggtatta cctccaggat   2400
gagcgtgcag gagcaccatg ggctacaaaa atagggtttc ccgttcagtg tgtcagtcaa   2460
gtcaggttct tggacgatac aactggactt ttgaacacca agagtttcac ttatcatgat   2520
ggctactacg atgctcccga tagggagttt agaggctttg ggatggtcga acagcttgaa   2580
tcgactgttt tcaacgccga tacgtcatca gaataccgcc aaacagctac catcaccaaa   2640
acctggtttc atacaggggc aatgacacca actaagtgcc gtctagagcg agcaacctct   2700
```

-continued

```
ggagctcttt tcggttctta ctggtgcgta gagtcattca agctcgaaga tcggcgtgac   2760
tgctgccggg ccctcaaagg aatgcagctc cgagaagaaa ttattggcca cgttgggact   2820
gcacttacag aacatgccta tcaagtgaca gatactgctc accaagtggt ccagctctct   2880
cctaggaaag gcgtattgca gccaggcaca tatcgttgcg tgccacgcga aatactcaag   2940
actcacaatg atcggtcgcc ggaatcatta ccacgctaca gccacgaact catcctagag   3000
acgaacagat tcaatgatag actgaagtca atggaaattt tctatgggca ctcaggcgga   3060
gaggccctgg attctgtcca gaaggaaagt gtcctgacgt acatagagaa cgaatattgt   3120
ctgcctgtcc tcgacaagga caatgggatc ttcgtaaagc caatgccgtc agtcactcgc   3180
aaatatcgta ttgttggtct ggactggtca agcaataaca tacaatcggc ctttaccaag   3240
tttactagtg gcagtttcca ggtattgcgg agtattcccg aagtcccata cacagatcag   3300
attctacctc catgttcttc agaagcccga gtaaagatcg aagagagacg gacattatat   3360
cgcaaccagg acttctctca agtacagcca ttacctctgg ggcaatttca ggcttactcg   3420
gtgatccatg gtattcttga cctagctgga ggagacagat ggtttcaagc cctgctcaag   3480
gactatttac ctgataattc agacttggat agctttatga ctacatatgg gtatatcaaa   3540
acaacggagg aaaacggcac tactctttgg tggcgccttt cttcgcgtaa tctttttggt   3600
cctgacgcaa aaaatgaact cgccaaggcc agaaagtgct tttacacacc gacgatcacc   3660
caggatccct ttgacaaccg gagtacagtt cagatggatg actataacct actgccaagg   3720
ctttctactg atgcggttgg aaatgtcacc aatgtggata tggattacag atacatgtct   3780
ccatcgtgtg tcgttgatcc aaaccgcaat cgaaccacct atagctacga cctgttgggt   3840
agagtcgtgg caacagcccg atctgggaaa gagaaagaat cagttggtga caatctcaac   3900
acaacagtca agctaccctc acaagctgac aaggatgttt tctttgcatg tccgacgcaa   3960
gaggctgctt tcaagctttt aggtggtgcc actagttacc gcctgtacta cgatgctcaa   4020
gccaagcatc ccagagcgct tttggatacc agtcccactg cctttatcga catcagtcga   4080
acttcccacc atgcggatgg agccagtgct agtgatattt ccatatcgat cacttacctg   4140
gatggcaatc ttgctgagct gcaaacgatc agcttgactg gcacagtcga ggatggatat   4200
aagtggaaca ttggtgaatg gagtttacga aatagcagag gggacccggt tcgcacgttt   4260
cagccatgct ataccgattc gcatgggttc attcattctt ctgagagcca gtcgaaaatg   4320
accaccatga tctatgatcc cctgggcaga ctagtcggta cattctatcc tgaccacgca   4380
tactcgaaag tgagatatga gacttgggca actacaaact acgacagagg ggatacagtc   4440
ttgatggacc tcgccgagga caaagatctc agtatctata ccagcgttct cgcaaaggag   4500
aactatagtc ccagctggca cgctagcgcg tcgacccaag agctttcacg cagggctgta   4560
gcaaaggttt cggaggttta cagtgagaca cccgataaga cttatctgga tgcgcaagag   4620
cgtccaattc taagaatcag agattgcaaa acggccaaga taaagacgcg gagtagttac   4680
agtctagcag ggcatttggc ccaaacaaca gatggtagag gtcgtcttgc tgaaagcgta   4740
acctctgact tgctaggccg tgacatactc cgtcaaggta tggacactgg catggttttt   4800
accttccacg actgcatgga ccgcactgtg atactgatgg atggccgtaa ctggaggcaa   4860
cggtcggtat acgatgctgc aggtagaaag acccatctct ggctctggca acacggtgga   4920
accgaattct tggcagaatt aattcgctat ggagaggctg ttgaaaacgc tgaggctttg   4980
aacctacgtg gaaaggtatg tgagatccgg gatcaatcag gaatccagaa gaacaaagtc   5040
```

-continued

```
tttgacttca aaggaaactt tgtcgagtca actacccagt tcacgactga atacaaaggc   5100
tcgatcaact ggggagctga gagcaacccc aagctggacc ccgaggttta cacggttcga   5160
aaggcttatg atgccatgga cagagtggtc gagtcatatg acgtcgaagg tgcagtcaca   5220
aggcatagtt atggcatctc tggacagctc aatcgggttt catacaagag cagagggcag   5280
aaggagtatc cctggaaaga ttacatgagc gacatcaggt atgcggctga tggacaaccg   5340
gagcaaatcc tgtacggaaa cggtgtcttg gcgacctttc agtatgactt agcgaccaga   5400
ctcatgaatc gaaagagact catccgccag aatgacaaga gagtcatgga agacacacaa   5460
tattcacacg atgttatgca tcnnnnnnnn nnnnnnnnnn nnnnnnnnnn nnnnnnnnnn   5520
nnnnnnnnnn nnnnnnnnnn nnnnnnnnnn nnnnnnnnnn nnnnnnnnnn nnnnnnnnnn   5580
nnnnnnnnnn nnnnnnnnnn nnnnnnnnnn nnnnnnnnnn nnnnnnnnnn nnnnnnnnnn   5640
nnnnnnnnnn nnnnnnnnnn nnnnnnnnnn nnnnnnnnnn nnnnnnnnnn nnnnnnnnnn   5700
nnnnnnnnnn nnnnnnnnnn nnnnnnnnnn nnnnnnnnnn nnnnnnnnnn nnnnnnnnnn   5760
nnnnnnnnnn nnnnnnnnnn nnnnnnnnnn nnnnnnnnnn nnnnnnnnnn nnnnnnnnnn   5820
nnnnnnnnnn nnnnnnnnnn nnnnnnnnnn nnnnnnnnnn nnnnnnnnnn nnnnnnnnnn   5880
nnnnnnnnnn nnnnnnnnnn nnnnnnnnnn nnnnnnnnnn nnnnnnnnnn nnnnnnnnnn   5940
nnnnnnnnnn nnnnnnnnnn nnnnnnnnnn nnnnnnnnnn nnnnnnnnnn nnnnnnnnnn   6000
nnnnnnnnnn nnnnnnnnnn nnnnnnnnnn nnnnnnnnnn nnnnnnnnnn nnnnnnnnnn   6060
nnnnnnnnnn nnnnnnnnnn nnnnnnnnnn nnnnnnnnnn nnnnnnnnnn nnnnnnnnnn   6120
nnnnnnnnnn nnnnnnnnnn nccagttacc ggcatagtgc agatagcagg gaaggagtcc   6180
caggtaggat gatggttgat agcattgctc aaaggggaaa acgccaccca ggcccaaaag   6240
gtcaaatgtg ggtgcggagc tatggcgtat gaggaaaaga gtcgggtcaa ggaaggcgag   6300
tctgaaaata ggctcagcta cacttcaaag agtggtcaaa cagaaaaatg gacgtacggc   6360
gatgggagcc aacactggct ttgctggtag tgtcactgcc ggtggcggga tgcattccat   6420
gtactgggat cctttcaacc gtctcaagtc ttgctcaagg caagtcaaga agagtggtgt   6480
accagaaact acatggtatg tgtacaacag tgaaggaaag agggtacgga aaataacgga   6540
gcgatcatcg tccgggtcgg atgatccaag aatgctgaaa gaaacaacct tcttttccaa   6600
tttgcacata taccagtgca agactgggga cggatctggc cacagcaagg ataaacgcta   6660
ccatctgatc catagtgccg aacagaaact cgtggccatt gctgaagagg acaaggctgt   6720
gtcttcagag tcttcccctc tagtcagata tcacatgtcc gacaagctag agttagatca   6780
ttcggggctt gtcataactt acgaggagta ttcacccttt ggatcaagct ccttttctct   6840
tcgacgatcg gaacaagagg catcccgcaa gtacagattt gctggctacg agagagataa   6900
agagaccggg ctctactact gcaacgcgcg gtactatgct ccgtggcttg ggcgatggat   6960
gtcaccagac cctatcggaa ccaaggatgg gctaaacttg tactgctact gcggtaatga   7020
cccggtgaac tacattgatc ctaccggaac tacgggtctg ttcaaggcca tgcgaatagc   7080
agcagtgcca ctagccaagg ccgcgatgag aatgaacgaa atcacaaaat cgggtgcagt   7140
gtttgagccc taccagcgat cctggctctc ggagatttcc aagccgagtc gaggctgctc   7200
ggcggctttc ctggatgatg ccggattctt gactgagaat gaaaagttga ggaacctgca   7260
ggaatacaac gcgaagatgg aacagcaggt acaacgtccg ctgagtcata tgtctccgga   7320
actcatgaag gaaatgggaa cgtacgacat taagcagtac ctcactgaat ttgggaagga   7380
aggtctaatt cagggaggca aggagctggc cttatttggt gctgccgcga tcggcacccg   7440
```

-continued

```
gattccccta ctaagcatgt cctcgccttt aggatttgtg cccggtattg tttatggcgt   7500

tgcctgcgat acggtcatag atgctgtagc ggagaagatt cgtgagggaa tggcgggtcc   7560

aaatgagtac gcgcaggaag acgcacagag ccacgtagaa acgatgaaca agttacggca   7620

gggtccgcgg gaattcgcac agggcttagc gcaggattgg ttcatgggcc atttccagga   7680

taaatgagat catcatttgc tttc                                          7704


<210> SEQ ID NO 34
<211> LENGTH: 1820
<212> TYPE: PRT
<213> ORGANISM: Fusarium verticillioides

<400> SEQUENCE: 34

Ala Ile Val Met Ser Gly Lys Met Asn Arg Lys Ser Arg Tyr His Pro
1               5                   10                  15

Ser Asp Ala Val Ala Pro Asn Thr Gly Ser Ser Thr Lys Ser Pro Pro
            20                  25                  30

Ser His Ser Ala Ser Thr Pro Ala Gly Lys Ala Ser Gln Gly Gly Gly
        35                  40                  45

Gln His Ala Ala Gln Thr Gly Gln Arg Leu Pro Ala Val Ile Ser Thr
    50                  55                  60

Pro Thr Leu Gln Lys Gly Ile Ala Gly Gly Ser His Arg Pro Ile Asp
65                  70                  75                  80

Gln Thr Phe Lys Met Asn Pro Leu Asn Gly Thr Met Ala Leu Ala Leu
                85                  90                  95

Pro Ile Pro Val Thr Glu Gly Arg Gly Gly Phe Gly Pro Lys Leu Glu
            100                 105                 110

Leu Ser Tyr Asn Ser Gly Ser Gly Asn Gly Tyr Phe Gly Leu Gly Trp
        115                 120                 125

Gln Leu Asn Leu Ser Ser Ile Thr Arg Met Thr Ser Lys Arg Thr Pro
    130                 135                 140

Met Tyr Asp Glu Thr Asp Thr Phe Leu Leu Ser Gly Glu Asp Glu Leu
145                 150                 155                 160

Val Arg Met Gly Asp Pro Glu Arg Ile Gly Asp Glu Phe Ser Val Gln
                165                 170                 175

Ser Tyr Gln Pro Arg Val Met Gly Asp Ala Leu Lys Ile Glu Gln Trp
            180                 185                 190

Ser Arg Leu Thr Asp Pro Ser Asp Val His Trp Arg Thr Ile Ser Gly
        195                 200                 205

Ser Asn Val Thr Cys Ile Tyr Gly Gln Ser Ser Gln Thr Arg Thr Ser
    210                 215                 220

Cys Lys Asp Gln Ser Gly Arg Thr Tyr Ile Phe Ser Trp Leu Leu Cys
225                 230                 235                 240

Ser Ser Tyr Asp Pro Phe Gly Asn Leu Ile Thr Tyr Glu Tyr Lys Asp
                245                 250                 255

Glu Asn Thr Gln Gly Phe Asp Thr Leu Ser Pro Glu Ala Arg Leu Gln
            260                 265                 270

Glu Gln Asn Arg Ala Met Glu Thr Val Gly Arg Ala Lys Tyr Leu Lys
        275                 280                 285

Ala Ile Lys Tyr Gly Asn Ala Leu Pro Asn Arg Asp Ile Ser Ser Trp
    290                 295                 300

Lys Pro Leu Glu His Asp Gly Gln Tyr His Phe Gln Val Val Leu Asp
305                 310                 315                 320
```

-continued

```
Tyr Gly Glu His Asp Ile Asp Asn Pro Asp Val Gln Ala Glu Ser Pro
                325                 330                 335

Trp Val Val Arg Gln Asp Arg Phe Ser Thr Ala Ala Ala Gly Phe Glu
            340                 345                 350

Val Arg Trp Leu Arg Leu Cys Arg Arg Ile Leu Met Phe His Tyr Phe
        355                 360                 365

Pro Lys Glu Leu Ser Glu Lys His Cys Leu Val Arg Ser Val Ser Met
    370                 375                 380

Gln Tyr Gln Glu Ser Ser Val Ala Ser Phe Leu Ser Ser Leu Thr Glu
385                 390                 395                 400

Arg Gly His Trp Phe Asn His Glu Thr Asn Glu Met Gln His Gln Ala
                405                 410                 415

Leu Pro Pro Tyr Thr Phe Gln Tyr Asn Met Pro Ile Asp Val Ser Ser
            420                 425                 430

Ala Lys Val Glu His Met Asn Thr Asp Asn Leu Pro Asn Leu Pro Ser
        435                 440                 445

Pro Gly Gly Asn Glu Trp Gln Trp Val Asp Leu Leu Gly Glu Gly Ala
    450                 455                 460

Pro Gly Leu Leu Glu Gln Arg Pro Asp Gly Ser Trp Asn Phe Arg Lys
465                 470                 475                 480

Asn Tyr Asn Ile Ile Asp Glu Ser Ser Val Pro Lys Phe Asp Ser Ser
                485                 490                 495

Met Thr Ile Pro Ala Arg Pro Asn Arg Asn Leu Gly Lys Ser Ala Tyr
            500                 505                 510

Phe Glu Asp Leu Asn Gln Asp Gly Lys Leu Glu Leu Val Cys Leu Asp
        515                 520                 525

Asp Ile Asn Arg Leu Glu Gly Phe Tyr His Gln Tyr Asp Glu Gly Trp
    530                 535                 540

Ile Gly Tyr Thr Thr Phe Ser Ser Thr Pro Asn Arg Asp Thr Thr Ala
545                 550                 555                 560

Val Phe Phe Lys Gln Leu Asp Leu Thr Gly Asn Gly Leu Ala Asp Leu
                565                 570                 575

Val Ala Val Asp Ala Val Asn Arg Glu Ile Met Trp Gln Glu Asn Leu
            580                 585                 590

Gly Ala Ala Gly Phe Ala Pro Leu Arg Glu Cys Val Asn Ser Thr Gly
        595                 600                 605

Val Pro Gln Leu Met Ser Asp Asp Pro Thr Val Gln Val Thr Leu Ala
    610                 615                 620

Asp Met Thr Gly Asp Gly Arg Ser Asp Val Val Gln Val Ser Ser Gly
625                 630                 635                 640

Tyr Val Lys Tyr Trp Gln Asn Leu Ser Tyr Gly Gln Phe Ser Asp Pro
                645                 650                 655

Val Cys Met Tyr Asn Ala Pro Lys Leu Asp Ser Asp Ile Ser Ile Ala
            660                 665                 670

Glu Arg Ile Arg Leu Val Asp Ile Asn Gly Ser Gly Thr Asn Asp Leu
        675                 680                 685

Ile Tyr Met Pro Ala Gly Gly Gly Leu His Val Tyr Phe Asn Gln Ala
    690                 695                 700

Gly Asn Gly Trp Ser Asp Pro Gln Ile Leu Glu Ser Phe Pro Ser Val
705                 710                 715                 720

Asp Gln Leu Ser Ser Val Ser Thr Val Asp Leu Phe Gly Lys Gly Thr
                725                 730                 735

Ala Cys Leu Cys Trp Ser Gly Lys Val Leu Gly Ser Asn Ser Ala Gln
```

-continued

```
            740                 745                 750

Thr Leu Tyr Tyr Val Asp Leu Ala Pro Gly Pro Lys Pro Asn Cys Leu
        755                 760                 765

Ala Thr Tyr Gln Asn Gly Arg Gly Ser Arg Val Glu Val Ser Tyr Arg
    770                 775                 780

Ser Ser Asn Trp Tyr Tyr Leu Gln Asp Glu Arg Ala Gly Ala Pro Trp
785                 790                 795                 800

Ala Thr Lys Ile Gly Phe Pro Val Gln Cys Val Ser Gln Val Arg Phe
                805                 810                 815

Leu Asp Asp Thr Thr Gly Leu Leu Asn Thr Lys Ser Phe Thr Tyr His
            820                 825                 830

Asp Gly Tyr Tyr Asp Ala Pro Asp Arg Glu Phe Arg Gly Phe Gly Met
        835                 840                 845

Val Glu Gln Leu Glu Ser Thr Val Phe Asn Ala Asp Thr Ser Ser Glu
    850                 855                 860

Tyr Arg Gln Thr Ala Thr Ile Thr Lys Thr Trp Phe His Thr Gly Ala
865                 870                 875                 880

Met Thr Pro Thr Lys Cys Arg Leu Glu Arg Ala Thr Ser Gly Ala Leu
                885                 890                 895

Phe Gly Ser Tyr Trp Cys Val Glu Ser Phe Lys Leu Glu Asp Arg Arg
            900                 905                 910

Asp Cys Cys Arg Ala Leu Lys Gly Met Gln Leu Arg Glu Glu Ile Ile
        915                 920                 925

Gly His Val Gly Thr Ala Leu Thr Glu His Ala Tyr Gln Val Thr Asp
    930                 935                 940

Thr Ala His Gln Val Val Gln Leu Ser Pro Arg Lys Gly Val Leu Gln
945                 950                 955                 960

Pro Gly Thr Tyr Arg Cys Val Pro Arg Glu Ile Leu Lys Thr His Asn
                965                 970                 975

Asp Arg Ser Pro Glu Ser Leu Pro Arg Tyr Ser His Glu Leu Ile Leu
            980                 985                 990

Glu Thr Asn Arg Phe Asn Asp Arg  Leu Lys Ser Met Glu  Ile Phe Tyr
        995                 1000                1005

Gly His  Ser Gly Gly Glu Ala  Leu Asp Ser Val Gln  Lys Glu Ser
    1010                 1015                 1020

Val Leu  Thr Tyr Ile Glu Asn  Glu Tyr Cys Leu Pro  Val Leu Asp
    1025                 1030                 1035

Lys Asp  Asn Gly Ile Phe Val  Lys Pro Met Pro Ser  Val Thr Arg
    1040                 1045                 1050

Lys Tyr  Arg Ile Val Gly Leu  Asp Trp Ser Ser Asn  Asn Ile Gln
    1055                 1060                 1065

Ser Ala  Phe Thr Lys Phe Thr  Ser Gly Ser Phe Gln  Val Leu Arg
    1070                 1075                 1080

Ser Ile  Pro Glu Val Pro Tyr  Thr Asp Gln Ile Leu  Pro Pro Cys
    1085                 1090                 1095

Ser Ser  Glu Ala Arg Val Lys  Ile Glu Glu Arg Arg  Thr Leu Tyr
    1100                 1105                 1110

Arg Asn  Gln Asp Phe Ser Gln  Val Gln Pro Leu Pro  Leu Gly Gln
    1115                 1120                 1125

Phe Gln  Ala Tyr Ser Val Ile  His Gly Ile Leu Asp  Leu Ala Gly
    1130                 1135                 1140

Gly Asp  Arg Trp Phe Gln Ala  Leu Leu Lys Asp Tyr  Leu Pro Asp
    1145                 1150                 1155
```

-continued

Asn Ser Asp Leu Asp Ser Phe Met Thr Thr Tyr Gly Tyr Ile Lys
1160 1165 1170

Thr Thr Glu Glu Asn Gly Thr Thr Leu Trp Trp Arg Leu Ser Ser
1175 1180 1185

Arg Asn Leu Phe Gly Pro Asp Ala Lys Asn Glu Leu Ala Lys Ala
1190 1195 1200

Arg Lys Cys Phe Tyr Thr Pro Thr Ile Thr Gln Asp Pro Phe Asp
1205 1210 1215

Asn Arg Ser Thr Val Gln Met Asp Asp Tyr Asn Leu Leu Pro Arg
1220 1225 1230

Leu Ser Thr Asp Ala Val Gly Asn Val Thr Asn Val Asp Met Asp
1235 1240 1245

Tyr Arg Tyr Met Ser Pro Ser Cys Val Val Asp Pro Asn Arg Asn
1250 1255 1260

Arg Thr Thr Tyr Ser Tyr Asp Leu Leu Gly Arg Val Val Ala Thr
1265 1270 1275

Ala Arg Ser Gly Lys Glu Lys Glu Ser Val Gly Asp Asn Leu Asn
1280 1285 1290

Thr Thr Val Lys Leu Pro Ser Gln Ala Asp Lys Asp Val Phe Phe
1295 1300 1305

Ala Cys Pro Thr Gln Glu Ala Ala Phe Lys Leu Leu Gly Gly Ala
1310 1315 1320

Thr Ser Tyr Arg Leu Tyr Tyr Asp Ala Gln Ala Lys His Pro Arg
1325 1330 1335

Ala Leu Leu Asp Thr Ser Pro Thr Ala Phe Ile Asp Ile Ser Arg
1340 1345 1350

Thr Ser His His Ala Asp Gly Ala Ser Ala Ser Asp Ile Ser Ile
1355 1360 1365

Ser Ile Thr Tyr Leu Asp Gly Asn Leu Ala Glu Leu Gln Thr Ile
1370 1375 1380

Ser Leu Thr Gly Thr Val Glu Asp Gly Tyr Lys Trp Asn Ile Gly
1385 1390 1395

Glu Trp Ser Leu Arg Asn Ser Arg Gly Asp Pro Val Arg Thr Phe
1400 1405 1410

Gln Pro Cys Tyr Thr Asp Ser His Gly Phe Ile His Ser Ser Glu
1415 1420 1425

Ser Gln Ser Lys Met Thr Thr Met Ile Tyr Asp Pro Leu Gly Arg
1430 1435 1440

Leu Val Gly Thr Phe Tyr Pro Asp His Ala Tyr Ser Lys Val Arg
1445 1450 1455

Tyr Glu Thr Trp Ala Thr Thr Asn Tyr Asp Arg Gly Asp Thr Val
1460 1465 1470

Leu Met Asp Leu Ala Glu Asp Lys Asp Leu Ser Ile Tyr Thr Ser
1475 1480 1485

Val Leu Ala Lys Glu Asn Tyr Ser Pro Ser Trp His Ala Ser Ala
1490 1495 1500

Ser Thr Gln Glu Leu Ser Arg Arg Ala Val Ala Lys Val Ser Glu
1505 1510 1515

Val Tyr Ser Glu Thr Pro Asp Lys Thr Tyr Leu Asp Ala Gln Glu
1520 1525 1530

Arg Pro Ile Leu Arg Ile Arg Asp Cys Lys Thr Ala Lys Ile Lys
1535 1540 1545

-continued

```
Thr Arg  Ser Ser Tyr Ser Leu  Ala Gly His Leu Ala  Gln Thr Thr
    1550                 1555                 1560

Asp Gly  Arg Gly Arg Leu Ala  Glu Ser Val Thr Ser  Asp Leu Leu
    1565                 1570                 1575

Gly Arg  Asp Ile Leu Arg Gln  Gly Met Asp Thr Gly  Met Val Phe
    1580                 1585                 1590

Thr Phe  His Asp Cys Met Asp  Arg Thr Val Ile Leu  Met Asp Gly
    1595                 1600                 1605

Arg Asn  Trp Arg Gln Arg Ser  Val Tyr Asp Ala Ala  Gly Arg Lys
    1610                 1615                 1620

Thr His  Leu Trp Leu Trp Gln  His Gly Gly Thr Glu  Phe Leu Ala
    1625                 1630                 1635

Glu Leu  Ile Arg Tyr Gly Glu  Ala Val Glu Asn Ala  Glu Ala Leu
    1640                 1645                 1650

Asn Leu  Arg Gly Lys Val Cys  Glu Ile Arg Asp Gln  Ser Gly Ile
    1655                 1660                 1665

Gln Lys  Asn Lys Val Phe Asp  Phe Lys Gly Asn Phe  Val Glu Ser
    1670                 1675                 1680

Thr Thr  Gln Phe Thr Thr Glu  Tyr Lys Gly Ser Ile  Asn Trp Gly
    1685                 1690                 1695

Ala Glu  Ser Asn Pro Lys Leu  Asp Pro Glu Val Tyr  Thr Val Arg
    1700                 1705                 1710

Lys Ala  Tyr Asp Ala Met Asp  Arg Val Val Glu Ser  Tyr Asp Val
    1715                 1720                 1725

Glu Gly  Ala Val Thr Arg His  Ser Tyr Gly Ile Ser  Gly Gln Leu
    1730                 1735                 1740

Asn Arg  Val Ser Tyr Lys Ser  Arg Gly Gln Lys Glu  Tyr Pro Trp
    1745                 1750                 1755

Lys Asp  Tyr Met Ser Asp Ile  Arg Tyr Ala Ala Asp  Gly Gln Pro
    1760                 1765                 1770

Glu Gln  Ile Leu Tyr Gly Asn  Gly Val Leu Ala Thr  Phe Gln Tyr
    1775                 1780                 1785

Asp Leu  Ala Thr Arg Leu Met  Asn Arg Lys Arg Leu  Ile Arg Gln
    1790                 1795                 1800

Asn Asp  Lys Arg Val Met Glu  Asp Thr Gln Tyr Ser  His Asp Val
    1805                 1810                 1815

Met His
    1820


<210> SEQ ID NO 35
<211> LENGTH: 494
<212> TYPE: PRT
<213> ORGANISM: Fusarium verticillioides

<400> SEQUENCE: 35

His Cys Ser Lys Gly Lys Thr Pro Pro Arg Pro Lys Arg Ser Asn Val
1               5                   10                  15

Gly Ala Glu Leu Trp Arg Met Arg Lys Arg Val Gly Ser Arg Lys Ala
            20                  25                  30

Ser Leu Lys Ile Gly Ser Ala Thr Leu Gln Arg Val Val Lys Gln Lys
        35                  40                  45

Asn Gly Arg Thr Ala Met Gly Ala Asn Thr Gly Phe Ala Gly Ser Val
    50                  55                  60

Thr Ala Gly Gly Gly Met His Ser Met Tyr Trp Asp Pro Phe Asn Arg
65                  70                  75                  80
```

-continued

```
Leu Lys Ser Cys Ser Arg Gln Val Lys Lys Ser Gly Val Pro Glu Thr
                85                  90                  95

Thr Trp Tyr Val Tyr Asn Ser Glu Gly Lys Arg Val Arg Lys Ile Thr
            100                 105                 110

Glu Arg Ser Ser Ser Gly Ser Asp Asp Pro Arg Met Leu Lys Glu Thr
        115                 120                 125

Thr Phe Phe Ser Asn Leu His Ile Tyr Gln Cys Lys Thr Gly Asp Gly
    130                 135                 140

Ser Gly His Ser Lys Asp Lys Arg Tyr His Leu Ile His Ser Ala Glu
145                 150                 155                 160

Gln Lys Leu Val Ala Ile Ala Glu Glu Asp Lys Ala Val Ser Ser Glu
                165                 170                 175

Ser Ser Pro Leu Val Arg Tyr His Met Ser Asp Lys Leu Glu Leu Asp
            180                 185                 190

His Ser Gly Leu Val Ile Thr Tyr Glu Glu Tyr Ser Pro Phe Gly Ser
        195                 200                 205

Ser Ser Phe Ser Leu Arg Arg Ser Glu Gln Glu Ala Ser Arg Lys Tyr
    210                 215                 220

Arg Phe Ala Gly Tyr Glu Arg Asp Lys Glu Thr Gly Leu Tyr Tyr Cys
225                 230                 235                 240

Asn Ala Arg Tyr Tyr Ala Pro Trp Leu Gly Arg Trp Met Ser Pro Asp
                245                 250                 255

Pro Ile Gly Thr Lys Asp Gly Leu Asn Leu Tyr Cys Tyr Cys Gly Asn
            260                 265                 270

Asp Pro Val Asn Tyr Ile Asp Pro Thr Gly Thr Thr Gly Leu Phe Lys
        275                 280                 285

Ala Met Arg Ile Ala Ala Val Pro Leu Ala Lys Ala Ala Met Arg Met
    290                 295                 300

Asn Glu Ile Thr Lys Ser Gly Ala Val Phe Glu Pro Tyr Gln Arg Ser
305                 310                 315                 320

Trp Leu Ser Glu Ile Ser Lys Pro Ser Arg Gly Cys Ser Ala Ala Phe
                325                 330                 335

Leu Asp Asp Ala Gly Phe Leu Thr Glu Asn Glu Lys Leu Arg Asn Leu
            340                 345                 350

Gln Glu Tyr Asn Ala Lys Met Glu Gln Gln Val Gln Arg Pro Leu Ser
        355                 360                 365

His Met Ser Pro Glu Leu Met Lys Glu Met Gly Thr Tyr Asp Ile Lys
    370                 375                 380

Gln Tyr Leu Thr Glu Phe Gly Lys Glu Gly Leu Ile Gln Gly Gly Lys
385                 390                 395                 400

Glu Leu Ala Leu Phe Gly Ala Ala Ala Ile Gly Thr Arg Ile Pro Leu
                405                 410                 415

Leu Ser Met Ser Ser Pro Leu Gly Phe Val Pro Gly Ile Val Tyr Gly
            420                 425                 430

Val Ala Cys Asp Thr Val Ile Asp Ala Val Ala Glu Lys Ile Arg Glu
        435                 440                 445

Gly Met Ala Gly Pro Asn Glu Tyr Ala Gln Glu Asp Ala Gln Ser His
    450                 455                 460

Val Glu Thr Met Asn Lys Leu Arg Gln Gly Pro Arg Glu Phe Ala Gln
465                 470                 475                 480

Gly Leu Ala Gln Asp Trp Phe Met Gly His Phe Gln Asp Lys
                485                 490
```

-continued

<210> SEQ ID NO 36
<211> LENGTH: 962
<212> TYPE: DNA
<213> ORGANISM: Fusarium verticillioides
<220> FEATURE:
<221> NAME/KEY: misc_feature
<222> LOCATION: (20)..(22)
<223> OTHER INFORMATION: beginning of the coding region corresponding to the first Glutamine of the deduced putative TC fused Class B/Class C protein (CAG)
<220> FEATURE:
<221> NAME/KEY: misc_feature
<222> LOCATION: (619)..(621)
<223> OTHER INFORMATION: Aspartic Acid codon (GAT) that starts the second portion of the putative TC fused Class B/Class C protein

<400> SEQUENCE: 36

```
atacgccaca gagtattagc agatgctgga ctggggagca gaggtataca caacagagac     60

attcttcaat gccctggggc agaatatccg tgttgttgcc ccgggaggtg actctctcaa    120

acgatccttt gatctcgctg ggcgattggc gaaggttgaa gcctacgcgt ctgtcagtag    180

tgttgttgcc acagcctcta tcgaccatgt cacatacgag cccgacgatc aagtgggctc    240

ggttctctac ggcaacggag cattggtcaa aaatacctat ggtatatctg atcacagact    300

actgaaaagt cgcaacacta gcactgagga gggtcgtgtg ctgcaggaca tctcatcctg    360

gtacgactgc atgggccgac tagttcgaag ggaagataag gcacaacaga ctctcttctt    420

tgacaattgt cgtatcagtc ttactgaaga ctttacctac gactctctcg gccagttggt    480

tgagtccggg ggttgtgagt tgacaaatct cctgacggtc ctgggagaac cagtccacca    540

gatcctcacc tacgtcgctc taccaatctt tcaggagacg ggaaacaaat ggcaccgttt    600

gtagagaggt atacctaaga tgtttgtgga aacatattga ggatggggca tggacttcag    660

tctgggagtg ggtggaccag aggatacaag tacgaagagc ctagccgcat tgatccaaat    720

gttcacaaca accgtctaag cagctccact gttggtaatt cgacgactca ctacggctac    780

aatggtattt caggaattgg tgggtgcatt gtgtccatgt ctggatactc agaccttcgc    840

tgggaccatc atgaccgtct ccgggcattt gccacgcaaa gggttacaga gggtgcaatg    900

gcagcaatgg cgttcagcat ctttgtatac ttgttttata tatagttctg tcacgattca    960

tt                                                                   962
```

<210> SEQ ID NO 37
<211> LENGTH: 194
<212> TYPE: PRT
<213> ORGANISM: Fusarium verticillioides

<400> SEQUENCE: 37

```
Gln Met Leu Asp Trp Gly Ala Glu Val Tyr Thr Thr Glu Thr Phe Phe
1               5                   10                  15

Asn Ala Leu Gly Gln Asn Ile Arg Val Val Ala Pro Gly Gly Asp Ser
            20                  25                  30

Leu Lys Arg Ser Phe Asp Leu Ala Gly Arg Leu Ala Lys Val Glu Ala
        35                  40                  45

Tyr Ala Ser Val Ser Ser Val Val Ala Thr Ala Ser Ile Asp His Val
    50                  55                  60

Thr Tyr Glu Pro Asp Asp Gln Val Gly Ser Val Leu Tyr Gly Asn Gly
65                  70                  75                  80

Ala Leu Val Lys Asn Thr Tyr Gly Ile Ser Asp His Arg Leu Leu Lys
                85                  90                  95
```

-continued

```
Ser Arg Asn Thr Ser Thr Glu Glu Gly Arg Val Leu Gln Asp Ile Ser
            100                 105                 110

Ser Trp Tyr Asp Cys Met Gly Arg Leu Val Arg Arg Glu Asp Lys Ala
        115                 120                 125

Gln Gln Thr Leu Phe Phe Asp Asn Cys Arg Ile Ser Leu Thr Glu Asp
    130                 135                 140

Phe Thr Tyr Asp Ser Leu Gly Gln Leu Val Glu Ser Gly Gly Cys Glu
145                 150                 155                 160

Leu Thr Asn Leu Leu Thr Val Leu Gly Glu Pro Val His Gln Ile Leu
                165                 170                 175

Thr Tyr Val Ala Leu Pro Ile Phe Gln Glu Thr Gly Asn Lys Trp His
            180                 185                 190

Arg Leu


<210> SEQ ID NO 38
<211> LENGTH: 109
<212> TYPE: PRT
<213> ORGANISM: Fusarium verticillioides
<220> FEATURE:
<221> NAME/KEY: misc_feature
<222> LOCATION: (1)..(2)
<223> OTHER INFORMATION: Xaa can be any naturally occurring amino acid

<400> SEQUENCE: 38

Xaa Xaa Asp Val Cys Gly Asn Ile Leu Arg Met Gly His Gly Leu Gln
1               5                   10                  15

Ser Gly Ser Gly Trp Thr Arg Gly Tyr Lys Tyr Glu Glu Pro Ser Arg
            20                  25                  30

Ile Asp Pro Asn Val His Asn Asn Arg Leu Ser Ser Ser Thr Val Gly
        35                  40                  45

Asn Ser Thr Thr His Tyr Gly Tyr Asn Gly Ile Ser Gly Ile Gly Gly
    50                  55                  60

Cys Ile Val Ser Met Ser Gly Tyr Ser Asp Leu Arg Trp Asp His His
65                  70                  75                  80

Asp Arg Leu Arg Ala Phe Ala Thr Gln Arg Val Thr Glu Gly Ala Met
                85                  90                  95

Ala Ala Met Ala Phe Ser Ile Phe Val Tyr Leu Phe Tyr
            100                 105


<210> SEQ ID NO 39
<211> LENGTH: 8242
<212> TYPE: DNA
<213> ORGANISM: Fusarium verticillioides
<220> FEATURE:
<221> NAME/KEY: misc_feature
<222> LOCATION: (21)..(23)
<223> OTHER INFORMATION: Beginning of the coding region corresponding to
      the first Glutamic Acid of the first portion of the deduced
      putative TC fused Class B/Class C protein (GAG).
<220> FEATURE:
<221> NAME/KEY: misc_feature
<222> LOCATION: (3424)..(4432)
<223> OTHER INFORMATION: n = a, g, c, or t (large gap in the DNA
      sequence, indicated as a string of 1009 n's)
<220> FEATURE:
<221> NAME/KEY: misc_feature
<222> LOCATION: (4435)..(4437)
<223> OTHER INFORMATION: TTG codon which specifies the first Leucine of
      the second portion of the deduced TC fused Class B/Class C protein

<400> SEQUENCE: 39

tatactccaa gacggactga gagattttta tttcatcatg ctctgtaggc cctttaccat     60
```

-continued

```
tttccatttt agtacagagt ccccagtcat ctgtcatgga tacaccgcaa gcagcaaaaa    120
cgcaaatacc gtcacgtgac cgaagtggtc ccaagattga gcatcgcgat gccgttggca    180
catcatcttc gtcccaacag gccgctagca aaggctcaac cgcagccaaa ggcacaggaa    240
gctcttcgtc cctctccatc ccagtgctcg actctgctgc ctttgcaact ggcaaaggcg    300
ggggagcatt acgatccatc gatagtaatt tttccgtaaa ccccaacacc ggcaccttgt    360
ccttcagcgt gcccttgcct gtgtcaaaat cacgtggtgg cttccagcca tcactttctc    420
tcgagtatga ttcaggccgt ggaaatggtg cctttggcat tggttggcga cttggcggta    480
tttcaagcat tgctcgcaag atgtctcgtc gtattccgac atatggtcaa gatgacgatg    540
gagaagacct ggacactttc acgctcactg gcgctgatga tttagtccct cttagcgacg    600
agactgtcga tggcttcgtc gtgaggcagt acgcaccccg tgtacgtggc gatacagaaa    660
tgcgtgttga gcgctggatg caaggcagcc atgttatctt ctggaggaca atttcgtctg    720
aaaatgtgac aaatatttat gggcgtgacg attcctctcg tgagatggag aatccacatc    780
gagtgtttgc atggttgctc tgtgaaagct atgatgcgta tggcaacgct atatctttca    840
catataagaa aggtgataat gaaggtatcg aagctttgcc tgcggacaga aaggcaactg    900
aaacgatgag agattctaaa gcactcacac gcgcgcgata tctcaagagc atccgatacg    960
gaaaccatac acccagtcga gatctcgaca gatggaagat tatccctgcc accgccaaca   1020
agacctatgg atggtgtttt agtattgtac tcgattacgg agaacatgac cttcagtgcc   1080
ctacaacgtt ggaatcttct cttccctggt ctgtccgaca ggatcctttc tcgacaggat   1140
cccgggggtt tgaggtacgc agcctccgtc tctgccggcg agttctcatg tttcatcatt   1200
tctctgagcc gggagaactc gggcgtgaag attatctggt cgcctcgatg gagattaatt   1260
atcaagaaag tcccgccggg tctgtcattg aacagatcac ctccaatggc catgtattcg   1320
acgcggctcg gggcgtgtat gccgcgcaga gcatggcgcc tctcaaacta cgctatagcg   1380
gcttgcctga cctcagaagt ttgccaatta ctaccgtctg cccgaccgca ttgcaaaatt   1440
tgcccatttc ccggcctgac gccgtcactc gctgggtaga cctggatggc gaaggctcac   1500
cgggcttgct tgtgcagcta gatggagcat ggtacttcca gcgcaatgaa agtcccttga   1560
tagcctgtag tgatgatgat agcagctcta tcactagttc tggggtggac acagaatcag   1620
acgctagcag catcagcgac tctgagtcgg ataagatgca ccttttaccc aaggacggct   1680
ttggtcctat ccatgaattg agagccattc cgggcctgaa agactttact cgcagcacct   1740
tcgaagatgt tgatggaaac ggacatcagg acgtggttgt tgtggatgaa caaggtcgcg   1800
catctgggtt ctacgagcga atagctagtg acgacggaga tgacggctgg actccattgc   1860
aattatttcc gcaagtcgtc aacatggacg ttcaaacagc cgaggcaaaa acccattcga   1920
tgagacttga tatgactggc aatggacgac cagacatact gctcgaggta gctggtggag   1980
gtagcggtct agcatggcat gaggcacttg gcaaaagagg catggatgct ctaagggaat   2040
gccagatagc caacgatgct ccatcaccca cagccccgcc actgaatctc acaggagatg   2100
atcgcacggc catttatcta gtggacatgt ctggcgacgg tcttcaggat atcgtgcgta   2160
tcaccaataa cctgataagt tattggccca atttgggata cggaagcttt ggccatgaaa   2220
tatctatgag actgccatgt cctataagcg aggatgacgc aagcttcaac gttctacgac   2280
tgcacctgct agacgtggat ggtagcggta ctacagatat catatacctt ccaccagaag   2340
gaggagccaa cgtctttttc aatcacagtg gcaatgcctt cagtgcgcca ttatctctac   2400
cccagttccc aagcatcagc cgactcacct cagtgtttgc cctggacttg ctgggaaaag   2460
```

-continued

```
gtaccagctg tctctgctgg gttggtccgc gggctggcag cggtactgat gaatttgtca   2520
tcaactacct cgaccttgca gctggaggga aaccccatct tctgtgccat ctcgacgatg   2580
gaaagggctc tgagacgcga attaattatc gtccatccac ggccttctac ctgagcgata   2640
aagccggagg ccagccctgg aaaacccgtc tgccgtttcc tgtacacgtt gtgcgcaagg   2700
cagtcagaca agaccatgtg tcacagacca agctgacaac aacctacgcc tatcgcgatg   2760
gctttttga tccgcatgat agagagtttc gcggctttgg aacggtgcac atttgggagc    2820
aagagcaaat gcgactcgca ccatctgtgt catcctcgtc cacaacgtat aagctgcctg   2880
ttagacatat aaagacttgg ttccacacgg gtgctacaga gtcatcttgg ctcccaacag   2940
gtactttcga acctcatcgt atgcagactg ttttaccaga caacgctggc ccatctgctg   3000
ctgctcatgt aagacgggag gcattccgag ccctcaaggg attgcagatg cgttctgaag   3060
tgtatcagaa agggaggtcg agctccagta acacacctat ctcaatttca gagacggcat   3120
tcgacatcca gcttctccag atgcctgtcg acagtcatat gaatgaaagg gccaagttca   3180
agcacgaaaa acctgggatc tcccgcgtgc ttccgcgcga gcagctgatg gagatctgtg   3240
agcggcagaa aggagaaaat gctcgtttgc agcacgaaat gatacttgaa cgaaacgagt   3300
acggctctgt ccgacgaaag ctgaccgtgt cgtatggttg tacaccggga tctcaagtat   3360
cctttgcatc catagttgag gctttgaaga atgggaaaca ggatgcagcg tctgctctcg   3420
agannnnnnn nnnnnnnnnn nnnnnnnnnn nnnnnnnnnn nnnnnnnnnn nnnnnnnnnn   3480
nnnnnnnnnn nnnnnnnnnn nnnnnnnnnn nnnnnnnnnn nnnnnnnnnn nnnnnnnnnn   3540
nnnnnnnnnn nnnnnnnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnnn nnnnnnnnnn   3660
nnnnnnnnnn nnnnnnnnnn nnnnnnnnnn nnnnnnnnnn nnnnnnnnnn nnnnnnnnnn   3720
nnnnnnnnnn nnnnnnnnnn nnnnnnnnnn nnnnnnnnnn nnnnnnnnnn nnnnnnnnnn   3780
nnnnnnnnnn nnnnnnnnnn nnnnnnnnnn nnnnnnnnnn nnnnnnnnnn nnnnnnnnnn   3840
nnnnnnnnnn nnnnnnnnnn nnnnnnnnnn nnnnnnnnnn nnnnnnnnnn nnnnnnnnnn   3900
nnnnnnnnnn nnnnnnnnnn nnnnnnnnnn nnnnnnnnnn nnnnnnnnnn nnnnnnnnnn   3960
nnnnnnnnnn nnnnnnnnnn nnnnnnnnnn nnnnnnnnnn nnnnnnnnnn nnnnnnnnnn   4020
nnnnnnnnnn nnnnnnnnnn nnnnnnnnnn nnnnnnnnnn nnnnnnnnnn nnnnnnnnnn   4080
nnnnnnnnnn nnnnnnnnnn nnnnnnnnnn nnnnnnnnnn nnnnnnnnnn nnnnnnnnnn   4140
nnnnnnnnnn nnnnnnnnnn nnnnnnnnnn nnnnnnnnnn nnnnnnnnnn nnnnnnnnnn   4200
nnnnnnnnnn nnnnnnnnnn nnnnnnnnnn nnnnnnnnnn nnnnnnnnnn nnnnnnnnnn   4260
nnnnnnnnnn nnnnnnnnnn nnnnnnnnnn nnnnnnnnnn nnnnnnnnnn nnnnnnnnnn   4320
nnnnnnnnnn nnnnnnnnnn nnnnnnnnnn nnnnnnnnnn nnnnnnnnnn nnnnnnnnnn   4380
nnnnnnnnnn nnnnnnnnnn nnnnnnnnnn nnnnnnnnnn nnnnnnnnnn nntcttgacc   4440
gaggctggtt tcgttcaact acccaaagac gatcgatggt ggaagccttc gagccgacag   4500
tctttttctg cgccctgcca tgctgctggc tccgagcttg tgagtgcccg caaaagtttc   4560
ttcacaccca ccatggaagc cgatgttttc cagaacacca ccagtgtgaa gatggacagc   4620
tacatgttgc tccccgaggt ctataccaac gctgcgggtc accagactaa agcagaaaat   4680
gactaccgca ccttaacagc ccgtgtcatg acggattgta acatgaatcg cactgcagct   4740
gaaggagatg cccttggtaa cacgcacgct gtatcacgca tgggcaaaga agaagagaaa   4800
```

-continued

```
ttgggcgatg accatgccgt ggagaaccta gtttcacaag ggctcataga cgacttcctc   4860
tttaatccgg ccgaggacaa ggcaattggt atgttgggtg gccgcgggtc tttgtcactg   4920
tactcgcatc gactcaatgg agacactcca ccttatcgga tcgatatcac tcgcgatact   4980
cacgcccatc cagatggaga cgatgaaagg cctttgaagc gcaacttccc agtcaaagta   5040
actttcttcg acccacaagg ccggacggtc caagagtcgc accttgcgtc atgggacaaa   5100
cagcgttggg acattactgg ctgtactgcg tttgatgcta agggccacgc gatacaaaca   5160
caccatgctt tcaccagctc gactccggcc tttgtgccag tttcaaagag aaacagccct   5220
gctacggtgc agtttgtaga tgctaccggt cgccaggttg ggcagctcga cccgggccat   5280
acatggagca aagtgcactt cacgccttgg gcacaatggg tgtttgacaa aggtgctact   5340
ttgggcattg aagatccagc ggaggacccg gatgttggag tctacatgtc tgcgcttgga   5400
agaggtgcat actccccttc atggcttgag atgcatcgaa gtgcaggtgg gattctacaa   5460
gctactggac agaaggccat ggacgcctac gccaatcatg cgatggtgct cctgtatgat   5520
ggtcgtggca atgggctgtc taagattcaa ggtgtgcgtc aagatagggc aacacaacca   5580
attgccgttc actatgaata tgacgctttg ggccatcttg cgcgtgaggt agatgctctt   5640
ggccgtacgg tgcagactac ccagtacaat cgccttggac aacaaatgat caagaagagc   5700
atggacaagt gcgaggagat atctctaagt gacattaatg gccaaccagt ctacctttgg   5760
gacctgggtc cgggctcacg acgtcgaatg gtctataaca atctgcgcca gcaaacagag   5820
acctgggttc gcgcgagctc acacgaacgc gaaattcttt ggactcgaac ggtgtataac   5880
agcaccaaca caagtgagtc caggtccatc aacatgctgg ggcaagtcat gaggatcgaa   5940
gaccaggccg gaacacgcaa gtttgacaag tatgacttca aaggcacagc cattgcggaa   6000
actcgggtgt tttctgagga atacaagact ggactagact ggtcggctgt ccctgttcca   6060
aagatgcaaa accacatgac ctaccactct agccttcgac tcgatgcagc cggcaggcca   6120
atcttcgaag aaaatgctca tggccgccaa acacgacggt gctacgatgt tcgcggtaat   6180
gtcgttcacc tgcaatctaa agcacatcag caagacagtt ggactgtaca tctccaagat   6240
tcaaccttca cctcagatct actacccgtg aatgtcactc gcggtaatgg caccaagacc   6300
cagcatgagt acgaccaata caccagactt ctaaccaaca gaagaaccag gcgctctgat   6360
agtagcctgg ttgaagacat tacccatata tacgactgca tgggccgcac ttcgcgaact   6420
ttggacgcag cacaagagac agtcttctac cgcaaccagc gaatagaacc tgttaacgag   6480
tactggtacg atttccatga tcgcctggtc aaggctacag gaagagagat ggtttcactg   6540
ggacagaaac agcaacaagg tcccttttc agacagcaca taaacggcga tgccaagcaa   6600
ttgacatgct atacggagac gtacagatac gatgacgccg gcaacatact cgagcaccgg   6660
cacgatatat cagatacgac catgccaaac tggactcgga ttcaccgata caatcaaacc   6720
agtcgtattg agcctgacaa gatgagcaat cgactgacat cggtgtcaat atctggcgta   6780
gaaagcaaac aatttgagta caatgccaat ggtgccacgg tatcactgcc agggttctcc   6840
tacgttggat gggaccctat ggattctctc cattgcgtat caactcagat tgtcaatcca   6900
ggagatgaaa cagcgattcc cgaaacaacg ttcttcgtct acgacaagga cggtacacgt   6960
gtcagaaaag tcacagaatc atcacgatca tgttgcaaga tgaaggagac attgtatctc   7020
ggccctgcag ctgaacactc cctgacctat tctggtgagg gcgtgactcc agactcggag   7080
gtgactacgt gccacctctt tcccgcgaca tcggaccctg gtaccaccgc ggtcgtaact   7140
atagagcact atgttaaagc agctaatcct aagctcggaa acaagactct acaacgctac   7200
```

-continued

```
aacctcagca acaatctcga agtggacgag gacggacaca ccatctccta tgaagagtat   7260

acgccgtttg ggactccaac atatgtaatc cgccagtctg gtattgacgc tcccagtgcg   7320

tttcgttttg ctgcataccg acgagatcga gagactggtg ggatgtacta ctgtaatgca   7380

agatattatg tgccgtggct cggtcgttgg atgtcgcccg atccactaga taccgttgat   7440

ggccctaacg tatacgcata ctgcggcaac aatcttgtca actgggcgga tccaaagggc   7500

acccttaagt ggaacatgca agatgtcaag aacgctattg tcccagctct caaatccgcc   7560

gcagttactg tccccagcgc tatagttagc ataggtacag cagcagtggc caacacgatc   7620

ctcacataca gggtcagttc aacccagtct gctctcacca atatggcatg gtcagctgca   7680

gcttacggct tgcaaaccgt cgctgcatct ttgccggtca tggtcaatgc cttcgcgggg   7740

tctgtgctgg cagagaggga taagcgagag gccgcaacca aggcagagat cattgataaa   7800

aagattaaat cactcgaaga taagaataaa acactcgaag agaagaacga atcactcgaa   7860

aaacagaata aagagttaaa agagcaggtt agatggctga aggagcacgg agaaaacctg   7920

gaaagggctg ttgtgtcact aagtgcggcg gtggggtttg tgctaccaga atttcaagac   7980

aagccatatc ccgaggacag tgaagaccaa cttcaagccg aattggagga ggaagataat   8040

ggcggatttg aggatgaaag cgatcttccg ggattattca taaatcaggt gatgagcgca   8100

cagaatcttg aagaagacaa cggagtgtct gaagtgagaa ggacaggagc agacgtaaac   8160

cagtcatctg ttgttaatcg gagggtcaac gcatctacaa atagagccat acacacagag   8220

ccttagattc aatcgaattg at                                             8242
```

```
<210> SEQ ID NO 40
<211> LENGTH: 1134
<212> TYPE: PRT
<213> ORGANISM: Fusarium verticillioides

<400> SEQUENCE: 40

Glu Ile Phe Ile Ser Ser Cys Ser Val Gly Pro Leu Pro Phe Ser Ile
1               5                   10                  15

Leu Val Gln Ser Pro Gln Ser Ser Val Met Asp Thr Pro Gln Ala Ala
            20                  25                  30

Lys Thr Gln Ile Pro Ser Arg Asp Arg Ser Gly Pro Lys Ile Glu His
        35                  40                  45

Arg Asp Ala Val Gly Thr Ser Ser Ser Ser Gln Gln Ala Ala Ser Lys
    50                  55                  60

Gly Ser Thr Ala Ala Lys Gly Thr Gly Ser Ser Ser Ser Leu Ser Ile
65                  70                  75                  80

Pro Val Leu Asp Ser Ala Ala Phe Ala Thr Gly Lys Gly Gly Gly Ala
                85                  90                  95

Leu Arg Ser Ile Asp Ser Asn Phe Ser Val Asn Pro Asn Thr Gly Thr
            100                 105                 110

Leu Ser Phe Ser Val Pro Leu Pro Val Ser Lys Ser Arg Gly Gly Phe
        115                 120                 125

Gln Pro Ser Leu Ser Leu Glu Tyr Asp Ser Gly Arg Gly Asn Gly Ala
    130                 135                 140

Phe Gly Ile Gly Trp Arg Leu Gly Gly Ile Ser Ser Ile Ala Arg Lys
145                 150                 155                 160

Met Ser Arg Arg Ile Pro Thr Tyr Gly Gln Asp Asp Asp Gly Glu Asp
                165                 170                 175

Leu Asp Thr Phe Thr Leu Thr Gly Ala Asp Asp Leu Val Pro Leu Ser
```

-continued

```
            180                 185                 190

Asp Glu Thr Val Asp Gly Phe Val Val Arg Gln Tyr Ala Pro Arg Val
        195                 200                 205

Arg Gly Asp Thr Glu Met Arg Val Glu Arg Trp Met Gln Gly Ser His
    210                 215                 220

Val Ile Phe Trp Arg Thr Ile Ser Ser Glu Asn Val Thr Asn Ile Tyr
225                 230                 235                 240

Gly Arg Asp Asp Ser Ser Arg Glu Met Glu Asn Pro His Arg Val Phe
                245                 250                 255

Ala Trp Leu Leu Cys Glu Ser Tyr Asp Ala Tyr Gly Asn Ala Ile Ser
            260                 265                 270

Phe Thr Tyr Lys Lys Gly Asp Asn Glu Gly Ile Glu Ala Leu Pro Ala
        275                 280                 285

Asp Arg Lys Ala Thr Glu Thr Met Arg Asp Ser Lys Ala Leu Thr Arg
    290                 295                 300

Ala Arg Tyr Leu Lys Ser Ile Arg Tyr Gly Asn His Thr Pro Ser Arg
305                 310                 315                 320

Asp Leu Asp Arg Trp Lys Ile Ile Pro Ala Thr Ala Asn Lys Thr Tyr
                325                 330                 335

Gly Trp Cys Phe Ser Ile Val Leu Asp Tyr Gly Glu His Asp Leu Gln
            340                 345                 350

Cys Pro Thr Thr Leu Glu Ser Ser Leu Pro Trp Ser Val Arg Gln Asp
        355                 360                 365

Pro Phe Ser Thr Gly Ser Arg Gly Phe Glu Val Arg Ser Leu Arg Leu
    370                 375                 380

Cys Arg Arg Val Leu Met Phe His His Phe Ser Glu Pro Gly Glu Leu
385                 390                 395                 400

Gly Arg Glu Asp Tyr Leu Val Ala Ser Met Glu Ile Asn Tyr Gln Glu
                405                 410                 415

Ser Pro Ala Gly Ser Val Ile Glu Gln Ile Thr Ser Asn Gly His Val
            420                 425                 430

Phe Asp Ala Ala Arg Gly Val Tyr Ala Ala Gln Ser Met Ala Pro Leu
        435                 440                 445

Lys Leu Arg Tyr Ser Gly Leu Pro Asp Leu Arg Ser Leu Pro Ile Thr
    450                 455                 460

Thr Val Cys Pro Thr Ala Leu Gln Asn Leu Pro Ile Ser Arg Pro Asp
465                 470                 475                 480

Ala Val Thr Arg Trp Val Asp Leu Asp Gly Glu Gly Ser Pro Gly Leu
                485                 490                 495

Leu Val Gln Leu Asp Gly Ala Trp Tyr Phe Gln Arg Asn Glu Ser Pro
            500                 505                 510

Leu Ile Ala Cys Ser Asp Asp Asp Ser Ser Ser Ile Thr Ser Ser Gly
        515                 520                 525

Val Asp Thr Glu Ser Asp Ala Ser Ser Ile Ser Asp Ser Glu Ser Asp
    530                 535                 540

Lys Met His Leu Leu Pro Lys Asp Gly Phe Gly Pro Ile His Glu Leu
545                 550                 555                 560

Arg Ala Ile Pro Gly Leu Lys Asp Phe Thr Arg Ser Thr Phe Glu Asp
                565                 570                 575

Val Asp Gly Asn Gly His Gln Asp Val Val Val Val Asp Glu Gln Gly
            580                 585                 590

Arg Ala Ser Gly Phe Tyr Glu Arg Ile Ala Ser Asp Asp Gly Asp Asp
        595                 600                 605
```

-continued

```
Gly Trp Thr Pro Leu Gln Leu Phe Pro Gln Val Val Asn Met Asp Val
    610                 615                 620

Gln Thr Ala Glu Ala Lys Thr His Ser Met Arg Leu Asp Met Thr Gly
625                 630                 635                 640

Asn Gly Arg Pro Asp Ile Leu Leu Glu Val Ala Gly Gly Gly Ser Gly
                645                 650                 655

Leu Ala Trp His Glu Ala Leu Gly Lys Arg Gly Met Asp Ala Leu Arg
            660                 665                 670

Glu Cys Gln Ile Ala Asn Asp Ala Pro Ser Pro Thr Ala Pro Pro Leu
        675                 680                 685

Asn Leu Thr Gly Asp Asp Arg Thr Ala Ile Tyr Leu Val Asp Met Ser
    690                 695                 700

Gly Asp Gly Leu Gln Asp Ile Val Arg Ile Thr Asn Asn Leu Ile Ser
705                 710                 715                 720

Tyr Trp Pro Asn Leu Gly Tyr Gly Ser Phe Gly His Glu Ile Ser Met
                725                 730                 735

Arg Leu Pro Cys Pro Ile Ser Glu Asp Asp Ala Ser Phe Asn Val Leu
            740                 745                 750

Arg Leu His Leu Leu Asp Val Asp Gly Ser Gly Thr Thr Asp Ile Ile
        755                 760                 765

Tyr Leu Pro Pro Glu Gly Gly Ala Asn Val Phe Phe Asn His Ser Gly
    770                 775                 780

Asn Ala Phe Ser Ala Pro Leu Ser Leu Pro Gln Phe Pro Ser Ile Ser
785                 790                 795                 800

Arg Leu Thr Ser Val Phe Ala Leu Asp Leu Leu Gly Lys Gly Thr Ser
                805                 810                 815

Cys Leu Cys Trp Val Gly Pro Arg Ala Gly Ser Gly Thr Asp Glu Phe
            820                 825                 830

Val Ile Asn Tyr Leu Asp Leu Ala Ala Gly Gly Lys Pro His Leu Leu
        835                 840                 845

Cys His Leu Asp Asp Gly Lys Gly Ser Glu Thr Arg Ile Asn Tyr Arg
    850                 855                 860

Pro Ser Thr Ala Phe Tyr Leu Ser Asp Lys Ala Gly Gly Gln Pro Trp
865                 870                 875                 880

Lys Thr Arg Leu Pro Phe Pro Val His Val Val Arg Lys Ala Val Arg
                885                 890                 895

Gln Asp His Val Ser Gln Thr Lys Leu Thr Thr Thr Tyr Ala Tyr Arg
            900                 905                 910

Asp Gly Phe Phe Asp Pro His Asp Arg Glu Phe Arg Gly Phe Gly Thr
        915                 920                 925

Val His Ile Trp Glu Gln Glu Gln Met Arg Leu Ala Pro Ser Val Ser
    930                 935                 940

Ser Ser Ser Thr Thr Tyr Lys Leu Pro Val Arg His Ile Lys Thr Trp
945                 950                 955                 960

Phe His Thr Gly Ala Thr Glu Ser Ser Trp Leu Pro Thr Gly Thr Phe
                965                 970                 975

Glu Pro His Arg Met Gln Thr Val Leu Pro Asp Asn Ala Gly Pro Ser
            980                 985                 990

Ala Ala Ala His Val Arg Arg Glu  Ala Phe Arg Ala Leu  Lys Gly Leu
        995                 1000                1005

Gln Met  Arg Ser Glu Val Tyr  Gln Lys Gly Arg Ser  Ser Ser Ser
    1010                1015                1020
```

-continued

```
Asn Thr  Pro Ile Ser Ile Ser  Glu Thr Ala Phe Asp  Ile Gln Leu
    1025                 1030                 1035

Leu Gln  Met Pro Val Asp Ser  His Met Asn Glu Arg  Ala Lys Phe
    1040                 1045                 1050

Lys His  Glu Lys Pro Gly Ile  Ser Arg Val Leu Pro  Arg Glu Gln
    1055                 1060                 1065

Leu Met  Glu Ile Cys Glu Arg  Gln Lys Gly Glu Asn  Ala Arg Leu
    1070                 1075                 1080

Gln His  Glu Met Ile Leu Glu  Arg Asn Glu Tyr Gly  Ser Val Arg
    1085                 1090                 1095

Arg Lys  Leu Thr Val Ser Tyr  Gly Cys Thr Pro Gly  Ser Gln Val
    1100                 1105                 1110

Ser Phe  Ala Ser Ile Val Glu  Ala Leu Lys Asn Gly  Lys Gln Asp
    1115                 1120                 1125

Ala Ala  Ser Ala Leu Glu
    1130


<210> SEQ ID NO 41
<211> LENGTH: 1267
<212> TYPE: PRT
<213> ORGANISM: Fusarium verticillioides
<220> FEATURE:
<221> NAME/KEY: misc_feature
<222> LOCATION: (1)..(4)
<223> OTHER INFORMATION: Xaa can be any naturally occurring amino acid

<400> SEQUENCE: 41

Xaa Xaa Xaa Xaa Leu Thr Glu Ala Gly Phe Val Gln Leu Pro Lys Asp
1               5                   10                  15

Asp Arg Trp Trp Lys Pro Ser Ser Arg Gln Ser Phe Ser Ala Pro Cys
            20                  25                  30

His Ala Ala Gly Ser Glu Leu Val Ser Ala Arg Lys Ser Phe Phe Thr
        35                  40                  45

Pro Thr Met Glu Ala Asp Val Phe Gln Asn Thr Thr Ser Val Lys Met
    50                  55                  60

Asp Ser Tyr Met Leu Leu Pro Glu Val Tyr Thr Asn Ala Ala Gly His
65                  70                  75                  80

Gln Thr Lys Ala Glu Asn Asp Tyr Arg Thr Leu Thr Ala Arg Val Met
                85                  90                  95

Thr Asp Cys Asn Met Asn Arg Thr Ala Ala Glu Gly Asp Ala Leu Gly
            100                 105                 110

Asn Thr His Ala Val Ser Arg Met Gly Lys Glu Glu Glu Lys Leu Gly
        115                 120                 125

Asp Asp His Ala Val Glu Asn Leu Val Ser Gln Gly Leu Ile Asp Asp
    130                 135                 140

Phe Leu Phe Asn Pro Ala Glu Asp Lys Ala Ile Gly Met Leu Gly Gly
145                 150                 155                 160

Arg Gly Ser Leu Ser Leu Tyr Ser His Arg Leu Asn Gly Asp Thr Pro
                165                 170                 175

Pro Tyr Arg Ile Asp Ile Thr Arg Asp Thr His Ala His Pro Asp Gly
            180                 185                 190

Asp Asp Glu Arg Pro Leu Lys Arg Asn Phe Pro Val Lys Val Thr Phe
        195                 200                 205

Phe Asp Pro Gln Gly Arg Thr Val Gln Glu Ser His Leu Ala Ser Trp
    210                 215                 220

Asp Lys Gln Arg Trp Asp Ile Thr Gly Cys Thr Ala Phe Asp Ala Lys
```

-continued

```
225                 230                 235                 240

Gly His Ala Ile Gln Thr His His Ala Phe Thr Ser Ser Thr Pro Ala
                245                 250                 255

Phe Val Pro Val Ser Lys Arg Asn Ser Pro Ala Thr Val Gln Phe Val
            260                 265                 270

Asp Ala Thr Gly Arg Gln Val Gly Gln Leu Asp Pro Gly His Thr Trp
        275                 280                 285

Ser Lys Val His Phe Thr Pro Trp Ala Gln Trp Val Phe Asp Lys Gly
    290                 295                 300

Ala Thr Leu Gly Ile Glu Asp Pro Ala Glu Asp Pro Asp Val Gly Val
305                 310                 315                 320

Tyr Met Ser Ala Leu Gly Arg Gly Ala Tyr Ser Pro Ser Trp Leu Glu
                325                 330                 335

Met His Arg Ser Ala Gly Gly Ile Leu Gln Ala Thr Gly Gln Lys Ala
            340                 345                 350

Met Asp Ala Tyr Ala Asn His Ala Met Val Leu Leu Tyr Asp Gly Arg
        355                 360                 365

Gly Asn Gly Leu Ser Lys Ile Gln Gly Val Arg Gln Asp Arg Ala Thr
    370                 375                 380

Gln Pro Ile Ala Val His Tyr Glu Tyr Asp Ala Leu Gly His Leu Ala
385                 390                 395                 400

Arg Glu Val Asp Ala Leu Gly Arg Thr Val Gln Thr Thr Gln Tyr Asn
                405                 410                 415

Arg Leu Gly Gln Gln Met Ile Lys Lys Ser Met Asp Lys Cys Glu Glu
            420                 425                 430

Ile Ser Leu Ser Asp Ile Asn Gly Gln Pro Val Tyr Leu Trp Asp Leu
        435                 440                 445

Gly Pro Gly Ser Arg Arg Arg Met Val Tyr Asn Asn Leu Arg Gln Gln
    450                 455                 460

Thr Glu Thr Trp Val Arg Ala Ser Ser His Glu Arg Glu Ile Leu Trp
465                 470                 475                 480

Thr Arg Thr Val Tyr Asn Ser Thr Asn Thr Ser Glu Ser Arg Ser Ile
                485                 490                 495

Asn Met Leu Gly Gln Val Met Arg Ile Glu Asp Gln Ala Gly Thr Arg
            500                 505                 510

Lys Phe Asp Lys Tyr Asp Phe Lys Gly Thr Ala Ile Ala Glu Thr Arg
        515                 520                 525

Val Phe Ser Glu Glu Tyr Lys Thr Gly Leu Asp Trp Ser Ala Val Pro
    530                 535                 540

Val Pro Lys Met Gln Asn His Met Thr Tyr His Ser Ser Leu Arg Leu
545                 550                 555                 560

Asp Ala Ala Gly Arg Pro Ile Phe Glu Glu Asn Ala His Gly Arg Gln
                565                 570                 575

Thr Arg Arg Cys Tyr Asp Val Arg Gly Asn Val Val His Leu Gln Ser
            580                 585                 590

Lys Ala His Gln Gln Asp Ser Trp Thr Val His Leu Gln Asp Ser Thr
        595                 600                 605

Phe Thr Ser Asp Leu Leu Pro Val Asn Val Thr Arg Gly Asn Gly Thr
    610                 615                 620

Lys Thr Gln His Glu Tyr Asp Gln Tyr Thr Arg Leu Leu Thr Asn Arg
625                 630                 635                 640

Arg Thr Arg Arg Ser Asp Ser Ser Leu Val Glu Asp Ile Thr His Ile
                645                 650                 655
```

-continued

```
Tyr Asp Cys Met Gly Arg Thr Ser Arg Thr Leu Asp Ala Ala Gln Glu
            660                 665                 670

Thr Val Phe Tyr Arg Asn Gln Arg Ile Glu Pro Val Asn Glu Tyr Trp
        675                 680                 685

Tyr Asp Phe His Asp Arg Leu Val Lys Ala Thr Gly Arg Glu Met Val
    690                 695                 700

Ser Leu Gly Gln Lys Gln Gln Gln Gly Pro Phe Phe Arg Gln His Ile
705                 710                 715                 720

Asn Gly Asp Ala Lys Gln Leu Thr Cys Tyr Thr Glu Thr Tyr Arg Tyr
                725                 730                 735

Asp Asp Ala Gly Asn Ile Leu Glu His Arg His Asp Ile Ser Asp Thr
            740                 745                 750

Thr Met Pro Asn Trp Thr Arg Ile His Arg Tyr Asn Gln Thr Ser Arg
        755                 760                 765

Ile Glu Pro Asp Lys Met Ser Asn Arg Leu Thr Ser Val Ser Ile Ser
    770                 775                 780

Gly Val Glu Ser Lys Gln Phe Glu Tyr Asn Ala Asn Gly Ala Thr Val
785                 790                 795                 800

Ser Leu Pro Gly Phe Ser Tyr Val Gly Trp Asp Pro Met Asp Ser Leu
                805                 810                 815

His Cys Val Ser Thr Gln Ile Val Asn Pro Gly Asp Glu Thr Ala Ile
            820                 825                 830

Pro Glu Thr Thr Phe Phe Val Tyr Asp Lys Asp Gly Thr Arg Val Arg
        835                 840                 845

Lys Val Thr Glu Ser Ser Arg Ser Cys Cys Lys Met Lys Glu Thr Leu
    850                 855                 860

Tyr Leu Gly Pro Ala Ala Glu His Ser Leu Thr Tyr Ser Gly Glu Gly
865                 870                 875                 880

Val Thr Pro Asp Ser Glu Val Thr Thr Cys His Leu Phe Pro Ala Thr
                885                 890                 895

Ser Asp Pro Gly Thr Thr Ala Val Val Thr Ile Glu His Tyr Val Lys
            900                 905                 910

Ala Ala Asn Pro Lys Leu Gly Asn Lys Thr Leu Gln Arg Tyr Asn Leu
        915                 920                 925

Ser Asn Asn Leu Glu Val Asp Glu Asp Gly His Thr Ile Ser Tyr Glu
    930                 935                 940

Glu Tyr Thr Pro Phe Gly Thr Pro Thr Tyr Val Ile Arg Gln Ser Gly
945                 950                 955                 960

Ile Asp Ala Pro Ser Ala Phe Arg Phe Ala Ala Tyr Arg Arg Asp Arg
                965                 970                 975

Glu Thr Gly Gly Met Tyr Tyr Cys Asn Ala Arg Tyr Tyr Val Pro Trp
            980                 985                 990

Leu Gly Arg Trp Met Ser Pro Asp  Pro Leu Asp Thr Val  Asp Gly Pro
        995                 1000                1005

Asn Val  Tyr Ala Tyr Cys Gly  Asn Asn Leu Val Asn  Trp Ala Asp
    1010                1015                1020

Pro Lys  Gly Thr Leu Lys Trp  Asn Met Gln Asp Val  Lys Asn Ala
    1025                1030                1035

Ile Val  Pro Ala Leu Lys Ser  Ala Ala Val Thr Val  Pro Ser Ala
    1040                1045                1050

Ile Val  Ser Ile Gly Thr Ala  Ala Val Ala Asn Thr  Ile Leu Thr
    1055                1060                1065
```

-continued

```
Tyr Arg  Val Ser Ser Thr Gln  Ser Ala Leu Thr Asn  Met Ala Trp
    1070                 1075                 1080

Ser Ala  Ala Ala Tyr Gly Leu  Gln Thr Val Ala Ala  Ser Leu Pro
    1085                 1090                 1095

Val Met  Val Asn Ala Phe Ala  Gly Ser Val Leu Ala  Glu Arg Asp
    1100                 1105                 1110

Lys Arg  Glu Ala Ala Thr Lys  Ala Glu Ile Ile Asp  Lys Lys Ile
    1115                 1120                 1125

Lys Ser  Leu Glu Asp Lys Asn  Lys Thr Leu Glu Glu  Lys Asn Glu
    1130                 1135                 1140

Ser Leu  Glu Lys Gln Asn Lys  Glu Leu Lys Glu Gln  Val Arg Trp
    1145                 1150                 1155

Leu Lys  Glu His Gly Glu Asn  Leu Glu Arg Ala Val  Val Ser Leu
    1160                 1165                 1170

Ser Ala  Ala Val Gly Phe Val  Leu Pro Glu Phe Gln  Asp Lys Pro
    1175                 1180                 1185

Tyr Pro  Glu Asp Ser Glu Asp  Gln Leu Gln Ala Glu  Leu Glu Glu
    1190                 1195                 1200

Glu Asp  Asn Gly Gly Phe Glu  Asp Glu Ser Asp Leu  Pro Gly Leu
    1205                 1210                 1215

Phe Ile  Asn Gln Val Met Ser  Ala Gln Asn Leu Glu  Glu Asp Asn
    1220                 1225                 1230

Gly Val  Ser Glu Val Arg Arg  Thr Gly Ala Asp Val  Asn Gln Ser
    1235                 1240                 1245

Ser Val  Val Asn Arg Arg Val  Asn Ala Ser Thr Asn  Arg Ala Ile
    1250                 1255                 1260

His Thr  Glu Pro
    1265
```

```
<210> SEQ ID NO 42
<211> LENGTH: 43
<212> TYPE: PRT
<213> ORGANISM: TcaC from Photorhabdus luminescens
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 42

Asp Ala Arg Lys Leu Val Ala Phe Ser Asp Met Leu Gly Ser Gly Gln
1               5                   10                  15

Gln His Leu Val Glu Ile Lys Ala Asn Xaa Arg Val Thr Cys Trp Pro
            20                  25                  30

Xaa Asn Leu Gly His Gly Arg Phe Gly Gln Pro
        35                  40
```

```
<210> SEQ ID NO 43
<211> LENGTH: 42
<212> TYPE: PRT
<213> ORGANISM: TcaC from Photorhabdus luminescens
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (32)..(32)
```

<223> OTHER INFORMATION: Xaa can be any naturally occurring amino acid

<400> SEQUENCE: 43

```
Ser Thr Glu Leu Val Ala Phe Ser Asp Leu Leu Gly Thr Gly Gln Gln
1               5                   10                  15

His Leu Ile Arg Ile Arg His Asn Xaa Glu Ile Arg Val Trp Pro Xaa
            20                  25                  30

Asn Leu Gly Arg Gly Arg Phe Gly Lys Gly
        35                  40
```

<210> SEQ ID NO 44
<211> LENGTH: 42
<212> TYPE: PRT
<213> ORGANISM: TcaC from Photorhabdus luminescens
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 44

```
His Pro Ser Ile Gln Phe Ala Asp Leu Thr Gly Ala Gly Leu Ser Asp
1               5                   10                  15

Leu Val Leu Ile Gly Pro Lys Xaa Ser Val Arg Leu Tyr Ala Xaa Asn
            20                  25                  30

Gln Arg Xaa Asn Gly Trp Arg Lys Gly Glu
        35                  40
```

<210> SEQ ID NO 45
<211> LENGTH: 41
<212> TYPE: PRT
<213> ORGANISM: TcaC from Photorhabdus luminescens
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 45

```
His Pro Gln Gly Gln Met Ala Asp Leu Val Gly Asp Gly Leu Ser Asp
1               5                   10                  15

Leu Ala Leu Ile Gly Pro Arg Xaa Ser Val Arg Leu Tyr Ala Xaa Asn
            20                  25                  30

Arg Arg Ala Asp Gly Phe Ala Ala Ala
        35                  40
```

<210> SEQ ID NO 46
<211> LENGTH: 40
<212> TYPE: PRT
<213> ORGANISM: TcaC from Photorhabdus luminescens

<400> SEQUENCE: 46

```
Asn Thr Cys Gln Leu Gln Val Ala Asp Ile Gln Gly Leu Gly Ile Ala
1               5                   10                  15

Ser Leu Ile Leu Thr Val Pro His Ile Ala Pro His His Trp Arg Cys
```

-continued

```
            20                  25                  30

Asp Leu Ser Leu Thr Lys Pro Trp
        35                  40


<210> SEQ ID NO 47
<211> LENGTH: 40
<212> TYPE: PRT
<213> ORGANISM: TcaC from Photorhabdus luminescens

<400> SEQUENCE: 47

Arg Phe Cys Gln Phe Ser Ala Val Asp Leu Leu Gly Leu Gly Phe Ser
1               5                   10                  15

Ser Leu Val Leu Thr Val Pro His Met Ala Pro Arg His Trp Ser Leu
            20                  25                  30

Tyr Tyr Ala Ala Asp Arg Thr Gly
        35                  40


<210> SEQ ID NO 48
<211> LENGTH: 40
<212> TYPE: PRT
<213> ORGANISM: TcaC from Photorhabdus luminescens
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 48

Gln Asp Asn Ala Ser Leu Met Asp Ile Asn Gly Asp Gly Gln Leu Asp
1               5                   10                  15

Trp Val Val Thr Ala Ser Gly Xaa Ile Arg Gly Tyr His Ser Xaa Gln
            20                  25                  30

Gln Pro Asp Gly Lys Trp Thr His
        35                  40


<210> SEQ ID NO 49
<211> LENGTH: 41
<212> TYPE: PRT
<213> ORGANISM: TcaC from Photorhabdus luminescens
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 49

Ala Pro Val Arg Gln Thr Leu Thr Asp Leu Thr Gly Asp Gly Arg Leu
1               5                   10                  15

Asp Trp Val Val Ala Gln Pro Gly Xaa Met Ala Gly Phe Phe Thr Xaa
            20                  25                  30

Leu Asn Pro Asp Arg Ser Trp Ser Lys
        35                  40


<210> SEQ ID NO 50
<211> LENGTH: 42
<212> TYPE: PRT
<213> ORGANISM: TcaC from Photorhabdus luminescens
<220> FEATURE:
<221> NAME/KEY: misc_feature
```

<222> LOCATION: (25)..(25)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 50

Asn Pro Glu Arg Leu Phe Leu Ala Asp Ile Asp Gly Ser Gly Thr Thr
1 5 10 15

Asp Leu Ile Tyr Ala Gln Ser Gly Xaa Ser Leu Leu Ile Tyr Leu Xaa
20 25 30

Asn Gln Ser Gly Asn Gln Phe Asp Ala Pro
35 40

<210> SEQ ID NO 51
<211> LENGTH: 42
<212> TYPE: PRT
<213> ORGANISM: TcaC from Photorhabdus luminescens
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 51

Asp Ser Ser Arg Val Arg Leu Ala Asp Leu Asp Gly Ser Gly Ala Ser
1 5 10 15

Asp Val Leu Tyr Leu Gln Ala Asp Xaa Gly Phe Gln Val Phe Met Xaa
20 25 30

Asn Gln Gly Gly Asn Gly Leu Ala Ala Ala
35 40

<210> SEQ ID NO 52
<211> LENGTH: 41
<212> TYPE: PRT
<213> ORGANISM: TcaC from Photorhabdus luminescens
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 52

Gln Gln Arg Tyr Gln Leu Val Asp Leu Arg Gly Glu Gly Leu Pro Gly
1 5 10 15

Met Leu Tyr Gln Asp Arg Gly Xaa Xaa Ala Trp Trp Tyr Lys Xaa Ala
20 25 30

Pro Gln Arg Gln Glu Asp Gly Asp Ser
35 40

<210> SEQ ID NO 53
<211> LENGTH: 41
<212> TYPE: PRT
<213> ORGANISM: TcaC from Photorhabdus luminescens
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature -continued
<222> LOCATION: (31)..(31)
<223> OTHER INFORMATION: Xaa can be any naturally occurring amino acid

<400> SEQUENCE: 53

```
Gly Gln Gln Tyr Gln Leu Val Asp Leu Tyr Gly Asp Gly Leu Pro Gly
1               5                   10                  15

Ile Leu Tyr Arg Asp Asp Lys Xaa Xaa Ala Trp Leu Tyr Arg Xaa Glu
            20                  25                  30

Pro Ile Arg Asp Thr Ala Gly Thr Ala
        35                  40
```

<210> SEQ ID NO 54
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 54

```
Ala Asp Ala Thr Gly Ala Leu Leu Thr Gln Thr Xaa Xaa Xaa Xaa Asp
1               5                   10                  15

Ala Lys Gly Asn Ile
            20
```

<210> SEQ ID NO 55
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 55

```
Phe Asp Ala Thr Gly Ala Leu Leu Thr Gln Thr Xaa Xaa Xaa Xaa Asp
1               5                   10                  15

Ala Lys Ser Asn Ile
            20
```

<210> SEQ ID NO 56
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 56

```
Ala Asp Ala Thr Gly Ala Val Leu Thr Thr Thr Xaa Xaa Xaa Xaa Asp
1               5                   10                  15

Ala Lys Gly Asn Leu
            20
```

<210> SEQ ID NO 57
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 57

-continued

```
Ala Asp Ala Thr Gly Ala Val Leu Thr Thr Thr Xaa Xaa Xaa Xaa Asp
1               5                   10                  15

Ala Lys Gly Asn Leu
            20


<210> SEQ ID NO 58
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 58

Tyr Ser Pro Leu Gly Ala Val Leu Thr Gln Thr Xaa Xaa Xaa Xaa Asp
1               5                   10                  15

Ala Gly Gly His Gln
            20


<210> SEQ ID NO 59
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 59

Phe Ser Ala Val Gly Ala Leu Leu Gln Thr Thr Xaa Xaa Xaa Xaa Asp
1               5                   10                  15

Ala Gly Gly His Leu
            20


<210> SEQ ID NO 60
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 60

Phe Asn Ala Gln Gly Glu Asp Leu Ala Gln Thr Xaa Xaa Xaa Xaa Asp
1               5                   10                  15

Ala Asn Gly Asn Val
            20


<210> SEQ ID NO 61
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 61

Phe Asn Ala Leu Gly Asp Ala Leu Ala Gln Thr Xaa Xaa Xaa Xaa Asp
1               5                   10                  15

Ala Met Gly Asn Thr
            20
```

-continued

<210> SEQ ID NO 62
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 62

```
Phe Asn Ala Gln Gly Glu Val Leu Lys Gln Thr Xaa Xaa Xaa Xaa Asp
1               5                   10                  15

Ala Ser Gly Asn Ser
            20
```

<210> SEQ ID NO 63
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (13)..(15)
<223> OTHER INFORMATION: Xaa can be any naturally occurring amino acid

<400> SEQUENCE: 63

```
Tyr Thr Val Ala Gly Leu Leu Lys Ser Ser Arg Leu Xaa Xaa Xaa Gln
1               5                   10                  15

Met Asn Gly Gln Ala Glu
            20
```

<210> SEQ ID NO 64
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (13)..(15)
<223> OTHER INFORMATION: Xaa can be any naturally occurring amino acid

<400> SEQUENCE: 64

```
Tyr Asn Arg Ala Gly Gln Leu Ile Gly Ser Trp Leu Xaa Xaa Xaa Thr
1               5                   10                  15

Ile Lys Asn Ser Ala Glu
            20
```

<210> SEQ ID NO 65
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 65

```
Tyr Asp Ala Gln Gln Arg Val Val Ser Glu Thr Xaa Xaa Xaa Xaa Ala
1               5                   10                  15

Gly Asn Gly Val Ile
            20
```

<210> SEQ ID NO 66
<211> LENGTH: 21
<212> TYPE: PRT
<213> ORGANISM: TccC3 from Photorhabdus luminescens
<220> FEATURE:
<221> NAME/KEY: misc_feature -continued
<222> LOCATION: (12)..(15)
<223> OTHER INFORMATION: Xaa can be any naturally occurring amino acid

<400> SEQUENCE: 66

Tyr Asp Ala Gln Gly His Val Thr Ser Glu Thr Xaa Xaa Xaa Xaa Ala
1 5 10 15

Gly Asn Gly Val Met
20

<210> SEQ ID NO 67
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 67

Tyr Asp Ala Phe Asn Gln Val Glu Gln Glu Thr Xaa Xaa Xaa Xaa Ala
1 5 10 15

Gly Asn Gly Val Val
20

<210> SEQ ID NO 68
<211> LENGTH: 21
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 68

Tyr Asp Ala His Gly Arg Ile Glu Ser Gln Thr Xaa Xaa Xaa Xaa Ala
1 5 10 15

Gly Asn Gly Val Ile
20

<210> SEQ ID NO 69
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (12)..(16)
<223> OTHER INFORMATION: Xaa can be any naturally occurring amino acid

<400> SEQUENCE: 69

Tyr Asp Ala Gln Leu Arg Pro Val Ala Ile Ile Xaa Xaa Xaa Xaa Xaa
1 5 10 15

Glu Asn Gly Arg Cys Val
20

<210> SEQ ID NO 70
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (12)..(16)
<223> OTHER INFORMATION: Xaa can be any naturally occurring amino acid

<400> SEQUENCE: 70

Tyr Asp Ala Gln Leu Arg Pro Leu Ala Ile Asn Xaa Xaa Xaa Xaa Xaa
1 5 10 15

-continued

Glu Ser Gly Arg Met Thr
20

<210> SEQ ID NO 71
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (12)..(16)
<223> OTHER INFORMATION: Xaa can be any naturally occurring amino acid

<400> SEQUENCE: 71

Tyr Asp Ser Ser Leu Arg Pro Val Ser Val Thr Xaa Xaa Xaa Xaa Xaa
1 5 10 15

Glu Gln Gly Leu Val Val
20

<210> SEQ ID NO 72
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (12)..(16)
<223> OTHER INFORMATION: Xaa can be any naturally occurring amino acid

<400> SEQUENCE: 72

Tyr Asp Leu His Leu Arg Pro Thr Arg Ile Ile Xaa Xaa Xaa Xaa Xaa
1 5 10 15

Glu Gln Asn Arg Cys Ala
20

<210> SEQ ID NO 73
<211> LENGTH: 20
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 73

Trp Thr Pro Arg Gly Glu Leu Lys Gln Val Asn Xaa Xaa Xaa Xaa Asn
1 5 10 15

Gly Pro Gly Asn
20

<210> SEQ ID NO 74
<211> LENGTH: 20
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 74

Trp Thr Pro Arg Gly Glu Leu Lys Gln Ala Asn Xaa Xaa Xaa Xaa Asn
1 5 10 15

Ser Ala Gly Asn
20

<210> SEQ ID NO 75
<211> LENGTH: 22

-continued

<212> TYPE: PRT
<213> ORGANISM: TccC3 from Photorhabdus luminescens
<220> FEATURE:
<221> NAME/KEY: misc_feature
<222> LOCATION: (20)..(21)
<223> OTHER INFORMATION: Xaa can be any naturally occurring amino acid

<400> SEQUENCE: 75

Trp Asn Thr Arg Gly Glu Leu Lys Gln Val Thr Pro Val Ser Arg Glu
1 5 10 15

Ser Ala Ser Xaa Xaa Asp
20

<210> SEQ ID NO 76
<211> LENGTH: 22
<212> TYPE: PRT
<213> ORGANISM: TccC3 from Photorhabdus luminescens

<400> SEQUENCE: 76

Trp Asn Thr Arg Gly Glu Leu Gln Gln Val Thr Leu Val Lys Arg Asp
1 5 10 15

Lys Gly Ala Asn Asp Asp
20

<210> SEQ ID NO 77
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (21)..(21)
<223> OTHER INFORMATION: Xaa can be any naturally occurring amino acid

<400> SEQUENCE: 77

Trp Thr Ala Arg Asn Glu Leu Leu Lys Val Thr Pro Val Val Arg Asp
1 5 10 15

Gly Ser Thr Asp Xaa Asp
20

<210> SEQ ID NO 78
<211> LENGTH: 22
<212> TYPE: PRT
<213> ORGANISM: TccC3 from Photorhabdus luminescens

<400> SEQUENCE: 78

Trp Asp Ala Arg Asn Gln Leu Gln His Ile Thr Thr Val Gln Arg Glu
1 5 10 15

Asp Gly Ser Asn Asp Asp
20

<210> SEQ ID NO 79
<211> LENGTH: 22
<212> TYPE: PRT
<213> ORGANISM: TccC3 from Photorhabdus luminescens

<400> SEQUENCE: 79

Trp Asp Val Arg Asn Gln Leu Gln His Ile Thr Thr Val Gln Arg Glu
1 5 10 15

Asp Gly Ser Ser Asp Asp
20

<210> SEQ ID NO 80
<211> LENGTH: 39
<212> TYPE: PRT

<213> ORGANISM: TccC3 from Photorhabdus luminescens

<400> SEQUENCE: 80

Phe Asp Ala Ser Gly Asn Leu Leu Ala Leu Gln Ala Gly Gln His Leu
1               5                   10                  15

Ser Trp Asp Arg Arg Asn Gln Leu Gln His Val Arg Pro Val Ile Arg
            20                  25                  30

Glu Asn Gly Met Asp Asp Ser
        35

<210> SEQ ID NO 81
<211> LENGTH: 22
<212> TYPE: PRT
<213> ORGANISM: TccC3 from Photorhabdus luminescens

<400> SEQUENCE: 81

Trp Asp Ser Gly Asn Arg Leu Ile Lys Val Asp Ala Val Thr Arg Ser
1               5                   10                  15

Glu Gln Pro Glu Asp Gly
            20

<210> SEQ ID NO 82
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (7)..(11)
<223> OTHER INFORMATION: Xaa can be any naturally occurring amino acid

<400> SEQUENCE: 82

Tyr Ser Ala Ala Gly Gln Xaa Xaa Xaa Xaa Xaa Lys Leu Arg Glu Glu
1               5                   10                  15

His Gly Asn Gly Ile Val
            20

<210> SEQ ID NO 83
<211> LENGTH: 22
<212> TYPE: PRT
<213> ORGANISM: TccC3 from Photorhabdus luminescens
<220> FEATURE:
<221> NAME/KEY: misc_feature
<222> LOCATION: (7)..(11)
<223> OTHER INFORMATION: Xaa can be any naturally occurring amino acid

<400> SEQUENCE: 83

Tyr Ser Ala Ala Gly Gln Xaa Xaa Xaa Xaa Xaa Lys Leu Arg Glu Glu
1               5                   10                  15

Ser Gly Asn Gly Val Ile
            20

<210> SEQ ID NO 84
<211> LENGTH: 22
<212> TYPE: PRT
<213> ORGANISM: TccC3 from Photorhabdus luminescens

<400> SEQUENCE: 84

Tyr Glu Pro Glu Thr Gln Arg Leu Ile Gly Ile Lys Thr Arg Arg Pro
1               5                   10                  15

Ser Asp Thr Lys Val Leu
            20

<210> SEQ ID NO 85

<211> LENGTH: 44
<212> TYPE: PRT
<213> ORGANISM: TccC3 from Photorhabdus luminescens
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid

<400> SEQUENCE: 85

```
Tyr Asp Ser Leu Xaa Xaa Xaa Xaa Xaa Xaa Xaa Tyr Gln Leu Ile Ser
1               5                   10                  15

Ala Thr Gly Arg Glu Met Ala Asn Ile Gly Gln Gln Asn Asn Gln Leu
            20                  25                  30

Pro Xaa Ser Pro Ala Leu Pro Ser Xaa Asp Asn Asn
        35                  40
```

<210> SEQ ID NO 86
<211> LENGTH: 44
<212> TYPE: PRT
<213> ORGANISM: TccC3 from Photorhabdus luminescens
<220> FEATURE:
<221> NAME/KEY: misc_feature
<222> LOCATION: (5)..(11)
<223> OTHER INFORMATION: Xaa can be any naturally occurring amino acid

<400> SEQUENCE: 86

```
Tyr Asp Thr Leu Xaa Xaa Xaa Xaa Xaa Xaa Xaa Tyr Gln Leu Ile Glu
1               5                   10                  15

Ala Ser Gly Arg Glu Val Arg Asn Gly Ala Ser His Gly Pro Ala Leu
            20                  25                  30

Pro Gly Leu Gln Ser Leu Pro Thr Ile Asp Pro Cys
        35                  40
```

<210> SEQ ID NO 87
<211> LENGTH: 44
<212> TYPE: PRT
<213> ORGANISM: TccC3 from Photorhabdus luminescens
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (34)..(38)
<223> OTHER INFORMATION: Xaa can be any naturally occurring amino acid

<400> SEQUENCE: 87

```
Tyr Asp Thr Leu Xaa Xaa Xaa Xaa Xaa Xaa Xaa Tyr Arg Leu Ile Ser
1               5                   10                  15

Ala Thr Gly Tyr Ser Asp Ala Pro Pro Ser Asp Arg Xaa Leu Gly Leu
            20                  25                  30

Pro Xaa Xaa Xaa Xaa Xaa Gln Ser Thr Asn Pro Asp
        35                  40
```

<210> SEQ ID NO 88

-continued

```
<211> LENGTH: 44
<212> TYPE: PRT
<213> ORGANISM: TccC3 from Photorhabdus luminescens
<220> FEATURE:
<221> NAME/KEY: misc_feature
<222> LOCATION: (34)..(41)
<223> OTHER INFORMATION: Xaa can be any naturally occurring amino acid

<400> SEQUENCE: 88

Tyr Asp Ala Ala Gly Asn Leu Leu Gln Met Arg His Glu Gly Ala His
1               5                   10                  15

Asn Phe Thr Arg Asn Met His Val Asp Pro Asp Ser Asn Arg Ser Leu
            20                  25                  30

Pro Xaa Xaa Xaa Xaa Xaa Xaa Xaa Xaa Asp Asn Asp
        35                  40


<210> SEQ ID NO 89
<211> LENGTH: 44
<212> TYPE: PRT
<213> ORGANISM: TccC3 from Photorhabdus luminescens
<220> FEATURE:
<221> NAME/KEY: misc_feature
<222> LOCATION: (34)..(41)
<223> OTHER INFORMATION: Xaa can be any naturally occurring amino acid

<400> SEQUENCE: 89

Tyr Asp Ala Ala Gly Asn Leu Leu Gln Met Arg His Glu Gly Ala His
1               5                   10                  15

Asn Phe Thr Arg Asn Met His Val Asp Pro Asp Ser Asn Arg Ser Leu
            20                  25                  30

Pro Xaa Xaa Xaa Xaa Xaa Xaa Xaa Xaa Asp Asp Glu
        35                  40


<210> SEQ ID NO 90
<211> LENGTH: 23
<212> TYPE: PRT
<213> ORGANISM: TccC3 from Photorhabdus luminescens
<220> FEATURE:
<221> NAME/KEY: misc_feature
<222> LOCATION: (13)..(14)
<223> OTHER INFORMATION: Xaa can be any naturally occurring amino acid

<400> SEQUENCE: 90

Tyr Asp Pro Val Gly Asn Ile Leu Ala Ile His Asn Xaa Xaa Asp Ala
1               5                   10                  15

Glu Ala Thr Arg Phe Tyr Arg
            20


<210> SEQ ID NO 91
<211> LENGTH: 23
<212> TYPE: PRT
<213> ORGANISM: TccC3 from Photorhabdus luminescens
<220> FEATURE:
<221> NAME/KEY: misc_feature
<222> LOCATION: (12)..(15)
<223> OTHER INFORMATION: Xaa can be any naturally occurring amino acid

<400> SEQUENCE: 91

Tyr Asn Ala Phe Gly Gln Leu Ile Ala Ser Arg Xaa Xaa Xaa Xaa Asp
1               5                   10                  15

Pro Arg Leu Glu Val Asp Asn
            20


<210> SEQ ID NO 92
<211> LENGTH: 25
```

-continued

<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 92

```
Gln Arg Leu Ala Tyr Asp Val Ala Xaa Xaa Xaa Gly Gln Leu Lys Gly
1               5                   10                  15

Cys Trp Leu Thr Leu Lys Gly Gln Ala
            20                  25
```

<210> SEQ ID NO 93
<211> LENGTH: 28
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 93

```
Gln Arg Leu Ala Tyr Asn Val Ala Xaa Xaa Xaa Gly Gln Leu Lys Gly
1               5                   10                  15

Ser Trp Leu Thr Leu Lys Asn Gln Ser Glu Gln Val
            20                  25
```

<210> SEQ ID NO 94
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 94

```
Gln Arg Met Ala Tyr Asp Val Ala Xaa Xaa Xaa Gly Leu Leu Ser Gly
1               5                   10                  15

Ser Trp Xaa Thr Leu Lys Asp Gly Thr Glu
            20                  25
```

<210> SEQ ID NO 95
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 95

```
Gln Arg Met Ala Tyr Asp Val Ala Xaa Xaa Xaa Gly Leu Leu Ser Gly
1               5                   10                  15

Ser Trp Leu Thr Leu Lys Asp Gly Thr Glu
            20                  25
```

<210> SEQ ID NO 96
<211> LENGTH: 25
<212> TYPE: PRT
<213> ORGANISM: TccC3 from Photorhabdus luminescens
<220> FEATURE:

<221> NAME/KEY: misc_feature
<222> LOCATION: (9)..(11)
<223> OTHER INFORMATION: Xaa can be any naturally occurring amino acid

<400> SEQUENCE: 96

Gln Gln Ser Thr Tyr Asp Val Ala Xaa Xaa Xaa Gly Gln Leu Asn Arg
1               5                   10                  15

Val Gln Leu Gln Ile Asn Gly Gln Thr
            20                  25

<210> SEQ ID NO 97
<211> LENGTH: 25
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 97

Gln Gln Ser Thr Tyr Asp Ile Ala Xaa Xaa Xaa Gly Gln Leu Val Gln
1               5                   10                  15

Val Gln Leu Gln Leu Asp Gly Gln Ala
            20                  25

<210> SEQ ID NO 98
<211> LENGTH: 29
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 98

Gln Arg Phe Ser His Gly Val Ala Xaa Xaa Xaa Gly Gln Leu His Ala
1               5                   10                  15

Val Glu Leu Thr Leu Ala Asn Thr Ala Gln Arg Gln Thr
            20                  25

<210> SEQ ID NO 99
<211> LENGTH: 20
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 99

Gln Ala Phe Gly Met Thr Val Ala Xaa Xaa Xaa Gly Gln Leu Lys Ala
1               5                   10                  15

Ala Gly Leu Thr
            20

<210> SEQ ID NO 100
<211> LENGTH: 19
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 100

Gln Leu Ser Thr His Asn Leu Ala Xaa Xaa Xaa Gly Gln Leu His Ser

-continued 1 5 10 15

Thr Asp Leu

<210> SEQ ID NO 101
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 101

Gln Val Leu Val Ser Ala Ile Gln Tyr Xaa Asp Ala Gln Glu Arg Val
1 5 10 15

Val Ser Glu Thr Ala Gly Asn Gly Val Met
20 25

<210> SEQ ID NO 102
<211> LENGTH: 24
<212> TYPE: PRT
<213> ORGANISM: TccC3 from Photorhabdus luminescens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 102

Gln Val Ile Leu Arg Ser Leu Thr Tyr Xaa Ser Ala Ala Gly Gln Lys
1 5 10 15

Leu Arg Glu Glu Ser Gly Asn Gly
20

<210> SEQ ID NO 103
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (9)..(10)
<223> OTHER INFORMATION: Xaa can be any naturally occurring amino acid

<400> SEQUENCE: 103

Ser Thr Ala Leu Tyr Ala Thr Glu Xaa Xaa Asp Gly Arg Leu Leu Ala
1 5 10 15

Leu Ser Ala Arg Arg Ala Asp Gly Leu Met
20 25

<210> SEQ ID NO 104
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (9)..(10)
<223> OTHER INFORMATION: Xaa can be any naturally occurring amino acid

<400> SEQUENCE: 104

Thr Lys Ala Leu His Asp Ala Ala Xaa Xaa Asn Gly Arg Leu Ile Glu
1 5 10 15

Leu Lys Gly Thr Arg Ala Asp Gly Gln Leu
20 25

<210> SEQ ID NO 105
<211> LENGTH: 26

-continued

```
<212> TYPE: PRT
<213> ORGANISM: TccC3 from Photorhabdus luminescens
<220> FEATURE:
<221> NAME/KEY: misc_feature
<222> LOCATION: (9)..(10)
<223> OTHER INFORMATION: Xaa can be any naturally occurring amino acid

<400> SEQUENCE: 105

Ser Arg Tyr Val Tyr Asp Leu Gln Xaa Xaa Asp Gly Arg Leu Ile Glu
1               5                   10                  15

Leu Ser Ala Leu Ser Ala Asp Gly Ser Val
            20                  25


<210> SEQ ID NO 106
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 106

Ser Cys Ala Ser Phe Asp Leu Ala Xaa Xaa Asp Gly Arg Met Ser Glu
1               5                   10                  15

Leu Ile Thr Tyr Arg Pro Xaa Gly Val Lys
            20                  25


<210> SEQ ID NO 107
<211> LENGTH: 30
<212> TYPE: PRT
<213> ORGANISM: TccC3 from Photorhabdus luminescens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 107

Glu Arg Arg Gln Tyr Gly Gly Ala Asp Xaa Thr Gln Gly His Asn Gln
1               5                   10                  15

Cys Asn Gln Cys Ile Arg His Asp Asp Pro Ala Gly Ser Arg
            20                  25                  30


<210> SEQ ID NO 108
<211> LENGTH: 30
<212> TYPE: PRT
<213> ORGANISM: TccC3 from Photorhabdus luminescens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 108

Glu Arg Phe Thr Tyr Gly Gly Pro Ala Xaa Thr Ala Glu Arg Asn Gln
1               5                   10                  15

Cys Asn Gln Leu Ile Arg His Asp Asp Thr Ala Gly Ser Arg
            20                  25                  30


<210> SEQ ID NO 109
<211> LENGTH: 30
<212> TYPE: PRT
<213> ORGANISM: TccC3 from Photorhabdus luminescens
<220> FEATURE:
```

```
<221> NAME/KEY: misc_feature
<222> LOCATION: (10)..(10)
<223> OTHER INFORMATION: Xaa can be any naturally occurring amino acid

<400> SEQUENCE: 109

Glu Arg Leu Ala Tyr Gly Gly Ala Asp Xaa Ala Ala Glu His Asn Gln
1               5                   10                  15

Cys Asn Gln Leu Ile Arg His Asp Asp Thr Ala Gly Ser Arg
            20                  25                  30


<210> SEQ ID NO 110
<211> LENGTH: 30
<212> TYPE: PRT
<213> ORGANISM: TccC3 from Photorhabdus luminescens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 110

Glu Arg Phe Thr Tyr Gly Gln Ala Gly Xaa Ala Ala Ala His Asn Gln
1               5                   10                  15

Cys Asn Gln Leu Val Arg His Asp Asp Thr Ala Gly Ser Arg
            20                  25                  30


<210> SEQ ID NO 111
<211> LENGTH: 24
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 111

Glu Trp Tyr Arg Tyr Asp Ser Asn Xaa Xaa Xaa Gly Met Arg Gln Leu
1               5                   10                  15

Lys Val Ser Glu Gln Pro Thr Gln
            20


<210> SEQ ID NO 112
<211> LENGTH: 24
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 112

Glu Trp Tyr Arg Tyr Asp Ser Asn Xaa Xaa Xaa Gly Ile Arg Gln Leu
1               5                   10                  15

Lys Val Asn Glu Gln Gln Thr Gln
            20


<210> SEQ ID NO 113
<211> LENGTH: 23
<212> TYPE: PRT
<213> ORGANISM: TccC3 from Photorhabdus luminescens
<220> FEATURE:
<221> NAME/KEY: misc_feature
<222> LOCATION: (10)..(12)
<223> OTHER INFORMATION: Xaa can be any naturally occurring amino acid

<400> SEQUENCE: 113

Arg Glu Trp Tyr Arg Tyr Gly Asn Asp Xaa Xaa Xaa Gly Met Arg Arg
```

-continued

```
1               5                   10                  15

Leu Lys Val Ser Glu Gln Gln
            20


<210> SEQ ID NO 114
<211> LENGTH: 30
<212> TYPE: PRT
<213> ORGANISM: TccC3 from Photorhabdus luminescens
<220> FEATURE:
<221> NAME/KEY: misc_feature
<222> LOCATION: (10)..(12)
<223> OTHER INFORMATION: Xaa can be any naturally occurring amino acid

<400> SEQUENCE: 114

Arg Glu Trp Tyr Arg Tyr Ser Gly Asp Xaa Xaa Xaa Gly Arg Arg Met
1               5                   10                  15

Leu Lys Ile Asn Glu Gln Gln Ala Ser Asn Asn Ala Gln Thr
            20                  25                  30


<210> SEQ ID NO 115
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (10)..(12)
<223> OTHER INFORMATION: Xaa can be any naturally occurring amino acid

<400> SEQUENCE: 115

Ser Glu Ser Tyr Arg Tyr Asp Ala Ala Xaa Xaa Xaa Ser Gln Arg Ile
1               5                   10                  15

Leu Lys Val Ser Arg Gln Lys Thr Asn Thr
            20                  25


<210> SEQ ID NO 116
<211> LENGTH: 28
<212> TYPE: PRT
<213> ORGANISM: TccC3 from Photorhabdus luminescens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 116

Glu Xaa Arg Tyr Val Tyr Asp Gly Gln Xaa Xaa Xaa Gly Gln Arg Cys
1               5                   10                  15

Arg Leu Ile Ser Thr Ala Gln Ala Ser Gly Arg Thr
            20                  25


<210> SEQ ID NO 117
<211> LENGTH: 28
<212> TYPE: PRT
<213> ORGANISM: TccC3 from Photorhabdus luminescens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 117
```

-continued

```
Glu Xaa Arg Tyr Val Tyr Asp Gly Gln Xaa Xaa Xaa Gly Gln Arg Cys
1               5                   10                  15

Arg Lys Ile Ser Thr Ala Gln Ala Ser Gly Arg Met
            20                  25


<210> SEQ ID NO 118
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 118

Glu Xaa Arg Tyr Ser Tyr Asp Ala Ser Xaa Xaa Xaa Gly Gln Arg Leu
1               5                   10                  15

Arg Lys Val Arg Thr Thr Gln Ala Lys Thr
            20                  25


<210> SEQ ID NO 119
<211> LENGTH: 24
<212> TYPE: PRT
<213> ORGANISM: TccC3 from Photorhabdus luminescens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid

<400> SEQUENCE: 119

Glu Xaa His Tyr Ala Tyr Asp Ala Ser Xaa Xaa Xaa Gly Gln Arg Leu
1               5                   10                  15

Arg Xaa Xaa Lys Thr Ala Lys Ala
            20


<210> SEQ ID NO 120
<211> LENGTH: 29
<212> TYPE: PRT
<213> ORGANISM: TccC3 from Photorhabdus luminescens
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid

<400> SEQUENCE: 120

Thr Glu Tyr Xaa Xaa Ser Tyr Glu Pro Glu Thr Gln Xaa Xaa Xaa Arg
1               5                   10                  15

Leu Ile Gly Ile Thr Thr Arg Arg Pro Ser Asp Ala Lys
            20                  25


<210> SEQ ID NO 121
<211> LENGTH: 29
```

-continued

```
<212> TYPE: PRT
<213> ORGANISM: TccC3 from Photorhabdus luminescens
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid

<400> SEQUENCE: 121

Thr Glu Tyr Xaa Xaa Arg Tyr Glu Pro Gln Thr Gln Xaa Xaa Xaa Arg
1               5                   10                  15

Leu Ile Gly Ile Lys Thr Thr Arg Pro Xaa Xaa Ala Lys
            20                  25


<210> SEQ ID NO 122
<211> LENGTH: 29
<212> TYPE: PRT
<213> ORGANISM: TccC3 from Photorhabdus luminescens
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 122

Gln Asp Leu Xaa Xaa Arg Tyr Glu Tyr Asp Pro Val Xaa Xaa Xaa Gly
1               5                   10                  15

Asn Val Xaa Ile Ser Ile Arg Asn Asp Ala Glu Ala Thr
            20                  25


<210> SEQ ID NO 123
<211> LENGTH: 31
<212> TYPE: PRT
<213> ORGANISM: TccC3 from Photorhabdus luminescens
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 123

Thr Tyr Thr Asn Tyr Thr Arg Arg Tyr Ser Tyr Asp His Ser Xaa Xaa
1               5                   10                  15

Xaa Gly Asn Leu Xaa Thr Gln Ile Arg His Ser Ser Ser Ala Thr
            20                  25                  30


<210> SEQ ID NO 124
<211> LENGTH: 29
<212> TYPE: PRT
<213> ORGANISM: TccC3 from Photorhabdus luminescens
<220> FEATURE:
<221> NAME/KEY: misc_feature
<222> LOCATION: (15)..(17)
```

-continued

```
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 124

Gln Val Ser Asn Tyr Thr Gln Ser Tyr Ser Tyr Asp Ala Ala Xaa Xaa
1               5                   10                  15

Xaa Gly Asn Leu Xaa Leu Gln Met Arg His Glu Gly Ala
            20                  25


<210> SEQ ID NO 125
<211> LENGTH: 32
<212> TYPE: PRT
<213> ORGANISM: TccC3 from Photorhabdus luminescens
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 125

Asp Arg Arg Asn Tyr Val Glu His Tyr Asp Tyr Asp His Gly Xaa Xaa
1               5                   10                  15

Xaa Asp Asn Leu Xaa Val Lys Thr Ile His Val Arg Asp Gly Thr Ser
            20                  25                  30


<210> SEQ ID NO 126
<211> LENGTH: 29
<212> TYPE: PRT
<213> ORGANISM: TccC3 from Photorhabdus luminescens
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 126

Arg Tyr Val Asp Phe Xaa Xaa Ala Thr Ser Phe Asp Ala Asn Xaa Xaa
1               5                   10                  15

Xaa Gly Asn Leu Xaa Leu Gln Leu Val Arg Gly Gln Thr
            20                  25


<210> SEQ ID NO 127
<211> LENGTH: 29
<212> TYPE: PRT
<213> ORGANISM: TccC3 from Photorhabdus luminescens
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
```

<400> SEQUENCE: 127

Gly Glu Val Asp Phe Xaa Xaa Ala Thr Ser Phe Asp Ala Asn Xaa Xaa
1               5                   10                  15

Xaa Gly Asn Leu Xaa Leu Gln Leu Val Arg Gly Gln Thr
            20                  25

<210> SEQ ID NO 128
<211> LENGTH: 28
<212> TYPE: PRT
<213> ORGANISM: TccC3 from Photorhabdus luminescens

<400> SEQUENCE: 128

Asn Gln Lys Ile Val Pro Glu Thr Thr Tyr Arg Tyr Asp Ala Leu Tyr
1               5                   10                  15

Gln Leu Ile Glu Ala Thr Gly Arg Glu Ala Asp Thr
            20                  25

<210> SEQ ID NO 129
<211> LENGTH: 26
<212> TYPE: PRT
<213> ORGANISM: TccC3 from Photorhabdus luminescens
<220> FEATURE:
<221> NAME/KEY: misc_feature
<222> LOCATION: (9)..(11)
<223> OTHER INFORMATION: Xaa can be any naturally occurring amino acid

<400> SEQUENCE: 129

Phe Arg Tyr Gln Tyr Ser Leu Ser Xaa Xaa Xaa Gly Val Pro Leu Arg
1               5                   10                  15

Thr Asp Ser Val Asp Ser Gly Ser Thr Leu
            20                  25

<210> SEQ ID NO 130
<211> LENGTH: 35
<212> TYPE: PRT
<213> ORGANISM: Fused Class B/C TC proteins from Prokaryotic and
      Archaeal Sources
<220> FEATURE:
<221> NAME/KEY: misc_feature
<222> LOCATION: (27)..(30)
<223> OTHER INFORMATION: Xaa can be any naturally occurring amino acid

<400> SEQUENCE: 130

Pro Glu Ser Gly Ile Ser Val Gly Asp Ile Asn Ala Asp Gly Leu Thr
1               5                   10                  15

Asp Val Leu Tyr His Asn Asn Gly Gln Val Xaa Xaa Xaa Xaa Glu Val
            20                  25                  30

Tyr Leu Ser
        35

<210> SEQ ID NO 131
<211> LENGTH: 18
<212> TYPE: PRT
<213> ORGANISM: Fused Class B/C TC proteins from Prokaryotic and
      Archaeal Sources

<400> SEQUENCE: 131

Ile Ser Ser Gly Thr Thr Ile Gly Asp Phe Asn Gly Asp Gly Leu Pro
1               5                   10                  15

Asp Phe

<210> SEQ ID NO 132

-continued

<211> LENGTH: 21
<212> TYPE: PRT
<213> ORGANISM: Fused Class B/C TC proteins from Prokaryotic and
Archaeal Sources

<400> SEQUENCE: 132

Pro Thr Thr Gln Phe Gln Pro Ile Asp Ile Asn Gly Asp Gly Glu Leu
1 5 10 15

Asp Val Ala Trp Leu
20

<210> SEQ ID NO 133
<211> LENGTH: 13
<212> TYPE: PRT
<213> ORGANISM: Fused Class B/C TC proteins from Prokaryotic and
Archaeal Sources

<400> SEQUENCE: 133

Asp Tyr Asn Ala Asp Gly His Ala Asp Val Ala Ile Tyr
1 5 10

<210> SEQ ID NO 134
<211> LENGTH: 32
<212> TYPE: PRT
<213> ORGANISM: Fused Class B/C TC proteins from Prokaryotic and
Archaeal Sources
<220> FEATURE:
<221> NAME/KEY: misc_feature
<222> LOCATION: (25)..(28)
<223> OTHER INFORMATION: Xaa can be any naturally occurring amino acid

<400> SEQUENCE: 134

Ala Asp Tyr Phe Ser Gly Asp Met Asn Gly Asp Arg Glu Glu Asp Tyr
1 5 10 15

Phe Ile Arg Gly Tyr Gln Ala Gly Xaa Xaa Xaa Xaa Glu Pro Ala Leu
20 25 30

<210> SEQ ID NO 135
<211> LENGTH: 35
<212> TYPE: PRT
<213> ORGANISM: Fused Class B/C TC proteins from Prokaryotic and
Archaeal Sources
<220> FEATURE:
<221> NAME/KEY: misc_feature
<222> LOCATION: (28)..(30)
<223> OTHER INFORMATION: Xaa can be any naturally occurring amino acid

<400> SEQUENCE: 135

Arg Arg Asn Thr Ile Ala Leu Gln Asp Tyr Asn Leu Asp Gly Arg Met
1 5 10 15

Asp Leu Val Leu Leu Ser Gly Val Gly Gly Tyr Xaa Xaa Xaa Val Val
20 25 30

Asp Val Ile
35

<210> SEQ ID NO 136
<211> LENGTH: 34
<212> TYPE: PRT
<213> ORGANISM: Fused Class B/C TC proteins from Prokaryotic and
Archaeal Sources
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(31)

```
<223> OTHER INFORMATION: Xaa can be any naturally occurring amino acid

<400> SEQUENCE: 136

Ser Gly Thr Thr Gly Val Leu Arg Asp Phe Asp Asn Asp Gly Lys Ala
1               5                   10                  15

Asp Val Val Thr Ile Thr Gly Xaa Gly Gly Xaa Xaa Xaa Xaa Xaa Ile
            20                  25                  30

Gly Ser


<210> SEQ ID NO 137
<211> LENGTH: 25
<212> TYPE: PRT
<213> ORGANISM: Fused Class B/C TC proteins from Prokaryotic and
      Archaeal Sources
<220> FEATURE:
<221> NAME/KEY: misc_feature
<222> LOCATION: (16)..(23)
<223> OTHER INFORMATION: Xaa can be any naturally occurring amino acid

<400> SEQUENCE: 137

Asp Val Asn Gly Asp Gly Leu Thr Asp Ala Leu Thr Glu Ser Arg Xaa
1               5                   10                  15

Xaa Xaa Xaa Xaa Xaa Xaa Xaa Val Tyr
            20                  25


<210> SEQ ID NO 138
<211> LENGTH: 35
<212> TYPE: PRT
<213> ORGANISM: Fused Class B/C TC proteins from Prokaryotic and
      Archaeal Sources

<400> SEQUENCE: 138

Glu Asp Lys Val Ile Arg Leu Leu Asp Val Asn Gly Asp Gly Leu Leu
1               5                   10                  15

Asp Leu Val Ser Glu Ser Lys Ser Asp Ser Thr Thr Lys Phe Asn Val
            20                  25                  30

Tyr His Trp
        35


<210> SEQ ID NO 139
<211> LENGTH: 33
<212> TYPE: PRT
<213> ORGANISM: Fused Class B/C TC proteins from Prokaryotic and
      Archaeal Sources
<220> FEATURE:
<221> NAME/KEY: misc_feature
<222> LOCATION: (26)..(29)
<223> OTHER INFORMATION: Xaa can be any naturally occurring amino acid

<400> SEQUENCE: 139

Gly Gly Ala Asn Tyr Val Phe Ser Asp Val Asn Gly Asp Ser His Thr
1               5                   10                  15

Asp Leu Ile Thr Phe Tyr Asp Glu Arg Xaa Xaa Xaa Xaa Leu Ser Ile
            20                  25                  30

His


<210> SEQ ID NO 140
<211> LENGTH: 37
<212> TYPE: PRT
<213> ORGANISM: Fused Class B/C TC proteins from Prokaryotic and
      Archaeal Sources
<220> FEATURE:
<221> NAME/KEY: misc_feature
<222> LOCATION: (26)..(29)
```

-continued

<223> OTHER INFORMATION: Xaa can be any naturally occurring amino acid

<400> SEQUENCE: 140

Gly Ser Gly Thr Cys Val Leu Ala Asp Val Asn Gly Asp Gly Ala Thr
1 5 10 15

Asp Ile Val Arg Tyr Asp Gly Leu Asn Xaa Xaa Xaa Xaa Leu Ser Ala
20 25 30

Gly Val Trp Leu Ser
35

<210> SEQ ID NO 141
<211> LENGTH: 17
<212> TYPE: PRT
<213> ORGANISM: Fused Class B/C TC proteins from Prokaryotic and Archaeal Sources

<400> SEQUENCE: 141

Gly Phe Gly Asp Phe Asn Gly Asp Gly Arg Leu Asp Leu Leu Val Gly
1 5 10 15

Asp

<210> SEQ ID NO 142
<211> LENGTH: 37
<212> TYPE: PRT
<213> ORGANISM: Fused Class B/C TC proteins from Prokaryotic and Archaeal Sources

<400> SEQUENCE: 142

Thr Glu Ala Pro Arg Glu Val Gly Asp Leu Asp Phe Asp Gly Arg Asp
1 5 10 15

Glu Ile Phe Gly Asp Tyr Ser Glu Ala Thr Asp Gln Arg Ser Gly Gly
20 25 30

Arg Glu Gly Glu Thr
35

<210> SEQ ID NO 143
<211> LENGTH: 31
<212> TYPE: PRT
<213> ORGANISM: Fused Class B/C TC proteins from Prokaryotic and Archaeal Sources
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (20)..(29)
<223> OTHER INFORMATION: Xaa can be any naturally occurring amino acid

<400> SEQUENCE: 143

Gly Ala Ser Gly Ile Gly Xaa Xaa Xaa Xaa Val Gly Xaa Xaa Asp Phe
1 5 10 15

Leu Gly Asn Xaa Xaa Xaa Xaa Xaa Xaa Xaa Xaa Xaa Xaa Gly Arg
20 25 30

<210> SEQ ID NO 144
<211> LENGTH: 17
<212> TYPE: PRT
<213> ORGANISM: Artificial Sequence
<220> FEATURE:
<223> OTHER INFORMATION: Synthetic peptide -continued

```
<400> SEQUENCE: 144

Ser Lys Thr Ala Ser Ala Ala Glu Glu Leu Lys Glu Ala Arg Lys
1               5                   10                  15

Ser Phe


<210> SEQ ID NO 145
<211> LENGTH: 22
<212> TYPE: PRT
<213> ORGANISM: Artificial Sequence
<220> FEATURE:
<223> OTHER INFORMATION: Synthetic peptide

<400> SEQUENCE: 145

Tyr His Tyr Asp Glu Lys Ser Leu Leu Ser Asp Asp Pro Arg Val Lys
1               5                   10                  15

Ser Asn Arg Leu Ser Arg
            20
```

The invention claimed is:

1. An isolated protein that potentiates toxin activity of a Class A toxin complex protein against an insect, wherein said protein comprises the amino acid sequence of SEQ ID NO:4.

2. A method of controlling an insect wherein said method comprises the step of contacting said insect with the protein of claim 1 and a Class A complex toxin.

3. A method of potentiating the toxin activity of a Class A toxin complex protein toxin wherein said method comprises providing the protein of claim 1 and the Class A complex toxin to an insect for ingestion.

* * * * *

UNITED STATES PATENT AND TRADEMARK OFFICE

CERTIFICATE OF CORRECTION

PATENT NO. : 7,812,131 B2
APPLICATION NO. : 11/366918
DATED : October 12, 2010
INVENTOR(S) : Ignacio Mario Larrinua et al.

It is certified that error appears in the above-identified patent and that said Letters Patent is hereby corrected as shown below:

On the title page item (73), Assignee's Correct name is "Dow AgroSciences LLC"

Signed and Sealed this
Fifth Day of July, 2011

David J. Kappos
*Director of the United States Patent and Trademark Office*